(12) United States Patent
Inaba et al.

(10) Patent No.: US 7,351,825 B2
(45) Date of Patent: Apr. 1, 2008

(54) CYCLOPROPANE COMPOUNDS AND PHARMACEUTICAL USE THEREOF

(75) Inventors: Takashi Inaba, Osaka (JP); Julia Haas, Boulder, CO (US); Makoto Shiozaki, Osaka (JP); Nicole M. Littmann, Erie, CO (US); Katsutaka Yasue, Osaka (JP); Steven W. Andrews, Longmont, CO (US); Atushi Sakai, Osaka (JP); Andrew M. Fryer, Erie, CO (US); Takafumi Matsuo, Osaka (JP); Ellen R. Laird, Longmont, CO (US); Akira Suma, Osaka (JP); Yuichi Shinozaki, Osaka (JP); Yoshikazu Hori, Osaka (JP); Hiroto Imai, Osaka (JP); Tamotsu Negoro, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 152 days.

(21) Appl. No.: 11/011,773

(22) Filed: Dec. 15, 2004

(65) Prior Publication Data

US 2006/0199826 A1 Sep. 7, 2006

Related U.S. Application Data

(60) Provisional application No. 60/529,116, filed on Dec. 15, 2003.

(51) Int. Cl.
| | |
|---|---|
| C07D 265/00 | (2006.01) |
| C07D 295/00 | (2006.01) |
| C07D 237/00 | (2006.01) |
| C07D 409/00 | (2006.01) |
| C07D 411/00 | (2006.01) |
| C07D 217/00 | (2006.01) |
| C07D 211/00 | (2006.01) |
| C07D 213/00 | (2006.01) |
| C07D 271/00 | (2006.01) |
| C07D 413/00 | (2006.01) |
| C07D 498/00 | (2006.01) |
| C07D 277/00 | (2006.01) |
| C07D 257/00 | (2006.01) |
| C07D 233/00 | (2006.01) |
| C07D 231/00 | (2006.01) |
| C07D 207/00 | (2006.01) |
| C07D 333/00 | (2006.01) |
| C07D 307/00 | (2006.01) |
| C07D 303/00 | (2006.01) |
| C07D 309/00 | (2006.01) |
| C07D 311/00 | (2006.01) |

(52) U.S. Cl. ............ 544/160; 544/224; 544/379; 546/147; 546/223; 546/235; 546/280.4; 546/293; 546/312; 546/316; 546/323; 546/335; 548/131; 548/143; 548/145; 548/204; 548/253; 548/340.1; 548/375.1; 548/569; 514/238.2; 514/247; 514/252.13; 514/307; 514/329; 514/331; 514/336; 514/347; 514/352; 514/354; 514/355; 514/357; 514/364; 514/365; 514/381; 514/399; 514/406; 514/428; 514/438; 514/445; 549/65; 549/77; 549/461; 560/12; 562/427; 562/430; 564/89

(58) Field of Classification Search .............. None
See application file for complete search history.

(56) References Cited

U.S. PATENT DOCUMENTS 3,313,842 A 4/1967 Kaiser et al.

(Continued)

FOREIGN PATENT DOCUMENTS

EP 0 757 037 A 2/1997

(Continued)

OTHER PUBLICATIONS

Co-Pending U.S. Appl. No. 11/011,781; Title: N-Substituted-N-Sulfonylaminocyclopropane Compounds and Pharmaceutical Use Thereof; U.S. Filing Date: Dec. 15, 2004.

(Continued)

*Primary Examiner*—Brian J. Davis
(74) *Attorney, Agent, or Firm*—Finnegan, Henderson, Farabow, Garrett & Dunner, LLP

(57) ABSTRACT

The present invention provides a compound having aggrecanase inhibitory activity and MMP-13 inhibitory activity, and useful as a therapeutic agent for osteoarthritis, rheumatoid arthritis and the like, more specifically, a cyclopropane compound of formula (1):

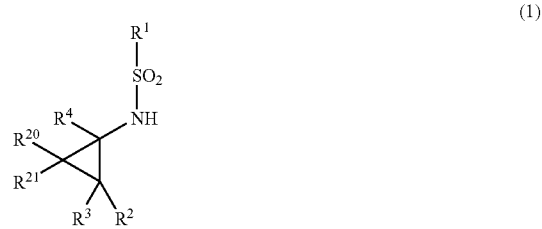

(1)

wherein $R^1$ is $-(CH_2)_m-X-(CH_2)_n-A^1$ etc., wherein m and n are the same or different and each is 0 to 6, X is a single bond, etc. and $A^1$ is a substituted $C_{3-14}$ hydrocarbon ring group, etc.; $R^2$ and $R^3$ are the same or different and each is a hydrogen atom, $-(CH_2)_p-X_1-(CH_2)_q-A^2$, etc., wherein p and q are the same or different and each is 0 to 6, $X_1$ is a single bond, etc. and $A^2$ is an optionally substituted $C_{3-14}$ hydrocarbon ring group, etc.; $R^4$ is $-CO_2R^9$, etc., wherein $R^9$ is a hydrogen atom, etc.; and $R^{20}$ and $R^{21}$ are the same or different and each is a hydrogen atom, $-(CH_2)_{m12}-X_{12}-(CH_2)_{m12}-R^{30}$, etc., wherein m12 and m12 are the same or different and each is 0 to 6, $X_{12}$ is a single bond, etc. and $R^{30}$ is a hydrogen atom, etc.; or a prodrug thereof or a pharmaceutically acceptable salt thereof.

33 Claims, No Drawings

U.S. PATENT DOCUMENTS

2005/0070588 A1    3/2005    Weinstein et al.

FOREIGN PATENT DOCUMENTS

| EP | 0 895 988 A | 2/1999 |
|---|---|---|
| EP | 0 950 656 A | 10/1999 |
| EP | 1 081 137 A | 3/2001 |
| EP | 1 088 819 A | 4/2001 |
| JP | A-2001-114765 | 4/2001 |
| JP | A-2002-284686 | 10/2002 |
| WO | WO 99/09000 | 2/1999 |
| WO | WO 00/09543 | 2/2000 |
| WO | WO01/47875 A1 | 7/2001 |
| WO | WO 01/77092 A | 10/2001 |
| WO | WO 03/053915 | 7/2003 |
| WO | WO 2004/041279 | 5/2004 |
| WO | WO 2004/055010 | 7/2004 |

OTHER PUBLICATIONS

Provisional U.S. Appl. No. 60/529,117; Title: Cyclopropane Compounds and Pharmaceutical Use Thereof; U.S. Filing Date: Dec. 15, 2003.

Patrick Y.S. Lam et al., *Discovery of 3-Amino-4-Chlorophenyl P1 as a Novel and Potent Benzamidine Mimic Via Solid-phase Synthesis of an Isoxazoline Library*, Bioorg. Med. Chem. Lett. 2003, 13, 1795-1799.

Nariyoshi Kawabata et al., *Copper(II) Halide Catalyzed Cyclopropanation of Olefins Involving Dehydrobromination of Bromomalonic Ester by Amine*, Bull. Chem. Soc. Jpn. 1982, 55, 2687-2688.

Isaac O. Donkor, et al., *Asymmetric Synthesis of 2, 3-Methanoleucine Stereoisomers from Common Intermediates*, Chirality 2000, 12, 551-557.

Joaquin Tamariz et al., *New Dienophiles: 1-Acetylvinyl Arenecarboxylates, Reactivity Toward Cylopentadiene and Exocyclic Dienes*, Helv. Chim. Acta 1981, 64, 188-197.

Yun Gao et al., *Vicinal Diol Cyclic Sulfates: Like Epoxides Only More Reactive*, J. Am. Chem. Soc. 1988, 110, 7538-7539.

Xiaohua Huang et al., *Expanding Pd-Catalyzed C-N Bond-Forming Processes: The First Amidation of Aryl Sulfonates, Aqueous Amination, and Complementarity with Cu-Catalyzed Reactions*, J. Am. Chem. Soc. 2003, 125, 6653-6655.

Fumio Toda, et al., *Efficient Solid-state Reactions of Alcohols: Dehydration, Rearrangement, and Substitution*, J. Chem. Soc. Chem. Commun. 1990, 18, 1270-1271.

Saeed Ahmad, et al. *Inhibition of Pig Kidney L=Aromatic Amino Acide Decarboxylase by 2,3-Methano-m-tyrosines*, J. Med Chem. 1992, 35, 1410-1417.

Yasuhisa Kohara, et al., *Synthesis and Angiotensin II Receptor Antagonistic Activities of Benzimidazole Derivatives Bearing Acidic Heterocycles as Novel Tetrazole Biososteres*, J. Med. Chem. 1996, 39, 5228-5235.

Francis Johnson, et al., *Polyfunctional Aliphatic Compounds. I. The Preparation of 3-Hydroxyglutaronitriles*, J. Org. Chem. 1962, 27, 2241-2243.

Donald A. McGowan et al., *(-)-Methyl cis-3-Hydroxy-4,5-oxycyclohex-1-enecarboxylate: Sterospecific Formation from and Conversion to (O)OMethyl Shikimate; Complex Formation with Bis(carbomethoxy) hydrazine*, J. Org. Chem. 1981, 46, 2381-2383.

Daniel Romo et al., *An Asymmetric Route to Enantiomerically Pure 1,2,3-Trisubstituted Cyclopropanes*, J. Org. Chem. 1992, 57, 6265-6270.

Andreas Reichelt, et al., *Design, Synthesis, and Evaluation of Matrix Metalloprotease Inhibitors Bearing Cyclopropane-Derived Peptidomimetics as P1' and P2' Replacements*, J. Org. Chem. 2002, 67, 4062-4075.

Ryan P. Wurz, et al., *An Expedient and Practical Method for the Synthesis of a Diverse Series of Cyclopropane α-Amino Acids and Amines*, J. Org. Chem. 2004, 69, 1262-1269.

F. Diederich et al., *Metal-catalzed Cross-coupling Reactions*, WILEY-VCH; New York, 1998, pp. 406-407, 416-419, and 452-453.

Georgia Georgakopoulou et al., $Rh^{11}$-*Catalyzed Thermal Cyclopropanations of a Phenyliodonium Bis(carbomethoxy)methylide with Alkenes and Dienes*, Synlett 2001, 12, 1843-1846.

Jonathan S. Baum et al., *Diazotransfer Reactions with p-Acetamidobenzenesulfonyl Azide*, Synth. Commun. 1987, 17, 1709-1716.

Frank L. Switzer, et al., *Synthesis of (±)2,3-Methanoproline: A Novel Inhibitor of Ethylene Biosynthesis*, Tetrahedron 1989, 45, 6091-6100.

Charles H. Stammer, *Cyclopropane Amino Acides 2,3-and 3,4-Methanoamino Acids)*, Tetrahedron 1990, 46, 2231-2254.

Georges Dewynter, et al., *Synthesis of N-sulfamoyloxazolidinones and—perhydrooxaziones Reactivity and Use as Donors in the Transsulfamoylation Reaction; Application to the Preparation of 2-Chloroethylnitrososulfamides. IV*, Tetrahedron 1996, 52, 14217-14227.

Damien Prim et al., *Palladium-catalysed reactions of aryl halides with soft, non-organometallic nucleophiles*, Tetrahedron 2002, 58, Issue 11, 2041-2075.

Jun-ichi Ohishi, *A New Cyclopropanation Method Mediated by Organosulfur Compounds*, Synthesis 1980, 9, 690-691.

Rogelio Jiménez et al., *1,3-Dipolar Cycloaddition Reactions Involving Captodative Olefins*, Heterocycles 1993, 35, 591-598.

English Derwent Abstract of JP 2002/284686, 2002.

English Derwent Abstract of JP 2001/114765, 2001.

International Search Report for PCT/US2004/041851 dated Apr. 18, 2005.

International Search Report for PCT/US2004/041852 dated Jun. 15, 2005.

Written Opinion of the International Searching Authority for PCT/US2004/041852 dated Jun. 15, 2005.

CYCLOPROPANE COMPOUNDS AND PHARMACEUTICAL USE THEREOF

This Application claims benefit of priority of U.S. provisional Application No. 60/529,116, filed Dec. 15, 2003, the contents of which are hereby incorporated by reference.

The present invention relates to a novel cyclopropane compound. In further detail, the present invention relates to a cyclopropane compound or a pharmaceutically acceptable salt thereof having an aggrecanase inhibitory activity or matrix metalloproteinase (MMP) inhibitory activity, a pharmaceutical composition which comprises this compound and a pharmaceutical use thereof.

Aggrecan is a main proteoglycan in cartilage, and decomposition of its core protein by protease is one of the early signs of a joint disorder associated with arthrodial cartilage destruction, such as rheumatoid arthritis and osteoarthritis. This process of decomposition leading to the cartilage destruction begins with the disappearance of aggrecan on the surface of cartilage, and progresses to the decomposition of collagen type II fiber. MMPs (Matrix metalloproteinases) that cleave Asn 341-Phe 342 and aggrecanase that cleaves Glu 373-Ala 374 are known as enzymes involved in this decomposition of aggrecan, and both are metal-proteases having zinc in the catalytic active center. The latter was determined to be ADAMTS (A Disintegrin and Metalloproteinase with Thrombospondin Motifs) in 1999. ADAMTS 1 to 20 have been identified so far, and ADAMTS 4 and 5 correspond to aggrecanase-1 and aggrecanase-2, respectively. Conventionally, MMP have been considered to mainly cause cartilage destruction, but many reports have documented that the aggrecan fragments found in the joint of osteoarthritis (OA) patients are predominantly the fragments cleaved by aggrecanases. Thus, aggrecanase is also considered to be a significant vicious factor for these disease states.

At present, conservative treatments and surgical treatments are available for treating OA. The conservative therapy includes body weight control, exercise therapy, physical therapy, drug therapy (administration of anti-inflammatory drug), hyperthermia, and the like. It is a general practice to inject hyaluronic acid into the joint in the course of these treatments to smoothen movement of the joint.

When improvement of conditions by the conservative treatments such as drug therapy, physical therapy, etc., is not achieved, a surgical treatment is performed. When the joint is highly deformed and causes a strong pain, an arthroplasty for embedding an artificial joint is performed as the final option. However, artificial joints have a life of only about 15 to 20 years, after which the QOL (Quality of Life) of the patient deteriorates.

At present, no drug that suppresses enzyme involved in cartilage destruction is available for OA treatment. When no improvement is made by a conservative treatment, cartilage destruction progresses and a surgical treatment will be required. Therefore, prevention of cartilage destruction before reaching the stage requiring a surgical treatment is important. A drug that inhibits aggrecanases involved in the destruction of cartilage is acknowledged to be an anti-OA drug having a sufficient cartilage destruction inhibitory activity. Without a surgical treatment, and moreover, such drug is expected to improve the QOL of patients.

Aggrecanase inhibitors have been developed as shown in the reports by DuPont (WO99/0900), Pfizer (JP-A-2001-114765) and the like, in which poor oral availability is a concern.

In addition, the MMP inhibitors under development include a compound that causes systemic connective tissue toxicity due to nonselective collagenase inhibition. It is proposed that the cause thereof is suppression of turnover of normal connective tissue collagen due to inhibition of collagenase-1 (MMP-1). It is clear, therefore, that the conventional products are not entirely satisfactory from the aspects of effective inhibition and occurrence of side effects.

The compound of the present invention possesses improved oral availability and shows strong aggrecanase inhibitory activity. While the compound is free of an MMP-1 inhibitory activity, it also has selective inhibitory activity of MMP-13, involved in joint destruction. Therefore, the compound is expected to suppress progress of joint diseases without causing side effects.

In addition, expressed in glioma, aggrecanase is suggested to be also involved in metastasis or tissue infiltration of tumor cells, like MMP, and in view of the current development of MMP inhibitor as an antimetastatic drug, the compound of the present invention having an inhibitory activity on both aggrecanase and MMP is expected to be a highly effective antitumor agent.

In bone metabolism, MMP suppresses decomposition of bone matrix and has a major part in bone resorption. In respiratory diseases, protease plays a key role in the course of destruction and remodeling of lung structure. MMP that uses an extracellular matrix (ECM), which is an architectural component of the protease, as a substrate is considered to be an important factor. Therefore, the compound of the present invention having MMP inhibitory activity is expected to be applicable to the bone resorption disorders and lung diseases, in which MMP is involved.

Various reports on compounds aiming at therapy of disorders such as OA, rheumatoid arthritis and the like by inhibition of aggrecanase have been published recently.

For example, JP-A-2002-284686 discloses a sulfonamide derivative having MMP-13 inhibitory activity and aggrecanase inhibitory activity. However, this publication does not include the compound having a structure, such as the structure of the compound of the present invention, or a disclosure suggestive thereof JP-A-2001-114765 discloses a hydroxamic acid derivative represented by the following formula:

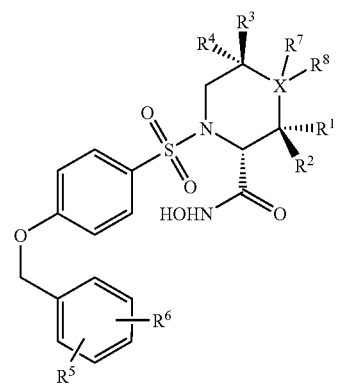

wherein X is carbon atom or nitrogen atom; $R^1$ and $R^2$ are each independently hydrogen atom, hydroxy or methyl, and at least one of $R^1$ and $R^2$ is methyl; $R^3$ and $R^4$ are each independently hydrogen atom, hydroxy or methyl, or $R^3$ and $R^4$ may be taken together to form carbonyl group; $R^5$ and $R^6$ are each independently hydrogen atom, halogen, cyano, methyl or ethyl; with the proviso that when X is carbon atom, $R^7$ and $R^8$ are both hydrogen atom and at least one of $R^1$, $R^2$, $R^3$ and $R^4$ is hydroxy; when X is carbon atom and $R^5$ is para-halo, at least one of $R^6$, $R^3$ and $R^4$ is not hydrogen atom; when X is nitrogen atom, $R^8$ is not present and $R^7$ is hydrogen atom or the group of the formula:

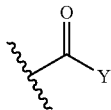

wherein Y is —$CH_2$—$NH_2$ or —NH—$CH_3$; when X is nitrogen atom and $R^7$ is H, $R^3$ and $R^4$ may be taken together to form carbonyl group, which has aggrecanase inhibitory activity. However, the compound of this publication has a piperidine ring or piperazine ring having substituent(s) as a skeletal structure. This publication does not include the compound having a cyclopropane structure, such as the structure of the compound of the present invention, or a disclosure suggestive thereof.

WO03/053915 discloses a cyclopropane derivative represented by the formula:

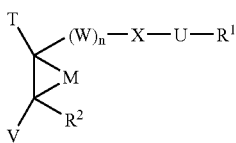

wherein M is —$(C(R^{30})(R^{40}))m$— wherein m is 1 to 6; T is $R^{21}$-substituted alkyl group, cycloalkyl group, heterocycloalkyl group, cycloalkenyl, heterocycloalkenyl, aryl group, heteroaryl group, —$OR^3$, —$C(O)R^4$, —$C(O)OR^3$, —$C(O)NR^{24}R^{25}$, —$C(O)NR^{24}OR^3$, —$C(O)SR^3$, —$NR^{24}R^{25}$, —$NR^{25}C(O)R^4$, —$NR^{25}C(O)OR^3 NR^{25}C(O)NR^{24}R^{25}$, —$NR^{25}C(O)NR^{24}OR^3$, —$SR^3$, —$S(O)_x NR^{24}R^{25}S(O)_x NR^{25} OR^3$, etc.; V is alkyl group, $R^{21}$-substituted alkyl group, cycloalkyl group, heterocycloalkyl group, cycloalkenyl, heterocycloalkenyl, aryl group, heteroaryl group, —$OR^3$, —$C(O)R^4$, —$(CR^{23}R^{24})_{n1}C(O)OR^3$, —$C(O)NR^{24}R^{25}$, —$(CR^{23}R^{24})_{n1}C(O)NR^{25}OR^3$, —$C(O)SR^3$, —$NR^{24}R^{25}$, —$NR^{25}C(O)R^4$, —$NR^{25}C(O)OR^4—NR^{25}C(O)NR^{24}R^{25}$, —$NR^{25}C(O)NR^{24}R^3$, —$SR^3$, —$S(O)xNR^{24}R^{25}$, —$S(O)xNR^{25}OR^3$, etc.; W is a covalent bond, —$(C(R^3)(R^4))_{n2}$-, —O—, —S—, etc.; X is alkylene, cycloalkylene, heterocycloalkylene, arylene, heteroarylene, —C≡C—, etc.; U is a covalent bond, —$(C(R^3)(R^4))_p$—, —Y—$(C(R^3)(R^4))q$-, —$(C(R^3)(R^4))$ t-Y—, —Y—, etc.; Y is —O—, —S(O)x-, etc.; n is 0 to 2; $R^1$ is alkyl group, $R^{21}$-substituted alkyl group, cycloalkyl group, heterocycloalkyl group, cycloalkenyl, heterocycloalkenyl, aryl group, heteroaryl group, etc.; $R^2$, $R^4$ and $R^5$ are each independently hydrogen atom, halo, alkyl group, etc.; $R^3$ is hydrogen atom, alkyl group, $R^{22}$-substituted alkyl group, etc.; $R^{23}$ is hydrogen atom, hydroxyl, halo, etc.; $R^{24}$ is hydrogen atom or alkyl; $R^{25}$ is hydrogen atom, hydroxyl, alkyl group, etc.; $R^{30}$ is hydrogen atom, etc.; $R^{40}$ is hydrogen atom, etc.; with the proviso that at least one of V and T is —$C(O)N(R^3)(OR^4)$, —$C(O)OR^3$ or —$C(O)NR^{24}R^{25}$. However, the compound of the formula disclosed in this publication is structurally different from the compound of the present invention. This publication does not include a compound having a structure of the compound of the present invention, or a disclosure suggestive thereof.

DISCLOSURE OF INVENTION

The present invention provides a compound having superior aggrecanase inhibitory activity and MMP inhibitory activity (particularly, MMP-13 inhibitory activity), and useful as a prophylactic or therapeutic agent for osteoarthritis, a prophylactic or therapeutic agent for rheumatoid arthritis, a prophylactic or therapeutic agent for a disorder such as joint injury, reactive arthritis, bone resorption disorder, cancer, asthma, allergic reaction, chronic pulmonary emphysema, fibroid lung, acute respiratory distress (ARDS), lung infection, interstitial pneumonia, etc. compound.

Some embodiments of the present invention provide an aggrecanase inhibitor, an MMP inhibitor, a prophylactic or therapeutic agent for osteoarthritis and a prophylactic or therapeutic agent for rheumatoid arthritis.

The present inventors have conducted intensive studies to obtain the above objects and found a cyclopropane compound represented by the following formula (1) has superior aggrecanase inhibitory activity and MMP-13 inhibitory activity, and useful as an aggrecanase inhibitor, an MMP inhibitor, a prophylactic or therapeutic agent for osteoarthritis and a prophylactic or therapeutic agent for rheumatoid arthritis, based on which findings the present invention has been completed.

Accordingly, the present invention relates the compounds [1] to [34] shown below and pharmaceutical use thereof.

[1] A cyclopropane compound of formula (1):

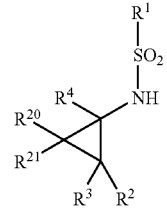

wherein
$R^1$ is selected from
(1) a substituted $C_{1-6}$ alkyl group
and
(2) —$(CH_2)_m$—X—$(CH_2)_n$-$A^1$,
wherein
m and n are the same or different and each is selected from 0 and an integer ranging from 1 to 6,
X is a linker selected from the following group A,
group A:
(a) a single bond,
(b) a $C_{1-6}$ alkylene group,
(c) a $C_{2-6}$ alkenylene group,
(d) a $C_{2-6}$ alkynylene group,
(e) —O—,
(f) —$N(R^5)$—,
(g) —$S(O)_{m1}$—,
(h) —CO—,
(i) —COO—,
(j) —OCO—,
(k) —$CON(R^5)$—,
(l) —$N(R^5)CO$—, (m) —SO$_2$N(R$^5$)—,
(n) —N(R$^5$)SO$_2$—,
(o) —N(R$^5$)CON(R$^6$)—,
(p) —N(R$^5$)SO$_2$N(R$^6$)—,
(q) —OCON(R$^5$)—,
(r) —N(R$^5$)COO—,
and
(s) —S(O)$_{m1}$—(CH$_2$)$_{n1}$—CO—;
wherein
R$^5$ and R$^6$ are the same or different and each is selected from a hydrogen atom, a C$_{1-6}$ alkyl group optionally substituted by halogen atoms or hydroxyl groups, a C$_{3-14}$ hydrocarbon ring group and a heterocyclic group,
m1 is selected from 0 and an integer ranging from 1 to 2 and
n1 is selected from an integer ranging from 1 to 2,
and
A$^1$ is selected from a substituted C$_{3-14}$ hydrocarbon ring group and a substituted heterocyclic group;
R$^2$ and R$^3$ are the same or different and each is selected from
(1) —(CH$_2$)$_p$—X$_1$—(CH$_2$)$_q$-A$^2$,
wherein
p and q are the same or different and each is selected from 0 and an integer ranging from 1 to 6,
X$_1$ is a linker selected from the above-mentioned group A and
A$^2$ is selected from an optionally substituted C$_{3-14}$ hydrocarbon ring group and an optionally substituted heterocyclic group,
and
(2) —(CH$_2$)$_{m8}$—X$_8$—(CH$_2$)$_{n8}$—R$^{27}$,
wherein
m8 and n8 are the same or different and each is selected from 0 and an integer ranging from 1 to 6,
X$_8$ is a linker selected from the above-mentioned group A and
R$^{27}$ is a substituent selected from the following group B,
group B:
(a) a hydrogen atom,
(b) a halogen atom,
(c) a hydroxyl group,
(d) a nitro group,
(e) a cyano group,
(f) a carboxyl group,
(g) an amino group,
(h) an amido group,
(i) a C$_{2-6}$ acyl group,
(j) a halogenated C$_{1-6}$ alkyl group,
(k) a C$_{1-6}$ alkyl group optionally substituted by hydroxyl groups,
(l) a C$_{2-6}$ alkenyl group optionally substituted by halogen atoms,
(m) a C$_{2-6}$ alkynyl group,
(n) a C$_{1-6}$ alkoxy group optionally substituted by hydroxyl groups,
(o) a C$_{1-6}$ alkoxy-C$_{1-6}$ alkyl group,
(p) a C$_{1-6}$ alkoxy-carbonyl group,
(q) a C$_{1-6}$ alkyl-aminocarbonyl group optionally substituted by halogen atoms,
(r) a mono(C$_{1-6}$ alkyl)amino group,
(s) a di(C$_{1-6}$ alkyl)amino group,
(t) a C$_{1-6}$ alkyl-carbonylamino group optionally substituted by halogen atoms,
(u) a C$_{1-6}$ alkylsulfonyl group and
(v) a C$_{1-6}$ alkylsulfonylamino group;

or A$_2$ and R$^{27}$ may be taken together to form an optionally substituted fused ring group,
or R$^2$ and R$^3$ may be taken together with a carbon atom bonded thereto to form the following ring

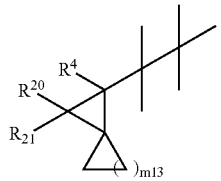

wherein m13 is selected from an integer ranging from 1 to 6, provided that R$^2$ and R$^3$ are not hydrogen atoms at the same time;
R$^4$ is selected from
(1) —CO$_2$R$^9$,
(2) —C(O)NHOR$^9$,
(3) —C(O)NH—SO$_2$—R$^9$,
(4) —C(O)NHR$^9$,
(5) —SH,
(6) —CH$_2$CO$_2$R$^9$,
(7) —C(O)R$^9$,
(8) —N(OH)COR$^9$,
(9) —SN$_2$H$_2$R$^9$,
(10) —SONHR$^9$,
(11) —CH$_2$CO$_2$H,
(12) —PO(OH)$_2$,
(13) —PO(OH)NHR$^9$,
(14) —CH$_2$SH,
(15) —CH$_2$OH,
(16) —(CH$_2$)$_{r1}$—PO(OH)—(CH$_2$)$_{r2}$—R$^9$,
(17) —NHR$^9$
(18) —NH—NHR$^9$
and
(19) —(CH$_2$)$_{r1}$—R$^{50}$
wherein
r1 and r2 are the same or different and each is selected from 0 and an integer ranging from 1 to 6,
R$^9$ is selected from
(1) a hydrogen atom,
(2) an optionally substituted C$_{1-10}$ alkyl group,
(3) an optionally substituted C$_{6-14}$ aryl-C$_{1-16}$ alkyl group and
(4) —(CH$_2$)$_{m9}$—X$_9$—(CH$_2$)$_{n9}$—R$^{28}$
wherein
m9 and n9 are the same or different and each is selected from 0 and an integer ranging from 1 to 6,
X$_9$ is a linker selected from the above-mentioned group A and
R$^{28}$ is a substituent selected from the following group C,
group C:
(a) a hydrogen atom,
(b) a halogen atom,
(c) a hydroxyl group,
(d) a nitro group,
(e) a cyano group,
(f) a carboxyl group,
(g) an amino group,
(h) an amido group,
(i) a C$_{2-6}$ acyl group,
(j) a halogenated C$_{1-6}$ alkyl group, (k) a $C_{1-6}$ alkyl group optionally substituted by hydroxyl groups, (l) a $C_{2-6}$ alkenyl group optionally substituted by halogen atoms, (m) a $C_{2-6}$ alkynyl group, (n) a $C_{1-6}$ alkoxy group optionally substituted by hydroxyl groups, (o) a $C_{1-6}$ alkoxy-$C_{1-6}$ alkyl group, (p) a $C_{1-6}$ alkoxy-carbonyl group, (q) a $C_{1-6}$ alkyl-aminocarbonyl group optionally substituted by halogen atoms, (r) a mono($C_{1-6}$ alkyl)amino group, (s) a di($C_{1-6}$ alkyl)amino group, (t) a $C_{1-6}$ alkyl-carbonylamino group optionally substituted by halogen atoms, (u) a $C_{1-6}$ alkylsulfonyl group, (v) a $C_{1-6}$ alkylsulfonylamino group, (w) a $C_{3-14}$ hydrocarbon ring group optionally substituted by 1 to 5 substituent(s) selected from the above-mentioned group B and (x) a heterocyclic group optionally substituted by 1 to 5 substituent(s) selected from the above-mentioned group B, and $R^{50}$ is selected from an optionally substituted $C_{3-14}$ hydrocarbon ring group and an optionally substituted heterocyclic group;

or $R^9$ of —C(O)NHR$^9$, $A^2$ and the cyclopropane ring may be taken together to form an optionally further substituted fused ring;

$R^{20}$ and $R^{21}$ are the same or different and each is selected from (1) —(CH$_2$)$_{m10}$—X$_{10}$—(CH$_2$)$_{n10}$-A$^3$, wherein m10 and n10 are the same or different and each is selected from 0 and an integer ranging from 1 to 6, $X_{10}$ is a linker selected from the above-mentioned group A and $A^3$ is selected from an optionally substituted $C_{3-14}$ hydrocarbon ring group and an optionally substituted heterocyclic group, and (2) —(CH$_2$)$_{m12}$—X$_{12}$—(CH$_2$)$_{n12}$—R$^{30}$, wherein m12 and n12 are the same or different and each is selected from 0 and an integer ranging from 1 to 6, $X_{12}$ is a linker selected from the above-mentioned group A and $R^{30}$ is a substituent selected from the above-mentioned group B;

or $A^2$, $R^{30}$ and the cyclopropane ring may be taken together to form a optionally further substituted fused ring, or $R^9$ of —CO$_2$R$^9$, $R^{20}$ and the cyclopropane ring may be taken together to form an optionally further substituted fused ring, or $R^{20}$ and $R^{21}$ may be taken together with a carbon atom bonded thereto to form the following ring

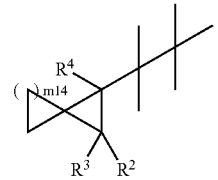

wherein m14 is selected from an integer ranging from 1 to 6; or a prodrug thereof or a pharmaceutically acceptable salt thereof [hereinafter sometimes referred to as compound (1)];

[2] The compound of [1] above, wherein the substituted $C_{3-14}$ hydrocarbon ring group or the substituted heterocyclic group in $A^1$ is a group of the following formula:

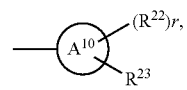

wherein ring $A^{10}$ is selected from a $C_{3-14}$ hydrocarbon ring group and a heterocyclic group, r is selected from an integer ranging from 1 to 4, $R^{22}$ is —(CH$_2$)$_{m4}$—X$_4$—(CH$_2$)$_{n4}$—R$^{24}$ wherein m4 and n4 are the same or different and each is selected from 0 and an integer ranging from 1 to 6, $X_4$ is a linker selected from the above-mentioned group A and $R^{24}$ is a substituent selected from the above-mentioned group B, wherein the substituents $R^{22}$ are the same or different when r is an integer selected from the range of 2 to 4, and $R^{23}$ is

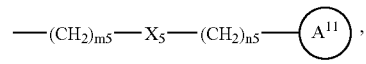

wherein m5 and n5 are the same or different and each is selected from 0 and an integer ranging from 1 to 6, $X_5$ is a linker selected from the above-mentioned group A and ring $A^{11}$ is selected from a $C_{3-14}$ hydrocarbon ring group and a heterocyclic group, and the ring $A^{11}$ is optionally substituted by 1 to 5 groups of the formula "—(CH$_2$)$_{m6}$—X$_6$—(CH$_2$)$_{n6}$—R$^{25}$", which are the same or different, wherein m6 and n6 are the same or different and each is selected from 0 and an integer ranging from 1 to 6, $X_6$ is a linker selected from the above-mentioned group A and $R^{25}$ is a substituent selected from the above-mentioned group C;

or the ring $A^{10}$ and the ring $A^{11}$ may be taken together with a substituent thereof to form an optionally substituted fused ring group;

the optionally substituted $C_{3-14}$ hydrocarbon ring group or the optionally substituted heterocyclic group in $A^2$ is a group of the following formula:

wherein
    ring $A^{12}$ is selected from a $C_{3-14}$ hydrocarbon ring group and a heterocyclic group, and the ring $A^{12}$ is optionally substituted by 1 to 5 groups of the formula "—$(CH_2)_{m7}$—$X_7$—$(CH_2)_{n7}$—$R^{26}$", which are the same or different, wherein
    m7 and n7 are the same or different and each is selected from 0 and an integer ranging from 1 to 6,
    $X_7$ is a linker selected from the above-mentioned group A and
    $R^{26}$ is a substituent selected from the above-mentioned group C;

or $R^{26}$ may be linked with $R^{27}$, together with ring $A^{12}$ to form an optionally substituted fused ring group, or $R^{26}$ may be linked with $R^9$ of —C(O)NHR$^9$ or $R^{30}$, together with the ring $A^{12}$ and the cyclopropane ring to form an optionally further substituted fused ring;

the optionally substituted $C_{3-14}$ hydrocarbon ring group or the optionally substituted heterocyclic group in $A^3$ is a group of the following formula:

wherein
    ring $A^{13}$ is selected from a $C_{3-14}$ hydrocarbon ring group and a heterocyclic group, and the ring $A^{13}$ is optionally substituted by 1 to 5 groups of the formula "—$(CH_2)_{m11}$—$X_{11}$—$(CH_2)_{n11}$—$R^{29}$", which are the same or different,
wherein
    m11 and n11 are the same or different and each is selected from 0 and an integer ranging from 1 to 6,
    $X_{11}$ is a linker selected from the above-mentioned group A and
    $R^{29}$ is a substituent selected from the above-mentioned group C;

or a prodrug thereof or a pharmaceutically acceptable salt thereof;

[3] The compound of [2] above, wherein $R^1$ is —$(CH_2)_m$—X—$(CH_2)_n$-$A^1$; or a prodrug thereof or a pharmaceutically acceptable salt thereof;

[4] The compound of [3] above, wherein m and n are 0 and X is a single bond; or a prodrug thereof or a pharmaceutically acceptable salt thereof;

[5] The compound of [4], wherein $A^1$ is

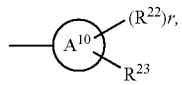

$R^{23}$ is

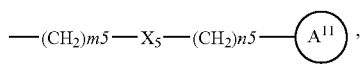

m5 and n5 are 0 and $X_5$ is a single bond; or a prodrug thereof or a pharmaceutically acceptable salt thereof;

[6] The compound of [5] above, wherein $R^4$ is selected from —$CO_2R^9$ and —C(O)NHOR$^9$; or a prodrug thereof or a pharmaceutically acceptable salt thereof;

[7] The compound of [6] above, wherein $R^9$ is a hydrogen atom; or a prodrug thereof or a pharmaceutically acceptable salt thereof;

[8] The compound of [7] above, wherein $R^2$ is —$(CH_2)_p$—$X_1$—$(CH_2)_q$-$A^2$; or a prodrug thereof or a pharmaceutically acceptable salt thereof;

[9] The compound of [8] above, wherein p and q are 0 and $X_1$ is a single bond; or a prodrug thereof or a pharmaceutically acceptable salt thereof;

[10] The compound of [1] above, which is selected from the group consisting of

4-[5-((1S,2R)-1-Carboxy-2-phenyl-cyclopropylsulfamoyl)-thiophen-2-yl]-3,6-dihydro-2H-pyridine-1-carboxylic acid tert-butyl ester, (1S,2R)-2-Phenyl-1-[5-(1,2,3,6-tetrahydro-pyridin-4-yl)-thiophene-2-sulfonylamino]-cyclopropanecarboxylic acid, 4-[5-((1S,2R)-1-Carboxy-2-phenyl-cyclopropylsulfamoyl)-thiophen-2-yl]-3,6-dihydro-2H-pyridine-1-carboxylic acid methyl ester, (1S,2R,3R)-1-[5-(4-Ethynyl-pyrazol-1-yl)-thiophene-2-sulfonylamino]-2-methyl-3-phenyl-cyclopropanecarboxylic acid, (1S,2R,3R)-2-Methyl-3-phenyl-1-[4-(5-trifluoromethyl-pyridin-2-yl)-piperazine-1-sulfonylamino]-cyclopropanecarboxylic acid, (1S,2R)-2-Methyl-2-phenyl-1-[5-(5-trifluoromethyl-isoxazol-3-yl)-thiophene-2-sulfonylamino]-cyclopropanecarboxylic acid, (1S,2R,3R)-2-Methyl-3-phenyl-1-[5-(5-trifluoromethyl-isoxazol-3-yl)-thiophene-2-sulfonylamino]-cyclopropanecarboxylic acid, (1R*,1aS*,8bS*)-1-[5-(4-Chloro-phenyl)-thiophene-2-sulfonylamino]-1,1a,2,3,4,8b-hexahydro-benzo[a]cyclopropan[c]cycloheptene-1-carboxylic acid, (1S,2R,3R)-1-{5-[5-(1,1-Difluoro-ethyl)-isoxazol-3-yl]-thiophene-2-sulfonylamino}-2-methyl-3-phenyl-cyclopropanecarboxylic acid, (1R*,2R*,3R*)-2-Hydroxymethyl-3-phenyl-1-[5-(5-trifluoromethyl-isoxazol-3-yl)-thiophene-2-sulfonylamino]-cyclopropanecarboxylic acid, (1S,2R,3R)-2-Methyl-3-phenyl-1-(4-phenylcarbamoyl-piperazine-1-sulfonylamino)-cyclopropanecarboxylic acid, (1S,2R)-1-[5-(3-Amino-4-chloro-phenyl)-thiophene-2-sulfonylamino]-2-methyl-2-phenyl-cyclopropanecarboxylic acid, (1R*,1aS*,6aS*)-1-[4-(3,5-Dichloro-benzyloxy)-benzene-sulfonylamino]-1,1a,6,6a-tetrahydro-cyclopropa[a]indene-1-carboxylic acid hydroxyamide, (1R*,2S*)-1-[5-(2-Methyl-5-trifluoromethyl-2H-pyrazol-3-yl)-thiophene-2-sulfonylamino]-2-phenyl-cyclopropanecarboxylic acid, (1R*,2S*)-1-[3-(4-Chloro-phenoxy)-azetidine-1-sulfonylamino]-2-phenyl-cyclopropanecarboxylic acid, (1R*,2S*)-1-[5-(1-Methyl-5-trifluoromethyl-1H-pyrazol-3-yl)-thiophene-2-sulfonylamino]-2-phenyl-cyclopropanecarboxylic acid, (1R*,2S*)-2-Phenyl-1-[5-(4-trifluoromethoxy-phenyl)-thiophene-2-sulfonylamino]-cyclopropanecarboxylic acid, (1R*,2S*)-1-[5-(3,4-Dichloro-phenyl)-thiophene-2-sulfonylamino]-2-phenyl-cyclopropanecarboxylic acid, (1R*,2S*)-2-Phenyl-1-[5-(4-trifluoromethyl-phenyl)-thiophene-2-sulfonylamino]-cyclopropanecarboxylic acid, (1R*,2S*)-2-Phenyl-1-(5-p-tolyl-thiophene-2-sulfonylamino)-cyclopropanecarboxylic acid, (1R*,2S*)-1-[5-(4-Fluoro-phenyl)-thiophene-2-sulfonylamino]-2-phenyl-cyclopropanecarboxylic acid, (1R*,2S*)-1-[5-(4-Chloro-phenyl)-thiophene-2-sulfonylamino]-2-[2-(pyridin-3-ylmethoxy)-phenyl]-cyclopropanecarboxylic acid, (1R*,2S*)-1-[5-(4-Chloro-phenyl)-thiophene-2-sulfonylamino]-2-[2-(pyridin-2-ylmethoxy)-phenyl]-cyclopropanecarboxylic acid, (1R*,2S*)-1-[5-(4-Chloro-phenyl)-thiophene-2-sulfonylamino]-2-[2-(pyridin-3-yloxy)-phenyl]-cyclopropahecarboxylic acid, (1R*,2S*)-1-[5-(4-Chloro-phenyl)-thiophene-2-sulfonylamino]-2-[2-(2-hydroxy-2-methyl-propoxy)-phenyl]-cyclopropanecarboxylic acid, (1S,2R)-1-[5-(5-Methyl-thiazol-2-yl)-thiophene-2-sulfonylamino]-2-phenyl-cyclopropanecarboxylic acid, (1S,2R)-1-[5-(6-Chloro-pyridin-3-yl)-thiophene-2-sulfonylamino]-2-phenyl-cyclopropanecarboxylic acid, (1R*,2S*)-2-Phenyl-1-[4-(3-trifluoromethyl-phenyl)-piperazine-1-sulfonylamino]-cyclopropanecarboxylic acid, (1R*,2S*)-2-Phenyl-1-[4-(4-trifluoromethyl-phenyl)-piperazine-1-sulfonylamino]-cyclopropanecarboxylic acid, (1R*,2S*)-1-[4-(4-Chloro-3-trifluoromethyl-phenyl)-piperazine-1-sulfonylamino]-2-phenyl-cyclopropanecarboxylic acid, (1R*,2S*)-1-[4-(3-Chloro-phenyl)-piperazine-1-sulfonylamino]-2-phenyl-cyclopropanecarboxylic acid, (1R*,2S*)-1-[5-(4-Chloro-phenyl)-thiophene-2-sulfonylamino]-2-[3-(pyridin-3-ylaminomethyl)-phenyl]-cyclopropanecarboxylic acid, (1S,2R)-1-[5-(6-Methoxy-pyridazin-3-yl)-thiophene-2-sulfonylamino]-2-phenyl-cyclopropanecarboxylic acid, (1S,2R)-1-(5'-Cyano-[2,2']bithiophenyl-5-sulfonylamino)-2-phenyl-cyclopropanecarboxylic acid, (1S,2R)-1-[5-(5-Hydroxy-5-trifluoromethyl-4,5-dihydro-isoxazol-3-yl)-thiophene-2-sulfonylamino]-2-phenyl-cyclopropanecarboxylic acid, (1R*,2S*)-2-(3-Benzyloxy-phenyl)-1-[5-(4-chloro-phenyl)-thiophene-2-sulfonylamino]-cyclopropanecarboxylic acid, (1R*,2S*)-1-[5-(4-Chloro-phenyl)-thiophene-2-sulfonylamino]-2-[3-(methyl-pyridin-3-ylmethyl-amino)-phenyl]-cyclopropanecarboxylic acid, (1R*,2S*)-2-Benzyl-1-[5-(4-chloro-phenyl)-thiophene-2-sulfonylamino]-cyclopropanecarboxylic acid, (1S,2R)-1-(5'-Methyl-[2,2']bithiophenyl-5-sulfonylamino)-2-phenyl-cyclopropanecarboxylic acid, (1R*,2S*)-1-[5-(4-Chloro-phenyl)-thiophene-2-sulfonylamino]-2-(4'-methyl-biphenyl-2-yl)-cyclopropanecarboxylic acid, (1R*,2S*)-1-[5-(4-Chloro-phenyl)-thiophene-2-sulfonylamino]-2-cyclohexyl-cyclopropanecarboxylic acid, (1R*,2S*)-1-[5-(4-Chloro-phenyl)-thiophene-2-sulfonylamino]-2-[3-(2-hydroxy-2-methyl-propoxy)-phenyl]-cyclopropanecarboxylic acid, (1S,2R)-2-Phenyl-1-[5-(5-trifluoromethyl-isoxazol-3-yl)-thiophene-2-sulfonylamino]-cyclopropanecarboxylic acid, (1S,2R)-2-Phenyl-1-[5-(5-trifluoromethyl-[1,2,4]oxadiazol-3-yl)-thiophene-2-sulfonylamino]-cyclopropanecarboxylic acid, (1S,2R)-1-[5-(5-Pentafluoroethyl-[1,2,4]oxadiazol-3-yl)-thiophene-2-sulfonylamino]-2-phenyl-cyclopropanecarboxylic acid, (1R*,2S*)-1-[5-(4-Chloro-phenyl)-thiophene-2-sulfonylamino]-2-vinyl-cyclopropanecarboxylic acid, (1R*,2S*)-1-[5-(4-Chloro-phenyl)-thiophene-2-sulfonylamino]-2-(4-oxo-4H-benzo[d][1,2,3]triazin-3-ylmethyl)-cyclopropanecarboxylic acid, (1R*,2R*)-1-[5-(4-Chloro-phenyl)-thiophene-2-sulfonylamino]-2-ethyl-cyclopropanecarboxylic acid, (1R*,2S*)-1-[5-(4-Chloro-phenyl)-thiophene-2-sulfonylamino]-2-[2-(2-dimethylamino-ethoxy)-phenyl]-cyclopropanecarboxylic acid, (1S,2R)-1-[5-(2-Methyl-thiazol-4-yl)-thiophene-2-sulfonylamino]-2-phenyl-cyclopropanecarboxylic acid, (1S,2R)-1-[5-(5-Methyl-[1,2,4]oxadiazol-3-yl)-thiophene-2-sulfonylamino]-2-phenyl-cyclopropanecarboxylic acid, (1R*,2R*)-1-[5-(4-Chloro-phenyl)-thiophene-2-sulfonylamino]-2-phenoxymethyl-cyclopropanecarboxylic acid, (1R*,2S*)-2-[2-(2-tert-Butylamino-ethoxy)-phenyl]-1-[5-(4-chloro-phenyl)-thiophene-2-sulfonylamino]-cyclopropanecarboxylic acid, (1S,2R)-1-[5-(4,4-Dimethyl-4,5-dihydro-oxazol-2-yl)-thiophene-2-sulfonylamino]-2-phenyl-cyclopropanecarboxylic acid, (1S,2R)-1-[5-(2-Methyl-thiazol-5-yl)-thiophene-2-sulfonylamino]-2-phenyl-cyclopropanecarboxylic acid, (1R*,2S*)-1-[5-(5-Chloro-pyridin-2-yl)-thiophene-2-sulfonylamino]-2-(3-pyrazol-1-ylmethyl-phenyl)-cyclopropanecarboxylic acid, (1R*,2S*)-1-[5-(5-Chloro-pyridin-2-yl)-thiophene-2-sulfonylamino]-2-(3-methoxymethyl-phenyl)-cyclopropanecarboxylic acid, (1R*,2S*)-1-[5-(4-Chloro-phenyl)-thiophene-2-sulfonylamino]-2-cyclobutyl-cyclopropanecarboxylic acid, (1R*,2S*)-1-[5-(4-Chloro-phenyl)-thiophene-2-sulfonylamino]-2-isopropyl-cyclopropanecarboxylic acid, (1S,2R)-2-Phenyl-1-[5-(4-trifluoromethyl-thiazol-2-yl)-thiophene-2-sulfonylamino]-cyclopropanecarboxylic acid, (1R*,2S*)-1-[5-(4-Chloro-phenyl)-thiophene-2-sulfonylamino]-2-cyclopentyl-cyclopropanecarboxylic acid, (1R*,2S*)-2-tert-Butyl-1-[5-(4-chloro-phenyl)-thiophene-2-sulfonylamino]-cyclopropanecarboxylic acid, (1R*,2S*)-1-[5-(4-Chloro-phenyl)-thiophene-2-sulfonylamino]-2-(2-hydroxymethyl-phenyl)-cyclopropanecarboxylic acid, (1R*,2S*)-1-[4-(4-Methoxy-phenyl)-piperazine-1-sulfonylamino]-2-phenyl-cyclopropanecarboxylic acid, (1R*,2S*)-1-[5-(4-Hydroxy-phenyl)-thiophene-2-sulfonylamino]-2-phenyl-cyclopropanecarboxylic acid, (1R*,2S*)-1-(5-Acetyl-thiophene-2-sulfonylamino)-2-phenyl-cyclopropanecarboxylic acid, (1R*,2S*)-1-[4-(4-Fluoro-phenyl)-piperazine-1-sulfonylamino]-2-phenyl-cyclopropanecarboxylic acid, (1R*,2S*)-2-Phenyl-1-[4-(5-trifluoromethyl-pyridin-2-yl)-piperazine-1-sulfonylamino]-cyclopropanecarboxylic acid, (1R*,2S*)-1-[5-(4-Chloro-phenyl)-thiophene-2-sulfonylamino]-2-{3-[(2-methoxy-ethyl)-methyl-carbamoyl]-phenyl}-cyclopropanecarboxylic acid, (1R*,2S*)-1-[5-(4-Chloro-phenyl)-thiophene-2-sulfonylamino]-2-pyridin-3-yl-cyclopropanecarboxylic acid, (1R*,2S*)-1-[5-(4-Chloro-phenyl)-thiophene-2-sulfonylamino]-2-{2-[(2-methoxy-ethyl)-methyl-carbamoyl]-phenyl}-cyclopropanecarboxylic acid, (1R*,2S*)-1-[5-(4-Chloro-phenyl)-thiophene-2-sulfonylamino]-2-[2-(2-hydroxy-ethylcarbamoyl)-phenyl]-cyclopropanecarboxylic acid, (1R*,2S*)-1-[5-(4-Chloro-phenyl)-thiophene-2-sulfonylamino]-2-[3-(morpholine-4-carbonyl)-phenyl]-cyclopropanecarboxylic acid, (1R*,2S*)-1-[5-(4-Chloro-phenyl)-thiophene-2-sulfonylamino]-2-[3-(2-hydroxy-1,1-dimethyl-ethylcarbamoyl)-phenyl]-cyclopropanecarboxylic acid, (1R*,2S*)-1-[5-(4-Chloro-phenyl)-thiophene-2-sulfonylamino]-2-[3-(2-hydroxy-ethylcarbamoyl)-phenyl]-cyclopropanecarboxylic acid, (1R*,2S*)-1-[5-(4-Chloro-phenyl)-thiophene-2-sulfonylamino]-2-[2-(morpholine-4-carbonyl)-phenyl]-cyclopropanecarboxylic acid, (1R*,2S*)-1-[5-(4-Chloro-phenyl)-thiophene-2-sulfonylamino]-2-[2-(4,4-dimethyl-4,5-dihydro-oxazol-2-yl)-phenyl]-cyclopropanecarboxylic acid, (1R*,2S*)-1-[5-(4-Chloro-phenyl)-thiophene-2-sulfonylamino]-2-[2-(2-hydroxy-1,1-dimethyl-ethylcarbamoyl)-phenyl]-cyclopropanecarboxylic acid, (1R*,2S*)-1-[5-(2-Methyl-oxazol-5-yl)-thiophene-2-sulfonylamino]-2-phenyl-cyclopropanecarboxylic acid, (1R*,2S*)-1-(4-Acetyl-benzenesulfonylamino)-2-phenyl-cyclopropanecarboxylic acid, (1R*,2S*)-1-(5-Benzenesulfonyl-thiophene-2-sulfonylamino)-2-phenyl-cyclopropanecarboxylic acid, (1R*,2S*)-1-(5-Chloro-thiophene-2-sulfonylamino)-2-phenyl-cyclopropanecarboxylic acid, (1R*,2S*)-2-Phenyl-1-(thiophene-2-sulfonylamino)-cyclopropanecarboxylic acid, (1S,2R)-1-{5-[5-(1,1-Difluoro-ethyl)-isoxazol-3-yl]-thiophene-2-sulfonylamino}-2-phenyl-cyclopropanecarboxylic acid, (1S,2R)-1-[5-(5-Methyl-isoxazol-3-yl)-thiophene-2-sulfonylamino]-2-phenyl-cyclopropanecarboxylic acid, (1R*,2S*)-1-[5-(4-Chloro-phenyl)-thiophene-2-sulfonylamino]-2-[3-(4-methyl-thiazol-2-yl)-phenyl]-cyclopropanecarboxylic acid, (1R*,2S*)-1-[5-(2-Methyl-oxazol-4-yl)-thiophene-2-sulfonylamino]-2-phenyl-cyclopropanecarboxylic acid, (1R*,2S*)-1-[5-(5-Chloro-2-methyl-oxazol-4-yl)-thiophene-2-sulfonylamino]-2-phenyl-cyclopropanecarboxylic acid, (1R*,2S*)-1-[5-(4-Chloro-phenyl)-thiophene-2-sulfonylamino]-2-(2-{[(2-methoxy-ethyl)-methyl-amino]-methyl}-phenyl)-cyclopropanecarboxylic acid, (1S,2R)-2-Phenyl-1-[5-(5-propyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-(2-morpholin-4-ylmethyl-phenyl)-cyclopropanecarboxylic acid, (1S,2R)-1-[5-(5-Ethyl-isoxazol-3-yl)-thiophene-2-sulfonylamino]-2-phenyl-cyclopropanecarboxylic acid, (1R*,2S*)-2-Phenyl-1-(5-propylcarbamoyl-thiophene-2-sulfonylamino)-cyclopropanecarboxylic acid, (1R*,2S*)-1-(5-Isopropylcarbamoyl-thiophene-2-sulfonylamino)-2-phenyl-cyclopropanecarboxylic acid, (1R*,2S*)-1-(5-Cyclopentylcarbamoyl-thiophene-2-sulfonylamino)-2-phenyl-cyclopropanecarboxylic acid, (1R*,2S*)-2-Phenyl-1-(5-phenylcarbamoyl-thiophene-2-sulfonylamino)-cyclopropanecarboxylic acid, (1R*,2S*)-2-Phenyl-1-[5-(3,3,3-trifluoro-propylcarbamoyl)-thiophene-2-sulfonylamino]-cyclopropanecarboxylic acid, (1S,2R)-1-[5-(5-Fluoromethyl-isoxazol-3-yl)-thiophene-2-sulfonylamino]-2-phenyl-cyclopropanecarboxylic acid, (1S,2R)-1-[5-(5-Difluoromethyl-isoxazol-3-yl)-thiophene-2-sulfonylamino]-2-phenyl-cyclopropanecarboxylic acid, (1S,2R)-1-(7-Bromo-9H-fluorene-2-sulfonylamino)-2-methyl-2-phenyl-cyclopropanecarboxylic acid, (1S,2R)-1-[5-(4-Chloro-phenyl)-thiophene-2-sulfonylamino]-2-methyl-2-phenyl-cyclopropanecarboxylic acid, (1S,2R)-1-(5'-Difluoromethyl-[2,2']bithiophenyl-5-sulfonylamino)-2-phenyl-cyclopropanecarboxylic acid, 5-((1R*,2S*)-1-Carboxy-2-phenyl-cyclopropylsulfamoyl)-thiophene-2-carboxylic acid, (1R*,2S*)-1-(5-Ethylcarbamoyl-thiophene-2-sulfonylamino)-2-phenyl-cyclopropanecarboxylic acid, (1R*,2S*)-1-(5-Cyclopropylcarbamoyl-thiophene-2-sulfonylamino)-2-phenyl-cyclopropanecarboxylic acid, (1R*,2S*)-2-Phenyl-1-[5-(2,2,2-trifluoro-ethylcarbamoyl)-thiophene-2-sulfonylamino]-cyclopropanecarboxylic acid, (1S,2R)-1-{5-[5-(1,1-Difluoro-ethyl)-isoxazol-3-yl]-thiophene-2-sulfonylamino}-2-methyl-2-phenyl-cyclopropanecarboxylic acid, (1R*,2S*)-2-[3-(2-Acetoxy-ethyl)-phenyl]—[5-(4-chloro-phenyl)-thiophene-2-sulfonylamino]-cyclopropanecarboxylic acid, (1R*,2S*)-1-[5-(4-Chloro-phenyl)-thiophene-2-sulfonylamino]-2-[3-(2-hydroxy-ethyl)-phenyl]-cyclopropanecarboxylic acid, (1S,2R)-1-[5-(5-Methoxymethyl-isoxazol-3-yl)-thiophene-2-sulfonylamino]-2-phenyl-cyclopropanecarboxylic acid, (1S,2R)-1-[5-(5-Pentafluoroethyl-isoxazol-3-yl)-thiophene-2-sulfonylamino]-2-phenyl-cyclopropanecarboxylic acid, (1S,2R)-2-Methyl-1-[5-(5-pentafluoroethyl-isoxazol-3-yl)-thiophene-2-sulfonylamino]-2-phenyl-cyclopropanecarboxylic acid, (1S,2R)-1-(5-Benzo[b]thiophen-2-yl-thiophene-2-sulfonylamino)-2-phenyl-cyclopropanecarboxylic acid, (1S,2R)-2-Phenyl-1-[5-(5-phenyl-isoxazol-3-yl)-thiophene-2-sulfonylamino]-cyclopropanecarboxylic acid, (1S,2R)-1-[5-(5-Fluoromethyl-[1,2,4]thiadiazol-3-yl)-thiophene-2-sulfonylamino]-2-phenyl-cyclopropanecarboxylic acid, (1R*,2S*)-2-Phenyl-1-(5-propionyl-thiophene-2-sulfonylamino)-cyclopropanecarboxylic acid, (1R*,2S*)-1-(5-Butyryl-thiophene-2-sulfonylamino)-2-phenyl-cyclopropanecarboxylic acid, (1S,2R)-1-(5-Benzo[b]thiophen-3-yl-thiophene-2-sulfonylamino)-2-phenyl-cyclopropanecarboxylic acid, (1S,2R)-1-[5-(5-Difluoromethyl-isothiazol-3-yl)-thiophene-2-sulfonylamino]-2-phenyl-cyclopropanecarboxylic acid, (1S,2R)-1-[5-(5-Fluoromethyl-isothiazol-3-yl)-thiophene-2-sulfonylamino]-2-phenyl-cyclopropanecarboxylic acid, (1S,2R)-1-[5-(5-Fluoromethyl-isothiazol-3-yl)-thiophene-2-sulfonylamino]-2-methyl-2-phenyl-cyclopropanecarboxylic acid, (1S,2R)-1-(5-Benzofuran-2-yl-thiophene-2-sulfonylamino)-2-phenyl-cyclopropanecarboxylic acid, (1R*,2R*)-1-[5-(4-Chloro-phenyl)-thiophene-2-sulfonylamino]-2-isopropyl-2-phenyl-cyclopropanecarboxylic acid, (1S,2R)-1-{5-[5-(1,1-Difluoro-ethyl)-isothiazol-3-yl]-thiophene-2-sulfonylamino}-2-phenyl-cyclopropanecarboxylic acid, (1R*,2S*)-2-Phenyl-1-(1,3,4,9-tetrahydro-beta-carboline-2-sulfonylamino)-cyclopropanecarboxylic acid, (1R*,2S*)-2-Phenyl-1-(3-phenyl-5,6-dihydro-8H-[1,2,4]triazolo[4,3-a]pyrazine-7-sulfonylamino)-cyclopropanecarboxylic acid, (1R*,2S*)-2-Phenyl-1-(2-phenyl-7,8-dihydro-5H-pyrido[4,3-d]pyrimidine-6-sulfonylamino)-cyclopropanecarboxylic acid, (1R*,2S*)-1-[4-(4-Chloro-phenoxy)-piperidine-1-sulfonylamino]-2-phenyl-cyclopropanecarboxylic acid, (1R*,2S*)-1-[5-(4-Chloro-phenyl)-thiophene-2-sulfonylamino]-2-ethyl-2-phenyl-cyclopropanecarboxylic acid, (1S,2R)-1-[5-(3-Hydroxy-3-methyl-but-1-ynyl)-thiophene-2-sulfonylamino]-2-phenyl-cyclopropanecarboxylic acid, (1S,2R)-1-[5-(5-Chloro-pyridin-2-yl)-thiophene-2-sulfonylamino]-2-methyl-2-phenyl-cyclopropanecarboxylic acid, (1S,2R)-1-[5-(3,3-Dimethyl-but-1-ynyl)-thiophene-2-sulfonylamino]-2-phenyl-cyclopropanecarboxylic acid, (1S,2R)-1-(5-Pent-1-ynyl-thiophene-2-sulfonylamino)-2-phenyl-cyclopropanecarboxylic acid, (1S,2R)-2-Phenyl-1-[5-(3-trifluoromethyl-phenyl)-thiophene-2-sulfonylamino]-cyclopropanecarboxylic acid, (1S,2R)-1-(5-Indolizin-2-yl-thiophene-2-sulfonylamino)-2-phenyl-cyclopropanecarboxylic acid, (1S,2R)-2-(3-Bromo-phenyl)-1-[5-(4-chloro-phenyl)-thiophene-2-sulfonylamino]-cyclopropanecarboxylic acid, (1S,2R)-1-[4-(5-Fluoromethyl-isoxazol-3-yl)-benzenesulfonylamino]-2-phenyl-cyclopropanecarboxylic acid, (1S,2S)-2-((R)-3-Benzyl-2-oxo-oxazolidin-5-yl)-1-[5-(4-chloro-phenyl)-thiophene-2-sulfonylamino]-cyclopropanecarboxylic acid, (1S,2S)-2-((S)-3-Benzyl-2-oxo-oxazolidin-5-yl)-1-[5-(4-chloro-phenyl)-thiophene-2-sulfonylamino]-cyclopropanecarboxylic acid, (1S,2R)-2-Phenyl-1-((E)-2-phenyl-ethenesulfonylamino)-cyclopropanecarboxylic acid, (1S,2R)-1-(7-Fluoro-9H-fluorene-2-sulfonylamino)-2-phenyl-cyclopropanecarboxylic acid, (1S,2R)-1-(7-Chloro-9H-fluorene-2-sulfonylamino)-2-phenyl-cyclopropanecarboxylic acid, (1R*,2S*)-1-(4-Phenoxy-piperidine-1-sulfonylamino)-2-phenyl-cyclopropanecarboxylic acid, (1R*,2S*)-2-Phenyl-1-[4-(4-trifluoromethyl-phenoxy)-piperidine-1-sulfonylamino]-cyclopropanecarboxylic acid, (1R*,2S*)-1-[4-(4-Fluoro-phenoxy)-piperidine-1-sulfonylamino]-2-phenyl-cyclopropanecarboxylic acid, (1R*,2S*)-2-Ethyl-1-(7-fluoro-9H-fluorene-2-sulfonylamino)-2-phenyl-cyclopropanecarboxylic acid, 1-[5-(4-Chloro-phenyl)-thiophene-2-sulfonylamino]-2,2-dimethyl-cyclopropanecarboxylic acid, (1R*,2S*)-2-Phenyl-1-(4-phenyl-3,6-dihydro-2H-pyridine-1-sulfonylamino)-cyclopropanecarboxylic acid, (1R*,2S*)-1-[4-(4-Chloro-phenyl)-3,6-dihydro-2H-pyridine-1-sulfonylamino]-2-phenyl-cyclopropanecarboxylic acid, (1R,2S)-2-(3-Bromo-phenyl)-1-[5-(4-chloro-phenyl)-thiophene-2-sulfonylamino]-cyclopropanecarboxylic acid, (1S,2R)-1-[(E)-2-(4-Chloro-phenyl)-ethenesulfonylamino]-2-phenyl-cyclopropanecarboxylic acid, (1S,2R)-1-[4-(5-Difluoromethyl-isoxazol-3-yl)-benzenesulfonylamino]-2-phenyl-cyclopropanecarboxylic acid, (1S,2R)-1-[(E)-2-(3-Chloro-phenyl)-ethenesulfonylamino]-2-phenyl-cyclopropanecarboxylic acid, (1S,2R)-2-Phenyl-1-[5-(4,5,6,7-tetrahydro-benzo[d]isoxazol-3-yl)-thiophene-2-sulfonylamino]-cyclopropanecarboxylic acid, (1R*,2S*)-1-[4-(5-Bromo-pyrimidin-2-yl)-piperazine-1-sulfonylamino]-2-phenyl-cyclopropanecarboxylic acid, (1R*,2S*)-1-(8-Chloro-3,4-dihydro-1H-pyrazino[1,2-a]indole-2-sulfonylamino)-2-phenyl-cyclopropanecarboxylic acid, (1R*,2S*)-1-(4-Benzothiazol-2-yl-piperazine-1-sulfonylamino)-2-phenyl-cyclopropanecarboxylic acid, (1R*,2S*)-1-(4-Benzyl-piperazine-1-sulfonylamino)-2-phenyl-cyclopropanecarboxylic acid, (1R*,2S*)-1-[4-(4-Chloro-benzoyl)-piperazine-1-sulfonylamino]-2-phenyl-cyclopropanecarboxylic acid, (1R*,2S*)-1-[4-(3-Chloro-benzoyl)-piperazine-1-sulfonylamino]-2-phenyl-cyclopropanecarboxylic acid, (1S,2R)-2-Phenyl-1-[(E)-2-(4-trifluoromethyl-phenyl)-ethenesulfonylamino]-cyclopropanecarboxylic acid, (1S,2R)-2-Phenyl-1-[(E)-2-(3-trifluoromethyl-phenyl)-ethenesulfonylamino]-cyclopropanecarboxylic acid, (1S,2R)-1-[5-(2-Oxo-pyrrolidin-1-yl)-thiophene-2-sulfonylamino]-2-phenyl-cyclopropanecarboxylic acid, (1S,2R)-1-[5-(2-Oxo-piperidin-1-yl)-thiophene-2-sulfonylamino]-2-phenyl-cyclopropanecarboxylic acid, (1R*,2S*)-1-(5-Amino-thiophene-2-sulfonylamino)-2-phenyl-cyclopropanecarboxylic acid, (1S,2R)-1-(2-Cyclohexyl-2,3-dihydro-1H-isoindole-5-sulfonylamino)-2-phenyl-cyclopropanecarboxylic acid, (1R*,2S*)-2-(2-Bromo-phenyl)-1-[5-(4-chloro-phenyl)-thiophene-2-sulfonylamino]-cyclopropanecarboxylic acid, (1R,2S)-2-(2-Bromo-phenyl)-1-[5-(4-chloro-phenyl)-thiophene-2-sulfonylamino]-cyclopropanecarboxylic acid, (1S,2R)-2-(3-Bromo-phenyl)-1-[5-(5-trifluoromethyl-isoxazol-3-yl)-thiophene-2-sulfonylamino]-cyclopropanecarboxylic acid, (1S,2R)-1-[5-(4-Chloro-phenyl)-thiophene-2-sulfonylamino]-2-(3-nitro-phenyl)-cyclopropanecarboxylic acid, (1S,2R)-2-Phenyl-1-[5-(3-trifluoromethyl-isoxazol-5-yl)-thiophene-2-sulfonylamino]-cyclopropanecarboxylic acid, (1S,2R)-1-[5-(1-Methyl-1,2,3,6-tetrahydro-pyridin-4-yl)-thiophene-2-sulfonylamino]-2-phenyl-cyclopropanecarboxylic acid, (1S,2R)-1-[5-(4-Chloro-phenyl)-thiophene-2-sulfonylamino]-2-{3-[(pyridin-3-ylmethyl)-amino]-phenyl}-cyclopropanecarboxylic acid, (1S,2R)-2-(3-amino-phenyl)-1-[5-(4-chloro-phenyl)-thiophene-2-sulfonylamino]-cyclopropanecarboxylic acid, 3-{(1R,2S)-2-Carboxy-2-[5-(4-chloro-phenyl)-thiophene-2-sulfonylamino]-cyclopropyl}-benzoic acid, (1S,2R)-1-[5-(4-Chloro-phenyl)-thiophene-2-sulfonylamino]-2-(3-dimethylamino-phenyl)-cyclopropanecarboxylic acid,
(1S,2R)-1-[5-(1-Acetyl-1,2,3,6-tetrahydro-pyridin-4-yl)-thiophene-2-sulfonylamino]-2-phenyl-cyclopropanecarboxylic acid,
(1S,2R)-2-(2-Bromo-phenyl)-1-[5-(4-chloro-phenyl)-thiophene-2-sulfonylamino]-cyclopropanecarboxylic acid,
(1R*,2S*)-2-[2-(2-Carboxy-ethyl)-phenyl]-1-[S-(4-chloro-phenyl)-thiophene-2-sulfonylamino]-cyclopropanecarboxylic acid,
(1R*,2S*)-2-[3-(2-Carboxy-ethyl)-phenyl]—[5-(4-chloro-phenyl)-thiophene-2-sulfonylamino]-cyclopropanecarboxylic acid,
(1R*,2S*)-2-(3-Carboxymethyl-phenyl)-1-[5-(4-chloro-phenyl)-thiophene-2-sulfonylamino]-cyclopropanecarboxylic acid,
(1S,2R)-1-[5-(4-Chloro-phenyl)-thiophene-2-sulfonylamino]-2-(3-hydroxymethyl-phenyl)-cyclopropanecarboxylic acid,
(1S,2R)-1-[5-(4-Chloro-phenyl)-thiophene-2-sulfonylamino]-2-[3-(methyl-pyridin-3-ylmethyl-amino)-phenyl]-cyclopropanecarboxylic acid,
(1R*,2S*)-3-{2-Carboxy-2-[5-(4-chloro-phenyl)-thiophene-2-sulfonylamino]-cyclopropyl}-benzoic acid methyl ester,
(1R*,2S*)-2-Phenyl-1-[4-(5-trifluoromethyl-pyridin-2-yl)-piperazine-1-sulfonylmethyl]-cyclopropanecarboxylic acid,
(1R*,2S*)-1-[4-(4-Chloro-phenyl)-piperazine-1-sulfonylmethyl]-2-phenyl-cyclopropanecarboxylic acid,
(1R*,2S*)-1-[5-(4-Chloro-phenyl)-thiophene-2-sulfonylmethyl]-2-phenyl-cyclopropanecarboxylic acid,
(1R*,2S*)-1-[5-(4-Chloro-phenyl)-thiophene-2-sulfonylamino]-2-(3-methoxycarbonylmethyl-phenyl)-cyclopropanecarboxylic acid,
(1R*,2S*)-1-[5-(4-Chloro-phenyl)-thiophene-2-sulfonylamino]-2-(3-dimethylcarbamoylmethyl-phenyl)-cyclopropanecarboxylic acid,
(1R*,2S*)-1-[5-(4-Chloro-phenyl)-thiophene-2-sulfonylamino]-2-[3-(2-morpholin-4-yl-2-oxo-ethyl)-phenyl]-cyclopropanecarboxylic acid,
(1R*,2S*)-1-[5-(4-Chloro-phenyl)-thiophene-2-sulfonylamino]-2-{3-[2-(4-methyl-piperazin-1-yl)-2-oxo-ethyl]-phenyl}-cyclopropanecarboxylic acid,
(1R,2S)-1-[5-(4-Chloro-phenyl)-thiophene-2-sulfonylamino]-2-phenyl-cyclopropanecarboxylic acid,
(1S,2R)-2-(2-Bromo-phenyl)-1-[5-(5-trifluoromethyl-isoxazol-3-yl)-thiophene-2-sulfonylamino]-cyclopropanecarboxylic acid,
(1R*,2S*)-1-[5-(4-Chloro-phenyl)-thiophene-2-sulfonylamino]-2-[2-(2-morpholin-4-yl-2-oxo-ethyl)-phenyl]-cyclopropanecarboxylic acid,
(1R*,2S*)-1-[5-(4-Chloro-phenyl)-thiophene-2-sulfonylamino]-2-{2-[2-(4-methyl-piperazin-1-yl)-2-oxo-ethyl]-phenyl}-cyclopropanecarboxylic acid,
(1R*,2S*)-2-{2-Carboxy-2-[5-(4-chloro-phenyl)-thiophene-2-sulfonylamino]-cyclopropyl}-benzoic acid,
(1R*,2S*)-1-[5-(4-Chloro-phenyl)-thiophene-2-sulfonylamino]-2-[3-(2-morpholin-4-yl-ethoxy)-phenyl]-cyclopropanecarboxylic acid,
(1R*,2S*)-1-[5-(4-Chloro-phenyl)-thiophene-2-sulfonylamino]-2-{3-[2-(4-methyl-piperazin-1-yl)-ethoxy]-phenyl}-cyclopropanecarboxylic acid,
(1R*,2S*)-2-(3-Nitro-phenyl)-1-[5-(5-trifluoromethyl-isoxazol-3-yl)-thiophene-2-sulfonylamino]-cyclopropanecarboxylic acid,
(1R*,2S*)-1-[5-(4-Chloro-phenyl)-thiophene-2-sulfonylamino]-2-[3-(4-methyl-piperazine-1-carbonyl)-phenyl]-cyclopropanecarboxylic acid,
(1R*,2S*)-2-(3-Amino-phenyl)-1-[5-(5-trifluoromethyl-isoxazol-3-yl)-thiophene-2-sulfonylamino]-cyclopropanecarboxylic acid,
(1R*,2R*)-2-(4-Bromo-phenyl)-1-[5-(4-chloro-phenyl)-thiophene-2-sulfonylamino]-cyclopropanecarboxylic acid,
(1R*,2S*)-2-(4-Bromo-phenyl)-1-[5-(4-chloro-phenyl)-thiophene-2-sulfonylamino]-cyclopropanecarboxylic acid,
(1R*,2S*) 1-[5-(4-Chloro-phenyl)-thiophene-2-sulfonylamino]-2-(2-dimethylcarbamoylmethyl-phenyl)-cyclopropanecarboxylic acid,
(1R*,2S*)-2-{2-Carboxy-2-[5-(4-chloro-phenyl)-thiophene-2-sulfonylamino]-cyclopropyl}-benzoic acid methyl ester,
(1S,2R)-1-[5-(4-Chloro-phenyl)-thiophene-2-sulfonylamino]-2-(2-hydroxymethyl-phenyl)-cyclopropanecarboxylic acid,
(1'R*,2'S*)-2-Acetyl-1,2,3,4-tetrahydro-isoquinoline-4-spiro-2'-{1-[5-(4-chloro-phenyl)-hiophene-2-sulfonylamino]-1'-cyclopropanecarboxylic acid},
(1R*,2S*)-1-[5-(4-Chloro-phenyl)-thiophene-2-sulfonylamino]-2-[3-(2-methoxycarbonyl-ethyl)-phenyl]-cyclopropanecarboxylic acid,
(1R*,2S*)-1-[5-(4-Chloro-phenyl)-thiophene-2-sulfonylamino]-2-[3-(3-morpholin-4-yl-3-oxo-propyl)-phenyl]-cyclopropanecarboxylic acid,
(1R*,2S*)-1-[5-(4-Chloro-phenyl)-thiophene-2-sulfonylamino]-2-{3-[3-(4-methyl-piperazin-1-yl)-3-oxo-propyl]-phenyl}-cyclopropanecarboxylic acid,
(1R*,2S*)-1-[5-(4-Chloro-phenyl)-thiophene-2-sulfonylamino]-2-[3-(3-oxo-3-thiomorpholin-4-yl-propyl)-phenyl]-cyclopropanecarboxylic acid,
(1R*,2S*)-2-(3-Carboxymethyl-phenyl)-1-[5-(5-trifluoromethyl-isoxazol-3-yl)-thiophene-2-sulfonylamino]-cyclopropanecarboxylic acid,
(1R*,2S*)-2-{3-[(Pyridin-3-ylmethyl)-amino]-phenyl}-1-[5-(5-trifluoromethyl-isoxazol-3-yl)-thiophene-2-sulfonylamino]-cyclopropanecarboxylic acid,
(1R*,2S*)-2-[3-(Methyl-pyridin-3-ylmethyl-amino)-phenyl]-1-[5-(5-trifluoromethyl-isoxazol-3-yl)-thiophene-2-sulfonylamino]-cyclopropanecarboxylic acid,
(1R*,2S*)-1-[5-(4-Chloro-phenyl)-thiophene-2-sulfonylamino]-2-(2-dimethylcarbamoyl-phenyl)-cyclopropanecarboxylic acid,
(1R*,2S*)-1-[5-(4-Chloro-phenyl)-thiophene-2-sulfonylamino]-2-[2-(4-methyl-piperazine-1-carbonyl)-phenyl]-cyclopropanecarboxylic acid,
(1R*,2S*)-2-(2-tert-Butoxycarbonylamino-phenyl)-1-[5-(4-chloro-phenyl)-thiophene-2-sulfonylamino]-cyclopropanecarboxylic acid,
(1aR*,7bS*)—S-(4-Chloro-phenyl)-thiophene-2-sulfonic acid (2-oxo-1,2,3,7b-tetrahydro-3-aza-cyclopropa[a]naphthalen-1a-yl)-amide,
(1R*,2S*)-2-(3-Methoxycarbonylmethyl-phenyl)-1-[5-(5-tr-ifluoromethyl-isoxazol-3-yl)-thiophene-2-sulfonylamino]-cyclopropanecarboxylic acid,
(1R*,2S*)-2-[3-(2-Morpholin-4-yl-2-oxo-ethyl)-phenyl]—[5-(5-trifluoromethyl-isoxazol-3-yl)-thiophene-2-sulfonylamino]-cyclopropanecarboxylic acid, (1R*,2S*)-2-{3-[2-(4-Methyl-piperazin-1-yl)-2-oxo-ethyl]-phenyl}-1-[5-(5-trifluoromethyl-isoxazol-3-yl)-thiophene-2-sulfonylamino]-cyclopropanecarboxylic acid, (1R*,2S*)-2-{3-[2-(4-Hydroxy-piperidin-1-yl)-2-oxo-ethyl]-phenyl}-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-[3-(3-dimethylamino-propionylamino)-phenyl]-cyclopropanecarboxylic acid, (1R*,2S*)-1-[5-(4-Chloro-phenyl)-thiophene-2-sulfonylamino]-2-{3-[3-(4-hydroxy-piperidin-1-yl)-3-oxo-propyl]-phenyl}-cyclopropanecarboxylic acid, (1R*,2S*)-2-(4-Benzyloxy-phenyl)-1-[5-(4-chloro-phenyl)-thiophene-2-sulfonylamino]-cyclopropanecarboxylic acid, (1R*,2S*)-1-[5-(4-Chloro-phenyl)-thiophene-2-sulfonylamino]-2-(4-hydroxymethyl-phenyl)-cyclopropanecarboxylic acid, (1R*,2S*)-1-[5-(4-Chloro-phenyl)-thiophene-2-sulfonylamino]-2-(3-hydroxy-propyl)-2-phenyl-cyclopropanecarboxylic acid, (1R*,2S*)-2-(3-Dimethylamino-phenyl)-1-[5-(5-trifluoromethyl-isoxazol-3-yl)-thiophene-2-sulfonylamino]-cyclopropanecarboxylic acid, (1R*,2R*)-1-[5-(4-Chloro-phenyl)-thiophene-2-sulfonylamino]-2-hydroxymethyl-2-phenyl-cyclopropanecarboxylic acid, (1R*,2S*)-2-[2-(3-Morpholin-4-yl-3-oxo-propyl)-phenyl]-1-[5-(5-trifluoromethyl-isoxazol-3-yl)-thiophene-2-sulfonylamino]-cyclopropanecarboxylic acid, (1R*,2S*)-2-[2-(2-Dimethylcarbamoyl-ethyl)-phenyl]-1-[5-(5-trifluoromethyl-isoxazol-3-yl)-thiophene-2-sulfonylamino]-cyclopropanecarboxylic acid, (1R*,2S*)-2-{2-[3-(4-Methyl-piperazin-1-yl)-3-oxo-propyl]-phenyl}-1-[5-(5-trifluoromethyl-isoxazol-3-yl)-thiophene-2-sulfonylamino]-cyclopropanecarboxylic acid, (1R*,2S*)-2-{3-[(4-trans-Hydroxy-cyclohexylcarbamoyl)-methyl]-phenyl}-1-[5-(5-trifluoromethyl-isoxazol-3-yl)-thiophene-2-sulfonylamino]-cyclopropanecarboxylic acid, (1R*,2S*)-2-[3-(3-Morpholin-4-yl-3-oxo-propyl)-phenyl]—S-(5-trifluoromethyl-isoxazol-3-yl)-thiophene-2-sulfonylamino]-cyclopropanecarboxylic acid, (1R*,2S*)-2-{3-[3-(4-Methyl-piperazin-1-yl)-3-oxo-propyl]-phenyl}-1-[5-(5-trifluoromethyl-isoxazol-3-yl)-thiophene-2-sulfonylamino]-cyclopropanecarboxylic acid, (1R*,2S*)-2-[3-(3-Hydroxy-propyl)-phenyl]-1-[5-(5-trifluoromethyl-isoxazol-3-yl)-thiophene-2-sulfonylamino]-cyclopropanecarboxylic acid, (1R*,2S*,3S*)-1-[5-(4-Chloro-phenyl)-thiophene-2-sulfonylamino]-2-methyl-3-phenyl-cyclopropanecarboxylic acid, (1R*,2S*)-4-Methyl-piperazine-1-carboxylic acid 3-(3-{2-carboxy-2-[5-(5-trifluoromethyl-isoxazol-3-yl)-thiophene-2-sulfonylamino]-cyclopropyl}-phenyl)-propyl ester, (1R*,2S*)-Morpholine-4-carboxylic acid 3-(3-{2-carboxy-2-[5-(5-trifluoromethyl-isoxazol-3-yl)-thiophene-2-sulfonylamino]-cyclopropyl}-phenyl)-propyl ester, (1R*,2S*)-2-[2-(2-Hydroxy-ethyl)-phenyl]-1-[5-(5-trifluoromethyl-isoxazol-3-yl)-thiophene-2-sulfonylamino]-cyclopropanecarboxylic acid, (1S,2R)-1-[5-(4-Methyl-pyrazol-1-yl)-thiophene-2-sulfonylamino]-2-phenyl-cyclopropanecarboxylic acid, (1R*,2S*)-Morpholine-4-carboxylic acid 2-(2-{2-carboxy-2-[5-(5-trifluoromethyl-isoxazol-3-yl)-thiophene-2-sulfonylamino]-cyclopropyl}-phenyl)-ethyl ester, (1R*,2S*)-2-[2-(2-Morpholin-4-yl-2-oxo-ethyl)-phenyl]-1-[5-(5-trifluoromethyl-isoxazol-3-yl)-thiophene-2-sulfonylamino]-cyclopropanecarboxylic acid, (1R,2S)-1-(7-Fluoro-9H-fluorene-2-sulfonylamino)-2-phenyl-cyclopropanecarboxylic acid, (1R*,2S*)-1-[5-(4-Chloro-phenyl)-thiophene-2-sulfonylamino]-2-(4-morpholin-4-yl-phenyl)-cyclopropanecarboxylic acid, (1R*,2S*)-1-[5-(4-Chloro-phenyl)-thiophene-2-sulfonylamino]-2-[4-(4-methyl-piperazin-1-yl)-phenyl]-cyclopropanecarboxylic acid, (1R*,2R*)-1-[5-(4-Chloro-phenyl)-thiophene-2-sulfonylamino]-2-[4-(4-methyl-piperazin-1-yl)-phenyl]-cyclopropanecarboxylic acid, (1R*,2S*)-2-(3-Hydroxy-propyl)-2-phenyl-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-(3-morpholin-4-yl-propyl)-2-phenyl-cyclopropanecarboxylic acid, (1R*,2S*)-2-3-[(Morpholine-4-carbonyl)-amino]-phenyl}-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-{3-[(morpholine-4-carbonyl)-amino]-phenyl}-cyclopropanecarboxylic acid, (1R*,2S*)-2-[2-(3-Hydroxy-propyl)-phenyl]-1-[5-(5-trifluoromethyl-isoxazol-3-yl)-thiophene-2-sulfonylamino]-cyclopropanecarboxylic acid, (1R*,2S*)-Morpholine-4-carboxylic acid 3-(2-{2-carboxy-2-[5-(5-trifluoromethyl-isoxazol-3-yl)-thiophene-2-sulfonylamino]-cyclopropyl}-phenyl)-propyl ester, (S)-2-Hydroxymethyl-pyrrolidine-1-carboxylic acid 3-(2-{(1R*,2S*)-2-carboxy-2-[5-(5-trifluoromethyl-isoxazol-3-yl)-thiophene-2-sulfonylamino]-cyclopropyl}-phenyl)-propyl ester, (R)-3-Hydroxy-pyrrolidine-1-carboxylic acid 3-(2-{(1R*,2S*)-2-carboxy-2-[5-(5-trifluoromethyl-isoxazol-3-yl)-thiophene-2-sulfonylamino]-cyclopropyl}-phenyl)-propyl ester, (1S,2R)-1-[5-(4-Methyl-piperidin-1-yl)-thiophene-2-sulfonylamino]-2-phenyl-cyclopropanecarboxylic acid, (1R*,2S*)-2-(3-Morpholin-4-yl-phenyl)-1-[5-(5-trifluoromethyl-isoxazol-3-yl)-thiophene-2-sulfonylamino]-cyclopropanecarboxylic acid, (1R*,2S*)-2-[3-(Morpholine-4-carbonyl)-phenyl]-1-[5-(5-trifluoromethyl-isoxazol-3-yl)-thiophene-2-sulfonylamino]-cyclopropanecarboxylic acid, (1R*,2S*)-2-(3-{2-[(Morpholine-4-carbonyl)-amino]-ethyl}-phenyl)-1-[5-(5-trifluoromethyl-isoxazol-3-yl)-thiophene-2-sulfonylamino]-cyclopropanecarboxylic acid, (1R*,2S*)-2-[3-(2-Morpholin-4-yl-acetylamino)-phenyl]-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-[3-(2-morpholin-4-yl-acetylamino)-phenyl]-cyclopropanecarboxylic acid, (1S,2R,3R)-1-[5-(4-Chloro-phenyl)-thiophene-2-sulfonylamino]-2-methyl-3-phenyl-cyclopropanecarboxylic acid, (1R*,2R*)-1-[5-(4-Chloro-phenyl)-thiophene-2-sulfonylamino]-2-(2-hydroxy-ethyl)-2-phenyl-cyclopropanecarboxylic acid, (1R*,2S*)-2-(3-Acetoxy-propyl)-2-phenyl-1-[5-(5-trifluoromethyl-isoxazol-3-yl)-thiophene-2-sulfonylamino]-cyclopropanecarboxylic acid, (1R*,2S*)-2-(4-Aminomethyl-phenyl)-1-[5-(4-chloro-phenyl)-thiophene-2-sulfonylamino]-cyclopropanecarboxylic acid, (1R*,2S*)-2-(4-Dimethylcarbamoyl-phenyl)-1-[5-(5-trifluoromethyl-isoxazol-3-yl)-thiophene-2-sulfonylamino]-cyclopropanecarboxylic acid, (1R*,2S*)-2-[3-(Morpholine-4-sulfonylamino)-phenyl]-1-[5-(5-trifluoromethyl-isoxazol-3-yl)-thiophene-2-sulfonylamino]-cyclopropanecarboxylic acid, (1R*,2S*)-2-[3-(2-Hydroxy-ethyl)-phenyl]-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-[3-(morpholine-4-sulfonylamino)-phenyl]-cyclopropanecarboxylic acid, (1R*,2S*)-2-[3-(2-Carbamoyloxy-ethyl)-phenyl]-1-[5-(5-trifluoromethyl-isoxazol-3-yl)-thiophene-2-sulfonylamino]-cyclopropanecarboxylic acid, (1R*,2S*)-2-(3-Acetoxy-propyl)-2-{4-[(2-methoxy-ethyl)-methyl-carbamoyl]-phenyl}-1-[5-(5-trifluoromethyl-isoxazol-3-yl)-thiophene-2-sulfonylamino]-cyclopropanecarboxylic acid, (1R*,2S*)-2-(3-Acetylamino-propyl)-1-[5-(4-chloro-phenyl)-thiophene-2-sulfonylamino]-2-phenyl-cyclopropanecarboxylic acid, (1R*,2S*)-1-[5-(4-Chloro-phenyl)-thiophene-2-sulfonylamino]-2-phenyl-2-(3-pyrazol-1-yl-propyl)-cyclopropanecarboxylic acid, (1R*,3S*)-1-[5-(4-Chloro-phenyl)-thiophene-2-sulfonylamino]-2,2-dimethyl-3-phenyl-cyclopropanecarboxylic acid, (1R*,3S*)-2,2-Dimethyl-3-phenyl-1-[5-(5-trifluoromethyl-isoxazol-3-yl)-thiophene-2-sulfonylamino]-cyclopropanecarboxylic acid, (1R*,2S*)-2-[3-(2-Oxo-pyrrolidin-1-yl)-phenyl]-1-[5-(5-trifluoromethyl-isoxazol-3-yl)-thiophene-2-sulfonylamino]-cyclopropanecarboxylic acid, (1R*,1aS*,6aS*)-1-[5-(5-Trifluoromethyl-isoxazol-3-yl)-thiophene-2-sulfonylamino]-1,1a,6,6a-tetrahydro-cyclopropa[a]indene-1-carboxylic acid, (1S,2R)-2-[4-(2-Carbamoyl-ethyl)-phenyl]-1-[5-(5-trifluoromethyl-isoxazol-3-yl)-thiophene-2-sulfonylamino]-cyclopropanecarboxylic acid, (1S,2R)-2-[4-(3-Morpholin-4-yl-3-oxo-propyl)-phenyl]-1-[5-(5-trifluoromethyl-isoxazol-3-yl)-thiophene-2-sulfonylamino]-cyclopropanecarboxylic acid, (1S,2R)-2-{4-[3-(4-Methyl-piperazin-1-yl)-3-oxo-propyl]-phenyl}-1-[5-(5-trifluoromethyl-isoxazol-3-yl)-thiophene-2-sulfonylamino]-cyclopropanecarboxylic acid, (1S,2R)-2-[4-(2-Methylcarbamoyl-ethyl)-phenyl]-1-[5-(5-trifluoromethyl-isoxazol-3-yl)-thiophene-2-sulfonylamino]-cyclopropanecarboxylic acid, (1S,2R)-2-[4-(2-Dimethylcarbamoyl-ethyl)-phenyl]-1-[5-(5-trifluoromethyl-isoxazol-3-yl)-thiophene-2-sulfonylamino]-cyclopropanecarboxylic acid, (1R*,2S*)-2-(3-Hydroxymethyl-phenyl)-1-[5-(5-trifluoromethyl-isoxazol-3-yl)-thiophene-2-sulfonylamino]-cyclopropanecarboxylic acid, (1R*,2S*)-2-(3-tert-Butoxycarbonylamino-propyl)-1-[5-(4-chloro-phenyl)-thiophene-2-sulfonylamino]-2-phenyl-cyclopropanecarboxylic acid, (1R*,2S*)-2-(3-Amino-propyl)-1-[5-(4-chloro-phenyl)-thiophene-2-sulfonylamino]-2-phenyl-cyclopropanecarboxylic acid, (1S,2R,3R)-1-(7-Bromo-9H-fluorene-2-sulfonylamino)-2-methyl-3-phenyl-cyclopropanecarboxylic acid, (1S,2R,3R)-2-Methyl-1-[5-(4-methyl-pyrazol-1-yl)-thiophene-2-sulfonylamino]-3-phenyl-cyclopropanecarboxylic acid, (1R,2S,3S)-2-Methyl-3-phenyl-1-[5-(5-trifluoromethyl-isoxazol-3-yl)-thiophene-2-sulfonylamino]-cyclopropanecarboxylic acid, (1R,2S)-2-(4-Aminomethyl-phenyl)-1-[5-(5-trifluoromethyl-isoxazol-3-yl)-thiophene-2-sulfonylamino]-cyclopropanecarboxylic acid, (1R,2S)-2-(4-Dimethylcarbamoylmethyl-phenyl)-1-[5-(5-trifluoromethyl-isoxazol-3-yl)-thiophene-2-sulfonylamino]-cyclopropanecarboxylic acid, (1R,2S)-2-[4-(2-Morpholin-4-yl-2-oxo-ethyl)-phenyl]-1-[5-(5-trifluoromethyl-isoxazol-3-yl)-thiophene-2-sulfonylamino]-cyclopropanecarboxylic acid, (1R,2S)-2-(4-Carbamoylmethyl-phenyl)-1-[5-(5-trifluoromethyl-isoxazol-3-yl)-thiophene-2-sulfonylamino]-cyclopropanecarboxylic acid, (1R,2S)-2-(4-Methylcarbamoylmethyl-phenyl)-1-[5-(5-trifluoromethyl-isoxazol-3-yl)-thiophene-2-sulfonylamino]-cyclopropanecarboxylic acid, (1R,2S)-2-{4-[2-(4-Methyl-piperazin-1-yl)-2-oxo-ethyl]-phenyl}-1-[5-(5-trifluoromethyl-isoxazol-3-yl)-thiophene-2-sulfonylamino]-cyclopropanecarboxylic acid, (1R*,2R*)-2-(2-Carbamoyloxy-ethyl)-1-[5-(4-chloro-phenyl)-thiophene-2-sulfonylamino]-2-phenyl-cyclopropanecarboxylic acid, (1S,2R,3R)-2-Methyl-3-phenyl-1-[5-(5-trifluoromethyl-isoxazol-3-yl)-thiophene-2-sulfonylamino]-cyclopropanecarboxylic acid amide, (1S,2R,3R)-2-Methyl-3-phenyl-1-[5-(5-trifluoromethyl-isoxazol-3-yl)-thiophene-2-sulfonylamino]-cyclopropanecarboxylic acid methylamide, (1R*,2S*)-1-[5-(4-Chloro-phenyl)-thiophene-2-sulfonylamino]-2-(3-cyclopentyloxycarbonylamino-propyl)-2-phenyl-cyclopropanecarboxylic acid, (1R*,2S*,3S*)-2-Ethyl-3-phenyl-1-[5-(5-trifluoromethyl-isoxazol-3-yl)-thiophene-2-sulfonylamino]-cyclopropanecarboxylic acid, (1S,2R)-2-[4-(2-Amino-ethyl)-phenyl] 1-[5-(5-trifluoromethyl-isoxazol-3-yl)-thiophene-2-sulfonylamino]-cyclopropanecarboxylic acid, (1R,2S)-2-[4-(2-Hydroxy-ethyl)-phenyl]-1-[5-(5-trifluoromethyl-isoxazol-3-yl)-thiophene-2-sulfonylamino]-cyclopropanecarboxylic acid, (1S,2R)-2-[4-(3-Hydroxy-propyl)-phenyl]-1-[5-(5-trifluoromethyl-isoxazol-3-yl)-thiophene-2-sulfonylamino]-cyclopropanecarboxylic acid, (1R*,2R*)-1-[5-(4-Chloro-phenyl)-thiophene-2-sulfonylamino]-2-(2-dimethylcarbamoyloxy-ethyl)-2-phenyl-cyclopropanecarboxylic acid, (1S,2R)-2-[3-(4-Isopropyl-piperazin-1-ylmethyl)-phenyl]-1-[5-(5-trifluoromethyl-isoxazol-3-yl)-thiophene-2-sulfonylamino]-cyclopropanecarboxylic acid, (1R*,1aS*,8bS*)1-[5-(5-Trifluoromethyl-isoxazol-3-yl)-thiophene-2-sulfonylamino]-1,1a,2,3,4,8b-hexahydro-benzo[a]cyclopropan[c]cycloheptene-1-carboxylic acid, (1R*,2R*)-Morpholine-4-carboxylic acid 2-carboxy-1-phenyl-2-[5-(5-trifluoromethyl-isoxazol-3-yl)-thiophene-2-sulfonylamino]-cyclopropylmethyl ester, (1S,2R)-1-[5-(4-Chloro-benzoyl)-thiophene-2-sulfonylamino]-2-phenyl-cyclopropanecarboxylic acid, (1R*,2R*)-2-(2-Isopropoxy-ethylcarbamoyloxymethyl)-2-phenyl-1-[5-(5-trifluoromethyl-isoxazol-3-yl)-thiophene-2-sulfonylamino]-cyclopropanecarboxylic acid, (1R*,2R*)-2-Phenyl-2-[(R)-1-(tetrahydro-furan-2-yl)methylcarbamoyloxymethyl]-1-[5-(5-trifluoromethyl-isoxazol-3-yl)-thiophene-2-sulfonylamino-cyclopropanecarboxylic acid, (1R*,2R*)-Piperidine-1-carboxylic acid 2-carboxy-1-phenyl-2-[5-(5-trifluoromethyl-isoxazol-3-yl)-thiophene-2-sulfonylamino]-cyclopropylmethyl ester, (1R*,2R*)-2-(3-Methyl-isoxazol-5-yl)-1-[5-(5-trifluoromethyl-isoxazol-3-yl)-thiophene-2-sulfonylamino]-cyclopropanecarboxylic acid, 5-(5-Trifluoromethyl-isoxazol-3-yl)-thiophene-2-sulfonic acid ((1S*,5S*,6S*)-2-oxo-6-phenyl-3-oxa-bicyclo[3.1.0]hex-1-yl)-amide, (1R*,2R*)-2-(5-Methyl-isoxazol-3-yl)-1-[5-(5-trifluoromethyl-isoxazol-3-yl)-thiophene-2-sulfonylamino]-cyclopropanecarboxylic acid, (1R*,2S*)-2-(5-Methyl-isoxazol-3-yl)-1-[5-(5-trifluoromethyl-isoxazol-3-yl)-thiophene-2-sulfonylamino]-cyclopropanecarboxylic acid, (1R*,2R*)-2-[5-(2-Hydroxy-ethyl)-isoxazol-3-yl]—[5-(5-trifluoromethyl-isoxazol-3-yl)-thiophene-2-sulfonylamino]-cyclopropanecarboxylic acid, (1R*,2S*)-2-[5-(2-Hydroxy-ethyl)-isoxazol-3-yl]-1-[5-(5-trifluoromethyl-isoxazol-3-yl)-thiophene-2-sulfonylamino]-cyclopropanecarboxylic acid, (1R*,2R*)-2-(5-Hydroxymethyl-isoxazol-3-yl)-1-[5-(5-trifluoromethyl-isoxazol-3-yl)-thiophene-2-sulfonylamino]-cyclopropanecarboxylic acid, (1R*,2S*)-2-(5-Hydroxymethyl-isoxazol-3-yl)-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-(3-isobutyrylamino-propyl)-2-phenyl-cyclopropanecarboxylic acid, (1R*,2R*)-2-Dimethylcarbamoyloxymethyl-2-phenyl-1-[5-(5-trifluoromethyl-isoxazol-3-yl)-thiophene-2-sulfonylamino]-cyclopropanecarboxylic acid, (1R*,2R*)-2-Ethylcarbamoyloxymethyl-2-phenyl-1-[5-(5-trifluoromethyl-isoxazol-3-yl)-thiophene-2-sulfonylamino]-cyclopropanecarboxylic acid, (1R*,2S*)-2-Morpholin-4-ylmethyl-2-phenyl-1-[5-(5-trifluoromethyl-isoxazol-3-yl)-thiophene-2-sulfonylamino]-cyclopropanecarboxylic acid, (1S,2R,3R)-2-Methyl-3-phenyl-1-[5-(5-trifluoromethyl-isoxazol-3-yl)-thiophene-2-sulfonylamino]-cyclopropanecarboxylic acid hydroxyamide, (1S,2R,3R)-1-[4-(2,4-Dichloro-benzyloxy)-benzenesulfonylamino]-2-methyl-3-phenyl-cyclopropanecarboxylic acid, (1S,2R,3R)-1-[4-(2,4-Dichloro-benzyloxy)-benzenesulfonylamino]-2-methyl-3-phenyl-cyclopropanecarboxylic acid hydroxyamide, (1R*,2R*,3S*)-1-[5-(4-Chloro-phenyl)-thiophene-2-sulfonylamino]-2-methyl-3-phenyl-cyclopropanecarboxylic acid, (1R*,2S*,3S*)-2-Ethyl-3-phenyl-1-[5-(5-trifluoromethyl-isoxazol-3-yl)-thiophene-2-sulfonylamino]-cyclopropanecarboxylic acid, (1S*,2R*,3R*)-2-Ethyl-3-phenyl-1-[5-(5-trifluoromethyl-isoxazol-3-yl)-thiophene-2-sulfonylamino]-cyclopropanecarboxylic acid, (1R*,2S*)-2-Phenyl-2-pyrrolidin-1-ylmethyl-1-[5-(5-trifluoromethyl-isoxazol-3-yl)-thiophene-2-sulfonylamino]-cyclopropanecarboxylic acid, (1R*,2S*)-2-Phenyl-2-piperidin-1-ylmethyl-1-[5-(5-trifluoromethyl-isoxazol-3-yl)-thiophene-2-sulfonylamino]-cyclopropanecarboxylic acid, (1R*,2R*)-2-Cyclopropylcarbamoyloxymethyl-2-phenyl-1-[5-(5-trifluoromethyl-isoxazol-3-yl)-thiophene-2-sulfonylamino]-cyclopropanecarboxylic acid, (1R*,2R*)-2-{[(2-Hydroxy-ethyl)-methyl-carbamoyloxy]-methyl}-2-phenyl-1-[5-(5-trifluoromethyl-isoxazol-3-yl)-thiophene-2-sulfonylamino]-cyclopropanecarboxylic acid, (1R*,2R*)-2-(2-Hydroxy-ethylcarbamoyloxymethyl)-2-phenyl-1-[5-(5-trifluoromethyl-isoxazol-3-yl)-thiophene-2-sulfonylamino]-cyclopropanecarboxylic acid, (1R*,2R*)-4-Methyl-piperazine-1-carboxylic acid 2-carboxy-1-phenyl-2-[5-(5-trifluoromethyl-isoxazol-3-yl)-thiophene-2-sulfonylamino]-cyclopropylmethyl ester, (1R*,2R*)-2-Carbamoyloxymethyl-2-phenyl-1-[5-(5-trifluoromethyl-isoxazol-3-yl)-thiophene-2-sulfonylamino]-cyclopropanecarboxylic acid, (1R*,2S*)-2-{[(2-Methoxy-ethyl)-methyl-amino]-methyl}-2-phenyl-1-[5-(5-trifluoromethyl-isoxazol-3-yl)-thiophene-2-sulfonylamino]-cyclopropanecarboxylic acid, (1R*,2R*)-1-[5-(4-Chloro-phenyl)-thiophene-2-sulfonylamino]-2-(2-dimethylamino-ethylsulfanylmethyl)-2-phenyl-cyclopropanecarboxylic acid, (1S,2R,3R)-2-Methyl-3-phenyl-1-[5-(3-trifluoromethyl-isoxazol-5-yl)-thiophene-2-sulfonylamino]-cyclopropanecarboxylic acid, (1R*,2S*)-2-(4-Fluoro-phenyl)-2-methyl-1-[5-(5-trifluoromethyl-isoxazol-3-yl)-thiophene-2-sulfonylamino]-cyclopropanecarboxylic acid, (1R*,2R*)-2-(4-Fluoro-phenyl)-2-methyl-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-morpholin-4-ylmethyl-2-phenyl-cyclopropanecarboxylic acid, (1R*,2S*)-2-(4-Methyl-piperazin-1-ylmethyl)-2-phenyl-1-[5-(5-trifluoromethyl-isoxazol-3-yl)-thiophene-2-sulfonylamino]-cyclopropanecarboxylic acid, (1R*,2S*)-2-Diethylaminomethyl-2-phenyl-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-((2R,6S)-2,6-dimethyl-morpholin-4-ylmethyl)-2-phenyl-cyclopropanecarboxylic acid, (1R*,2R*)-1-[5-(4-Chloro-phenyl)-thiophene-2-sulfonylamino]-2-(2-hydroxy-ethylsulfanylmethyl)-2-phenyl-cyclopropanecarboxylic acid, (1R*,2S*)-1-[5-(4-Chloro-phenyl)-thiophene-2-sulfonylamino]-2-imidazol-1-ylmethyl-2-phenyl-cyclopropanecarboxylic acid, (1R*,2R*)-1-[5-(4-Chloro-phenyl)-thiophene-2-sulfonylamino]-2-(2-hydroxy-ethoxymethyl)-2-phenyl-cyclopropanecarboxylic acid, (1R*,2R*)-1-[5-(4-Chloro-phenyl)-thiophene-2-sulfonylamino]-2-phenyl-2-(propane-2-sulfonylmethyl)-cyclopropanecarboxylic acid, (1R*,2R*)-1-[5-(4-Chloro-phenyl)-thiophene-2-sulfonylamino]-2-isopropylsulfanylmethyl-2-phenyl-cyclopropanecarboxylic acid,
(1R*,1aS*,7bS*)-1-[5-(4-Chloro-phenyl)-thiophene-2-sulfonylamino]-1a,2,3,7b-tetrahydro-1H-cyclopropa[a]naphthalene-1-carboxylic acid,
(1R*,1aS*,7bS*)-1-[5-(5-Trifluoromethyl-isoxazol-3-yl)-thiophene-2-sulfonylamino]-1a,2,3,7b-tetrahydro-1H-cyclopropa[a]naphthalene-1-carboxylic acid,
(1R*,2R*)-1-[5-(4-Chloro-phenyl)-thiophene-2-sulfonylamino]-2-ethoxycarbonylmethylsulfanylmethyl-2-phenyl-cyclopropanecarboxylic acid,
(1S,2R,3R)-1-[5-(5-Difluoromethyl-isoxazol-3-yl)-thiophene-2-sulfonylamino]-2-methyl-3-phenyl-cyclopropanecarboxylic acid,
(1S,2R,3R)-1-[5-(3-Difluoromethyl-isoxazol-5-yl)-thiophene-2-sulfonylamino]-2-methyl-3-phenyl-cyclopropanecarboxylic acid,
(1R*,1aS*,7bS*)-1-[4-(2,4-Dichloro-benzyloxy)-benzenesulfonylamino]-1a,2,3,7b-tetrahydro-1H-cyclopropa[a]naphthalene-1-carboxylic acid,
(1R*,2R*)-2-Benzyloxymethyl-1-[5-(4-chloro-phenyl)-thiophene-2-sulfonylamino]-2-phenyl-cyclopropanecarboxylic acid,
(1R*,2R*)-1-[5-(4-Chloro-phenyl)-thiophene-2-sulfonylamino]-2-dimethylcarbamoylmethylsulfanylmethyl-2-phenyl-cyclopropanecarboxylic acid,
(1R*,2R*)-2-Carboxymethylsulfanylmethyl-1-[5-(4-chloro-phenyl)-thiophene-2-sulfonylamino]-2-phenyl-cyclopropanecarboxylic acid,
(1R*,2R*)-1-[5-(4-Chloro-phenyl)-thiophene-2-sulfonylamino]-2-(2-morpholin-4-yl-2-oxo-ethylsulfanylmethyl)-2-phenyl-cyclopropanecarboxylic acid,
(1R*,1aS*,7bS*)-1-[4-(2,4-Dichloro-benzyloxy)-benzenesulfonylamino]-1a,2,3,7b-tetrahydro-1H-cyclopropa[a]naphthalene-1-carboxylic acid hydroxyamide,
(1R*,2S*)-2-Aminomethyl-1-[S-(4-chloro-phenyl)-thiophene-2-sulfonylamino]-2-phenyl-cyclopropanecarboxylic acid,
(1R*,2S*)-1-[5-(4-Chloro-phenyl)-thiophene-2-sulfonylamino]-2-(2-oxo-oxazolidin-3-ylmethyl)-2-phenyl-cyclopropanecarboxylic acid,
(1R*,1aS*,8bS*)-1-[4-(2,4-Dichloro-benzyloxy)-benzenesulfonylamino]-1,1a,2,3,4,8b-hexahydro-benzo[a]cyclopropan[c]cycloheptene-1-carboxylic acid,
(1R*,1aS*,7bS*)-1-[5-(4-Chloro-phenyl)-thiophene-2-sulfonylamino]-1a,2,3,7b-tetrahydro-1H-cyclopropa[a]naphthalene-1-carboxylic acid hydroxyamide,
(1R*,1aS*,8bS*)-1-[5-(5-Chloro-pyridin-2-yl)-thiophene-2-sulfonylamino]-1,1a,2,3,4,8b-hexahydro-benzo[a]cyclopropan[c]cycloheptene-1-carboxylic acid,
(1S,2R,3R)-1-[5-(5-Chloro-pyridin-2-yl)-thiophene-2-sulfonylamino]-2-methyl-3-phenyl-cyclopropanecarboxylic acid,
(1S,2R,3R)-2-Methyl-1-[5-(4-methyl-imidazol-1-yl)-thiophene-2-sulfonylamino]-3-phenyl-cyclopropanecarboxylic acid,
(1R*,2S*)-1-[5-(4-Chloro-phenyl)-thiophene-2-sulfonylamino]-2-phenyl-2-{[(pyridine-2-carbonyl)-amino]-methyl}-cyclopropanecarboxylic acid,
(1R*,1aS*,8bS*)-1-[5-(4-Chloro-phenyl)-thiophene-2-sulfonylamino]-1a,2,3,8b-tetrahydro-1H-4-oxa-benzo[a]cyclopropan[c]cycloheptene-1-carboxylic acid,
(1R*,1aS*,8bS*)-1-[5-(5-Trifluoromethyl-isoxazol-3-yl)-thiophene-2-sulfonylamino]-1a,2,3,8b-tetrahydro-1H-4-oxa-benzo[a]cyclopropan[c]cycloheptene-1-carboxylic acid,
(1S,2R)-2-Phenyl-1-[5-(5-trifluoromethyl-isoxazol-3-yl)-furan-2-sulfonylamino]-cyclopropanecarboxylic acid,
(1S,2R,3R)-2-Methyl-3-phenyl-1-[5-(5-trifluoromethyl-isoxazol-3-yl)-furan-2-sulfonylamino]-cyclopropanecarboxylic acid,
(1R*,1aS*,8bS*)-1-[5-(5-Trifluoromethyl-isoxazol-3-yl)-furan-2-sulfonylamino]-1,1a,2,3,4,8b-hexahydro-benzo[a]cyclopropan[c]cycloheptene-1-carboxylic acid,
(1S,2R,3R)-2-Methyl-1-[5-(5-methyl-isoxazol-3-yl)-thiophene-2-sulfonylamino]-3-phenyl-cyclopropanecarboxylic acid,
(1R*,1aS*,8bS*)-1-[5-(5-Methyl-isoxazol-3-yl)-thiophene-2-sulfonylamino]-1,1a,2,3,4,8b-hexahydro-benzo[a]cyclopropan[c]cycloheptene-1-carboxylic acid,
(1R*,2S*)-2-(Acetylamino-methyl)-1-[5-(4-chloro-phenyl)-thiophene-2-sulfonylamino]-2-phenyl-cyclopropanecarboxylic acid,
(1R*,2S*)-2-(Butyrylamino-methyl)-1-[5-(4-chloro-phenyl)-thiophene-2-sulfonylamino]-2-phenyl-cyclopropanecarboxylic acid,
(1R*,2S*)-1-[5-(4-Chloro-phenyl)-thiophene-2-sulfonylamino]-2-(3,3-dimethyl-ureidomethyl)-2-phenyl-cyclopropanecarboxylic acid,
(1R*,2S*)-1-[5-(4-Chloro-phenyl)-thiophene-2-sulfonylamino]-2-[(cyclopropanecarbonyl-amino)-methyl]-2-phenyl-cyclopropanecarboxylic acid,
(1R*,2S*)-1-[5-(4-Chloro-phenyl)-thiophene-2-sulfonylamino]-2-[(cyclohexanecarbonyl-amino)-methyl]-2-phenyl-cyclopropanecarboxylic acid,
(1R*,2S*)-1-[5-(4-Chloro-phenyl)-thiophene-2-sulfonylamino]-2-{[(morpholine-4-carbonyl)-amino]-methyl}-2-phenyl-cyclopropanecarboxylic acid,
(1S,2R)-1-[5-(5-Difluoromethyl-isoxazol-3-yl)-thiophene-2-sulfonylamino]-2-methyl-2-phenyl-cyclopropanecarboxylic acid,
(1R*,1aS*,8bS*) 1-[5-(5-Difluoromethyl-isoxazol-3-yl)-thiophene-2-sulfonylamino]-1,1a,2,3,4,8b-hexahydro-benzo[a]cyclopropan[c]cycloheptene-1-carboxylic acid,
(1R*,2S*)-1-[5-(4-Chloro-phenyl)-thiophene-2-sulfonylamino]-2-(ethoxycarbonylamino-methyl)-2-phenyl-cyclopropanecarboxylic acid,
(1R*,2S*)-1-[5-(4-Chloro-phenyl)-thiophene-2-sulfonylamino]-2-phenyl-2-{[((S)-tetrahydro-furan-2-carbonyl)-amino]-methyl}-cyclopropanecarboxylic acid,
(1R*,2R*)-1-[5-(4-Chloro-phenyl)-thiophene-2-sulfonylamino]-2-methoxymethyl-2-phenyl-cyclopropanecarboxylic acid,
(1S,2R)-1-[5-(1-Methyl-1H-pyrazol-4-yl)-thiophene-2-sulfonylamino]-2-phenyl-cyclopropanecarboxylic acid,
(1S,2R)-1-[5-(4-Nitro-phenyl)-thiophene-2-sulfonylamino]-2-phenyl-cyclopropanecarboxylic acid,
(1R*,1aS*,8bS*)-1-[5-(4-Chloro-phenyl)-thiophene-2-sulfonylamino]-1,1a,2,3,4,8b-hexahydro-4-aza-benzo[a]cyclopropan[c]cycloheptene-1-carboxylic acid,
(1R*,1aS*,8bS*)-1-[4-(2,4-Dichloro-benzyloxy)-benzenesulfonylamino]-1,1a,2,3,4,8b-hexahydro-benzo[a]cyclopropan[c]cycloheptene-1-carboxylic acid hydroxyamide,
(1R*,1aS*,8bS*)-1-[5-(4-Chloro-phenyl)-thiophene-2-sulfonylamino]-1,1a,2,3,4,8b-hexahydro-benzo[a]cyclopropan[c]cycloheptene-1-carboxylic acid hydroxyamide,
(1R*,2S*)-1-[5-(4-Chloro-phenyl)-thiophene-2-sulfonylamino]-2-(isopropylamino-methyl)-2-phenyl-cyclopropanecarboxylic acid,
(1R*,2S*)-1-[5-(4-Chloro-phenyl)-thiophene-2-sulfonylamino]-2-phenyl-2-{[(thiazol-2-ylmethyl)-amino]-methyl}-cyclopropanecarboxylic acid, (1R*,2S*)-1-[5-(4-Chloro-phenyl)-thiophene-2-sulfonylamino]-2-phenyl-2-{[(pyridine-3-carbonyl)-amino]-methyl}-cyclopropanecarboxylic acid,
(1R*,2S*)-1-[5-(4-Chloro-phenyl)-thiophene-2-sulfonylamino]-2-[(3-hydroxy-propionylamino)-methyl]-2-phenyl-cyclopropanecarboxylic acid,
(1R*,2S*)-1-[5-(4-Chloro-phenyl)-thiophene-2-sulfonylamino]-2-[(3-ethyl-ureido)-methyl]-2-phenyl-cyclopropanecarboxylic acid,
(1R*,2S*)-1-[5-(4-Chloro-phenyl)-thiophene-2-sulfonylamino]-2-(isobutyrylamino-methyl)-2-phenyl-cyclopropanecarboxylic acid,
(1R*,2S*)-1-[5-(4-Chloro-phenyl)-thiophene-2-sulfonylamino]-2-[(2-methoxy-acetylamino)-methyl]-2-phenyl-cyclopropanecarboxylic acid,
(1R*,2S*)-1-[5-(4-Chloro-phenyl)-thiophene-2-sulfonylamino]-2-[(2-hydroxy-acetylamino)-methyl]-2-phenyl-cyclopropanecarboxylic acid,
(1R*,2S*)-1-[5-(4-Chloro-phenyl)-thiophene-2-sulfonylamino]-2-(3-oxo-morpholin-4-ylmethyl)-2-phenyl-cyclopropanecarboxylic acid,
(1S,2R,3R)-1-[4-(5-Difluoromethyl-isoxazol-3-yl)-benzenesulfonylamino]-2-methyl-3-phenyl-cyclopropanecarboxylic acid,
(1S,2R)-1-[5-(4-Acetylamino-phenyl)-thiophene-2-sulfonylamino]-2-methyl-2-phenyl-cyclopropanecarboxylic acid,
(1S,2R)-1-[5-(5-Methoxymethyl-isoxazol-3-yl)-thiophene-2-sulfonylamino]-2-methyl-2-phenyl-cyclopropanecarboxylic acid,
(1S,2R,3R)-2-methyl-1-[5-(5-Methoxymethyl-isoxazol-3-yl)-thiophene-2-sulfonylamino]-3-phenyl-cyclopropanecarboxylic acid,
(1R*,2R*)-2-Carboxymethoxymethyl-1-[5-(4-chloro-phenyl)-thiophene-2-sulfonylamino]-2-phenyl-cyclopropanecarboxylic acid,
(1S,2R)-1-[5-(4-Chloro-2-fluoro-phenyl)-thiophene-2-sulfonylamino]-2-methyl-2-phenyl-cyclopropanecarboxylic acid,
(1S,2R,3R)-1-[5-(4-Chloro-2-fluoro-phenyl)-thiophene-2-sulfonylamino]-2-methyl-3-phenyl-cyclopropanecarboxylic acid,
(1S,2R,3R)-1-[5-(5-Isopropyl-isoxazol-3-yl)-thiophene-2-sulfonylamino]-2-methyl-3-phenyl-cyclopropanecarboxylic acid,
(1R*,2R*)-2-Ethoxycarbonylmethylsulfanylmethyl-2-phenyl-1-[5-(5-trifluoromethyl-isoxazol-3-yl)-thiophene-2-sulfonylamino]-cyclopropanecarboxylic acid,
(1R*,2R*)-2-Carboxymethylsulfanylmethyl-2-phenyl-1-[5-(5-trifluoromethyl-isoxazol-3-yl)-thiophene-2-sulfonylamino]-cyclopropanecarboxylic acid,
(1R*,1aS*,4R*,8bS*)-1-[5-(4-Chloro-phenyl)-thiophene-2-sulfonylamino]-4-hydroxy-1,1a,2,3,4,8b-hexahydro-benzo[a]cyclopropan[c]cycloheptene-1-carboxylic acid,
(1R*,1aS*,4S*,8bS*)-1-[5-(4-Chloro-phenyl)-thiophene-2-sulfonylamino]-4-hydroxy-1,1a,2,3,4,8b-hexahydro-benzo[a]cyclopropan[c]cycloheptene-1-carboxylic acid,
(1S,2R)-1-[5-(3-Chloro-4-fluoro-phenyl)-thiophene-2-sulfonylamino]-2-methyl-2-phenyl-cyclopropanecarboxylic acid,
(1S,2R)-1-[5-(5-Bromo-pyrimidin-2-yl)-thiophene-2-sulfonylamino]-2-methyl-2-phenyl-cyclopropanecarboxylic acid,
(1aR*,8bS*)-5-(4-Chloro-phenyl)-thiophene-2-sulfonic acid (2-oxo-2,3,4,8b-tetrahydro-1H-3-aza-benzo[a]cyclopropan[c]cyclohepten-1a-yl)-amide,
(1S,2R)-1-[5-(5-Fluoro-pyridin-2-yl)-thiophene-2-sulfonylamino]-2-methyl-2-phenyl-cyclopropanecarboxylic acid,
(1S,2R,3R)-2-Methyl-1-[5-(5-methyl-oxazol-2-yl)-thiophene-2-sulfonylamino]-3-phenyl-cyclopropanecarboxylic acid,
(1S,2R)-2-Methyl-1-[5-(5-methyl-oxazol-2-yl)-thiophene-2-sulfonylamino]-2-phenyl-cyclopropanecarboxylic acid,
(1S,2R,3R)-1-[5-(5-Dimethylamino-isoxazol-3-yl)-thiophene-2-sulfonylamino]-2-methyl-3-phenyl-cyclopropanecarboxylic acid,
(1S,2R)-1-[5-(3-Cyano-4-fluoro-phenyl)-thiophene-2-sulfonylamino]-2-methyl-2-phenyl-cyclopropanecarboxylic acid,
(1S,2R)-2-Methyl-1-(5-morpholin-4-yl-thiophene-2-sulfonylamino)-2-phenyl-cyclopropanecarboxylic acid,
(1S,2R)-1-[5-(3-Difluoromethyl-isoxazol-5-yl)-thiophene-2-sulfonylamino]-2-methyl-2-phenyl-cyclopropanecarboxylic acid,
(1S,2R)-1-[5-(5-Dimethylamino-isoxazol-3-yl)-thiophene-2-sulfonylamino]-2-methyl-2-phenyl-cyclopropanecarboxylic acid,
(1S,2R,3R)-1-(5-Ethynyl-thiophene-2-sulfonylamino)-2-methyl-3-phenyl-cyclopropanecarboxylic acid,
(1S,2R,3R)-1-(5-Acetyl-thiophene-2-sulfonylamino)-2-methyl-3-phenyl-cyclopropanecarboxylic acid,
(1S,2R,3R)-1-[4-(4-Chloro-phenyl)-piperazine-1-sulfonylamino]-2-methyl-3-phenyl-cyclopropanecarboxylic acid,
(1S,2R,3R)-1-(5-Bromo-thiophene-2-sulfonylamino)-2-methyl-3-phenyl-cyclopropanecarboxylic acid,
(1S,2R,3R)-2-Methyl-3-phenyl-1-[4-(4-trifluoromethyl-phenyl)-piperazine-1-sulfonylamino]-cyclopropanecarboxylic acid,
(1R*,2R*)-1-[5-(4-Chloro-phenyl)-thiophene-2-sulfonylamino]-2-(2-methoxy-ethoxymethyl)-2-phenyl-cyclopropanecarboxylic acid,
(1R*,1aS*,8bS*)-1-[5-(4-Chloro-phenyl)-thiophene-2-sulfonylamino]-4-methyl-1,1a,2,3,4,8b-hexahydro-4-aza-benzo[a]cyclopropan[c]cycloheptene-1-carboxylic acid,
(1R*,1aS*,6aS*)-1-[5-(4-Chloro-phenyl)-thiophene-2-sulfonylamino]-1,1a,6,6a-tetrahydro-cyclopropa[a]indene-1-carboxylic acid,
(1R*,2R*)-1-[5-(4-Chloro-phenyl)-thiophene-2-sulfonylamino]-2-methylsulfanylmethyl-2-phenyl-cyclopropanecarboxylic acid,
(1S,2R,3R)-1-[5-(5-Cyclopropyl-isoxazol-3-yl)-thiophene-2-sulfonylamino]-2-methyl-3-phenyl-cyclopropanecarboxylic acid,
(1S,2R)-1-[5-(4-Chloro-3-fluoro-phenyl)-thiophene-2-sulfonylamino]-2-methyl-2-phenyl-cyclopropanecarboxylic acid,
(1S,2R,3R)-1-[5-(4-Chloro-3-fluoro-phenyl)-thiophene-2-sulfonylamino]-2-methyl-3-phenyl-cyclopropanecarboxylic acid,
(1S,2R)-2-Methyl-1-[4-(4-methyl-cyclohexyl)-benzenesulfonylamino]-2-phenyl-cyclopropanecarboxylic acid,
(1R*,1aS*,4R*,8bS*)-4-Hydroxy-1-[5-(5-trifluoromethyl-isoxazol-3-yl)-thiophene-2-sulfonylamino]-1,1a,2,3,4,8b-hexahydro-benzo[a]cyclopropan[c]cycloheptene-1-carboxylic acid,
(1R*,1aS*,4S*,8bS*)-4-Hydroxy-1-[5-(5-trifluoromethyl-isoxazol-3-yl)-thiophene-2-sulfonylamino]-1,1a,2,3,4,8b-hexahydro-benzo[a]cyclopropan[c]cycloheptene-1-carboxylic acid,
(1R*,1aS*,8bS*)-4-Acetyl-1-[5-(4-chloro-phenyl)-thiophene-2-sulfonylamino]-1,1a,2,3,4,8b-hexahydro-4-aza-benzo[a]cyclopropan[c]cycloheptene-1-carboxylic acid, (1R*,2R*)-1-[5-(4-Chloro-phenyl)-thiophene-2-sulfonylamino]-2-methanesulfonylmethyl-2-phenyl-cyclopropanecarboxylic acid,
(1S,2R,3R)-1-[4-(4-Chloro-phenyl)-3,6-dihydro-2H-pyridine-1-sulfonylamino]-2-methyl-3-phenyl-cyclopropanecarboxylic acid,
(1S,2R,3R)-2-Methyl-1-[4-(4-methyl-cyclohexyl)-piperazine-1-sulfonylamino]-3-phenyl-cyclopropanecarboxylic acid,
(1S,2R)-1-[5-(4-Isopropyl-piperazin-1-yl)-thiophene-2-sulfonylamino]-2-methyl-2-phenyl-cyclopropanecarboxylic acid,
(1S,2R,3R)-1-[5-(4-Chloro-pyrazol-1-yl)-thiophene-2-sulfonylamino]-2-methyl-3-phenyl-cyclopropanecarboxylic acid,
(1S,2R,3R)-1-(8-Chloro-3,4-dihydro-1H-benzo[4,5]imidazol[1,2-a]pyrazine-2-sulfonylamino)-2-methyl-3-phenyl-cyclopropanecarboxylic acid,
(1R*,1aS*,6aS*)-1-[4-(2,4-Dichloro-benzyloxy)-benzenesulfonylamino]-1,1a,6,6a-tetrahydro-cyclopropa[a]indene-1-carboxylic acid,
(1R*,1aS*,6aS*)-1-[5-(4-Chloro-phenyl)-thiophene-2-sulfonylamino]-1,1a,6,6a-tetrahydro-cyclopropa[a]indene-1-carboxylic acid hydroxyamide,
(1S,2R)-1-[5-(3,5-Dichloro-phenyl)-thiophene-2-sulfonylamino]-2-methyl-2-phenyl-cyclopropanecarboxylic acid,
(1S,2R)-1-(5-Benzo[1,3]dioxol-5-yl-thiophene-2-sulfonylamino)-2-methyl-2-phenyl-cyclopropanecarboxylic acid,
(1S,2R,3R)-2-Methyl-1-[5-(1-methyl-1H-imidazol-4-yl)-thiophene-2-sulfonylamino]-3-phenyl-cyclopropanecarboxylic acid,
(1S,2R,3R)-2-Methyl-1-[5-(5-methyl-[1,2,4]oxadiazol-3-yl)-thiophene-2-sulfonylamino]-3-phenyl-cyclopropanecarboxylic acid,
(1S,2R)-1-[5-(3-Amino-phenyl)-thiophene-2-sulfonylamino]-2-methyl-2-phenyl-cyclopropanecarboxylic acid,
(1S,2R)-1-[5-(3-Methanesulfonylamino-phenyl)-thiophene-2-sulfonylamino]-2-methyl-2-phenyl-cyclopropanecarboxylic acid,
(1S,2R,3R)-1-[4-(4-Chloro-phenyl)-[1,4]diazepane-1-sulfonylamino]-2-methyl-3-phenyl-cyclopropanecarboxylic acid,
(1S,2R)-1-[5-(4,4-Difluoro-piperidin-1-yl)-thiophene-2-sulfonylamino]-2-methyl-2-phenyl-cyclopropanecarboxylic acid,
(1S,2R,3R)-2-Methyl-3-phenyl-1-(5-quinoxaiin-2-yl-thiophene-2-sulfonylamino)-cyclopropanecarboxylic acid,
(1S,2R,3R)-1-[4-(5-Chloro-pyridin-2-yl)-piperazine-1-sulfonylamino]-2-methyl-3-phenyl-cyclopropanecarboxylic acid,
(1S,2R,3R)-1-[4-(4-Bromo-phenyl)-piperazine-1-sulfonylamino]-2-methyl-3-phenyl-cyclopropanecarboxylic acid,
(1S,2R,3R)-1-[4-(4-Chloro-3-fluoro-phenyl)-piperazine-1-sulfonylamino]-2-methyl-3-phenyl-cyclopropanecarboxylic acid,
(1S,2R,3R)-1-[4-(4-Chloro-2-fluoro-phenyl)-piperazine-1-sulfonylamino]-2-methyl-3-phenyl-cyclopropanecarboxylic acid,
(1S,2R,3R)-1-[4-(5-Chloro-pyridin-2-yl)-[1,4]diazepane-1-sulfonylamino]-2-methyl-3-phenyl-cyclopropanecarboxylic acid,
(1S,2R,3R)-1-[4-(5-Fluoro-pyridin-2-yl)-[1,4]diazepane-1-sulfonylamino]-2-methyl-3-phenyl-cyclopropanecarboxylic acid,
(1S,2R,3R)-1-(4-Benzothiazol-2-yl-piperazine-1-sulfonylamino)-2-methyl-3-phenyl-cyclopropanecarboxylic acid,
(1S,2R,3R)-1-(4-Benzoxazol-2-yl-piperazine-1-sulfonylamino)-2-methyl-3-phenyl-cyclopropanecarboxylic acid,
(1S,2R,3R)-2-Methyl-1-[4-(5-methyl-[1,3,4]thiadiazol-2-yl)-piperazine-1-sulfonylamino]-3-phenyl-cyclopropanecarboxylic acid,
(1S,2R)-1-[5-(3,5-Difluoro-pyridin-2-yl)-thiophene-2-sulfonylamino]-2-methyl-2-phenyl-cyclopropanecarboxylic acid,
(1S,2R)-1-[5-(3,3-Difluoro-pyrrolidin-1-yl)-thiophene-2-sulfonylamino]-2-methyl-2-phenyl-cyclopropanecarboxylic acid,
(1S,2R,3R)-2-Methyl-1-[5-(2-oxo-2,3-dihydro-benzothiazol-6-yl)-thiophene-2-sulfonylamino]-3-phenyl-cyclopropanecarboxylic acid,
(1S,2R,3R)-2-Methyl-1-[5-(2-methyl-benzothiazol-5-yl)-thiophene-2-sulfonylamino]-3-phenyl-cyclopropanecarboxylic acid,
(1S,2R,3R)-1-(5-Benzo[1,3]dioxol-5-yl-thiophene-2-sulfonylamino)-2-methyl-3-phenyl-cyclopropanecarboxylic acid,
(1S,2R,3R)-1-[4-(3-Chloro-phenyl)-[1,4]diazepane-1-sulfonylamino]-2-methyl-3-phenyl-cyclopropanecarboxylic acid,
(1S,2R,3R)-1-[4-(4-Fluoro-phenyl)-[1,4]diazepane-1-sulfonylamino]-2-methyl-3-phenyl-cyclopropanecarboxylic acid,
(1S,2R)-1-(4-Benzoylamino-benzenesulfonylamino)-2-phenyl-cyclopropanecarboxylic acid,
(1S,2R)-2-Phenyl-1-(4-phenylcarbamoyl-benzenesulfonylamino)-cyclopropanecarboxylic acid,
(1S,2R,3R)-2-Methyl-1-[4-(5-methyl-isoxazol-3-yl)-piperazine-1-sulfonylamino]-3-phenyl-cyclopropanecarboxylic acid,
(1S,2R,3R)-2-Methyl-1-[4-(5-methyl-isoxazol-3-yl)-3-oxo-piperazine-1-sulfonylamino]-3-phenyl-cyclopropanecarboxylic acid,
(1S,2R)-1-[5-(4-Chloro-3-nitro-phenyl)-thiophene-2-sulfonylamino]-2-methyl-2-phenyl-cyclopropanecarboxylic acid,
(1S,2R)-3-[5-((1S,2R)-1-Carboxy-2-methyl-2-phenyl-cyclopropylsulfamoyl)-thiophen-2-yl]-benzoic acid ethyl ester,
3-[5-((1S,2R)-1-Carboxy-2-methyl-2-phenyl-cyclopropylsulfamoyl)-thiophen-2-yl]-benzoic acid,
(1S,2R)-1-[5-(3-Acetylamino-phenyl)-thiophene-2-sulfonylamino]-2-methyl-2-phenyl-cyclopropanecarboxylic acid,
(1S,2R)-1-[6-(4-Methyl-pyrazol-1-yl)-pyridine-3-sulfonylamino]-2-phenyl-cyclopropanecarboxylic acid,
(1S,2R)-1-[6-(4-Methoxy-pyrazol-1-yl)-pyridine-3-sulfonylamino]-2-phenyl-cyclopropanecarboxylic acid,
(1S,2R,3R)-2-Methyl-1-[4-(2-methyl-benzothiazol-5-yl)-piperazine-1-sulfonylamino]-3-phenyl-cyclopropanecarboxylic acid,
(1S,2R,3R)-2-Methyl-1-[4-(5-methyl-thiazol-2-yl)-piperazine-1-sulfonylamino]-3-phenyl-cyclopropanecarboxylic acid,
(1S,2R)-1-[5-(2,3-Dihydro-benzo[1,4]dioxin-6-yl)-thiophene-2-sulfonylamino]-2-methyl-2-phenyl-cyclopropanecarboxylic acid,
(1R*,1aS*,7bS*)-1-[5-(5-Trifluoromethyl-isoxazol-3-yl)-thiophene-2-sulfonylamino]-1a,2,3,7b-tetrahydro-1H-cyclopropa[a]naphthalene-1-carboxylic acid hydroxyamide,
(1S,2R)-1-[5-(3-Hydroxy-3H-benzotriazol-5-yl)-thiophene-2-sulfonylamino]-2-methyl-2-phenyl-cyclopropanecarboxylic acid, (1S,2R)-1-[5-(4-Chloro-3-dimethylamino-phenyl)-thiophene-2-sulfonylamino]-2-methyl-2-phenyl-cyclopropanecarboxylic acid,
(1R*,2S*)-2-Phenyl-(6-phenyl-imidazo[2,1-b]thiazole-2-sulfonylamino)-cyclopropanecarboxylic acid,
(1R*,2S*)-1-[6-(4-Chloro-phenyl)-imidazol[2,1-b]thiazole-2-sulfonylamino]-2-phenyl-cyclopropanecarboxylic acid,
(1R*,2S*)-1-[6-(4-Fluoro-phenyl)-imidazol[2,1-b]thiazole-2-sulfonylamino]-2-phenyl-cyclopropanecarboxylic acid,
(1S,2R,3R)-1-[5-(4-Methoxy-pyrazol-1-yl)-thiophene-2-sulfonylamino]-2-methyl-3-phenyl-cyclopropanecarboxylic acid,
(1S,2R,3R)-1-[5-(1H-Indol-2-yl)-thiophene-2-sulfonylamino]-2-methyl-3-phenyl-cyclopropanecarboxylic acid,
(1S,2R,3R)-1-[5-(4-Bromo-pyrazol-1-yl)-thiophene-2-sulfonylamino]-2-methyl-3-phenyl-cyclopropanecarboxylic acid,
(1R*,1aS*,6aS*)-1-[5-(5-Trifluoromethyl-isoxazol-3-yl)-thiophene-2-sulfonylamino]-1,1a,6,6a-tetrahydro-cyclopropa[a]indene-1-carboxylic acid hydroxyamide,
(1S,2R,3R)-1-[5-(3-Amino-4-chloro-phenyl)-thiophene-2-sulfonylamino]-2-methyl-3-phenyl-cyclopropanecarboxylic acid,
(1S,2R,3R)-1-(5-Benzo[2,1,3]thiadiazol-5-yl-thiophene-2-sulfonylamino)-2-methyl-3-phenyl-cyclopropanecarboxylic acid,
(1S,2R)-1-[5-(4-Chloro-pyrazol-1-yl)-thiophene-2-sulfonylamino]-2-methyl-2-phenyl-cyclopropanecarboxylic acid,
(1S,2R,3R)-2-Methyl-3-phenyl-1-(6-phenyl-imidazo[2,1-b]thiazole-2-sulfonylamino)-cyclopropanecarboxylic acid,
(1S,2R,3R)-1-[3-(4-Chloro-phenoxy)-pyrrolidine-1-sulfonylamino]-2-methyl-3-phenyl-cyclopropanecarboxylic acid,
(1S,2R,3R)-1-[3-(3-Chloro-phenoxy)-pyrrolidine-1-sulfonylamino]-2-methyl-3-phenyl-cyclopropanecarboxylic acid,
(1S,2R,3R)-1-[4-(4-Chloro-phenyl)-3-oxo-piperazine-1-sulfonylamino]-2-methyl-3-phenyl-cyclopropanecarboxylic acid,
(1S,2R,3R)-1-[4-(6-Chloro-pyridazin-3-yl)-piperazine-1-sulfonylamino]-2-methyl-3-phenyl-cyclopropanecarboxylic acid,
(1S,2R,3R)-2-Methyl-1-[3-oxo-4-(4-trifluoromethyl-phenyl)-piperazine-1-sulfonylamino]-3-phenyl-cyclopropanecarboxylic acid,
(1S,2R,3R)-1-(5-Bromo-1,3-dihydro-isoindole-2-sulfonylamino)-2-methyl-3-phenyl-cyclopropanecarboxylic acid,
(1S,2R)-2-Methyl-2-phenyl-1-[4-(4-trifluoromethyl-pyrazol-1-yl)-benzenesulfonylamino]-cyclopropanecarboxylic acid,
(1S,2R,3R)-2-Methyl-3-phenyl-1-[4-(4-trifluoromethyl-pyrazol-1-yl)-benzenesulfonylamino]-cyclopropanecarboxylic acid,
(1R*,2S*,3S*)-1-(5-Benzyl-thiophene-2-sulfonylamino)-2-methyl-3-phenyl-cyclopropanecarboxylic acid,
(1R*,2S*,3S*)-1-[5-(3-Hydroxy-phenyl)-thiophene-2-sulfonylamino]-2-methyl-3-phenyl-cyclopropanecarboxylic acid,
4-((1S,2R)-1-Carboxy-2-phenyl-cyclopropylsulfamoyl)-piperazine-1-carboxylic acid isopropyl ester,
(1S,2R)-1-[4-(3-Methyl-butyl)-piperazine-1-sulfonylamino]-2-phenyl-cyclopropanecarboxylic acid,
(1S,2R)-1-(4-Ethylcarbamoyl-piperazine-1-sulfonylamino)-2-phenyl-cyclopropanecarboxylic acid,
(1S,2R)-1-[4-(3-Methyl-butyryl)-piperazine-1-sulfonylamino]-2-phenyl-cyclopropanecarboxylic acid,
(1S,2R,3R)-2-Methyl-3-phenyl-1-[5-(3-trifluoromethyl-pyrazol-1-yl)-thiophene-2-sulfonylamino]-cyclopropanecarboxylic acid,
(1S,2R)-2-Methyl-1-[5-(methyl-phenyl-amino)-thiophene-2-sulfonylamino]-2-phenyl-cyclopropanecarboxylic acid,
(1S,2R)-1-[5-(4-Chloro-3-methoxy-phenyl)-thiophene-2-sulfonylamino]-2-methyl-2-phenyl-cyclopropanecarboxylic acid,
(1S,2R,3R)-1-(5-Benzo[2,1,3]oxadiazol-5-yl-thiophene-2-sulfonylamino)-2-methyl-3-phenyl-cyclopropanecarboxylic acid,
(1S,2R)-2-Methyl-2-phenyl-1-(6-phenyl-imidazo[2,1-b]thiazole-2-sulfonylamino)-cyclopropanecarboxylic acid,
(1S,2R)-1-(6-Methoxymethyl-imidazo[2,1-b]thiazole-2-sulfonylamino)-2-methyl-2-phenyl-cyclopropanecarboxylic acid,
(1S,2R,3R)-1-[6-(4-Chloro-pyrazol-1-ylmethyl)-imidazol[2,1-b]thiazole-2-sulfonylamino]-2-methyl-3-phenyl-cyclopropanecarboxylic acid,
1-[5-((1S,2R,3R)-1-Carboxy-2-methyl-3-phenyl-cyclopropylsulfamoyl)-thiophen-2-yl]-1H-pyrazole-4-carboxylic acid ethyl ester,
1-[5-((1S,2R,3R)-1-Carboxy-2-methyl-3-phenyl-cyclopropylsulfamoyl)-thiophen-2-yl]-1H-pyrazole-4-carboxylic acid,
(1S,2R,3R)-1-{5-[4-(1-Hydroxy-1-methyl-ethyl)-pyrazol-1-yl]-thiophene-2-sulfonylamino}-2-methyl-3-phenyl-cyclopropanecarboxylic acid,
(1S,2R,3R)-1-[5-(4-Methanesulfonyl-pyrazol-1-yl)-thiophene-2-sulfonylamino]-2-methyl-3-phenyl-cyclopropanecarboxylic acid,
(1R*,2S*,3S*)-1-[5-(3-Hydroxymethyl-phenyl)-thiophene-2-sulfonylamino]-2-methyl-3-phenyl-cyclopropanecarboxylic acid,
(1S,2R)-2-Methyl-2-phenyl-1-(5-pyridin-4-yl-thiophene-2-sulfonylamino)-cyclopropanecarboxylic acid,
(1S,2R)-2-Methyl-2-phenyl-1-(5-pyridin-3-yl-thiophene-2-sulfonylamino)-cyclopropanecarboxylic acid,
(1S,2R,3R)-1-(6,7-Dimethoxy-3,4-dihydro-1H-isoquinoline-2-sulfonylamino)-2-methyl-3-phenyl-cyclopropanecarboxylic acid,
(1S,2R,3R)-1-(4-Benzylcarbamoyl-piperazine-1-sulfonylamino)-2-methyl-3-phenyl-cyclopropanecarboxylic acid,
(1S,2R,3R)-2-Methyl-1-[4-(3-methyl-butyl)-piperazine-1-sulfonylamino]-3-phenyl-cyclopropanecarboxylic acid,
(1S,2R,3R)-2-Methyl-1-(4-phenethyl-piperazine-1-sulfonylamino)-3-phenyl-cyclopropanecarboxylic acid,
4-((1S,2R,3R)-1-Carboxy-2-methyl-3-phenyl-cyclopropylsulfamoyl)-piperazine-1-carboxylic acid benzyl ester,
(1S,2R,3R)-2-Methyl-3-phenyl-1-(4-pyridin-4-yl-piperazine-1-sulfonylamino)-cyclopropanecarboxylic acid,
(1S,2R,3R)-1-[4-(2-Methoxy-ethyl)-piperazine-1-sulfonylamino]-2-methyl-3-phenyl-cyclopropanecarboxylic acid,
(1S,2R,3R)-1-(3,4-Dihydro-1H-isoquinoline-2-sulfonylamino)-2-methyl-3-phenyl-cyclopropanecarboxylic acid,
(1S,2R,3R)-1-[4-(4-Methoxy-benzyl)-piperazine-1-sulfonylamino]-2-methyl-3-phenyl-cyclopropanecarboxylic acid,
(1S,2R,3R)-2-Methyl-3-phenyl-1-[4-((E)-3-phenyl-allyl)-piperazine-1-sulfonylamino]-cyclopropanecarboxylic acid,
(1S,2R,3R)-1-(5-Chloro-1,3-dihydro-isoindole-2-sulfonylamino)-2-methyl-3-phenyl-cyclopropanecarboxylic acid,
(1R*,2R*,3R*)-2-Methoxymethyl-3-phenyl-1-[5-(5-trifluoromethyl-isoxazol-3-yl)-thiophene-2-sulfonylamino]-cyclopropanecarboxylic acid, (1R*,2S*,3S*)-2-Methyl-1-[5-(3-morpholin-4-ylmethyl-phenyl)-thiophene-2-sulfonylmethyl]-3-phenyl-cyclopropanecarboxylic acid,
(1R*,2S*,3S*)-2-Methyl-1-(5-phenethyl-thiophene-2-sulfonylamino)-3-phenyl-cyclopropanecarboxylic acid,
(1S,2R,3R)-2-Methyl-3-phenyl-1-(5-pyrazol-1-yl-thiophene-2-sulfonylamino)-cyclopropanecarboxylic acid,
(1S,2R,3R)-1-[5-(4-Iodo-pyrazol-1-yl)-thiophene-2-sulfonylamino]-2-methyl-3-phenyl-cyclopropanecarboxylic acid,
(1S,2R)-1-[5-(2,2-Difluoro-benzo[1,3]dioxol-5-yl)-thiophene-2-sulfonylamino]-2-methyl-2-phenyl-cyclopropanecarboxylic acid,
(1S,2R,3R)-1-{5-[4-(1-Chloro-vinyl)-pyrazol-1-yl]-thiophene-2-sulfonylamino}-2-methyl-3-phenyl-cyclopropanecarboxylic acid,
(1S,2R,3R)-1-[5-(4-Acetyl-pyrazol-1-yl)-thiophene-2-sulfonylamino]-2-methyl-3-phenyl-cyclopropanecarboxylic acid,
(1S,2R,3R)-1-{5-[4-(1-Hydroxy-ethyl)-pyrazol-1-yl]-thiophene-2-sulfonylamino}-2-methyl-3-phenyl-cyclopropanecarboxylic acid,
(1S,2R,3R)-1-(5-Hydroxy-1,3-dihydro-isoindole-2-sulfonylamino)-2-methyl-3-phenyl-cyclopropanecarboxylic acid,
(1S,2R,3R)-1-[3-(3-Chloro-benzyloxy)-pyrrolidine-1-sulfonylamino]-2-methyl-3-phenyl-cyclopropanecarboxylic acid,
(1S,2R,3R)-1-[3-(4-Chloro-benzyloxy)-pyrrolidine-1-sulfonylamino]-2-methyl-3-phenyl-cyclopropanecarboxylic acid,
(1S,2R,3R)-1-[3-(2,5-Dichloro-benzyloxy)-pyrrolidine-1-sulfonylamino]-2-methyl-3-phenyl-cyclopropanecarboxylic acid,
(1S,2R,3R)-1-(5-Isopropylamino-1,3-dihydro-isoindole-2-sulfonylamino)-2-methyl-3-phenyl-cyclopropanecarboxylic acid,
(1S,2R,3R)-1-[3-(2,4-Dichloro-benzyloxy)-pyrrolidine-1-sulfonylamino]-2-methyl-3-phenyl-cyclopropanecarboxylic acid,
(1S,2R)-1-[6-(4-Chloro-pyrazol-1-yl)-pyridine-3-sulfonylamino]-2-phenyl-cyclopropanecarboxylic acid,
3-[5-((1S,2R,3R)-1-Carboxy-2-methyl-3-phenyl-cyclopropylsulfamoyl)-thiophen-2-yl]-isoxazole-5-carboxylic acid ethyl ester,
(1S,2R,3R)-2-Methyl-3-phenyl-1-[6-(4-trifluoromethyl-pyrazol-1-yl)-pyridine-3-sulfonylamino]-cyclopropanecarboxylic acid,
(1S,2R,3R)-1-[6-(4-Chloro-pyrazol-1-yl)-pyridine-3-sulfonylamino]-2-methyl-3-phenyl-cyclopropanecarboxylic acid,
(1S,2R)-2-Phenyl-1-[6-(4-trifluoromethyl-pyrazol-1-yl)-pyridine-3-sulfonylamino]-cyclopropanecarboxylic acid,
(1R*,2S*)-1-[5-(4-Chloro-phenyl)-thiophene-2-sulfonylamino]-2-(3-methoxy-propyl)-2-phenyl-cyclopropanecarboxylic acid,
(1R*,2S*)-1-[5-(4-Chloro-phenyl)-thiophene-2-sulfonylamino]-2-(3-methoxy-propyl)-2-phenyl-cyclopropanecarboxylic acid,
(1S,2R,3R)-1-[5-(4-Hydroxymethyl-pyrazol-1-yl)-thiophene-2-sulfonylamino]-2-methyl-3-phenyl-cyclopropanecarboxylic acid,
(1S,2R)-2-Methyl-2-phenyl-1-[5-((E)-3,3,3-trifluoro-propenyl)-thiophene-2-sulfonylamino]-cyclopropanecarboxylic acid,
(1S,2R)-2-Methyl-2-phenyl-1-[5-((Z)-3,3,3-trifluoro-propenyl)-thiophene-2-sulfonylamino]-cyclopropanecarboxylic acid,
(1S,2R)-1-[5-(4-Chloro-3-hydroxymethyl-phenyl)-thiophene-2-sulfonylamino]-2-methyl-2-phenyl-cyclopropanecarboxylic acid,
(1S,2R,3R)-1-[5-(4-Chloro-3-hydroxymethyl-phenyl)-thiophene-2-sulfonylamino]-2-methyl-3-phenyl-cyclopropanecarboxylic acid,
(1S,2R)-1-[5-(2,4-Dichloro-phenyl)-thiophene-2-sulfonylamino]-2-methyl-2-phenyl-cyclopropanecarboxylic acid,
(1S,2R)-1-[5-(4-Cyano-phenyl)-thiophene-2-sulfonylamino]-2-methyl-2-phenyl-cyclopropanecarboxylic acid,
(1S,2R)-1-(7-Chloro-9H-fluorene-2-sulfonylamino)-2-methyl-2-phenyl-cyclopropanecarboxylic acid,
(1S,2R,3R)-1-(7-Chloro-9H-fluorene-2-sulfonylamino)-2-methyl-3-phenyl-cyclopropanecarboxylic acid,
(1S,2R,3R)-1-(5-Imidazo[1,2-a]pyridin-2-yl-thiophene-2-sulfonylamino)-2-methyl-3-phenyl-cyclopropanecarboxylic acid,
(1S,2R,3R)-1-(5-Imidazo[1,2-a]pyrimidin-2-yl-thiophene-2-sulfonylamino)-2-methyl-3-phenyl-cyclopropanecarboxylic acid,
(1S,2R)-2-Methyl-2-phenyl-1-[5-(4-trifluoromethyl-phenyl)-thiophene-2-sulfonylamino]-cyclopropanecarboxylic acid,
(1S,2R)-1-[5-(4-Acetyl-phenyl)-thiophene-2-sulfonylamino]-2-methyl-2-phenyl-cyclopropanecarboxylic acid,
(1S,2R)-1-[5-(4-Hydroxymethyl-phenyl)-thiophene-2-sulfonylamino]-2-methyl-2-phenyl-cyclopropanecarboxylic acid,
(1S,2R)-1-{5-[3-(2-Hydroxy-ethoxy)-phenyl]-thiophene-2-sulfonylamino}-2-methyl-2-phenyl-cyclopropanecarboxylic acid,
(1S,2R)-1-{5-[3-(3-Hydroxy-propoxy)-phenyl]-thiophene-2-sulfonylamino}-2-methyl-2-phenyl-cyclopropanecarboxylic acid,
(1S,2R,3R)-2-Methyl-3-phenyl-1-[5-(4-trifluoromethyl-pyrazol-1-yl)-thiophene-2-sulfonylamino]-cyclopropanecarboxylic acid,
(1S,2R,3R)-1-[5-(5-Carbamoyl-isoxazol-3-yl)-thiophene-2-sulfonylamino]-2-methyl-3-phenyl-cyclopropanecarboxylic acid,
(1S,2R,3R)-1-[5-(5-Cyano-isoxazol-3-yl)-thiophene-2-sulfonylamino]-2-methyl-3-phenyl-cyclopropanecarboxylic acid,
(1S,2R,3R)-1-[5-(4-Cyano-pyrazol-1-yl)-thiophene-2-sulfonylamino]-2-methyl-3-phenyl-cyclopropanecarboxylic acid,
(1S,2R)-1-[5-(3,4-Difluoro-phenyl)-thiophene-2-sulfonylamino]-2-methyl-2-phenyl-cyclopropanecarboxylic acid,
(1S,2R)-1-[5-(4-Hydroxy-phenyl)-thiophene-2-sulfonylamino]-2-methyl-2-phenyl-cyclopropanecarboxylic acid,
(1S,2R)-1-[5-(4-Amino-phenyl)-thiophene-2-sulfonylamino]-2-methyl-2-phenyl-cyclopropanecarboxylic acid,
(1S,2R,3R)-1-[5-(1H-Benzoimidazol-2-yl)-thiophene-2-sulfonylamino]-2-methyl-3-phenyl-cyclopropanecarboxylic acid,
(1S,2R)-2-Methyl-2-phenyl-1-(5-phenyl-benzo[b]thiophene-3-sulfonylamino)-cyclopropanecarboxylic acid,
(1S,2R)-2-Methyl-1-[5-(3-methyl-3H-[1,2,3]triazol-4-yl)-thiophene-2-sulfonylamino]-2-phenyl-cyclopropanecarboxylic acid,
(1S,2R)-2-Methyl-1-[5-(1-methyl-1H-[1,2,3]triazol-4-yl)-thiophene-2-sulfonylamino]-2-phenyl-cyclopropanecarboxylic acid, (1R*,2S*)-2-(3-Methoxy-propyl)-2-phenyl-1-[5-(5-trifluoromethyl-isoxazol-3-yl)-thiophene-2-sulfonylamino]-cyclopropanecarboxylic acid, (1S,2R)-1-[5-(3-Fluoro-4-hydroxy-phenyl)-thiophene-2-sulfonylamino]-2-methyl-2-phenyl-cyclopropanecarboxylic acid, (1S,2R,3R)-2-Methyl-3-phenyl-1-[5-(4-trifluoromethyl-phenyl)-thiophene-2-sulfonylamino]-cyclopropanecarboxylic acid, (1S,2R,3R)-1-(5-Benzothiazol-2-yl-thiophene-2-sulfonylamino)-2-methyl-3-phenyl-cyclopropanecarboxylic acid, (1S,2R)-1-[5-(3-Hydroxymethyl-4-methoxy-phenyl)-thiophene-2-sulfonylamino]-2-methyl-2-phenyl-cyclopropanecarboxylic acid, (1S,2R)-1-[5-(4-Cyano-3-fluoro-phenyl)-thiophene-2-sulfonylamino]-2-methyl-2-phenyl-cyclopropanecarboxylic acid, (1S,2R)-1-[5-(3-Fluoro-4-hydroxymethyl-phenyl)-thiophene-2-sulfonylamino]-2-methyl-2-phenyl-cyclopropanecarboxylic acid, (1S,2R)-1-[5-(3-Chloro-4-methoxy-phenyl)-thiophene-2-sulfonylamino]-2-methyl-2-phenyl-cyclopropanecarboxylic acid, (1S,2R,3R)-2-Methyl-3-phenyl-1-(2-phenyl-3H-benzoimidazole-5-sulfonylamino)-cyclopropanecarboxylic acid, (1R*,2R*,3S*)-2,3-Dimethyl-2-phenyl-1-[5-(5-trifluoromethyl-isoxazol-3-yl)-thiophene-2-sulfonylamino]-cyclopropanecarboxylic acid, (1R*,2S*,3R*)-2,3-Dimethyl-2-phenyl-1-[5-(5-trifluoromethyl-isoxazol-3-yl)-thiophene-2-sulfonylamino]-cyclopropanecarboxylic acid, (1S,2R)-2-Methyl-2-phenyl-1-[5-(4-trifluoromethyl-pyrazol-1-yl)-thiophene-2-sulfonylamino]-cyclopropanecarboxylic acid, (1S,2R)-1-[5-(4-Fluoro-3-hydroxy-phenyl)-thiophene-2-sulfonylamino]-2-methyl-2-phenyl-cyclopropanecarboxylic acid, (1S,2R)-1-[5-(3,4-Difluoro-5-hydroxy-phenyl)-thiophene-2-sulfonylamino]-2-methyl-2-phenyl-cyclopropanecarboxylic acid, (1S,2R)-1-[5-(4-Methanesulfonyl-pyrazol-1-yl)-thiophene-2-sulfonylamino]-2-methyl-2-phenyl-cyclopropanecarboxylic acid, (1S,2R)-1-[5-(4-Hydroxymethyl-pyrazol-1-yl)-thiophene-2-sulfonylamino]-2-methyl-2-phenyl-cyclopropanecarboxylic acid, (1S,2R,3R)-1-[5-(5-Chloro-1H-benzoimidazol-2-yl)-thiophene-2-sulfonylamino]-2-methyl-3-phenyl-cyclopropanecarboxylic acid, (1S,2R)-1-[5-(4-Bromo-pyrazol-1-yl)-thiophene-2-sulfonylamino]-2-phenyl-cyclopropanecarboxylic acid, (1S,2R)-1-{5-[3-(1,1-Difluoro-2-hydroxy-ethyl)-phenyl]-thiophene-2-sulfonylamino}-2-methyl-2-phenyl-cyclopropanecarboxylic acid, (1S,2R,3R)-1-[5-(5-Methoxy-1H-benzoimidazol-2-yl)-thiophene-2-sulfonylamino]-2-methyl-3-phenyl-cyclopropanecarboxylic acid, (1R*,2S*)-2-(4-Chloro-phenyl)-2-methyl-1-[5-(5-trifluoromethyl-isoxazol-3-yl)-thiophene-2-sulfonylamino]-cyclopropanecarboxylic acid, (1R*,2S*)-2-(3-Methoxy-phenyl)-2-methyl-1-[5-(5-trifluoromethyl-isoxazol-3-yl)-thiophene-2-sulfonylamino]-cyclopropanecarboxylic acid, (1R*,2S*)-2-(3-Fluoro-phenyl)-2-methyl-1-[5-(5-trifluoromethyl-isoxazol-3-yl)-thiophene-2-sulfonylamino]-cyclopropanecarboxylic acid, (1R*,2S*)-2-(3-Chloro-phenyl)-2-methyl-1-[5-(5-trifluoromethyl-isoxazol-3-yl)-thiophene-2-sulfonylamino]-cyclopropanecarboxylic acid, (1R*,2S*)-2-(2-Methoxy-phenyl)-2-methyl-1-[5-(5-trifluoromethyl-isoxazol-3-yl)-thiophene-2-sulfonylamino]-cyclopropanecarboxylic acid, (1R*,2S*)-2-(3-Methanesulfonyl-phenyl)-2-methyl-1-[5-(5-trifluoromethyl-isoxazol-3-yl)-thiophene-2-sulfonylamino]-cyclopropanecarboxylic acid, (1R*,2S*)-2-(2-Fluoro-phenyl)-2-methyl-1-[5-(5-trifluoromethyl-isoxazol-3-yl)-thiophene-2-sulfonylamino]-cyclopropanecarboxylic acid, (1R*,2S*)-2-(2-Chloro-phenyl)-2-methyl-1-[5-(5-trifluoromethyl-isoxazol-3-yl)-thiophene-2-sulfonylamino]-cyclopropanecarboxylic acid, (1R*,2S*)-2-Methyl-2-pyridin-3-yl-1-[5-(5-trifluoromethyl-isoxazol-3-yl)-thiophene-2-sulfonylamino]-cyclopropanecarboxylic acid, (1S,2R)-2-(3-Fluoro-phenyl)-2-methyl-1-[5-(5-trifluoromethyl-isoxazol-3-yl)-thiophene-2-sulfonylamino]-cyclopropanecarboxylic acid, (1S,2R)-2-(3-Chloro-phenyl)-2-methyl-1-[5-(5-trifluoromethyl-isoxazol-3-yl)-thiophene-2-sulfonylamino]-cyclopropanecarboxylic acid, (1S,2R)-2-(4-Chloro-phenyl)-2-methyl-1-[5-(5-trifluoromethyl-isoxazol-3-yl)-thiophene-2-sulfonylamino]-cyclopropanecarboxylic acid, (1S,2R)-2-(4-Fluoro-phenyl)-2-methyl-1-[5-(5-trifluoromethyl-isoxazol-3-yl)-thiophene-2-sulfonylamino]-cyclopropanecarboxylic acid, (1S,2R,3R)-2-Methyl-3-phenyl-1-(2-phenyl-imidazo[1,2-a]pyridine-6-sulfonylamino)-cyclopropanecarboxylic acid, (1S,2R,3R)-2,3-Dimethyl-2-phenyl-1-[5-(5-trifluoromethyl-isoxazol-3-yl)-thiophene-2-sulfonylamino]-cyclopropanecarboxylic acid, (1S,2R)-2-(3-Methoxy-phenyl)-2-methyl-1-[5-(5-trifluoromethyl-isoxazol-3-yl)-thiophene-2-sulfonylamino]-cyclopropanecarboxylic acid, and (1S,2R,3R)-1-{5-[5-(1,1-Difluoro-ethyl)-isoxazol-3-yl]-thiophene-2-sulfonylamino}-2,3-dimethyl-2-phenyl-cyclopropanecarboxylic acid;

or a prodrug thereof or a pharmaceutically acceptable salt thereof;

[11] The compound of [1] above, which is represented by the formula (1'):

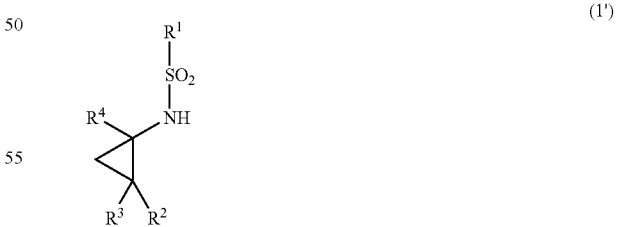

wherein $R^1$ is selected from (1) a substituted $C_{1-6}$ alkyl group, and (2) —$(CH_2)_m$—X—$(CH_2)_n$-$A^1$, wherein m and n are the same or different and each is selected from 0 and an integer ranging from 1 to 6, X is selected from a single bond, a $C_{1-6}$ alkylene group, a $C_{2-6}$ alkenylene group, a $C_{2-6}$ alkynylene group, —O—, —N(R$^5$)—, —S(O)$_{m1}$—, —CO—, —CON(R$^5$)—, —N(R$^5$)CO—, —SO$_2$N(R$^5$)—, —N(R$^5$)SO$_2$—, —N(R$^5$)CON(R$^6$)—, —N(R$^5$)SO$_2$N(R$^6$)—, —OCON(R$^5$)— and —N(R$^5$)COO—, wherein R$^5$ and R$^6$ are the same or different and each is selected from a hydrogen atom and a $C_{1-6}$ alkyl group, m1 is selected from 0 and an integer ranging from 1 to 2, A$^1$ is selected from a substituted $C_{3-14}$ hydrocarbon ring group and a substituted heterocyclic group;

R$^2$ and R$^3$ are the same or different and each is selected from
(1) a hydrogen atom,
(2) a $C_{1-6}$ alkyl group,
(3) a halogenated $C_{1-6}$ alkyl group,
and
(4) —(CH$_2$)$_p$—X$_1$—(CH$_2$)$_q$-A$^2$, provided that R$^2$ and R$^3$ are not hydrogen atoms at the same time, wherein p and q are the same or different and each is selected from 0 and an integer ranging from 1 to 6, X$_1$ is selected from a single bond, a $C_{1-6}$ alkylene group, a $C_{2-6}$ alkenylene group, a $C_{2-6}$ alkynylene group, —O—, —N(R$^7$)—, —S(O)$_{m2}$—, —CO—, —CON(R$^7$)—, —N(R$^7$)CO—, —SO$_2$N(R$^7$)—, —N(R$^7$)SO$_2$—, —N(R$^7$)CON(R$^8$)—, —N(R$^7$)SO$_2$N(R$^8$)—, —OCON(R$^7$)— and —N(R$^7$)COO—, wherein R$^7$ and R$^8$ are the same or different and each is selected from a hydrogen atom and a $C_{1-6}$ alkyl group, m2 is selected from 0 and an integer ranging from 1 to 2, r is selected from 0 and an integer ranging from 1 to 2, and A$^2$ is selected from an optionally substituted $C_{3-14}$ hydrocarbon ring group and an optionally substituted heterocyclic group;

and

R$^4$ is selected from
(1) —CO$_2$R$^9$,
(2) —C(O)NHOR$^9$,
(3) —C(O)NH—SO$_2$—R$^9$,
(4) —C(O)NHR$^9$,
(5) —SH,
(6) —CH$_2$CO$_2$R$^9$,
(7) —C(O)R$^9$,
(8) —N(OH)COR$^9$,
(9) —SN$_2$H$_2$R$^9_1$,
(10) —SONHR$^9$,
(11) —CH$_2$CO$_2$H,
(12) —PO(OH)$_2$,
(13) —PO(OH)NHR$^9$,
(14) —CH$_2$SH
and
(15) —CH$_2$OH wherein R$^9$ is selected from a hydrogen atom, an optionally substituted $C_{1-10}$ alkyl group and an optionally substituted $C_{6-14}$ aryl-$C_{1-6}$ alkyl group;

or a prodrug thereof or a pharmaceutically acceptable salt thereof;

[12] The compound of [11] above, wherein R$^1$ is —(CH$_2$)$_m$—X—(CH$_2$)$_n$-A$^1$ and A$^1$ is selected from
(1) an optionally substituted fused $C_{6-14}$ hydrocarbon ring group,
(2) an optionally substituted fused heterocyclic group, and
(3) —V—W-Z, wherein V is selected from an optionally substituted $C_{3-14}$ hydrocarbon ring group and an optionally substituted heterocyclic group;

W is —(CH$_2$)$_t$—X$_2$—(CH$_2$)$_u$—;

wherein t and u are the same or different and each is selected from 0 and an integer ranging from 1 to 6, X$_2$ is selected from a single bond, a $C_{1-6}$ alkylene group, a $C_{2-6}$ alkenylene group, a $C_{2-6}$ alkynylene group, —O—, —N(R$^{10}$)—, —S(O)$_{m3}$—, —CO—, —CON(R$^{10}$)—, —N(R$^{10}$)CO—, —SO$_2$N(R$^{10}$)—, —N(R$^{10}$)SO$_2$—, —N(R$^{10}$)CON(R$^{11}$)—, —N(R$^{10}$)SO$_2$N(R$^{11}$)—, —OCON(R$^{10}$)— and —N(R$^{10}$)COO—, wherein R$^{10}$ and R$^{11}$ are the same or different and each is selected from a hydrogen atom and a $C_{1-6}$ alkyl group, m3 is selected from 0 and an integer ranging from 1 to 2, Z is selected from an optionally substituted $C_{1-6}$ alkyl group, a halogen atom, a nitro group, a cyano group, a $C_{1-6}$ alkoxy group, a hydroxyl group, a halogenated $C_{1-6}$ alkyl group, a halogenated $C_{1-6}$ alkoxy group, a carboxyl group, a $C_{1-6}$ alkoxy-carbonyl group, an amino group, a mono($C_{1-6}$ alkyl)amino group, a di($C_{1-6}$ alkyl)amino group, an optionally substituted $C_{3-14}$ hydrocarbon ring group and an optionally substituted heterocyclic group;

or a prodrug thereof or a pharmaceutically acceptable salt thereof;

[13] The compound of [12] above, wherein m and n are 0, and X is a single bond; or a prodrug thereof or a pharmaceutically acceptable salt thereof;

[14] The compound of [13] above, wherein t and u are 0; or a prodrug thereof or a pharmaceutically acceptable salt thereof;

[15] The compound of [14] above, wherein R$^4$ is selected from —CO$_2$R$^9$ and —C(O)NHOR$_9$; or a prodrug thereof or a pharmaceutically acceptable salt thereof;

[16] The compound of [15] above, wherein R$^9$ is a hydrogen atom; or a prodrug thereof or a pharmaceutically acceptable salt thereof;

[17] The compound of [16] above, wherein R$^2$ is —(CH$_2$)$_p$—X$_1$—(CH$_2$)$_q$-A$^2$; or a prodrug thereof or a pharmaceutically acceptable salt thereof;

[18] The compound of [11] above, which is selected from the group consisting of (1S,2R)-1-(4'-chloro-biphenyl-4-sulfonylamino)-2-phenyl-cyclopropanecarboxylic acid, (1R*,2S*)-1-[4-(2,4-dichloro-benzyloxy)-benzenesulfonylamino]-2-phenyl-cyclopropanecarboxylic acid hydroxyamide, (1R*,2S*)-1-(4'-chloro-biphenyl-4-sulfonylamino)-2-{3-[(pyridin-3-ylmethyl)-amino]-phenyl}-cyclopropanecarboxylic acid, (1R*,2S*)-1-[5-(4-chloro-phenyl)-thiophene-2-sulfonylamino]-2-(2-methoxy-phenyl)-cyclopropanecarboxylic acid, (1S,2R)-1-(4'-chloro-biphenyl-4-sulfonylamino)-2-phenyl-cyclopropanecarboxylic acid, (1R,2R)-1-(4'-chloro-biphenyl-4-sulfonylamino)-2-phenyl-cyclopropanecarboxylic acid, (1R,2S)-1-(4'-chloro-biphenyl-4-sulfonylamino)-2-phenyl-cyclopropanecarboxylic acid, (1R,2R)-2-benzyl-1-(4'-chloro-biphenyl-4-sulfonylamino)-cyclopropanecarboxylic acid, (1S,2S)-2-benzyl-1-(4'-chloro-biphenyl-4-sulfonylamino)-cyclopropanecarboxylic acid, (1R*,2S*)-1-(4'-chloro-biphenyl-4-sulfonylamino)-2-(3-phenoxy-phenyl)-cyclopropanecarboxylic acid,
(1R*,2S*)-1-(4'-chloro-biphenyl-4-sulfonylamino)-2-[3-(4-chloro-phenoxy)-phenyl]-cyclopropanecarboxylic acid,
(1R*,2S*)-1-(4'-chloro-biphenyl-4-sulfonylamino)-2-(3-methoxy-phenyl)-cyclopropanecarboxylic acid,
(1R*,2S*)-1-(4'-chloro-biphenyl-4-sulfonylamino)-2-(2-methoxy-phenyl)-cyclopropanecarboxylic acid,
(1R*,2S*)-1-(4'-chloro-biphenyl-4-sulfonylamino)-2-(2-phenoxy-phenyl)-cyclopropanecarboxylic acid,
(1R*,2S*)-1-(4'-chloro-biphenyl-4-sulfonylamino)-2-(4-methoxy-phenyl)-cyclopropanecarboxylic acid,
(1R*,2S*)-1-(4'-chloro-biphenyl-4-sulfonylamino)-2-(4-phenoxy-phenyl)-cyclopropanecarboxylic acid,
(1R*,2S*)-1-(4'-chloro-biphenyl-4-sulfonylamino)-2-(3-nitro-phenyl)-cyclopropanecarboxylic acid,
(1R*,2S*)-2-(3-amino-phenyl)-1-(4'-chloro-biphenyl-4-sulfonylamino)-cyclopropanecarboxylic acid,
(1R*,2S*)-1-(4'-chloro-biphenyl-4-sulfonylamino)-2-piperidine-4-yl-cyclopropanecarboxylic acid,
(1R*,2S*)-1-(4'-chloro-biphenyl-4-sulfonylamino)-2-(3-isobutoxy-phenyl)-cyclopropanecarboxylic acid,
(1R*,2S*)-1-(4'-chloro-biphenyl-4-sulfonylamino)-2-(3-dimethylamino-phenyl)-cyclopropanecarboxylic acid,
(1R*,2S*)-1-(4'-chloro-biphenyl-4-sulfonylamino)-2-(3-trifluoromethyl-phenyl)-cyclopropanecarboxylic acid,
(1R*,2S*)-2-(3-bromo-phenyl)-1-(4'-chloro-biphenyl-4-sulfonylamino)-cyclopropanecarboxylic acid,
(1R*,2S*)-1-(4'-chloro-biphenyl-4-sulfonylamino)-2-phenyl-cyclopropanecarboxylic acid,
(1R*,2S*)-1-(4'-chloro-biphenyl-4-sulfonylamino)-2-(3,5-diphenoxy-phenyl)-cyclopropanecarboxylic acid,
(1R*,2S*)-2-biphenyl-3-yl-1-(4'-chloro-biphenyl-4-sulfonylamino)-cyclopropanecarboxylic acid,
(1R*,2S*)-2-(3-benzyloxycarbonylamino-phenyl)-1-(4'-chloro-biphenyl-4-sulfonylamino)-cyclopropanecarboxylic acid,
(1R*,2S*)-1-(4'-chloro-biphenyl-4-sulfonylamino)-2-(3-isobutoxycarbonylamino-phenyl)-cyclopropanecarboxylic acid,
(1R*,2S*)-1-(biphenyl-4-sulfonylamino)-2-phenyl-cyclopropanecarboxylic acid,
(1R*,2S*)-1-(4-phenoxy-benzenesulfonylamino)-2-phenyl-cyclopropanecarboxylic acid,
(1R*,2S*)-1-(4'-bromo-biphenyl-4-sulfonylamino)-2-phenyl-cyclopropanecarboxylic acid,
(1S,2R)-2-phenyl-1-[5-(5-trifluoromethyl-[1,2,4]oxadiazol-3-yl)-thiophene-2-sulfonylamino]-cyclopropanecarboxylic acid,
(1R*,2S*)-1-[4-(2-methyl-2H-tetrazol-5-yl)-benzenesulfonylamino]-2-phenyl-cyclopropanecarboxylic acid,
(1R*,2S*)-1-[4-(2-ethyl-2H-tetrazol-5-yl)-benzenesulfonylamino]-2-phenyl-cyclopropanecarboxylic acid,
(1R*,2S*)-2-phenyl-1-[4-(2-propyl-2H-tetrazol-5-yl)-benzenesulfonylamino]-cyclopropanecarboxylic acid,
(1R*,2S*)-1-[4-(2-isopropyl-2H-tetrazol-5-yl)-benzenesulfonylamino]-2-phenyl-cyclopropanecarboxylic acid,
(1R*,2S*)-1-(dibenzofurane-2-sulfonylamino)-2-phenyl-cyclopropanecarboxylic acid,
(1R*,2S*)-1-(4'-chloro-biphenyl-4-sulfonylamino)-2-(3-methanesulfonylamino-phenyl)-cyclopropanecarboxylic acid,
(1S,2R)-1-[5-(5-pentafluoroethyl-[1,2,4]oxadiazol-3-yl)-thiophene-2-sulfonylamino]-2-phenyl-cyclopropanecarboxylic acid,
(1R*,2S*)-2-(3-acetylamino-phenyl)-1-(4'-chloro-biphenyl-4-sulfonylamino)-cyclopropanecarboxylic acid,
(1R*,2S*)-1-(4'-chloro-biphenyl-4-sulfonylamino)-2-(3-methoxycarbonylamino-phenyl)-cyclopropanecarboxylic acid,
(1R*,2S*)-4-{3-[2-carboxy-2-(4'-chloro-biphenyl-4-sulfonylamino)-cyclopropyl]-phenylamino}-piperidine-1-carboxylic acid tert-butyl ester,
(1R*,2S*)-2-(3-benzylamino-phenyl)-1-(4'-chloro-biphenyl-4-sulfonylamino)-cyclopropanecarboxylic acid,
(1R*,2S*)-1-(4'-chloro-biphenyl-4-sulfonylamino)-2-(3-hydroxy-phenyl)-cyclopropanecarboxylic acid,
(1R*,2S*)-1-(4'-chloro-biphenyl-4-sulfonylamino)-2-cyclohexyl-cyclopropanecarboxylic acid,
(1R*,2S*)-2-phenyl-1-(4-thiophen-2-yl-benzenesulfonylamino)-cyclopropanecarboxylic acid,
(1R*,2S*)-2-phenyl-1-(4-thiophen-3-yl-benzenesulfonylamino)-cyclopropanecarboxylic acid,
(1R*,2S*)-1-[4-(4-methyl-thiophen-2-yl)-benzenesulfonylamino]-2-phenyl-cyclopropanecarboxylic acid,
5-[4-((1R*,2S*)-1-Carboxy-2-phenyl-cyclopropylsulfamoyl)-phenyl]-thiophene-2-carboxylic acid,
(1R*,2S*)-1-(9-oxo-9H-fluorene-2-sulfonylamino)-2-phenyl-cyclopropanecarboxylic acid,
(1R*,2S*)-4-[2-carboxy-2-(4'-chloro-biphenyl-4-sulfonylamino)-cyclopropyl]-piperidine-1-carboxylic acid tert-butyl ester,
(1R*,2S*)-2-(3-benzenesulfonylamino-phenyl)-1-(4'-chloro-biphenyl-4-sulfonylamino)-cyclopropanecarboxylic acid,
(1R*,2S*)-1-(4'-methoxy-biphenyl-4-sulfonylamino)-2-phenyl-cyclopropanecarboxylic acid,
(1R*,2S*)-1-(9H-fluorene-2-sulfonylamino)-2-phenyl-cyclopropanecarboxylic acid,
(1R*,2S*)-1-[4-(5-methyl-[1,2,4]oxadiazol-3-yl)-benzenesulfonylamino]-2-phenyl-cyclopropanecarboxylic acid,
(1R*,2S*)-2-phenyl-1-[4-(5-phenyl-[1,2,4]oxadiazol-3-yl)-benzenesulfonylamino]-cyclopropanecarboxylic acid,
(1R*,2S*)-2-phenyl-1-(5-phenyl-thiophene-2-sulfonylamino)-cyclopropanecarboxylic acid,
(1R*,2S*)-1-(4'-chloro-biphenyl-4-sulfonylamino)-2-(2-hydroxy-phenyl)-cyclopropanecarboxylic acid,
(1R*,2S*)-2-phenyl-1-[4-(5-phenyl-[1,3,4]oxadiazol-2-yl)-benzenesulfonylamino]-cyclopropanecarboxylic acid,
(1R*,2S*)-1-(5-bromo-thiophene-2-sulfonylamino)-2-phenyl-cyclopropanecarboxylic acid,
(1R*,2S*)-1-(4'-chloro-biphenyl-4-sulfonylamino)-2-[3-(pyridin-2-ylamino)-phenyl]-cyclopropanecarboxylic acid,
(1R*,2S*)-1-(4'-chloro-biphenyl-4-sulfonylamino)-2-{3-[(pyridin-2-carbonyl)-amino]-phenyl}-cyclopropanecarboxylic acid,
(1R*,2S*)-1-(4'-chloro-biphenyl-4-sulfonylamino)-2-{3-[(pyridin-4-carbonyl)-amino]-phenyl}-cyclopropanecarboxylic acid,
(1R*,2S*)-1-(4'-chloro-biphenyl-4-sulfonylamino)-2-{3-[(pyridin-3-carbonyl)-amino]-phenyl}-cyclopropanecarboxylic acid,
(1R*,2S*)-1-[4-(2,4-dichloro-benzyloxy)-benzenesulfonylamino]-2-phenyl-cyclopropanecarboxylic acid,
(1R*,2S*)-1-(4'-chloro-biphenyl-4-sulfonylamino)-2-[3-(2-hydroxy-ethoxy)-phenyl]-cyclopropanecarboxylic acid,
(1R*,2S*)-1-(4'-chloro-biphenyl-4-sulfonylamino)-2-[3-(2-dimethylamino-acetylamino)-phenyl]-cyclopropanecarboxylic acid,
(1R*,2S*)-1-(4'-chloro-biphenyl-4-sulfonylamino)-2-[3-(pyridin-3-yloxy)-phenyl]-cyclopropanecarboxylic acid,
(1R*,2S*)-1-[5-(4-chloro-phenyl)-thiophene-2-sulfonylamino]-2-phenyl-cyclopropanecarboxylic acid, (1R*,2S*)-1-[5-(4-methoxy-phenyl)-thiophene-2-sulfonylamino]-2-phenyl-cyclopropanecarboxylic acid,
(1R*,2S*)-1-[5-(4-dimethylamino-phenyl)-thiophene-2-sulfonylamino]-2-phenyl-cyclopropanecarboxylic acid,
(1R*,2S*)-1-(7-bromo-9H-fluorene-2-sulfonylamino)-2-phenyl-cyclopropanecarboxylic acid,
(1R*,2S*)-1-(4'-chloro-biphenyl-4-sulfonylamino)-2-[3-(2-pyrrolidin-1-yl-ethoxy)-phenyl]-cyclopropanecarboxylic acid,
(1R*,2S*)-1-(4'-chloro-biphenyl-4-sulfonylamino)-2-[3-(2-morpholin-4-yl-ethoxy)-phenyl]-cyclopropanecarboxylic acid,
(1R*,2S*)-1-(4'-chloro-biphenyl-4-sulfonylamino)-2-[3-(2-pyrazol-1-yl-ethoxy)-phenyl]-cyclopropanecarboxylic acid,
(1R*,2S*)-1-(4'-chloro-biphenyl-4-sulfonylamino)-2-[3-(pyridin-3-ylmethoxy)-phenyl]-cyclopropanecarboxylic acid,
(1R*,2S*)-1-(4'-chloro-biphenyl-4-sulfonylamino)-2-(2-methyl-1,2,3,4-tetrahydro-isoquinolin-7-yl)-cyclopropanecarboxylic acid,
(1R*,2S*)-1-(4'-chloro-biphenyl-4-sulfonylamino)-2-(2-isopropyl-1,2,3,4-tetrahydro-isoquinolin-7-yl)-cyclopropanecarboxylic acid,
(1R*,2S*)-2-(2-benzyl-1,2,3,4-tetrahydro-isoquinolin-7-yl)-1-(4'-chloro-biphenyl-4-sulfonylamino)-cyclopropanecarboxylic acid,
(1R*,2S*)-1-(7-fluoro-9H-fluorene-2-sulfonylamino)-2-phenyl-cyclopropanecarboxylic acid,
(1S*,2S*)-1-(7-fluoro-9H-fluorene-2-sulfonylamino)-2-phenyl-cyclopropanecarboxylic acid,
(1R*,2S*)-1-[4-(2-ethyl-thiazol-4-yl)-benzenesulfonylamino]-2-phenyl-cyclopropanecarboxylic acid,
(1R*,2S*)-1-(4'-chloro-biphenyl-4-sulfonylamino)-2-[3-(2-imidazol-1-yl-ethoxy)-phenyl]-cyclopropanecarboxylic acid,
(1R*,2S*)-2-(2-benzyloxy-phenyl)-1-[5-(4-chloro-phenyl)-thiophene-2-sulfonylamino]-cyclopropanecarboxylic acid,
(1S,2R)-1-[5-(4-chloro-phenyl)-thiophene-2-sulfonylamino]-2-phenyl-cyclopropanecarboxylic acid,
(1R*,2S*)-1-[5-(4-chloro-phenyl)-thiophene-2-sulfonylamino]-2-[3-(2-hydroxy-ethoxy)-phenyl]-cyclopropanecarboxylic acid,
(1R*,2S*)-2-(2-benzyloxy-phenyl)-1-[5-(4-chloro-phenylethynyl)-thiophene-2-sulfonylamino]-cyclopropanecarboxylic acid,
(1R*,2S*)-1-[5-(4-chloro-phenyl)-thiophene-2-sulfonylamino]-2-[3-(pyridin-3-yloxy)-phenyl]-cyclopropanecarboxylic acid,
(1S,2R)-2-phenyl-1-(1-phenyl-1H-pyrazole-4-sulfonylamino)-cyclopropanecarboxylic acid,
(1R*,2S*)-1-(4'-chloro-biphenyl-4-sulfonylamino)-2-{3-[(3H-imidazol-4-ylmethyl)-amino]-phenyl}-cyclopropanecarboxylic acid,
(1S,2R)-1-(7-bromo-9H-fluorene-2-sulfonylamino)-2-phenyl-cyclopropanecarboxylic acid,
(1R*,2S*)-1-[4-(2-methyl-thiazol-4-yl)-benzenesulfonylamino]-2-phenyl-cyclopropanecarboxylic acid,
(1R*,2S*)-1-[4-(1-hydroxy-ethyl)-benzenesulfonylamino]-2-phenyl-cyclopropanecarboxylic acid,
(1R*,2S*)-1-(7-chloro-9H-fluorene-2-sulfonylamino)-2-phenyl-cyclopropanecarboxylic acid,
(1R*,2S*)-1-[3-(6-chloro-pyridazin-3-yl)-benzenesulfonylamino]-2-phenyl-cyclopropanecarboxylic acid,
(1S*,2S*)-1-(7-chloro-9H-fluorene-2-sulfonylamino)-2-phenyl-cyclopropanecarboxylic acid,
(1S,2R)-1-[1-(4-chloro-phenyl)-1H-pyrazole-4-sulfonylamino]-2-phenyl-cyclopropanecarboxylic acid,
(1R*,2S*)-1-[5-(4-chloro-phenyl)-thiophene-2-sulfonylamino]-2-(3-dimethylaminomethyl-phenyl)-cyclopropanecarboxylic acid,
(1R*,2S*)-1-(4'-chloro-biphenyl-4-sulfonylamino)-2-[3-(1-methyl-piperidine-4-ylamino)-phenyl]-cyclopropanecarboxylic acid,
(1S,2R)-1-[2-(4-chloro-phenyl)-thiazole-5-sulfonylamino]-2-phenyl-cyclopropanecarboxylic acid,
(1R*,2S*)-1-(4'-chloro-biphenyl-4-sulfonylamino)-2-{3-[(1-methyl-1H-imidazol-2-ylmethyl)-amino]-phenyl}-cyclopropanecarboxylic acid,
(1R*,2S*)-1-[5-(4-chloro-phenyl)-thiophene-2-sulfonylamino]-2-(2-hydroxy-phenyl)-cyclopropanecarboxylic acid,
(1R*,2S*)-1-[5-(4-chloro-phenyl)-thiophene-2-sulfonylamino]-2-[3-(4-methyl-piperazin-1-ylmethyl)-phenyl]-cyclopropanecarboxylic acid,
(1R*,2S*)-1-[5-(4-chloro-phenyl)-thiophene-2-sulfonylamino]-2-(3-{[methyl-(1-methyl-piperidine-4-yl)-amino]-methyl}-phenyl)-cyclopropanecarboxylic acid,
(1R*,2S*)-1-(4'-chloro-biphenyl-4-sulfonylamino)-2-[3-(2-hydroxy-acetylamino)-phenyl]-cyclopropanecarboxylic acid,
(1S,2R)-1-[5-(4-chloro-phenyl)-4-methyl-thiophene-2-sulfonylamino]-2-phenyl-cyclopropanecarboxylic acid,
(1R*,2S*)-1-[5-(4-chloro-phenyl)-thiophene-2-sulfonylamino]-2-[3-(pyridin-3-ylmethoxy)-phenyl]-cyclopropanecarboxylic acid,
(1R*,2S*)-1-[5-(4-chloro-phenyl)-thiophene-2-sulfonylamino]-2-[3-(pyridin-2-ylmethoxy)-phenyl]-cyclopropanecarboxylic acid,
(1R,2S)-1-(7-bromo-9H-fluorene-2-sulfonylamino)-2-phenyl-cyclopropanecarboxylic acid,
(1S,2R)-1-[5-(3-chloro-phenyl)-thiophene-2-sulfonylamino]-2-phenyl-cyclopropanecarboxylic acid,
(1R*,2S*)-1-(4'-chloro-biphenyl-4-sulfonylamino)-2-[3-(pyridine-3-sulfonylamino)-phenyl]-cyclopropanecarboxylic acid,
(1R*,2S*)-1-(4'-chloro-biphenyl-4-sulfonylamino)-2-{3-[(1H-imidazol-2-ylmethyl)-amino]-phenyl}-cyclopropanecarboxylic acid,
(1R*,2S*)-3-{2-carboxy-2-[5-(4-chloro-phenyl)-thiophene-2-sulfonylamino]-cyclopropyl}-benzoic acid,
(1R*,2S*)-1-(4'-chloro-biphenyl-4-sulfonylamino)-2-(3-dimethylcarbamoylmethoxy-phenyl)-cyclopropanecarboxylic acid,
(1R*,2S*)-1-[5-(4-chloro-phenyl)-thiophene-2-sulfonylamino]-2-(3-methoxy-phenyl)-cyclopropanecarboxylic acid,
(1R*,2S*)-1-[5-(4-chloro-phenyl)-thiophene-2-sulfonylamino]-2-(3-hydroxy-phenyl)-cyclopropanecarboxylic acid,
(1R*,2S*)-2-(3-carbamoylmethoxy-phenyl)-1-(4'-chloro-biphenyl-4-sulfonylamino)-cyclopropanecarboxylic acid,
(1R*,2S*)-1-(4'-chloro-biphenyl-4-sulfonylamino)-2-(3-methylcarbamoylmethoxy-phenyl)-cyclopropanecarboxylic acid,
(1R*,2S*)-2-(3-carboxymethoxy-phenyl)-1-(4'-chloro-biphenyl-4-sulfonylamino)-cyclopropanecarboxylic acid,
(1R*,2S*)-1-(5-isooxazol-3-yl-thiophene-2-sulfonylamino)-2-phenyl-cyclopropanecarboxylic acid,
(1R*,2S*)-2-phenyl-1-[5-(5-trifluoromethyl-isooxazol-3-yl)-thiophene-2-sulfonylamino]-cyclopropanecarboxylic acid, (1S*,2R*)-1-(7-chloro-dibenzofurane-3-sulfonylamino)-2-phenyl-cyclopropanecarboxylic acid,
(1S*,2S*)-1-(7-chloro-dibenzofurane-3-sulfonylamino)-2-phenyl-cyclopropanecarboxylic acid,
(1S,2R)-1-[5-(2-chloro-phenyl)-thiophene-2-sulfonylamino]-2-phenyl-cyclopropanecarboxylic acid,
(1S,2R)-1-[5-(2,4-dichloro-phenyl)-thiophene-2-sulfonylamino]-2-phenyl-cyclopropanecarboxylic acid,
(1S,2R)-1-(2-benzofuran-2-yl-ethansulfonylamino)-2-phenyl-cyclopropanecarboxylic acid,
(1R*,2S*)-1-[5-(4-chloro-phenyl)-thiophene-2-sulfonylamino]-2-(3-nitro-phenyl)-cyclopropanecarboxylic acid,
(1R*,2S*)-2-(3-amino-phenyl)-1-[5-(4-chloro-phenyl)-thiophene-2-sulfonylamino]-cyclopropanecarboxylic acid,
(1R*,2S*)-1-[5-(4-chloro-phenyl)-thiophene-2-sulfonylamino]-2-{3-[(pyridin-3-ylmethyl)-amino]-phenyl}-cyclopropanecarboxylic acid,
(1R*,2S*)-1-[5-(4-chloro-phenyl)-thiophene-2-sulfonylamino]-2-(3-methanesulfonylamino-phenyl)-cyclopropanecarboxylic acid,
(1S,2R)-1-[5-(5-chloro-pyridin-2-yl)-thiophene-2-sulfonylamino]-2-phenyl-cyclopropanecarboxylic acid,
(1R*,2S*)-1-[5-(4-chloro-phenyl)-thiophene-2-sulfonylamino]-2-(3-trifluoromethanesulfonylamino-phenyl)-cyclopropanecarboxylic acid,
(1R*,2S*)-1-[5-(4-chloro-phenyl)-thiophene-2-sulfonylamino]-2-(3-dimethylamino-phenyl)-cyclopropanecarboxylic acid,
(1R*,2S*)-1-[5-(4-chloro-phenyl)-thiophene-2-sulfonylamino]-2-(3-hydroxymethyl-phenyl)-cyclopropanecarboxylic acid,
(1R*,2S*)-1-[5-(4-chloro-phenyl)-thiophene-2-sulfonylamino]-2-(3-ureido-phenyl)-cyclopropanecarboxylic acid,
(1R*,2S*)-1-[5-(4-chloro-phenyl)-thiophene-2-sulfonylamino]-2-[3-(pyridine-3-sulfonylamino)-phenyl]-cyclopropanecarboxylic acid,
(1R*,2S*)-2-(3-carbamoyl-phenyl)-1-[5-(4-chloro-phenyl)-thiophene-2-sulfonylamino]-cyclopropanecarboxylic acid,
(1R*,2S*)-1-[5-(4-chloro-phenyl)-thiophene-2-sulfonylamino]-2-[2-(2-hydroxy-ethoxy)-phenyl]-cyclopropanecarboxylic acid,
(1R*,2S*)-2-(2-carboxymethoxy-phenyl)-1-[5-(4-chloro-phenyl)-thiophene-2-sulfonylamino]-cyclopropanecarboxylic acid,
(1R*,2S*)-1-(3-phenoxy-benzenesulfonylamino)-2-phenyl-cyclopropanecarboxylic acid,
(1R*,2S*)-1-[3-(4-fluoro-phenoxy)-benzenesulfonylamino]-2-phenyl-cyclopropanecarboxylic acid,
(1R*,2S*)-1-[3-(4-chloro-phenoxy)-benzenesulfonylamino]-2-phenyl-cyclopropanecarboxylic acid,
(1R*,2S*)-1-[3-(3,4-dichloro-phenoxy)-benzenesulfonylamino]-2-phenyl-cyclopropanecarboxylic acid,
(1R*,2S*)-1-[4-(4-chloro-phenyl)-piperazin-1-sulfonylamino]-2-phenyl-cyclopropanecarboxylic acid,
(1R*,2S*)-2-[2-(benzylcarbamoyl-methoxy)-phenyl]-1-[5-(4-chloro-phenyl)-thiophene-2-sulfonylamino]-cyclopropanecarboxylic acid,
(1R*,2S*)-1-[5-(4-chloro-phenyl)-thiophene-2-sulfonylamino]-2-[2-(2-morpholin-4-yl-2-oxo-ethoxy)-phenyl]-cyclopropanecarboxylic acid,
(1R*,2S*)-1-[5-(4-chloro-phenyl)-thiophene-2-sulfonylamino]-2-[2-(isopropylcarbamoyl-methoxy)-phenyl]-cyclopropanecarboxylic acid,
(1R*,2S*)-1-[5-(4-chloro-phenyl)-thiophene-2-sulfonylamino]-2-[3-(pyridin-3-ylaminomethyl)-phenyl]-cyclopropanecarboxylic acid,
and
(1R*,2S*)-1-[5-(4-chloro-phenyl)-thiophene-2-sulfonylamino]-2-methyl-2-phenyl-cyclopropanecarboxylic acid;
or a prodrug thereof or a pharmaceutically acceptable salt thereof;

[19] A pharmaceutical composition comprising a compound of any of [1] to [18] above, a prodrug thereof or a pharmaceutically acceptable salt thereof, and a pharmaceutically acceptable carrier;
[20] An aggrecanase inhibitor comprising a compound of any of [1] to [18] above, or a prodrug thereof or a pharmaceutically acceptable salt thereof as an active ingredient;
[21] An MMP inhibitor comprising a compound of any of [1] to [18] above, or a prodrug thereof or a pharmaceutically acceptable salt thereof as an active ingredient;
[22] The MMP inhibitor of [21] above, which is an MMP-13 inhibitor;
[23] A prophylactic or therapeutic agent for osteoarthritis comprising a compound of any of [1] to [18] above, a prodrug thereof or a pharmaceutically acceptable salt thereof as an active ingredient;
[24] A prophylactic or therapeutic agent for rheumatoid arthritis comprising a compound of any of [1] to [18] above, a prodrug thereof or a pharmaceutically acceptable salt thereof as an active ingredient;
[25] A method for preventing or treating osteoarthritis, which comprises administering a compound of any of [1] to [18] above, a prodrug thereof or a pharmaceutically acceptable salt thereof to a mammal;
[26] A method for preventing or treating rheumatoid arthritis, which comprises administering a compound of any of [1] to [18] above, a prodrug thereof or a pharmaceutically acceptable salt thereof to a mammal;
[27] The agent of [23] above, which is used in combination with a different therapeutic agent for osteoarthritis;
[28] The agent of [23] above, which is used in combination with a different therapeutic agent for rheumatoid arthritis;
[29] The agent of [24] above, which is used in combination with a different therapeutic agent for osteoarthritis;
[30] The agent of [24] above, which is used in combination with a different therapeutic agent for rheumatoid arthritis;
[31] The method of [25] above, which is used in combination with a different therapeutic agent for osteoarthritis;
[32] The method of [25] above, which is used in combination with a different therapeutic agent for rheumatoid arthritis;
[33] The method of [26] above, which is used in combination with a different therapeutic agent for osteoarthritis;
[34] The method of [26] above, which is used in combination with a different therapeutic agent for rheumatoid arthritis.

DETAILED DESCRIPTION OF THE INVENTION

The definitions of respective substituents and moieties used in the present specification are as follows.
In the present specification, "$C_{1-6}$" means that the number of carbon atoms ranges from 1 to 6.
The "single bond" means a direct connection. In —$(CH_2)_m$—X—$(CH_2)_n$-$A^1$, for example, when X is a "single bond", it is —$(CH_2)_m$—$(CH_2)_n$-$A^1$.

The "halogen atom" is a fluorine atom, a chlorine atom, a bromine atom or an iodine atom, preferably a fluorine atom, a chlorine atom or a bromine atom.

The "$C_{1-10}$ alkyl group" is a straight chain or branched chain alkyl group having 1 to 10 carbon atoms, and is exemplified by methyl, ethyl, propyl, isopropyl, butyl, isobutyl, sec-butyl, tert-butyl, pentyl, isopentyl, neo-pentyl, tert-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. In some embodiments of the present invention, it is a straight chain or branched chain alkyl group having 1 to 6 carbon atoms.

The "$C_{1-6}$ alkyl group" is a straight chain or branched chain alkyl group having 1 to 6 carbon atoms, and is exemplified by methyl, ethyl, propyl, isopropyl, butyl, isobutyl, sec-butyl, tert-butyl, pentyl, isopentyl, tert-pentyl, hexyl and the like. In some embodiments of the present invention, it is a straight chain or branched chain alkyl group having 1 to 4 carbon atoms.

The "$C_{2-6}$ alkenyl group" is a straight chain or branched chain alkenyl group having 2 to 6 carbon atoms, and is exemplified by ethenyl (vinyl), 1-propenyl, 2-propenyl (allyl), isopropenyl, 1-butenyl, 2-butenyl, 3-butenyl, 1-methyl-1-propenyl, 1-methyl-2-propenyl, 2-methyl-2-propenyl, 1-ethylvinyl, 1-pentenyl, 2-pentenyl, 3-pentenyl, 4-pentenyl, 1,2-dimethyl-1-propenyl, 1,2-dimethyl-2-propenyl, 1-ethyl-1-propenyl, 1-ethyl-2-propenyl, 1-methyl-1-butenyl, 1-methyl-2-butenyl, 2-methyl-1-butenyl, 1-isopropylvinyl, 2,4-pentadienyl, 1-hexenyl, 2-hexenyl, 3-hexenyl, 4-hexenyl, 5-hexenyl, 2,4-hexadienyl, 1-methyl-1-pentenyl and the like. In some embodiments of the present invention, it is a straight chain or branched chain alkenyl group having 2 to 4 carbon atoms.

The "$C_{2-6}$ alkynyl group" is a straight chain or branched chain alkynyl group having 2 to 6 carbon atoms, and is exemplified by ethynyl, propynyl, butynyl, 2-pentynyl, 3-pentynyl, 2-hexynyl, 3-hexynyl and the like.

The "$C_{1-6}$ alkoxy group" is an alkyloxy group wherein the alkyl moiety thereof is the above-defined $C_{1-6}$ alkyl group. Examples thereof include methoxy, ethoxy, propoxy, isopropyloxy, butoxy, isobutyloxy, tert-butyloxy, pentyloxy, hexyloxy and the like. In some embodiments of the present invention, it is an alkoxy group wherein the alkyl moiety thereof is a straight chain or branched chain alkyl group having 1 to 4 carbon atoms.

The "halogenated $C_{1-6}$ alkyl group" is the above-defined $C_{1-6}$ alkyl group except that it is substituted by the above-defined halogen atom. Examples thereof include fluoromethyl, difluoromethyl, trifluoromethyl, bromomethyl, chloromethyl, 1,2-dichloromethyl, 2,2-dichloromethyl, 2,2,2-trifluoroethyl and the like. In some embodiments of the present invention, it is a halogenated alkyl group wherein the alkyl moiety thereof is a straight chain or branched chain alkyl group having 1 to 4 carbon atoms.

The "halogenated $C_{1-6}$ alkoxy group" is the above-defined $C_{1-6}$ alkoxy group except that it is substituted by the above-defined halogen atom. Examples thereof include fluoromethoxy, difluoromethoxy, trifluoromethoxy, bromomethoxy, chloromethoxy, 1,2-dichloromethoxy, 2,2-dichloromethoxy, 2,2,2-trifluoroethoxy and the like. In some embodiments of the present invention, it is a halogenated alkoxy group wherein the alkoxy moiety thereof is a straight chain or branched chain alkoxy group having 1 to 4 carbon atoms.

The "mono ($C_{1-6}$ alkyl)amino group" is a mono-alkylamino group wherein the alkyl moiety thereof is the above-defined $C_{1-6}$ alkyl group. Examples thereof include methylamino, ethylamino, propylamino, isopropylamino, butylamino, isobutylamino, tert-butylamino, pentylamino, hexylamino and the like. In some embodiments of the present invention, it is a mono-alkylamino group wherein the alkyl moiety thereof is a straight chain or branched chain alkyl group having 1 to 4 carbon atoms.

The "di($C_{1-6}$ alkyl)amino group" is a di-alkylamino group wherein the alkyl moiety thereof is the above-defined $C_{1-6}$ alkyl group. Examples thereof include dimethylamino, diethylamino, dipropylamino and the like. In some embodiments of the present invention, it is a di-alkylamino group wherein the alkyl moiety thereof is a straight chain or branched chain alkyl group having 1 to 4 carbon atoms.

The "$C_{1-6}$ alkoxy-carbonyl group" is an alkyloxycarbonyl group wherein the alkoxy moiety thereof is the above-defined $C_{1-6}$ alkoxy group. Examples thereof include methoxycarbonyl, ethoxycarbonyl, propoxycarbonyl, isopropyloxycarbonyl, butoxycarbonyl, isobutyloxycarbonyl, tert-butyloxycarbonyl, pentyloxycarbonyl, hexyloxycarbonyl and the like. In some embodiments of the present invention, it is an alkoxycarbonyl group wherein the alkyl moiety thereof is a straight chain or branched chain alkyl group having 1 to 4 carbon atoms.

The "$C_{1-6}$ alkoxy-$C_{1-6}$ alkyl group" is an alkoxy-alkyl group wherein the alkoxy moiety thereof is the above-defined $C_{1-6}$ alkoxy group and the alkyl moiety thereof is the above-defined $C_{1-6}$ alkyl group. Examples thereof include methoxymethyl, ethoxymethyl, propoxymethyl, butoxymethyl, pentyloxymethyl, hexyloxymethyl, methoxyethyl, ethoxyethyl, propoxyethyl, butoxyethyl, pentyloxyethyl, hexyloxyethyl and the like. In some embodiments of the present invention, it is a $C_{1-4}$ alkoxy-$C_{1-4}$ alkyl group wherein the alkoxy moiety thereof is a straight chain or branched chain alkoxy group having 1 to 4 carbon atoms and the alkyl moiety thereof is a straight chain or branched chain alkyl group having 1 to 4 carbon atoms.

The "$C_{1-6}$ alkyl-aminocarbonyl group" is a mono-alkylamino-carbonyl group wherein the alkyl moiety thereof is the above-defined $C_{1-6}$ alkyl group. Examples thereof include methylaminocarbonyl, ethylaminocarbonyl, propylaminocarbonyl, isopropylaminocarbonyl, butylaminocarbonyl, isobutylaminocarbonyl, tert-butylaminocarbonyl, pentylaminocarbonyl, hexylaminocarbonyl and the like. In some embodiments of the present invention, it is a $C_{1-4}$ alkyl-aminocarbonyl group wherein the alkyl moiety thereof is a straight chain or branched chain alkyl group having 1 to 4 carbon atoms.

The "$C_{1-6}$ alkyl-carbonylamino group" is a mono-alkylcarbonyl-amino group wherein the alkyl moiety thereof is the above-defined $C_{1-6}$ alkyl group. Examples thereof include methylcarbonylamino, ethylcarbonylamino, propylcarbonylamino, isopropylcarbonylamino, butylcarbonylamino, isobutylcarbonylamino, tert-butylcarbonylamino, pentylcarbonylamino, hexylcarbonylamino and the like. In some embodiments of the present invention, it is a mono-alkylcarbonyl-amino group wherein the alkyl moiety thereof is a straight chain or branched chain alkyl group having 1 to 4 carbon atoms.

The "$C_{1-6}$ alkylsulfonyl group" is an alkylsulfonyl group wherein the alkyl moiety thereof is the above-defined $C_{1-6}$ alkyl group. Examples thereof include methanesulfonyl, ethanesulfonyl, propanesulfonyl, butanesulfonyl, penanesulfonyl, hexanesulfonyl and the like. In some embodiments of the present invention, it is an alkylsulfonyl group wherein the alkyl moiety thereof is a straight chain or branched chain alkyl group having 1 to 4 carbon atoms. The "$C_{1-6}$ alkylsulfonylamino group" is an alkylsulfonyl-amino group wherein the alkyl moiety thereof is the above-defined $C_{1-6}$ alkyl group. Examples thereof include methanesulfonylamino, ethanesulfonylamino, propanesulfonylamino, butanesulfonylamino, pentanesulfonylamino, hexanesulfonylamino and the like. In some embodiments of the present invention, it is an alkylsulfonylamino group wherein the alkyl moiety thereof is a straight chain or branched chain alkyl group having 1 to 4 carbon atoms.

The "$C_{1-6}$ alkylene group" is a straight chain or branched chain alkylene group having 1 to 6 carbon atoms, and is exemplified by methylene, ethylene, trimethylene, tetramethylene, pentamethylene, hexamethylene and the like.

The "$C_{2-6}$ alkenylene group" is a straight chain or branched chain alkenylene group having 2 to 6 carbon atoms, and is exemplified by vinylene, propenylene, 1-butenylene, 1,3-butadienylene and the like.

The "$C_{2-6}$ alkynylene group" is a straight chain or branched chain alkynylene group having 2 to 6 carbon atoms, such as a straight chain or branched chain alkynylene group having 2 to 4 carbon atoms, for example ethynylene.

The "$C_{2-6}$ acyl group" is an alkanoyl group having 2 to 6 carbon atoms, and is exemplified by, acetyl, propionyl, butyryl, pivaloyl and the like. In some embodiments of the present invention, it is acetyl, pivaloyl and the like.

The "substituted $C_{1-6}$ alkyl group" is the above-defined $C_{1-6}$ alkyl group except that it is substituted by 1 to 5, for example 1 to 3, substituent(s). The substituent of the substituted $C_{1-6}$ alkyl group include
(i) a halogen atom,
(ii) a nitro group,
(iii) a cyano group,
(iv) a $C_{1-6}$ alkxy group,
(v) a hydroxyl group,
(vi) a halogenated $C_{1-6}$ alkxy group,
(vii) a carboxyl group,
(viii) a $C_{1-6}$ alkoxy-carbonyl group,
(ix) an amino group,
(x) a mono ($C_{1-6}$ alkyl)amino group,
(xi) a di($C_{1-6}$ alkyl)amino group,
(xii) an optionally substituted $C_{3-14}$ hydrocarbon ring group,
(xiii) an optionally substituted heterocyclic group,
(xiv) —W-Z (as defined above),
(xv) —$W^1$-$Z^1$ (defined below),
(xvi) a group selected from the above-mentioned group B,
(xvii) a group selected from the above-mentioned group C, and the like.

The "optionally substituted $C_{1-6}$ alkyl group" includes the above-defined substituted $C_{1-6}$ alkyl group and an unsubstituted $C_{1-6}$ alkyl group.

The "optionally substituted $C_{1-6}$ alkyl group" is that wherein the above-defined $C_{1-10}$ alkyl group is optionally substituted by 1 to 5, for example 1 to 3, substituent(s) and includes an unsubstituted $C_{1-10}$ alkyl group. Substituents of the optionally substituted $C_{1-10}$ alkyl group include substituents similar to those mentioned above for a substituted $C_{1-6}$ alkyl group. In some embodiments, it is a straight chain or branched chain alkyl group having 1 to 6 carbon atoms, which is substituted or unsubstituted by the above-mentioned substituents.

The "$C_{3-14}$ hydrocarbon ring group" is a saturated or unsaturated cyclic hydrocarbon group having 3 to 14 carbon atoms and includes a $C_{6-14}$ aryl group, a $C_{3-10}$ cycloalkyl group, a $C_{3-8}$ cycloalkenyl group and the like.

The "$C_{6-14}$ aryl group" is an aromatic hydrocarbon group having 6 to 14 carbon atoms. Examples thereof include phenyl, naphthyl, azulenyl, anthryl, phenanthryl and the like, for example, some embodiments include phenyl.

The "$C_{3-10}$ cycloalkyl group" is a saturated cycloalkyl group having 3 to 10 carbon atoms. Examples thereof include cyclopropyl, cyclobutyl, cyclopentyl, cyclohexyl, cycloheptyl, cyclooctyl, adamantyl, norbornanyl and the like, for example, some embodiments include cyclopentyl, cyclohexyl or cycloheptyl.

The "$C_{3-8}$ cycloalkenyl group" is a cycloalkenyl group having at least 1, preferably 1 or 2, double bond(s) and 3 to 8 carbon atoms. Examples thereof include cyclopropenyl, cyclobutenyl, cyclopentenyl, cyclopentadienyl, cyclohexenyl (e.g., 2,4-cyclohexadien-1-yl, 2,5-cyclohexadien-1-yl, etc.), cycloheptenyl, cyclooctenyl and the like.

The "substituted $C_{3-14}$ hydrocarbon ring group" is the above-defined $C_{3-14}$ hydrocarbon ring group except that it is substituted by 1 to 5, for example 1 to 3, substituent(s). The substituent of the substituted $C_{3-14}$ hydrocarbon ring group include
(i) an optionally substituted $C_{1-6}$ alkyl group,
(ii) a halogen atom,
(iii) a nitro group,
(iv) a cyano group,
(v) a $C_{1-6}$ alkoxy group,
(vi) a hydroxyl group,
(vii) a halogenated $C_{1-6}$ alkyl group,
(viii) a halogenated $C_{1-6}$ alkoxy group,
(ix) a carboxyl group,
(x) a $C_{1-6}$ alkoxy-carbonyl group,
(xi) an amino group,
(xii) a mono($C_{1-6}$alkyl)amino group,
(xiii) a di($C_{1-6}$alkyl)amino group,
(xiv) an optionally substituted $C_{3-14}$ hydrocarbon ring group,
(xv) an optionally substituted heterocyclic group,
(xvi) —W-Z (as defined above),
(xvii) —$W^1$-$Z^1$ (defined below),
(xviii) a group represented by the formula —$(CH^2)_{m4}$—$X_4$—$(CH_2)_{n4}$—$R^{24}$ wherein each symbol is as defined above,
(xix) a group represented by the formula

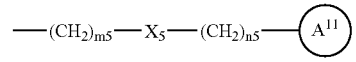

wherein each symbol is as defined above,
(xx) a group selected from the above-mentioned group B,
(xxi) a group selected from the above-mentioned group C, and the like.

The "substituted $C_{3-14}$ hydrocarbon ring group" may take together with the substituent(s) to form an "optionally substituted fused $C_{6-14}$ hydrocarbon ring group" or an "optionally substituted fused heterocyclic group".

The "fused $C_{6-14}$ hydrocarbon ring group" in the "optionally substituted fused $C_{6-14}$ hydrocarbon ring group" includes, for example, a saturated or unsaturated (including partially unsaturated and completely unsaturated) fused hydrocarbon ring group having 6 to 14 carbon atoms, wherein $C_{3-14}$ hydrocarbon ring groups defined above have been fused. Examples thereof include indenyl, indanyl, 1,4-dihydronaphthyl, fluorenyl, 9-oxo-fluorenyl, 1,2,3,4-tetrahydronaphthyl (1,2,3,4-tetrahydro-2-naphthyl, 5,6,7,8-tetrahydro-2-naphthyl and the like), perhydronaphthyl and the like. For example, it is a fused ring group of phenyl and a different ring group, and fluorenyl, 9-oxo-fluorenyl and the like.

Examples of substituent of the "optionally substituted fused $C_{6-14}$ hydrocarbon ring group" include substituents similar to those mentioned above for the "substituted $C_{3-14}$ hydrocarbon ring group".

The "optionally substituted $C_{3-14}$ hydrocarbon ring group" includes the "substituted $C_{3-14}$ hydrocarbon ring group" and an unsubstituted $C_{3-14}$ hydrocarbon ring group.

The "heterocyclic group" is a 5-membered or 6-membered saturated or unsaturated (including partially unsaturated and completely unsaturated) monocyclic heterocyclic group having, as an atom constituting the ring, at least 1, for example 1 to 4, heteroatoms selected from an oxygen atom, a nitrogen atom and a sulfur atom, besides a carbon atom.

The "saturated monocyclic heterocyclic group" include, for example, pyrrolidinyl, 2-oxo-pyrrolidinyl, tetrahydrofuryl, tetrahydrothienyl, imidazolidinyl, 2-oxo-imidazolidinyl, 2,4-dioxo-imidazolidinyl, pyrazolydinyl, 1,3-dioxolanyl, 1,3-oxathiolanyl, oxazolidinyl, 2-oxo-oxazolidinyl, thiazolidinyl, 2-oxo-thiazolidinyl, 2,4-dioxo-thiazolidinyl, 4-oxo-2-thioxo-thiazolidinyl, piperidinyl, 2-oxopiperidinyl, piperazinyl, 2,5-dioxopiperazinyl, hexahydropyridazinyl, 3-oxotetrahydropyridazinyl, 2-oxotetrahydropyrimidinyl, tetrahydropyranyl, tetrahydrothiopyranyl, dioxanyl, morpholinyl, 3-oxomorpholinyl, thiomorpholinyl, 3-oxothiomorpholinyl, 2-oxopyrrolidinyl, 2-oxopiperidinyl, 4-oxopiperidinyl, 2,6-dioxopiperidinyl, 2-oxo-1,3-oxazinanyl, 2-oxo-1,3-thiazinanyl, azetidinyl, 1,4-diazepanyl,

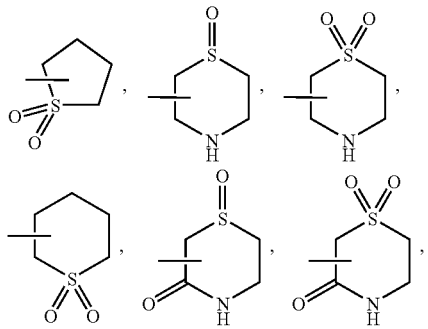

and the like, preferably, pyrrolidinyl, piperidinyl and morpholinyl.

The "unsaturated monocyclic heterocyclic group" includes, for example, pyrrolyl, 1,5-dihydro-2-oxopyrrolyl, furyl, thienyl, imidazolyl, 1,2-dihydro-2-oxoimidazolyl, 1,3-dihydro-2-oxoimidazolyl, pyrazolyl, 1,2-dihydro-3-oxopyrazolyl, oxazolyl, 2-oxo-oxazolyl, isoxazolyl, thiazolyl, 2-oxothiazolyl, isothiazolyl, 1,2,4-triazolyl, 3-oxo-1,2,4-triazolyl, 1,2,3-triazolyl, tetrazolyl, 1,3,4-oxadiazolyl, 1,2,4-oxadiazolyl, 5-oxo-1,2,4-oxadiazolyl, 1,3,4-thiadiazinyl, 1,3,4-thiadiazolyl, 2-thioxo-1,3,4-thiadiazolyl, 3-oxo-1,4-oxazinyl, 1,2,4-thiadiazolyl, 5-oxo-1,2,4-thiadiazolyl, furazanyl, pyridyl, 2-oxopyridyl, 4-oxopyridyl, 2-thioxopyridyl, 4-thioxopyridyl, pyrimidinyl, 2-oxopyrimidinyl, 3,4-dihydro-4-oxopyrimidinyl, 2,4,6-trioxopyrimidinyl, pyridazinyl, 3-oxopyridazinyl, pyrazinyl, 1,3,5-triazinyl, imidazolinyl, pyrazolinyl, oxazolinyl (2-oxazolinyl, 3-oxazolinyl, 4-oxazolinyl), isoxazolinyl, thiazolinyl, isothiazolinyl, pyranyl, 2-oxopyranyl, 4-oxopyranyl, 4-thioxopyranyl and the like, such as, imidazolyl, pyrazolyl, isoxazolyl, thiazolyl, 1,2,4-triazolyl, tetrazolyl, 1,3,4-oxadiazolyl, pyridyl, pyrimidinyl, pyridazinyl, pyrazinyl and oxazolinyl.

The "substituted heterocyclic group" is the above-defined heterocyclic group except that it is substituted by 1 to 5, for example 1 to 3, substituent(s). As the substituent thereof, examples include substituents similar to those mentioned above for "substituted $C_{3-14}$ hydrocarbon ring group".

The "substituted heterocyclic group" may take together with the substituent(s) thereof to form an "optionally substituted fused heterocyclic group".

The "fused heterocyclic group" in the "optionally substituted fused heterocyclic group" includes, for example, a 6-membered to 14-membered saturated or unsaturated (including partially unsaturated and completely unsaturated) fused heterocyclic group having, as an atom constituting the ring, at least 1, for example 1 to 4, heteroatoms selected from an oxygen atom, a nitrogen atom and a sulfur atom, besides a carbon atom. The fused heterocyclic group may be a fused ring group of a saturated or unsaturated heterocyclic group defined above and a $C_{3-14}$ hydrocarbon ring group defined above, or may be a fused ring group of saturated or unsaturated heterocyclic groups defined above. Examples thereof include indolyl, isoindolyl, 2,3-dihydroindolyl, 2,3-dihydroisoindolyl, 1,3-dihydro-2-oxoisoindolyl, 2,3-dihydro-1-oxoisoindolyl, 1,3-dihydro-1,3-dioxoisoindolyl, benzimidazolyl, indazolyl, 4,5,6,7-tetrahydroindazolyl, benzotriazolyl, benzothiazolyl, benzoisothiazolyl, 4,5,6,7-tetrahydrobenzoisothiazolyl, 2-oxobenzothiazolyl, benzothiophenyl, dibenzothiophenyl, 4,5,6,7-tetrahydrobenzothiophenyl, benzofuranyl, dibenzofuranyl, isobenzofuranyl, 4,5,6,7-tetrahydrobenzofuranyl, 4,5,6,7-tetrahydroisobenzofuranyl, benzoxazolyl, benzoisooxazolyl, 2-oxobenzoxazolyl, 4,5,6,7-tetrahydroisobenzoxazolyl, indolizinyl, quinolyl, isoquinolyl, 1,2-dihydro-2-oxoquinolyl, quinazolinyl, quinoxalinyl, cinnolinyl, phthalazinyl, quinolidinyl, carbazolyl, puryl, pteridinyl, indolinyl, isoindolinyl, 4,5,6,7-tetrahydroindolyl, 4,5,6,7-tetrahydroisoindolyl, 5,6,7,8-tetrahydroquinolyl, 1,2,3,4-tetrahydroquinolyl, 2-oxo-1,2,3,4-tetrahydroquinolyl, 1,2,3,4-tetrahydroisoquinolyl, 2-oxo-1,2,3,4-tetrahydroisoquinolyl, 1,3-benzodioxolyl, 3,4-methylenedioxypyridyl, 4,5-ethylenedioxypyrimidinyl, chromenyl, chromanyl, isochromanyl, 1,2,4-benzotriazinyl, 6,7-dihydropyrindinyl, 6,7-dihydrocyclopentapyrazinyl, 6,7-dihydrocyclopentapyridazinyl, 6,7-dihydrocyclopentapyrimidinyl, 2,3,4,5-tetrahydrobenzoazepinyl,

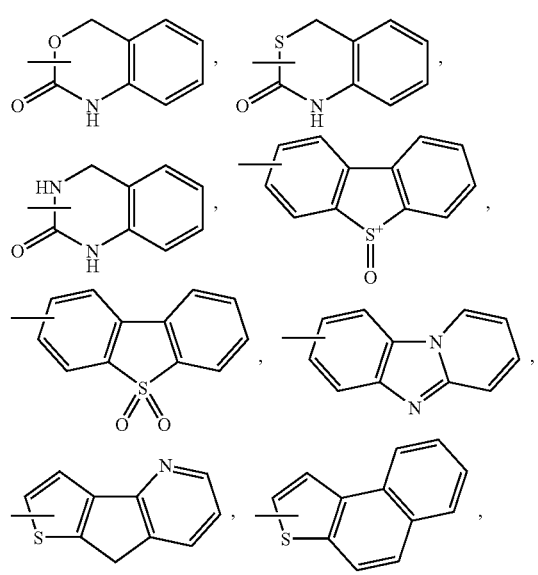

-continued

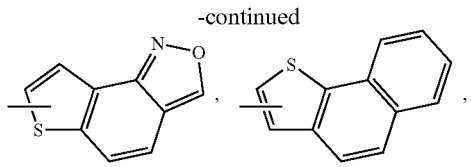

and the like, for example, some embodiments include benzofuranyl, dibenzofuranyl, or isoquinolyl.

Examples of substituents of the "optionally substituted fused heterocyclic group" include substituents similar to those mentioned above for "substituted heterocyclic group".

The "optionally substituted heterocyclic group" includes the above-defined "substituted heterocyclic group" and the unsubstituted heterocyclic group.

The "$C_{6-14}$ aryl-$C_{1-6}$ alkyl group" is an arylalkyl group wherein the alkyl moiety thereof is the above-defined $C_{1-6}$ alkyl group and the aryl moiety is the above-defined $C_{6-14}$ aryl group. Examples thereof include benzyl, phenethyl, 3-phenylpropyl, 2-phenylpropyl, 4-phenylbutyl and the like. In some embodiments of the present invention, it is an arylalkyl group wherein the alkyl moiety thereof is a straight chain alkyl group having 1 to 4 carbon atoms and the aryl moiety is phenyl.

The "optionally substituted $C_{6-14}$ aryl-$C_{1-6}$ alkyl group" is that wherein the above-defined $C_{6-14}$ aryl-$C_{1-6}$ alkyl group is optionally substituted by 1 to 5, preferably 1 to 3, substituent(s) and includes an unsubstituted $C_{6-14}$ aryl-$C_{1-6}$ alkyl group. Substituents of the optionally substituted $C_{6-14}$ aryl-$C_{1-6}$ alkyl group include substituents similar to those mentioned above for the substituted $C_{3-14}$ hydrocarbon ring group. In some embodiments of the present invention, it is a phenyl-$C_{1-4}$ alkyl group substituted or unsubstituted by the above-mentioned substituents.

Each symbol in the formula (1) of preferable compounds of the formula (1) is explained in the following.

In some embodiments of the inventive compounds of formula (1), $R^1$ is for example —$(CH_2)_m$—X—$(CH_2)_n$-$A^1$ wherein each symbol is as defined above.

m and n are the same or different and each is for example 0 or an integer ranging from 1 to 2, preferably 0.

X is for example a single bond or a $C_{2-6}$ alkenylene group (e.g., vinylene), preferably a single bond.

$A^1$ is for example a group of the following formula

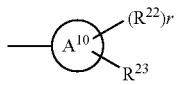

wherein each symbol is as defined above.

The $C_{3-14}$ hydrocarbon ring group at ring $A^{10}$ is for example a $C_{6-14}$ aryl group, preferably phenyl.

The heterocyclic group at ring $A^{10}$ is for example a saturated monocyclic heterocyclic group (e.g., azetidinyl, pyrrolidinyl, piperazinyl, piperazinonyl, piperidinyl, 1,4-diazepanyl, 3-oxo-piperazinyl) or an unsaturated monocyclic heterocyclic group (e.g., thienyl, methylthienyl, pyrazolyl, thiazolyl, pyridyl, 1,2,3,6-tetrahydropyridyl), preferably thienyl, azetidinyl, pyrrolidinyl, piperazinyl, piperazinonyl, piperidinyl, thienyl, pyridyl, 1,2,3,6-tetrahydropyridyl or 3-oxo-piperazinyl.

r is for example 0 or an integer ranging from 2 to 4.

$R^{22}$ is —$(CH_2)_{m4}$—$X_4$—$(CH_2)_{n4}$—$R^{24}$ wherein each symbol is as defined above.

m4 and n4 is for example 0 or an integer ranging from 1 to 2, preferably 0.

$X_4$ is for example a single bond, —O—, —CO—, a $C_{2-6}$ alkynylene group (e.g., ethynylene) or —CON($R^5$)—(preferably $R^5$ is hydrogen atom), preferably a single bond.

$R^{24}$ is for example a halogen atom (e.g., a chlorine atom, a bromine atom, a fluorine atom), a halogenated $C_{1-6}$ alkyl group (e.g., trifluoromethyl) or a $C_{1-6}$ alkyl group optionally substituted by hydroxyl groups (e.g., methyl, ethyl, propyl, isopropyl, t-butyl, 1-hydroxyethyl, 1-hydroxy-1-methylethyl).

The substituents $R^{22}$ are the same or different when r is an integer selected from the range of 2 to 4, $R^{23}$ is

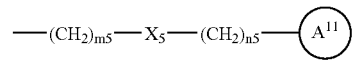

wherein each symbol is as defined above.

m5 and n5 are the same or different and each is for example 0 or an integer ranging from 1 to 2, preferably 0.

$X_5$ is for example a single bond, —O—, —CO—, —S(O)$_{m1}$—(preferably m1 is 2) or —CON($R^5$)—(preferably $R^5$ is a hydrogen atom), preferably a single bond.

The $C_{3-14}$ hydrocarbon ring group at ring $A^{11}$ is for example a $C_{3-10}$ cycloalkyl group (e.g., cyclopropyl, cyclopentyl) or a $C_{6-14}$ aryl group (e.g., phenyl), preferably cyclopropyl, cyclopentyl and phenyl.

The heterocyclic group at ring $A^{11}$ is for example a saturated monocyclic heterocyclic group (e.g., pyrrolidinyl, 2-oxo-pyrrolidinyl, 2-oxo-piperidinyl, morpholinyl, piperazinyl, piperidinyl) or an unsaturated monocyclic heterocyclic group (e.g., pyrazolyl, imidazolyl, thiazolyl, pyridyl, 3,6-dihydro-2H-pyridyl, 1,2,3,6-tetrahydro-pyridyl, pyridazinyl, pyrimidinyl, 1,2,3-triazolyl, thienyl, oxazolyl, 4,5-dihydro-oxazolyl, 1,2,4-oxadiazolyl, 1,3,4-oxadiazolyl, tetrazolyl, isooxazolyl, 4,5-dihydroisooxazolyl, isothiazolyl, 1,2,4-thiadiazolyl, 1,3,4-thiadiazolyl).

The ring $A^{11}$ is optionally substituted by 1 to 5 groups of the formula "—$(CH_2)_{m6}$—$X_6$—$(CH_2)_{n6}$—$R^{25}$", which are the same or different. The number of substituents is for example 1 or 2.

m6 and n6 are the same or different and each is for example 0 or an integer ranging from 1 to 2, preferably 0.

$X_6$ is for example a single bond, —O—, —CO— or —COO—, preferably a single bond.

$R^{25}$ is for example (a) a halogen atom (e.g., a chlorine atom, a bromine atom, a fluorine atom),
(b) a hydroxyl group,
(c) a cyano group,
(d) a carboxyl group,
(e) an amino group,
(f) a halogenated $C_{1-6}$ alkyl group (e.g., fluoromethyl, difluoromethyl, trifluoromethyl, pentafluoroethyl, 1,1-difluoroethyl),
(g) a $C_{1-6}$ alkyl group optionally substituted by hydroxyl groups (e.g., methyl, ethyl, propyl, isopropyl, t-butyl),
(h) a $C_{1-6}$ alkoxy group optionally substituted by hydroxyl groups, (e.g., methoxy),
(i) a di($C_{1-6}$ alkyl)amino group (e.g., dimethylamino) or (j) a $C_{3-14}$ hydrocarbon ring group optionally substituted by 1 to 5 substituent(s) selected from the above-mentioned group B (e.g., a $C_{6-14}$ aryl group, preferably phenyl).

The ring $A^{11}$ is may take together with a group of the formula "—$(CH_2)_{m6}$—$X_6$—$(CH_2)_{n6}$—$R^{25}$" to form an optionally substituted fused ring group. The optionally substituted fused ring group is for example the above-defined "optionally substituted fused $C_{6-14}$ hydrocarbon ring group", the above-defined "optionally substituted fused heterocyclic group" or the like.

The "fused $C_{6-14}$ hydrocarbon ring group" in the "optionally substituted fused $C_{6-14}$ hydrocarbon ring group" is for example 9H-fluorenyl or 9-oxo-9H-fluorenyl, preferably 9H-fluorenyl. The substituent thereof is for example a halogen atom (e.g., a chlorine atom, a bromine atom, a fluorine atom). The number of substituents is for example 1. Examples thereof include 9H-fluoren-2-yl, 9-oxo-9H-fluoren-2-yl, 7-bromo-9H-fluoren-2-yl, 7-fluoro-9H-fluoren-2-yl, 7-chloro-9H-fluoren-2-yl and the like.

The "fused heterocyclic group" in the "optionally substituted fused heterocyclic group" is for example benzothienyl, benzothiazolyl, benzooxazolyl, benzofuranyl, benzoimidazolyl, indolyl, 5-indolizinyl, 4,5,6,7-tetrahydrobenzo[d]isooxazolyl, 1,3-benzodioxolyl, 5-quinoxalinyl, 2-oxo-2,3-dihydro-benzothiazolyl, 1,4-benzodioxanyl, 3H-benzotriazolyl, benzo[2,1,3]thiadiazolyl, benzo[2,1,3]oxadiazolyl, benzo[1,3]dioxazolyl, imidazo[1,2-a]pyrimidinyl or the like. The substituent thereof is for example a hydroxyl group, a halogen atom (e.g., a chlorine atom, a fluorine atom), a $C_{1-6}$ alkyl group (e.g., methyl), a $C_{1-6}$ alkoxy group (e.g., methoxy) or the like. The number of substituents is for example 1 or 2.

The ring $A^{10}$ and the ring $A^{11}$ may be taken together with a substituent thereof to form an optionally substituted fused ring group. The optionally substituted fused ring group is for example the above-defined "optionally substituted fused $C_{6-14}$ hydrocarbon ring group", the above-defined "optionally substituted fused heterocyclic group" or the like.

The "fused $C_{6-14}$ hydrocarbon ring group" in the "optionally substituted fused $C_{6-14}$ hydrocarbon ring group" is for example 9H-fluorenyl or 9-oxo-9H-fluorenyl, preferably 9H-fluorenyl. The substituent thereof is for example a halogen atom (e.g., a chlorine atom, a bromine atom, a fluorine atom) or the like. The number of substituents is for example 1. Examples thereof include 9H-fluoren-2-yl, 9-oxo-9H-fluoren-2-yl, 7-bromo-9H-fluoren-2-yl, 7-fluoro-9H-fluoren-2-yl, 7-chloro-9H-fluoren-2-yl and the like.

The "fused heterocyclic group" in the "optionally substituted fused heterocyclic group" is for example benzofuranyl, dibenzofuranyl, 1,3,4,9-tetrahydro-β-carbolinyl, 5,6-dihydro-8H-[1,2,4]triazolo[4,3-a]pyrazinyl, 7,8-dihydro-5H-pyrido[4,3-d]pyrimidinyl, 3,4-dihydro-1H-pyrazino[1,2-a]indolyl, 2,3-dihydro-1H-isoindolyl, 3,4-dihydro-1H-benzo[4,5]imidazo[1,2-a]pyrazinyl, imidazo[2,1-b]thiazolyl, 1,3-dihydroisoindolyl, imidazothiazolyl, 3,4-dihydroisoquinolyl, dihydroisoindolyl, benzo[b]thienyl, benzoimidazolyl, imidazo[1,2-a]pyridyl or the like. The substituent thereof is for example a hydroxyl group, a halogen atom (e.g., a chlorine atom, a bromine atom, a fluorine atom), a $C_{1-6}$ alkoxy group (e.g., methoxy), an optionally substituted $C_{3-14}$ hydrocarbon ring group (e.g., an optionally substituted $C_{3-10}$ cycloalkyl group (e.g., cyclohexyl), an optionally substituted $C_{6-14}$ aryl group (e.g., phenyl, chlorophenyl, fluorophenyl), an optionally substituted heterocyclic group (e.g., chloropyrazolyl), a $C_{1-6}$ alkoxy-$C_{1-6}$ alkyl group (e.g., methoxymethyl) or a $C_{1-6}$ alkyl-amino group (e.g., isopropylamino). The number of substituents is for example 1 or 2.

In some embodiments of the inventive compounds of formula (1), $R^2$ and $R^3$ are the same or different and each is —$(CH_2)_p$—$X_1$—$(CH_2)_q$-$A^2$, wherein each symbol is as defined above, or —$(CH_2)_{m8}$—$X_8$—$(CH_2)_{n8}$—$R^{27}$, wherein each symbol is as defined above, preferably, one of them is —$(CH_2)_{m8}$—$X_8$—$(CH_2)_{n8}$—$R^{27}$ (preferably hydrogen atom or a $C_{1-6}$ alkyl group optionally substituted by hydroxyl groups), and the other is —$(CH_2)_p$—$X_1$—$(CH_2)_q$-$A^2$, wherein each symbol is as defined above.

p and q are the same or different and each is for example 0 or an integer ranging from 1 to 2, preferably 0.

$X_1$ is for example a single bond, —O—, —N($R^5$)— (preferably $R^5$ is a hydrogen atom, a $C_{1-6}$ alkyl group optionally substituted by hydroxyl groups (e.g., methyl)), —S(O)$_{m1}$— (preferably m1 is 0), —CO—, —COO—, —OCO—, —N($R^5$)CO—(preferably $R^5$ is a hydrogen atom), —OCON($R^5$)—(preferably $R^5$ is a hydrogen atom) or —S(O)$_{m1}$—$(CH_2)_{n1}$—CO— (preferably m1 is 0 and n1 is 1), preferably a single bond.

$A^2$ is for example a group of the following formula

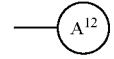

wherein each symbol is as defined above.

The $C_{3-14}$ hydrocarbon ring group at ring $A^{12}$ is for example a $C_{6-14}$ aryl group (preferably phenyl) or a $C_{3-8}$ cycloalkyl group (preferably cyclopropyl, cyclobutyl, cyclopentyl, cyclohexyl).

The heterocyclic group at ring $A^{12}$ is for example a saturated monocyclic heterocyclic group (e.g., pyrrolidinyl, piperidinyl, piperazinyl, tetrahydrofuryl, 2-oxazolidonyl, morpholinyl, 3-oxo-morpholinyl) or an unsaturated monocyclic heterocyclic group (e.g., pyrazolyl, pyridyl, imidazolyl, thiazolyl, isooxazolyl).

The ring $A^{12}$ is optionally substituted by 1 to 5 groups of the formula "—$(CH_2)_{m7}$—$X_7$—$(CH_2)_{n7}$—$R^{26}$", which are the same or different. The number of substituents is for example 1 or 2.

m7 and n7 are the same or different and each is for example 0 or an integer ranging from 1 to 2, preferably 0.

$X_7$ is for example a single bond, —O—, —N($R^5$), —S(O)$_{m1}$—, —CO—, —COO—, —OCO—, —CON($R^5$)—, —N($R^5$)CO—, —N($R^5$)SO$_2$—, —OCON($R^5$)— or —N($R^5$)COO—(preferably $R^5$ is a hydrogen atom and a $C_{1-6}$ alkyl group optionally substituted by hydroxyl groups (e.g., methyl), and m1 is 2), preferably a single bond.

$R^{26}$ is for example
(a) a halogen atom (e.g., a chlorine atom, a bromine atom, a fluorine atom),
(b) a hydroxyl group,
(c) a nitro group,
(d) a carboxyl group,
(e) an amino group,
(f) a halogenated $C_{1-6}$ alkyl group (e.g., trifluoromethyl),
(g) a $C_{1-6}$ alkyl group optionally substituted by hydroxyl groups (e.g., methyl, isobutyl, hydroxymethyl, 1-hydroxy-1-methyl-ethyl, 2-hydroxy-1,1-dimethylethyl),
(h) a $C_{1-6}$ alkoxy group optionally substituted by hydroxyl groups, (e.g., methoxy, tert-butoxy),
(i) a mono($C_{1-6}$ alkyl)amino group (e.g., methylamino, t-butylamino), (j) a di($C_{1-6}$ alkyl)amino group (e.g., dimethylamino),
(k) a $C_{1-6}$ alkylsulfonyl group (e.g., methanesulfonyl),
(l) a $C_{3-14}$ hydrocarbon ring group optionally substituted by 1 to 5 substituent(s) selected from the above-mentioned group B.
wherein the "$C_{3-14}$ hydrocarbon ring group" is for example a $C_{3-10}$ cycloalkyl group (e.g., cyclohexyl) or a $C_{6-14}$ aryl group (e.g., phenyl), the substituent thereof is for example a halogen atom (e.g., chlorine atom), a hydroxyl group or a $C_{1-6}$ alkyl group optionally substituted by hydroxyl groups (e.g., methyl), and the number of substituents is for example 1;
or
(m) a heterocyclic group optionally substituted by 1 to 5 substituent(s) selected from the above-mentioned group B,
wherein the "heterocyclic group" is for example a saturated monocyclic heterocyclic group (e.g., piperidinyl, pyrrolidinyl, 2-oxo-pyrrolidinyl, morpholinyl, piperazinyl), an unsaturated monocyclic heterocyclic group (e.g., pyridyl, pyrazolyl, thiazolyl, imidazolyl, 4,5-dihydro-oxazolyl) or the like, the substituent thereof is for example a hydroxyl group, a $C_{1-6}$ alkyl group optionally substituted by hydroxyl groups (e.g., methyl, hydroxymethyl, isopropyl) or a $C_{1-6}$ alkoxy-carbonyl group (e.g., tert-butoxy carbonyl), and the number of substituents is for example 1.

The ring $A^{12}$ is may take together with a group of the formula "—$(CH_2)_{m7}$—$X_7$—$(CH_2)_{n7}$—$R^{26}$" to form an optionally substituted fused ring group. The optionally substituted fused ring group is for example the above-defined "optionally substituted fused $C_{6-14}$ hydrocarbon ring group", the above-defined "optionally substituted fused heterocyclic group" or the like.

The "fused $C_{6-14}$ hydrocarbon ring group" in the "optionally substituted fused $C_{6-14}$ hydrocarbon ring group" is for example 9H-fluorenyl or 9-oxo-9H-fluorenyl. The substituent thereof is for example a halogen atom (e.g., a chlorine atom, a bromine atom, a fluorine atom), and the number of substituents is for example 1.

The "fused heterocyclic group" in the "optionally substituted fused heterocyclic group" is for example tetrahydroisoquinolyl or 4-oxo-4H-benzo[d][1,2,3]triazinyl. The substituent thereof is for example a $C_{1-6}$ alkyl group (e.g., methyl, isopropyl) or a $C_{1-6}$ alkyl group substituted by $C_{6-14}$ aryl groups (e.g., benzyl), and the number of substituents is for example 1.

m8 and n8 in —$(CH_2)_{m8}$—$X_8$—$(CH_2)_{n8}$—$R^{27}$ are for example the same or different and each is 0 or an integer ranging from 1 to 2.

The $X_8$ is for example a single bond, —O—, —$N(R^5)$—, —$S(O)_{m1}$—, —OCO—, —$N(R^5)CO$—, —$OCON(R^5)$— or —$S(O)_{m1}$—$(CH_2)_{n1}$—CO— (preferably $R^5$ is a hydrogen atom, a $C_{1-6}$ alkyl group optionally substituted by hydroxyl groups (e.g., methyl), m1 is 0, 1 or 2 and n1 is 1).

$R^{27}$ is for example
(a) a hydrogen atom
(b) a hydroxyl group,
(c) a carboxyl group,
(d) an amino group,
(e) a $C_{1-6}$ alkyl group optionally substituted by hydroxyl groups (e.g., methyl, ethyl, isopropyl, t-butyl, hydroxymethyl, 2-hydroxyethyl),
(f) a $C_{2-6}$ alkenyl group optionally substituted by halogen atoms (e.g., vinyl),
(g) a $C_{1-6}$ alkoxy group optionally substituted by hydroxyl groups, (e.g., methoxy, ethoxy, isopropoxy, t-butoxy),
(h) a mono($C_{1-6}$ alkyl)amino group (e.g., ethylamino), or
(i) a di($C_{1-6}$ alkyl)amino group (e.g., dimethylamino, diethylamino).

$A^2$ and $R^{27}$ may be taken together to form an optionally substituted fused ring group. $R^{26}$ may be linked with $R^{27}$ together with the ring $A^{12}$ to form an optionally substituted fused ring group. The optionally substituted fused ring group is for example the above-defined "optionally substituted fused $C_{6-14}$ hydrocarbon ring group", the above-defined "optionally substituted fused heterocyclic group" or the like. Examples thereof include 1,2,3,4-tetrahydroisoquinoline and the like. The substituent thereof is for example a substituent selected from the above-mentioned group C, preferably a $C_{2-6}$ acyl group (e.g., acetyl). The number of substituents is for example 1.

$R^2$ and $R^3$ may be taken together with a carbon atom bonded thereto to form the following ring

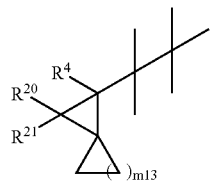

wherein each symbol is as defined above.
m13 is for example an integer of 1 to 4, preferably 1.
Provided that $R^2$ and $R^3$ are not hydrogen atoms at the same time.

In some embodiments of the inventive compounds of formula (1), $R^{20}$ and $R^{21}$ are the same or different and each is —$(CH_2)_{m10}$—$X_{10}$—$(CH_2)_{n10}$-$A^3$, wherein each symbol is as defined above, or —$(CH_2)_{m12}$—$X_{12}$—$(CH_2)_{n12}$—$R^{30}$, wherein each symbol is as defined above, preferably —$(CH_2)_{m12}$—$X^{12}$—$(CH_2)_{n12}$—$R^{30}$ (more preferably a hydrogen atom or a $C_{1-6}$ alkyl group optionally substituted by hydroxyl groups).

m10 and n10 are the same or different and each is for example 0 or an integer ranging from 1 to 2, preferably 0.
$X_{10}$ is for example a single bond.
$A^3$ is for example, a group of the following formula

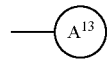

wherein each symbol is as defined above.
m12 and n12 are the same or different and each is for example 0 or an integer ranging from 1 to 2, preferably 0.
$X_{12}$ is for example a single bond.
$R^{30}$ is for example
(a) a hydrogen atom,
(b) a $C_{1-6}$ alkyl group optionally substituted by hydroxyl groups (e.g., methyl, ethyl, 2-hydroxymethyl) or
(c) a $C_{1-6}$ alkoxy-$C_{1-6}$ alkyl group (e.g., methoxymethyl).

$A^2$, $R^{30}$ and the cyclopropane ring may be taken together to form an optionally further substituted fused ring. $R^{26}$ may be linked with $R^{30}$, together with the ring $A^{12}$ and the cyclopropane ring to form an optionally further substituted fused ring.

The "fused ring" is for example a fused $C_{6-14}$ hydrocarbon ring in the above-defined fused $C_{6-14}$ hydrocarbon ring group or a fused heterocyclic ring in the above-defined fused heterocyclic group, wherein the above-defined $C_{3-14}$ hydrocarbon ring group and/or the above-defined heterocyclic group are/is fused with the cyclopropane ring, or the like. Examples thereof include 1,1a,2,3,4,8b-hexahydro-benzo[a]cyclopropa[c]cycloheptene, 1,1a,6,6a-tetrahydro-cyclopropa[a]indene, 1a,2,3,7b-tetrahydro-1H-cyclopropa[a]naphthalene, 1a,2,3,8b-tetrahydro-1H-4-oxa-benzo[a]cyclopropa[c]cycloheptene, 1,1a,2,3,4,8b-hexahydro-4-aza-benzo[a]cyclopropa[c]cycloheptene and the like. The "fused ring" is optionally further substituted, and the substituent thereof is for example a substituent selected from the above-mentioned group C, preferably a hydroxyl group or a $C_{2-6}$ acyl group (e.g., acetyl). The number of substituents is for example 1.

$R^{20}$ and $R^{21}$ may be taken together with a carbon atom bonded thereto to form the following ring

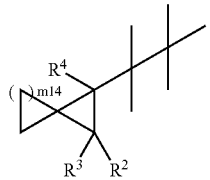

wherein each symbol is as defined above.

m14 is for example an integer of 1 to 4, preferably 1.

In some embodiments of the inventive compounds of formula (1), $R^4$ is for example $—CO_2R^9$, $—C(O)NHOR^9$ or $—(CH_2)_{r1}—R^{50}$, preferably $—CO_2R^9$, wherein each symbol is as defined above.

$R^9$ is for example a hydrogen atom or $—(CH_2)_{m9}—X^9—(CH_2)_{n9}—R^{28}$, wherein each symbol is as defined above.

m9 and n9 are the same or different and each is for example 0 or an integer ranging from 1 to 2.

$X_9$ is for example a single bond.

$R^{28}$ is for example a $C_{3-14}$ hydrocarbon ring group optionally substituted by 1 to 5 substituent(s) selected from the above-mentioned group B, a heterocyclic group optionally substituted by 1 to 5 substituent(s) selected from the above-mentioned group B or the like.

r1 is for example 0 or an integer ranging from 1 to 2.

The "optionally substituted $C_{3-14}$ hydrocarbon ring group" at $R^{28}$ and $R^{50}$ is for example the above-defined "optionally substituted fused $C_{3-14}$ hydrocarbon ring group" or the like.

The "optionally substituted heterocyclic group" at $R^{28}$ and $R^{50}$ is for example the above-defined "optionally substituted heterocyclic group" or the like. Examples thereof include 1-hydroxy-1H-pyridin-2-one, 3-hydroxy-1H-pyridin-2-one, 3-hydroxy-1,2-dimethyl-1H-pyridin-4-one, 3-hydroxy-pyran-4-one, 3-hydroxy-2-methyl-pyran-4-one, 3-hydroxy-1H-pyridin-2-one, 1-hydroxy-1H-pyridine-2-thione, 3-hydroxy-1,2-dimethyl-1H-pyridine-4-thione, 3-hydroxy-1H-pyridine-2-thione, 3-hydroxy-pyran-4-thione, 3-hydroxy-2-methyl-pyran-4-thione, 3H-[1,3,4]thiadiazole-2-thione, barbituric acid, 2-thioxo-thiazolidin-4-one, thiazolidine-2,4-dione, imidazolidine-2,4-dione, 6H-1,3,4-thiazine, nitropyrimidine and the like.

$R^9$ of $—C(O)NHR^9$, $A^2$ and the cyclopropane ring may be taken together to form an optionally further substituted fused ring. $R^{26}$ may be linked with $R^9$ of $—C(O)NHR^9$ or $R^{30}$, together with the ring $A^{12}$ and the cyclopropane ring to form an optionally further substituted fused ring.

The "fused ring" is for example a fused $C_{6-14}$ hydrocarbon ring in the above-defined fused $C_{6-14}$ hydrocarbon ring group or a fused heterocyclic ring in the above-defined fused heterocyclic group, wherein the above-defined $C_{3-14}$ hydrocarbon ring group and/or the above-defined heterocyclic group are/is fused with the cyclopropane ring, or the like. Examples thereof include 2-oxo-1,2,3,7b-tetrahydro-3-aza-cyclopropa[a]naphthalene, 2-oxo-2,3,4,8b-tetrahydro-1H-3-aza-benzo[a]cyclopropa[c]cycloheptene and the like. The "fused ring" is optionally further substituted, and the substituent thereof is for example a substituent selected from the above-mentioned group C. The number of substituents is for example 1.

$R^9$ of $—CO_2R^9$, $R^{20}$ and the cyclopropane ring may be taken together to form an optionally further substituted fused ring. The "fused ring" is for example a fused $C_{6-14}$ hydrocarbon ring in the above-defined fused $C_{6-14}$ hydrocarbon ring group or a fused heterocyclic ring in the above-defined fused heterocyclic group, wherein the above-defined $C_{3-14}$ hydrocarbon ring group and/or the above-defined heterocyclic group are/is fused with the cyclopropane ring, or the like. Examples thereof include 2-oxo-3-oxa-bicyclo[3.1.0]hexyl and the like. The "fused ring" is optionally further substituted, and the substituent thereof is for example a substituent selected from the above-mentioned group C. The number of substituents is for example 1.

As the compound represented by the formula (1), the following compound is preferable.

[Compound A]

A compound wherein $R^1$ is the formula $—(CH_2)_m—X—(CH_2)_n-A^1$ wherein each symbol is as defined above., preferably m and n are 0, X is a single bond, and $A^1$ is a group of the following formula:

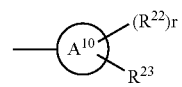

wherein ring $A^{10}$, r and $R^{22}$ are as defined above, $R^{23}$ is

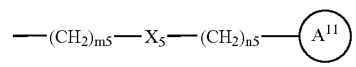

wherein each symbol is as defined above, preferably m5 and n5 are 0 and $X_5$ is a single bond;

$R^2$ is $—(CH_2)_p—X_1—(CH_2)_q-A^2$, wherein each symbol is as defined above, preferably p and q are 0, $X_1$ is a single bond, and A is a group of the following formula:

wherein each symbol is as defined above;

$A^3$ at $R^{20}$ and $R^{21}$ is a group of the following formula:

wherein each symbol is as defined above; and
$R^4$ is —CO$_2$R$^9$ or —C(O)NHOR$^9$, wherein each symbol is as defined above, preferably $R^9$ is hydrogen atom.

As the compound represented by the formula (1), the compound represented by the following formula (1') is also preferable:

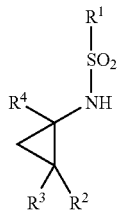

(1')

wherein
$R^1$ is selected from
(1) a substituted $C_{1-6}$ alkyl group,
and
(2) —(CH$_2$)$_m$—X—(CH$_2$)$_n$-A$^1$,
wherein
m and n are the same or different and each is selected from 0 and an integer ranging from 1 to 6,
X is selected from a single bond, a $C_{1-6}$ alkylene group, a $C_{2-6}$ alkenylene group, a $C_{2-6}$ alkynylene group, —O—, —N(R$^5$)—, —S(O)$_{m1}$—, —CO—, —CON(R$^5$)—, —N(R$^5$)CO—, —SO$_2$N(R$^5$)—, —N(R$^5$)SO$_2$—, —N(R$^5$)CON(R$^6$)—, —N(R$^5$)SO$_2$N(R$^6$)—, —OCON(R$^5$)— and —N(R$^5$)COO—,
wherein
$R^5$ and $R^6$ are the same or different and each is selected from a hydrogen atom and a $C_{1-6}$ alkyl group,
m1 is selected from 0 and an integer ranging from 1 to 2,
$A^1$ is selected from a substituted $C_{3-14}$ hydrocarbon ring group and a substituted heterocyclic group;
$R^2$ and $R^3$ are the same or different and each is selected from
(1) a hydrogen atom,
(2) a $C_{1-6}$ alkyl group,
(3) a halogenated $C_{1-6}$ alkyl group,
and
(4) —(CH$_2$)$_p$—X$_1$—(CH$_2$)$_q$-A$^2$, provided that $R^2$ and $R^3$ are not hydrogen atoms at the same time,
wherein
p and q are the same or different and each is selected from 0 and an integer ranging from 1 to 6,
$X_1$ is selected from a single bond, a $C_{1-6}$ alkylene group, a $C_{2-6}$ alkenylene group, a $C_{2-6}$ alkynylene group, —O—, —N(R$^7$)—, —S(O)$_{m2}$—, —CO—, —CON(R$^7$)—, —N(R$^7$)CO—, —SO$_2$N(R$^7$)—, —N(R$^7$)SO$_2$—, —N(R$^7$)CON(R$^8$)—, —N(R$^7$)SO$_2$N(R$^8$)—, —OCON(R$^7$)— and —N(R$^7$)COO—,
wherein
$R^7$ and $R^8$ are the same or different and each is selected from a hydrogen atom and a $C_{1-6}$ alkyl group,
m2 is selected from 0 and an integer ranging from 1 to 2,
r is selected from 0 and an integer ranging from 1 to 2, and $A^2$ is selected from an optionally substituted $C_{3-14}$ hydrocarbon ring group and an optionally substituted heterocyclic group; and
$R^4$ is selected from
(1) —CO$_2$R$^9$$_1$,
(2) —C(O)NHOR$^9$,
(3) —C(O)NH—SO$_2$—R$^9$,
(4) —C(O)NHR$^9$,
(5) —SH,
(6) —CH$_2$CO$_2$R$^9$,
(7) —C(O)R$^9$,
(8) —N(OH)COR$^9$,
(9) —SN$_2$H$_2$R$^9$$_1$,
(10) —SONHR$^9$,
(11) —CH$_2$CO$_2$H,
(12) —PO(OH)$_2$,
(13) —PO(OH)NHR$^9$,
(14) —CH$_2$SH
and
(15) —CH$_2$OH
wherein
$R^9$ is selected from a hydrogen atom, an optionally substituted $C_{1-10}$ alkyl group and an optionally substituted $C_{6-14}$ aryl-$C_{1-6}$ alkyl group.

In some embodiments of the inventive compounds of formula (1'), $R^1$ is —(CH$_2$)$_m$—X—(CH$_2$)$_n$-A$^1$ wherein each symbol is as defined above.

m and n are the same or different and each is selected from 0 and an integer ranging from 1 to 2, preferably 0.

X is for example a single bond.

$A^1$ is for example
(1) an optionally substituted fused $C_{6-14}$ hydrocarbon ring group;
such as an optionally substituted 9H-fluorenyl or an optionally substituted 9-oxo-9H-fluorenyl. The substituent thereof is for example at least one halogen atom (e.g., a chlorine atom, a bromine atom, a fluorine atom), and the number of substituents is for example 1. Examples thereof include 9H-fluoren-2-yl, 9-oxo-9H-fluoren-2-yl, 7-bromo-9H-fluoren-2-yl, 7-fluoro-9H-fluoren-2-yl, 7-chloro-9H-fluoren-2-yl and the like.
(2) an optionally substituted fused heterocyclic group;
such as an optionally substituted benzofuranyl or optionally substituted dibenzofuranyl. The substituent thereof is for example at least one halogen atom (e.g., a chlorine atom), and the number of substituents is for example 1. Examples thereof include 2-benzofuran-2-yl, dibenzofuran-2-yl, dibenzofuran-3-yl, 7-chloro-dibenzofuran-3-yl, 8-chloro-dibenzofuran-3-yl and the like. or
(3) —V—W-Z, wherein each symbol is as defined above.
The optionally substituted $C_{3-14}$ hydrocarbon ring group at V is for example a $C_{6-14}$ aryl group (e.g., phenyl).
The optionally substituted heterocyclic group at V is for example an optionally substituted saturated monocyclic heterocyclic group (e.g., piperazinyl) or an optionally substituted unsaturated monocyclic heterocyclic group (e.g., thienyl, methylthienyl, pyrazolyl, thiazolyl). The substituent thereof is for example a $C_{1-6}$ alkyl group (e.g., methyl).
t and u at W represented by —(CH$_2$)t-X$_2$—(CH$_2$)$_u$— are for example the same or different and each is 0 or an integer ranging from 1 to 2, more preferably 0.
The $X_2$ at W is for example selected from a single bond, a $C_{2-6}$ alkynylene group and —O—, preferably a single bond.
The $C_{2-6}$ alkynylene group at $X_2$ is for example ethynylene.

Z is for example selected from an optionally substituted $C_{1-6}$ alkyl group, a halogen atom, an optionally substituted $C_{3-14}$ hydrocarbon ring group and an optionally substituted heterocyclic group.

The optionally substituted $C_{1-6}$ alkyl group at Z is for example selected from a $C_{1-6}$ alkyl group substituted by a hydroxyl group (e.g., 1-hydroxyethyl).

The halogen atom at Z is for example selected from a chlorine atom, a bromine atom and a fluorine atom.

The optionally substituted $C_{3-14}$ hydrocarbon ring group at Z is for example selected from an optionally substituted $C_{6-14}$ aryl group, such as phenyl. The substituent thereof is for example selected from a halogen atom (e.g., a chlorine atom, a bromine atom), a $C_{1-6}$ alkoxy group (e.g., methoxy) and a di($C_{1-6}$ alkyl)amino group (e.g., dimethylamino), and the number of the substituent is for example 1 or 2. Examples thereof include phenyl, chlorophenyl (e.g., 2-chlorophenyl, 3-chlorophenyl, 4-chlorophenyl), dichlorophenyl (e.g., 2,4-dichlorophenyl, 3,4-dichlorophenyl), bromophenyl, methoxyphenyl (e.g., 4-methoxyphenyl), dimethylaminophenyl and the like.

The optionally substituted heterocyclic group at Z is for example selected from an optionally substituted unsaturated monocyclic heterocyclic group (e.g., 1,2,4-oxadiazolyl, 1,3,4-oxadiazolyl, tetrazolyl, thiophenyl, thiazolyl, pyridazinyl, isooxazolyl, pyridyl). The substituent thereof is for example selected from a halogen atom (e.g., a chlorine atom, a bromine atom), a $C_{1-6}$ alkyl group (e.g., methyl, ethyl, propyl, isopropyl), a halogenated $C_{1-6}$ alkyl group (e.g., trifluoromethyl, pentafluoroethyl), a $C_{1-6}$ alkoxy group (e.g., methoxy), a di($C_{1-6}$ alkyl)amino group (e.g., dimethylamino), a carboxyl group and a $C_{6-14}$ aryl group (e.g., phenyl), and the number of substituents is for example 1 or 2. Examples thereof include 5-trifluoromethyl-1,2,4-oxadiazol-3-yl, 5-pentafluoroethyl-1,2,4-oxadiazol-3-yl, 5-methyl-1,2,4-oxadiazol-3-yl, 5-phenyl-1,2,4-oxadiazol-3-yl, 5-phenyl-1,3,4-oxadiazol-2-yl, 2-methyl-2H-tetrazol-5-yl, 2-ethyl-2H-tetrazol-5-yl, 2-propyl-2H-tetrazol-5-yl, 2-isopropyl-2H-tetrazol-5-yl, thiophen-2-yl, thiophen-3-yl, 4-methyl-thiophen-2-yl, 5-carboxy-thiophen-2-yl, 2-ethyl-thiazol-4-yl, 2-methyl-thiazol-4-yl, 6-chloro-pyridazin-3-yl, isoxazol-3-yl, 5-trifluoromethyl-isoxazol-3-yl, 5-chloro-pyridin-2-yl and the like.

In some embodiments of the inventive compounds of formula (1'), $R^2$ and $R^3$ are the same or different and each is selected from a hydrogen atom, a $C_{1-6}$ alkyl group and —$(CH_2)_p$—$X_1$—$(CH_2)_q$-$A^2$, in one embodiment, one of them is a hydrogen atom or a $C_{1-6}$ alkyl group, and the other is —$(CH_2)_p$—$X_1$—$(CH_2)_q$-$A^2$.

The $C_{1-6}$ alkyl group at $R^2$ and $R^3$ is for example methyl.

p and q are the same or different and each is for example selected from 0 and an integer ranging from 1 to 2, preferably 0.

$X_1$ is for example a single bond.

$A^2$ is for example (1) an optionally substituted fused $C_{6-14}$ hydrocarbon ring group;

such as an optionally substituted 9H-fluorenyl or an optionally substituted 9-oxo-9H-fluorenyl. The substituent thereof is for example at least one halogen atom (e.g., a chlorine atom, a bromine atom, a fluorine atom), and the number of substituents is for example 1. Examples thereof include 9H-fluoren-2-yl, 9-oxo-9H-fluoren-2-yl, 7-bromo-9H-fluoren-2-yl, 7-fluoro-9H-fluoren-2-yl, 7-chloro-9H-fluoren-2-yl and the like.

(2) an optionally substituted fused heterocyclic group;

such as an optionally substituted tetrahydroisoquinolyl. The substituent thereof is for example selected from a $C_{1-6}$ alkyl group (e.g., methyl, isopropyl) and a $C_{1-6}$ alkyl group substituted by a $C_{6-14}$ aryl group (e.g., benzyl), and the number of substituents is for example 1. Examples thereof include 2-methyl-1,2,3,4-tetrahydroisoquinolin-7-yl, 2-isopropyl-1,2,3,4-tetrahydroisoquinolin-7-yl, 2-benzyl-1,2,3,4-tetrahydroisoquinolin-7-yl and the like. or (3) —$V^1$—$W^1$-$Z^1$ $V^1$ is an optionally, substituted $C_{3-14}$ hydrocarbon ring group or an optionally substituted heterocyclic group;

$W^1$ is —$X_3$—$(CH_2)_{t1}$—$X_4$—$(CH_2)_{u1}$— wherein t1 and u1 are the same or different and each is selected from 0 and an integer ranging from 1 to 6, $X_3$ and $X_4$ are the same or different and each is selected from a single bond, a $C_{1-6}$ alkylene group, a $C_{2-6}$ alkenylene group, a $C_{2-6}$ alkynylene group, —O—, —N($R^{12}$)—, —S(O)$_{m4}$—, —CO—, —CON($R^{12}$)—, —N($R^{12}$)CO—, —SO$_2$N($R^{12}$)—, —N($R^{12}$)SO$_2$—, —N($R^{12}$)CON($R^{13}$)—, —N($R^{12}$)SO$_2$N($R^{13}$)—, —OCON($R^{12}$)— and —N($R^{12}$)COO—, wherein $R^{12}$ and $R^{13}$ are the same or different and each is selected from a hydrogen atom and a $C_{1-6}$ alkyl group, and m4 is selected from 0 and an integer ranging from 1 to 2, and $Z^1$ is selected from an optionally substituted $C_{1-6}$ alkyl group, a halogen atom, a nitro group, a cyano group, a $C_{1-6}$ alkoxy group, a hydroxyl group, a halogenated $C_{1-6}$ alkyl group, a halogenated $C_{1-6}$ alkoxy group, a carboxyl group, a $C_{1-6}$ alkoxy-carbonyl group, an amino group, a mono($C_{1-6}$ alkyl)amino group, a di($C_{1-6}$ alkyl)amino group, an optionally substituted $C_{3-14}$ hydrocarbon ring group and an optionally substituted heterocyclic group.

The optionally substituted $C_{3-14}$ hydrocarbon ring group at $V^1$ is preferably an optionally substituted $C_{6-14}$ aryl group (for example phenyl) or a $C_{3-8}$ cycloalkyl group (for example cyclohexyl).

The optionally substituted heterocyclic group at $V^1$ is for example optionally substituted saturated monocyclic heterocyclic group (e.g., piperidinyl).

t1 and u1 at $W^1$ are the same or different and each is for example selected from 0 and an integer ranging from 1 to 2, preferably 0.

$X_3$ and $X_4$ at $W^1$ are the same or different and each is for example selected from a single bond, —O—, —CO—, —N($R^{12}$)—, —CON($R^{12}$)—, —N($R^{12}$)CO—, —N($R^{12}$)SO$_2$— and —N($R^{12}$)COO—, wherein $R^{12}$ is for example selected from a hydrogen atom and methyl.

$Z^1$ is for example selected from an optionally substituted $C_{1-6}$ alkyl group, a halogen atom, a nitro group, a hydroxyl group, a halogenated $C_{1-6}$ alkyl group, an amino group, a di($C_{1-6}$ alkyl)amino group, an optionally substituted $C_{3-14}$ hydrocarbon ring group and an optionally substituted heterocyclic group.

The optionally substituted $C_{1-6}$ alkyl group at $Z^1$ is for example methyl or isobutyl.

The halogen atom at $Z^1$ is for example a bromine atom.

The $C_{1-6}$ alkoxy group at $Z^1$ is for example tert-butoxy.

The halogenated $C_{1-6}$ alkyl group at $Z^1$ is for example trifluoromethyl.

The di($C_{1-6}$ alkyl)amino group at $Z^1$ is for example dimethylamino.

The optionally substituted $C_{3-14}$ hydrocarbon ring group at $Z^1$ is for example an optionally substituted $C_{6-14}$ aryl group, for example phenyl. The substituent thereof is for example at least one halogen atom (e.g., a chlorine atom), and the number of substituents is for example 1. Examples thereof include phenyl, 4-chlorophenyl and the like.

The optionally substituted heterocyclic group at Z, is for example selected from an optionally substituted saturated monocyclic heterocyclic group and an optionally substituted unsaturated monocyclic heterocyclic group.

The optionally substituted saturated monocyclic heterocyclic group at Z, is for example selected from an optionally substituted piperidinyl group, an optionally substituted pyrrolidinyl group, an optionally substituted morpholinyl group and an optionally substituted piperazinyl group. The substituent thereof is for example selected from a $C_{1-6}$ alkyl group (e.g., methyl) and $C_{1-6}$ alkoxy-carbonyl group (e.g., tert-butoxycarbonyl group), and the number of substituents is for example 1. Examples thereof include 1-methyl-piperidin-4-yl, 1-tert-butoxycarbonyl group-piperidin-4-yl, pyrrolidin-1-yl, morpholin-4-yl, 4-methyl-piperazin-1-yl and the like.

The optionally substituted saturated monocyclic heterocyclic group at $Z^1$ is for example selected from an optionally substituted pyridyl group, an optionally substituted pyrazolyl group and an imidazolyl group. The substituent thereof is for example a $C_{1-6}$ alkyl group (e.g., methyl), and the number of substituents is for example 1. Examples thereof include pyridin-3-yl, pyrazol-1-yl, 3H-imidazol-4-yl, 1H-imidazol-2-yl, 1-methyl-1H-imidazol-2-yl and the like.

In the compounds represented by the formula (1'), $R^4$ is for example selected from —$CO_2R^9$ and —$C(O)NHOR^9$, such as —$CO_2R^9$ wherein $R^9$ is for example a hydrogen atom.

The "pharmaceutically acceptable salt" may be any as long as it forms a non-toxic salt with a compound of the above-mentioned formula (1). Such salt can be obtained by reacting the compound with an inorganic acid such as hydrochloric acid, sulfuric acid, phosphoric acid, hydrobromic acid and the like; or an organic acid such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid and the like; or an inorganic bases such as sodium, potassium, lithium, calcium, magnesium, ammonium and the like; or an organic bases such as methylamine, diethylamine, triethylamine, triethanolamine, ethylenediamine, tris(hydroxymethyl)methylamine, guanidine, choline, cinchonine N-methyl-D-glucamine and the like; or an amino acid such as lysine, histidine, arginine, alanine and the like. The present invention encompasses water-retaining product, hydrate and solvate of each compound.

The compounds of the above-mentioned formula (1) have various isomers. For example, E compound and Z compound are present as geometric isomers, and when the compound has an asymmetric carbon, an enantiomer and a diastereomer are present due to the asymmetric carbon. A tautomer may be also present. The present invention encompasses all of these isomers and mixtures thereof.

The present invention also encompasses prodrug and metabolite of the compound represented by the formula (1).

The "prodrug" means a derivative having a chemically modified drug molecule, which does not show physiological activity by itself, but which shows inherent efficacy by reverting to the original compound in a body after administration. The "prodrug" in the present invention means a derivative of cyclopropane compound (1) having a group capable of chemical or metabolic decomposition and showing a pharmaceutical activity by hydrolysis or solvolysis or by decomposition under physiological condition. For example, those wherein a hydroxyl group of the compound is substituted by —CO-alkyl group, —$CO_2$-alkyl group, —CONH-alkyl group, —CO-alkenyl, —$CO_2$-alkenyl, —CONH-alkenyl, —CO-aryl group, —$CO_2$-aryl group, —CONH-aryl group, —CO-heterocyclic ring, —$CO_2$-heterocyclic ring, —CONH-heterocyclic ring (the alkyl group, alkenyl, aryl group, heterocyclic ring are optionally substituted by halogen atom, alkyl group, hydroxyl group, alkoxy group, carboxyl group, amino group, amino acid residue, —$PO_3H_2$, —$SO_3H$, —$OPO_3H_2$, —$OSO_3H$, and the like.), or —CO-polyethylene glycol residue, —$CO_2$-polyethylene glycol residue, —CO-polyethylene glycol mono alkyl ether residue, —$CO_2$-polyethylene glycol mono alkyl ether residue, —$PO_3H_2$, saccharides (e.g., glucose), or other known macromolecule for a prodrug and the like;

those wherein an amino group of the compound is substituted by —CO-alkyl group, —$CO_2$-alkyl group, —CO-alkenyl, —$CO_2$-alkenyl, —$CO_2$-aryl group, —CO-aryl group, —CO-heterocyclic ring, —$CO_2$-heterocyclic ring (the alkyl group, alkenyl, aryl group, heterocyclic ring are optionally substituted by halogen atom, alkyl group, hydroxyl group, alkoxy group, carboxyl group, amino group, amino acid residue, —$PO_3H_2$, —$SO_3H$, —$OPO_3H_2$, —$OSO_3H$, and the like.), or —CO-polyethylene glycol residue, —$CO_2$-polyethylene glycol residue, —CO-polyethylene glycol mono alkyl ether residue, —$CO_2$-polyethylene glycol mono alkyl ether residue, —$PO_3H_2$, saccharides (e.g., glucose), or other known macromolecule for a prodrug and the like; and those wherein a carboxyl group of the compound is substituted by alkoxy group, aryloxy group (the alkoxy group, aryloxy group are optionally substituted by halogen atom, alkyl group, hydroxyl group, alkoxy group, carboxyl group, amino group, amino acid residue, —$PO_3H_2$, —$SO_3H$, —$OPO_3H_2$, —$OSO_3H$, and the like.), or polyethylene glycol residue, polyethylene glycol mono alkyl ether residue, saccharides (e.g., glucose), or other known macromolecule for a prodrug and the like are mentioned as examples of embodiments of the present invention.

These prodrugs can be produced, for example, according to a method known per se by one of skill in the pertinent field, such as esterification, acylation, alkoxycarbonylation, and the like.

When the inventive compound is used as a pharmaceutical preparation, the inventive compound is generally admixed with pharmaceutically acceptable carriers, excipients, diluents, fillers, disintegrators, stabilizers, preservatives, buffers, emulsifiers, aromatics, coloring agents, sweeteners, thickeners, correctives, solubilizers, and other additives such as water, vegetable oil, alcohol such as ethanol, benzyl alcohol and the like, polyethylene glycol, glycerol triacetate, gelatin, lactose, carbohydrate such as starch and the like, magnesium stearate, talc, lanolin, petrolatum and the like, and prepared into a dosage form, for example, of tablets, pills, powders, granules, suppositories, injections, eye drops, liquids, capsules, troches, aerosols, elixirs, suspensions, emulsions, syrups and the like, which can be administered systemically or topically and orally or parenterally.

While the dose of the inventive compound varies depending on the age, body weight, general condition, treatment effect, administration route and the like, it is generally from 1 mg to 1000 mg for an adult per dose, which is given one to several times a day.

The inventive compound (1) can be administered to mammals (human, mouse, rat, rabbit, dog, cat, cattle, pig, monkey, etc.) as an aggrecanase inhibitor, an MMP inhibitor, a prophylactic or therapeutic agent for osteoarthritis (OA), a prophylactic or therapeutic agent for rheumatoid arthritis (RA), a prophylactic or therapeutic agent for a disorder mediated by aggrecanase, such as joint injury, reactive arthritis, cancer, asthma, allergic reaction, chronic pulmonary emphysema, fibroid lung, acute respiratory distress (ARDS), lung infection, interstitial pneumonia, bone resorption disorder, and the like.

The compound (1) of the present invention can be administered to mammals along with other therapeutic agents for osteoarthritis, for the purpose of prevention or treatment of osteoarthritis. The compound (1) of the present invention can be also administered to mammals along with other therapeutic agents for rheumatoid arthritis, for the purpose of prevention or treatment of rheumatoid arthritis.

"Prevention" include, for example, both preventing recurrence of the disease and preventing initial occurrence of the disease.

In the case of combined administration, the compound of the present invention can be administered simultaneously with other therapeutic agents for osteoarthritis or other therapeutic agents for rheumatoid arthritis (hereinafter combination drug) or administered at certain time intervals. In the case of combined administration, a pharmaceutical composition containing the compound of the present invention and a combination drug can be administered. Alternatively, a pharmaceutical composition containing the compound of the present invention and a pharmaceutical composition containing a combination drug may be administered separately. The administration route may be the same or different.

In the case of a combined administration, the compound of the present invention can be administered once a day or several times a day in a single dose of 1 mg to 1000 mg, or may be administered in a smaller dose. The combination drug can be administered in a dose generally used for the prevention or treatment of osteoarthritis or rheumatoid arthritis or in a smaller dose.

In addition, a compound having aggrecanase inhibitory activity or MMP inhibitory activity as does the compound (1) of the present invention, a prodrug thereof and a pharmaceutically acceptable salt thereof can be used as prophylactic or therapeutic agents for diseases mediated by aggrecanase, such as osteoarthritis, rheumatoid arthritis, and the like.

Examples of the production method of the compound (1) of the present invention are given in the following. However, the production method of the compound of the present invention is not limited to these examples.

It is also possible to previously protect, as necessary, the functional groups other than those involved in the reactions to be mentioned below, and to deprotect them at a later stage.

The treatment after reaction in each step may be a conventional one, for which typical methods, such as isolation and purification, crystallization, recrystallization, column chromatography, preparative HPLC and the like, can be appropriately selected and combined.

The compound (2), which is a starting material in the following production methods, is commercially available or can be easily synthesized by a method known per se by one of skill in the art.

Production Method 1

This production method is a production method for compound (1) wherein $R^2$ is a hydrogen atom and $R^4$ is a hydroxyl group or a hydroxyamino group.

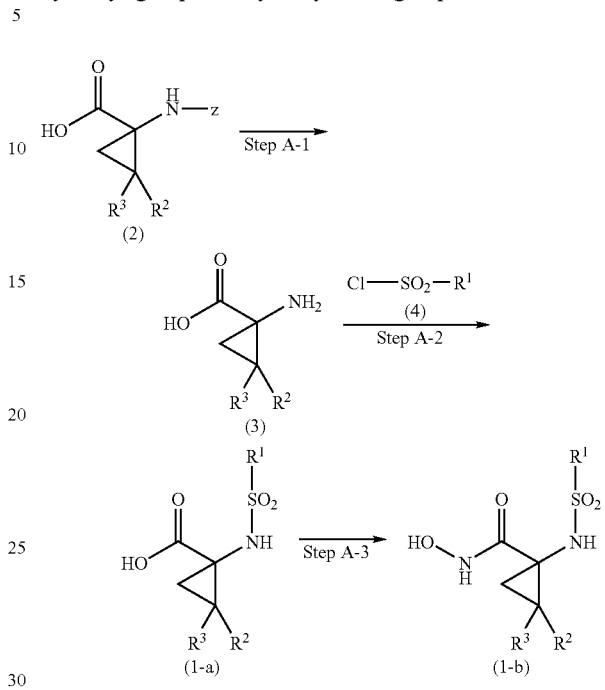

wherein $R^1$ and $R^3$ are as defined above and Z is a protective group of amino group (e.g., benzyloxycarbonyl, tert-butoxycarbonyl, etc.)

Step A-1

General deprotection is performed. A compound of the formula (2) is reacted in the presence of an acid in a solvent to give a compound of the formula (3).

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, dichloroethane, etc.; ester solvents such as ethyl acetate, methyl acetate, butyl acetate, etc.; polar solvents such as acetone, N,N-dimethylformamide, etc.; etc. can be mentioned, which may be used alone or in combination. A preferable solvent in this reaction is dioxane.

As the acid to be used for the reaction is, for example, inorganic acids such as hydrochloric acid, sulfuric acid, nitric acid, etc.; and organic acids such as trifluoroacetic acid, trichloroacetic acid, acetic acid, methanesulfonic acid, p-toluenesulfonic acid, etc. can be mentioned, with preference given to hydrochloric acid.

The reaction temperature is generally −30° C. to 60° C., preferably 0° C. to room temperature.

The reaction time is generally 1 hr to 24 hr, preferably 2 hr to 12 hr.

The obtained compound (3) can be used in the next reaction without isolation.

Step A-2

General sulfonylation is performed. A compound of the formula (3) is reacted with a compound of the formula (4) in a solvent in the presence of a base to give a compound of the formula (1-a), which is one of the objective compounds.

As the base to be used for the reaction is, for example, alkali metal hydrides such as sodium hydride, potassium hydride, etc.; alkali metal carbonates such as sodium carbonate, potassium carbonate, cesium carbonate, sodium hydrogen carbonate, potassium hydrogen carbonate, etc.; alkali metal carboxylates such as sodium acetate, potassium acetate, etc.; alkali metal phosphate such as sodium phosphate, potassium phosphate, etc.; organic bases such as triethylamine, diisopropylethylamine, pyridine, N-methylmorpholine, N,N-dimethylaminopyridine, etc. can be mentioned, with preference given to triethylamine and N,N-dimethylaminopyridine.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, dichloroethane, etc.; ester solvents such as ethyl acetate, methyl acetate, butyl acetate, etc.; polar solvents such as acetone, N,N-dimethylformamide, water, etc.; etc. can be mentioned, which may be used alone or in combination. A preferable solvent in this reaction is a mixed solvent of dioxane and water.

The reaction temperature is generally −30° C. to 60° C., preferably 0° C. to room temperature.

The reaction time is generally 2 hr to 24 hr, preferably 4 hr to 12 hr.

Step A-3

General amidation is performed. A compound of the formula (1-a) is reacted with a hydroxyamine derivative using a condensing agent in a solvent in the presence of a base to give a compound of the formula (1-b), which is one of the objective compounds.

As the base to be used for the reaction, for example, alkali metal carbonates such as sodium carbonate, potassium carbonate, cesium carbonate, sodium hydrogen carbonate, potassium hydrogen carbonate, etc.; alkali metal carboxylates such as sodium acetate, potassium acetate, etc.; alkali metal phosphates such as sodium phosphate, potassium phosphate, etc.; and organic bases such as triethylamine, diisopropylethylamine, pyridine, N-methylmorpholine, etc. can be mentioned, with preference given to N-methylmorpholine.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, dichloroethane, etc.; ester solvents such as ethyl acetate, methyl acetate, butyl acetate, etc.; and polar solvents such as acetone, N,N-dimethylformamide, acetonitrile, etc.; etc. can be mentioned, which may be used alone or in combination. Preferable solvents in this reaction are tetrahydrofuran and N,N-dimethylformamide.

As the condensing agent, any condensing agent used for general peptide condensation method (e.g., acid chloride method, mixed acid anhydride method, etc.) can be used, with preference given to a combination of ethyl chlorocarbonate and N-methylmorpholine.

As the hydroxyamine derivative to be used for the reaction, for example, O-(trimethylsilyl)hydroxylamine, etc. can be mentioned.

The reaction temperature is generally 0° C. to 100° C., preferably room temperature to 60° C.

The reaction time is generally 1 hr to 24 hr, preferably 2 hr to 12 hr.

Production Method 2

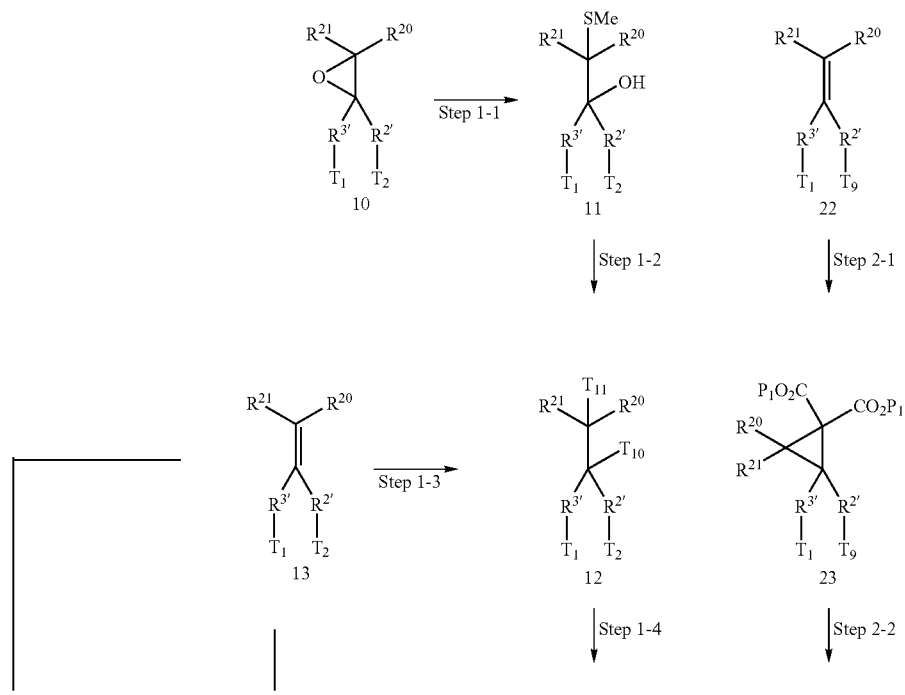

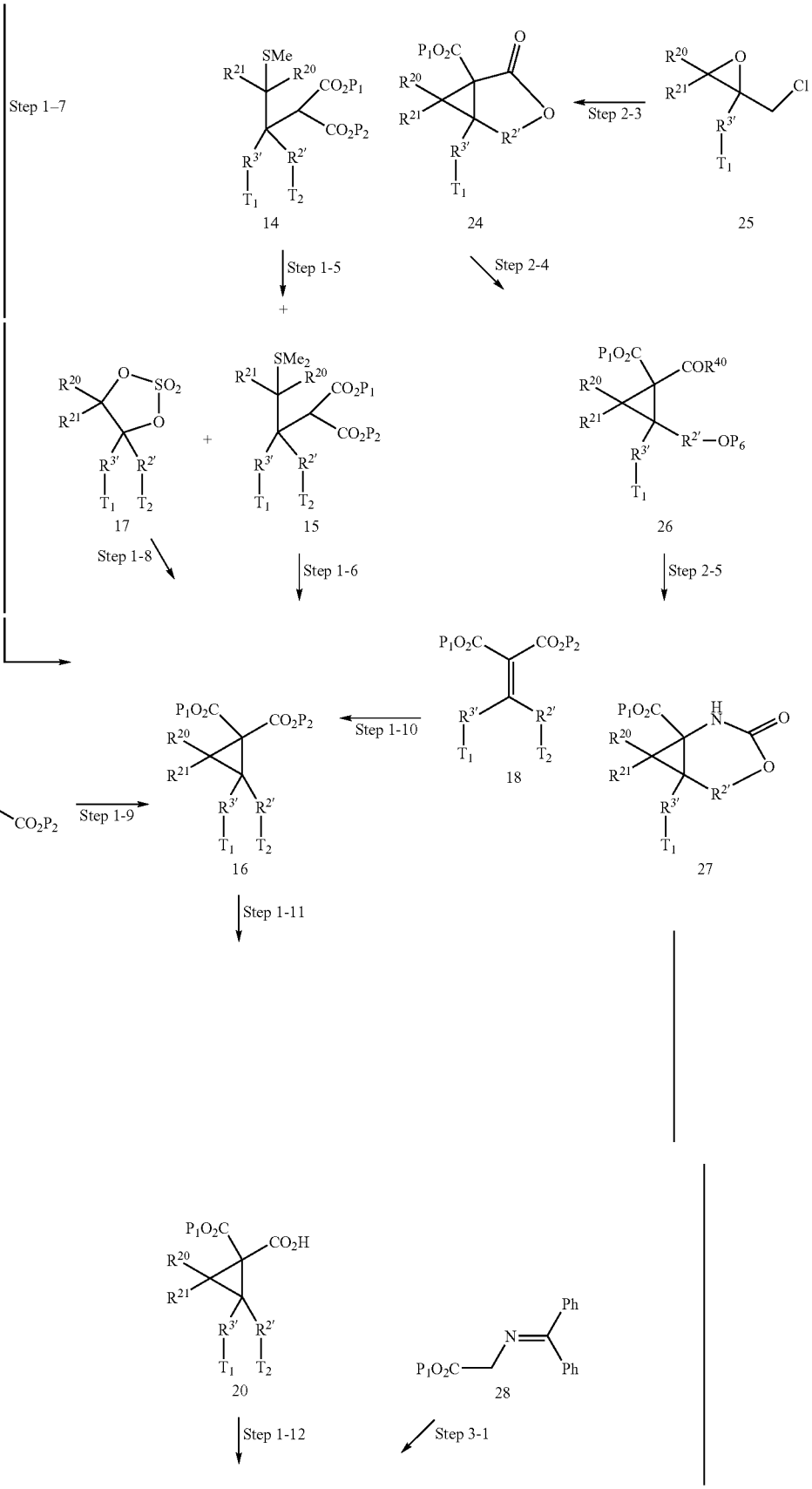

-continued
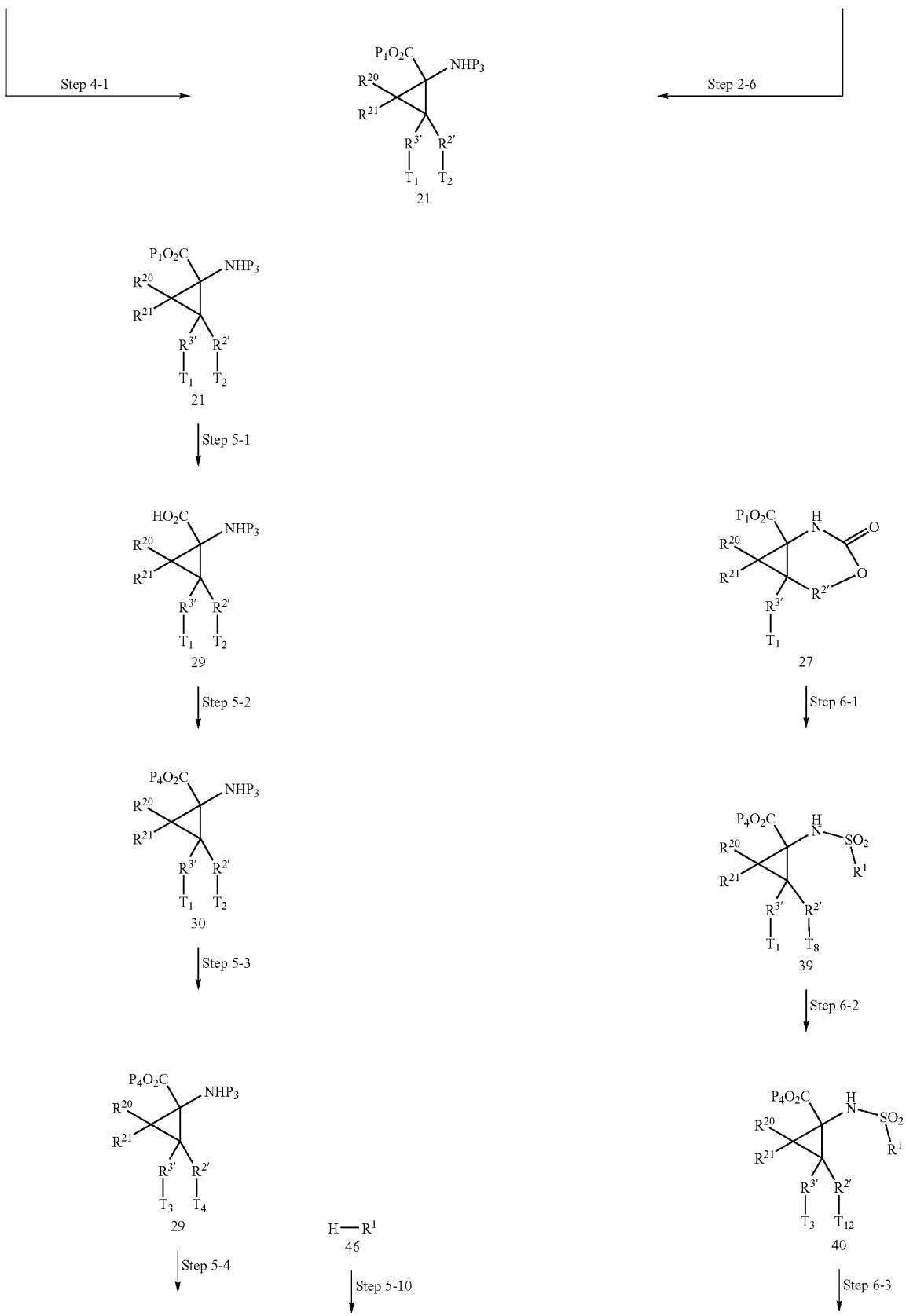

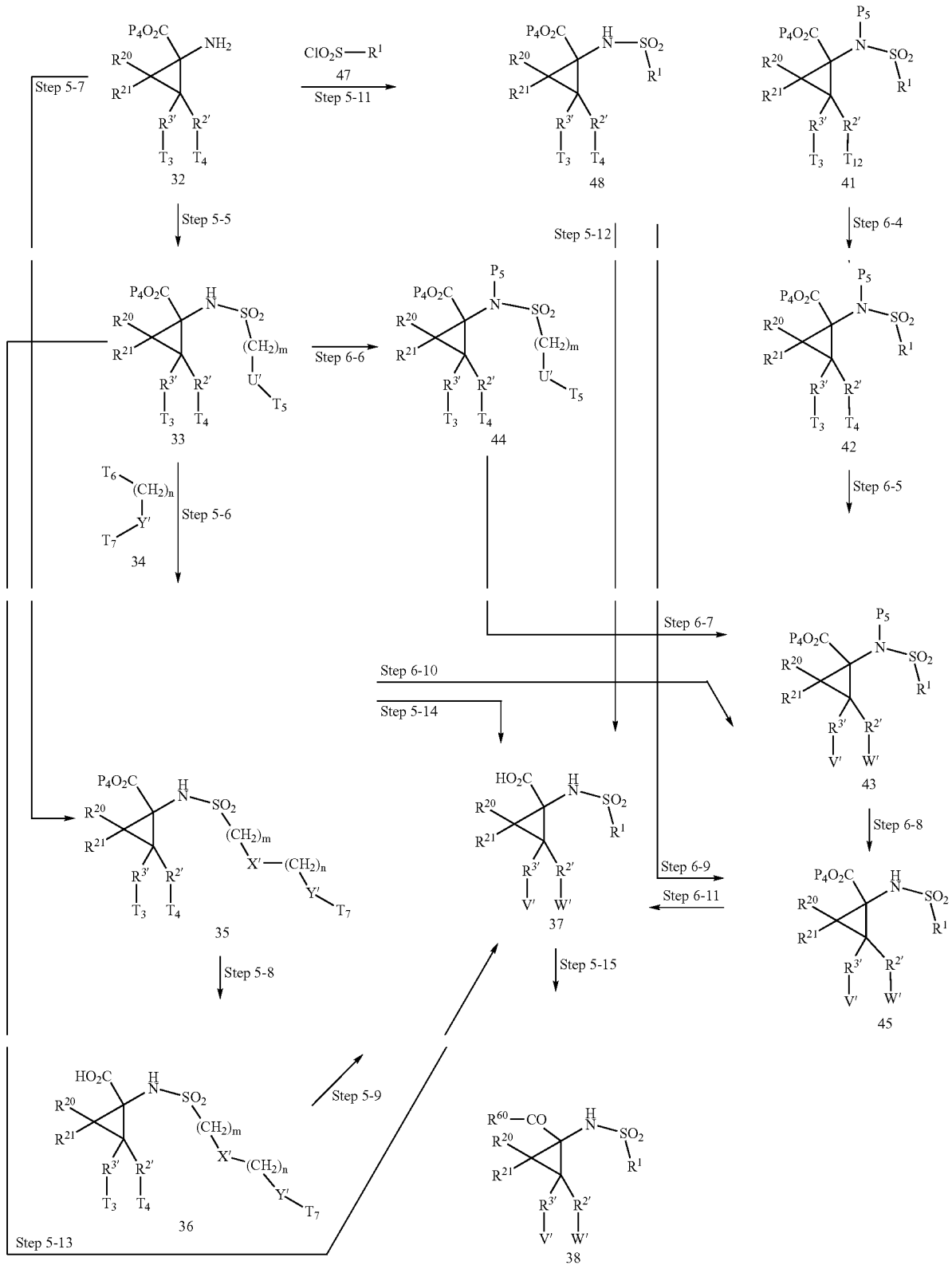

wherein as $R^2$, the same substituents as for $R^2$ can be mentioned;

as $R^3$, the same substituents as for $R^3$ can be mentioned;

$R^{40}$ is an amino group or a hydroxy group;

$R^{60}$ is —$OR^9$, —$NHOR^9$, —$NH$—$SO_2$—$R^9$, —$NHR^9$ or —$R^9_1$, wherein $R^9$ is as defined above (provided that when $R^{60}$ is —$OR^9$, then $R^9$ should not be a hydrogen atom);

U', X' and Y' are the same or different and each is an optionally substituted $C_{3-14}$ hydrocarbon ring group or an optionally substituted heterocyclic group;

$T_1$, $T_2$, $T_3$, $T_4$, $T_5$, $T_6$, $T_7$, $T_8$, $T_9$, $T_{10}$, $T_{11}$, $T_{12}$, V' and W' are substituents to be used for subsequent conversion of functional group and, for example, a hydrogen atom, an alkyl group, a halogen atom, a haloalkyl group, an amino group, a hydroxyl group, a formyl group, an alkylcarbonyl group, an alkylboranyl group, an alkoxyboranyl group, a hydroxyboranyl group, a methylthio group, a benzenesulfonyloxy group, a p-toluenesulfonyloxy group, a methanesulfonyloxy group, a trifluoromethanesulfonyloxy group, a nitro group, a cyano group, an alkoxycarbonyl group, an amido group, an azido group, an alkoxy group, a carboxyl group, etc. can be mentioned, and when conversion of functional group is not necessary, $T_1$, $T_2$, $T_3$ and $T_4$ remain in V' or W' in the molecule of the compound of the claim;

$P_1$, $P_2$ and $P_4$ are conventional protecting groups of carboxyl group, and as the protecting group, for example, a methyl group, an ethyl group, a t-butyl group, a benzyl group, a p-methoxybenzyl group, an allyl group, a t-butyldimethylsilyl group, etc. can be mentioned, wherein, depending on the step, $P_4$ may be a hydrogen atom;

$P_3$ is a conventional protecting group of amino group, and as the protecting group, a t-butoxycarbonyl group, a benzyloxycarbonyl group, a 9-fluorenylmethoxycarbonyl group, etc. can be mentioned, wherein, depending on the step, $P_3$ may be a hydrogen atom;

$P_5$ is an alkyl type protecting group of nitrogen atom, and an allyl group, a trichloroethyl group, a trimethylsilylethyl group, a benzyl group and a p-methoxybenzyl group can be mentioned, wherein, depending on the step, $P_5$ may be a hydrogen atom.;

$P_6$ is a conventional protecting group of a hydroxyl group, and as the protecting group, for example, ethers such as a tetrahydropyranyl group, a benzyl group, a methoxymethyl group, a benzyloxymethyl group, a trimethylsilylethyloxymethyl group, etc.; esters such as a pivaloyl group, an acetyl group, a benzoyl group, etc.; silyl ether protecting groups such as a trimethylsilyl group, a t-butyldimethylsilyl group, a t-butyldiphenylsilyl group, etc.; etc. can be mentioned, wherein, depending on the step, $P_6$ may be a hydrogen atom.

Step 1-1

In this Step, the epoxide of the formula 10 is reacted with MeSH in the presence of a base to give an alcohol of the formula 11. For the reaction, a base is used, but an alkali metal salt of MeSH such as sodium thiomethoxide can be also used.

As the base, for example, alkyl lithiums such as butyl lithium, t-butyl lithium, s-butyl lithium, etc.; alkali metal hydrides such as sodium hydride, potassium hydride, etc.; metal alcoholates such as potassium t-butoxide, sodium ethoxide, sodium methoxide, etc.; alkali metal amides such as lithium diisopropylamide, sodium bis(trimethylsilyl)amide, lithium bis(trimethylsilyl)amide, etc.; alkali metal carbonates such as sodium carbonate, potassium carbonate, sodium hydrogen carbonate, potassium hydrogen carbonate, etc.; alkali metal hydroxides such as lithium hydroxide, sodium hydroxide, potassium hydroxide, etc.; alkali metal carboxylate such as sodium acetate, potassium acetate, etc.; alkali metal phosphates such as sodium phosphates, potassium phosphates, etc.; organic bases such as triethylamine, pyridine, N-methylmorpholine, 2,6-lutidine, 1,8-diazabicyclo[5.4.0]undec-7-ene, etc.; etc. can be mentioned, with preference given to alkali metal hydroxide.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is alcohol solvent, and a mixed solvent of methanol and water is more preferable.

The reaction temperature is generally 0° C. to 100° C., preferably room temperature to 80° C.

The reaction time is 1 hr to 48 hr, preferably 1 hr to 12 hr.

Thus obtained compound of the formula 11 can be used in the next reaction without isolation.

Step 1-2

In this Step, the alcohol of the formula 11 obtained in Step 1-1 is converted to a halide or sulfonate of the formula 12.

Either $T_{10}$ or $T_{11}$ of compound 12 obtained by this Step is a methylthio group (MeS group), and one of $T_{10}$ and $T_{11}$ is a leaving groups such as Cl, Br, I, OMs, OTs, $OSO_2Ph$, OTf, etc. Depending on the substituents $R^{2'}$, $R^{3'}$, $R^{20}$, $R^{21}$, $T_1$ and $T_2$, compound 12 becomes a mixture of isomers. For example, when the alcohol of the formula 11 is converted into a compound of formula 12 wherein one of $T_{11}$ and $T_{10}$ is Cl, the reagent to be used for this Step includes thionyl chloride, phosphorous oxychloride, phosphorus pentachloride, hydrogen chloride and the like, with preference given to thionyl chloride. In this case, the reaction can be also carried out in the presence of a base.

As the base, organic bases such as triethylamine, pyridine, N-methylmorpholine, 2,6-lutidine, 1,8-diazabicyclo[5.4.0]undec-7-ene, etc.; etc. can be mentioned, with preference given to pyridine.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, acetonitrile, etc.; etc. can be mentioned, which may be used alone or in combination. A preferable solvent in this reaction is hydrocarbon solvent, and toluene is more preferable.

The reaction temperature is generally −20° C. to 50° C., preferably 0° C. to room temperature.

The reaction time is 1 hr to 48 hr, preferably 1 hr to 6 hr.

Thus obtained compound of the formula 12 can be used in the next reaction without isolation.

When one of $T_{11}$ and $T_{10}$ is sulfonate, the compound can be obtained with sulfonyl chloride in the presence of a base. As the sulfonyl chloride, methanesulfonyl chloride, p-toluenesulfonyl chloride, benzenesulfonyl chloride; etc. can be mentioned, with preference given to methanesulfonyl chloride. In this case, the reaction is carried out in the presence of a base.

As the base, organic bases such as triethylamine, pyridine, N-methylmorpholine, 2,6-lutidine, 1,8-diazabicyclo[5.4.0]undec-7-ene, etc.; etc. can be mentioned, with preference given to pyridine.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, acetonitrile, etc.; etc. can be mentioned, which may be used alone or in combination. A preferable solvent in this reaction is hydrocarbon solvent, and toluene is more preferable.

The reaction temperature is generally −20° C. to 50° C., preferably 0° C. to room temperature.

The reaction time is 1 hr to 48 hr, preferably 1 hr to 6 hr.

Thus obtained compound of the formula 12 can be used in the next reaction without isolation.

Step 1-3

In this Step, the alkene of the formula 13 is reacted with sulfenyl halide based on the method known from Synthesis (1980, 9, 690-691) to give a compound of the formula 12. For example, when methanesulfenyl chloride obtained from sulfuryl chloride and dimethyl disulfide is used as a reaction reagent, one of $T_{10}$ and $T_{11}$ in the product 12 is a methylthio group (MeS group) and one of them is Cl (leaving group). Depending on the substituent $R^{2'}$, $R^{3'}$, $R^{20}$, $R^{21}$, $T_1$ and $T_2$, compound 12 becomes a mixture of isomers.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, acetonitrile, etc.; etc. can be mentioned, which may be used alone or in combination. A preferable solvent in this reaction is ether solvent, and 1,2-dimethoxyethane is more preferable.

The reaction temperature is generally −78° C. to 50° C., preferably −50° C. to room temperature.

The reaction time is 1 hr to 48 hr, preferably 1 hr to 12 hr.

Thus obtained compound of the formula 12 can be used in the next reaction without isolation.

Step 1-4

In this Step, one of $T_{10}$ and $T_{11}$, the leaving group in the compound of the formula 14 obtained in Step 1-2 or 1-3 is substituted by a malonic acid diester based on the method known from Synthesis (1980, 9, 690-691) to give the halide of the formula 12). The reaction is carried out in the presence of a base.

As the base, for example, alkyl lithiums such as butyl lithium, t-butyl lithium, s-butyl lithium, etc.; alkali metal hydrides such as sodium hydride, potassium hydride, etc.; metal alcoholates such as potassium t-butoxide, sodiumt-butoxide, sodium ethoxide, sodium methoxide, etc.; alkali metal amides such as lithium diisopropylamide, sodium bis(trimethylsilyl)amide, lithium bis(trimethylsilyl)amide, etc.; alkali metal carbonates such as sodium carbonate, potassium carbonate, sodium hydrogen carbonate, potassium hydrogen carbonate, etc.; organic bases such as triethylamine, pyridine, N-methylmorpholine, 2,6-lutidine, 1,8-diazabicyclo[5.4.0]undec-7-ene, etc.; etc. can be mentioned. A preferable base is metal alcoholate, and when, for example, $P_1$ and $P_2$ are each ethyl, sodium ethoxide is preferable.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; alcohol solvents such as methanol, ethanol, isopropyl alcohol, t-butyl alcohol, etc.; polar solvents such as N,N-dimethylformamide, dimethyl sulfoxides such as, etc.; etc. can be mentioned, which may be used alone or in combination. A preferable solvent in this reaction is alcohol solvent, and when, for example, $P_1$ and $P_2$ are each an ethyl group, ethanol is more preferable.

The reaction temperature is generally −50° C. to 100° C., preferably 0° C. to room temperature to 50° C.

The reaction time is 1 hr to 48 hr, preferably 1 hr to 12 hr.

Thus obtained compound of the formula 14 can be used in the next reaction without isolation.

Step 1-5

In this Step, divalent sulfur in the compound of the formula 14 obtained in Step 1-4 is alkylated by a conventional method based on the method known from Synthesis (1980, 9, 690-691) to give a sulfonium salt of the formula 15). As the reagent for the sulfonium salt formation, methyl iodide, methyl p-toluenesulfonate, methyl trifluoromethanesulfonate, dimethyl sulfate; etc. can be mentioned, with preference given to dimethyl sulfate or methyl p-toluenesulfonate.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is hydrocarbon solvent, and no solvent is more preferable.

The reaction temperature is generally 0° C. to 150° C., preferably 50° C. to 120° C.

The reaction time is 1 hr to 48 hr, preferably 6 hr to 18 hr.

Thus obtained compound of the formula 15 can be used in the next reaction without isolation.

Step 1-6

In this Step, the compound of the formula 15 obtained in Step 1-5 is treated with a base to form a cyclopropane skeleton based on the method known from Synthesis (1980, 9, 690-691), thereby affording a compound of the formula 16.

As the base, for example, alkyl lithiums such as butyl lithium, t-butyl lithium, s-butyl lithium, etc.; alkali metal hydrides such as sodium hydride, potassium hydride, etc.; metal alcoholates such as potassium t-butoxide, sodium ethoxide, sodium methoxide, etc.; alkali metal amides such as lithium diisopropylamide, sodium bis(trimethylsilyl)amide, lithium bis(trimethylsilyl)amide, etc.; alkali metal carbonates such as sodium carbonate, potassium carbonate, sodium hydrogen carbonate, potassium hydrogen carbonate, etc.; alkali metal hydroxides such as lithium hydroxide, sodium hydroxide, potassium hydroxide, etc.; alkali metal carboxylates such as sodium acetate, potassium acetate, etc.; organic bases such as triethylamine, pyridine, N-methylmorpholine, 2,6-lutidine, 1,8-diazabicyclo[5.4.0]undec-7-ene, etc.; etc. can be mentioned. A preferable base is metal alcoholate and when, for example, $P_1$ and $P_2$ are both an ethyl group, sodium ethoxide is more preferable.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; alcohol solvents such as methanol, ethanol, isopropyl alcohol, t-butyl alcohol, etc.; polar solvents such as N,N-dimethylformamide, dimethyl sulfoxide, acetonitrile, etc.; etc. can be mentioned, which may be used alone or in combination. A solvent preferable for this reaction are alcohol solvents and when, for example, $P_1$ and $P_2$ are each an ethyl group, ethanol is more preferable.

The reaction temperature is generally −30° C. to 100° C., preferably 0° C. to 80° C.

The reaction time is 1 hr to 48 hr, preferably 1 hr to 12 hr.

Thus obtained compound of the formula 16 can be used in the next reaction without isolation.

Step 1-7

In this Step, the alkene of the formula 13 is reacted with bromomalonic acid diester in the presence of a catalyst and a base based on the method known from Bull. Chem. Soc. Jpn. (2, 55, 2687-2688) to give a compound of the formula 16.

As the catalyst, copper chloride, copper bromide, copper iodide, etc. can be used, with preference given to copper (II) bromide. As the base, for example, alkyl lithium such as butyl lithium, t-butyl lithium, s-butyl lithium, etc.; alkali metal hydrides such as sodium hydride, potassium hydride, etc.; metal alcoholates such as potassium t-butoxide, sodium ethoxide, sodium methoxide, etc.; alkali metal amides such as lithium diisopropylamide, sodium bis(trimethylsilyl)amide, lithium bis(trimethylsilyl)amide, etc.; alkali metal carbonates such as sodium carbonate, potassium carbonate, sodium hydrogen carbonate, potassium hydrogen carbonate, etc.; alkali metal hydroxides such as lithium hydroxide, sodium hydroxide, potassium hydroxide, etc.; alkali metal carboxylates such as sodium acetate, potassium acetate, etc.; alkali metal phosphate such as sodium phosphate, potassium phosphate, etc.; organic bases such as triethylamine, pyridine, N-methylmorpholine, 2,6-lutidine, 1,8-diazabicyclo[5.4.0]undec-7-ene, etc.; etc. can be mentioned. A preferable base is organic base, and 1,8-diazabicyclo[5.4.0]undec-7-ene is more preferable.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is hydrocarbon solvent, and toluene is more preferable.

The reaction temperature is generally −20° C. to 100° C., preferably 0° C. to room temperature.

The reaction time is 1 hr to 48 hr, preferably 6 hr to 24 hr.

Thus obtained compound of the formula 16 can be used in the next reaction without isolation.

This Step can be also achieved by a conventional method using diazomalonic acid diester or the method known from Synlett (2001, 12, 1843-1846). In the latter case, for example, a compound of the formula 16 can be also obtained by reacting the alkene of the formula 13 with bis(methoxycarbonyl) (phenyliodono)methanide in the presence of a catalyst.

As the catalyst, rhodium complexes and copper complexs can be used, with preference given to rhodium (II) acetate dimer.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is halogenated solvent, and no solvent is more preferable.

The reaction temperature is generally room temperature to 180° C., preferably 80° C. to 150° C.

The reaction time is 10 min to 48 hr, preferably 10 min to 6 hr.

Thus obtained compound of the formula 16 can be used in the next reaction without isolation.

Step 1-8

In this Step, the cyclic sulfonate of the formula 17 is reacted with malonic acid diester based on the method known from Chirality (2000, 12, 551-557) to give a compound of the formula 16.

The reaction is carried out in the presence of a base, and as the base, for example, alkyl lithiums such as butyl lithium, t-butyl lithium, s-butyl lithium, etc.; alkali metal hydride such as sodium hydride, potassium hydride, etc.; metal alcoholates such as potassium t-butoxide, sodium ethoxide, sodium methoxide, etc.; alkali metal amides such as lithium diisopropylamide, sodium bis(trimethylsilyl)amide, lithium bis(trimethylsilyl)amide, etc.; etc. can be mentioned. A preferable base is alkali metal hydride, and sodium hydride is more preferable.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; alcohol solvents such as methanol, ethanol, isopropyl alcohol, t-butyl alcohol, etc.; polar solvents such as N,N-dimethylformamide, dimethyl sulfoxide, acetonitrile, etc.; etc. can be mentioned, which may be used alone or in combination. A preferable solvent in this reaction is ether solvent, and 1,2-dimethoxyethane is more preferable.

The reaction temperature is generally 0° C. to 100° C., preferably room temperature to 50° C.

The reaction time is 1 hr to 48 hr, preferably 1 hr to 12 hr.

Thus obtained compound of the formula 16 can be used in the next reaction without isolation.

Step 1-9

In this Step, the malonic acid diester of the formula 19, which has a double bond in a molecule, is cyclized to afford a compound of the formula 16 based on the method known from J. Org. Chem. (2002, 67, 4062-4075). That is, this Step is a two-step reaction comprising treating compound 19 with sulfonyl azide in the presence of a base into a diazomalonate derivative, which is then treated with a transition metal catalyst in the coexistence of a ligand to give compound 16.

As the base to be used for the first step, for example, alkyl lithiums such as butyl lithium, t-butyl lithium, s-butyl lithium, etc.; alkali metal hydrides such as sodium hydride, potassium hydride, etc.; metal alcoholates such as potassium t-butoxide, sodium ethoxide, sodium methoxide, etc.; alkali metal amides such as lithium diisopropylamide, sodium hexamethyl disilazide, lithium hexamethyl disilazide, etc.; alkali metal carbonates such as sodium carbonate, potassium carbonate, sodium hydrogencarbonate, potassium hydrogen carbonate, etc.; etc. can be mentioned, with preference given to potassium carbonate.

As the sulfonyl azide, benzenesulfonyl azide, p-toluenesulfonyl azide, p-acetylaminobenzenesulfonyl azide; etc. can be mentioned, with preference given to p-toluenesulfonyl azide.

As the solvent, for example, ether solvents such as diethyl ether, tetrahydrofuran (THF), dioxane, 1,2-dimethoxyethane, diglyme, etc.; polar solvents such as N,N-dimethylformamide, dimethyl sulfoxide, acetonitrile, etc.; etc. can be mentioned, which may be used alone or in combination. A preferable solvent in this reaction is polar solvent, and acetonitrile is more preferable.

The reaction temperature is generally −20° C. to 100° C., preferably 0° C. to 50° C.

The reaction time is 1 hr to 48 hr, preferably 1 hr to 24 hr.

Thus obtained diazomalonate can be used in the next reaction without isolation.

As the transition metal catalyst to be used in the subsequent cyclization reaction, rhodium complexes and copper complexs can be used, with preference given to copper (I) iodide. As the ligand to be used simultaneously, trimethyl phosphite, triethyl phosphite and triphenyl phosphite can be mentioned, with preference given to triethyl phosphite.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; and polar solvents such as acetone, N,N-dimethylformamide, dimethyl sulfoxide, acetonitrile, etc.; can be mentioned, which may be used alone or in combination. A preferable solvent in this reaction is toluene.

The reaction temperature is generally room temperature to 150° C., preferably 50° C. to 130° C.

The reaction time is 1 hr to 48 hr, preferably 2 hr to 12 hr.

Thus obtained compound of the formula 16 can be used in the next reaction without isolation.

Step 1-10

In this Step, the alkylidenemalonic acid diester of the formula 18 is reacted with sulfonium methylide based on the method known from J. Med. Chem. (1992, 35, 1410-1417) to give a compound of the formula 16. Sulfonium methylide is produced by treating trimethylsulfoxonium or trimethylsufonium halide with a base.

As the base, for example, alkyl lithiums such as butyl lithium, t-butyl lithium, s-butyl lithium, etc.; alkali metal hydrides such as sodium hydride, potassium hydride, etc.; metal alcoholates such as potassium t-butoxide, sodium ethoxide, sodium methoxide, etc.; alkali metal amides such as lithium diisopropylamide, sodium bis(trimethylsilyl)amide, lithium bis(trimethylsilyl)amide, etc.; etc. can be mentioned. A preferable base is alkali metal hydride, and sodium hydride is more preferable.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; polar solvents such as N,N-dimethylformamide, dimethyl sulfoxide, etc.; etc. can be mentioned, which may be used alone or in combination. A preferable solvent in this reaction is polar solvent, and dimethyl sulfoxide is more preferable.

The reaction temperature is generally −78° C. to 100° C., preferably 0° C. to 60° C.

The reaction time is 30 min to 48 hr, preferably 1 hr to 12 hr.

Thus obtained compound of the formula 16 can be used in the next reaction without isolation.

Step 1-11

In this Step, one of the esters of cyclopropane dicarboxylic acid diester of the formula 16 obtained in Step 1-6, 1-7, 1-8, 1-9 or 1-10 is selectively hydrolyzed to give a monoester of the formula 20. While the selectivity varies depending on $R^{2'}$, $R^{3'}$, $R^{20}$, $R^{21}$, $T_1$ and $T_2$, one of the two esters of less hindered or of being assisted by neighboring functional groups is preferentially hydrolyzed.

While the hydrolysis conditions vary depending on the kind of $P_1$ and $P_2$, when, for example, $P_2$ is a methyl group, the base includes, for example, alkali metal carbonates such as sodium carbonate, potassium carbonate, etc.; and alkali metal hydroxides such as lithium hydroxide, sodium hydroxide, potassium hydroxide, etc.; etc., with preference given to sodium hydroxide.

As the solvent, for example, ether solvents such as diethyl ether, tetrahydrofuran (THF), dioxane, 1,2-dimethoxyethane, diglyme, etc.; alcohol solvents such as methanol, ethanol, isopropyl alcohol, t-butyl alcohol, etc.; polar solvents such as water, etc.; etc. can be mentioned, which may be used alone or in combination. A preferable solvent in this reaction is alcohol solvent, and a mixed solvent of ethanol or methanol and water is more preferable.

The reaction temperature is generally 0° C. to 100° C., preferably 0° C. to room temperature.

The reaction time is 1 hr to 48 hr, preferably 6 hr to 24 hr.

Thus obtained compound of the formula 20 can be used in the next reaction without isolation.

When $P_1$ and $T_2$ are combined and forming single bond, the compound of the formula 16 is lactone and this Step may be performed by leading the compound to an intermediate (Weinreb amide). In this case, a $CO_2P_1$ moiety of the resulting compound 20 is CONMe(OMe). $T_2$ is a hydroxyl group derived from lactone, or a substituent derived from the hydroxyl group such as alkyl ether, etc.

Step 1-12

In this Step, the dicarboxylic acid monoester of the formula 20 obtained in Step 1-11 is led to a compound of the formula 21. In this Curtius rearrangement reaction, acyl azide obtained by converting compound 20 to an activated ester by a conventional method and reacting the ester with metal azide may be used as an intermediate. Alternatively, compound 21 can also be obtained from compound 20 via acyl azide by the use of diphenylphophonic azide. In addition, this Step can be applied to a compound wherein a $CO_2P_1$ moiety of compound 20, which is a starting material, is Weinreb amide (CONMe(OMe)).

As the base, for example, organic bases such as triethylamine, diisopropylethylamine, pyridine, N-methylmorpholine, 2,6-lutidine, 1,8-diazabicyclo[5.4.0]undec-7-ene etc. can be mentioned, with preference given to triethylamine or diisopropylethylamine.

As the solvent, for example, ether solvents such as diethyl ether, tetrahydrofuran (THF), dioxane, 1,2-dimethoxyethane, diglyme, etc.; hydrocarbon solvents such as benzene, toluene, xylene, etc.; alcohol solvents such as benzyl alcohol, fluorenylmethyl alcohol, t-butyl alcohol, etc.; polar solvents such as N,N-dimethylformamide, dimethyl sulfoxide etc.; etc. can be mentioned, which may be used alone or in combination. The solvent is appropriately chosen depending on $P_3$. For example, when $P_3$ is t-butoxycarbonyl, t-butyl alcohol is used. The reaction temperature is generally 0° C. to 150° C., preferably room temperature to 120° C.

The reaction time is 1 hr to 48 hr, preferably 6 hr to 48 hr.

Thus obtained compound of the formula 21 can be used in the next reaction without isolation.

Step 2-1

In this Step, the alkene of the formula 22 is led to a cyclopropane derivative of the formula 23 by the method known from Synlett (2001, 12, 1843-1846) or a method using diazomalonic acid diester derived from malonic acid diester by a conventional method with a catalyst. In the formula of this Step, $T_9$ is a protected hydroxyl group. When, for example, diazomalonic acid diester is used, the catalyst is preferably rhodium complex, copper complex, etc., and rhodium (II) acetate dimer is more preferable. As the malonic acid diester, diethyl malonate, dimethyl malonate, dibenzyl malonate, di-t-butyl malonate, etc. can be mentioned, with preference given to dimethyl malonate.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, dimethyl sulfoxide, acetonitrile, etc.; etc. can be mentioned, which may be used alone or in combination. A preferable solvent in this reaction is hydrocarbon solvent, and no solvent is more preferable.

The reaction temperature is generally room temperature to 150° C., preferably 50° C. to 120° C.

The reaction time is 1 min to 48 hr, preferably 10 min to 3 hr.

Thus obtained compound of the formula 23 can be used in the next reaction without isolation.

Step 2-2

In this Step, the protecting group of the substituent $T_9$ (protected hydroxyl group) of the compound of the formula 23 obtained in Step 2-1 is removed to give a lactone of the formula 24. The reaction conditions are appropriately chosen depending on the kind of the protecting group in $T_9$. For example, when the protecting group is t-butyldiphenylsilyl group, deprotection is possible with an acid or fluoride.

As the acid, hydrochloric acid, sulfuric acid, phosphoric acid, acetic acid, trifluoroacetic acid, methanesulfonic acid, trifluoromethanesulfonic acid, etc. can be mentioned, with preference given to trifluoroacetic acid.

As the fluoride source, hydrogen fluoride, hydrogen fluoride-pyridine, tetrabutylammonium fluoride, potassium fluoride, cesium fluoride; etc. can be mentioned, with preference given to tetrabutylammonium fluoride.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is ether solvent, and THF is more preferable.

The reaction temperature is generally 0° C. to 100° C., preferably room temperature to 50° C.

The reaction time is 1 hr to 48 hr, preferably 1 hr to 12 hr.

Thus obtained compound of the formula 24 can be used in the next reaction without isolation.

Step 2-3

In this Step, the epichlorohydrin of the formula 25 is reacted with malonic acid diester to give a lactone derivative condensed with the cyclopropane of the formula 24. $R^{2'}$ in the compound of the formula 24 obtained by this Step is methylene. The reaction is carried out in the presence of a base. The kind of malonic acid diester is appropriately chosen depending on $P_1$, and dimethyl malonate, diethyl malonate, di-t-butyl malonate, dibenzyl malonate, etc. can be mentioned, with preference given to di-t-butyl malonate.

As the base, for example, alkyl lithium such as butyl lithium, t-butyl lithium, s-butyl lithium, etc.; alkali metal hydride such as sodium hydride, potassium hydride, etc.; metal alcoholates such as potassium t-butoxide, sodium ethoxide, sodium methoxide, etc.; alkali metal amides such as lithium diisopropylamide, sodium bis(trimethylsilyl)amide, lithium bis(trimethylsilyl)amide, etc.; alkali metal carbonates such as sodium carbonate, potassium carbonate, sodium hydrogen carbonate, potassium hydrogen carbonate, etc.; etc. can be mentioned, with preference given to potassium t-butoxide.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; alcohol solvents such as methanol, ethanol, isopropyl alcohol, t-butyl alcohol, etc.; polar solvents such as acetone, N,N-dimethylformamide, dimethyl sulfoxide, acetonitrile, etc.; etc. can be mentioned, which may be used alone or in combination. A preferable solvent in this reaction is a mixed solvent of t-butyl alcohol and THF.

The reaction temperature is generally 0° C. to 150° C., preferably room temperature to 80° C.

The reaction time is 1 hr to 48 hr, preferably 6 hr to 24 hr.

Thus obtained compound of the formula 24 can be used in the next reaction without isolation.

This Step can also include optical resolution process. When $P_1$ is a t-butyl group, deprotection with an acid is performed and the obtained racemic carboxylic acid is led to a diastereomeric salt of a chiral amine and recrystallized. The obtained chiral acid is subjected to t-butyl esterification again to give an optically active compound 24. As the acid to be used for deprotection under acidic conditions, mineral acids such as hydrochloric acid, sulfuric acid, phosphoric acid, nitric acid, etc., organic acids such as trifluoroacetic acid, methanesulfonic acid, p-toluenesulfonic acid, trifluoromethanesulfonic acid and the like can be mentioned, with preference given to hydrochloric acid or trifluoroacetic acid.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, acetonitrile, water, etc.;

etc. can be mentioned. Preferable solvents in this reaction are ethyl acetate and dioxane.

The reaction temperature is generally room temperature to 100° C., preferably room temperature to 80° C.

The reaction time is 1 hr to 48 hr, preferably 2 hr to 24 hr.

As the chiral amine to be used for optical resolution, alkaloids such as cinchonine, quinidine, cinchonidine, quinine, brucine, strychinine, etc.; amino acids or alcohols derived from amino acids such as alanine, phenylalanine, alaninol, phenylalaninol, etc.; phenethylamine, naphthylethylamine; etc. can be mentioned, with preference given to quinidine.

As the solvent to be used for recrystallization, for example, ether solvents such as diethyl ether, tetrahydrofuran (THF), dioxane, 1,2-dimethoxyethane, etc.; hydrocarbon solvents such as benzene, toluene, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, 2-butanone, acetonitrile, water, etc.; etc. can be mentioned, which may be used alone or in combination. A preferable solvent in this recrystallization is ethanol.

For t-butyl esterification, a method using isobutene in the presence of an acid catalyst to give t-butyl ester, or a method using N,N-dimethylformamide di-t-butylacetal can be mentioned. For example, when N,N-dimethylformamide di-t-butylacetal is used, as the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, dimethyl sulfoxide, acetonitrile, etc.; etc. can be mentioned, which may be used alone or in combination. A preferable solvent in this reaction is hydrocarbon solvent, and toluene is more preferable.

The reaction temperature is generally room temperature to 150° C., preferably room temperature to 110° C.

The reaction time is 1 hr to 24 hr, preferably 2 hr to 12 hr.

Thus obtained compound of the formula 24 can be used in the next reaction without isolation.

Step 2-4

In this Step, the lactone of the formula 24 obtained in Step 2-2 or 2-3 is subjected to ring opening and a hydroxyl group is protected as necessary. The reaction conditions are appropriately chosen depending on the kind of $R^{2'}$, $R^{40}$ and $P_6$. For example, when $P_6$ is a t-butyldimethylsilyl group and $R^{40}$ is OH, this Step comprises three reactions including hydrolysis of compound 24 with alkali metal carbonates or alkali metal hydroxides to give alkali metal carboxylate, subsequent protection of newly formed hydroxyl group and carboxyl group with t-butyldimethylsilyl chloride, and selective hydrolysis of carboxylic acid silyl ester with a base.

As the alkali metal carbonates used in the hydrolysis of lactone, potassium carbonate, sodium carbonate, etc. can be mentioned. As the alkali metal hydroxides, sodium hydroxide, potassium hydroxide; etc. can be mentioned, with preference given to sodium hydroxide.

As the solvent used in the hydrolysis, for example, ether solvents such as diethyl ether, tetrahydrofuran (THF), dioxane, 1,2-dimethoxyethane, diglyme, etc.; alcohol solvents such as methanol, ethanol, isopropyl alcohol, t-butyl alcohol, etc.; polar solvents such as water, etc.; etc. can be mentioned, which may be used alone or in combination. A preferable solvent in this reaction is ether solvent, and a mixed solvent of THF and water is more preferable.

The reaction temperature is generally 0° C. to 100° C., preferably room temperature to 80° C.

The reaction time is 1 hr to 48 hr, preferably 1 hr to 12 hr.

The subsequent protection of the newly formed hydroxyl group with a t-butyldimethylsilyl group is performed in the presence of a base. As the base, for example, organic bases such as triethylamine, pyridine, N-methylmorpholine, imidazol, etc.; etc. can be mentioned, with preference given to imidazol.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, dimethyl sulfoxide, acetonitrile, etc.; etc. can be mentioned, which may be used alone or in combination. A preferable solvent in this reaction is polar solvent, and N,N-dimethylformamide is more preferable.

The hydrolysis of carboxylic acid silyl ester can be performed in one-pot together with the above-mentioned reaction. That is, after the completion of the above-mentioned reaction, water and an alcohol solvent, and a base are added to the reaction, whereby carboxylic acid silyl ester can be selectively hydrolyzed.

As the alcohol solvents, methanol can be preferably used.

As the base, alkali metal carbonates such as sodium carbonate, potassium carbonate, sodium hydrogen carbonate, potassium hydrogen carbonate, etc.; alkali metal hydroxides such as lithium hydroxide, sodium hydroxide, potassium hydroxide, etc.; etc. can be mentioned. A preferable base is alkali metal carbonate, and potassium carbonate is more preferable.

The reaction temperature is generally 0° C. to 100° C., preferably 0° C. to 50° C.

The reaction time is 1 hr to 48 hr, preferably 1 hr to 12 hr.

Thus obtained compound of the formula 26 can be used in the next reaction without isolation.

For example, the compound of the formula 26 wherein $R^{40}$ is a $NH_2$ group and $P_6$ is a hydrogen atom can be obtained by treating the lactone of the formula 24 obtained in Step 2-3 with ammonia.

As the solvent, for example, ether solvents such as diethyl ether, tetrahydrofuran (THF), dioxane, 1,2-dimethoxyethane, diglyme, etc.; alcohol solvents such as methanol, ethanol, isopropyl alcohol, t-butyl alcohol, etc.; polar solvents such as N,N-dimethylformamide, dimethyl sulfoxide, acetonitrile, water, etc.; etc. can be mentioned, which may be used alone or in combination. A preferable solvent in this reaction is a mixed solvent of methanol, water and THF.

The reaction temperature is generally 0° C. to 100° C., preferably 0° C. to 50° C.

The reaction time is 1 hr to 48 hr, preferably 6 hr to 24 hr.

Thus obtained compound of the formula 26 can be used in the next reaction without isolation.

Step 2-5

In this Step, the compound of the formula 26 obtained in Step 2-4 is led to a cyclic urethane of the formula 27. For example, when $R^{40}$ is OH and $P_6$ is a trialkylsilyl-protecting group, compound 27 can be obtained by a Curtius rearrangement reaction and subsequent deprotection of the trialkylsilyl protecting group. That is, compound 26 is treated with diphenylphophonic azide in the presence of a base to give an isocyanate, which is then led to compound 27 by addition of a fluoride to the reaction to deprotect the silyl group.

As the base, organic bases such as triethylamine, pyridine, N-methylmorpholine, 2,6-lutidine, 1,8-diazabicyclo[5.4.0]undec-7-ene, etc.; etc. can be mentioned, with preference given to triethylamine.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, acetonitrile, water, etc.; etc. can be mentioned, which may be used alone or in combination. A preferable solvent in this reaction is polar solvent, and N,N-dimethylformamide is more preferable.

The reaction temperature is generally room temperature to 150° C., preferably room temperature to 80° C.

The reaction time is 10 min to 48 hr, preferably 10 min to 6 hr.

As the fluoride source, after completion of Curtius rearrangement, hydrogen fluoride, hydrogen fluoride-pyridine, tetrabutylammonium fluoride, potassium fluoride, cesium fluoride; etc. can be mentioned, with preference given to cesium fluoride. The reaction temperature for this reaction is generally 0° C. to 100° C., preferably room temperature to 80° C.

The reaction time is 1 hr to 48 hr, preferably 1 hr to 6 hr.

Thus obtained compound of the formula 27 can be used in the next reaction without isolation.

In addition, for example, a Hofmann rearrangement reaction can be used for the compound of the formula 26 wherein $R^{40}$ is $NH_2$ and $P_6$ is a hydrogen atom. As the oxidizing agent to be used for the Hofmann rearrangement, N-bromosuccinimide, N-chlorosuccinimide, sulfuryl chloride, bromine, iodosobenzene diacetate and the like can be used, with preference given to iodosobenzene diacetate.

The reaction may be carried out in the presence of a base, and as the base, alkali metal carbonates such as sodium carbonate, potassium carbonate, sodium hydrogen carbonate, potassium hydrogen carbonate, etc.; alkali metal hydroxides such as lithium hydroxide, sodium hydroxide, potassium hydroxide, etc.; etc. can be mentioned, with preference given to sodium hydroxide.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, acetonitrile, water, etc.; etc. can be mentioned, which may be used alone or in combination. A preferable solvent in this reaction is a mixed solvent of acetonitrile, ethyl acetate and water.

The reaction temperature is generally −20° C. to 100° C., preferably 0° C. to room temperature.

The reaction time is 1 hr to 48 hr, preferably 1 hr to 12 hr.

Thus obtained compound of the formula 27 can be used in the next reaction without isolation.

Step 2-6

In this Step, the cyclic urethane of the formula 27 obtained in Step 2-5 is subjected to ring opening reaction to give an N-protected alcohol of the formula 21. In the compound of the formula 21 obtained by this Step, $T_2$ is OH. For example, when $R^{2'}$ is methylene and $P_3$ is a t-butoxycarbonyl group, this Step comprises two sequential reactions. The first step is protection of a nitrogen atom of compound 27 with a t-butoxycarbonyl group, and the second step is hydrolysis of cyclic urethane. In this case, as the butoxycarbonylation reagent to be used in the first step, for example, di-t-butyl dicarbonate is used and the reaction is carried out in the presence of a base as necessary.

As the base to be used in the first step, for example, alkyl lithiums such as butyl lithium, t-butyl lithium, s-butyl lithium, etc.; alkali metal hydrides such as sodium hydride, potassium hydride, etc.; alkali metal amides such as lithium diisopropylamide, sodium bis(trimethylsilyl)amide, lithium bis(trimethylsilyl)amide, etc.; etc. can be mentioned. A preferable base is one of alkali metal hydrides, and sodium hydride is more preferable.

As the solvent, for example, ether solvents such as diethyl ether, tetrahydrofuran (THF), dioxane, 1,2-dimethoxyethane, diglyme, etc.; polar solvents such as N,N-dimethylformamide, dimethyl sulfoxide, etc.; etc. can be mentioned, which may be used alone or in combination. A preferable solvent in this reaction is ether solvent, and THF is more preferable.

The reaction temperature is generally −20° C. to 100° C., preferably 0° C. to 50° C.

The reaction time is 1 hr to 48 hr, preferably 1 hr to 24 hr.

The second step is hydrolysis with a base.

As the base to be used in the second step, for example, alkali metal carbonates such as sodium carbonate, potassium carbonate, cesium carbonate, sodium hydrogen carbonate, potassium hydrogen carbonate, etc.; alkali metal hydroxides such as lithium hydroxide, sodium hydroxide, potassium hydroxide, etc.; etc. can be mentioned, with preference given to alkali metal carbonate, and cesium carbonate is more preferable.

As the solvent, for example, ether solvents such as diethyl ether, tetrahydrofuran (THF), dioxane, 1,2-dimethoxyethane, diglyme, etc.; alcohol solvents such as methanol, ethanol, isopropyl alcohol, t-butyl alcohol, etc.; polar solvents such as N,N-dimethylformamide, dimethyl sulfoxide, water, etc.; etc. can be mentioned, which may be used alone or in combination. A preferable solvent in this reaction is alcohol solvent, and methanol is more preferable.

The reaction temperature is generally 0° C. to 100° C., preferably room temperature to 50° C.

The reaction time is 10 min to 24 hr, preferably 30 min to 6 hr.

Thus obtained compound of the formula 21 can be used in the next reaction without isolation.

Step 3-1

In this Step, the glycine derivative of the formula 28 is reacted with dihaloalkane or dihaloalkene in the presence of a base to give a cyclopropane derivative of the formula 21. Dihaloalkane and dihaloalkene are appropriately chosen depending on $R^{20}$, $R^{21}$, $R^{2'}$, $R^{3'}$, T and $T_2$.

As the base, for example, alkyl lithiums such as butyl lithium, t-butyl lithium, s-butyl lithium, etc.; alkali metal hydrides such as sodium hydride, potassium hydride, etc.; metal alcoholates such as potassium t-butoxide, sodium ethoxide, sodium methoxide, etc.; alkali metal amides such as lithium diisopropylamide, sodium bis(trimethylsilyl)amide, lithium bis(trimethylsilyl)amide, etc.; etc. can be mentioned, with preference given to metal alcoholate, and potassium t-butoxide is more preferable.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; polar solvents such as N,N-dimethylformamide, dimethyl sulfoxide, etc.; etc. can be mentioned, which may be used alone or in combination. A preferable solvent in this reaction is ether solvent, and THF is more preferable.

The reaction temperature is generally −100° C. to 50° C., preferably −78° C. to room temperature.

The reaction time is 1 hr to 24 hr, preferably 1 hr to 8 hr.

Thus obtained compound of the formula 21 can be used in the next reaction without isolation.

Step 4-1

In this Step, the alkene of the formula 13 is reacted with nitroacetic acid ester, in the presence of iodosobenzene diacetate and a catalyst based on the method known from J. Org. Chem. (2004, 69, 1262-1269), and the compound of the formula 21 is obtained via a subsequent reductive reaction.

The catalyst to be used for the reaction is rhodium complex or copper complex, with preference given to a rhodium (II) pivalate dimer.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is water or no solvent.

The reaction temperature is generally −20° C. to 100° C., preferably room temperature to 40° C.

The reaction time is 1 hr to 48 hr, preferably 2 hr to 24 hr.

As the reduction condition employed for the subsequent reaction, hydrogenation reaction in the presence of a palladium catalyst, reductive reaction using tin (II) chloride, iron, zinc and the like under acidic conditions reductive reaction using sodium borohydride in the presence of copper acetate can be mentioned, with preference given to conditions using zinc in the presence of hydrochloric acid.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is alcohol solvent, and isopropyl alcohol is more preferable.

The reaction temperature is generally −20° C. to 100° C., preferably 0° C. to room temperature.

The reaction time is 1 hr to 48 hr, preferably 2 hr to 12 hr.

Thus obtained compound of the formula 21 can be used in the next reaction without isolation.

Step 5-1

In this Step, the ester of the formula 21 obtained in Step 1-12, 2-6, 3-1 or 4-1 is led to a carboxylic acid of the formula 29 by a-conventional method. The reaction conditions are appropriately chosen depending on $P_1$ and when, for example, $P_1$ is a methyl group or ethyl group, hydrolysis with a conventional base can be performed. In addition, when, for example, $P_1$ is a t-butyl group, deprotection with an acid can be performed. Thus obtained racemic compound 29 can be subjected to optical resolution using a chiral amine, to give compound 29 of optically active.

As a base to be used for hydrolysis under basic conditions, for example, alkali metal carbonates such as cesium carbonate, sodium carbonate, potassium carbonate, etc.; alkali metal hydroxides such as lithium hydroxide, sodium hydroxide, potassium hydroxide, etc.; etc. can be mentioned, with preference given to sodium hydroxide. As an acid to be used for deprotection under acidic conditions, mineral acids such as hydrochloric acid, sulfuric acid, phosphoric acid, nitric acid, etc.; organic acids such as trifluoroacetic acid, methanesulfonic acid, p-toluenesulfonic acid, trifluoromethanesulfonic acid, etc.; etc. can be mentioned, with preference given to hydrochloric acid or trifluoroacetic acid.

As the solvent, for example, for hydrolysis under basic conditions, ether solvents such as diethyl ether, tetrahydrofuran (THF), dioxane, 1,2-dimethoxyethane, diglyme, etc.; alcohol solvents such as methanol, ethanol, isopropyl alcohol, t-butyl alcohol, etc.; polar solvents such as water, etc.; etc. can be mentioned, which may be used alone or in combination. A preferable solvent in this reaction is a mixed solvent of ether and alcohol, and a mixed solvent of methanol, THF and water is more preferable.

The reaction temperature is generally room temperature to 100° C., preferably room temperature to 80° C.

The reaction time is 1 hr to 48 hr, preferably 2 hr to 24 hr. For deprotection under acidic conditions, as the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, acetonitrile, water, etc.; etc. can be mentioned. A preferable solvent is ethyl acetate, dioxane, dichloromethane, chloroform or no solvent.

Thus obtained compound of the formula 29 can be used in the next reaction without isolation.

In addition, an optically active compound of the formula 29 can be obtained by recrystallization of diastereomeric salt of the racemate with chiral amine.

As the chiral amine, alkaloids such as cinchonine, quinidine, cinchonidine, quinine, brucine, strychinine, etc.; amino acids or alcohols derived from amino acid such as alanine, phenylalanine, alaninol, phenylalaninol, etc.; phenethylamine, naphthylethylamine; etc. can be mentioned, with preference given to quinidine.

As the solvent to be used for recrystallization, for example, ether solvents such as diethyl ether, tetrahydrofuran (THF), dioxane, 1,2-dimethoxyethane, etc.; hydrocarbon solvents such as benzene, toluene, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, 2-butanone, acetonitrile, water, etc.; etc. can be mentioned, which may be used alone or in combination. A preferable solvent in this recrystallization is isopropyl alcohol, acetone, ethyl acetate or a mixed solvent thereof.

This Step is performed as necessary or may be omitted.

The compound of the formula 21 can be treated as the compound of the formula 30, 31 or 32.

Step 5-2

In this Step, the carboxylic acid of the formula 29 obtained in Step 5-1 is protected using a protecting group $P_4$ by a conventional method. While $P_4$ is appropriately chosen depending on $P_3$, $T_1$, or $T_2$, when, for example, $P_4$ is a t-butyl group, a method using isobutene in the presence of an acid catalyst or a method using N,N-dimethylformamide di-tert-butyl acetal can be mentioned.

When, for example, N,N-dimethylformamide di-tert-butyl acetal is used, as the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, dimethyl sulfoxide, acetonitrile, etc.; etc. can be mentioned, which may be used alone or in combination. A preferable solvent in this reaction is a hydrocarbon solvent, and toluene is more preferable.

The reaction temperature is generally room temperature to 150° C., preferably room temperature to 110° C.

The reaction time is 1 hr to 24 hr, preferably 2 hr to 12 hr.

Thus obtained compound of the formula 30 can be used in the next reaction without isolation.

This Step is performed as necessary, or may be omitted when the next Step and the following Steps have no problem, and the compound of the formula 29 wherein $P_4$ is a hydrogen atom may be used as a starting material of the subsequent Steps.

Step 5-3

In this Step, substituent $T_1$ on $R^{3'}$ and/or substituent $T_2$ on $R^{2'}$ of the compound of the formula 30 are/is converted to $T_3$ and/or $T_4$, respectively, under conventional conditions.

For example, when $R^{3'}$ is an aromatic ring and T, is a halogen atom, so-called Negishi reaction, Suzuki-Miyaura reaction (Metal-catalyzed Cross Coupling Reactions; WILEY-VCH; New York, 1998), Buchwald reaction, Ullmann reaction (Tetrahedron 2002, 11, 2041-2075; J. Am. Chem. Soc. 2003, 125, 6653-6655) and the like can be applied, whereby a compound of the formula 31 wherein $T_3$ is alkoxycarbonyl alkyl, carbonylamino group, alkoxycarbonyl group, aryl group, arylamino group, alkylamino group or aryl alkoxy group can be obtained respectively.

When, for example, $R^{2'}$ is an alkyl chain and $T_2$ is a hydroxyl group, for example, a compound of the formula 31 wherein $T_4$ is an amino group or alkylamino group can be obtained by a conventional method. Thus obtained compound of the formula 31 can be used in the next reaction without isolation.

When $T_1$ and $T_2$ are hydrogen atoms or when further conversion is not necessary, this Step is omitted and the compound of the formula 30 can be treated as a compound of the formula 31.

Step 5-4

In this Step, $P_3$, which is a nitrogen-protecting group in the compound of the formula 31, is deprotected by a conventional method. When Step(s) 5-1, 5-2 and/or 5-3 are/is omitted, this Step is also a step for deprotecting $P_3$ of the compounds of the formulas 21, 29 or 30. In addition, this Step can be applied to compound 31, wherein a $CO_2P_4$ moiety is Weinreb amide (CONMe(OMe)). The reaction conditions are appropriately chosen depending on $P_3$ or $P_4$, when, for example, $P_3$ is a t-butoxycarbonyl group and $P_4$ is a t-butyl group, deprotection can be performed under acidic conditions.

As the acid, mineral acids such as hydrochloric acid, sulfuric acid, phosphoric acid, etc.; organic acids such as acetic acid, trifluoroacetic acid, methanesulfonic acid, p-toluenesulfonic acid, etc. can be mentioned, with preference given to p-toluenesulfonic acid.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is ether solvent, alcohol solvent or acetonitrile.

The reaction temperature is generally 0° C. to 100° C., preferably room temperature to 50° C.

The reaction time is 1 hr to 72 hr, preferably 6 hr to 48 hr.

Thus obtained compound of the formula 32 can be used in the next reaction without isolation.

When $P_3$ is a hydrogen atom, this Step is not necessary, and the compound of the formula 31 can be treated as a compound of the formula 32.

Step 5-5

In this Step, the compound of the formula 32 obtained in Step 5-4 is led to a sulfonamide or sulfamide of the formula 33. $T_5$ in the compound of the formula 33 obtained in this Step is a substituent, which is further led to other functional group in the next Step 5-6, 5-13 or 6-7.

When the compound of the formula 33 is a sulfonamide derivative, the compound 33 can be obtained by a conventional reaction of the compound of the formula 32 with $ClSO_2$—$(CH_2)$m-U-$T_5$ or $O(SO_2$—$(CH_2)$m-U-$T_5)_2$ in the presence of a base, for example.

As the base, organic bases such as triethylamine, pyridine, N-methylmorpholine, 2,6-lutidine, 1,8-diazabicyclo[5.4.0]undec-7-ene, etc.; etc. can be mentioned, with preference given to pyridine or 2,6-lutidine. These may be used as solvents.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as N,N-dimethylformamide, acetonitrile, etc.; etc. can be mentioned, which may be used alone or in combination. A preferable solvent in this reaction is halogenated solvent or ether solvent, and chloroform or THF is more preferable.

The reaction temperature is generally 0° C. to 100° C., preferably room temperature to 50° C.

The reaction time is 1 hr to 72 hr, preferably 1 hr to 48 hr.

When the compound of the formula 33 is a sulfamide derivative, based on the method known in Tetrahedron (1996, 52, 14217-14227), the derivative can be synthesized by two consecutive reactions. The first step is a reaction of 2-haloethanol with chlorosulfonyl isocyanate and then with the compound of the formula 32 in the presence of a base, to give an oxazolidin-2-one-3-ylsulfamide, and the second step is a reaction of the compound obtained above with a desired amine to give a sulfamide of the formula 33.

As the 2-haloethanol, for example, 2-chloroethanol, 2-bromoethanol and 2-iodoethanol can be mentioned, with preference given to 2-chloroethanol.

As the base, for example, organic bases such as triethylamine, pyridine, N-methylmorpholine, 2,6-lutidine, 1,8-diazabicyclo[5.4.0]undec-7-ene, etc.; etc. can be mentioned. A preferable base is organic base, and N-methylmorpholine is more preferable.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, N,N-dimethylacetamide, dimethyl sulfoxide, acetonitrile, etc.; etc. can be mentioned, which may be used alone or in combination. A preferable solvent in this reaction is polar solvent, and acetonitrile is more preferable.

The reaction temperature is generally −20° C. to 100° C., preferably 0° C. to 50° C.

The reaction time is 1 hr to 48 hr, preferably 1 hr to 24 hr.

The second step is a nucleophilic substitution reaction with amine.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, dimethyl sulfoxide, acetonitrile, etc.; etc. can be mentioned, which may be used alone or in combination. A preferable solvent in this reaction is polar solvent, and acetonitrile is more preferable.

The reaction temperature is generally −20° C. to 100° C., preferably 0° C. to 100° C.

The reaction time is 1 hr to 48 hr, preferably 1 hr to 24 hr.

Thus obtained compound of the formula 33 can be used in the next reaction without isolation.

Step 5-6

In this Step, the compound of the formula 33 obtained in Step 5-5 is reacted with the compound of the formula 34 to give a compound of the formula 35. $T_7$ in the compound of the formula 35 obtained in this Step is a substituent that can be led to the other substituents in Step 5-9, 5-14 or 6-10. In addition, U' in the compound of the formula 33 changes structure by reacting with the compound of the formula 34, thereby forming a new ring X', or may remain the structure (U'=X').

As for one of the examples of structural change of U' with this reaction, can be mentioned the case, in which U'-$T_5$ is 2-aminothiazol-4-yl and the compound of the formula 34 is an α'-haloacetone possessing $T_7$ at the α-position. In this case, U'-$T_5$ structurally changes to an imidazo[2.1-b]thiazol-2-yl group possessing $CH_2T_7$ at the 6-position. As the solvent in this case, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is ester solvent, and ethyl acetate is more preferable.

The reaction temperature is generally 0° C. to 100° C., preferably room temperature to 80° C.

The reaction time is 1 hr to 48 hr, preferably 6 hr to 24 hr.

Thus obtained compound of the formula 35 can be used in the next reaction without isolation.

Step 5-7

In this Step, the compound of the formula 32 obtained in Step 5-4 is directly led to the compound of the formula 35 without going through the compound of the formula 33. $T_7$ in the compound of the formula 35 obtained in this Step is a substituent that can be converted to the other substituent in Step 5-9, 5-14 or 6-10. when the compound of the formula 35 is a sulfonamide derivative, for example, $ClSO_2$—$(CH_2)_m$—X'—$(CH_2)_n$—Y'-$T_7$ or $O(SO_2$—$(CH_2)_m$—X'—$(CH_2)_n$—Y'-$T_7)_2$ is reacted with the compound of the formula 32, and when the compound of the formula 35 is a sulfamide derivative, for example, the compound can be obtained from the compound of the formula 32 by a method similar to that of Step 5-5. Thus obtained compound of the formula 35 can be used in the next reaction without isolation.

Step 5-8

In this Step, the carboxyl group-protecting group of the compound of the formula 35 obtained in Step 5-6 or 5-7 is deprotected by a conventional method. $T_7$ in the compound of the formula 36 obtained in this Step is a substituent that can be converted to the other substituent in Step 5-9. The reaction conditions are similar to those in Step 5-1.

Thus obtained compound of the formula 36 can be used in the next reaction without isolation.

Step 5-9

In this Step, $T_7$ in the compound of the formula 36 obtained in Step 5-8 is modified by a conventional method to give a compound of the formula 37. By this Step, a $(CH_2)_m$—X'—$(CH_2)_n$—Y'-$T_7$ moiety in the compound of the formula 36 is converted to $R^1$ of the compound of the formula 37. In this Step, $T_3$ and $T_4$ do not change and correspond to V' and W', respectively. The reaction conditions are appropriately chosen depending on the kind of $T_7$ and desired compound, when, for example, $T_7$ is a protecting group of an amino group involved in Y', this can be deprotected by a conventional method and the amino group can be led to amide, urethane, urea, alkylamine by a conventional method. When, for example, Y' is an aromatic ring and $T_7$ is a halogen atom, $T_7$ on Y' can be led to other substituents by methods known in literature, such as so-called Sonogashira reaction, Heck reaction, Negishi reaction, Suzuki-Miyaura reaction (Metal-catalyzed Cross Coupling Reactions; WILEY-VCH; New York, 1998), Buchwald reaction, Ullmann reaction (Tetrahedron 2002, 11, 2041-2075; J. Am. Chem. Soc. 2003, 125, 6653-6655) and the like. It can be led to alkyne by the Sonogashira reaction, to alkene by Heck reaction, to an aromatic ring by Suzuki-Miyaura reaction, to amine by Buchwald reaction, and to ether by Ullmann reaction.

Step 5-10

In this Step, a hydrogen atom of the compound of the formula 46 is replaced with a chlorosulfonyl group. After leading the compound of the formula 46 to a sulfonic acid derivative, the derivative is subsequently chlorinated to give the sulfonyl chloride derivative of the formula 47. As the sulfonylation agent, sulfuric acid, chlorosulfonic acid and chlorosulfonic acid trimethylsilyl ester can be mentioned. As the solvent, no solvent, or halogenated solvents such as dichloromethane, chloroform, carbon tetrachloride, 1,2-dichloroethane, etc.; ester solvents such as ethyl acetate, methyl acetate, butyl acetate, etc.; polar solvents such as acetic acid, sulfuric acid, etc.; etc. can be mentioned, which may be used alone or in combination. A preferable solvent in this reaction is halogenated solvent, and chloroform is more preferable.

The reaction temperature is generally −20° C. to 100° C., preferably 0° C. to 50° C.

The reaction time is 1 hr to 72 hr, preferably 1 hr to 48 hr.

The subsequent chlorination reaction is a conventional synthetic method for a sulfonyl chloride derivative, and as the chlorinating agent to be used for the reaction, for example, thionyl chloride, phosphorous oxychloride, phosphorus pentachloride and chlorosulfonic acid can be mentioned, with preference given to thionyl chloride. As the solvent, no solvent, or hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, etc.; etc. can be mentioned, which may be used alone or in combination. A preferable solvent in this reaction is no solvent, and a mixed solvent of thionyl chloride, which is a chlorinating agent, and a catalytic amount of N,N-dimethylformamide is more preferable.

The reaction temperature is generally 0° C. to 100° C., preferably room temperature to 80° C.

The reaction time is 1 hr to 48 hr, preferably 3 hr to 24 hr.

Thus obtained compound of the formula 47 can be used in the next reaction without isolation.

Step 5-11

In this Step, the amine of the formula 32 obtained in Step 5-4 is led to a sulfonamide derivative or sulfamide derivative of the formula 48. In addition, this Step can be also applied to a compound 32, wherein a $CO_2P_4$ moiety is Weinreb amide (CONMe(OMe)). When the compound of the formula 48 is a sulfonamide derivative, for example, the derivative can be obtained by a reaction with the $ClSO_2$—$R^1$ of the formula 47 obtained in Step 5-10, or $O(SO_2$—$R^1)_2$. The reaction conditions are the same as those in Step 5-5. When the compound of the formula 48 is a sulfamide derivative, the same procedure as in Step 5-5 can be applied.

Thus obtained compound of the formula 48 can be used in the next reaction without isolation.

Step 5-12

In this Step, the carboxyl-protecting group in the compound of the formula 48 obtained in Step 5-11 is deprotected and $T_4$ in compound 48 is converted to W' to give the compound of the formula 37.

$P_4$ is deprotected and $T_4$ is led to the other substituent simultaneously under the same conditions. In addition, $P_4$ and $T_4$ may be combined together to form a single bond, and when compound 48 is lactone, this Step can be also achieved by hydrolyzing the lactone to hydroxycarboxylic acid. In this case, the reaction is carried out by a base. As the base, alkali metal carbonates such as sodium carbonate, potassium carbonate, sodium hydrogen carbonate, potassium hydrogen carbonate, etc.; alkali metal hydroxides such as lithium hydroxide, sodium hydroxide, potassium hydroxide, etc.; etc. can be mentioned, with preference given to sodium hydroxide.

As the solvent, for example, ether solvents such as diethyl ether, tetrahydrofuran (THF), dioxane, 1,2-dimethoxyethane, diglyme, etc.; alcohol solvents such as methanol, ethanol, isopropyl alcohol, t-butyl alcohol, etc.; polar solvents such as water, etc.; can be mentioned, which may be used alone or in combination. A preferable solvent is alcohol solvent, and a mixed solvent of methanol and water is more preferable.

The reaction temperature is generally 0° C. to 100° C., preferably room temperature to 60° C.

The reaction time is 1 hr to 48 hr, preferably 1 hr to 12 hr.

Thus obtained compound of the formula 37 can be used in the next reaction without isolation.

Step 5-13

In this Step, a carboxyl group of the compound of the formula 33 obtained in Step 5-5 is deprotected and then $T^5$ is modified by a conventionally known method to give the compound of the formula 37. By this Step, a $(CH_2)_m$-U'-$T_5$ moiety in the compound of the formula 33 is converted to $R^1$ in the compound of the formula 37. In this Step, a substituent $T_3$ at $R^{3'}$ and a substituent $T_4$ at $R^{2'}$ are the same as V' and W', respectively.

The reaction conditions are appropriately chosen depending on the kind of $T_5$ and a desired compound. For example, reductive alkylation of amino group, conversion to a hydroxymethyl group by reduction of alkoxycarbonyl group, conversion of halomethyl group to an alkoxymethyl group by substitution by alkoxide and the like can be mentioned. When T5 is a protecting group of amine included in U', this is deprotected under conventional conditions and the amine was reacted with a desired isocyanide to give a urea derivative 37. In this case, the conditions of the deprotection are the same as in Step 5-4. As the isocyanide, methyl isocyanate, phenyl isocyanate and the like can be mentioned and the reaction with these is carried out in the presence of a base. As the base, organic bases such as triethylamine, pyridine, N-methylmorpholine, 2,6-lutidine, etc.; etc. can be mentioned, with preference given to triethylamine.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, acetonitrile, etc.; etc. can be mentioned, which may be used alone or in combination. A preferable solvent in this reaction is ether solvent, and THF is more preferable.

The reaction temperature is generally −20° C. to 100° C., preferably 0° C. to room temperature.

The reaction time is 1 hr to 24 hr, preferably 1 hr to 6 hr.

Thus obtained compound of the formula 37 can be used in the next reaction without isolation.

Step 5-14

In this Step, $T_7$ of the compound of the formula 35 obtained in Step 5-6 or 5-7 is modified by a conventionally known method and $P_4$, which is a protecting group of carboxyl group, is simultaneously deprotected to give a compound of the formula 37. In this Step, a substituent $T_3$ at $R^{3'}$ and a substituent $T_4$ at $R^{2'}$ correspond to V' and W', respectively. For example, when $T_7$ is a nitro group and $P_4$ is a t-butyl group, the compound of the formula 37 can be obtained using a conventional reducing agent of a nitro group in the presence of an acid. In this case, as a conventional reducing agent of a nitro group, for example, tin (II) chloride, iron, zinc can be mentioned, with preference given to tin (II) chloride. As the acid, hydrochloric acid, acetic acid, sulfuric acid, nitric acid, etc. can be mentioned, with preference given to hydrochloric acid.

As the solvent, for example, ether solvents such as diethyl ether, tetrahydrofuran (THF), dioxane, 1,2-dimethoxyethane, diglyme, etc.; alcohol solvents such as methanol, ethanol, isopropyl alcohol, t-butyl alcohol, etc.; polar solvents such as water, etc.; etc. can be mentioned, which may be used alone or in combination. A preferable solvent in this reaction is alcohol solvent, and ethanol is more preferable.

The reaction temperature is generally room temperature to 150° C., preferably room temperature to 100° C.

The reaction time is 1 hr to 48 hr, preferably 1 hr to 12 hr.

Thus obtained compound of the formula 37 can be used in the next reaction without isolation.

Step 5-15

In this Step, the carboxylic acid of the formula 37 obtained in Step 5-9, 5-12, 5-13, 5-14 or 6-11 is led to a compound of the formula 38. For example, when $R^{60}$ is a NHOH group, carboxylic acid is converted to activated ester or acid chloride in a solvent, and a hydroxylamine or its equivalent wherein a hydroxylamine or hydroxyl group is protected is added to give a compound of the formula 38. This Step may be performed in the presence of a base. When a hydroxylamine equivalent wherein the hydroxyl group is protected is used, deprotection is necessary after the reaction.

As the activated ester, aryl imidazole, mixed acid anhydride, hydroxybenzotriazole ester, hydroxysuccinimide ester and the like can be mentioned, which are prepared by known methods. For preparation of acyl chloride, thionyl chloride, oxalyl chloride and the like are used. The reaction temperature for preparation of the activated ester or acyl chloride is generally –78° C. to 50° C., preferably –20° C. to room temperature.

The reaction time is 10 min to 6 hr, preferably 30 min to 6 hr. As the hydroxylamine equivalent wherein a hydroxyl group is protected, O-(trimethylsilyl)hydroxylamine, O-(benzyl)hydroxylamine; etc. can be mentioned, with preference given to O-(trimethylsilyl)hydroxylamine.

The temperature of the reaction with the hydroxylamine equivalent wherein the hydroxyl group is protected is generally –78° C. to 50° C., preferably –20° C. to room temperature.

The reaction time is 10 min to 6 hr, preferably 30 min to 6 hr.

As the base, organic bases such as triethylamine, pyridine, N-methylmorpholine, 2,6-lutidine, 1,8-diazabicyclo[5.4.0]undec-7-ene, etc.; etc. can be mentioned, with preference given to N-methylmorpholine.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; etc. can be mentioned, which may be used alone or in combination. A preferable solvent in this reaction is ether solvent, and THF is more preferable.

When a compound of the formula (1) wherein $R^4$ is a substituent other than —$COR^{60}$ is desired, such compound can be produced from a compound of the formula 38 or 37 by a known method.

Step 6-1

In this Step, the cyclic urethane of the formula 27 obtained in Step 2-5 is sulfonylated and subsequently subjected to ring opening reaction with a nucleophilic agent to give a sulfonamide derivative of the formula 39. For example, when the nucleophilic agent is a base (hydroxide ion), $T_8$ in the compound of the formula 39 obtained by this Step is a hydroxyl group. When, for example, the nucleophilic agent is alkylamine, $T_8$ in the compound of the formula 39 obtained by this Step is an alkylcarbamoyloxy group. In this Step, moreover, the substituents $T_1$ at $R^{3'}$ and $P_1$, a carboxylic protecting group of acid do not change and correspond to $T_3$ and $P_4$, respectively.

The sulfonylation agent is appropriately depending on the desired $R^1$, and $ClSO_2$—$R^1$ or $O(SO_2$—$R^1)_2$ is used for the reaction. The reaction is carried out in the presence of a base, and as the base, for example, alkyl lithiums such as n-butyl lithium, t-butyl lithium, s-butyl lithium, etc.; alkali metal hydrides such as sodium hydride, potassium hydride, etc.; alkali metal amides such as lithium diisopropylamide, sodium bis(trimethylsilyl)amide, lithium bis(trimethylsilyl)amide, etc.; etc. can be mentioned, with preference given to sodium hydride.

As the solvent, for example, ether solvents such as diethyl ether, tetrahydrofuran (THF), dioxane, 1,2-dimethoxyethane, diglyme, etc.; polar solvents such as N,N-dimethylformamide, dimethyl sulfoxide, etc.; etc. can be mentioned, which may be used alone or in combination. A preferable solvent in this reaction is ether solvent, and a mixed solvent of THF and 15-crown-5-ether is more preferable.

The reaction temperature is generally –20° C. to 100° C., preferably 0° C. to 50° C.

The reaction time is 1 hr to 48 hr, preferably 1 hr to 24 hr.

When, for example, the nucleophilic agent in the subsequent ring-opening reactions is a base (hydroxyl anion), this reaction is conventional hydrolysis in the presence of a base, and the base to be used for the reaction includes, for example, alkali metal carbonates such as sodium carbonate, potassium carbonate, cesium carbonate, sodium hydrogen carbonate, potassium hydrogen carbonate, etc.; alkali metal hydroxides such as lithium hydroxide, sodium hydroxide, potassium hydroxide, etc.; etc. can be mentioned, with preference given to alkali metal hydroxide, and sodium hydroxide is more preferable.

As the solvent, for example, ether solvents such as diethyl ether, tetrahydrofuran (THF), dioxane, 1,2-dimethoxyethane, diglyme, etc.; alcohol solvents such as methanol, ethanol, isopropyl alcohol, t-butyl alcohol, etc.; polar solvents such as N,N-dimethylformamide, dimethyl sulfoxide, water, etc.; etc. can be mentioned, which may be used alone or in combination. A preferable solvent in this reaction is polar solvent, and a mixed solvent of THF, methanol and water is more preferable.

The reaction temperature is generally 0° C. to 100° C., preferably room temperature to 50° C.

The reaction time is 10 min to 48 hr, preferably 30 min to 24 hr.

Thus obtained compound of the formula 39 can be used in the next reaction without isolation.

When the nucleophilic agent is alkylamine, for example, isopropylamine, morpholine, benzylamine, etc. can be mentione as the alkylamine.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc. such as, etc.; halogenated solvents such as dichloromethane, chloroform, carbon tetrachloride, 1,2-dichloroethane, etc.; polar solvents such as N,N-dimethylformamide, dimethyl sulfoxide, acetonitrile, etc.; etc. can be mentioned, which may be used alone or in combination. A preferable solvent in this reaction is ether solvent, and THF is more preferable.

The reaction temperature is generally 0° C. to 100° C., preferably room temperature to 80° C.

The reaction time is 1 hr to 24 hr, preferably 1 hr to 12 hr.

Thus obtained compound of the formula 39 can be used in the next reaction without isolation.

Step 6-2

In this Step, a substituent $T_8$ at $R^{2'}$ in the compound of the formula 39 obtained in Step 6-1 is led to $T_{12}$ under conventional conditions. For example, when $R^{2'}$ is an alkyl chain and $T_8$ is a hydroxyl group, this step includes protection of the hydroxyl group ($T_8$) with a conventional protecting group transforming into $T_{12}$.

$T_{12}$ is appropriately chosen according to $P_4$, or $T_3$, $R^1$, and when, for example, $T_{12}$ is a hydroxyl group protected by tetrahydropyranyl ether, a method using 3,4-dihydro-2H-pyran in the presence of an acid catalyst can be mentioned. In this case, as the acid, p-toluenesulfonic acid, pyridinium p-toluenesulfonate, camphorsulfonic acid, methanesulfonic acid, benzenesulfonic acid, hydrochloric acid, etc. can be mentioned.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, dimethyl sulfoxide, acetonitrile, etc.; etc. can be mentioned, which may be used alone or in combination. A preferable solvent in this reaction is halogenated solvent, and chloroform is more preferable.

The reaction temperature is generally room temperature to 100° C., preferably room temperature to 70° C.

The reaction time is 1 hr to 24 hr. preferably 2 hr to 12 hr.

Thus obtained compound of the formula 40 can be used in the next reaction without isolation.

This Step is performed as necessary or may be omitted. In this case, the compound of the formula 39 can be treated as a compound of the formula 45.

Step 6-3

In this Step, a sulfonamide group of the compound of the formula 40 obtained in Step 6-2 is protected with a protecting group $P_5$ by a conventional method. $P_5$ is appropriately chosen depending on $P_4$, $T_3$, $T_{12}$ or $R^1$. When, for example, $P_5$ is a 2-trimethylsilylethyl group, a method using Mitsunobu reagents such as diethyl azodicarboxylate, etc. in the presence of 2-trimethylsilylethyl alcohol can be mentioned. As the solvent in this case, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, dimethyl sulfoxide, acetonitrile, etc.; etc. can be mentioned, which may be used alone or in combination. A preferable solvent in this reaction is ether solvent, and THF is more preferable.

The reaction temperature is generally room temperature to 100° C., preferably room temperature to 50° C.

The reaction time is 1 hr to 96 hr, preferably 2 hr to 24 hr.

Thus obtained compound of the formula 41 can be used in the next reaction without isolation.

Step 6-4

In this Step, a substituent $T_{12}$ at $R^{2'}$ in the compound of the formula 41 obtained in Step 6-3 is led to $T_4$ in a compound of the formula 42. For example, deprotection reaction of a hydroxyl group by a conventional method and the like can be mentioned. In this case, $T_4$ is a hydroxyl group, and as $T_{12}$, for example, a hydroxyl group protected by tetrahydropyranyl ether, acetoxy group, t-butoxy group, or t-butyldimethylsilyloxy group, etc. can be mentioned. The reaction conditions are appropriately chosen depending on $P_4$, $P_5$, $T_3$, $T_{12}$ and $R^1$. For example, when $P_4$ is a t-butyl group, $P_5$ is a 2-trimethylsilylethyl group and $T_{12}$ is a hydroxyl group protected with tetrahydropyranyl ether, the deprotection can be carried out in the presence of an acid catalyst.

As the acid, mineral acids such as hydrochloric acid, sulfuric acid, phosphoric acid, etc.; organic acids such as acetic acid, trifluoroacetic acid, methanesulfonic acid, p-toluenesulfonic acid, etc. can be mentioned, with preference given to p-toluenesulfonic acid.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is alcohol solvent, and methanol is more preferable.

The reaction temperature is generally 0° C. to 100° C., preferably room temperature to 50° C.

The reaction time is 30 min to 48 hr, preferably 1 hr to 12 hr.

Thus obtained compound of the formula 42 can be used in the next reaction without isolation.

Step 6-5

In this Step, a substituent $T_3$ at $R^{3'}$ and/or a substituent $T_4$ at $R^{2'}$ of the compound of the formula 42 obtained in Step 6-4 are/is converted to V' and/or W', respectively, under conventional conditions. For example, when $R^{3'}$ is a benzene ring and $T_3$ is a halogen atom, so-called Negishi reaction, Suzuki-Miyaura reaction (Metal-catalyzed Cross Coupling Reactions; WILEY-VCH; New York, 1998), Buchwald reaction, Ullmann reaction (Tetrahedron 2002, 11, 2041-2075; J. Am. Chem. Soc. 2003, 125, 6653-6655) and the like can be applied, whereby the compound of the formula 43, wherein V' is an alkoxycarbonyl alkyl, an aryl group, an arylamino group or an aryl alkoxy group can be obtained. When, for example, $R^{2'}$ is an alkyl chain and $T_4$ is a hydroxyl group, for example, the compound of the formula 43 wherein W' is an alkoxy group or acyloxy group can be obtained by a conventional method.

Step 6-6

In this Step, the sulfonamide group of the compound of the formula 33 obtained in Step 5-5 is protected with a protecting group $P_5$ by a conventional method. While $P_5$ can be appropriately chosen depending on $P_4$, $T_3$, $T_4$ or $T_5$, when, for example, $P_5$ is a 2-trimethylsilylethyl group, a method using Mitsunobu reagents such as diethyl azodicarboxylate, etc. in the presence of 2-trimethylsilylethyl alcohol can be mentioned.

As the solvent in this case, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; ester solvents such as ethyl acetate, methyl acetate, butyl acetate, etc.; polar solvents such as acetone, N,N-dimethylformamide, dimethyl sulfoxide, acetonitrile, etc.; etc. can be mentioned, which may be used alone or in combination. A preferable solvent in this reaction is ether solvent, and THF is more preferable.

The reaction temperature is generally room temperature to 100° C., preferably room temperature to 50° C.

The reaction time is 1 hr to 96 hr, preferably 2 hr to 24 hr.

Thus obtained compound of the formula 44 can be used in the next reaction without isolation.

This Step is performed as necessary, or may be omitted when the next Step and the following Steps proceed without protection. In this case, the compound of the formula 33 may be treated as the compound of the formula 44 wherein $P_5$ is a hydrogen atom.

Step 6-7

In this Step, a substituent $T_5$ at U' of the compound of the formula 44 obtained in Step 6-6 is led to the other substituent under conventional conditions to give a compound of the formula 43. In this Step, a substituent $T_3$ at $R^{3'}$ and a substituent $T_4$ at $R^{2'}$ do not change and correspond to V' and W', respectively.

For example, when U' is an aromatic ring and $T_5$ is a halogen atom, so-called Negishi reaction, Suzuki-Miyaura reaction (Metal-catalyzed Cross Coupling Reactions; WILEY-VCH; New York, 1998), Buchwald reaction, Ullmann reaction (Tetrahedron 2002, 11, 2041-2075; J. Am. Chem. Soc. 2003, 125, 6653-6655) and the like can be applied, whereby a compound of the formula 43, wherein $R^1$ is a biaryl group or arylaminoaryl group can be obtained, for example.

Step 6-8

In this Step, $P_5$, which is a protecting group of sulfonamide, in the compound of the formula 43 obtained in Step 6-5 or 6-7 is deprotected by a conventional method. The reaction conditions are appropriately chosen depending on $P_4$, and, for example, when $P_4$ is a t-butyl group and $P_5$ is a 2-trimethylsilylethyl group, deprotection can be performed using an acid or fluoride.

As the acid, acetic acid, hydrochloric acid, sulfuric acid, phosphoric acid, trifluoroacetic acid, methanesulfonic acid, trifluoromethanesulfonic acid, etc. can be mentioned, with preference given to trifluoroacetic acid. As the fluoride source, hydrogen fluoride, hydrogen fluoride-pyridine, tetrabutylammonium fluoride, potassium fluoride, etc. can be mentioned, with preference given to tetrabutylammonium fluoride.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; ester solvents such as ethyl acetate, methyl acetate, butyl acetate, etc.; polar solvents such as acetone, N,N-dimethylformamide, dimethyl sulfoxide, acetonitrile, water, etc.; etc. can be mentioned, which may be used alone or in combination. A preferable solvent in this reaction is ether solvent, and THF is more preferable.

The reaction temperature is generally 0° C. to 120° C., preferably room temperature to 100° C.

The reaction time is 1 hr to 48 hr, preferably 1 hr to 12 hr.

Thus obtained compound of the formula 45 can be used in the next reaction without isolation.

When Step 6-6 is omitted, this Step can be also omitted.

Step 6-9

In this Step, $T_3$ and/or $T_4$ of the compound of the formula 48 obtained in Step 5-11 are/is converted to V' and/or W'. The reaction conditions are appropriately chosen depending on $P_4$, $T_3$, $T_4$, V' and W' and when, for example, $R^{3'}$ and/or $R^{2'}$ are/is an aromatic ring and $T_3$ and/or $T_4$ are/is a halogen atom, so-called Negishi reaction, Suzuki-Miyaura reaction (Metal-catalyzed Cross Coupling Reactions; WILEY-VCH; New York, 1998), Buchwald reaction, Ullmann reaction (Tetrahedron 2002, 11, 2041-2075; J. Am. Chem. Soc. 2003, 125, 6653-6655) and the like can be applied, whereby the compound of the formula 45, wherein V' and/or W' are/is an alkoxycarbonyl alkyl group, a carbonylamino group, an alkoxycarbonyl group, an aryl group, an arylamino group, an alkylamino group or an aryl alkoxy group can be obtained.

In addition, when, for example, $T_3$ and/or $T_4$ are/is a nitro group, they can be converted to an amino group under conventional reduction conditions. It is also possible to be followed by reductive alkylation. As the reduction conditions, hydrogenation reaction in the presence of a palladium catalyst, reductive reaction under acidic conditions using tin (II) chloride, iron, zinc, etc., and reductive reaction using sodium borohydride in the presence of copper acetate can be mentioned. A preferable reducing agent in this reaction is sodium borohydride in the presence of copper (II) acetate.

As the solvent, for example, ether solvents such as diethyl ether, tetrahydrofuran (THF), dioxane, 1,2-dimethoxyethane, diglyme, etc.; hydrocarbon solvents such as benzene, toluene, hexane, xylene, etc.; halogenated solvents such as dichloromethane, chloroform, carbon tetrachloride, 1,2-dichloroethane, etc.; alcohol solvents such as methanol, ethanol, isopropyl alcohol, t-butyl alcohol, etc.; polar solvents such as N,N-dimethylformamide, acetonitrile, water, etc.; etc. can be mentioned, which may be used alone or in combination. A preferable solvent in this reaction is alcohol solvent, and a mixed solvent of chloroform and ethanol is more preferable.

The reaction time is 10 min to 12 hr, preferably 30 min to 6 hr.

For example, when $T_3$ and/or $T_4$ are/is an azido group, for example, the compound can be led to compound 45 wherein V' and/or W' are/is an alkylamino group or an amino group by a conventional method. For example, when W' is an alkylamino group, this Step is achieved by subjecting the amino group obtained via a conventional reduction step to reductive alkylation. In this case, the reducing agent for azide reduction is, for example, trialkylphosphine, with preference given to triphenyl phosphine. The subsequent reductive alkylation is performed by a conventional method.

Thus obtained compound of the formula 45 can be used in the next reaction without isolation. This Step is performed as necessary or may be omitted. In this case, the compound of the formula 48 can be treated as the compound of the formula 45.

Step 6-10

In this Step, $T_7$ of the compound of the formula 35 obtained in Step 5-6 or 5-7 is modified by a conventional method to give the compound of the formula 45. By this Step, a $(CH_2)_m$—$X'$—$(CH_2)_n$—$Y'$-$T_7$ moiety in the compound of the formula 35 is converted to $R^1$ in the compound of the formula 45. The reaction conditions are appropriately chosen depending on $T_7$ and the desired compound. For example, conversion of an alkoxycarbonyl group to a hydroxymethyl group, conversion of a halomethyl group to an alkoxymethyl group and the like can be mentioned.

Thus obtained compound of the formula 45 can be used in the next reaction without isolation.

Step 6-11

In this Step, a protecting group of the carboxyl group in the compound of the formula 45 obtained in Step 6-8, 6-9 or 6-10 is deprotected to give a compound of the formula 37. This Step can be also applied to a compound wherein a $CO_2P_4$ moiety of compound 45 is Weinreb amide (CONMe(OMe)). The reaction conditions are appropriately chosen depending on the kind of $P_4$ and the same as those in Step 5-1. In addition, this Step is performed as necessary, or omitted when $P_4$ is a hydrogen atom.

The production methods described in the specification are among the examples of the production method of the compound of the present invention, and compounds other than those explained in the above can be produced by combining conventional methods known in the field of organic synthetic chemistry.

The compound represented by the formula (1) and production method thereof of the present invention is explained in detail in the following by way of Examples. It is needless to say that the present invention is not limited by these Examples.

PREPARATION EXAMPLE 1-1

(2R*,3R*)-3-methylsulfanyl-2-phenyl-butan-2-ol (step 1-1)

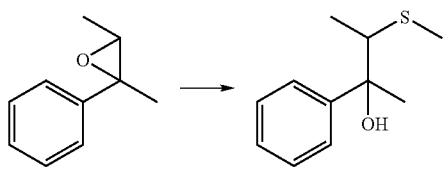

To a solution of trans-2,3-dimethyl-2-phenyloxirane (14 g, 76 mmol) in methanol (100 mL) was added 15% aqueous sodium methyl mercaptan solution (61 mL, 190 mmol) under nitrogen atmosphere at room temperature, and the mixture was warmed to 60° C. and stirred for 2 hours. The mixture was concentrated under reduced pressure, and the residue was extracted twice with diethyl ether (50 mL), sequentially washed with water (50 ml) and saturated aqueous sodium chloride solution (50 mL), and dried over sodium sulfate. The resultant mixture was filtered and the solvent was evaporated to give the title compound (16 g, yield 99%) as a colorless oil.

PREPARATION EXAMPLE 1-2

(1R*,2R*)-(1-chloro-1-methyl-2-methylsulfanyl-propyl)benzene or (1R*,2R*)-(2-chloro-1-methyl-1-methylsulfanyl-propyl)benzene(step 1-2)

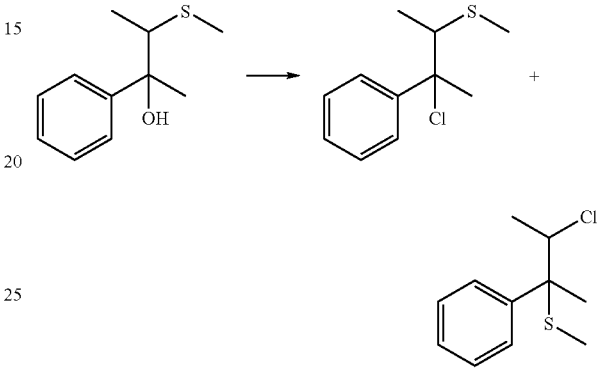

To a solution of (2R*,3R*)-3-methylsulfanyl-2-phenyl-butan-2-ol (1.0 g, 5.1 mmol) obtained in Preparation Example 1-1 in toluene (3.0 mL) was added dropwise a solution of thionyl chloride (0.67 mL, 9.2 mmol) in toluene (2.0 mL) under argon atmosphere at 0° C., and the mixture was stirred for 1 hour. The solution was evaporated to give a mixture of two kinds of regioisomers of the title compound (1.0 g, yield 100%) as a yellow oil.

PREPARATION EXAMPLE 1-3

1-(1-chloro-1-methyl-2-methylsulfanyl-ethyl)-4-fluoro-benzene or 1-(2-chloro-1-methyl-1-methylsulfanyl-ethyl)-4-fluoro-benzene (step 1-3)

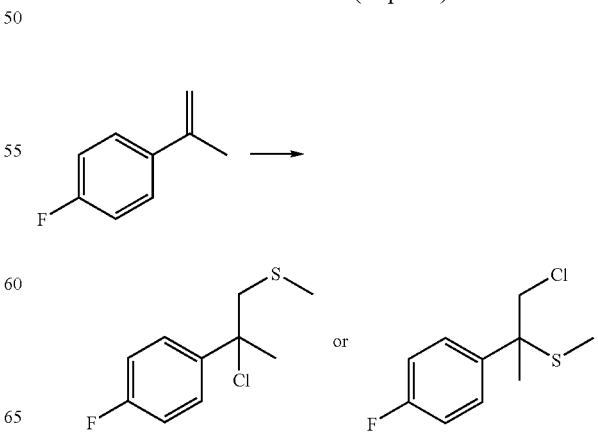

This procedure was performed according to the method described in Synthesis (1980, 9690-9691).

While cooling to −40° C., sulfuryl chloride (2.9 mL, 37 mmol) was added dropwise to a solution of dimethyl disulfide (3.3 mL, 37 mmol) in 1,2-dimethoxyethane (20 mL) under nitrogen atmosphere, and the mixture was stirred for 10 min. The obtained solution was added dropwise to a solution of 4-fluoro-α-methylstyrene (10 g, 73 mmol) in 1,2-dimethoxyethane (20 mL) while maintaining a temperature below −30° C. After stirring for 1 hour at room temperature, the solution was evaporated to give a crude product of the title compound. The obtained product was used in the next step without further purification.

PREPARATION EXAMPLE 1-4 diethyl 2-[1-(4-fluorophenyl)-1-methyl-2-methylsulfanyl-ethyl]malonate (step 1-4)

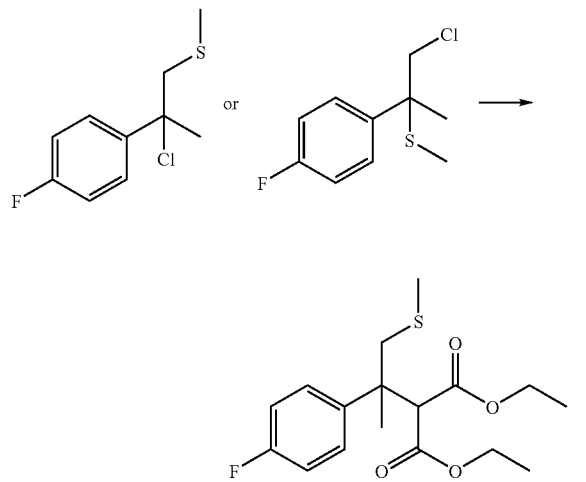

This procedure was performed according to the method described in Synthesis (1980, 9690-9691).

To a solution of diethyl malonate (12 mL, 81 mmol) in ethanol (40 mL) was added dropwise 21% sodium ethoxide ethanol solution (29 mL, 77 mmol) under nitrogen atmosphere under ice-cooling. The mixture was warmed to room temperature, stirred for 1 hour, and cooled again with ice. The crude product (73 mmol) of 1-(1-chloro-1-methyl-2-methylsulfanyl-ethyl)-4-fluorobenzene or 1-(2-chloro-1-methyl-1-methylsulfanyl-ethyl)-4-fluorobenzene obtained in Example 1-3 was added dropwise to the mixture while maintaining a temperature below 4° C. The obtained solution was stirred for 1 hour at room temperature and concentrated under reduced pressure. The residue was neutralized by adding a 2N aqueous hydrochloric acid solution and the aqueous layer was extracted with ethyl acetate (50 mL). The organic layer was dried over magnesium sulfate, filtrated and the solvent was evaporated. Then the obtained residue was purified by silica gel chromatography (hexane: ethyl acetate=20:1 to 5:1) to give the title compound (24 g, yield 84%) as a pale-yellow oil.

PREPARATION EXAMPLE 1-5

[3,3-bis-ethoxycarbonyl-2-(4-fluorophenyl)-2-methylpropyl]dimethylsulfonium p-toluenesulfonate (step 1-5)

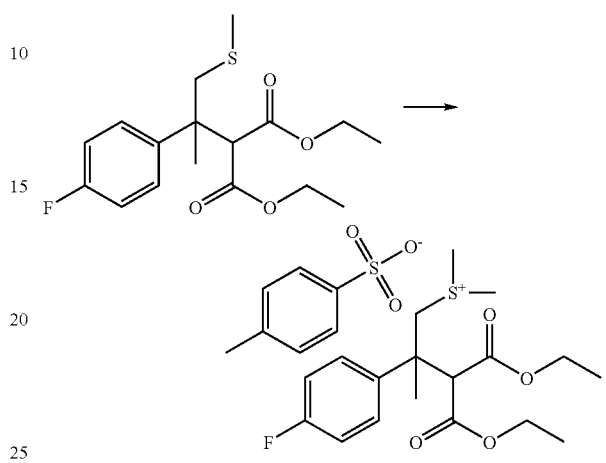

This procedure was performed according to the method described in Synthesis (1980, 9690-9691).

Diethyl 2-[1-(4-fluorophenyl)-1-methyl-2-methylsulfanylethyl]malonate (1.0 g, 2.9 mmol) obtained in Preparation Example 1-4 and methyl p-toluenesulfonate (0.47 mL, 3.1 mmol) were mixed under nitrogen atmosphere, and the mixture was stirred for 12 hours at 100° C. The obtained solution was cooled to room temperature to give a crude product of the title compound as a pale-yellow oil. The obtained product was used in the next step without purification.

PREPARATION EXAMPLE 1-6

2-(4-fluorophenyl)-2-methyl-cyclopropane-1,1-dicarboxylic acid diethyl ester (step 1-6)

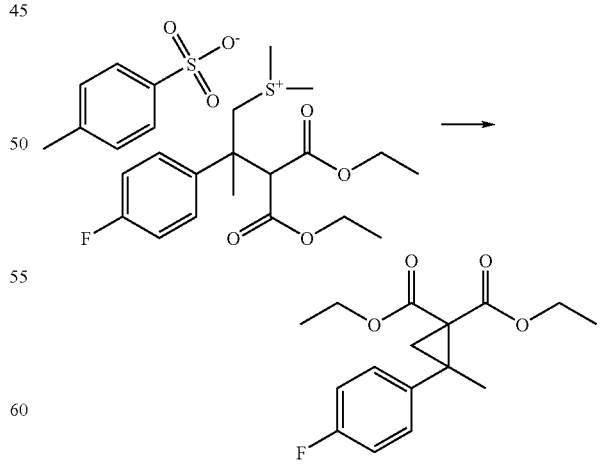

This procedure was performed according to the method described in Synthesis (1980, 9690-9691).

Under ice-cooling and under nitrogen atmosphere, a solution of 21% sodium ethoxide in ethanol (1.6 mL, 4.4 mmol)

was added to a solution of the crude product (2.9 mmol) of [3,3-bis-ethoxycarbonyl-2-(4-fluorophenyl)-2-methylpropyl]dimethylsulfonium p-toluenesulfonate in ethanol (10 mL), which was obtained in Preparation Example 1-5, and the mixture was stirred for 1 hour. The obtained solution was concentrated under reduced pressure, and the residue was neutralized by the addition of a 2N aqueous hydrochloric acid solution, and the aqueous layer was extracted with ethyl acetate (10 mL). The organic layer was dried over magnesium sulfate and filtrated, and the solvent was evaporated. Then, the obtained residue was purified by silica gel chromatography (hexane:ethyl acetate=20:1 to 5:1) to give the title compound (0.64 g, yield 75%) as a pale-yellow oil.

PREPARATION EXAMPLE 1-7

2-methyl-2-phenyl-cyclopropane-1,1-dicarboxylic acid diethyl ester (step 1-7)

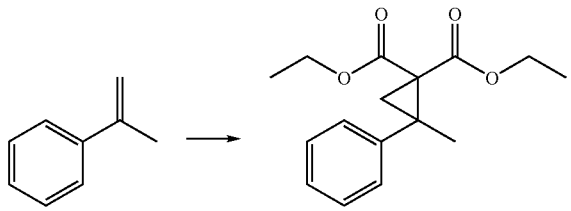

This procedure was performed according to the method described in Bull. Chem. Soc. Jpn. (1982, 55, 2687-2688).

To a solution of α-methylstyrene (570 mL, 4.4 mol), 1,8-diazabicyclo[5.4.0]undec-7-ene (240 mL, 1.6 mol) and copper (II) bromide (9.8 g, 44 mmol) in toluene (700 mL) was added diethyl bromomalonate (210 g, 0.88 mol) at 0° C., and the mixture was stirred for 22 hours at room temperature. The obtained solution was washed with saturated aqueous ammonium chloride solution and saturated aqueous sodium chloride solution, and dried over sodium sulfate. Then, the solution was filtered and the solvent was evaporated. The obtained residue was separated and purified by silica gel chromatography (hexane:ethyl acetate=20:1) to give the title compound (110 g, yield 45%) as a colorless oil.

PREPARATION EXAMPLE 1-7-2

(2R*,3R*)-2-methyl-3-phenyl-cyclopropane-1,1-dicarboxylic acid dimethyl ester (step 1-7)

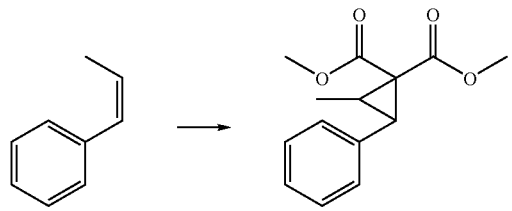

This procedure was performed according to the method described in Synlett (2001, 12, 1843-1846).

To a mixture of bis(methoxycarbonyl)(phenyliodono)methanide (30 g, 90 mmol) synthesized by a known method and cis-β-methylstyrene (60 g) was added rhodium (II) acetate dimer (0.16 g, 0.72 mmol). After stirring for 20 min. at 120° C., the mixture was concentrated under reduced pressure. The procedure was repeated twice, and the obtained residues were combined. Then a mixed solvent of hexane:ethyl acetate=5:1 (360 mL) and silica gel (30 g) were added, and the mixture was stirred for 30 min. Silica gel was removed and the mixture was concentrated under reduced pressure to give the title compound (38 g, yield 85%) as a pale-yellow oil.

PREPARATION EXAMPLE 1-8

(R)-2-benzyl-cyclopropane-1,1-dicarboxylic acid dimethyl ester (step 1-8)

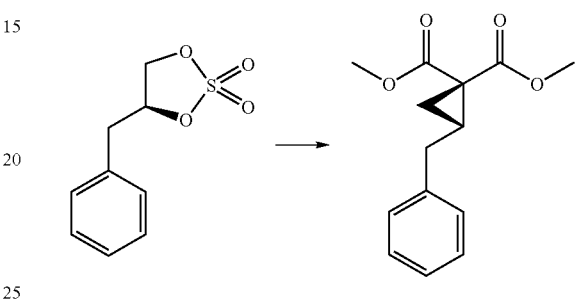

A solution of (S)-4-benzyl-[1,3,2]dioxathiolane 2,2-dioxide (1.6 g, 7.5 mmol) in 1,2-dimethoxyethane (12 mL), which was synthesized from diol obtained by reducing L-phenyllactic acid according to J. Am. Chem. Soc. (1988, 110, 7538-7539), and dimethyl malonate (0.86 mL, 7.5 mmol) was added dropwise to a suspension of sodium hydride (liquid paraffin 40% added, 0.63 g, 16 mmol) in 1,2-dimethoxyethane (25 mL) under argon atmosphere at 0° C. The mixture was warmed to room temperature and stirred for 2.5 hours. To the obtained solution was added saturated aqueous ammonium chloride solution (20 mL). The organic layer was extracted twice with diethyl ether (10 mL), washed with saturated aqueous sodium chloride solution (30 mL), and dried over sodium sulfate. After filtration and evaporation, the obtained residue was purified by silica gel chromatography (hexane:ethyl acetate=9:1) to give the title compound (0.88 g, yield 47%).

PREPARATION EXAMPLE 1-9 a) t-butyl(Z)-3-phenyl-allyl 2-diazomalonate

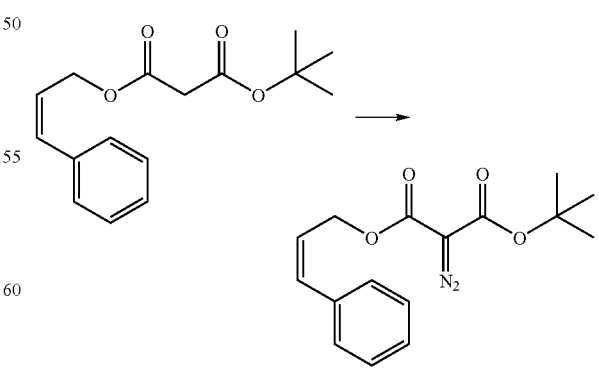

To malonic acid t-butyl ester (Z)-3-phenyl allyl ester (15 g, 54 mmol) was added tolylsulfonylazide (12 g, 60 mmol), $K_2CO_3$ (8.3 g, 60 mmol) in acetonitrile (110 mL). After stirring overnight at room temperature, the reaction mixture was concentrated and diluted with EtOAc. After washing with water (×2) and brine and drying over Na₂SO₄, a crude product was purified by column chromatography using 10:1 hexanes/EtOAc to afford 16 g (100%) of the desired product.

b) (1R*,5R*,6R*)-2-oxo-6-phenyl-3-oxa-bicyclo[3.1.0]hexane-1-carboxylic acid t-butyl ester (step 1-9)

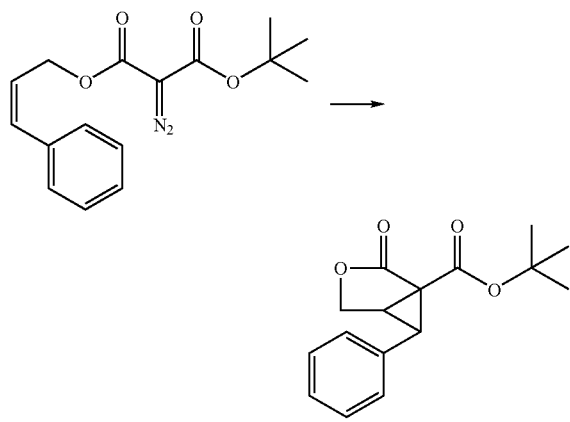

To the 2-diazomalonic acid t-butyl ester (Z)-3-phenyl-allyl ester (16 g, 54 mmol) above were added triethyl phosphite (0.090 g, 0.54 mmol) and copper (I) iodide (0.10 g, 0.54 mmol) in toluene (490 mL). After heating at 130° C. for 5 hours, the solid was filtered off and the filtrate was concentrated. The reaction mixture was purified by column chromatography using dichloromethane as an eluent. Purification afforded 5.2 g of the desired diastereomer and 2.8 g of the other diastereomer.

PREPARATION EXAMPLE 1-10

2-(3-benzyloxyphenyl)-cyclopropane-1,1-dicarboxylic acid dimethyl ester (step 1-10)

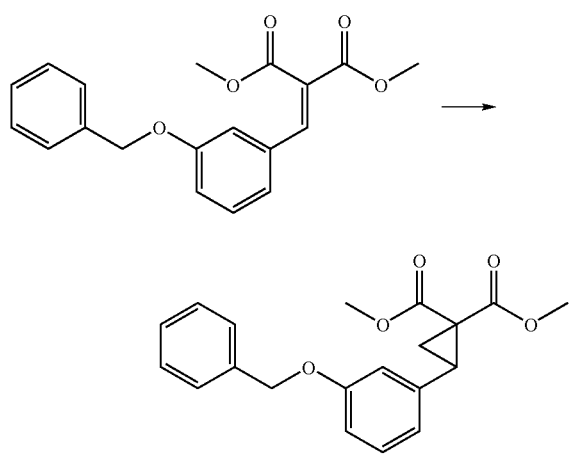

This procedure was performed according to the method described in J. Med. Chem. (1992, 35, 1410-1417).

While water-bathing, to a suspension of sodium hydride (liquid paraffin 40% added, 5.0 g, 0.13 mol) in dimethyl sulfoxide (180 mL) was gradually added trimethylsulfoxonium iodide (28 g, 0.13 mmol) under argon atmosphere, and the mixture was stirred for 30 min. Then dimethyl 2-(3-benzyloxybenzylidene) malonate (37 g, 0.11 mol) synthesized by the method described in the above-mentioned reference was added dropwise. After stirring for 1 hour at 50° C., saturated aqueous ammonium chloride solution (200 mL) and toluene (100 mL) were added to the obtained solution. The mixture was separated into layers and extracted with toluene (100 mL). The organic layer was sequentially washed with water (100 mL) and saturated aqueous sodium chloride solution (20 mL) and dried over magnesium sulfate. After filtration and evaporation, the obtained residue was separated and purified by silica gel chromatography (hexane:chloroform=4:1) to give the title compound (31 g, 79%) as a pale-yellow oil.

PREPARATION EXAMPLE 1-11

(1R*,2R*,3R*)-2-methyl-3-phenylcyclopropane-1,1-dicarboxylic acid mono-methyl ester (step 1-11)

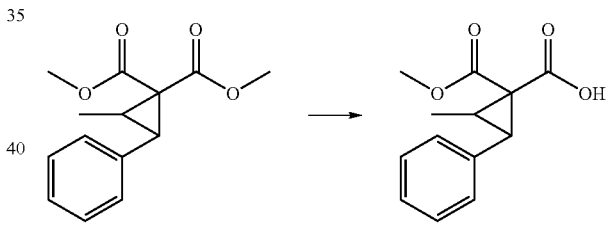

To a solution of (2R*,3R*)-2-methyl-3-phenyl-cyclopropane-1,1-dicarboxylic acid dimethyl ester (39 g, 0.16 mol) obtained in Preparation Example 1-7-2 in methanol (390 mL) was added 4N aqueous sodium hydroxide solution (160 mL, 0.62 mol) at 0° C., and the mixture was stirred for 18 hours at room temperature. After the mixture was concentrated under reduced pressure, diethyl ether and water were added and the mixture was stirred. After the organic layer was removed, concentrated hydrochloric acid was added to the aqueous layer under ice-cooling until the pH level read about 1. The organic layer was extracted with ethyl acetate, washed with saturated aqueous sodium chloride solution, and dried over sodium sulfate. The solution was filtrated and the solvent was evaporated. The obtained crude product was azeotroped with toluene, and diethyl ether and hexane were added gradually. The precipitated crystals were filtrated and dried under reduced pressure to give the title compound (35 g, yield 96%) as while crystals.

PREPARATION EXAMPLE 1-11-2

(1R*,5S*,6S*)-2-oxo-6-phenyl-3-oxa-bicyclo[3.1.0]hexane-1-carboxylic acid(step 1-11)

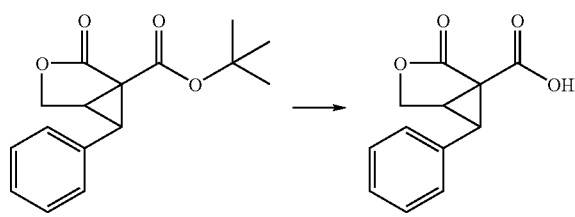

To 0.18 g (0.65 mmol) of (1R*,5R*,6R*)-2-oxo-6-phenyl-3-oxa-bicyclo[3.1.0]hexane-1-carboxylic acid t-butyl ester were added 1 mL of trifluoroacetic acid and 2 mL of dichloroethane. After stirring at room temperature for 20 min, the reaction mixture was concentrated and dried under high vacuum to afford 0.14 g (98%) of the desired acid.

PREPARATION EXAMPLE 1-11-3 a) (1R*,2R*,3R*)-2-hydroxymethyl-1-(methoxy-methyl-carbamoyl)-3-phenyl-cyclopropanecarboxylic acid t-butyl ester

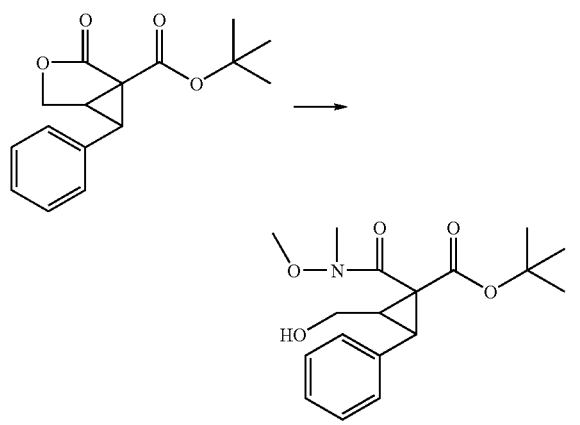

In a 100 mL round-bottomed flask, a solution of N,O-dimethyl hydroxylamine HCl was suspended in 20 mL of dichloromethane. After cooling to 0° C., trimethyl aluminum (2 M in toluene. 3.83 mL, 7.66 mmol) was added dropwise and the mixture was stirred at 0° C. for 45 min. A solution of the previously described (1R*,5R*,6R*)-2-oxo-6-phenyl-3-oxa-bicyclo[3.1.0]hexane-1-carboxylic acid tert-butyl ester (0.3 g, 1 mmol) in 10 mL of dichloromethane was added dropwise to the cooled stirring solution. After stirring at 0° C. for 5 min, the reaction mixture was warmed to room temperature and stirred for 3 hours. After the reaction was completed, the reaction mixture was again cooled in an ice bath and acidified with 10 mL of 1N HCl, extracted with dichloromethane (×3), dried over MgSO₄ and concentrated to afford 0.32 g (86%) of the desired product as a clear oil.

b) (1R*,2R*,3R*)-2-methoxymethyl-1-(methoxy-methyl-carbamoyl)-3-phenyl-cyclopropanecarboxylic acid t-butyl ester

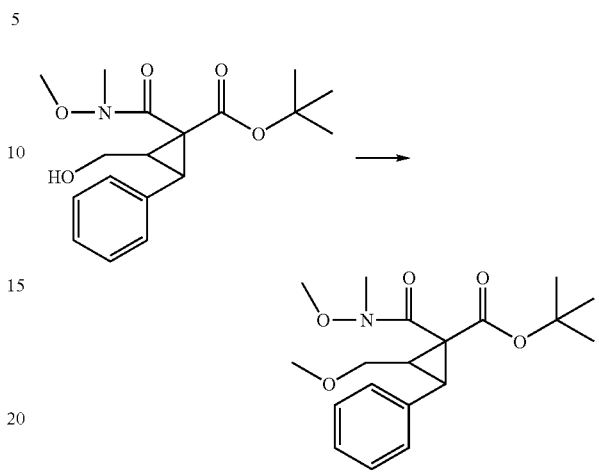

The above (1R*,2R*,3R*)-2-hydroxymethyl-1-(methoxy-methyl-carbamoyl)-3-phenyl-cyclopropanecarboxylic acid t-butyl ester (0.050 g, 0.15 mmol) was dissolved in 1 mL of methyl iodide. To this solution was added silver oxide (0.69 g, 3.0 mmol) and the mixture was stirred overnight at room temperature under N₂ (in the dark). This reaction was incomplete and additional methyl iodide and silver oxide were added. After stirring overnight, the reaction appeared stalled. The catalyst was filtered off through celite and the residue was rinsed with ether. The filtrate was concentrated to a clear oil and purified by prep-TLC using 1:1 hexanes/EtOAc to afford 30 mg of the desired product (58%). This reaction was repeated numerous times to bring up more material. Note: If a huge excess of silver oxide was not used, the reaction often led to a reversion to the lactone product.

c) (1R*,2R*,3R*)-2-methoxymethyl-1-(methoxy-methyl-carbamoyl)-3-phenyl-cyclopropanecarboxylic acid (step 1-11)

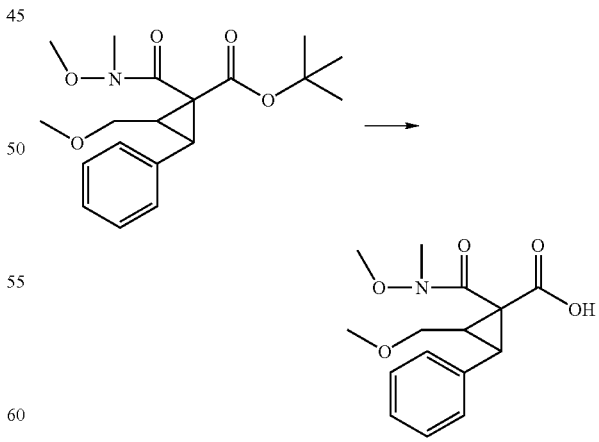

(1R*,2R*,3R*)-2-methoxymethyl-1-(methoxy-methyl-carbamoyl)-3-phenyl-cyclopropanecarboxylic acid t-butyl ester (30 mg, 0.086 mmol) was dissolved in 1 mL of trifluoroacetic acid and 1 mL of dichloromethane. After stirring at room temperature for 2 hours, the reaction mixture was concentrated and azeotroped with toluene. The product was dried under high vacuum before use.

PREPARATION EXAMPLE 1-12

(1R*,2S*,3S*)-1-t-butoxycarbonylamino-2-methyl-3-phenyl-cyclopropanecarboxylic acid methyl ester (step 1-12)

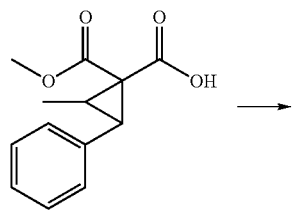

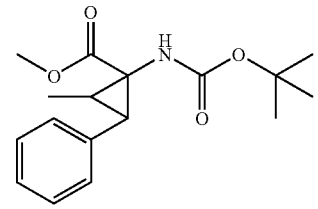

To a solution of 2-methyl-3-phenylcyclopropane-1,1-dicarboxylic acid mono-methyl ester (36 g, 0.16 mol) obtained in Preparation Example 1-11 and triethylamine (35 mL, 0.25 mol) in t-butylalcohol (370 mL) was added diphenylphosphoryl azide (44 mL, 0.20 mol). After stirring for 2 hours at room temperature, the mixture was warmed gradually and refluxed for 7 hours. After the solvent was evaporated under reduced pressure, a mixed solvent of hexane:ethyl acetate=4:1 (750 mL) and silica gel (200 g) were added and the mixture was stirred for 30 min. Then silica gel was removed, and the mixture was concentrated under reduced pressure. Hexane was added to the obtained residue, and the precipitated crystals were filtrated to give the title compound (35 g, yield 74%) as a white solid.

PREPARATION EXAMPLE 1-12-2

[(1R*,5R*,6R*)-2-oxo-6-phenyl-3-oxa-bicyclo[3.1.0]hexa-1-yl]carbamic acid t-butyl ester (step 1-12)

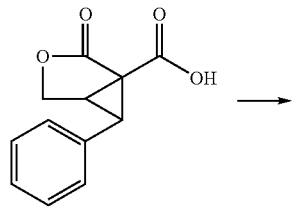

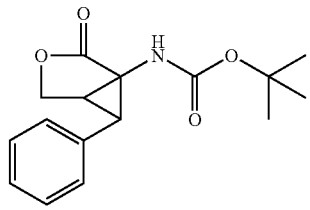

To 0.20 g (0.92 mmol) of (1R*,5S*,6S*)-2-oxo-6-phenyl-3-oxa-bicyclo[3.1.0]hexane-1-carboxylic acid were added diphenylphosphoryl azide (0.33 g, 1.2 mmol) and diisopropylethylamine (0.32 mL, 1.8 mmol) in tert-butyl alcohol. After heating at 90° C. for 2 hours, the reaction mixture was concentrated and purified using column chromatography (3:1 hexanes/EtOAc). The desired product was isolated as a white solid (0.23 g, yield 85%).

PREPARATION EXAMPLE 1-12-3

[(1R*,2R*,3R*)-2-methoxymethyl-1-(methoxy-methyl-carbamoyl)-3-phenyl-cyclopropyl]carbamic acid t-butyl ester (step 1-12)

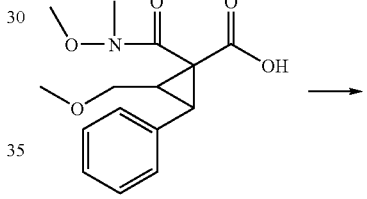

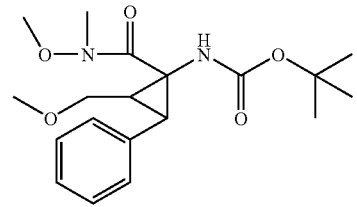

(1R*,2R*,3R*)-2-methoxymethyl-1-(methoxy-methyl-carbamoyl)-3-phenyl-1-cyclopropanecarboxylic acid (0.10 g, 0.34 mmol) was dissolved in 8 mL of t-butyl alcohol. To this solution were added diisopropylethylamine (0.15 g, 0.85 mmol) and 4 Å molecular sieves. Then diphenylphosphoryl azide (0.11 mL, 0.51 mmol) was added in one portion. The reaction mixture was heated to 90° C. overnight. After cooling, the reaction mixture was poured into saturated NaHCO$_3$ and extracted with EtOAc (2×). The combined organic layers were washed with brine and dried over MgSO$_4$. The crude product was purified using column chromatography (5:1->1:1 hexanes/EtOAc gradient) to afford the desired product (stains slightly with KMnO$_4$ stain). A white solid (69 mg, 56% yield) was isolated, which contained about 50% desired product and 50% lactone. This material was carried through to the next step. NOTE: the above reaction was run in very dilute t-butyl alcohol and using 4 Å molecular sieves to prevent formation of free amine and subsequent self-condensation to form a urea byproduct.

PREPARATION EXAMPLE 2-1

2-[2-(t-butyldiphenylsilanyloxy)ethyl]-2-phenyl-cyclopropane-1,1-dicarboxylic acid dimethyl ester (step 2-1)

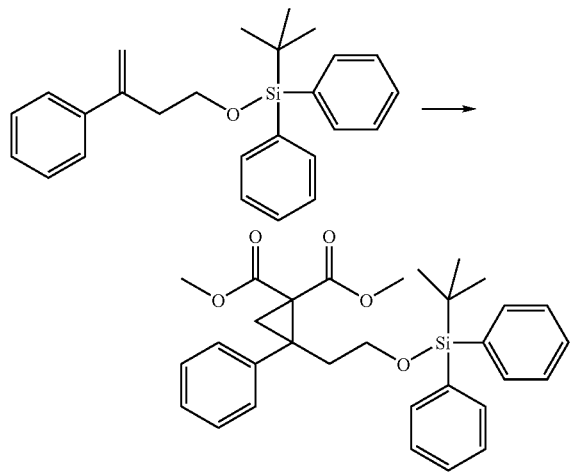

To a mixture of t-butyldiphenyl-(3-phenyl-3-butenyloxy)-silane (3.0 g, 7.0 mmol) and dimethyl diazomalonate (1.1 g, 7.0 mmol), which was synthesized by the method described in Synth. Commun. (1987, 17, 1709-1716), was added rhodium (II) acetate dimmer (62 mg, 0.14 mmol) under argon atmosphere, and the mixture was heated at 100° C. for 10 min. After cooling to room temperature, the mixture was diluted with chloroform (4 mL), separated and purified by silica gel chromatography (hexane:ethyl acetate=100:0 to 4:1) to give the title compound (2.5 g, yield 70%) as a colorless oil.

PREPARATION EXAMPLE 2-2

(1R*,6R*)-2-oxo-6-phenyl-3-oxa-bicyclo[4.1.0]heptan-1-carboxylic acid methyl ester (step 2-2)

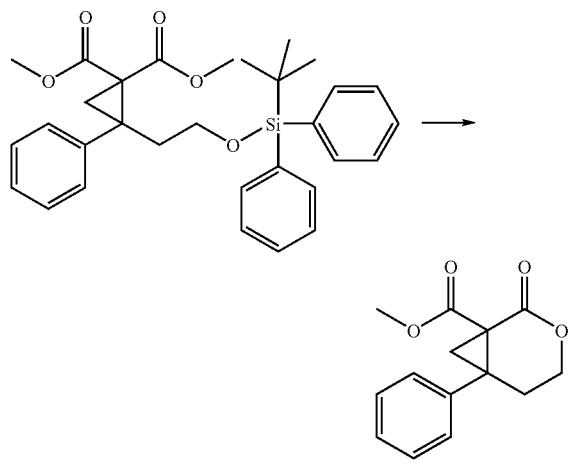

To a solution of 2-[2-(t-butyldiphenylsilanyloxy)ethyl]-2-phenyl-cyclopropane-1,1-dicarboxylic acid dimethyl ester (1.3 g, 2.5 mmol) obtained in Preparation Example 2-1 in tetrahydrofuran (13 mL) was added tetrabutylammonium fluoride trihydrate (1.2 g, 3.7 mmol) under argon atmosphere at 0° C., and the mixture was stirred at room temperature for 12 hours. The obtained solution was diluted with ethyl acetate and washed with saturated aqueous sodium chloride solution. The aqueous layer was extracted twice with ethyl acetate, and the combined organic layers were dried over sodium sulfate. After filtration and evaporation, the obtained residue was separated and purified by silica gel chromatography (hexane:ethyl acetate=10:1 to 1:1) to give the title compound (0.41 g, yield 67%) as a white solid.

PREPARATION EXAMPLE 2-3

(1R*,5S*)-2-oxo-5-phenyl-3-oxa-bicyclo[3.1.0]hexane-1-carboxylic acid t-butyl ester (step 2-3)

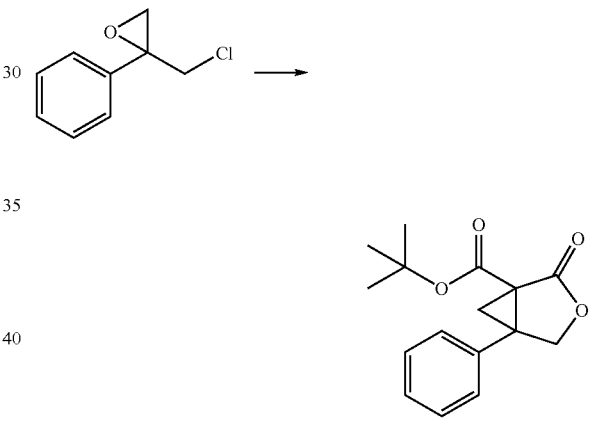

Under nitrogen atmosphere, potassium t-butoxide (110 g, 0.78 mol) was added to a solution of di-t-butyl malonate (170 g, 0.78 mol) in t-butyl alcohol (1.5 L) in 3 portions at room temperature. After stirring at room temperature for 1 hour, the mixture was heated to 70° C. Then a solution of 2-chloromethyl-2-phenyloxirane (120 g) in tetrahydrofuran (500 mL) synthesized by the method described in J. Org. Chem. (1962, 27, 2241-2243) was added dropwise over 90 min. After stirring for 12 hours at 70° C., the mixture was cooled to room temperature and the solvent was evaporated. 10% Aqueous citric acid solution (500 mL) was added to the residue. The mixture was extracted with ethyl acetate (2.0 L), sequentially washed with water (500 mL) and saturated aqueous sodium chloride solution (200 mL), and dried over magnesium sulfate. After filtration and evaporation, the title compound (120 g, 3 step, yield 54%) was recrystallized from a mixed solution of hexane:diisopropyl ether=1:1 (600 mL) as a white solid.

PREPARATION EXAMPLE 2-3-2

(1R,5S)-2-oxo-5-phenyl-3-oxa-bicyclo[3.1.0]hexane-1-carboxylic acid t-butyl ester (step 2-3)

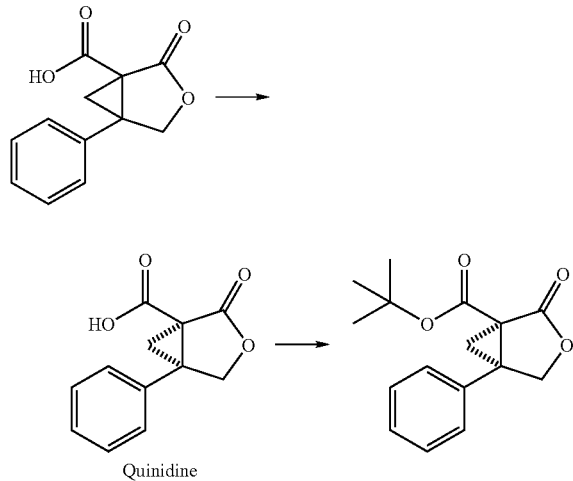

Quinidine

To a suspension of the starting material (7.0 g, 32 mmol) obtained by deprotecting t-butyl group of (1R*,5S*)-2-oxo-5-phenyl-3-oxa-bicyclo[3.1.0]hexane-1-carboxylic acid t-butyl ester obtained in Preparation Example 2-3 in ethanol (210 mL) was added quinidine (10 g, 32 mmol) at room temperature. After stirring at room temperature for 5 hours, the resultant precipitate was filtrated to give an optically active compound as a quinidine salt. The quinidine salt was suspended in ethyl acetate (80 mL) and water (60 mL). Then 1 N aqueous hydrochloric acid solution (20 mL, 20 mmol) was added to the suspension at 0° C. and the mixture was stirred.

After the organic layer was washed with saturated aqueous sodium chloride solution and dried over magnesium sulfate, an optically active carboxylic acid compound (3.3 g, yield 47%, optical purity 96% ee) was obtained as a white amorphous form after filtration and evaporation. The compound was esterificated in a similar manner as in Example 5-2 to give the title compound [4.0 g, yield 95%, $[\alpha]^{25}_D$-62.9° (c0.275, MeOH)] as white crystals.

PREPARATION EXAMPLE 2-4 a) sodium (1R*,2S*)-1-t-butoxycarbonyl-2-hydroxymethyl-2-phenyl-cyclopropanecarboxylate

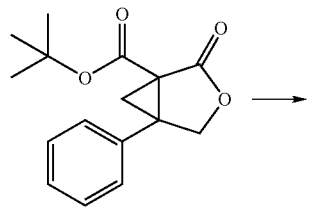

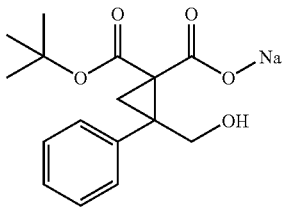

To a solution of (1R*,5S*)-2-oxo-5-phenyl-3-oxa-bicyclo[3.1.0]hexane-1-carboxylic acid t-butyl ester (30 g, 0.11 mol) obtained in Preparation Example 2-3 in tetrahydrofuran (300 mL) was added 4N aqueous sodium hydroxide solution (29 mL, 0.11 mol) at room temperature. After stirring at 60° C. for 2.5 hours, the mixture was concentrated under reduced pressure. Then the mixture was azeotroped with toluene to remove water. The title compound (39 g) was obtained as a white amorphous form. The obtained product was used in the next step without purification.

b) (1R*,2S*)-2-(t-butyldimethylsilanyloxymethyl)-2-phenyl-cyclopropane-1,1-dicarboxylic acid mono-t-butyl ester (step 2-4)

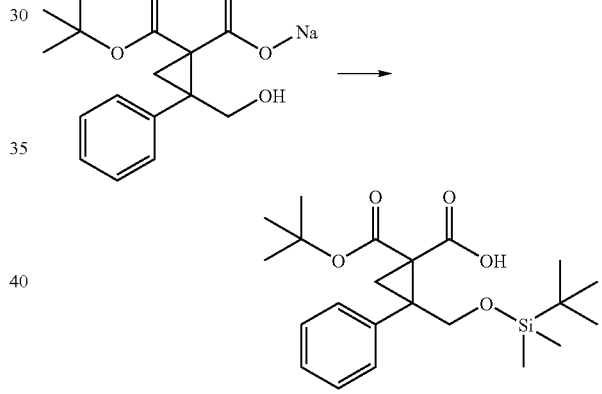

Imidazol (18 g, 0.27 mol) was added to a suspension of sodium (1R*,2S*)-1-t-butoxycarbonyl-2-hydroxymethyl-2-phenyl-cyclopropanecarboxylate (38 g, 0.11 mol) obtained in the above-mentioned Example a) in N,N-dimethylformamide (190 mL) under argon atmosphere at 0° C., and t-butyldimethylsilyl chloride (35 g, 0.24 mol) was further added in 2 portions. After warming to room temperature, the mixture was stirred for 12 hours. Then water (76 mL) and methanol (76 mL) were added to the mixture at 0° C., which was followed by addition of potassium carbonate (30 g, 0.21 mol). After the obtained suspension was stirred for 3 hours at room temperature, toluene (190 mL) was added and the mixture was separated into layers using 10% aqueous citric acid solution (400 mL) while adjusting pH to about 5. The aqueous layer was extracted twice with toluene, and the combined organic layer was sequentially washed with 10% aqueous citric acid solution and saturated aqueous sodium chloride solution, and dried over sodium sulfate. After filtration and evaporation, the product was azeotroped with xylene to remove t-butyldimethylsilanol. The title compound (44 g) was obtained as white crystals. The obtained product was used in the next step without purification.

PREPARATION EXAMPLE 2-4-2

(1R*,2S*)-cis-1-carbamoyl-2-(2-hydroxyethyl)-2-phenylcyclopropanecarboxylic acid methyl ester (Preparation Example 2-4)

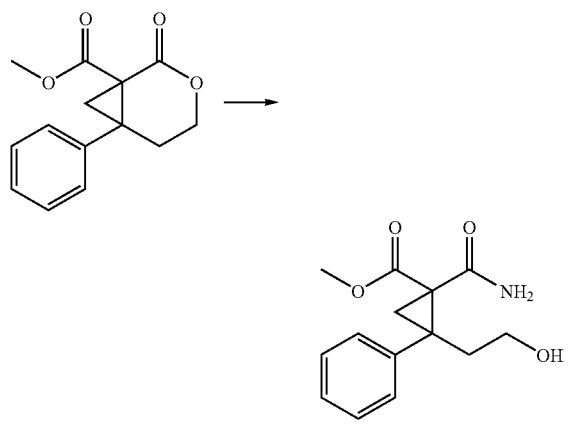

To a solution of (1R,6R*)-2-oxo-6-phenyl-3-oxa-bicyclo[4.1.0]heptan-1-carboxylic acid methyl ester (0.29 g, 1.2 mmol) obtained in Preparation Example 2-2 in a tetrahydrofuran:methanol=1:1 mixture (6 mL) was added 28% ammonia in water (6 mL) at room temperature, and the mixture was stirred for 12 hours. The obtained solution was concentrated under reduced pressure to give the title compound (0.32 g) as a colorless oil. The obtained product was used in the next step without purification.

PREPARATION EXAMPLE 2-5

(1R*,6R*)-3-oxo-6-phenyl-4-oxa-2-aza-bicyclo[4.1.0]heptan-1-carboxylic acid t-butyl ester (Preparation Example 2-5)

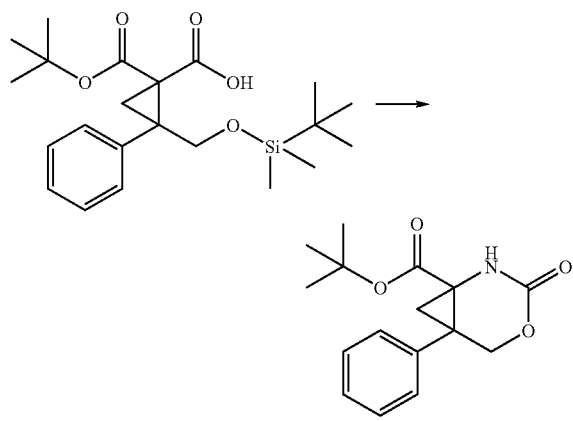

To a solution of (1R*,2S*)-2-(t-butyldimethylsilanyloxymethyl)-2-phenyl-cyclopropane-1,1-dicarboxylic acid mono-t-butyl ester (42 g, 0.10 mol) obtained in Preparation Example 2-4 in N,N-dimethylformamide (310 mL) were sequentially added triethylamine (15 mL, 0.11 mol) and diphenylphosphoryl azide (24 mL, 0.11 mol) under argon atmosphere. After stirring at 80° C. for 30 min., the mixture was cooled to room temperature over 1 hour. Then, cesium fluoride (30 g, 0.20 mol) was added at once, and the mixture was stirred at 50° C. for 1.5 hours. To the obtained suspension were added water (300 mL), toluene (150 mL), diethyl ether (150 mL) and tetrahydrofuran (100 mL), and the insoluble solid was filtrated. The filtrate was separated into layers, and the aqueous layer was extracted twice with toluene. The residue was sequentially washed with 1N aqueous sodium hydroxide solution and water and dried over sodium sulfate. After filtration and evaporation, the obtained residue and the above-mentioned solid were combined. A mixed solvent of hexane:diisopropyl ether=2:1 (150 mL) was added and the mixture was stirred at room temperature for 30 min. After the obtained crystal was filtrated, the residue was dried under reduced pressure to give the title compound (21 g, 3 steps, yield 73%) as a white solid.

PREPARATION EXAMPLE 2-5-2

(1R*,7R*)-3-oxo-7-phenyl-4-oxa-2-azabicyclo[5.1.0]octane-1-carboxylic acid methyl ester (step 2-5)

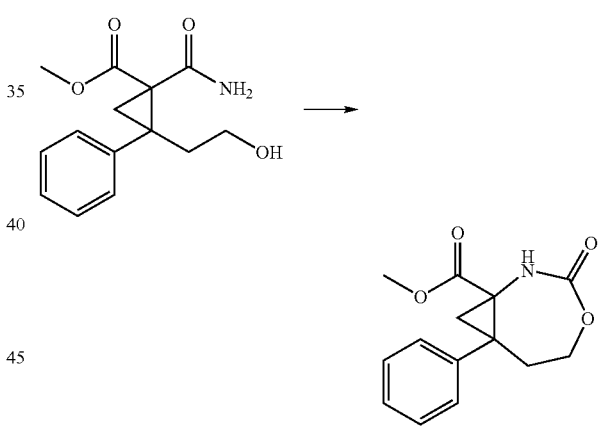

To a solution of (1R*,2S*)-cis-1-carbamoyl-2-(2-hydroxyethyl)-2-phenylcyclopropanecarboxylic acid methyl ester (0.30 g, 1.1 mmol) obtained in Preparation Example 2-4-2 in an ethyl acetate:acetonitrile:water=1:2:1 mixture (12 mL) was added iodobenzene diacetate (0.48 g, 1.5 mmol) at 0° C. After stirring at room temperature for 1.5 hours, iodobenzene diacetate (64 mg, 0.23 mmol) was further added, and the mixture was stirred for 1.5 hours. After the obtained solution was diluted with ethyl acetate and separated into layers, the aqueous layer was extracted twice with ethyl acetate. The combined organic layers were washed with saturated aqueous sodium chloride solution, and dried over sodium sulfate. After filtration and evaporation, the obtained residue was separated and purified by silica gel chromatography (hexane:ethyl acetate=40:1 to 1:2) to give the title compound (0.11 g, 35%) as a white solid.

PREPARATION EXAMPLE 2-6

(1R*,2R*)-1-t-butoxycarbonylamino-2-hydroxymethyl-2-phenylcyclopropanecarboxylic acid t-butyl ester (step 2-6)

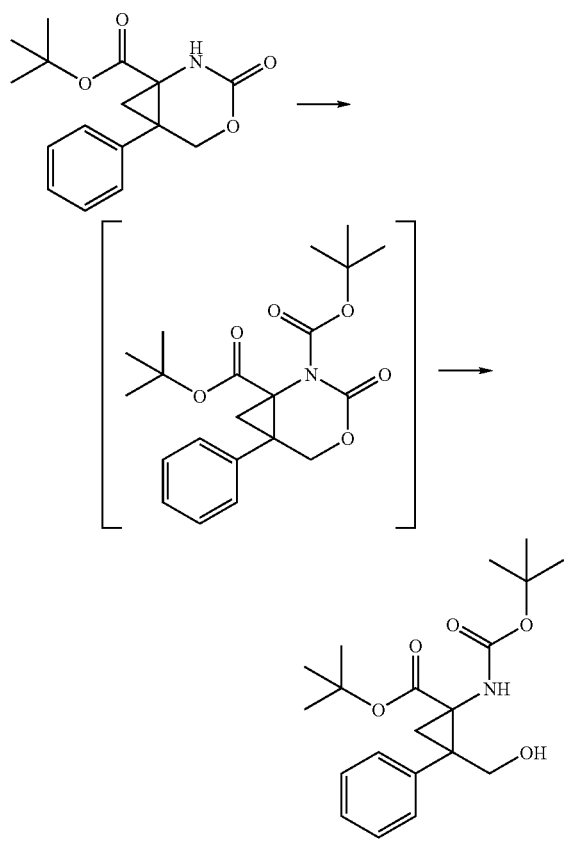

To a solution of (1R*,6R*)-3-oxo-6-phenyl-4-oxa-2-aza-bicyclo[4.1.0]heptan-1-carboxylic acid t-butyl ester (2.0 g, 6.9 mmol) obtained in Preparation Example 2-5 in tetrahydrofuran (40 mL) was added sodium hydride (liquid paraffin 40% added, 0.61 g, 15 mmol) under nitrogen atmosphere at 0° C., and the mixture was stirred for 30 min. Then a solution of di-t-butyl dicarbonate (2.4 g, 11 mmol) in tetrahydrofuran (20 mL) was added dropwise to the obtained solution. After stirring at 0° C. for 5 min., the mixture was warmed to room temperature and stirred for 20 hours. Then, acetic acid (1 mL) and water (30 mL) were added to the obtained solution, and the solution was extracted three times with ethyl acetate (50 mL). The residue was washed with water (30 mL) and saturated aqueous sodium chloride solution (30 mL), and dried over sodium sulfate. After filtration and evaporation, hexane (20 mL) was added to the obtained residue to allow precipitation of crystals. The crystals were filtrated and dried under reduced pressure to give (1R*,6R*)-3-oxo-6-phenyl-4-oxa-2-aza-bicyclo[4.1.0]heptan-1,2-dicarboxylic acid di-t-butyl (2.1 g) as a crude product.

To the obtained solution of (1R*,6R*)-3-oxo-6-phenyl-4-oxa-2-aza-bicyclo[4.1.0]heptan-1,2-dicarboxylic acid di-t-butyl ester (2.1 g, 5.5 mmol) in methanol (42 mL) was added cesium carbonate (0.54 g, 1.7 mmol) at room temperature. After stirring for 30 min., the mixture was concentrated to about half the amount under reduced pressure, and then saturated aqueous sodium chloride solution (40 mL) was added to the obtained residue. The mixture was extracted three times with ethyl acetate (30 mL), washed with water (50 mL) and saturated aqueous sodium chloride solution (50 mL), and dried over sodium sulfate. After filtration and evaporation, hexane (20 mL) was added to the obtained residue to allow precipitation of crystals. The crystals were filtrated and dried under reduced pressure to give the title compound (1.9 g, yield 74%) as a colorless amorphous form.

PREPARATION EXAMPLE 3-1

(1R,2S*)-1-amino-2-vinyl-cyclopropanecarboxylic acid ethyl ester (step 3-1)

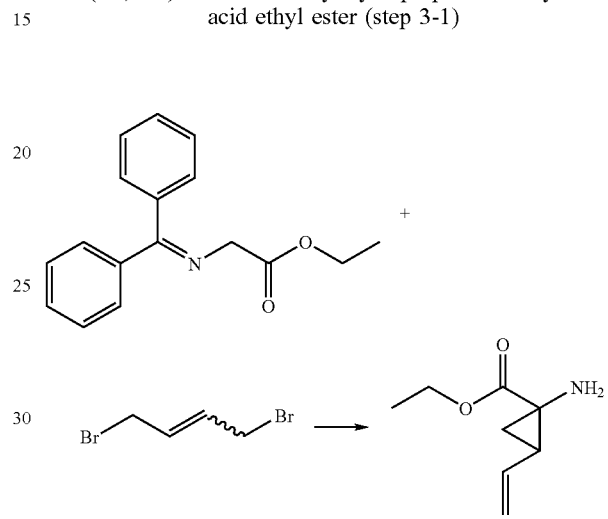

The title compound was synthesized according to the method described in WO0009543.

PREPARATION EXAMPLE 4-1

1-amino-1,1a,2,3,4,8b-hexahydrobenzo[a]cyclopropa[c]cyclohepten-1-carboxylic acid ethyl ester (step 4-1)

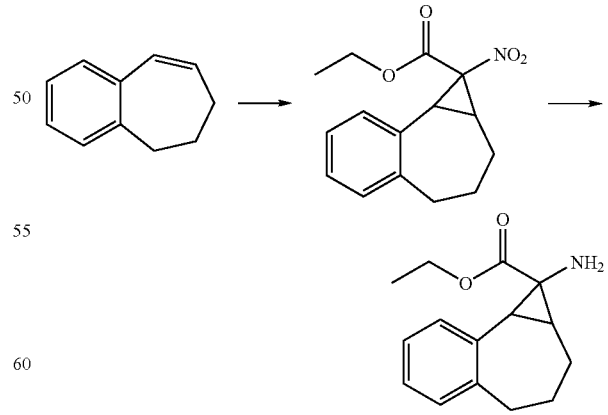

Nitroethyl acetate (3.8 mL, 34 mmol), rhodium (II) pivalate dimmer (0.11 g, 0.17 mmol) and iodobenzene diacetate (12 g, 38 mmol) were gradually added to 6,7-dihydro-5H-benzocycloheptene (5.0 g, 35 mmol) synthesized by the method described in J. Chem. Soc. Chem. Commun. (1990, 18, 1270-1271) under argon atmosphere, and the mixture was stirred at 40° C. for 14 hours. The obtained solution was cooled to room temperature, and separated and purified by silica gel chromatography (hexane:ethyl acetate=20:1) to give 1-nitro-1,1a,2,3,4,8b-hexahydrobenzo[a]cyclopropane[c]cyclohepten-1-carboxylic acid ethyl ester (1.5 g, yield 17%).

To the obtained solution of 1-nitro-1,1a,2,3,4,8b-hexahydrobenzo[a]cyclopropane[c]cyclohepten-1-carboxylic acid ethyl ester (1.9 g, 7.0 mmol) in isopropylalcohol (140 mL) were gradually added aqueous solution of 1N hydrochloric acid (70 mL, 70 mmol) and zinc powder (9.1 g, 0.14 mol), and the mixture was stirred at room temperature for 4 hours. The obtained solution was cooled to 0° C. Then, saturated aqueous sodium hydrogen carbonate solution (150 mL) was added to the solution, and the mixture was filtrated. After the filtrate was separated into layers, the aqueous layer was extracted twice with ethyl acetate (100 mL) and dried over magnesium sulfate. After filtration and evaporation, the obtained residue was separated and purified by silica gel chromatography (chloroform:methanol=30:1) to give the title compound (1.5 g, yield 87%) as a pale-yellow oil.

PREPARATION EXAMPLE 5-1

(1R*,2S*,3S*)-1-t-butoxycarbonylamino-2-methyl-3-phenyl-cyclopropanecarboxylic acid (step 5-1)

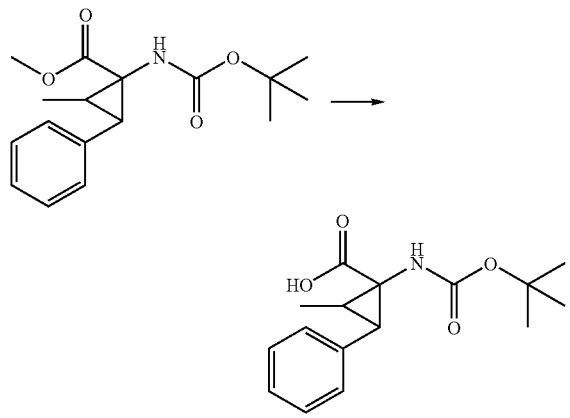

To a solution of (1R*,2S*,3S*)-1-t-butoxycarbonylamino-2-methyl-3-phenyl-cyclopropanecarboxylic acid methyl ester (37 g, 0.12 mol) obtained in Preparation Example 1-12 in a methanol:tetrahydrofuran=15:1 mixture (610 mL) was added 4N aqueous sodium hydroxide solution (95 mL, 0.38 mol), and the mixture was refluxed for 6 hours. The mixture was allowed to cool to room temperature and the solvent was evaporated. 4N aqueous hydrochloric acid solution was added to the residue at 0° C. until the pH level read about 3. After the aqueous layer was extracted with ethyl acetate (800 mL), the organic layer was washed with saturated aqueous sodium chloride solution. The solution was dried over magnesium sulfate and the solvent was evaporated under reduced pressure to give the title compound (38 g) as a crude product of a pale-yellow oil. The obtained product was used in the next step without further purification.

PREPARATION EXAMPLE 5-1-2

(1S,2R,3R)-1-t-butoxycarbonylamino-2-methyl-3-phenyl-cyclopropanecarboxylic acid (step 5-1)

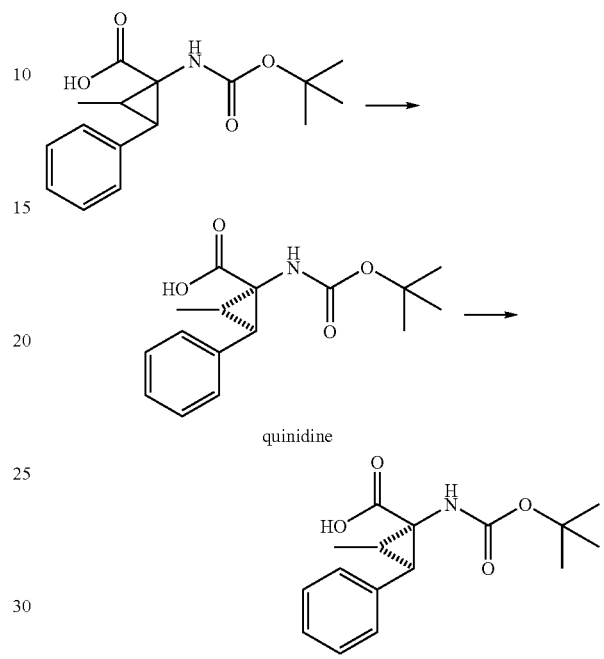

To a solution of (1R,2S*,3S*)-1-t-butoxycarbonylamino-2-methyl-3-phenyl-cyclopropanecarboxylic acid (38 g) obtained in Preparation Example 5-1 in isopropylalcohol (380 mL) was added quinidine (40 g, 0.12 mmol), and the mixture was stirred at room temperature for 20 hours. The obtained crystal was filtrated to give an optical active quinidine salt (28 g, 44 mmol) as a white solid. The quinidine salt was suspended in ethyl acetate (250 mL) and water (250 mL), and the suspension was stirred after addition of 1N aqueous hydrochloric acid solution (88 mL, 88 mmol) at 0° C. The organic layer was washed with saturated aqueous sodium chloride solution, and dried over magnesium sulfate. The title compound [13 g, 2 steps, yield 37%, $[\alpha]^{25}_D$+111° (c1.00, MeOH), optical purity 97% ee] was obtained as a white amorphous form by filtration and evaporation.

PREPARATION EXAMPLE 5-2

(1S,2R,3R)-1-t-butoxycarbonylamino-2-methyl-3-phenyl-cyclopropanecarboxylic acid t-butyl ester (step 5-2)

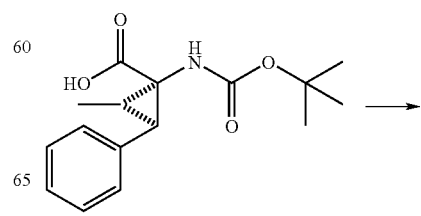

-continued

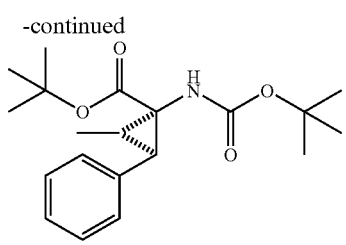

Under argon atmosphere, N,N-dimethylformamide di-t-butylacetal (5.0 mL, 21 mmol) was added dropwise to a solution of (1S,2R,3R)-1-t-butoxycarbonylamino-2-methyl-3-phenyl-cyclopropanecarboxylic acid (1.5 g, 5.2 mmol) obtained in Preparation Example 5-1 in toluene (15 mL) at 80° C. over 15 min, and the mixture was stirred for 1 hour. The obtained solution was cooled to 0° C. After saturated aqueous sodium hydrogen carbonate solution (15 mL) was added to the mixture, the organic layer was washed three times with water (10 mL) and dried over magnesium sulfate. Then, the title compound (1.8 g, yield 99%) was obtained as a pale-yellow oil by filtration and evaporation. The obtained product was used in the next step without further purification.

PREPARATION EXAMPLE 5-3

(1R*,2S*)-1-t-butoxycarbonylamino-2-[2-(2-ethoxy-carbonyl-ethyl)-phenyl]-cyclopropanecarboxylic acid methyl ester (step 5-3)

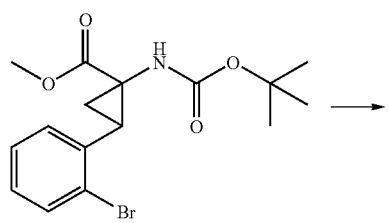

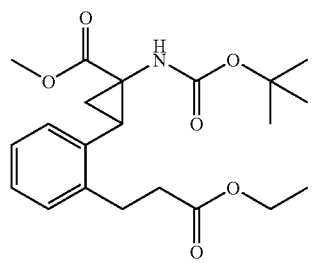

To a solution of (1R*,2S*)-2-(2-bromo-phenyl)-1-t-butoxycarbonylamino-cyclopropanecarboxylic acid methyl ester (50 mg, 0.14 mmol) obtained in a similar manner as described in Preparation Example 1-12 in tetrahydrofuran (0.5 mL) were added dibenzylidene acetone palladium (7.8 mg, 14 μmol), 1,2,3,4,5-pentaphenyl-1'-(di-t-butylphosphino) ferrocene (9.6 mg, 14 μmol) and 0.5M solution of 3-ethoxy-3-oxopropylzinc bromide in tetrahydrofuran (0.81 mL, 0.41 mmol), and the mixture was stirred at room temperature for 2 hours. To the mixture were added 1N aqueous hydrochloric acid solution (0.5 mL) and water (5.0 mL), and the mixture was extracted twice with ethyl acetate (10 mL). Then the organic layer was sequentially washed with water (5.0 mL) and saturated aqueous sodium chloride solution (5.0 mL), and dried over magnesium sulfate. After filtration and evaporation, the obtained residue was separated and purified by silica gel chromatography (hexane: ethyl acetate=5:1) to give the title compound (50 mg, yield 95%) as a brown oil.

PREPARATION EXAMPLE 5-4

(1S,2R,3R)-1-amino-2-methyl-3-phenyl-cyclopropanecarboxylic acid t-butyl ester (step 5-4)

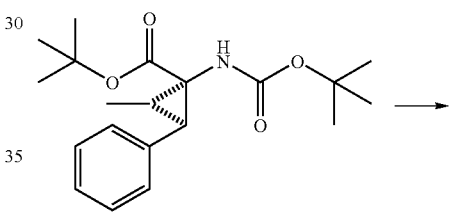

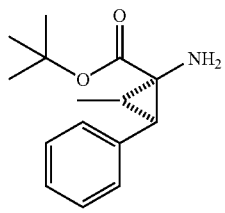

Under argon atmosphere, p-toluenesulfonic acid monohydrate (3.5 g, 18 mmol) was added to a solution of (1S,2R,3R)-1-t-butoxycarbonylamino-2-methyl-3-phenyl-cyclopropanecarboxylic acid t-butyl ester (3.2 g, 9.1 mmol) obtained in Preparation Example 5-2 in acetonitrile (30 mL) at 0° C., and the mixture was stirred at room temperature for 16 hours. The obtained solution was cooled to 0° C., and 1N aqueous sodium hydroxide solution (20 mL) was added. The aqueous layer was extracted twice with ethyl acetate (15 mL) and dried over magnesium sulfate. Then, the residue was filtrated and the solvent was evaporated to give a crude product of the title compound (1.8 g, yield 99%) as a crude product of a pale-yellow oil. The obtained product was used in the next step without purification.

PREPARATION EXAMPLE 5-4-2

(1R*,2S*)-1-amino-2-azidomethyl-2-phenyl-cyclopropanecarboxylic acid t-butyl ester (step 5-4)

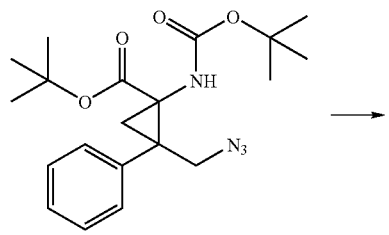

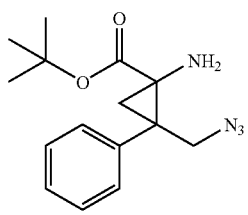

p-Toluenesulfonic acid monohydrate (5.2 g, 27 mmol) was added to a solution of the crude product (5.0 g) of (1R*,2S*)-2-azidomethyl-1-t-butoxycarbonylamino-2-phenyl-cyclopropanecarboxylic acid t-butyl ester, which was made from (1R*,2S*)-1-t-butoxycarbonylamino-2-hydroxymethyl-2-phenyl-cyclopropanecarboxylic acid t-butyl ester obtained in Preparation Example 2-6 by general method step 5-3, in acetonitrile (40 mL). The mixture was stirred at room temperature for 14 hours. After water (16 mL) was added, the mixture was further stirred for 7 hours and separated into layers by adding ethyl acetate (50 mL). The organic layer was washed with saturated aqueous sodium hydrogen carbonate solution (30 mL), water (30 mL) and saturated aqueous sodium chloride solution (50 mL), and dried over sodium sulfate. The residue was filtrated and the solvent was evaporated to give a crude product of the title compound (2.8 g). The obtained product was used in the next step without further purification.

PREPARATION EXAMPLE 5-4-3

(1R*,5R*,6R*)-1-amino-6-phenyl-3-oxa-bicyclo[3.1.0]hexane-2-one (step 5-4)

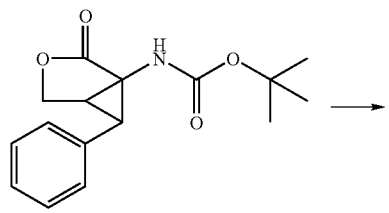

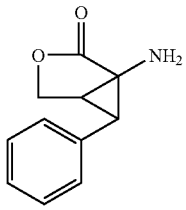

[(1R*,5R*,6R*)-2-oxo-6-phenyl-3-oxa-bicyclo[3.1.0]hex-1-yl]-carboxylic acid t-butyl ester (0.22 g, 0.76 mmol) was dissolved in 4 mL of dichloroethane and 2 mL of trifluoroacetic acid. This reaction was started at 0° C. and the reaction mixture was warmed to room temperature over 30 min. After concentration, the reaction mixture was diluted with saturated NaHCO$_3$ (5 mL) and extracted with dichloromethane (5×10 mL). The combined organic layers were washed with brine (×2), dried over Na$_2$SO$_4$ and concentrated to afford a free base as a clear oil (yield 97%).

PREPARATION EXAMPLE 5-4-4

(1R*,2R*,3R*)-1-amino-2-methoxymethyl-3-phenyl-cyclopropanecarboxylic acidmethoxy-methyl-amide hydrochloride (step 5-4)

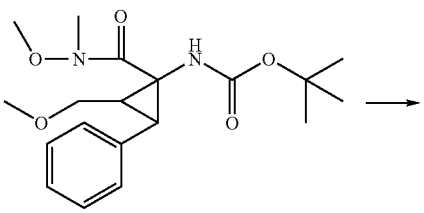

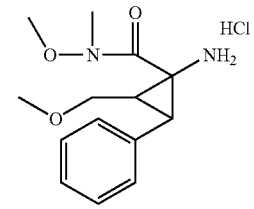

[(1R*,2R*,3R*)-2-methoxymethyl-1-(methoxy-methyl-carbamoyl)-3-phenyl-cyclopropyl]-carbamic acid t-butyl ester (25 mg, 0.69 mmol) was dissolved in 4 mL of HCl in dioxane (4M). After stirring at room temperature for 1 hour, the solution was concentrated and dried under high vacuum to afford 100% of an HCl salt product.

PREPARATION EXAMPLE 5-5

(1S,2R,3R)-1-(5-bromothiophene-2-sulfonylamino)-2-methyl-3-phenylcyclopropanecarboxylic acid t-butyl ester (step 5-5)

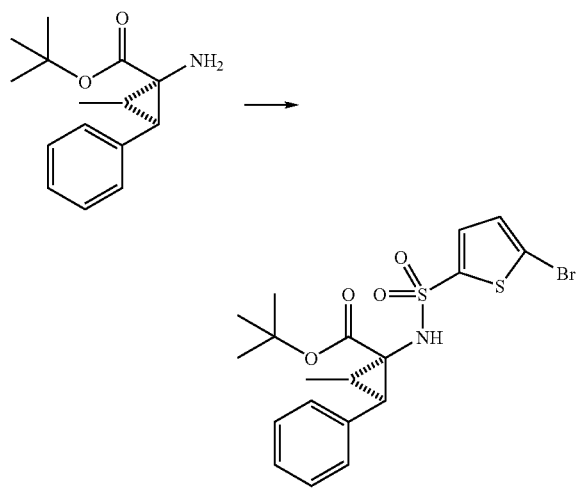

To a solution of (1S,2R,3R)-1-amino-2-methyl-3-phenyl-cyclopropanecarboxylic acid t-butyl ester (2.7 g, 11 mmol) obtained in Preparation Example 5-4 in pyridine (25 mL) was added 5-bromothiophene-2-sulfonyl chloride (3.4 g, 13 mmol) at room temperature under argon atmosphere. After stirring, the mixture was concentrated under reduced pressure. The obtained residue was separated and purified by silica gel chromatography (hexane:ethyl acetate=10:1) to give a crude product of the title compound as a pale-yellow oil. The crude product was washed with water to give the title compound (2.9 g, yield 58%) as a yellow solid.

PREPARATION EXAMPLE 5-5-2

4-[(1S,2R,3R)-1-t-butoxycarbonyl-2-methyl-3-phenyl-cyclopropylsulfamoyl]-piperazine-1-carboxylic acid t-butyl ester (step 5-5)

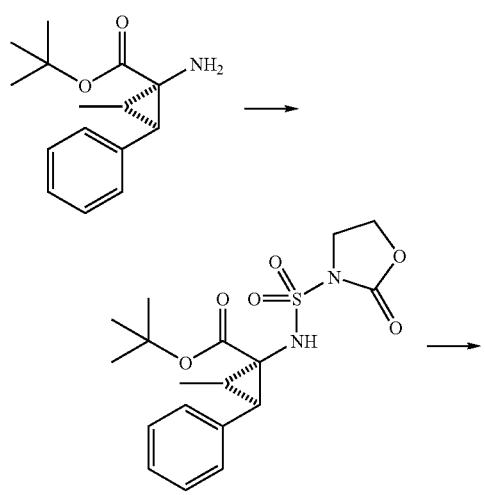

-continued

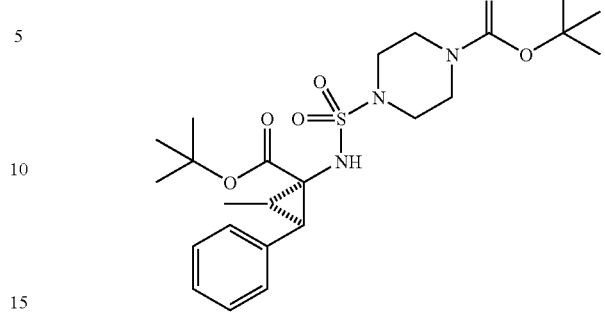

To a solution of chlorosulfonyl isocyanate (18 μL, 0.20 mmol) in acetonitrile (2 mL) was added 2-chloroethanol (14 μL, 0.20 mmol) at 0° C. The mixture was stirred at 0° C. for 30 min and then at room temperature for 1 hour. To this reaction mixture were added N-methylmorpholine (89 μL, 0.81 mmol) and (1S,2R,3R)-1-amino-2-methyl-3-phenyl-cyclopropanecarboxylic acid t-butyl ester (50 mg, 0.20 mmol). The reaction mixture was then stirred at 50° C. for 3 hours. This crude solution was used directly in the next step.

Under argon atmosphere, this (1S,2R,3R)-2-methyl-1-(2-oxo-oxazolidine-3-sulfonylamino)-3-phenyl-cyclopropanecarboxylic acid t-butyl ester (0.61 mmol) and t-butyl-1-piperazinecarboxylic acid (0.14 g, 0.73 mmol) were mixed, and the mixture was refluxed for 18 hours under heating. The obtained solution was concentrated under reduced pressure, and the residue was purified by silica gel chromatography (hexane:ethyl acetate=10:0 to 5:1) to give the title compound (0.24 g, yield 79%).

PREPARATION EXAMPLE 5-6

(1S,2R)-1-(6-bromomethyl-imidazo[2,1-b]thiazol-2-sulfonylamino)-2-methyl-2-phenyl-cyclopropanecarboxylic acid methyl ester (step 5-6)

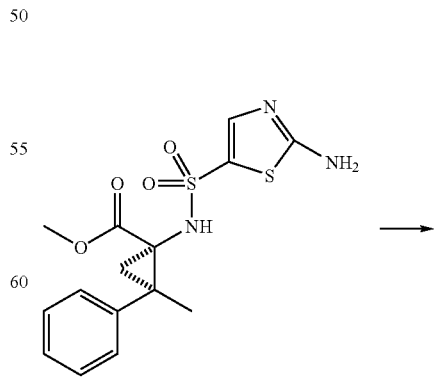

-continued

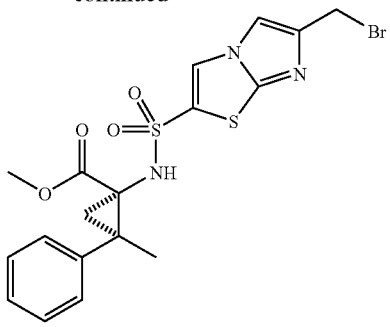

To a solution of (1S,2R)-1-(2-amino-thiazol-5-sulfonylamino)-2-methyl-2-phenyl-cyclopropanecarboxylic acid methyl ester (0.21 g, 0.58 mmol) in ethyl acetate (6.4 mL) was added 1,3-dibromoacetone (0.18 mL, 0.87 mmol), and the mixture was stirred at 60° C. for 18 hours. After cooling to room temperature, the mixture was washed with saturated aqueous sodium hydrogen carbonate solution and saturated aqueous sodium chloride solution, and dried over sodium sulfate. After filtration and evaporation, the obtained residue was separated and purified by silica gel chromatography (hexane:ethyl acetate=1:1) to give the title compound (68 mg, yield 24%) as a pale-yellow solid.

PREPARATION EXAMPLE 5-7

(1S,2R,3R)-1-[5-(4-iodo-pyrazole-1-yl)-thiophene-2-sulfonylamino-2-methyl-3-phenyl-cyclopropanecarboxylic acid t-butyl ester (step 5-7)

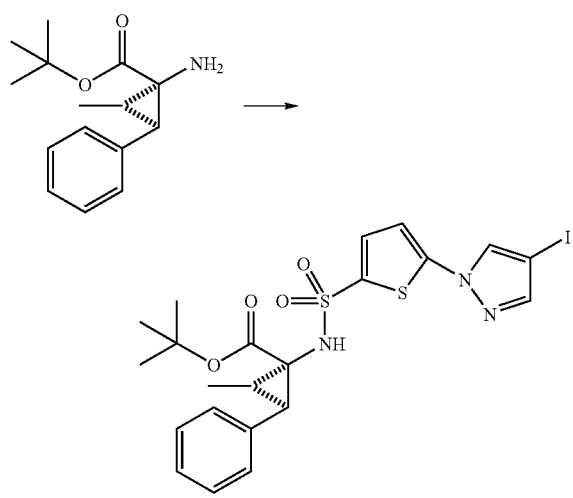

To a solution of (1S,2R,3R)-1-amino-2-methyl-3-phenyl-cyclopropanecarboxylic acid t-butyl ester (1.7 g, 6.7 mmol) obtained in Preparation Example 5-4 in chloroform (17 mL) was sequentially added triethylamine (1.4 mL, 10 mmol) and 5-(4-iodo-pyrazole-1-yl)-thiophene-2-sulfonyl chloride (3.0 g, 8.0 mmol) at room temperature under nitrogen atmosphere. The obtained solution was warmed to 50° C., and stirred for 2 hours. Then, the obtained solution was purified by silica gel chromatography (hexane:ethyl acetate=7:3) to give the title compound as a pale-yellow crude product. The crude product was slurry-washed with diisopropyl ether:hexane=1:1 (30 mL) to give the title compound (3.2 g, yield 82%) as a colorless amorphous form.

PREPARATION EXAMPLE 5-10 a) 1-(3-thiophene-2-yl-isoxazole-5-yl)-ethanone

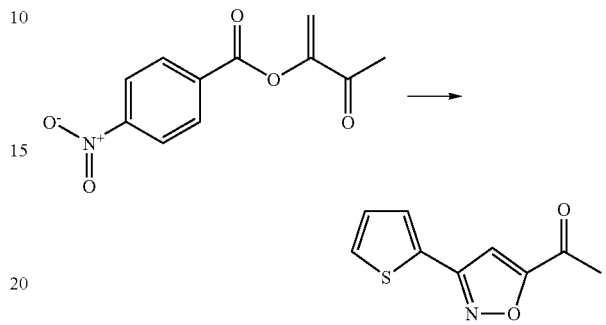

The title compound was synthesized according to the method described in known Heterocycles (1993, 35, 591-598).

To a solution of 4-nitro-benzoic acid 1-methylene-2-oxopropyl ester (10 g, 43 mmol) synthesized by the method of Helv. Chim. Acta (1981, 64, 188-197) and 2-thiophenecarbohydroxymoyl chloride (10 g, 62 mmol) synthesized by the method of Bioorg. Med. Chem. Lett. (2003, 13, 1795-1799) in chloroform (100 mL) was added dropwise triethylamine (9.0 mL, 62 mmol) under argon atmosphere at 0° C. over 30 min., and the mixture was stirred for 30 min. Then triethylamine (6.0 mL, 42 mmol) was added dropwise and the mixture was warmed gradually to room temperature.

After stirring at room temperature for 12 hours, water (100 mL) was added to the obtained solution, and the mixture was filtrated through celite. The filtrate was separated into layers and extracted with chloroform (100 mL). After the organic layer was washed with 1N aqueous sodium hydroxide solution (40 mL), 1N aqueous hydrochloric acid solution (80 mL) and saturated aqueous sodium chloride solution (40 mL) were added sequentially, and the mixture was dried over sodium sulfate. After filtration and evaporation, the obtained residue was separated and purified by silica gel chromatography (hexane:chloroform=1:1) to give the title compound (5.4 g, yield 66%) as pale-brown crystals.

b) 5-(1,1-difluoroethyl)-3-thiophene-2-yl-isoxazole

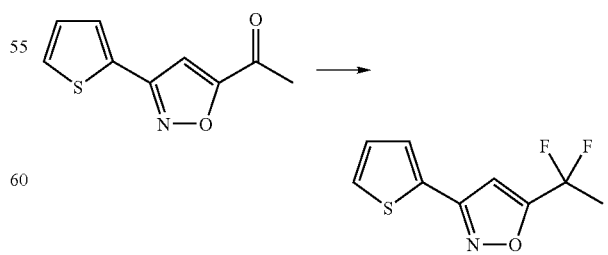

Under argon atmosphere, to a suspension of 1-(3-thiophene-2-yl-isoxazole-5-yl)-ethanone (6.0 g, 31 mmol) obtained in Preparation Example 5-10-a) in dichloromethane (30 mL) was added dropwise diethylaminosulfur trifluoride (DAST) (16 mL, 0.12 mol) over 5 min. at 0° C., and the suspension was warmed gradually to room temperature. After stirring at room temperature for 23 hours, the obtained solution was transferred to a separatory funnel and added dropwise over 30 min to 4N aqueous sodium hydroxide solution (105 mL) cooled at 0° C. Then the obtained solution was warmed gradually to room temperature and filtrated through celite. The filtrate was separated into layers and extracted with chloroform (60 mL). Then the organic layer was sequentially washed with saturated aqueous sodium hydrogen carbonate solution (90 mL), 1N aqueous hydrochloric acid solution (60 mL) and saturated aqueous sodium chloride solution (30 mL), and dried over magnesium sulfate. After filtration and evaporation, the obtained residue was separated and purified by silica gel chromatography (hexane:ethyl acetate=15:1) to give the title compound (6.2 g, 94%) as a brown oil.

c) 5-[5-(1,1-difluoroethyl)-isoxazol-3-yl]-thiophene-2-sulfonic acid

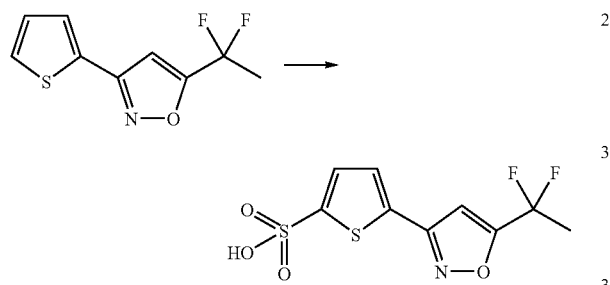

Under argon atmosphere, to a solution of 5-(1,1-difluoroethyl)-3-thiophene-2-yl-isoxazole (6.2 g, 31 mmol) obtained in Preparation Example 5-10-b) in chloroform (100 mL) was added chlorosulfonic acid (2.5 mL, 38 mmol), and the mixture was stirred at room temperature for 3 days. The obtained solution was filtrated and dried under reduced pressure to give the title compound (7.9 g, yield 93%) as a pale-brown powder.

d) 5-[5-(1,1-difluoroethyl)-isoxazol-3-yl]-thiophene-2-sulfonic acid chloride (step 5-10)

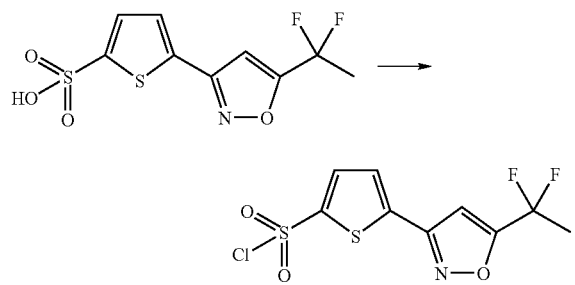

To a suspension of 5-[5-(1,1-difluoroethyl)-isoxazol-3-yl]-thiophene-2-sulfonic acid (9.5 g, 32 mmol) obtained in Preparation Example 5-10-c) in thionyl chloride (50 mL) was added dimethylformamide (1.0 mL) under argon atmosphere, and the suspension was stirred at 80° C. for 16 hours. The obtained solution was concentrated, and chloroform (100 mL) was added. After azeotropic removal of residual solvent with chloroform, chloroform (50 mL) was added to the residue. The obtained mixture was extracted twice, sequentially washed with water (20 mL) and saturated aqueous sodium chloride solution (10 mL), and dried over magnesium sulfate. After filtration and evaporation, the obtained residue was separated and purified by silica gel chromatography (hexane:ethyl acetate=15:1) to give the title compound (6.9 g, 68%) as a yellow solid.

PREPARATION EXAMPLE 5-11

(1S,2R,3R)-1-{5-[5-(1,1-difluoro-ethyl)-isoxazol-3-yl]-thiophene-2-sulfonylamino}-2-methyl-3-phenyl-cyclopropanecarboxylic acid t-butyl ester (step 5-11)

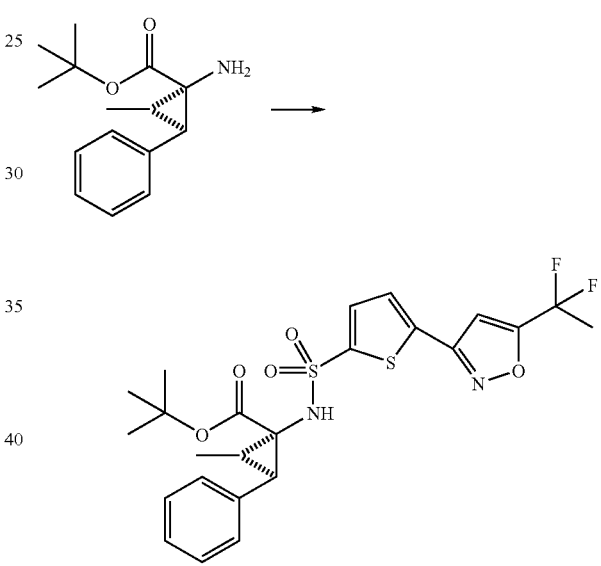

To a solution of (1S,2R,3R)-1-amino-2-methyl-3-phenyl-cyclopropanecarboxylic acid t-butyl ester (3.0 g, 12 mmol) obtained in Preparation Example 5-4 in tetrahydrofuran (60 mL) were sequentially added 5-[5-(1,1-difluoroethyl)-isoxazol-3-yl]-thiophene-2-sulfonic acid chloride (3.8 g, 12 mmol) obtained in Example 5-10 and 2,6-lutidine (3.1 mL, 27 mmol) at room temperature under argon atmosphere. The obtained solution was warmed to 50° C., and stirred for 15 hours. Then, to the obtained solution was added saturated aqueous sodium chloride solution (60 mL), and the mixture was extracted twice with ethyl acetate (60 mL), sequentially washed with 2N aqueous hydrochloric acid solution (30 mL) and saturated aqueous sodium chloride solution (10 mL), and dried over magnesium sulfate. After filtration and evaporation, the obtained crude product was separated and purified by silica gel chromatography (hexane:ethyl acetate=10:1). The crude product was slurry-washed with hexane (60 mL) to give the title compound (3.8 g, 60%) as a pale-yellow solid.

PREPARATION EXAMPLE 5-11-2

(1R*,1aS*,8bS*)-1-[5-(4-chloro-phenyl) thiophene-2-sulfonylamino]-1,1a,2,3,4,8b-hexahydrobenzo[a]cyclopropa[c]cyclohepten-1-carboxylic acid ethyl ester (step 5-11)

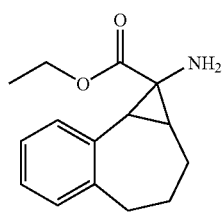

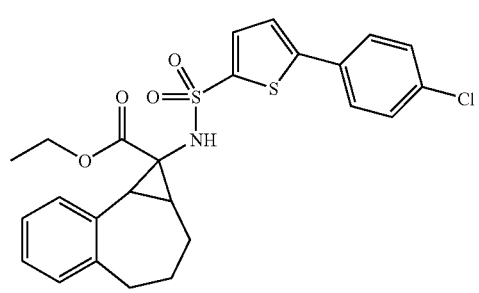

To a solution of (1R*,1aS*,8bS*)-1-amino-1,1a,2,3,4,8b-hexahydrobenzo[a]cyclopropa[c]cyclohepten-1-carboxylic acid ethyl ester (0.22 g, 0.91 mmol) obtained in Preparation Example 4-1 in pyridine (2.0 mL) was added 5-(4-chlorophenyl)-thiophene-2-sulfonyl chloride (0.32 g, 1.1 mmol) at room temperature under argon atmosphere. After stirring for 4 hours, the mixture was concentrated under reduced pressure. The obtained residue was separated and purified by silica gel chromatography (hexane:ethyl acetate=10:1) to give the title compound (0.26 g, yield 56%) as a pale-yellow amorphous form.

PREPARATION EXAMPLE 5-11-3

(1S,2R,3R)-2-methyl-1-[4-(5-trifluoromethyl-pyridin-2-yl)-piperazine-1-sulfonylamino]-3-phenyl-cyclopropanecarboxylic acid t-butyl ester (step 5-11)

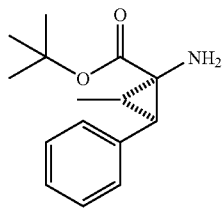

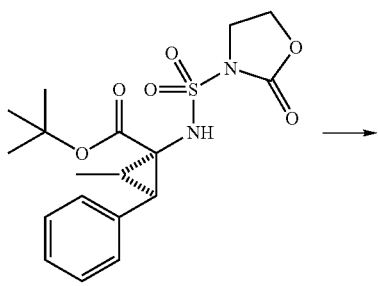

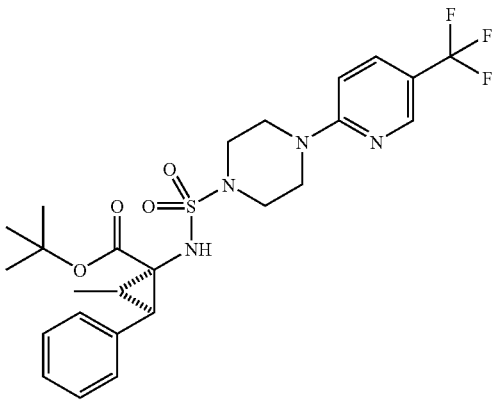

To a solution of chlorosulfonyl isocyanate (18 µL, 0.20 mmol) in acetonitrile (2 mL) was added 2-chloroethanol (14 µL, 0.20 mmol) at 0° C. The mixture was stirred at 0° C. for 30 min and then at room temperature for 1 hour. To this reaction mixture were added N-methylmorpholine (89 µL, 0.81 mmol) and (1S,2R,3R)-1-amino-2-methyl-3-phenyl-cyclopropanecarboxylic acid tert-butyl ester (50 mg, 0.20 mmol). The reaction mixture was then stirred at 50° C. for 3 hours. This crude solution was used directly in the next step.

To the crude (1S,2R,2R)-2-methyl-1-(2-oxo-oxazolidine-3-sulfonylamino)-3-phenyl-cyclopropanecarboxylic acid tert-butyl ester (120 mg, 0.30 mmol) was added commercially available 1-(5-trifluoromethyl-pyridin-2-yl)-piperazine (70 mg, 0.30 mmol) and the reaction mixture was heated at 80° C. for 30 min. N,N-dimethylacetamide (0.5 mL) was added to completely dissolve piperazine. After heating for 24 hours, the reaction mixture was diluted with ethyl acetate and the organic layer was washed with saturated sodium hydrogen carbonate solution and saturated sodium chloride solution. After drying over magnesium sulfate, the solvent was removed in vacuo. The crude material was purified using prep TLC eluting with 1:1 Hexanes/ethyl acetate ($R_f$ 0.7) to afford the desired sulfamide in a 20% isolated yield.

PREPARATION EXAMPLE 5-11-4

5-(5-trifluoromethyl-isoxazol-3-yl)-thiophene-2-sulfonic acid[(1R*,5R*,6R*)-2-oxo-6-phenyl-3-oxa-bicyclo[3.1.0]hexan-1-yl]-amide (step 5-11)

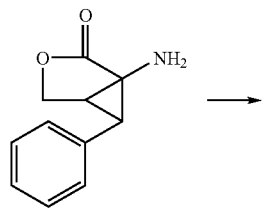

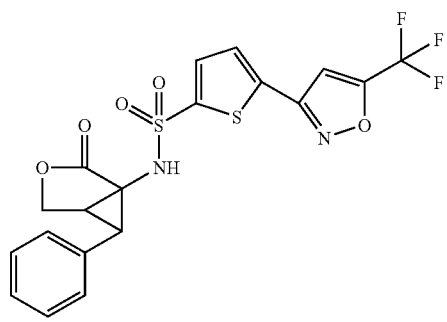

(1R*,5R*,6R*)-1-amino-6-phenyl-3-oxa-bicyclo[3.1.0]hexan-2-one (0.14 g, 0.74 mmol) was dissolved in 3 mL of pyridine. After cooling to 0° C., 5-(5-trifluoromethyl-isoxazol-3-yl)-thiophene-2-sulfonyl chloride (0.31 g, 0.96 mmol) was added in one portion. The reaction mixture was warmed to room temperature and stirred overnight. After concentration, the reaction mixture was diluted with EtOAc, washed with 10% citric acid, water (×2), 5% NaHCO₃ and brine and dried over Na₂SO₄. After concentration, the crude product was purified by column chromatography using 2:1 hexanes/EtOAc to afford 0.26 g (75%) of the desired product.

PREPARATION EXAMPLE 5-11-5

(1R*,2R*,3R*)-2-methoxymethyl-3-phenyl-1-[5-(5-trifluoromethyl-isoxazol-3-yl)-thiophene-2-sulfonylamino]-cyclopropanecarboxylic acid methoxy-methyl-amide (step 5-11)

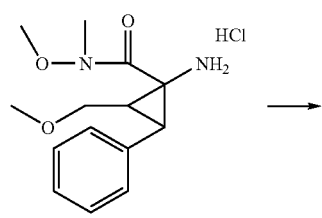

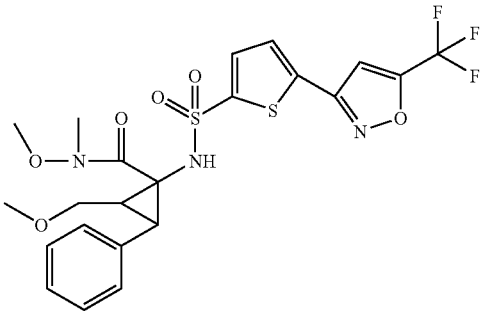

The (1R*,2R*,3R*)-1-amino-2-methoxymethyl-3-phenyl-cyclopropanecarboxylic acid methoxy-methyl-amide hydrochloride (22 mg, 0.082 mmol) was dissolved in 1 mL of pyridine. To this solution was added 5-(5-trifluoromethyl-isoxazol-3-yl)-thiophene-2-sulfonyl chloride (25 mg, 0.079 mmol) and the mixture was stirred at room temperature overnight. After concentration, the reaction mixture was diluted with EtOAc and washed with sat. NaHCO₃ (2×) and brine. After drying over MgSO₄, the solution was concentrated and purified using prep-TLC (1:1 hexanes/EtOAc) to afford 13 mg of the desired product (32%).

PREPARATION EXAMPLE 6-1

(1R*,2R*)-1-[5-(4-chloro-phenyl)-thiophene-2-sulfonylamino]-2-hydroxymethyl-2-phenyl-cyclopropanecarboxylic acid t-butyl ester (step 6-1)

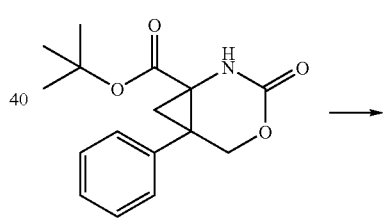

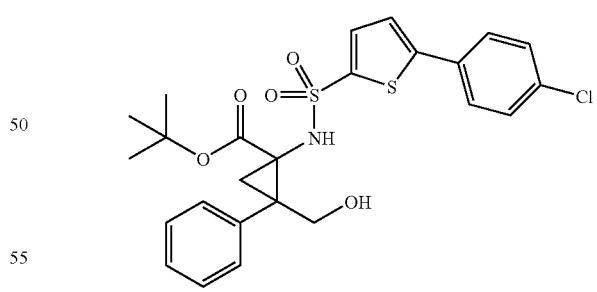

To a solution of (1R*,6R*)₃-oxo-6-phenyl-4-oxa-2-aza-bicyclo[4.1.0]heptan-1-carboxylic acid t-butyl ester (5.0 g, 17 mmol) obtained in Preparation Example 2-5 in tetrahydrofuran (50 mL) was sequentially added 15-crown-5 (0.34 mL, 1.7 mmol) and sodium hydride (liquid paraffin 40% added, 1.7 g, 41 mmol) at 0° C. under nitrogen atmosphere. After stirring for 5 min., the mixture was further stirred at room temperature for 30 min. The obtained solution was cooled to 0° C., and 5-(4-chlorophenyl)-thiophene-2-sulfonyl chloride (6.1 g, 21 mmol) was added. After stirring at 0° C. for 15 min., the mixture was stirred at room temperature for 6 hours. To the obtained solution were sequentially added tetrahydrofuran (50 mL), methanol (100 mL) and 2N aqueous sodium hydroxide solution (17 mL, 69 mmol). After stirring for 15 hours, the mixture was concentrated to about half the amount under reduced pressure. To the obtained solution was added 5% aqueous potassium hydrogen sulfate solution until the pH level read about 6. Then the solution was extracted three times with ethyl acetate (50 mL), washed with water (30 mL) and saturated aqueous sodium chloride solution (30 mL), and dried over sodium sulfate. After filtration and evaporation, the obtained residue was purified by silica gel chromatography (hexane:ethyl acetate=7:3) to give the title compound (3.6 g, yield 40%) as a pale-yellow amorphous form.

PREPARATION EXAMPLE 6-2

(1R*,2R*)-1-[5-(4-chloro-phenyl)-thiophene-2-sulfonylamino]-2-phenyl-2-(tetrahydro-pyran-2-yloxymethyl)-cyclopropanecarboxylic acid t-butyl ester (step 6-2)

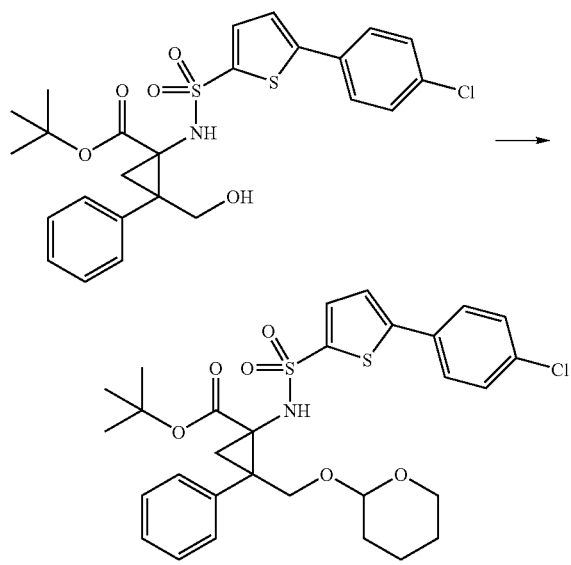

To a solution of (1R*,2R*)-1-[5-(4-chloro-phenyl)-thiophene-2-sulfonylamino]-2-hydroxymethyl-2-phenyl-cyclopropanecarboxylic acid t-butyl ester (4.5 g, 8.7 mmol) obtained in Preparation Example 6-1 in chloroform (45 mL) were sequentially added 3,4-dihydro-2H-pyran (2.0 mL, 22 mmol) and p-toluenesulfonic acid monohydrate (0.17 g, 0.87 mmol) at room temperature under nitrogen atmosphere. After stirring for 1 hour, saturated aqueous sodium hydrogen carbonate solution (40 mL) was added to the mixture. Then the aqueous layer was extracted three times with ethyl acetate (20 mL). The organic layer was washed with water (30 mL) and saturated aqueous sodium chloride solution (30 mL), and dried over sodium sulfate. After filtration and evaporation, the obtained residue was purified by silica gel chromatography (hexane:ethyl acetate=7:3) to give the title compound (4.9 g, yield 93%) as a pale-yellow powder.

PREPARATION EXAMPLE 6-3

(1R*,2R*)-1-[[5-(4-chloro-phenyl)-thiophene-2-sulfonyl]-(2-trimethylsilanyl-ethyl)-amino]-2-phenyl-2-(tetrahydro-pyran-2-yloxymethyl)-cyclopropanecarboxylic acid t-butyl ester (step 6-3)

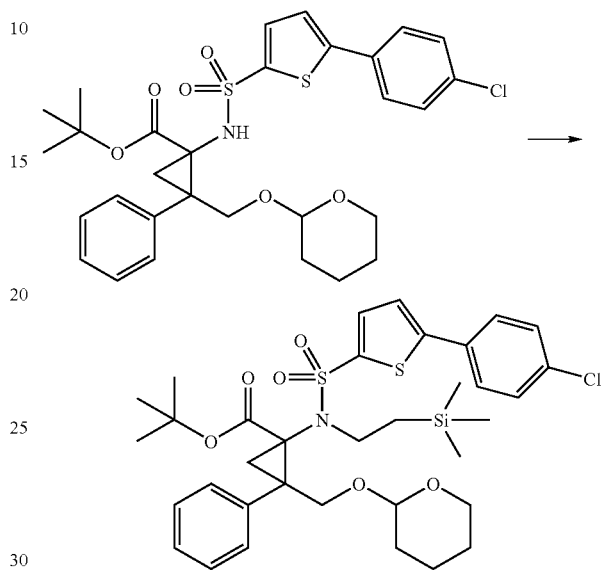

To a solution of (1R*,2R*)-1-[5-(4-chloro-phenyl)-thiophene-2-sulfonylamino]-2-phenyl-2-(tetrahydro-pyran-2-yloxymethyl)-cyclopropanecarboxylic acid t-butyl ester (4.9 g, 8.0 mmol) obtained in Preparation Example 6-2, triphenylphosphine (3.2 g, 12 mmol) and 2-trimethylsilylethanol (1.7 mL, 12 mmol) in tetrahydrofuran (49 mL) was dropwise added azodicarboxylic acid diisopropyl ester (2.4 mL, 12 mmol) at room temperature under nitrogen atmosphere, and the mixture was stirred for 15 hours. The obtained solution was purified by silica gel chromatography (hexane:ethyl acetate=4:1) to give the title compound (5.1 g, yield 91%) as a pale-yellow amorphous form.

PREPARATION EXAMPLE 6-4

(1R*,2R*)-1-[[5-(4-chloro-phenyl)-thiophene-2-sulfonyl]-(2-trimethylsilanyl-ethyl)-amino]-2-hydroxymethyl-2-phenyl-cyclopropanecarboxylic acid t-butyl ester (step 6-4)

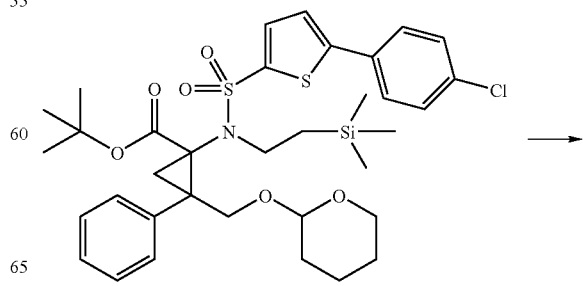

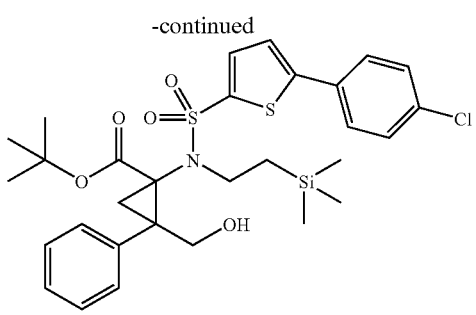

To a solution of (1R*,2R*)-1-[[5-(4-chloro-phenyl)-thiophene-2-sulfonyl](2-trimethylsilanyl-ethyl)-amino]-2-phenyl-2-(tetrahydro-pyran-2-yloxymethyl)-cyclopropanecarboxylic acid t-butyl ester (5.1 g, 7.3 mmol) obtained in Preparation Example 6-3 in methanol (50 mL) was added p-toluenesulfonic acid monohydrate (0.14 g, 0.73 mmol) at room temperature under nitrogen atmosphere. After stirring for 1 hour, saturated aqueous sodium hydrogen carbonate solution (10 mL) was added. The mixture was extracted three times with ethyl acetate (20 mL). The organic layer was washed twice with water (30 mL) and also washed twice with saturated aqueous sodium chloride solution (30 mL), and dried over sodium sulfate. After filtration and evaporation, the obtained residue was purified by silica gel chromatography (hexane:ethyl acetate=7:3) to give the title compound 35 (4'0.5 g, yield 99%) as a pale-yellow amorphous form.

PREPARATION EXAMPLE 6-5

(1R*,2R*)-1-[[5-(4-chloro-phenyl)-thiophene-2-sulfonyl]-(2-trimethylsilanyl-ethyl)-amino]-2-methoxymethyl-2-phenyl-cyclopropanecarboxylic acid t-butyl ester (step 6-5)

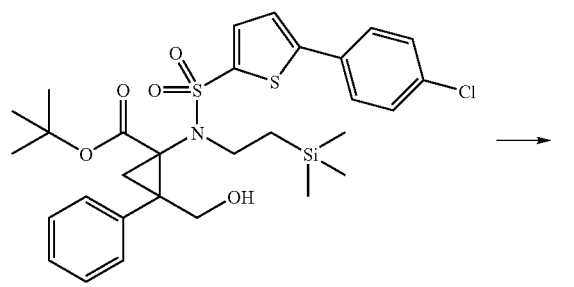

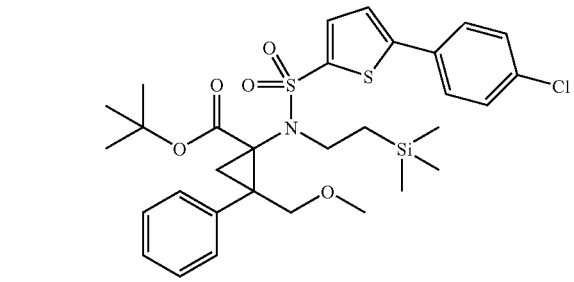

To a solution of (1R*,2R*)—[[5-(4-chloro-phenyl)-thiophene-2-sulfonyl]-(2-trimethylsilanyl-ethyl)-amino]-2-hydroxymethyl-2-phenyl-cyclopropanecarboxylic acid t-butyl ester (0.10 g, 0.16 mmol) obtained in Preparation Example 6-4 in tetrahydrofuran (1.0 mL) were sequentially added methyl iodide (20 μL, 0.32 mmol) and sodium hydride (liquid paraffin 40% added, 13 mg, 0.32 mmol) at 0° C. under nitrogen atmosphere. After stirring for 30 min., the mixture was further stirred at room temperature for 26 hours. To the obtained solution were added 5% aqueous potassium hydrogen sulfate solution (1.0 mL) and ethyl acetate (2.0 mL). The aqueous layer was extracted three times with ethyl acetate (2.0 mL). The organic layer was washed with water (5.0 mL) and saturated aqueous sodium chloride solution (5.0 mL), and dried over sodium sulfate. After filtration and evaporation, the obtained residue was purified by silica gel chromatography (hexane:ethyl acetate=7:3) to give the title compound (99 mg, yield 98%) as a pale-yellow oil.

PREPARATION EXAMPLE 6-6

(1R*,2S*)-1-[(5-bromo-thiophene-2-sulfonyl)-(2-trimethylsilanyl-ethyl)-amino]-2-methyl-2-phenyl-cyclopropanecarboxylic acid t-butyl ester (step 6-6)

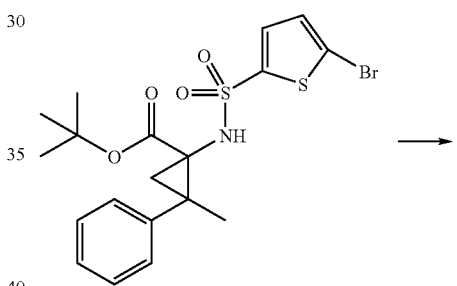

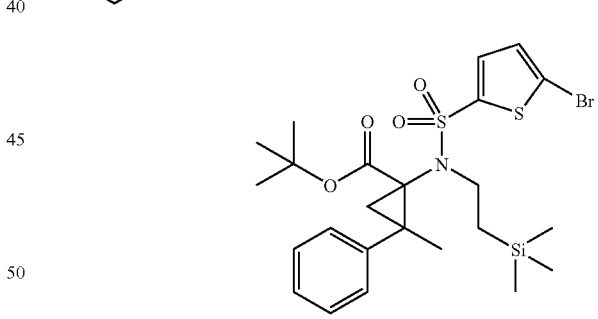

To a solution of (1R*,2S*)-1-(5-bromo-thiophene-2-sulfonylamino)-2-methyl-2-phenyl-cyclopropanecarboxylic acid t-butyl ester (0.90 g, 1.9 mmol) obtained in a similar manner as in Preparation Example 5-5 in tetrahydrofuran (9.0 mL) were sequentially added triphenylphosphine (0.75 g, 2.8 mmol), 2-trimethylsilylethanol (0.33 mL, 2.8 mmol) and azodicarboxylic acid diisopropyl ester (0.56 mL, 2.8 mmol) under argon atmosphere, and the mixture was stirred at room temperature for 12 hours. After evaporation, the obtained residue was separated and purified by silica gel chromatography (hexane:ethyl acetate=20:1) to give the title compound (0.90 g, yield 83%) as a colorless oil.

PREPARATION EXAMPLE 6-7

(1S,2R)-1-(5-benzo[1,3]dioxo-5-yl-thiophene-2-sulfonylamino)-2-methyl-2-phenyl-cyclopropanecarboxylic acid t-butyl ester (step 6-7)

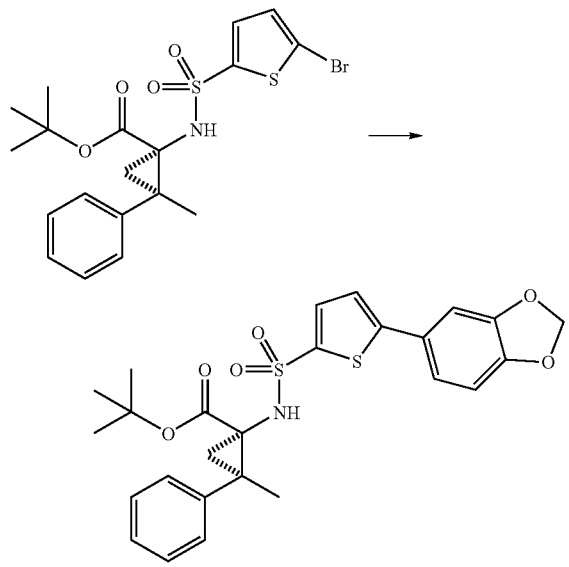

To a solution of (1S,2R)-1-(5-bromo-thiophene-2-sulfonylamino)-2-methyl-2-phenyl-cyclopropanecarboxylic acid t-butyl ester (52 mg, 0.11 mmol) obtained in a similar manner as in Preparation Example 5-5 in 1,2-dimethoxyethane (1.0 mL) were sequentially added 0,3,4-(methylenedioxy)phenylboronic acid (24 mg, 0.15 mmol), potassium carbonate (46 mg, 0.33 mmol) and a catalytic amount of tetrakis(triphenylphosphine)palladium (0) under argon atmosphere. After stirring at 80° C. for 8 hours, the mixture was filtrated through celite. After evaporation, the obtained residue was separated and purified by silica gel chromatography (hexane:ethyl acetate=10:1) to give the title compound (65 mg, purity 80%) as a colorless amorphous form.

PREPARATION EXAMPLE 6-7-2

(1R*,2S*)-2-methyl-1-[(5-morpholin-4-yl-thiophene-2-sulfonyl)-(2-trimethylsilanyl-ethyl)-amino]-2-phenyl-cyclopropanecarboxylic acid t-butyl ester (step 6-7)

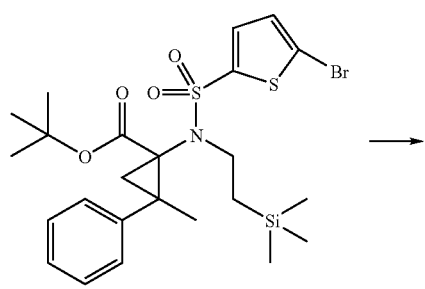

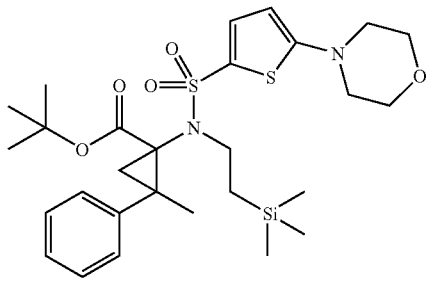

To a solution of (1R*,2S*)-1-[(5-bromo-thiophene-2-sulfonyl)-(2-trimethylsilanyl-ethyl)-amino]-2-methyl-2-phenyl-cyclopropanecarboxylic acid t-butyl ester (52 mg, 91 μmol) obtained in Preparation Example 6-6 in toluene (1.0 mL) were added sodium t-butoxide (26 mg, 0.27 mmol), 2-dicyclohexylphosphino-2', 4', 6'-triisopropyl-1,1'-biphenyl (13 mg, 27 μmol), tris(dibenzylideneacetone)dipalladium (9.0 mg, 9.0 μmol) and morpholine (40 μL, 0.46 mmol) under argon atmosphere, and the mixture was stirred for 6 hours under refluxing. The obtained suspension was cooled to 0° C. and water (1.0 mL) was added. The mixture was extracted twice with ethyl acetate (5.0 mL). The organic layer was sequentially washed with water (1.0 mL) and saturated aqueous sodium chloride solution (1.0 mL), and dried over magnesium sulfate. After filtration and evaporation, the obtained residue was separated and purified by silica gel chromatography (hexane:ethyl acetate=10:1) to give the title compound (36 mg, yield 70%) as a white solid.

PREPARATION EXAMPLE 6-8

(1R*,2S*)-2-methyl-1-(5-morpholin-4-yl-thiophene-2-sulfonylamino)-2-phenyl-cyclopropanecarboxylic acid t-butyl ester (step 6-8)

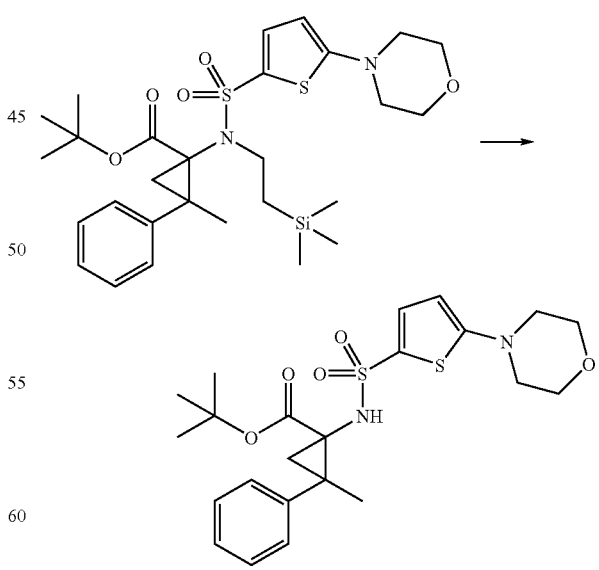

To (1R*,2S*)-2-methyl-1-[(5-morpholin-4-yl-thiophene-2-sulfonyl)-(2-trimethylsilanyl-ethyl)-amino]-2-phenyl-cyclopropanecarboxylic acid t-butyl ester (36 mg, 63 μmol) obtained in Preparation Example 6-7-2 was added 1.0 M solution of tetrabutylammonium fluoride in tetrahydrofuran (1.0 mL) under argon atmosphere, and the mixture was stirred for 12 hours under refluxing. The obtained solution was cooled to 0° C. and water (1.0 mL) was added. The mixture was extracted twice with ethyl acetate (5.0 mL). The organic layer was sequentially washed with water (1.0 mL) and saturated aqueous sodium chloride solution (1.0 mL), and dried over magnesium sulfate. After filtration and evaporation, the obtained residue was separated and purified by silica gel chromatography (hexane:ethyl acetate=3:1) to give the title compound (22 mg, yield 73%) as a white solid.

PREPARATION EXAMPLE 6-9

(1R*,2S*)-2-(3-amino-phenyl)-1-[5-(5-trifluoromethyl-isoxazol-3-yl)-thiophene-2-sulfonylamino]-cyclopropanecarboxylic acid t-butyl ester (step 6-9)

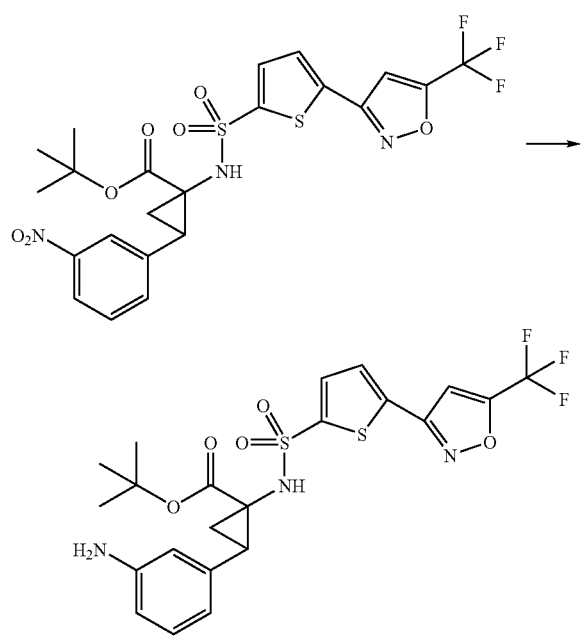

To a solution of (1R*,2S*)-2-(3-nitro-phenyl)-1-[5-(5-trifluoromethyl-isoxazol-3-yl)-thiophene-2-sulfonylamino]-cyclopropanecarboxylic acid t-butyl ester (0.46 g, 0.82 mmol) obtained in a similar manner as in Preparation Example 5-11 in a ethanol:chloroform=1:1 (5.0 mL) mixture was added copper (II) acetate (0.23 g, 1.2 mmol), and the mixture was stirred at room temperature for 5 min. to give a homogenous blue solution. Then sodium borohydride (0.22 g, 5.8 mmol) was added slowly at room temperature, and the mixture was stirred for 30 min. After the obtained solution was diluted with diethyl ether (5.0 mL) and ethyl acetate (5.0 mL), the organic layer was sequentially washed with saturated aqueous sodium hydrogen carbonate solution (10 mL) and saturated aqueous sodium chloride solution (10 mL), and dried over sodium sulfate. After filtration and evaporation, the residue were gradually added ethyl acetate and hexane to allow precipitation of crystals. The crystals was filtrated to give the title compound (0.20 g, yield 46%) as a pale-yellow powder.

PREPARATION EXAMPLE 6-9-2

1-[5-(4-chloro-phenyl)-thiophene-2-sulfonylamino]-2-(isopropylamino-methyl)-2-phenyl-cyclopropanecarboxylic acid t-butyl ester (step 6-9)

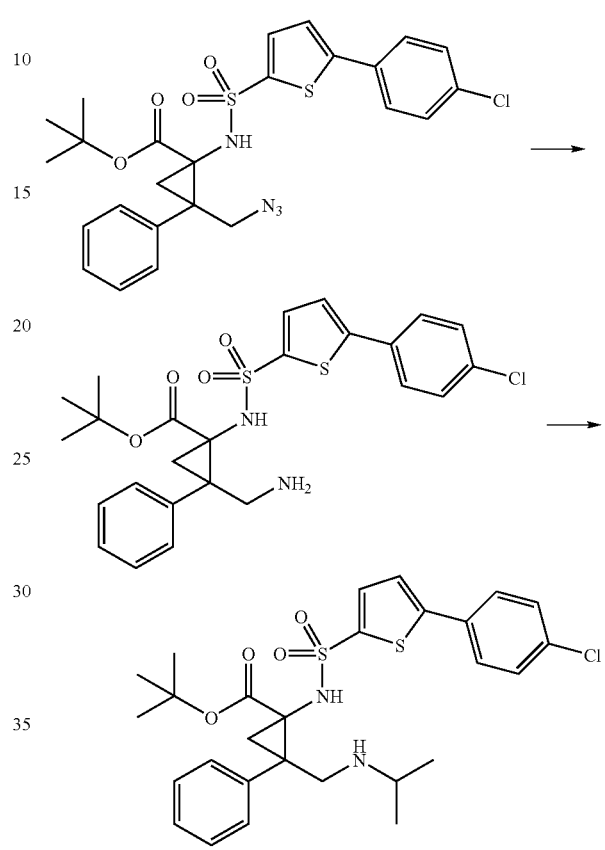

To a solution of 2-azidomethyl-1-[5-(4-chloro-phenyl)-thiophene-2-sulfonylamino]-2-phenyl-cyclopropanecarboxylic acid t-butyl ester (2.2 g, 4.0 mmol), which was produced in a similar manner as in Preparation Example 5-11 from (1R*,2S*)-1-amino-2-azidomethyl-2-phenyl-cyclopropanecarboxylic acid t-butyl ester obtained in Preparation Example 5-4-2, in toluene (22 mL) was added triphenylphosphine (1.1 g, 4.2 mmol) under argon atmosphere, and the mixture was stirred at room temperature for 3 hours. To the obtained solution was added water (20 mL) and the mixture was stirred at 100° C. for 1 hour. After evaporation, the obtained residue was purified by silica gel chromatography (chloroform:methanol=100:1 to 20:1) to give 2-aminomethyl-1-[5-(4-chloro-phenyl)-thiophene-2-sulfonylamino]-2-phenyl-cyclopropanecarboxylic acid t-butyl ester (1.8 g, yield 86%).

To the obtained 2-aminomethyl-1-[5-(4-chloro-phenyl)-thiophene-2-sulfonylamino]-2-phenyl-cyclopropanecarboxylic acid t-butyl ester (60 mg, 0.12 mmol) in tetrahydrofuran (1.0 mL) were added acetone (13 μL, 0.17 mmol) and sodium triacetoxyborohydride (37 mg, 0.17 mmol) at 0° C. under argon atmosphere, and the mixture was stirred at room temperature for 20 hours. To the obtained solution was added acetic acid (50 μL), and the mixture was further stirred for 21 hours. Then saturated aqueous sodium hydrogen carbonate solution (2.0 mL) was added and the aqueous layer was extracted with ethyl acetate (3.0 mL). The organic layer was washed with water (2.0 mL) and saturated aqueous sodium chloride solution (2.0 mL), and dried over magnesium sulfate. After filtration and evaporation, the obtained residue was purified by silica gel chromatography (chloroform:methanol=25:2) to give the title compound (45 mg, yield 69%) as a pale-yellow oil.

PREPARATION EXAMPLE 6-10

(1S,2R)-1-(6-methoxymethyl-imidazo[2,1-b]thiazol-2-sulfonylamino)-2-methyl-2-phenyl-cyclopropanecarboxylic acid methyl ester (step 6-10)

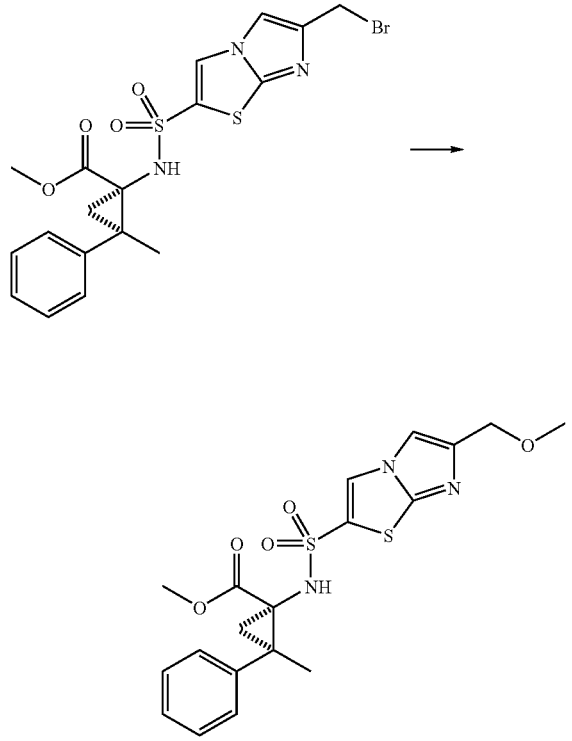

To a solution of (1S,2R)-1-(6-bromomethyl-imidazo[2,1-b]thiazol-2-sulfonylamino)-2-methyl-2-phenyl-cyclopropanecarboxylic acid methyl ester (32 mg, 65 μmol) obtained in Preparation Example 5-6 in dimethylformamide (3.0 mL) were added methanol (0.60 mL) and a solution of 28% sodium methoxide in methanol (0.13 mL, 0.65 mmol) under argon atmosphere, and the mixture was stirred for 18 hours. To the mixture was added saturated aqueous ammonium chloride solution (15 mL), and the aqueous layer was extracted with ethyl acetate (15 mL). The organic layer was washed with saturated aqueous sodium chloride solution and dried over sodium sulfate. After filtration and evaporation, the obtained residue was separated and purified by silica gel chromatography (hexane:ethyl acetate=1:2) to give the title compound (25 mg, yield 88%) as a white solid.

PREPARATION EXAMPLE 6-11

(1R*,2R*,3R*)-2-methoxymethyl-3-phenyl-1-[5-(5-trifluoromethyl-isoxazol-3-yl)-thiophene-2-sulfonylamino]-cyclopropanecarboxylic acid (step 6-11)

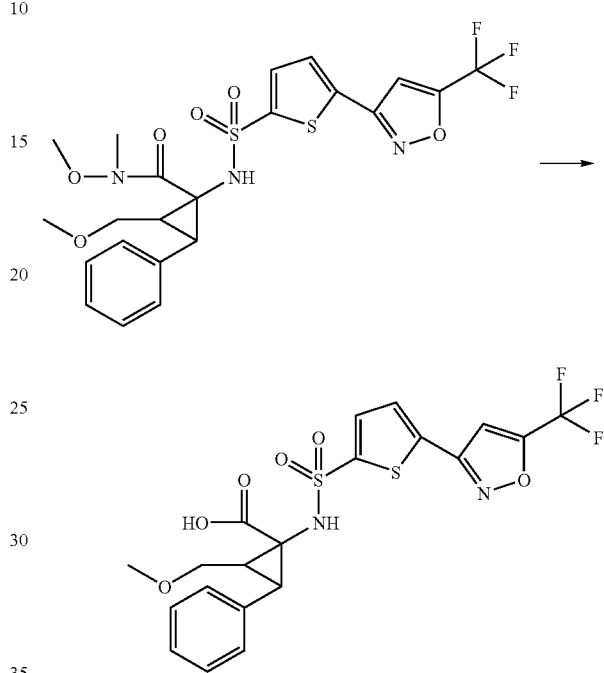

(1R*,2R*,3R*)-2-methoxymethyl-3-phenyl-1-[5-(5-trifluoromethyl-isoxazol-3-yl)-thiophene-2-sulfonylamino]-cyclopropanecarboxylic acid methoxy-methyl-amide (55 mg, 0.10 mmol) was dissolved in 6 mL of dichloromethane. Diisobutylaluminum hydride (1M, 0.22 mL, 0.22 mmol) was added dropwise at −78° C. This mixture was monitored by LC/MS and supplemental diisobutylaluminum hydride was repeatedly added until the reaction was completed. After quenching with methanol, the reaction mixture was partitioned between dichloromethane and 1N HCl. The organic layer was washed with brine, dried over MgSO$_4$ and concentrated. The crude product was used directly in the next step.

The crude mixture (assumed 0.1 mmol) was dissolved in 12 mL of 3:1 acetone/water. To this solution were added NaClO$_2$ (31 mg, 0.34 mmol, 3.4 equiv), NaH$_2$PO$_4$ (12 mg, 0.10 mmol, 1.0 equiv) and 2-methyl-2-butene (few drops). After stirring at room temperature for 4 hours, the reaction mixture was concentrated and partitioned between EtOAc and water. The aqueous solution was further extracted with EtOAc (×2). The combined organic layers were dried over MgSO$_4$ and concentrated to give a yellow oil. This material was given to our purification group to purify and quite a lot of material was lost during repeated purifications. Further purification using prep TLC afforded the product (2 mg) in a 50% purity.

EXAMPLE 1

(1S,2R)-1-(4'-Chlorobiphenyl-4-sulfonylamino)-2-phenylcyclopropanecarboxylic acid a)
(1S,2R)-1-Amino-2-phenylcyclopropanecarboxylic acid

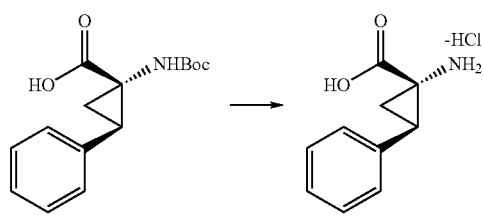

To commercially available (1R,2S)-1-tert-butoxycarbonylamino-2-phenylcyclopropanecarboxylic acid (130 mg, 0.45 mmol) was added 4N hydrochloric acid—1,4-dioxane solution (2.0 mL, 16 v/w) and the mixture was stirred for 1 hr at room temperature. Diethyl ether (1.0 mL) was added thereto and the mixture was stirred for 5 min, after which the resulting crystals were collected by filtration. The crystals were washed with diethyl ether (1.0 mL) and dried under reduced pressure to give the title compound (81 mg, white powder, yield 84%).

$^1$H-NMR (DMSO, 300 MHz): 1.84 (dd, J=6.0, 9.0 Hz, 1H), 2.03 (dd, J=6.0, 9.0 Hz, 1H), 2.99 (t, J=10.5 Hz, 1H), 7.20-7.40 (m, 5H), 8.29 (br, 3H)

b) (1S,2R)-1-(4'-Chlorobiphenyl-4-sulfonylamino)-2-phenylcyclopropanecarboxylic acid

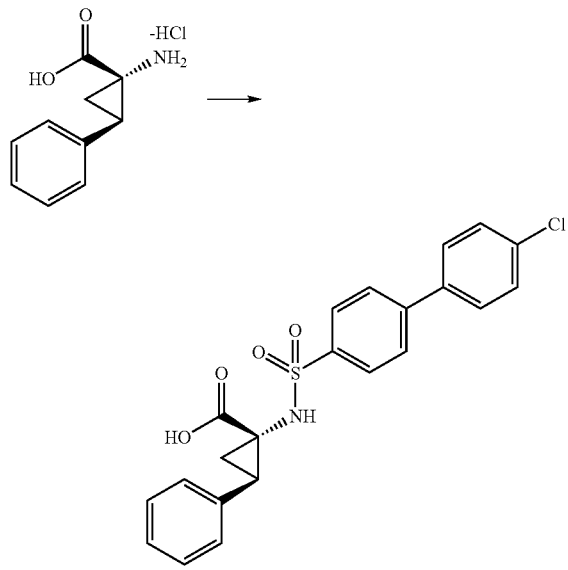

To a suspension of (1S,2R)-1-amino-2-phenylcyclopropanecarboxylic acid (80 mg, 0.38 mol) obtained in Example 1-a) in 1,4-dioxane:water=1:1 (3.2 mL, 40 v/w) were successively added triethylamine (0.18 mL, 1.3 mmol), 4-chlorobiphenylsulfonic acid chloride (110 mg, 1.1 mol) and N,N-dimethylaminopyridine (9.0 mg, 0.20 mmol) at 0° C. The mixture was stirred for 12 hr at room temperature, and 1N hydrochloric acid was added thereto until its pH reached approximately 1. The organic layer was extracted twice with ethyl acetate (4.0 mL) and concentrated. Then, the obtained crude product was separated and purified by thin-layer silica gel chromatography (chloroform:methanol=7:1) to give the title compound (60 mg, white amorphous solid, 37%).

EXAMPLE 1-2

1-[4-(2,4-Dichlorobenzyloxy)benzenesulfonylamino]-2-phenylcyclopropanecarboxylic acid hydroxyamide

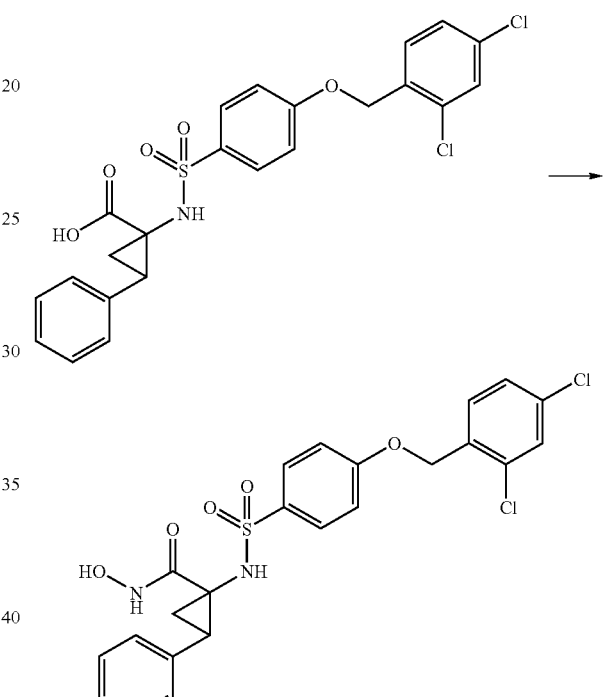

Under an argon atmosphere of, 1-[4-(2,4-dichlorobenzyloxy)benzenesulfonylamino]-2-phenylcyclopropanecarboxylic acid (120 mg, 0.24 mmol) obtained in the same manner as in Example 1 was dissolved in tetrahydrofuran (1.2 mL, 10 v/w) and a methylene chloride solution of 2N oxalyl chloride (0.13 mL, 0.26 mmol) and a catalytic amount of N,N-dimethylformamide were added dropwise thereto at −20° C. After warming to 0° C. over 1 hr, O-(trimethylsilyl)hydroxylamino (0.064 mL, 0.52 mmol) and N-methylmorpholine (0.052 mL, 0.48 mmol) were successively added dropwise thereto. The mixture was stirred at 0° C. for 1.5 hr, and 1N-hydrochloric acid (1.0 mL) and water (5.0 mL) were added thereto. The mixture was extracted twice with ethyl acetate (5.0 mL). The organic layer was successively washed with water (5.0 mL) and saturated brine (5.0 mL), and dried over magnesium sulfate (1.0 g). After filtration, the solvent was evaporated off under reduced pressure, and the obtained crude product was purified by silica gel chromatography (chloroform:methanol=10:1). The solvent was evaporated off, and diethyl ether was added to the obtained colorless oil. The mixture was stirred for 10 min at room temperature and the precipitated crystals were collected by filtration and dried under reduced pressure to give the title compound (88 mg, yield 73%) as a white solid. Melting point 164.0-169.0° C.

(Examples 1-3 to 1-149)

In the same manner as in Examples 1 and 1-2, the compounds of Examples 1-3 to 1-149 were obtained.

The structural formulas of the compounds of Examples 1 to 1-149 are shown in Tables 1-1 to 1-30.

EXAMPLE 2

4-[5-((1S,2R)-1-carboxy-2-phenyl-cyclopropane-sulfamoyl)-thiophene-2-yl]-3,6-dihydro-2H-pyridin-1-carboxylic acid t-butyl ester (step 5-8)

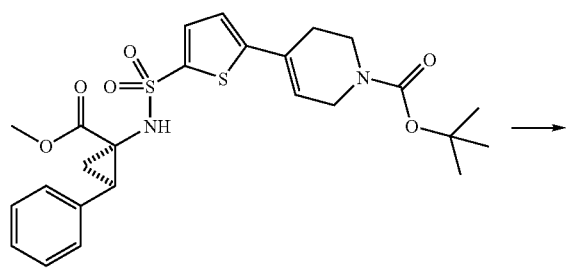

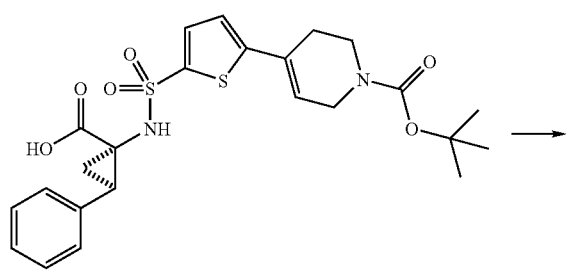

The title compound (0.11 g, yield 90%) was obtained in a similar manner as in Preparation Example 5-1 from 4-{5-[(1S,2R)-1-methoxycarbonyl-2-phenyl-cyclopropyl-sulfamyl]-thiophen-2-yl}-3,6-dihydro-2H-pyridin-1-carboxylic acid t-butyl ester (0.13 g, 0.24 mmol).

EXAMPLE 2-2

(1S,2R)-2-phenyl-1-[5-(1,2,3,6-tetrahydro-pyridin-4-yl)-thiophene-2-sulfonylamino]-cyclopropanecarboxylic acid hydrochloride (step 5-9)

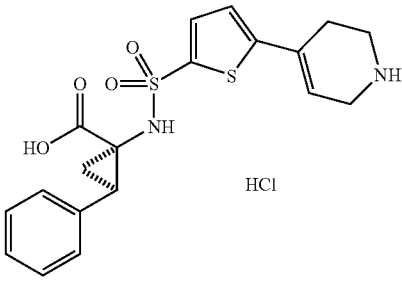

To a solution of 4-[5-((1S,2R)-1-carboxy-2-phenyl-cyclopropanesulfamoyl)-thiophen-2-yl]-3,6-dihydro-2H-pyridin-1-carboxylic acid t-butyl ester (0.11 g, 0.22 mmol) obtained in Example 2 in methanol (0.86 mL) was added 4N hydrochloric acid dioxane solution (2.2 mL) under argon atmosphere, and the mixture was stirred at room temperature for 1 hour. The title compound (0.11 g, yield 100%) was obtained by evaporation under reduced pressure.

EXAMPLE 2-3

4-[5-((1S,2R)-1-carboxy-2-phenyl-cyclopropane-sulfamoyl)-thiophene-2-yl]-3,6-dihydro-2H-pyridin-1-carboxylic acid methyl ester (step 5-9)

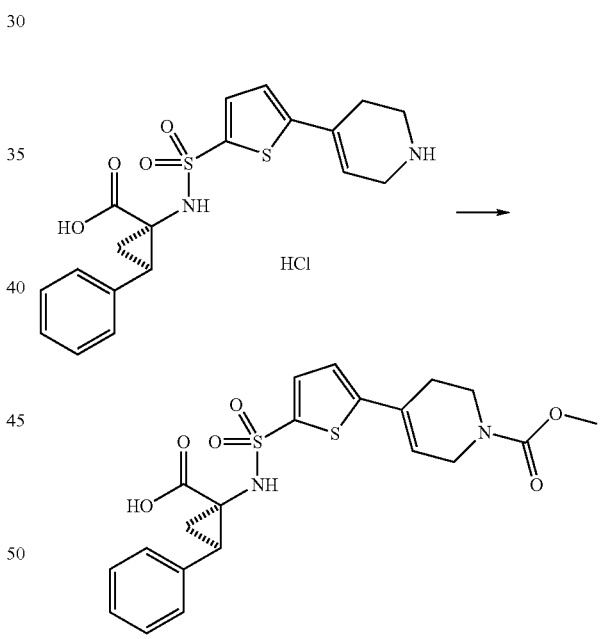

To a solution of (1S,2R)-2-phenyl-1-[5-(1,2,3,6-tetrahydro-pyridin-4-yl)-thiophene-2-sulfonylamino]-cyclopropanecarboxylic acid hydrochloride (30 mg, 69 μmol) obtained in Example 2-2 in chloroform (0.60 mL) were added triethylamine (39 μL, 0.28 mmol) and methyl chlorocarbonate (6.4 μL, 83 μmol) under argon atmosphere, and the mixture was stirred at room temperature for 18 hours. Saturated aqueous ammonium chloride solution, a small amount of ethyl acetate and diisopropyl ether were added to the mixture to allow precipitation of crystal, and the obtained crystals were filtrated to give the title compound (13 mg, yield 42%).

EXAMPLE 2-4

(1S,2R,3R)-1-[5-(4-ethynyl-pyrazole-1-yl)-thiophene-2-sulfonylamino]-2-methyl-3-phenyl-cyclopropanecarboxylic acid (step 5-9)

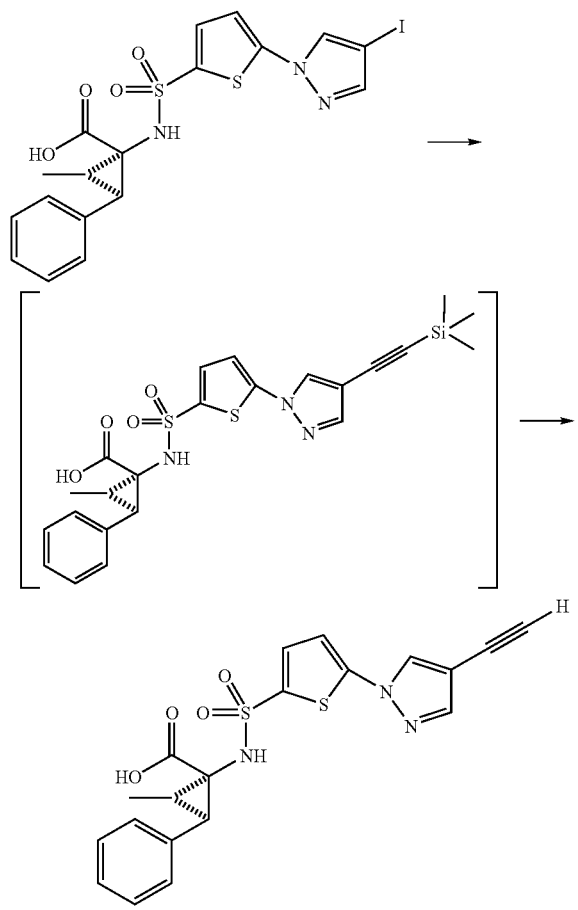

To a solution of a deprotected compound of (1S,2R,3R)-1-[5-(4-iodo-pyrazol-1-yl)-thiophene-2-sulfonylamino-2-methyl-3-phenyl-cyclopropanecarboxylic acid t-butyl ester (0.10 g, 0.19 mmol) obtained in Preparation Example 5-7 in chloroform (1.0 mL) were sequentially added triethylamine (0.13 mL, 0.94 mmol), trimethylsilylacetylene (54 µL, 0.38 mmol), copper iodide (I) (1.8 mg, 9.4 mmol) and dichlorobis(triphenylphosphine)palladium (II) (6.6 mg, 9.4 µmol) at room temperature under nitrogen atmosphere. After stirring for 1 hour without any modification, 5% aqueous potassium hydrogen sulfate solution (1 mL) was added to the mixture. The aqueous layer was extracted three times with ethyl acetate (2 mL). The organic layer was washed with water (3 mL) and saturated aqueous sodium chloride solution (3 mL), and dried over sodium sulfate. After filtration and evaporation, the obtained crude product was purified by silica gel chromatography (hexane:ethyl acetate=1:1) to give (1S,2R,3R)-2-methyl-3-phenyl-1-[5-(4-trimethylsilanylethynyl-pyrazol-1-yl)-thiophene-2-sulfonylamino]-cyclopropanecarboxylic acid (75 mg, yield 79%) as a brown oil.

To a solution of (1S,2R,3R)-2-methyl-3-phenyl-1-[5-(4-trimethylsilanylethynyl-pyrazol-1-yl)-thiophene-2-sulfonylamino]-cyclopropanecarboxylic acid (66 mg, 0.13 mmol) in methanol (1.0 mL) was added potassium carbonate (36 mg, 0.26 mmol) at room temperature. After stirring for 1 hour without any modification, to the mixture was added 5% aqueous potassium hydrogen sulfate solution (3.0 mL). The aqueous layer was extracted three times with ethyl acetate (2.0 mL). The organic layer was washed with water (3.0 mL) and saturated aqueous sodium chloride solution (3.0 mL), and dried over sodium sulfate. After filtration and evaporation of the residue, chloroform (1.0 mL) was added to the obtained residue to allow precipitation of crystals. After slurry-washing and filtration, the residue was dried under reduced pressure to give the title compound (54 mg, yield 98%) as a pale-yellow powder.

EXAMPLE 2-5

(1S,2R,3R)-2-methyl-3-phenyl-1-[4-(5-trifluoromethyl-pyridin-2-yl)-piperazine-1-sulfonylamino]-cyclopropanecarboxylic acid (step 6-11)

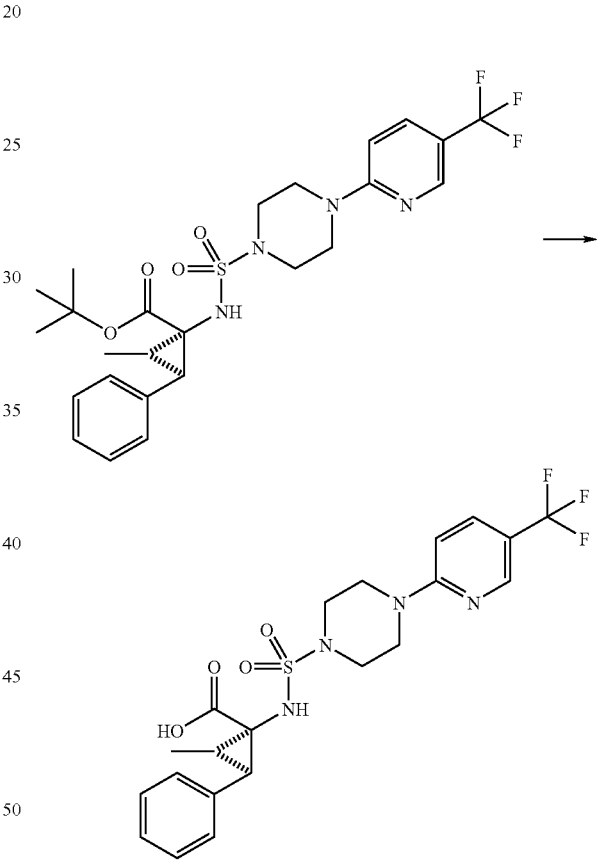

To a solution of (1S,2R,3R)-2-methyl-3-phenyl-1-[4-(5-trifluoromethyl-pyridin-2-yl)-piperazine-1-sulfonylamino]-cyclopropanecarboxylic acid t-butyl ester (33 mg, 0.061 mmol) obtained in Preparation Example 5-11-3 in dichloromethane (1.5 mL) was added trifluoroacetic acid (1.5 mL). The reaction mixture was stirred at room temperature for 3 hours. The excess trifluoroacetic acid was removed by azeotropic distillation (twice) with toluene. Toluene was removed by azeotroping twice with dichloromethane and drying under hivac. The material was purified by prep TLC eluting with 9:1 chloroform/methanol (Rf 0.3). The product was further purified by dissolving in a small amount of dichloromethane and adding hexane to allow precipitation of the product as a white solid (88% yield).

EXAMPLE 2-6

(1S,2R)-2-methyl-2-phenyl-1-[5-(5-trifluoromethyl-isoxazol-3-yl)-thiophene-2-sulfonylamino]-cyclopropanecarboxylic acid (step 6-11)

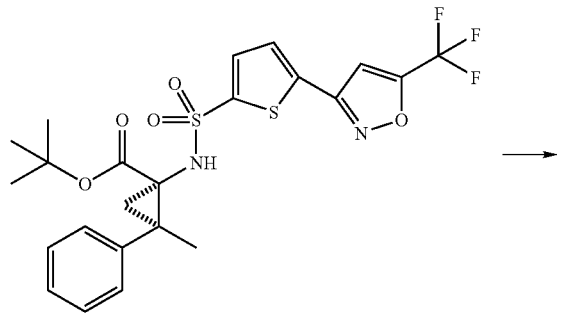

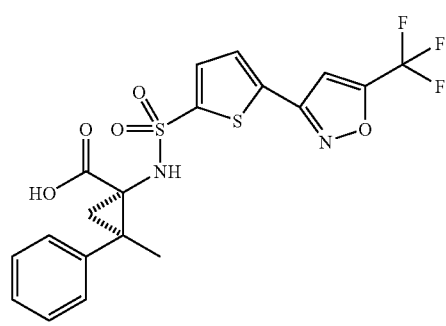

To a solution of (1S,2R)-2-methyl-2-phenyl-1-[5-(5-trifluoromethyl-isoxazol-3-yl)-thiophene-2-sulfonylamino]-cyclopropanecarboxylic acid t-butyl ester (5.0 g, 9.4 mmol) obtained in a similar manner as in Preparation Example 5-11 in chloroform (50 mL) was added trifluoroacetic acid (25 mL), and the mixture was stirred at room temperature for 21 hours. The solvent was evaporated under reduced pressure. After azeotropic removal of residual solvent with methanol, the residue was dissolved in a small amount of methanol. To the mixture was added water at 0° C. to allow precipitation of crystals. The crystals were filtrated and dried to give the title compound (4.3 g, yield 97%, $[\alpha]^{25}_D$+72.60 (c1.00, MeOH), m.p. 130-132° C.) as a white amorphous form.

EXAMPLE 2-7

(1S,2R,3R)-2-methyl-3-phenyl-1-[5-(5-trifluoromethyl-isoxazol-3-yl)-thiophene-2-sulfonylamino]-cyclopropanecarboxylic acid (step 6-11)

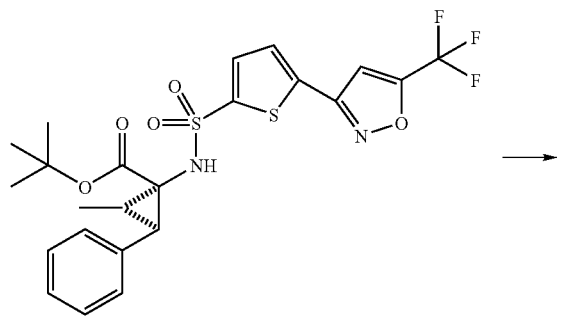

-continued

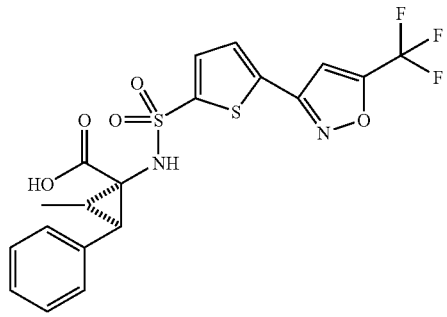

(1S,2R,3R)-2-methyl-3-phenyl-1-[5-(5-trifluoromethyl-isoxazol-3-yl)-thiophene-2-sulfonylamino]-cyclopropanecarboxylic acid t-butyl ester (7.2 g, 14 mmol) obtained in a similar manner as in Preparation Example 5-11 was deprotected in a similar manner as in Example 2-6 to give the title compound [5.9 g, yield 90%, $[\alpha]^{25}_D$+81.0° (c 1.10, MeOH)] as white crystals.

EXAMPLE 2-8

(1R*,1aS*,8bS*)-1-[5-(4-chloro-phenyl) thiophene-2-sulfonylamino]-1,1a,2,3,4,8b-hexahydrobenzo[a]cyclopropane[c]cyclohepten-1-carboxylic acid (step 6-11)

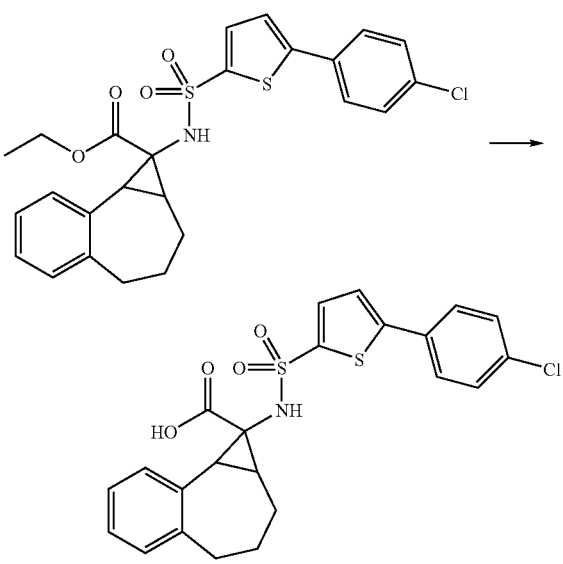

To a solution of (1R*,1aS*,8bS*)-1-[5-(4-chloro-phenyl) thiophene-2-sulfonylamino]-1,1a,2,3,4,8b-hexahydrobenzo[a]cyclopropane[c]cyclohepten-1-carboxylic acid ethyl ester (0.25 g, 0.50 mmol) obtained in Preparation Example 5-11-2 in a methanol:tetrahydrofuran=1:1 (5.0 mL) mixture was added 4N aqueous sodium hydroxide solution (1.0 mL, 4.0 mmol), and the mixture was refluxed for 5 days. After putting back to room temperature, ethyl acetate (5.0 mL) and 1N aqueous hydrochloric acid solution (5.0 mL) were sequentially added to the mixture. After separating into layers, the aqueous layer was extracted twice with ethyl acetate (100 mL), and dried over magnesium sulfate. After filtration and evaporation, the residue was separated and purified by silica gel chromatography (hexane:ethyl acetate=1:1) to give the title compound (0.15 g, yield 65%) as a white amorphous form.

EXAMPLE 2-9

(1S,2R,3R)-1-{5-[5-(1,1-difluoro-ethyl)-isoxazol-3-yl]-thiophene-2-sulfonylamino}-2-methyl-3-phenyl-cyclopropanecarboxylic acid (step 6-11)

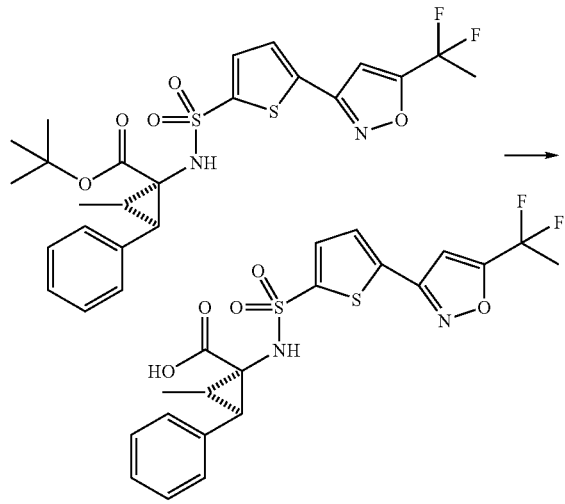

To a solution of (1S,2R,3R)-1-{5-[5-(1,1-difluoro-ethyl)-isoxazol-3-yl]-thiophene-2-sulfonylamino}-2-methyl-3-phenyl-cyclopropanecarboxylic acid t-butyl ester (4.1 g, 7.8 mmol) obtained in Preparation Example 5-11 in chloroform (40 mL) was added trifluoroacetic acid (20 mL), and the mixture was stirred at room temperature for 20 hours. Then the mixture was evaporated under reduced pressure. The residue was azeotroped with a mixed solvent of chloroform and hexane, and dissolved in methanol (30 mL). After treatment with activated carbon (1 g), the solvent was evaporated and the residue was dissolved in methanol (30 mL). To the obtained solution was added water at 0° C. to allow precipitation of crystals. The crystals were filtrated and dried to give the title compound [3.3 g, yield 90%, $[\alpha]^{25}_D$ +83.6° (c 0.45, MeOH), m.p. 177-178° C.] as white crystals.

EXAMPLE 2-10

(1R*,2R*,3R*)-2-hydroxymethyl-3-phenyl-1-[5-(5-trifluoromethyl-isoxazol-3-yl)-thiophene-2-sulfonylamino]-cyclopropanecarboxylic acid (step 5-12)

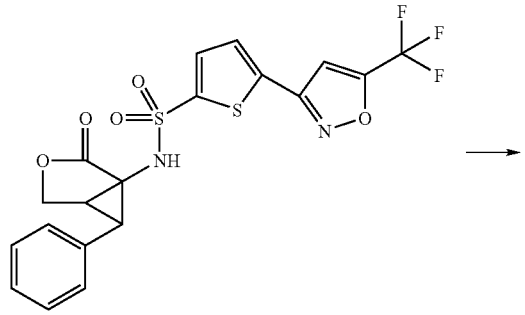

-continued

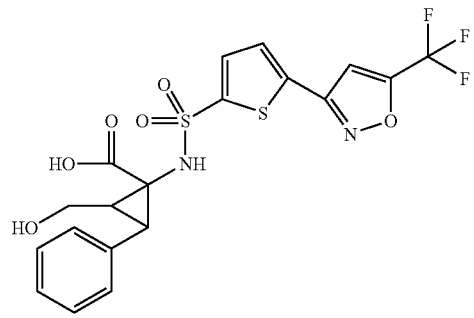

To 5-(5-trifluoromethyl-isoxazol-3-yl)-thiophene-2-sulfonic acid [(1R*,5R*,6R*)-2-oxo-6-phenyl-3-oxa-bicyclo[3.1.0]hex-1-yl]-amide (53 mg, 11 mmol) were added LiOH—H$_2$O (11 mg, 0.27 mmol), 1 mL of THF and 0.5 mL of water. After stirring overnight at room temperature, the reaction mixture was concentrated, diluted with water (2 mL), and acidified to pH 4 with 2N KHSO$_4$. The product was extracted with EtOAc, washed with water (×2), brine and dried over Na$_2$SO$_4$. After concentrating, the product was precipitated from dichloromethane/hexane to afford the desired product as a white solid (46 mg, 86% yield).

EXAMPLE 2-11

(1S,2R,3R)-2-methyl-3-phenyl-1-(4-phenylcarbamoyl-piperazine-1-sulfamoylamino)-cyclopropanecarboxylic acid (step 5-13)

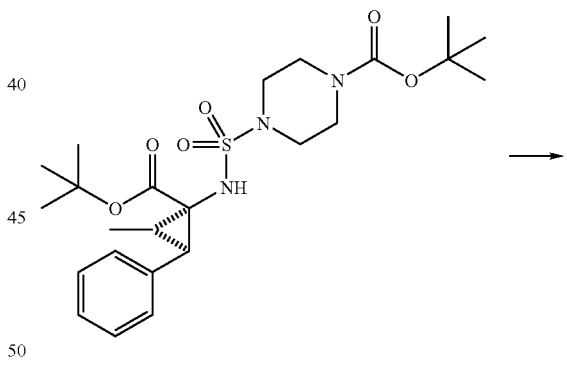

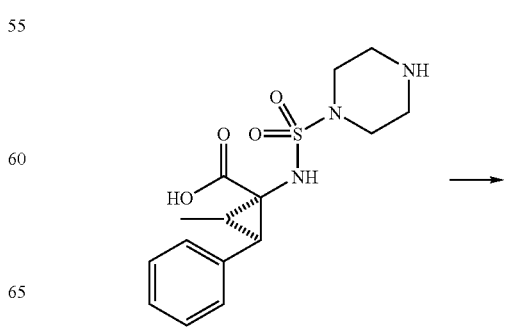

-continued

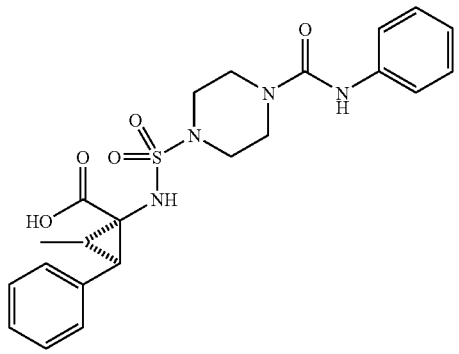

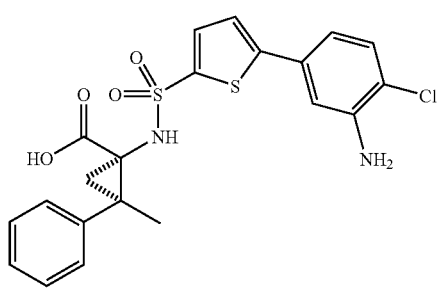

4-((1S,2R,3R)-1-t-butoxycarbonyl-2-methyl-3-phenyl-cyclopropylsulfamoyl)-piperazine-1-carboxylic acid t-butyl ester (0.24 g, 0.48 mmol) obtained in Preparation Example 5-5-2, dioxane (0.20 mL) and 4N hydrochloric acid in dioxane (2.0 mL) were mixed, and the mixture was stirred at room temperature for 16 hours. After the obtained solution was concentrated, the residue was slurry-washed with ethyl acetate (5.0 mL) to give (1S,2R,3R)-2-methyl-3-phenyl-1-(piperazine-1-sulfamoylamino)-cyclopropanecarboxylic acid (0.15 g, yield 84%) as a white solid.

To a solution of the obtained (1S,2R,3R)-2-methyl-3-phenyl-1-(piperazine-1-sulfamoylamino)-cyclopropanecarboxylic acid (20 mg, 53 μmol) in tetrahydrofuran (1.0 mL) were added triethylamine (11 μL, 80 μmol) and phenyl isocyanate (8.7 μL, 80 μmol) at 0° C., and the mixture was stirred for 3 hours. To the obtained solution was added 10% aqueous potassium hydrogen sulfate solution (1.0 mL), and the aqueous layer was extracted twice with ethyl acetate (2.0 mL). After the organic layer was concentrated, the residue was purified by silica gel chromatography (chloroform:methanol=10:1) to give the title compound (20 mg, yield 80%) as a colorless amorphous form.

EXAMPLE 2-12

(1S,2R)-1-[5-(3-amino-4-chloro-phenyl)-thiophene-2-sulfonylamino]-2-methyl-2-phenyl-cyclopropanecarboxylic acid (step 5-14)

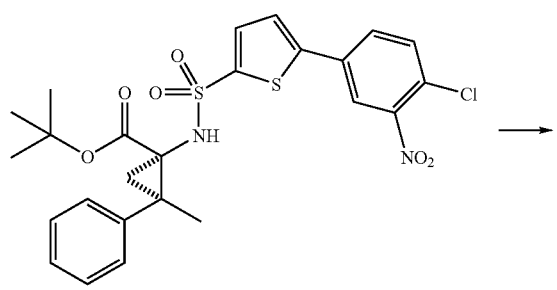

To a solution of (1S,2R)-1-[5-(4-chloro-3-nitro-phenyl)-thiophene-2-sulfonylamino]-2-methyl-2-phenyl-cyclopropanecarboxylic acid t-butyl ester (23 mg, 41 μmol), which was obtained from (1S,2R,3R)-1-amino-2-methyl-3-phenyl-cyclopropanecarboxylic acid t-butyl ester obtained in Preparation Example 5-4 by the general method of steps 5-5 and 5-6, in ethanol (0.30 mL) was added tin dichloride dihydrate (37 mg, 0.16 mmol), and the mixture was stirred at 100° C. for 2 hours. To the obtained solution were added saturated aqueous sodium hydrogen carbonate solution (1.0 mL) and methanol (1.0 mL), and the mixture was filtrated. The eluent was evaporated and the residue was separated and purified by silica gel chromatography (chloroform:methanol=9:1) to give the title compound (8.3 mg, yield 43%) as a white amorphous form.

EXAMPLE 2-13

(1R*,1aS*,6aS*)-1-[4-(2,4-dichloro-benzyloxy)-benzenesulfonylamino]-1,1a,6,6a-tetrahydro-cyclopropa[a]inden-1-carboxylic acid hydroxyamide (step 5-15)

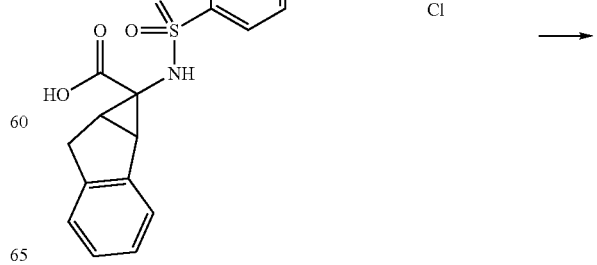

-continued

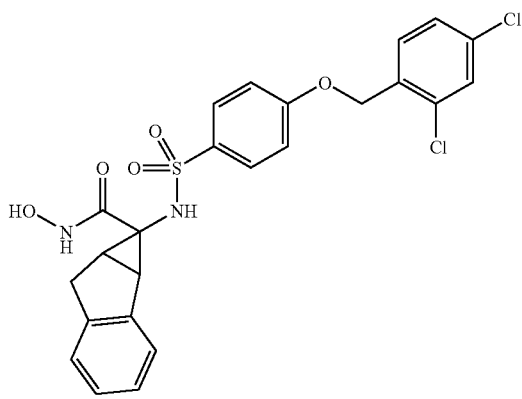

After (1R*,1aS*,6aS*)-1-[4-(2,4-dichloro-benzyloxy)-benzenesulfonylamino]-1,1a,6,6a-tetrahydro-cyclopropane[a]inden-1-carboxylic acid (92 mg, 0.18 mmol) obtained in a similar manner as in Preparation Example 6-11 was azeotroped with toluene, the residue was dissolved in tetrahydrofuran (2.0 mL). Under argon atmosphere, 2 M oxalyl chloride dichloromethane solution (0.12 mL, 0.24 mmol) and a catalytic amount of N,N-dimethylformamide were sequentially added dropwise at −20° C. After stirring at 0° C. for 1 hour, O-(trimethylsilyl)hydroxylamine (59 μL, 0.48 mmol) and N-methylmorpholin (40 μL, 0.36 mmol) were sequentially added dropwise at −20° C. After stirring at 0° C. for 1 hour, 1N aqueous hydrochloric acid solution (1.0 mL) was added, and the mixture was extracted twice with ethyl acetate (20 mL). The organic layer was washed with water (3.0 mL) and dried over magnesium sulfate. After filtration and evaporation, the obtained residue was purified by silica gel chromatography (hexane:ethyl acetate=1:1). Further, diisopropyl ether was added to the obtained residue to allow precipitation. After filtration, a white solid (43 mg, yield 46%) was obtained under reduced pressure.

(Example 2-14 to 2-625)

The compounds of Examples 2-14 to 2-625 were produced from the compounds obtained in Preparation Examples or by known preparation methods and using similar methods of Examples 1, 1-2, 2-1 to 2-13.

The structural formulas of the compounds of Examples 2 to 2-625 are shown in Tables 2-1 to 2-125.

TABLE 1-1

| Example | Structural formula | NMR |
|---------|--------------------|-----|
| 1 | | (DMSO-d6-300) 1.50(dd, J=6.0, 9.0Hz, 1H), 1.88-1.97(m, 1H), 2.57-2.66(m, 1H), 7.12-7.26(m, 5H), 7.57(dd, J=3.0, 6.0Hz, 2H), 7.78(dd, J=3.0, 6.0Hz, 2H), 7.85(br, 4H) |
| 1-2 | | (DMSO-d6-300) 1.01-1.10(m, 1H), 1.90(dd, J=6.0, 9.0Hz, 1H), 2.40-2.52(m, 1H); 5.24(s, 2H), 7.07-7.24(m, 7H), 7.49(dd, J=3.0, 9.0Hz, 1H), 7.65(d, J=9.0Hz, 1H), 7.72(d, J=3.0Hz, 1H), 7.76(d, J=6.0Hz, 2H), 8.50(brs, 2H), 10.20(brs, 1H) |

TABLE 1-1-continued

| Example | Structural formula | NMR |
|---|---|---|
| 1-3 | | (DMSO-d6-300) 1.45(dd, J=9.8, 4.8Hz, 1H), 1.73(dd, J=8.2, 5.2Hz, 1H), 2.37(t, J=9.20Hz, 1H), 4.21(d, J=5.5Hz, 2H), 6.00-6.09(m, 1H), 6.29-6.50(m, 3H), 6.85(t, J=7.7Hz, 1H), 7.32(dd, J=7.9, 4.9Hz, 1H), 7.53-7.60(m, 2H), 7.68-7.80(m, 3H), 7.85(s, 4H), 8.42(dd, J=4.8, 1.8Hz, 1H), 8.55(d, J=1.8Hz, 1H) |
| 1-4 | | (DMSO-d6-300) 0.84(dd, J=3.0, 9.0Hz, 1H), 0.97(dd, J=6.0, 9.0Hz, 1H), 2.58(t, J=9.0Hz, 1H), 3.75(s, 3H), 6.81(t, J=7.5Hz, 1H), 6.89(brd, J=9.0Hz, 1H), 7.03(brd, J=9.0Hz, 1H), 7.17(t, J=9.0Hz, 1H), 7.53(brd, J=9.0Hz, 2H), 7.56(d, J=3.0Hz, 1H), 7.58(d, J=3.0Hz, 1H), 7.76(brd, J=9.0Hz, 2H), 9.01(br, 1H), 11.98(br, 1H) |
| 1-5 | | (DMSO-d6-300) 1.79-1.87(m, 1H), 1.96-2.03(m, 1H), 2.53-2.58(m, 1H), 7.10-7.16(m, 2H), 7.20-7.28(m, 3H), 7.58(d, J=9.0Hz, 2H), 7.74-7.86(m, 6H) |

TABLE 1-2

| Example | Structural formula | NMR |
|---|---|---|
| 1-6 | | (DMSO-d6-300) 1.79-1.87(m, 1H), 1.96-2.03(m, 1H), 2.53-2.58(m, 1H), 7.10-7.16(m, 2H), 7.20-7.28(m, 3H), 7.58(d, J=9.0Hz, 2H), 7.74-7.86(m, 6H) |

TABLE 1-2-continued
| Example | Structural formula | NMR |
|---|---|---|
| 1-7 | 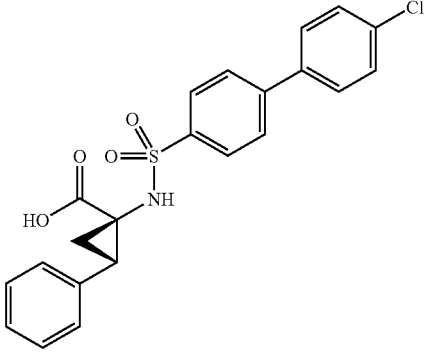 | (DMSO-d6-300)<br>1.50(dd, J=6.0, 9.0Hz, 1H), 1.88-1.97(m, 1H), 2.57-2.66(m, 1H), 7.12-7.26(m, 5H), 7.57(dd, J=3.0, 6.0Hz, 2H), 7.78(dd, J=3.0, 6.0Hz, 2H), 7.85(br, 4H) |
| 1-8 | 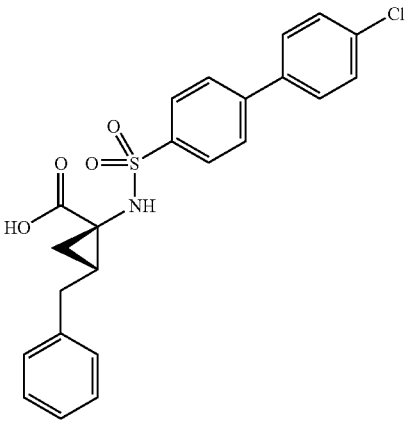 | (DMSO-d6-300)<br>1.18-1.26(m, 1H), 1.31-1.41(m, 1H), 1.58-1.71(m, 1H), 2.69-2.78(m, 2H), 7.13-7.32(m, 5H), 7.58(brd, J=9.0Hz, 2H), 7.74-7.81(m, 4H), 7.85 (brd, J=9.0, Hz, 2H) |
| 1-9 | 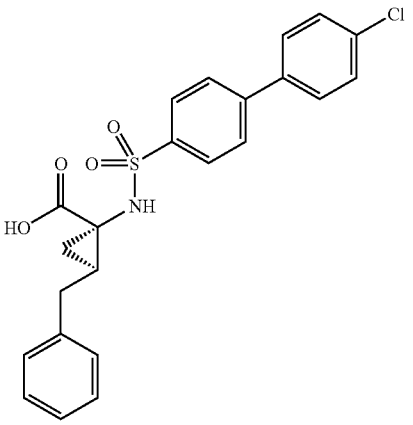 | (DMSO-d6-300)<br>0.60(dd, J=3.0, 9.0Hz, 1H), 0.67(dd, J=3.0, 6.0Hz, 1H), 0.82(dd, J=6.0, 9.0Hz, 1H), 2.73(t, J=7.5Hz, 2H), 7.16-7.32(m, 5H), 7.58(d, J=9.0Hz, 2H), 7.78(d, J=9.0Hz, 4H), 7.86(d, J=9.0Hz, 2H) |

TABLE 1-2-continued

| Example | Structural formula | NMR |
|---|---|---|
| 1-10 | | (CDCL3-400) 1.81-1.93(m, 1H), 1.96-2.05(m, 1H), 2.81(t, J=8.0Hz, 1H), 5.84(brs, 1H), 6.76-6.85(m, 2H), 6.87-6.94(m, 3H), 7.07(t, J=8.0Hz, 1H), 7.14(t, J=8.0Hz, 1H), 7.28(d, J=8.0Hz, 2H), 7.43(d, J=8.0Hz, 2H), 7.50(d, J=8.0Hz, 2H), 7.61(d, J=8.0Hz, 2H), 7.88(d, J=8.0Hz, 2H) |

TABLE 1-3

| Example | Structural formula | NMR |
|---|---|---|
| 1-11 | | (DMSO-d6-300) 1.48-1.56(m, 1H), 1.84-1.93(m, 1H), 2.56-2.65(m, 1H), 6.81(br, 2H), 6.95(d, J=9.0Hz, 2H), 6.97-7.03(m, 1H), 7.25(t, J=9.0Hz, 1H), 7.39(d, J=9.0Hz, 2H), 7.57(dd, J=3.0, 9.0Hz, 2H), 7.77(dd, J=3.0, 9.0Hz, 2H), 7.83(br, 4H), 7.89(d, J=3.0Hz, 1H) |
| 1-12 | | (DMSO-d6-300) 1.45(dd, J=6.0, 12.0Hz, 1H), 1.93(dd, J=6.0, 9.0Hz, 1H), 2.64(t, J=10.5Hz, 1H), 3.69(s, 3H), 6.72-6.81(m, 3H), 7.15(t, J=7.5Hz, 1H), 7.57(d, J=9.0Hz, 2H), 7.78(d, J=9.0Hz, 2H), 7.83-7.91(m, 4H) |
| 1-13 | | (DMSO-d6-300) 1.50-1.62(m, 1H), 1.79-1.92(m, 1H), 2.42-2.55(m, 1H), 3.74(s, 3H), 6.78(t, J=7.5Hz, 1H), 6.87(d, J=9.0Hz, 1H), 6.99(d, J=9.0Hz, 1H), 7.14(t, J=7.5Hz, 1H), 7.57(d, J=9.0Hz, 2H), 7.78(d, J=9.0Hz, 2H), 7.87(s, 4H) |

TABLE 1-3-continued

| Example | Structural formula | NMR |
|---|---|---|
| 1-14 | 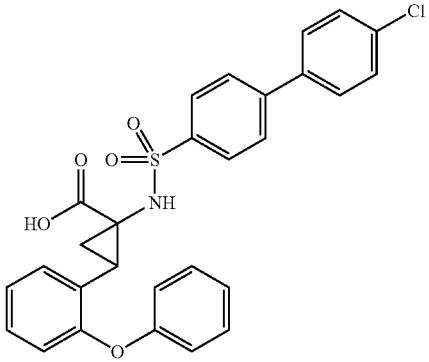 | (DMSO-d6-300)<br>1.49(dd, J=5.7, 9.4Hz, 1H),<br>1.97(dd, J=5.7, 8.7Hz, 1H),<br>2.59(dd, J=8.7, 9.4Hz, 1H),<br>6.69(d, J=7.9Hz, 1H), 6.94-<br>7.04(m, 3H), 7.09-7.22(m, 3H),<br>7.38(dd, J=7.5, 8.3Hz, 2H),<br>7.57(d, J=8.7Hz, 2H), 7.77(d,<br>J=8.3Hz, 2H), 7.85(s, 4H),<br>8.83(s, 1H), 12.20(s, 1H). |
| 1-15 | 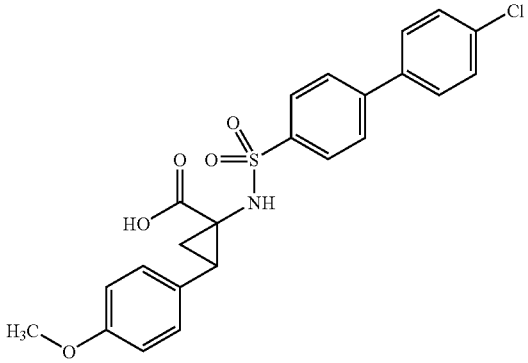 | (DMSO-d6-300)<br>1.43(dd, J=5.7, 9.4Hz, 1H),<br>1.92(dd, J=5.7, 8.7Hz, 1H),<br>2.61(dd, J=8.7, 9.4Hz, 1H),<br>3.69(s, 3H), 6.81(d, J=8.7Hz,<br>2H), 7.12(d, J=8.7Hz, 2H),<br>7.57(d, J=8.3Hz, 2H), 7.78(d,<br>J=8.6Hz, 2H), 7.87(s, 4H),<br>8.90(s, 4H), 12.05(s, 4H). |

TABLE 1-4

| Example | Structural formula | NMR |
|---|---|---|
| 1-16 | 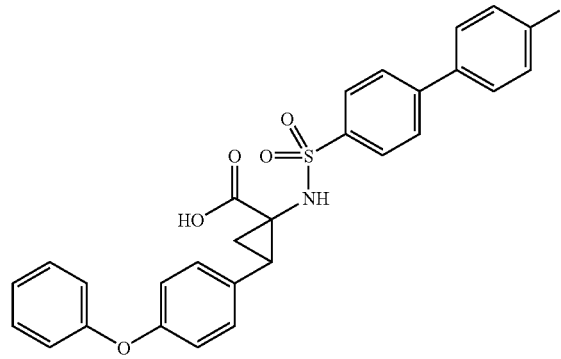 | (DMSO-d6-300)<br>1.50(dd, J=6.0, 9.0Hz, 1H),<br>1.92(dd, J=6.0, 9.0Hz, 1H),<br>2.57-2.67(m, 1H), 6.87(d,<br>J=9.0Hz, 2H), 6.94(d, J=9.0Hz,<br>2H), 7.12(t, J=7.5Hz, 1H),<br>7.20(d, J=9.0Hz, 2H), 7.31-<br>7.41(m, 2H), 7.57(d, J=9.0Hz,<br>2H), 7.78(d, J=9.0Hz, 2H),<br>7.87(s, 4H) |

TABLE 1-4-continued
| Example | Structural formula | NMR |
|---|---|---|
| 1-17 | 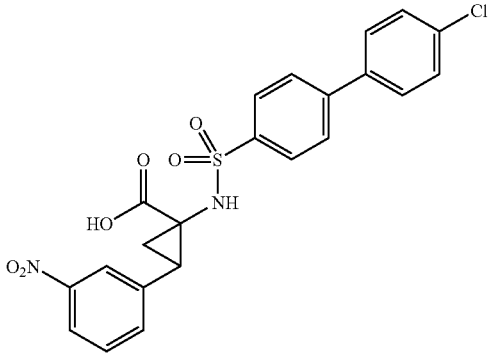 | (CDCL3-300) 2.08-2.20(m, 2H), 3.01(t, J=9.0Hz, 1H), 5.79(brs, 1H), 7.39-7.59(m, 3H), 7.69(d, J=9.0Hz, 2H), 7.96(d, J=9.0Hz, 2H), 8.03-8.11(m, 2H) |
| 1-18 | 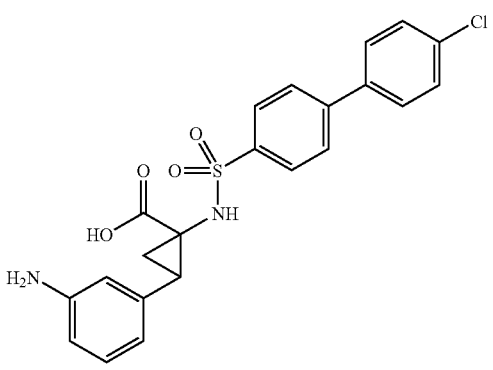 | (DMSO-d6-300) 1.37(dd, J=6.0, 12.0Hz, 1H), 1.81(dd, J=3.0, 9.0Hz, 1H), 2.45-2.54(m, 1H), 4.93(brs, 1H), 6.32-6.45(m, 3H), 6.85(t, J=7.5Hz, 1H), 7.57(d, J=9.0Hz, 2H), 7.78(d, J=9.0Hz, 2H), 7.74-7.90(m, 4H), 8.92(brs, 1H) |
| 1-19 | 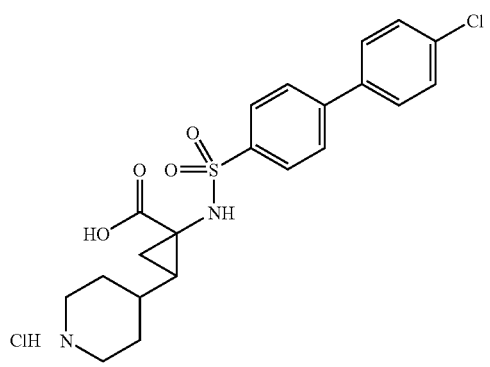 | (DMSO-d6-300) 1.04-1.84(m, 8H), 2.60-2.95(m, 2H), 3.15-3.28(m, 2H), 7.58(d, J=9.0Hz, 2H), 7.74-7.91(m, 6H), 8.36-8.87(m, 3H), 12.60(brs, 1H) |
| 1-20 | 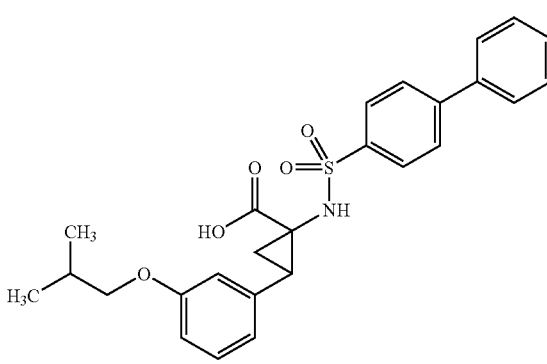 | (DMSO-d6-300) 0.93(d, J=6.0Hz, 6H), 1.55(dd, J=6.0, 9.0Hz, 1H), 1.76(dd, J=6.0, 9.0Hz, 1H), 1.88-1.99(m, 1H), 2.41(t, J=9.0Hz, 1H), 3.61(d, J=6.0Hz, 2H), 6.62-6.70(m, 3H), 7.04(t, J=7.5Hz, 1H), 7.57(d, J=9.0Hz, 2H), 7.77(d, J=9.0Hz, 2H), 7.84(d, J=9.0Hz, 2H), 7.87(d, J=9.0Hz, 2H) |

TABLE 1-5

| Example | Structural formula | NMR |
|---|---|---|
| 1-21 | | (DMSO-d6-300) 1.42(dd, J=3.0, 9.0Hz, 1H), 1.90(dd, J=6.0, 9.0Hz, 1H), 2.61(t, J=9.0Hz, 1H), 2.83(s, 6H), 6.47-6.58(m, 3H), 7.03(t, J=7.5Hz, 1H), 7.57(d, J=9.0Hz, 2H), 7.78(d, J=9.0Hz, 2H), 7.82-7.91(m, 4H), 8.91(brs, 1H), 12.05(brs, 1H) |
| 1-22 | | (DMSO-d6-300) 1.58(dd, J=6.0, 9.0Hz, 1H), 2.07(dd, J=6.0, 9.0Hz, 1H), 2.81(t, J=9.0Hz, 1H), 7.48-7.60(m, 4H), 7.57(d, J=9.0Hz, 2H), 7.78(d, J=9.0Hz, 2H), 7.87(s, 4H), 8.96(brs, 1H), 12.26(brs, 1H) |
| 1-23 | | (DMSO-d6-300) 1.52(dd, J=5.7, 9.8Hz, 1H), 2.00(dd, J=5.7, 8.7Hz, 1H), 2.71(dd, J=8.7, 9.8Hz, 1H), 7.19-7.26(m, 2H), 7.35-7.41(m, 2H), 7.57(d, J=8.3Hz, 2H), 7.78(d, J=8.7Hz, 2H), 7.87(s, 4H), 8.93(s, 1H), 12.27(s, 1H). |
| 1-24 | | (DMSO-d6-300) 0.92(d, J=6.8Hz, 6H), 1.47(dd, J=5.3, 9.4Hz, 1H), 1.90(dd, J=5.3, 8.7Hz, 1H), 2.00-2.12(m, 1H), 2.16(d, J=6.8Hz, 2H), 2.66(dd, J=8.7, 9.4Hz, 1H), 6.86(d, J=7.2Hz, 1H), 7.14(dd, J=7.5, 8.3Hz, 1H), 7.44(d, J=8.3Hz, 1H), 7.47(d, 1H), 7.57(d, J=8.7Hz, 2H), 7.78(d, J=8.7Hz, 2H), 7.87(s, 4H), 8.96(s, 1H), 9.78(s, 1H), 12.12(s, 1H). |

TABLE 1-5-continued

| Example | Structural formula | NMR |
|---|---|---|
| 1-25 | | (DMSO-d6-300)<br>1.46(dd, J=5.7, 9.4Hz, 1H),<br>1.88(dd, J=5.7, 8.7Hz, 1H),<br>2.65(dd, J=8.7, 9.4Hz, 1H),<br>6.43(s, 1H), 6.64(s, 2H),<br>6.99(d, J=7.5Hz, 4H), 7.14(t,<br>J=7.5Hz, 2H), 7.38(t, J=7.5Hz,<br>4H), 7.57(d, J=8.6Hz, 2H),<br>7.73-7.89(m, 6H), 8.88(s, 1H),<br>12.29(s, 1H) |

TABLE 1-6

| Example | Structural formula | NMR |
|---|---|---|
| 1-26 | | (DMSO-d6-300)<br>1.56(dd, J=6.0, 12.0Hz, 1H),<br>1.96(dd, J=6.0, 9.0Hz, 1H),<br>2.65(t, J=9.0Hz, 1H),<br>7.17(brd, J=9.0Hz, 1H), 7.25-<br>7.37(m, 2H), 7.39-7.46(m, 4H),<br>7.53-7.59(m, 4H), 7.76(d,<br>J=9.0Hz, 2H), 7.85(d, J=9.0Hz,<br>2H), 7.88(d, J=9.0Hz, 2H) |
| 1-27 | | (DMSO-d6-300)<br>1.55(dd, J=6.0, 9.0Hz, 1H),<br>1.55(dd, J=6.0, 9.0Hz, 1H),<br>1.73(dd, J=3.0, 6.0Hz, 1H),<br>2.40(t, J=9.0Hz, 1H), 5.12(s,<br>2H), 6.75(d, J=9.0Hz, 1H),<br>7.04(t, J=9.0Hz, 1H), 7.20-<br>7.43(m, 6H), 7.56(d, J=9.0Hz,<br>2H), 7.77(d, J=9.0Hz, 2H),<br>7.84(d, J=9.0Hz, 2H), 7.88(d,<br>J=9.0Hz, 2H), 9.61(s, 1H) |

TABLE 1-6-continued

| Example | Structural formula | NMR |
|---|---|---|
| 1-28 | | (DMSO-d6-300) 0.92(d, J=6.0Hz, 6H), 1.44(dd, J=6.0, 9.0Hz, 1H), 1.89(dd, J=6.0, 12.0Hz, 1H), 2.66(t, J=9.0Hz, 1H), 3.85(d, J=6.0Hz, 2H), 6.83(d, J=9.0Hz, 1H), 7.13(t, J=7.5Hz, 1H), 7.28(d, J=9.0Hz, 1H), 7.57(d, J=9.0Hz, 2H), 7.78(d, J=9.0Hz, 2H), 7.87(s, 4H), 8.97(s, 1H), 9.55(s, 1H) |
| 1-29 | | (METHANOL-d4-400) 1.84(dd, J=6.0, 9.0Hz, 1H), 2.09(dd, J=6.0, 9.0Hz, 1H), 2.77(t, J=9.0Hz, 1H), 7.11-7.25(m, 5H), 7.39(t, J=6.0Hz, 1H), 7.46(t, J=6.0Hz, 2H), 7.67(d, J=6.0Hz, 2H), 7.78(d, J=6.0Hz, 2H), 7.95(d, J=6.0Hz, 2H) |
| 1-30 | | (METHANOL-d4-400) 1.84(dd, J=8.0, 4.0Hz, 1H), 2.07(dd, J=4.0, 8.0Hz, 1H), 2.76(t, J=8.0Hz, 1H), 7.03(d, J=8.0Hz, 2H), 7.07(d, J=8.0Hz, 2H), 7.13-7.26(m, 6H), 7.41(t, J=8.0Hz, 2H), 7.84(d, J=8.0Hz, 2H) |

TABLE 1-7

| Example | Structural formula | NMR |
|---|---|---|
| 1-31 | | (METHANOL-d4-400) 1.83(dd, J=4.0, 8.0Hz, 1H), 2.08(dd, J=8.0, 4.0Hz, 1H), 2.77(t, J=8.0Hz, 1H), 7.11-7.28(m, 5H), 7.57-7.65(m, 4H), 7.78(d, J=8.0Hz, 2H), 7.95(d, J=8.0Hz, 2H) |

TABLE 1-7-continued

| Example | Structural formula | NMR |
|---|---|---|
| 1-32 | | (DMSO-d6-300) 1.63(dd, J=6.0, 9.0Hz, 1H), 2.04(dd, J=6.0, 9.0Hz, 1H), 2.75(t, J=9.0Hz, 1H), 7.10-7.27(m, 5H), 7.70(d, J=3.0Hz, 1H), 7.94(d, J=3.0Hz, 1H) |
| 1-33 | | (ACETONE-d6-400) 1.86(dd, J=8.0, 4.0Hz, 1H), 2.13 (dd, J=4.0, 8.0Hz, 1H), 2.85(t, J=8.0Hz, 1H), 4.48(s, 3H), 7.14-7.30(m, 5H), 8.06(d, J=8.0Hz, 2H), 8.27(d, J=8.0Hz, 2H) |
| 1-34 | | (ACETONE-d6-400) 1.67(t, J=8.0Hz, 3H), 1.86(dd, J=4.0, 8.0Hz, 1H), 2.13(dd, J=4.0, 8.0Hz, 1H), 2.82(t, J=8.0Hz, 1H), 4.81(q, J=8.0Hz, 2H), 7.13-7.30(m, 5H), 8.06(d, J=8.0Hz, 2H), 8.28(d, J=8.0Hz, 2H) |
| 1-35 | | (METHANOL-d4-400) 1.24(t, J=6.0Hz, 3H), 1.87(dd, J=8.0, 4.0Hz, 1H), 2.02-2.13(m, 3H), 2.76(t, J=8.0Hz, 1H), 4.70(t, J=6.0Hz, 3H), 7.12-7.26(m, 5H), 8.03(d, J=8.0Hz, 2H), 8.27(d, J=8.0Hz, 2H) |

TABLE 1-8
| Example | Structural formula | NMR |
|---|---|---|
| 1-36 | 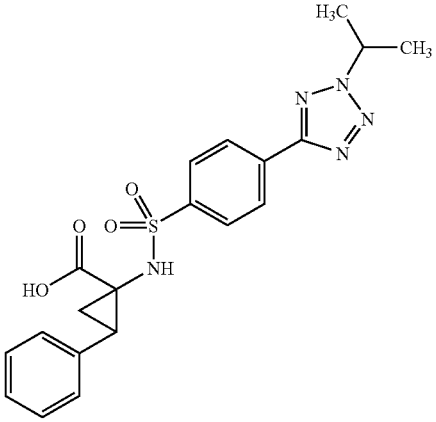 | (METHANOL-d4-400) 1.69(d, J=6.7Hz, 6H), 1.87(dd, J=9.8, 5.9Hz, 1H), 2.10(dd, J=8.6, 5.5 Hz, 1H), 2.7 (t, J=9.2Hz, 1H), 5.19(Septet, J=6.7Hz, 1H), 7.11-7.27(m, 5H), 8.01-8.06(m, 2H), 8.25-8.29(m, 2H) |
| 1-37 | 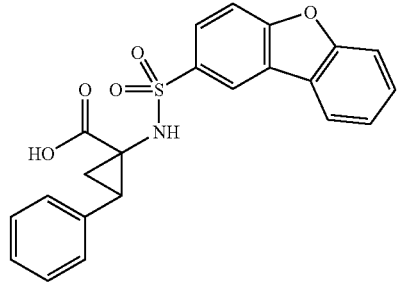 | (METHANOL-d4-400) 1.91(dd, J=9.8, 5.5Hz, H1), 2.11(dd, J=8.6, 5.5Hz, 1H), 2.80(t, J=9.0Hz, 1H)7.10-7.25(m, 4H), 7.43(t, J=8.1Hz, 1H), 7.53-7.58(m, 1H), 7.62-7.66(m, 1H), 7.72(d, J=9.4Hz, 1H), 8.01-8.05(m, 1H), 8.08-8.14(m, 2H), 8.57-8.60(m, 1H) |
| 1-38 | 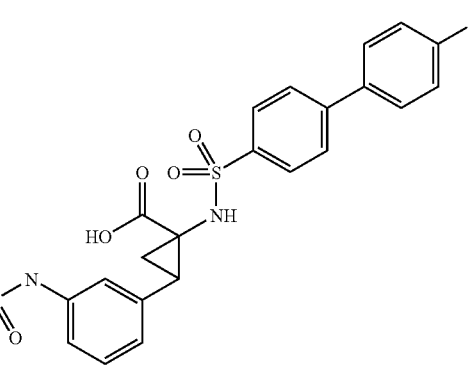 | (DMSO-d6-300) 1.49(dd, J=5.2, 9.8Hz, 1H), 1.92(dd, J=5.2, 9.0Hz, 1H), 2.69(dd, J=9.0, 9.8Hz, 1H), 2.92(s, 3H), 6.96(d, J=7.9Hz, 1H), 7.01(d, J=7.9Hz, 1H), 7.11(s, 1H), 7.20(t, J=7.9Hz, 1H), 7.57(d, J=8.7Hz, 2H), 7.78(d, J=8.6Hz, 2H), 7.87(s, 4H), 8.99(s, 1H), 9.67(s, 1H), 12.17(s, 1H) |
| 1-39 | 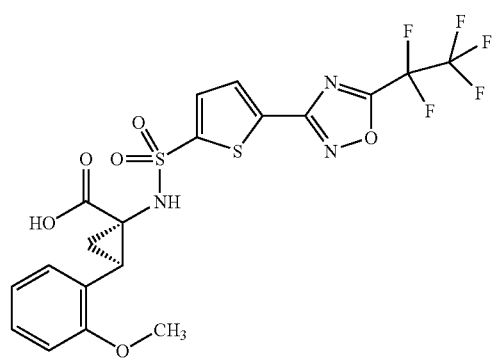 | (DMSO-d6-300) 1.62(dd, J=6.0, 9.0Hz, 1H), 2.03(dd, J=6.0, 9.0Hz, 1H), 2.75(t, J=9.0Hz, 1H), 7.11-7.27(m, 5H), 7.70(d, J=3.0Hz, 1H), 7.94(d, J=3.0Hz, 1H) |

TABLE 1-8-continued
| Example | Structural formula | NMR |
|---|---|---|
| 1-40 |  | (DMSO-d6-300) 1.46(dd, J=6.0, 9.0Hz, 1H), 1.89(dd, J=6.0, 9.0Hz, 1H), 2.01(s, 3H), 2.64(t, J=9.0Hz, 1H), 6.86(d, J=9.0Hz, 1H), 7.14(t, J=7.5Hz, 1H), 7.38-7.46(m, 2H), 7.57(d, J=9.0Hz, 2H), 7.78(d, J=9.0Hz, 2H), 7.87(s, 4H), 8.93(brs, 1H), 9.86(s, 1H), 12.13(brs, 1H) |
TABLE 1-9
| Example | Structural formula | NMR |
|---|---|---|
| 1-41 | 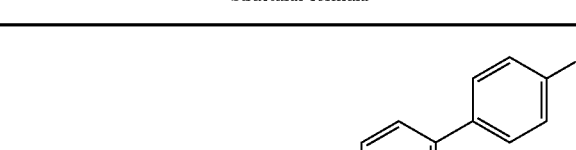 | (DMSO-d6-300) 1.46(dd, J=6.0, 9.0Hz, 1H), 1.88(dd, J=6.0, 9.0Hz, 1H), 2.64(t, J=9.0Hz, 1H), 3.64(s, 3H), 6.83(d, J=9.0Hz, 1H), 7.13(t, J=7.5Hz, 1H), 7.27(d, J=9.0Hz, 1H), 7.35(s, 1H), 7.57(d, J=9.0Hz, 2H), 7.78(d, J=9.0Hz, 2H), 7.87(s, 4H), 8.95(brs, 1H), 9.57(s, 1H), 12.11(brs, 1H) |
| 1-42 | | (DMSO-d6-300) 1.12-1.26(m, 2H), 1.34-1.39 (m, 2H), 1.40(s, 9H), 1.80-1.89(m, 2H)2.56(t, J=9.0, 1H), 2.80-2.96(m, 2H), 3.27-3.35(m, 1H), 3.81-3.89(m, 2H), 5.36-5.43 (m, 1H), 6.36-6.43 (m, 3H), 6.92 (t, J=7.5Hz, 1H), 7.58 (d, J=9.0Hz, 2H), 7.79 (d, J=9.0Hz, 2H), 7.86 (dJ=9.0Hz, 2H) 7.89 (d, J=9.0Hz, 2H)8.91 (s, 1H), 12.07(s, 1H) |

TABLE 1-9-continued
| Example | Structural formula | NMR |
|---|---|---|
| 1-43 | 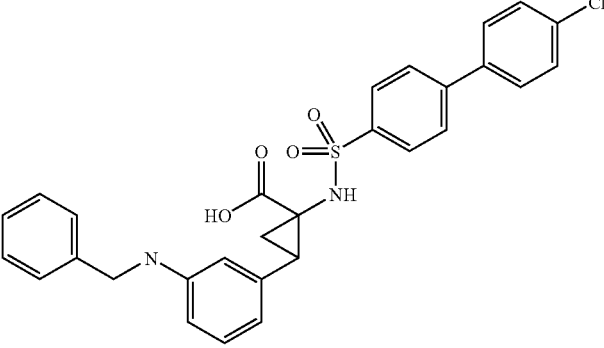 | (DMSO-d6-300) 1.35(dd, J=6.0, 9.0Hz, 1H), 1.83(dd, J=6.0, 9.0Hz, 1H), 2.53(t, J=9.0Hz, 1H), 4.20(d, J=3.0Hz, 2H), 6.12(t, J=6.0Hz, 1H), 6.37(t, J=6.0Hz, 2H), 6.49(s, 1H), 6.89(t, J=7.5Hz, 1H), 7.17-7.25(m, 1H), 7.26-7.36(m, 4H), 7.26-7.36(m, 4H), 7.57(d, J=9.0Hz, 2H), 7.78(d, J=9.0Hz, 2H), 8.90(brs, 1H), 12.07(brs, 1H) |
| 1-44 | 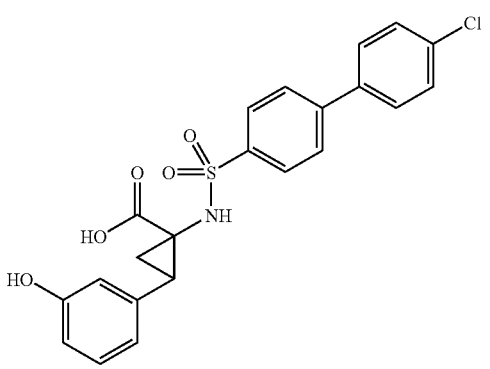 | (DMSO-d6-300) 1.42(dd, J=6.0, 9.0Hz, 1H), 1.87(dd, J=6.0, 9.0Hz, 1H), 2.59(t, J=9.0Hz, 1H), 6.57(d, J=9.0Hz, 1H), 6.63(m, 2H), 7.01(t, J=9.0Hz, 1H), 7.57(d, J=9.0Hz, 2H), 7.78(d, J=9.0Hz, 2H), 7.84-7.90(m, 4H) |
| 1-45 | 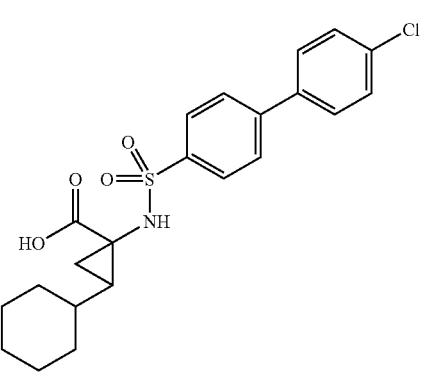 | (DMSO-d6-300) 0.94-1.29(m, 9H), 1.49-1.70(m, 5H), 7.54-7.61(m, 2H), 7.72-7.90(m, 6H), 8.53-8.74(m, 1H) |
TABLE 1-10
| Example | Structural formula | NMR |
|---|---|---|
| 1-46 | 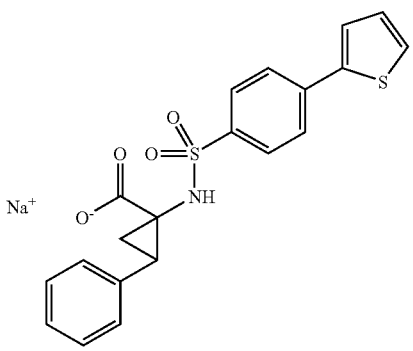 | (ACETONE-d6-500) 1.84-1.92(m, 1H), 2.13-2.20(m, 1H), 2.83-2.89(m, 1H), 7.13-7.30(m, 6H), 7.80-7.92(m, 1H), 8.03-8.08(m, 3H), 8.22-8.33(m, 3H) |

TABLE 1-10-continued
| Example | Structural formula | NMR |
|---|---|---|
| 1-47 | 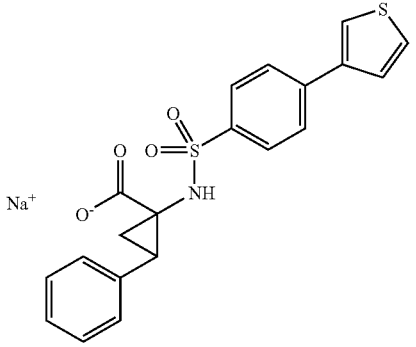 | (METHANOL-d4-400) 1.48-1.56(m, 1H), 1.83-1.90(m, 1H), 2.31-2.38(m, 1H), 7.02-7.08(m, 1H), 7.09-7.16(m, 3H), 7.18-7.22(m, 2H), 7.43-7.47(m, 1H), 7.49-7.52(m, 1H), 7.71-7.77(m, 2H), 7.71-7.77(m, 2H) |
| 1-48 | 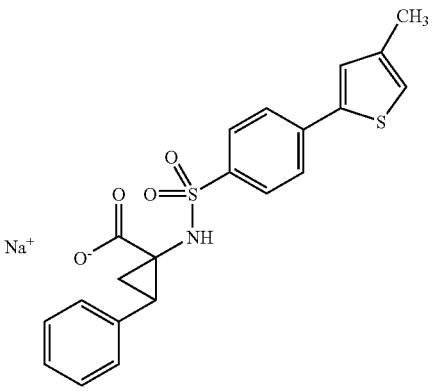 | (ACETONE-d6-400) 1.83-1.89(m, 1H), 1.96(s, 3H), 2.09-2.15(m, 1H), 2.82-2.89(m, 1H), 7.14-7.30(m, 6H), 7.45-7.48(m, 1H), 7.71-7.73(m, 1H), 7.78-7.83(m, 2H), 7.88-7.94(m, 2H) |
| 1-49 | 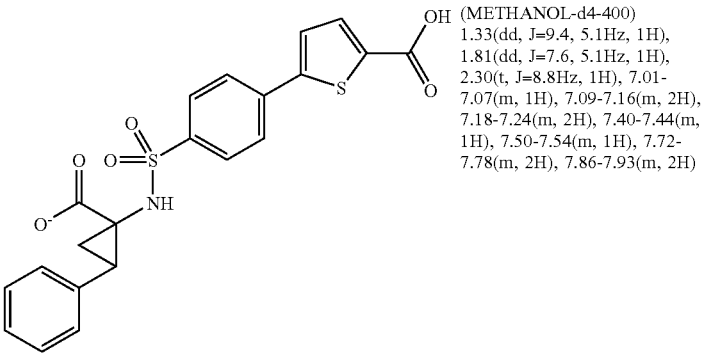 | (METHANOL-d4-400) 1.33(dd, J=9.4, 5.1Hz, 1H), 1.81(dd, J=7.6, 5.1Hz, 1H), 2.30(t, J=8.8Hz, 1H), 7.01-7.07(m, 1H), 7.09-7.16(m, 2H), 7.18-7.24(m, 2H), 7.40-7.44(m, 1H), 7.50-7.54(m, 1H), 7.72-7.78(m, 2H), 7.86-7.93(m, 2H) |
| 1-50 | 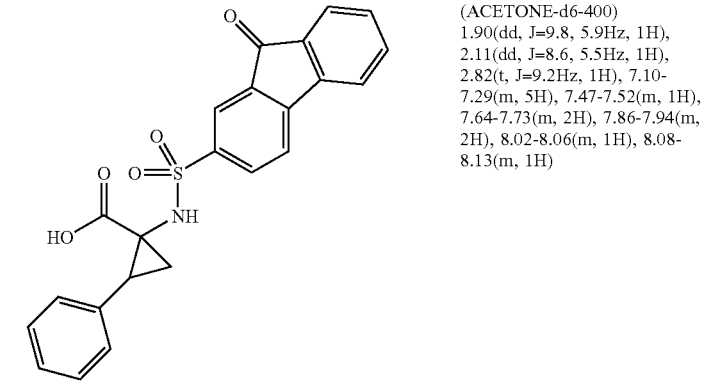 | (ACETONE-d6-400) 1.90(dd, J=9.8, 5.9Hz, 1H), 2.11(dd, J=8.6, 5.5Hz, 1H), 2.82(t, J=9.2Hz, 1H), 7.10-7.29(m, 5H), 7.47-7.52(m, 1H), 7.64-7.73(m, 2H), 7.86-7.94(m, 2H), 8.02-8.06(m, 1H), 8.08-8.13(m, 1H) |

TABLE 1-11
| Example | Structural formula | NMR |
|---------|-------------------|-----|
| 1-51 | 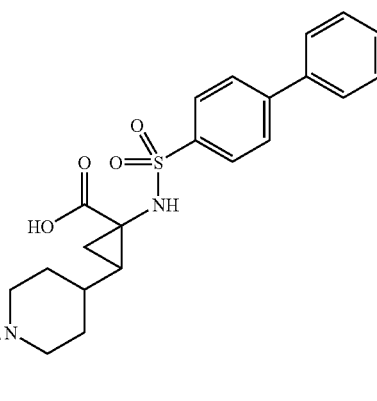 | (DMSO-d6-300)<br>0.99-1.64(m, 17H), 2.55-2.78(m, 2H), 3.76-3.98(m, 2H), 7.57(d, J=6.0Hz, 2H), 7.78(d, J=9.0Hz, 2H), 7.80(d, J=9.0Hz, 2H), 7.87(d, J=9.0Hz, 2H), 8.64(brs, 1H), 12.55(brs, 1H) |
| 1-52 | 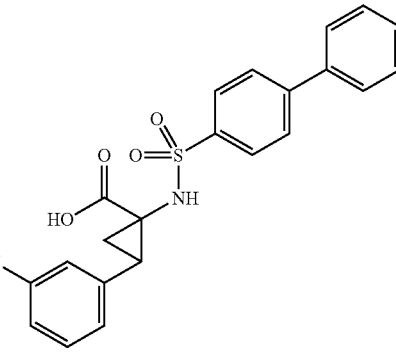 | (DMSO-d6-300)<br>1.45(dd, J=9.5, 4.9Hz, 1H), 1.77-1.85(m, 1H), 2.51-2.61(m, 1H), 6.79-6.86 (m, 2H), 7.00-7.09(m, 2H), 7.45-7.63(m, 6H), 7.68-7.81(m, 5H), 7.86(s, 4H) |
| 1-53 | 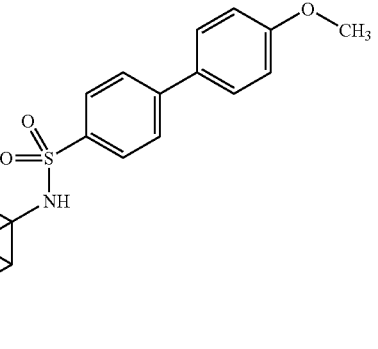 | (MeOH-d4-400)<br>1.83(dd, J=9.8, 5.5Hz, 1H), 2.09(dd, J=8.6, 5.9Hz, 1H), 2.77(t, J=9.2Hz, 1H), 3.83(s, 3H), 7.00-7.04(m, 2H), 7.14-7.28(m, 5H), 7.61-7.66(m, 2H), 7.73-7.77(m, 2H), 7.89-7.93(m, 2H) |
| 1-54 | 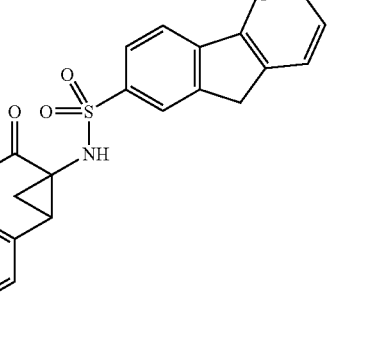 | (ACETONE-d6-400)<br>1.88(dd, J=9.8, 5.5Hz, 1H), 2.10(dd, J=8.6, 5.9Hz, 1H), 2.80(t, J=9.2Hz, 1H), 7.12-7.27(m, 5H), 7.38-7.48(m, 2H), 7.63-7.68(m, 1H), 7.69-7.83(m, 1H), 7.91-8.03(m, 3H), 8.08(s, 1H) |

TABLE 1-11-continued

| Example | Structural formula | NMR |
|---|---|---|
| 1-55 | | (ACETONE-d6-400) 1.83(dd, J=4.0, 8.0Hz, 1H), 2.11(dd, J=4.0, 8.0Hz, 1H), 2.68(s, 3H), 2.86(t, J=10.0Hz, 1H), 7.12-7.28(m, 5H), 8.04(d, J=8.0Hz, 2H), 8.19(d, J=8.0Hz, 2H) |

TABLE 1-12

| Example | Structural formula | NMR |
|---|---|---|
| 1-56 | | (ACETONE-d6-400) 1.85(dd, J=8.0, 12.0Hz, 1H), 2.08-2.13(m, 1H), 2.81(t, J=10.0Hz, 1H), 7.12-7.26(m, 5H), 7.64-7.77(m, 3H), 8.08(d, J=8.0Hz, 2H), 8.24(d, J=8.0Hz, 2H), 8.30(d, J=8.0Hz, 2H) |
| 1-57 | | (ACETONE-d6-400) 1.94(dd, J=4.0, 8.0Hz, 1H), 2.17(dd, J=4.0, 8.0Hz, 1H), 2.91(t, J=10.0Hz, 1H), 7.15-7.31(m, 5H), 7.38-7.49(m, 4H), 7.61(dd, J=1.0, 4.0Hz, 1H), 7.71(dt, J=8.0, 1.0Hz, 2H), 7.95(brs, 1H) |
| 1-58 | | (DMSO-d6-300) 1.85(dd, J=6.0, 9.0Hz, 1H), 1.96(dd, J=6.0, 9.0Hz, 1H), 2.77(t, J=9.0Hz, 1H), 6.61-6.71(m, 2H), 6.81(d, J=6.0Hz, 1H), 7.01-7.09(m, 1H), 7.58(d, J=9.0Hz, 2H), 7.71-7.90(m, 7H), 9.45(brs, 1H), 12.39(brs, 1H) |

TABLE 1-12-continued

| Example | Structural formula | NMR |
|---|---|---|
| 1-59 | | (ACETONE-d6-400) 1.86(dd, J=4.0, 8.0Hz, 1H), 2.05-2.09(m, 1H), 2.78(t, J=10.0Hz, 1H), 7.13-7.26(m, 5H), 7.62-7.68(m, 3H), 8.10(d, J=8.0Hz, 2H), 8.20(dd, J=4.0, 8.0Hz, 2H), 8.32(d, J=8.0Hz, 2H) |
| 1-60 | | (CDCL3-400) 2.13-2.22(m, 2H), 2.98(t, J=10.0Hz, 1H), 5.93(s, 1H), 6.94(d, J=4.0Hz, 1H), 7.17-7.22(m, 2H), 7.24-7.33(m, 3H), 7.36(d, J=4.0Hz, 1H) |

TABLE 1-13

| Example | Structural formula | NMR |
|---|---|---|
| 1-61 | | (DMSO-d6-300) 1.45(dd, J=5.2, 9.4Hz, 1H), 1.92(dd, J=5.2, 8.7Hz, 1H), 2.67(dd, J=8.7, 9.4Hz, 1H), 6.68-6.76(m, 2H), 6.82(d, J=8.3Hz, 1H), 7.12(t, J=7.9Hz, 1H), 7.42(s, 1H), 7.49-7.61(m, 2H), 7.57(d, J=8.7Hz, 2H), 7.78(d, J=8.7Hz, 2H), 7.88(s, 4H), 8.13(dd, J=1.1, 4.9Hz, 1H), 8.93(s, 1H), 8.96(s, 1H), 12.13(s, 1H) |
| 1-62 | | (DMSO-d6-300) 1.47-1.57(m, 1H), 1.83-1.95(m, 1H), 2.54-2.65(m, 1H), 6.96(d, J=9.0Hz, 1H), 7.19(t, J=7.5Hz), 1H), 7.55(d, J=9.0Hz, 2H), 7.64-7.73(m, 3H), 7.77(d, J=9.0Hz, 2H), 7.83-7.93(m, 4H), 8.07(t, J=7.5Hz, 1H), 8.15(d, J=9.0Hz, 1H), 8.70-8.74(m, 1H), 10.45(brs, 1H) |

TABLE 1-13-continued

| Example | Structural formula | NMR |
|---|---|---|
| 1-63 | | (DMSO-d6-300) 1.51(dd, J=6.0, 9.0Hz, 1H), 1.95(dd, J=6.0, 9.0Hz, 1H), 2.73(t, J=9.0Hz, 1H), 6.99(d, J=9.0Hz, 1H), 7.25(t, J=7.5Hz, 1H), 7.57(d, J=9.0Hz, 2H), 7.59(t, J=9.0Hz, 1H), 7.70(s, 1H), 7.78(d, J=9.0Hz, 2H), 7.84(d, J=6.0Hz, 2H), 7.86-7.91(m, 4H), 8.78(d, J=6.0Hz, 2H), 8.99(s, 1H), 10.46(s, 1H), 12.16(brs, 1H) |
| 1-64 | | (DMSO-d6-400) 1.51(dd, J=9.5, 4.6Hz, 1H), 1.89-1.95(m, 1H), 2.60-2.72(m, 1H), 6.95(d, J=8.3Hz, 1H), 7.21(t, J=8.3Hz, 1H), 7.49-7.78(m, 8H), 7.87(s, 4H), 8.24-8.28(m, 1H), 8.74(dd, J=4.9, 1.6Hz, 1H), 9.07(d, J=1.9Hz, 1H), 10.39(s, 1H) |
| 1-65 | | (DMSO-d6-300) 1.42(dd, J=5.4, 9.3Hz, 1H), 1.92(t, J=7.4Hz, 1H), 2.63(t, J=9.4Hz, 1H), 5.22(s, 2H), 7.10-7.29(m, 7H), 7.49(dd, J=2.1, 8.1Hz, 1H), 7.64(d, J=8.1Hz, 1H), 7.71(d, J=2.1Hz, 1H), 7.74(d, J=9.0Hz, 2H), 8.71(brs, 1H), 12.07(brs, 1H) |

TABLE 1-14

| Example | Structural formula | NMR |
|---|---|---|
| 1-66 | | (DMSO-d6-300) 1.41-1.50(m, 1H), 1.88-1.97(m, 1H), 2.64(t, J=9.0Hz, 1H), 3.64(br, 2H), 3.86(br, 2H), 4.78(br, 1H), 6.71-6.80(m, 3H), 7.14(t, J=7.5Hz, 1H), 7.57(d, J=6.0Hz, 2H), 7.78(d, J=6.0Hz, 2H), 7.83(br, 4H), 8.81(br, 1H) |

TABLE 1-14-continued

| Example | Structural formula | NMR |
|---|---|---|
| 1-67 | | (DMSO-d6-300) 1.39-1.55(m, 1H), 1.86-1.96(m, 1H), 2.26(s, 6H), 2.58-2.68(m, 1H), 3.03(s, 2H), 6.85-6.90(m, 1H), 7.15(t, J=7.5Hz, 1H), 7.45-7.72(m, 5H), 7.75-7.81(m, 2H), 7.87(s, 4H), 9.60(s, 1H) |
| 1-68 | | (DMSO-d6-300) 1.51-1.59(m, 1H), 1.70-1.79(m, 1H), 2.39-2.52(m, 1H), 6.75-6.88(m, 2H), 6.99(d, J=9.0Hz, 1H), 7.20(t, J=9.0Hz, 1H),nl 7.31-7.40(m, 2H), 7.55(d, J=6.0Hz, 2H), 7.75(d, J=6.0Hz, 2H), 7.83(d, J=9.0Hz, 2H), 7.89(d, J=9.0Hz, 2H), 8.28-8.32(m, 2H) |
| 1-69 | | (ACETONE-d6-400) 1.96(dd, J=4.0, 8.0Hz, 1H), 2.19(dd, J=4.0, 8.0Hz, 1H), 2.92(t, J=8.0Hz, 1H), 7.15-7.33(m, 5H), 7.47-7.54(m, 3H), 7.62(d, J=4.0Hz, 1H), 7.74(d, J=8.0Hz, 2H), 8.00(s, 1H) |
| 1-70 | | (ACETONE-d6-400) 1.95(dd, J=8.0, 12.0Hz, 1H), 2.17(dd, J=8.0, 12.0Hz, 1H), 2.91(t, J=10.0Hz, 1H), 3.85(s, 3H), 7.02(d, J=8.0Hz, 2H), 7.15-7.34(m, 6H), 7.57(d, J=4.0Hz, 1H), 7.64(d, J=8.0Hz, 2H), 7.86(s, 1H) |

TABLE 1-15

| Example | Structural formula | NMR |
|---|---|---|
| 1-71 | | (ACETONE-d6-400) 1.95(dd, J=8.0, 8.0Hz, 1H), 2.18(dd, J=8.0, 8.0Hz, 1H), 2.93(t, J=10.0Hz, 1H), 3.17(s, 6H), 7.15-7.33(m, 5H), 7.53(d, J=4.0Hz, 1H), 7.63(d, J=8.0Hz, 1H), 7.87(d, J=12.0Hz, 2H), 7.92(d, J=8.0Hz, 2H) |
| 1-72 | | (DMSO-d6-300) 1.50(dd, J=6.0, 9.0Hz, 1H), 1.96(dd, J=6.0, 9.0Hz, 1H), 2.68(t, J=9.0Hz, 1H), 4.05(s, 2H), 7.11-7.29(m, 5H), 7.64(dd, J=3.0, 9.0Hz, 1H), 7.83(dd, J=3.0, 9.0Hz, 1H), 7.87(d, J=3.0Hz, 1H), 7.98(d, J=9.0Hz, 1H), 8.00(d, J=3.0Hz, 1H), 8.10(d, J=6.0Hz, 1H), 8.88(brs, 1H), 12.04(brs, 1H) |
| 1-73 | | (DMSO-d6-300) 1.47(dd, J=6.0, 9.0Hz, 1H), 1.72(br, 4H), 1.95(dd, J=6.0, 9.0Hz, 1H), 2.65(t, J=9.0Hz, 1H), 2.76(br, 4H), 3.01(br, 2H), 4.08(t, J=4.5Hz, 2H), 6.74-6.85(m, 3H), 7.16(t, J=7.5Hz, 1H), 7.57(d, J=9.0Hz, 2H), 7.78(d, J=9.0Hz, 2H), 7.85(br, 4H), 8.83(br, 1H) |
| 1-74 | | (DMSO-d6-300) 1.58-1.71(m, 2H), 2.26(t, J=9.0Hz, 1H), 2.41(t, J=6.0Hz, 4H), 2.57(t, J=6.0Hz, 2H), 3.55(t, J=4.5Hz, 4H), 3.91(t, J=6.0Hz, 2H), 6.97(t, J=9.0Hz, 1H), 7.57(d, J=9.0Hz, 2H), 7.75-7.93(m, 7H) |

TABLE 1-15-continued
| Example | Structural formula | NMR |
|---|---|---|
| 1-75 | 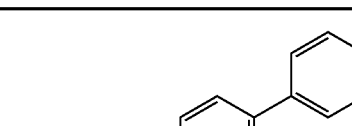 | (DMSO-d6-300) 1.54(dd, J=6.0, 9.0Hz, 1H), 1.77-1.87(m, 1H), 4.23(t, J=4.5Hz, 2H), 4.44(t, J=4.5Hz, 2H), 6.22(t, J=3.0Hz, 1H), 6.63-6.76(m, 3H), 7.07(t, J=7.5Hz, 1H), 7.44(dd, J=0.0, 0.0Hz, 1H), 7.56(d, J=9.0Hz, 2H), 7.74(d, J=3.0Hz, 1H), 7.77(d, J=9.0Hz, 2H), 7.81-7.89(m, 4H) |
TABLE 1-16
| Example | Structural formula | NMR |
|---|---|---|
| 1-76 | | (DMSO-d6-300) 1.47(dd, J=6.0, 9.0Hz, 1H), 1.97(dd, J=6.0, 9.0Hz, 1H), 2.68(t, J=9.0Hz, 1H), 5.15(s, 2H), 6.82-6.91(m, 3H), 7.19(t, J=9.0Hz, 1.H), 7.57(d, J=9.0Hz, 2H), 7.66(dd, J=6.0, 9.0Hz, 1H), 7.78(d, J=9.0Hz, 2H), 7.85-7.92(m, 4H), 8.12(d, J=9.0Hz, 1H), 8.67(d, J=6.0Hz, 1H), 8.78(s, 1H), 8.94(s, 1H), 11.91-12.38(m, 1H) |
| 1-77 | | (DMSO-d6-400) 1.44(dd, J=9.8, 5.2Hz, 1H), 1.87(dd, J=8.2, 5.5Hz, 1H), 2.28(s, 3H), 2.48-2.58(m, 3H), 2.69-2.73(m, 2H), 3.36(s, 2H), 6.75-6.79(m, 1H), 6.91(s, 2H), 7.53-7.58(m, 2H), 7.71-7.80(m, 3H), 7.85(s, 4H) |
| 1-78 | | (DMSO-d6-400) 0.99(d, J=6.5Hz, 6H), 1.45(dd, J=10.0, 5.1Hz, 1H), 1.78-1.84(m, 1H), 2.45-2.49(m, 1H), 2.57-2.69(m, 4H), 2.72-2.83(m, 1H), 3.46(s, 2H), 6.64-6.72(m, 1H), 6.86(s, 2H), 7.52-7.58(m, 2H), 7.71-7.79(m, 3H), 7.85(s, 4H) |

TABLE 1-16-continued

| Example | Structural formula | NMR |
|---|---|---|
| 1-79 | | (DMSO-d6-400) 1.47(dd, J=9.8, 4.7Hz, 1H), 1.72-1.78(m, 1H), 2.37-2.44(m, 1H), 2.56-2.62(m, 2H), 2.67-2.72(m, 2H), 3.36(s, 2H), 3.56(s, 2H), 6.60-6.64(m, 1H), 6.85(s, 2H), 7.21-7.27(m, 1H), 7.29-7.33(m, 4H), 7.53-7.58 (m, 2H), 7.73-7.77(m, 2H), 7.80-7.87(m, 5H) |
| 1-80 | | (ACETONE-d4-400) 1.87(dd, J=5.9, 9.8Hz, 1H), 2.11(dd, J=5.9, 8.7Hz, 1H), 2.82(dd, J=8.7, 9.8Hz, 1H), 4.05(s, 2H), 7.11-7.28(m, 6H), 7.41-7.47(m, 1H), 7.65-7.74(brs, 1H), 7.90-7.94(m, 1H), 7.98-8.03(m, 2H), 8.06-8.09(m, 1H) |

TABLE 1-17

| Example | Structural formula | NMR |
|---|---|---|
| 1-81 | | (ACETONE-d4-400) 2.01-2.06(m, 1H), 2.21(dd, J=5.9, 7.9Hz, 1H), 2.72(dd, J=7.9, 9.4Hz, 1H), 4.06(s, 2H), 6.85(s, 1H), 7.14-7.20(m, 2H), 7.20-7.30(m, 4H), 7.46(d, J=9.0Hz, 1H), 7.85(d, J=8.2Hz, 1H), 7.96(s, 1H), 8.00(d, J=8.2Hz, 1H), 8.03(dd, J=8.6, 5.5Hz, 1H) |
| 1-82 | | (METHANOL-d4-400) 1.42(t, J=7.5Hz, 3H), 1.76-1.88(m, 1H), 2.00-2.14(m, 1H), 2.66-2.77(m, 1H), 3.09(q, J=7.5Hz, 2H), 7.10-7.30(m, 5H), 7.85(s, 1H), 7.93(d, J=7.9Hz, 2H), 8.07(d, J=7.9Hz, 2H) |

TABLE 1-17-continued

| Example | Structural formula | NMR |
|---------|---|---|
| 1-83 | | (DMSO-d6-300) 1.46(dd, J=6.0, 12.0Hz, 1H), 1.95(dd, J=6.0, 9.0Hz, 1H), 2.66(t, J=7.5Hz, 1H), 4.21(t, J=6.0Hz, 2H), 4.41(t, J=6.0Hz, 2H), 6.72-6.84(m, 3H), 7.10-7.19(m, 2H), 7.39(s, 1H), 7.57(d, J=9.0Hz, 2H), 7.78(d, J=9.0Hz, 2H), 7.82-7.91(m, 4H), 8.13(s, 1H), 8.91(s, 1H) |
| 1-84 | | (DMSO-d6-300) 1.62-1.76(m, 1H), 1.93-2.05(m, 1H), 2.62-2.74(m, 1H), 5.16(s, 2H), 6.79(t, J=7.5Hz, 1H), 6.86(d, J=9.0Hz, 1H), 7.02-7.14(m, 2H), 7.24-7.39(m, 3H), 7.47-7.61(m, 6H), 7.76(d, J=9.0Hz, 2H), 8.91(brs, 1H), 12.17(brs, 1H) |
| 1-85 | | (ACETONE-d6-300) 1.94(dd, J=6.0, 9.0Hz, 1H), 2.16(dd, J=6.0, 9.0Hz, 1H), 2.91(t, J=10.5Hz, 1H), 7.15-7.31(m, 5H), 7.44-7.52(m, 3H), 7.61(d, J=3.0Hz, 1H), 7.74(d, J=9.0Hz, 2H), 7.95(brs, 1H) |

TABLE 1-18

| Example | Structural formula | NMR |
|---------|---|---|
| 1-86 | | (DMSO-d6-300) 1.71(dd, J=6.0, 9.0Hz, 1H), 1.78(dd, J=6.0, 9.0Hz, 1H), 2.27(t, J=9.0Hz, 1H), 3.64(t, J=6.0Hz, 2H), 3.86(t, J=6.0Hz, 2H), 6.61(dd, J=3.0, 9.0Hz, 1H), 6.69-6.73 (m, 2H), 7.00(t, J=9.0Hz, 1H), 7.52(d, J=9.0Hz, 2H), 7.55(d, J=6.0Hz), 1H), 7.59(d, J=6.0Hz, 1H) |

TABLE 1-18-continued
| Example | Structural formula | NMR |
|---|---|---|
| 1-87 | 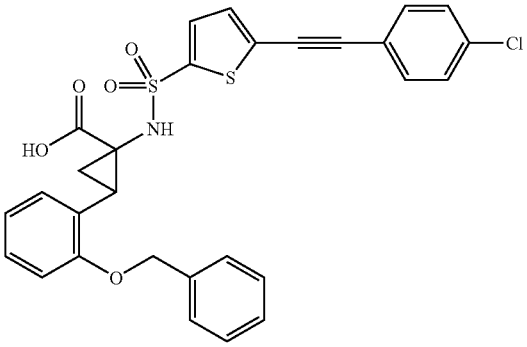 | (DMSO-d6-300) 0.82(dd, J=3.0, 9.0Hz, 1H), 0.99(dd, J=6.0, 9.0Hz, 1H), 2.70(t, J=10.5Hz, 1H), 5.17(s, 2H), 6.76-6.89(m, 2H), 7.02-7.14(m, 2H), 7.26-7.41(m, 3H), 7.43-7.58(m, 6H), 7.60-7.67(m, 2H), 8.98(br, 1H), 11.96(br, 1H) |
| 1-88 | 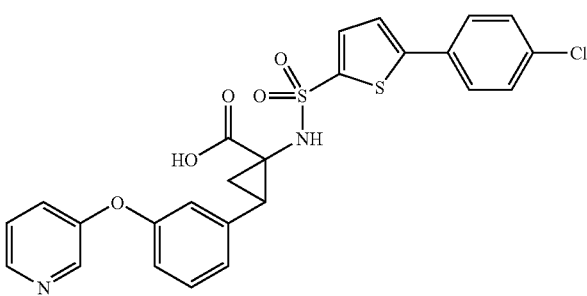 | (DMSO-d6-300) 1.63(dd, J=6.0, 9.0Hz, 1H), 2.02(dd, J=6.0, 9.0Hz, 1H), 2.77(t, J=9.0Hz, 1H), 6.88-6.96(m, 2H), 7.08(d, J=6.0Hz, 1H), 7.28-7.44(m, 3H), 7.49-7.59(m, 4H), 7.75(d, J=9.0Hz, 2H), 8.31-8.37(m, 2H), 9.16(s, 1H), 12.33(brs, 1H) |
| 1-89 | 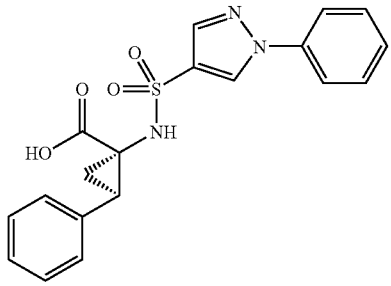 | (DMSO-d6-300) 1.71(dd, J=6.0, 9.0Hz, 1H), 1.99(dd, J=6.0, 9.0Hz, 1H), 2.70(t, J=9.0Hz, 1H), 7.11-7.27(m, 5H), 7.40(t, J=7.5Hz, 1H), 7.54(t, J=7.5Hz, 2H), 7.90(d, J=6.0Hz, 2H), 7.99(s, 1H), 8.97(s, 1H), 12.01(br, 1H) |
| 1-90 | 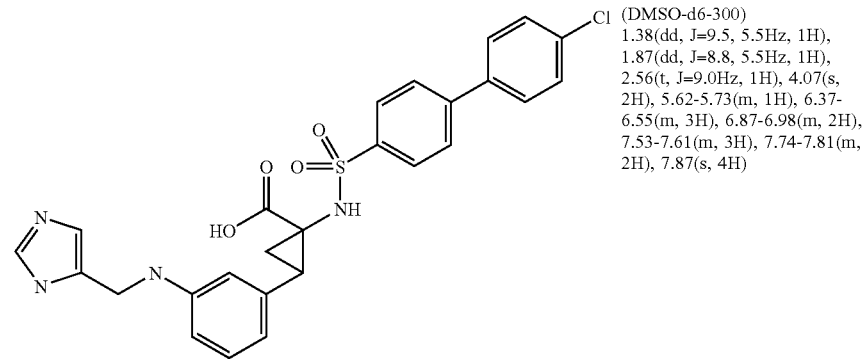 | (DMSO-d6-300) 1.38(dd, J=9.5, 5.5Hz, 1H), 1.87(dd, J=8.8, 5.5Hz, 1H), 2.56(t, J=9.0Hz, 1H), 4.07(s, 2H), 5.62-5.73(m, 1H), 6.37-6.55(m, 3H), 6.87-6.98(m, 2H), 7.53-7.61(m, 3H), 7.74-7.81(m, 2H), 7.87(s, 4H) |

TABLE 1-19

| Example | Structural formula | NMR |
|---|---|---|
| 1-91 | | (DMSO-d6-300) 1.50(dd, J=6.0, 9.0Hz, 1H), 1.96(dd, J=6.0, 9.0Hz, 1H), 2.68(t, J=9.0Hz, 1H), 4.05(s, 2H), 7.13-7.28 (m, 5H), 7.64(dd, J=3.0, 9.0Hz, 1H), 7.83(dd, J=3.0, 9.0Hz, 1H), 7.87(d, J=0.0Hz, 1H), 7.98(d, J=9.0Hz, 1H), 8.00(d, J=0.0Hz, 1H), 8.10(d, J=9.0Hz, 1H), 8.83(brs, 1H), 11.98(brs, 1H) |
| 1-92 | | (METHANOL-d4-400) 1.81(dd, J=5.5, 9.8Hz, 1H), 2.03-2.09(m, 1H), 2.72(dd, J=9.0, 9.8Hz, 1H), 2.75(s, 3H), 7.10-7.28(m, 5H), 7.83(s, 1H), 7.92(d, J=8.6Hz, 2H), 8.05(d, J=8.7Hz, 2H) |
| 1-93 | | (METHANOL-d4-400) 1.44(d, J=6.7Hz, 3H), 1.72(dd, J=5.1, 9.4Hz, 1H), 1.99-2.06(m, 1H), 2.67(dd, J=9.0, 9.4Hz, 1H), 4.82-4.94(m, 1H), 7.10-7.25(m, 5H), 7.53(d, J=8.3Hz, 2H), 7.85(d, J=8.2Hz, 2H) |
| 1-94 | | (ACETONE-d4-400) 1.88(dd, J=5.9, 9.8Hz, 1H), 2.12(dd, J=5.9, 8.6Hz, 1H), 2.84(dd, J=8.6, 9.8Hz, 1H), 4.04(s, 2H), 7.12-7.29(m, 5H), 7.47(d, J=8.2Hz, 1H), 7.67(s, 1H), 7.94(d, J=8.2Hz, 1H), 7.97(d, J=8.2Hz, 1H), 8.02(d, J=8.2Hz, 1H), 8.09(s, 1H) |

TABLE 1-19-continued

| Example | Structural formula | NMR |
|---------|--------------------|-----|
| 1-95 | | (ACETONE-d6-400) 0.93(dd, J=4.0, 8.0Hz, 1H), 1.07(dd, J=4.0, 8.0Hz, 1H), 2.90(t, J=8.0Hz, 1H), 7.13-7.30(m, 5H), 7.78(t, J=8.0Hz, 1H), 7.88(br, 1H), 7.94(d, J=12.0Hz, 1H), 8.06-8.11(m, 1H), 8.32(d, J=12.0Hz, 1H), 8.39-8.41(m, 1H), 8.67-8.68(m, 1H) |

TABLE 1-20

| Example | Structural formula | NMR |
|---------|--------------------|-----|
| 1-96 | | (ACETONE-d6-400) 2.08-2.09(m, 1H), 1.11(dd, J=4.0, 8.0Hz, 1H), 2.74(t, J=8.0Hz, 1H), 4.12(s, 2H), 6.93(br, 1H), 7.16-7.18(m, 2H), 7.24-7.29(m, 3H), 7.42-7.50(m, 2H), 7.66(brd, J=8.0Hz, 1H), 7.91(brd, J=8.0Hz, 1H), 8.00(br, 1H), 8.53(d, J=8.0Hz, 1H) |
| 1-97 | | (DMSO-d6-300) 1.69(dd, J=6.0, 9.0Hz, 1H), 2.01(dd, J=6.0, 9.0Hz, 1H), 2.74(t, J=9.0Hz, 1H), 7.16-7.28(m, 5H), 7.60(d, J=9.0Hz, 2H), 7.95(d, J=9.0Hz, 2H), 8.01(s, 1H), 9.02(s, 1H), 12.13(br, 1H) |
| 1-98 | | (DMSO-d6-300) 1.65(dd, J=6.0, 9.0Hz, 1H), 1.99 (dd, J=6.0, 9.0Hz, 1H), 2.09 (s, 6H), 2.69(t, J=9.0Hz, 1H), 3.30(s, 2H), 7.04-7.21(m, 4H), 7.50-7.59(m, 4H), 7.76(d, J=9.0Hz, 2H) |

TABLE 1-20-continued
| Example | Structural formula | NMR |
|---|---|---|
| 1-99 | 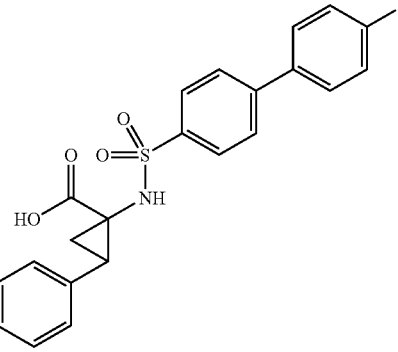 | (DMSO-d6-300)<br>1.30-1.48(m, 3H), 1.81-1.93(m, 3H), 2.28(s, 3H), 2.17-2.32(m, 1H), 2.46-2.59(m, 1H), 2.78-2.92(m, 2H), 3.08-3.25(m, 2H), 5.34(brs, 1H), 6.32-6.45(m, 3H), 6.90(t, J=9.0Hz, 1H), 7.57(d, J=9.0Hz, 2H), 7.78(d, J=9.0Hz, 2H), 7.82-7.91(m, 4H), 8.83(brs, 1H) |
| 1-100 | 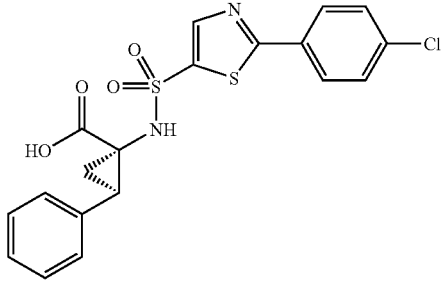 | (DMSO-d6-300)<br>1.70(dd, J=5.6, 9.8Hz, 1H), 2.07(dd, J=5.6, 8.7Hz, 1H), 2.81(dd, J=8.7, 9.8Hz, 1H), 7.14-7.30(m, 5H), 7.62(d, J=8.7Hz, 2H), 8.03(d, J=9.1Hz, 2H), 8.27(s, 1H), 9.49(s, 1H), 12.27(s, 1H) |
TABLE 1-21
| Example | Structural formula | NMR |
|---|---|---|
| 1-101 | 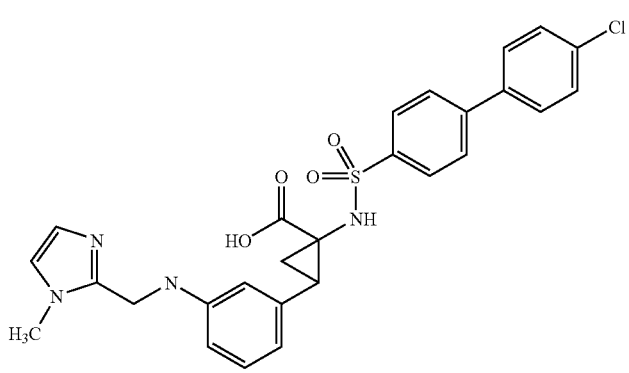 | (DMSO-d6-300)<br>1.42(dd, J=10.3, 5.5Hz, 1H), 1.83(dd, J=8.4, 5.2Hz, 1H), 2.45-2.54(m, 1H), 3.60(s, 3H), 4.20(d, J=4.4Hz, 2H), 5.82-5.90(m, 1H), 6.42(d, J=7.7Hz, 1H), 6.51-6.59(m, 2H), 6.78(s, 1H), 6.91(t, J=7.3Hz, 1H), 7.05(s, 1H), 7.57(d, J=8.4Hz, 2H), 7.78(d, J=8.4Hz, 2H), 7.87(s, 4H) |
| 1-102 | 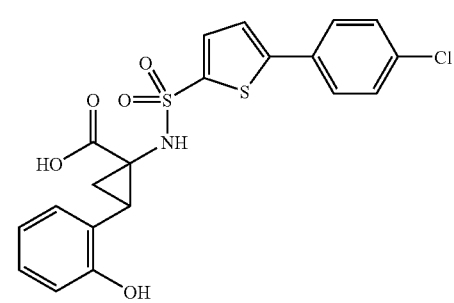 | (DMSO-d6-300)<br>0.81(dd, J=6.0, 9.0Hz, 1H), 0.98(dd, J=6.0, 9.0Hz, 1H), 2.60(t, J=9.0Hz, 1H), 6.62-6.76(m, 2H), 6.93-7.05(m, 2H), 7.49-7.61(m, 4H), 7.72-7.80(m, 2H), 8.99(br, 1H), 9.16(br, 1H), 11.92(br, 1H) |

TABLE 1-21-continued

| Example | Structural formula | NMR |
|---|---|---|
| 1-103 | | (DMSO-d6-300) 1.65(dd, J=6.0, 9.0Hz, 1H), 1.97(dd, J=6.0, 9.0Hz, 1H), 2.13(s, 3H), 223-2.36(m, 8H), 2.66(t, J=9.0Hz, 1H), 7.04-7.21(m, 4H), 7.49-7.59(m, 4H), 7.76(d, J=9.0Hz, 2H) |
| 1-104 | | (DMSO-d6-300) 1.01-1.50(m, 4H), 1.62(dd, J=6.0, 9.0Hz, 1H), 1.85-1.92(m, 1H), 2.14(s, 3H), 2.23-2.31(m, 2H), 2.37(s, 3H), 2.81-2.96(m, 3H), 7.05-7.19(m, 4H), 7.48-7.57(m, 4H), 7.73(d, J=9.0Hz, 2H) |
| 1-105 | | (METHANOL-d4-300) 1.85(dd, J=6.0, 9.0Hz, 1H), 2.06(dd, J=6.0, 9.0Hz, 1H), 2.73(t, J=9.0Hz, 1H), 4.07(s, 2H), 7.03(d, J=9.0Hz, 1H), 7.17(t, J=9.0Hz, 1H), 7.42-7.50(m, 4H), 7.67(d, J=9.0Hz, 2H), 7.78(d, J=9.0Hz, 2H), 7.96(d, J=9.0Hz, 2H) |

TABLE 1-22

| Example | Structural formula | NMR |
|---|---|---|
| 1-106 | | (DMSO-d6-300) 1.62(dd, J=6.0, 12.0Hz, 1H), 1.98(dd, J=6.0, 9.0Hz, 1H), 2.26(s, 3H), 2.67(t, J=9.0Hz, 1H), 7.14-7.27(m, 5H), 7.47(s, 1H), 7.54(d, J=9.0Hz, 2H), 7.55(d, J=9.0Hz, 2H) |

TABLE 1-22-continued

| Example | Structural formula | NMR |
|---|---|---|
| 1-107 | | (DMSO-d6-300) 1.60(dd, J=6.0, 12.0Hz, 1H), 2.01(dd, J=6.0, 9.0Hz, 1H), 2.74(t, J=9.0Hz, 1H), 5.18(s, 2H), 6.85-6.92(m, 3H), 7.21(t, J=7.5Hz, 1H), 7.53(d, J=9.0Hz, 2H), 7.56(d, J=6.0Hz, 1H), 7.58(d, J=6.0Hz, 1H), 7.68-7.75(m, 1H), 7.76(d, J=9.0Hz, 2H), 8.17-8.21(m, 1H), 8.70(d, J=6.0Hz, 1H), 8.81(s, 1H), 9.18(s, 1H), 12.20(brs, 1H) |
| 1-108 | | (DMSO-d6-300) 1.59(dd, J=6.0, 12.0Hz, 1H), 2.00(dd, J=6.0, 9.0Hz, 1H), 2.73(t, J=9.0Hz, 1H), 5.11(s, 2H), 6.82-6.88(m, 2H), 6.89(s, 1H), 7.18(t, J=7.5Hz, 1H), 7.34(dd, J=6.0, 9.0Hz, 1H), 7.49(d, J=6.0Hz, 2H), 7.53(t, J=3.0Hz, 1H), 7.56(d, J=3.0Hz, 1H), 7.58(d, J=3.0Hz, 1H), 7.76(d, J=9.0Hz, 2H), 7.82(dt, J=3.0, 9.0Hz, 1H), 7.55-7.59(m, 1H), 9.17(s, 1H), 12.23(brs, 1H) |
| 1-109 | | (DMSO-d6-300) 1.50(dd, J=5.7, 9.8Hz, 1H), 1.96(dd, J=5.7, 8.3Hz, 1H), 2.68(dd, J=8.3, 9.8Hz, 1H), 4.05(s, 2H), 7.12-7.28(m, 5H), 7.64(dd, J=1.5, 8.3Hz, 1H), 7.83(dd, J=1.5, 8.3Hz, 1H), 7.87(d, J=1.5Hz, 1H), 7.98(d, J=8.3Hz, 1H), 8.00(d, J=1.5Hz, 1H), 8.10(d, J=8.3Hz, 1H), 8.88(s, 1H), 12.05(s, 1H) |
| 1-110 | | (DMSO-d6-300) 1.62(dd, J=5.7, 9.8Hz, 1H), 2.04(dd, J=5.7, 8.7Hz, 1H), 2.76(dd, J=8.7, 9.8Hz, 1H), 7.15-7.30(m, 5H), 7.43-7.53(m, 2H), 7.57(d, J=3.8Hz, 1H), 7.65(d, J=3.7Hz, 1H), 7.68(ddd, J=1.8, 2.7, 6.4Hz, 1H), 7.81-7.84(m, 1H), 9.21(s, 1H), 12.20(s, 1H) |

TABLE 1-23

| Example | Structural formula | NMR |
|---|---|---|
| 1-111 | | (DMSO-d6-300) 1.49(dd, J=9.5, 5.5Hz, 1H), 1.73(dd, J=8.2, 4.9Hz, 1H), 2.39(t, J=9.2Hz, 1H), 6.69-6.79(m, 3H), 6.91-6.99(m, 2H), 7.50(dd, J=8.1, 4.8Hz, 1H), 7.56(d, J=8.4Hz, 2H), 7.78(d, J=8.4Hz, 2H), 7.81-7.91(m, 4H), 8.00-8.08(m, 1H), 8.65-8.70(m, 1H), 8.85(d, J=2.2Hz, 1H) |
| 1-112 | | (DMSO-d6-300) 1.37(dd, J=9.9, 5.5Hz, 1H), 1.86(dd, J=8.1, 5.6Hz, 1H), 2.56(t, J=9.5Hz, 1H), 4.18 (d, J=4.4Hz, 2H), 5.86-5.93(m, 1H), 6.40-6.55 (m, 2H), 6.89-6.96 (m, 3H), 7.53-7.61(m, 2H), 7.74-7.82 (m, 2H), 7.87 (s, 4H) |
| 1-113 | | (DMSO-d6-300) 1.69(dd, J=6.0, 9.0Hz, 1H), 2.06(dd, J=6.0, 9.0Hz, 1H), 2.81(t, J=9.0Hz, 1H), 7.34-7.47(m, 2H), 7.49-7.59(m, 4H), 7.72-7.80(m, 3H), 7.86(s, 1H) |
| 1-114 | | (DMSO-d6-300) 1.46(dd, J=3.0, 9.0Hz, 1H), 1.93(dd, J=6.0, 9.0Hz, 1H), 2.63(t, J=9.0Hz, 1H), 2.83(s, 3H), 2.98(s, 3H), 4.70(s, 2H), 6.68-6.83(m, 3H), 7.13(t, J=9.0Hz, 1H), 7.57(d, J=9.0Hz, 2H), 7.78(d, J=9.0Hz, 2H), 7.83-7.91(m, 4H), 8.89(brs, 1H), 12.16(brs, 1H) |

TABLE 1-23-continued
| Example | Structural formula | NMR |
|---|---|---|
| 1-115 | 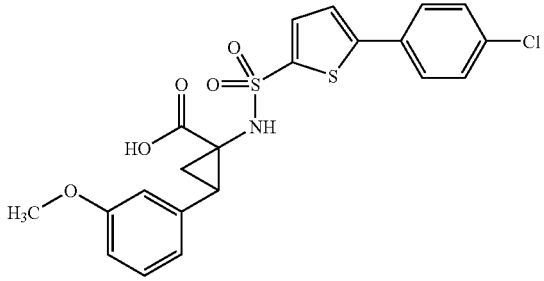 | (DMSO-d6-300) 1.66-1.74(m, 1H), 1.78-1.87(m, 1H), 2.34-2.45(m, 1H), 3.66(s, 3H), 6.63-6.77(m, 3H), 7.03-7.10(m, 1H), 7.52(d, J=9.0Hz, 2H), 7.54-7.59(m, 2H), 7.75(d, J=9.0Hz, 2H) |
TABLE 1-24
| Example | Structural formula | NMR |
|---|---|---|
| 1-116 | 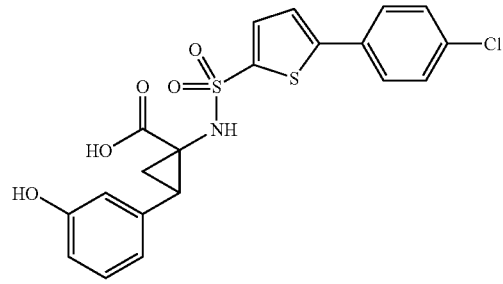 | (DMSO-d6-300) 1.55-1.61(m, 1H) 1.85-1.93(m, 1H), 2.58(t, J=9.0Hz, 1H), 6.53-6.65(m, 3H), 7.00(t, J=7.5Hz, 1H), 7.51-7.58(m, 4H), 7.75(d, J=6.0Hz, 1H) |
| 1-117 | 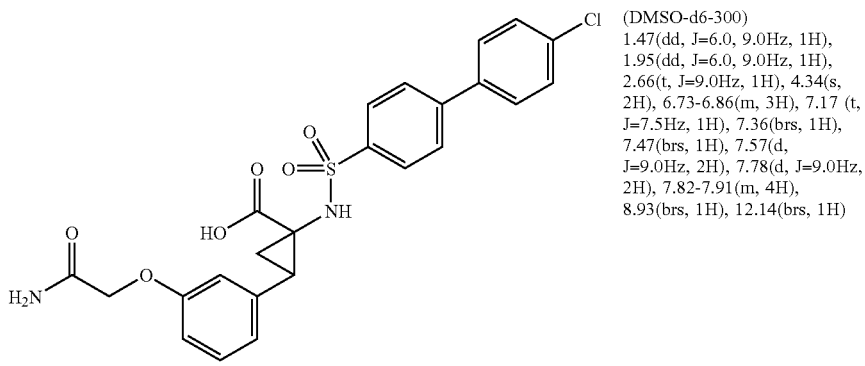 | (DMSO-d6-300) 1.47(dd, J=6.0, 9.0Hz, 1H), 1.95(dd, J=6.0, 9.0Hz, 1H), 2.66(t, J=9.0Hz, 1H), 4.34(s, 2H), 6.73-6.86(m, 3H), 7.17 (t, J=7.5Hz, 1H), 7.36(brs, 1H), 7.47(brs, 1H), 7.57(d, J=9.0Hz, 2H), 7.78(d, J=9.0Hz, 2H), 7.82-7.91(m, 4H), 8.93(brs, 1H), 12.14(brs, 1H) |
| 1-118 | 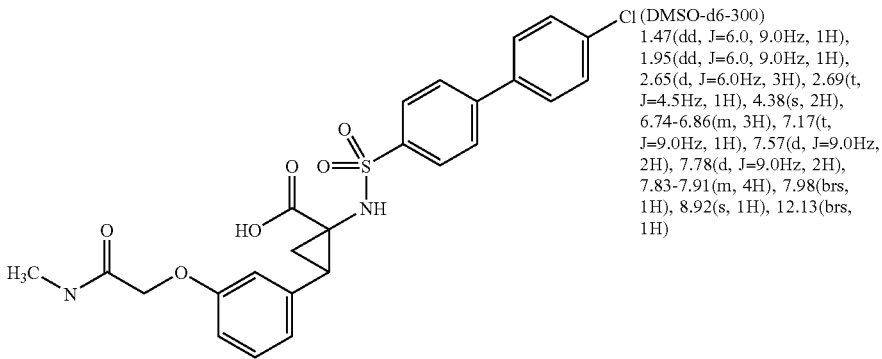 | (DMSO-d6-300) 1.47(dd, J=6.0, 9.0Hz, 1H), 1.95(dd, J=6.0, 9.0Hz, 1H), 2.65(d, J=6.0Hz, 3H), 2.69(t, J=4.5Hz, 1H), 4.38(s, 2H), 6.74-6.86(m, 3H), 7.17(t, J=9.0Hz, 1H), 7.57(d, J=9.0Hz, 2H), 7.78(d, J=9.0Hz, 2H), 7.83-7.91(m, 4H), 7.98(brs, 1H), 8.92(s, 1H), 12.13(brs, 1H) |

TABLE 1-24-continued

| Example | Structural formula | NMR |
|---|---|---|
| 1-119 | | (DMSO-d6-300) 1.45(dd, J=6.0, 9.0Hz, 1H), 1.95(dd, J=6.0, 9.0Hz, 1H), 2.65(t, J=9.0Hz, 1H), 4.59(s, 2H), 6.6.8-6.84(m, 3H), 7.16(t, J=7.5Hz, 1H), 7.57(d, J=9.0Hz, 2H), 7.78(d, J=9.0Hz, 2H), 7.83-7.91(m, 4H), 8.92(s, 1H), 12.18(brs, 1H), 12.91(brs, 1H) |
| 1-120 | | (ACETONE-d6-400) 1.94-1.99(m, 1H), 2.17-2.22(m, 1H), 2.94(t, J=10.0Hz, 1H), 6.94(d, J=1.0Hz, 1H), 7.16-7.31(m, 5H), 7.65(d, J=4.0Hz, 1H), 7.69(d, J=4.0Hz, 1H), 8.55(d, J=1.0Hz, 1H) |

TABLE 1-25

| Example | Structural formula | NMR |
|---|---|---|
| 1-121 | | (ACETONE-d6-400) 0.97(dd, J=8.0, 12.0Hz, 1H), 1.10(dd, J=8.0, 12.0Hz, 1H), 2.95(t, J=8.0Hz, 1H), 7.17-7.31(m, 5H), 7.72(d, J=8.0Hz, 1H), 7.81(d, J=8.0Hz, 1H), 7.82-7.85(m, 2H), 8.24(br, 1H) |
| 1-122 | | (ACETONE-d6-400) 0.95(dd, J=8.0, 12.0Hz, 1H), 1.07(dd, J=8.0, 8.0Hz, 1H), 2.87(t, J=8.0Hz, 1H), 7.13-7.27(m, 5H), 7.13-7.27(m, 5H), 3.74(dt, J=12.0, 2.0Hz, 1H), 7.82(d, J=4.0Hz, 1H), 3.97(dt, J=8.0, 2.0Hz, 1H), 3.97(dt, J=8.0, 2.0Hz, 1H), 8.21(d, J=8.0Hz, 1H), 8.28(d, J=8.0Hz, 1H) |

TABLE 1-25-continued

| Example | Structural formula | NMR |
|---|---|---|
| 1-123 | 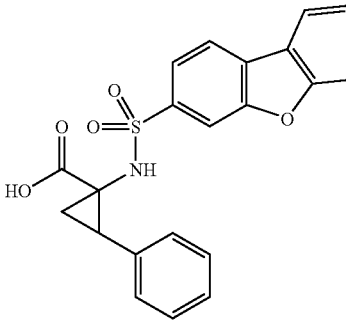 | (ACETONE-d6-400) 1.28-1.32(m, 1H), 0.95(dd, J=8.0, 12.0Hz, 1H), 2.13-2.17(m, 1H), 7.13-7.28(m, 5H), 7.65(ddd, J=0.0, 4.0, 8.0Hz, 5H), 7.76(dd, J=1.0, 12.0Hz, 1H), 7.96(dt, J=1.0, 8.0Hz, 1H), 8.14(d, J=1.0Hz, 1H), 8.31(d, J=4.0Hz, 1H), 8.34(d, J=12.0Hz, 1H) |
| 1-124 | 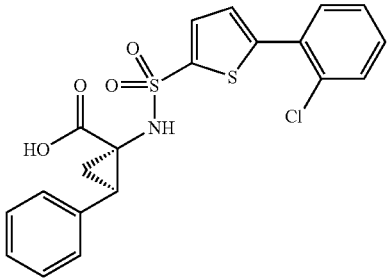 | (DMSO-d6-300) 1.60(dd, J=5.7, 9.8Hz, 1H), 2.04(dd, J=5.7, 8.6Hz, 1H), 2.76(dd, J=8.6, 9.8Hz, 1H), 7.14-7.30(m, 5H), 7.45(d, J=3.4Hz, 1H), 7.46(d, J=3.7Hz, 1H), 7.48(d, J=3.0Hz, 1H), 7.60(d, J=3.8Hz, 1H), 7.63(dd, J=3.4, 6.0Hz, 1H), 7.72(dd, J=3.8, 6.0Hz, 1H), 9.21(s, 1H), 12.22(s, 1H) |
| 1-125 | 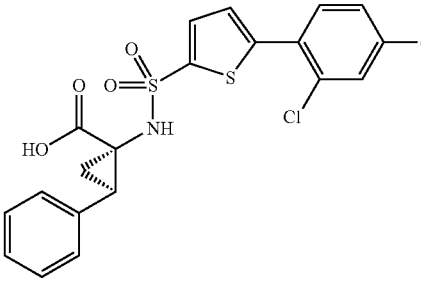 | (DMSO-d6-300) 1.60(dd, J=6.0, 9.4Hz, 1H), 2.05(dd, J=5.6, 8.7Hz, 1H), 2.77(dd, J=8.7, 9.4Hz, 1H), 7.15-7.31(m, 5H), 7.49(d, J=3.8Hz, 1H), 7.56(dd, J=2.2, 8.3Hz, 1H), 7.61(d, J=4.2Hz, 1H), 7.75(d, J=8.3Hz, 1H), 7.82(d, J=1.9Hz, 1H), 9.23(s, 1H), 12.23(s, 1H) |

TABLE 1-26

| Example | Structural formula | NMR |
|---|---|---|
| 1-126 | 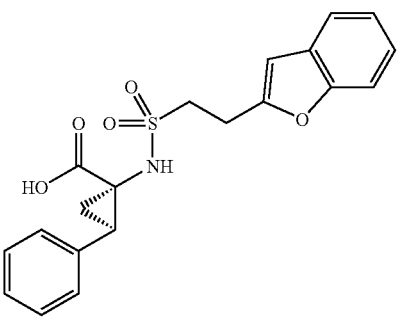 | (CDCL3-300) 1.89(dd, J=6.0, 9.0Hz, 1H), 2.17(dd, J=6.0, 9.0Hz, 1H), 3.02(t, J=9.0Hz, 1H), 3.30(t, J=7.5Hz, 2H), 3.45-3.54(m, 2H), 5.46(br, 1H), 6.45(br, 1H), 7.14-7.27(m, 7H), 7.41(d, J=9.0Hz, 1H), 7.51(dd, J=3.0, 6.0Hz, 1H) |

TABLE 1-26-continued

| Example | Structural formula | NMR |
|---|---|---|
| 1-127 | | (DMSO-d6-300) 1.77(dd, J=9.6, 5.6Hz, 1H), 2.06(dd, J=8.8, 5.1Hz, 1H), 2.78(t, J=8.8Hz, 1H), 7.49-7.61(m, 5H), 7.63-7.69(m, 1H), 7.72-7.78(m, 3H), 8.01-8.08(m, 2H) |
| 1-128 | | (DMSO-d6-300) 1.52(dd, J=9.5, 5.5Hz, 1H), 1.80(dd, J=8.4, 5.1Hz, 1H), 2.42-2.50(m, 1H), 6.28-6.41(m, 3H), 6.81(t, J=7.7Hz, 1H), 7.45-7.54(m, 5H), 7.68-7.74(m, 2H) |
| 1-129 | | (DMSO-d6-400) 1.54(dd, J=9.7, 5.0Hz, 1H), 1.78(dd, J=8.7, 5.0Hz, 1H), 2.40(t, J=9.0Hz, 1H), 4.20(d, J=5.6Hz, 1H), 6.05(t, J=6.0Hz, 1H), 6.32(dd, J=8.1, 1.9Hz, 1H), 6.37(d, J=7.7Hz, 1H), 6.46-6.49(m, 1H), 6.83(t, J=7.8Hz, 1H), 7.29(dd, J=7.7, 4.9Hz, 1H), 7.45-7.53(m, 4H), 7.66-7.73(m, 3H), 8.39(dd, J=4.9, 1.6Hz, 1H), 8.52(d, J=2.1Hz, 1H) |
| 1-130 | | (DMSO-d6-300) 1.69(dd, J=6.0, 12.0Hz, 1H), 1.81(dd, J=6.0, 9.0Hz, 1H), 2.44(t, J=9.0Hz, 1H), 2.94(s, 3H), 6.93(brd, J=9.0Hz, 1H), 6.96(brd, J=9.0Hz, 1H), 7.09(d, J=6.0Hz, 1H), 7.13(d, J=9.0Hz, 1H), 7.52(d, J=9.0Hz, 2H), 7.55(d, J=3.0Hz, 1H), 7.62(d, J=3.0Hz, 1H), 7.75(d, J=9.0Hz, 2H) |

TABLE 1-27

| Example | Structural formula | NMR |
|---|---|---|
| 1-131 | | (CDCL3-300) 1.62(dd, J=6.0, 9.0Hz, 1H), 2.00(dd, J=6.0, 9.0Hz, 1H), 2.71(t, J=9.0Hz, 1H), 7.14-7.27(m, 5H), 7.59(d, J=3.0Hz, 1H), 7.85(d, J=3.0Hz, 1H), 8.04(dd, J=238494.0, 9.0Hz, 1H), 8.09(d, J=6.0Hz, 1H), 8.64(d, J=3.0Hz, 1H), 12.20(brs, 1H) |

TABLE 1-27-continued

| Example | Structural formula | NMR |
|---|---|---|
| 1-132 | | (DMSO-d6-300) 1.63(dd, J=3.0, 9.0Hz, 1H), 1.97(dd, J=6.0, 9.0Hz, 1H), 2.75(t, J=9.0Hz, 1H), 7.05-7.13(m, 3H), 7.26(t, J=7.5Hz, 1H), 7.53(d, J=9.0Hz, 2H), 7.57(s, 2H), 7.76(d, J=9.0Hz, 2H), 9.22(s, 1H), 11.85(brs, 1H), 12.27(brs, 1H) |
| 1-133 | | (DMSO-d6-300) 1.58(dd, J=6.0, 9.0Hz, 1H), 1.99(dd, J=6.0, 9.0Hz, 1H), 2.70(t, J=9.0Hz, 1H), 6.60-6.76(m, 3H), 7.10(t, J=9.0Hz, 1H), 7.53(d, J=9.0Hz, 2H), 7.56(d, J=3.0Hz, 1H), 7.58(d, J=3.0Hz, 1H), 7.76(d, J=9.0Hz, 2H), 9.17(s, 1H) |
| 1-134 | | (CDCL3-300) 2.03(dd, J=6.0, 9.0Hz, 1H), 2.09-2.17(m, 1H), 2.88(t, J=9.0Hz, 1H), 4.48(s, 2H), 6.46(brs, 1H), 7.07-7.28(m, 5H), 7.37(d, J=9.0Hz, 2H), 7.50(d, J=9.0Hz, 2H), 7.56(d, J=6.0Hz, 1H) |
| 1-135 | | (DMSO-d6-300) 1.58(dd, J=6.0, 9.0Hz, 1H), 1.94(dd, J=6.0, 9.0Hz, 1H), 2.70(t, J=9.0Hz, 1H), 5.81(brs, 2H), 6.75(d, J=6.0Hz, 1H), 7.08(t, J=7.5Hz, 1H), 7.22-7.31(m, 2H), 7.49-7.58(m, 4H), 7.76(d, J=9.0Hz, 2H), 8.52(brs, 1H), 9.20(brs, 1H) |

TABLE 1-28

| Example | Structural formula | NMR |
|---------|-------------------|-----|
| 1-136 | | (DMSO-d6-300) 1.58(dd, J=6.0, 9.0Hz, 1H), 1.90(dd, J=6.0, 9.0Hz, 1H), 2.69(t, J=9.0Hz, 1H), 6.87(d, J=6.0Hz, 1H), 6.94(d, J=6.0Hz, 1H), 7.09(s, 1H), 7.12(t, J=6.0Hz, 1H), 7.53(d, J=9.0Hz, 2H), 7.54-7.59(m, 3H), 7.76(d, J=9.0Hz, 2H), 8.05(dt, J=9.0, 6.0Hz, 1H), 8.76(dd, J=1.0, 6.0Hz, 1H), 8.87(d, J=1.0Hz, 1H), 9.21(s, 1H), 10.41(s, 1H) |
| 1-137 | | (METHANOL-d4-300) 1.77-1.86(m, 1H), 2.13(dd, J=6.0, 9.0Hz, 1H), 2.71(t, J=10.5Hz, 1H), 7.25-7.52(m, 5H), 7.58-7.76(m, 5H) |
| 1-138 | | (DMSO-d6-300) 0.84(dd, J=6.0, 12.0Hz, 1H), 0.99(dd, J=6.0, 9.0Hz, 1H), 2.64(t, J=9.0Hz, 1H), 3.73-3.82(m, 2H), 3.85-4.03(m, 2H), 4.75(br, 1H), 6.82(t, J=7.5Hz, 1H), 6.90(d, J=9.0Hz, 1H), 7.04(d, J=9.0Hz, 1H), 7.15(t, J=9.0Hz, 1H), 7.53(brd, J=9.0Hz, 2H), 7.57(d, J=6.0Hz, 1H), 7.59(d, J=3.0Hz, 1H), 7.76(brd, J=9.0Hz, 2H), 8.82(br, 1H), 11.95(br, 1H) |
| 1-139 | | (DMSO-d6-300) 0.88(dd, J=6.0, 9.0Hz, 1H), 1.00(dd, J=6.0, 9.0Hz, 1H), 2.64(t, J=9.0Hz, 1H), 2.64(t, J=9.0Hz, 1H), 4.56(d, J=15.0Hz, 1H), 4.66(d, J=15.0Hz, 1H), 6.79-6.89(m, 2H), 7.02-7.09(m, 1H), 7.10-7.20(m, 1H), 7.49-7.60(m, 4H), 7.71-7.78(m, 2H), 8.69(brs, 1H), 11.90(brs, 1H), 12.83(brs, 1H) |
| 1-140 | | (ACETONE-d6-400) 0.92(dd, J=4.0, 8.0Hz, 1H), 1.04(dd, J=8.0, 12.0Hz, 1H), 2.83(t, J=10.0Hz, 1H), 7.11(dt, J=8.0, 2.0Hz, 1H), 7.16-7.28(m, 7H), 7.40-7.46(m, 3H), 7.57(t, J=8.0Hz, 1H), 7.62(dt, J=10.0, 1.0Hz, 1H), 7.80(br, 1H) |

TABLE 1-29

| Example | Structural formula | NMR |
|---|---|---|
| 1-141 | 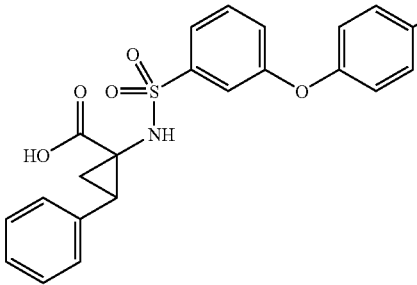 | (ACETONE-d6-400)<br>0.92(dd, J=8.0, 12.0Hz, 1H),<br>1.05(dd, J=4.0, 8.0Hz, 1H),<br>2.84(t, J=10.0Hz, 1H), 7.13-<br>7.28(m, 9H), 7.41(t, J=2.0Hz,<br>1H), 7.57(t, J=8.0Hz, 1H),<br>7.62(dt, J=8.0, 2.0Hz, 1H),<br>7.78(br, 1H) |
| 1-142 | 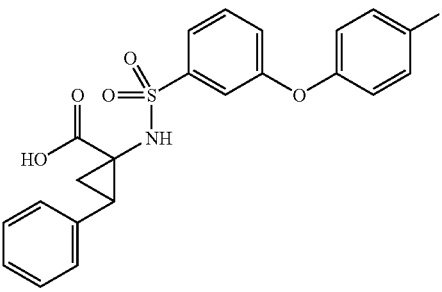 | (ACETONE-d6-400)<br>0.93(dd, J=4.0, 8.0Hz, 1H),<br>1.05(dd, J=4.0, 8.0Hz, 1H),<br>2.85(t, J=10.0Hz, 1H), 7.12(d,<br>J=8.0Hz, 2H), 7.16-7.30(m,<br>6H), 7.41-7.46(m, 3H), 7.59(t,<br>J=8.0Hz, 1H), 7.67(d, J=8.0Hz,<br>1H), 7.82(br, 1H) |
| 1-143 | 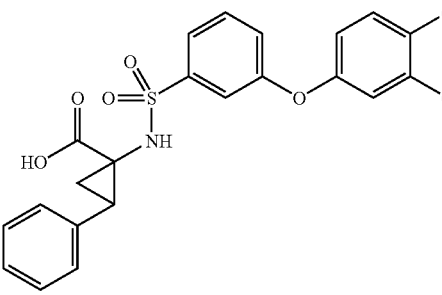 | (ACETONE-d6-400)<br>0.93(dd, J=4.0, 8.0Hz, 1H),<br>1.06(dd, J=4.0, 8.0Hz, 1H),<br>2.86(t, J=10.0Hz, 1H),<br>7.08(dd, J=4.0, 8.0Hz, 1H),<br>7.16-7.28(m, 4H), 7.34-7.37(m,<br>2H), 7.52(t, J=2.0Hz, 1H),<br>7.59(d, J=8.0Hz, 1H), 7.62(t,<br>J=8.0Hz, 1H), 7.70(dt, J=8.0,<br>2.0Hz, 1H), 7.86(brs, 1H) |
| 1-144 | 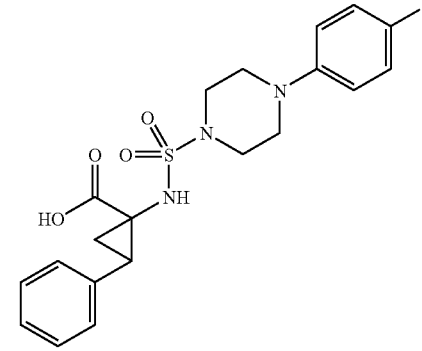 | (METHANOL-d4-400)<br>0.97(dd, J=4.0, 8.0Hz, 1H),<br>1.05(dd, J=4.0, 8.0Hz, 1H),<br>2.78(t, J=10.0Hz, 1H), 3.15-<br>3.25(m, 4H), 3.33-3.42(m, 4H),<br>6.94(d, J=8.0Hz, 2H), 7.15-<br>7.29(m, 7H), 8.38(brs, 1H) |

TABLE 1-29-continued

| Example | Structural formula | NMR |
|---|---|---|
| 1-145 | | (DMSO-d6-300) 1.68(dd, J=6.0, 9.0Hz, 1H), 1.98-2.08(m, 1H), 2.68-2.80(m, 1H), 4.35(ddd, J=6.0, 15.0, 27.0Hz, 1H), 4.54(dd, J=15.0, 21.0Hz, 2H), 6.78-6.93(m, 2H), 7.03-7.32(m, 7H), 7.48-7.62(m, 4H), 7.74(d, J=9.0Hz, 2H), 8.32(brs, 1H), 9.08(brs, 1H), 12.22(brs, 1H) |

TABLE 1-30

| Example | Structural formula | NMR |
|---|---|---|
| 1-146 | | (DMSO-d6-300) 1.76(dd, J=6.0, 12.0Hz, 1H), 1.96-2.08(m, 1H), 2.55-2.67(m, 1H), 3.40-3.68(m, 4H), 4.75(dd, J=15.0, 45.0Hz, 2H), 6.78-6.94(m, 2H), 7.05(d, J=6.0Hz, 1H), 7.15(t, J=9.0Hz, 1H), 7.47-7.62(m, 4H), 7.75(d, J=6.0Hz, 2H), 8.90(brs, 1H), 12.02(brs, 1H) |
| 1-147 | | (DMSO-d6-300) 1.10(d, J=6.0Hz, 3H), 1.15(d, J=6.0Hz, 3H), 1.55-1.66(m, 1H), 1.91-2.02(m, 1H), 2.60-2.75(m, 1H), 3.92-4.05(m, 1H), 4.36(d, J=15.0Hz, 1H), 4.47(d, J=15.0Hz, 1H), 6.80-6.89(m, 2H), 7.04-7.08(m, 1H), 7.13-7.20(m, 1H), 7.53(d, J=9.0Hz, 2H), 7.57(d, J=6.0Hz, 1H), 7.60(d, J=6.0Hz, 1H), 7.76(d, J=9.0Hz, 2H) |
| 1-148 | | (ACETONE-d6-300) 1.94(dd, J=6.0, 9.0Hz, 1H), 2.17(dd, J=6.0, 9.0Hz, 1H), 2.92(t, J=9.0Hz, 1H), 4.11(s, 3H), 7.15-7.33(m, 6H), 7.63(d, J=6.0Hz, 1H), 7.70(d, J=6.0Hz, 1H), 8.15(d, J=9.0Hz, 1H) |

TABLE 1-30-continued

| Example | Structural formula | NMR |
|---|---|---|
| 1-149 | | (DMSO-d6-400)<br>1.38-1.41(m, 1H), 1.39(s, 3H), 2.09(d, J=5.3Hz, 1H), 7.11(m, 5H), 7.49-7.57(m, 4H), 7.71-7.76(m, 2H), 9.19(brs, 1H), 12.11(brs, 1H). |

TABLE 2-1

| Example | Structural formula | NMR |
|---|---|---|
| 2 | | (DMSO-d6-400)<br>1.41(s, 9H), 1.55(dd, J=9.7, 5.1Hz, 1H), 1.94(dd, J=8.3, 5.6Hz, 1H), 2.40-2.47(m, 2H), 2.62(t, J=9.0Hz, 1H), 3.48-3.55(m, 2H), 3.94-4.02(m, 2H), 6.26(brs, 1H), 7.43(d, J=3.7Hz, 1H), 7.11-7.24(m, 5H), 7.43(d, J=3.7Hz, 1H) |
| 2-2 | | (DMSO-d6-400)<br>1.53(dd, J=10.2, 5.6Hz, 1H), 1.97-2.02(m, 1H), 2.66(brs, 2H), 2.71(t, J=9.3Hz, 1H), 3.26-3.32(m, 2H), 3.73(brs, 2H), 6.27(brs, 1H), 7.14-7.27(m, 6H), 7.48(d, J=4.2Hz, 1H), 9.18(brs, 2H) |
| 2-3 | | (DMSO-d6-400)<br>1.60(dd, J=9.3, 5.6Hz, 1H), 1.84(dd, J=8.3, 5.1Hz, 1H), 2.43-2.50(m, 3H), 3.56(t, J=5.8Hz, 2H), 3.62(s, 3H), 4.03(brs, 2H), 6.26(brs, 1H), 7.21-7.07(m, 6H), 7.44(d, J=3.7Hz, 1H) |

TABLE 2-1-continued

| Example | Structural formula | NMR |
|---|---|---|
| 2-4 | | (DMSO-d6-300)<br>1.26(d, J=6.8Hz, 3H), 2.00(dq, J=10.5, 6.8Hz, 1H), 2.79(d, J=10.5Hz, 1H), 4.24(s, 1H), 7.13-7.17(m, 5H), 7.38(d, J=4.1Hz, 1H), 7.51(d, J=4.1Hz, 1H), 7.98(s, 1H), 8.91(s, 1H), 9.06(brs, 1H), 12.29(brs, 1H) |
| 2-5 | | (CDCl3-400)<br>1.33(d, J=6.6Hz, 3H), 2.18(brs, 1H), 3.10(d, J=10.8Hz, 1H), 3.31(brs, 4H), 3.69(brs, 4H), 6.65(d, J=9.0Hz, 1H), 7.21-7.28(m, 5H), 7.66(dd, J=2.3, 9.0Hz, 1H), 8.37(s, 1H) |

TABLE 2-2

| Example | Structural formula | NMR |
|---|---|---|
| 2-6 | | (DMSO-d6-400)<br>1.40(s, 3H), 1.43(d, J=5.6Hz, 1H), 2.12(d, J=5.6Hz, 1H), 7.13-7.26(m, 5H), 7.68(d, J=3.7Hz, 1H), 7.85(d, J=3.7Hz, 1H), 8.17(s, 1H), 9.41(brs, 1H), 12.14(brs, 1H) |
| 2-7 | | (DMSO-d6-300)<br>1.27(d, J=6.8Hz, 3H), 2.00(dd, J=10.2, 6.4Hz, 1H), 2.79(d, J=10.2Hz, 1H), 7.09-7.35(m, 5H), 7.70(d, J=3.8Hz, 1H), 7.85(d, J=3.8Hz, 1H), 8.17(s, 1H), 9.28(brs, OH), 12.34(brs, 1H) |

TABLE 2-2-continued

| Example | Structural formula | NMR |
|---|---|---|
| 2-8 | | (DMSO-d6-400) 1.45-1.59(m, 2H), 1.68-1.84(m, 3H), 2.44(dd, J=13.0, 6.0Hz, 1H), 2.69(d, J=9.3Hz, 1H), 3.00(td, J=13.0, 5.6Hz, 1H), 6.95-7.10(m, 4H), 7.48-7.61(m, 4H), 7.70-7.76(m, 2H) |
| 2-9 | | (MeOH-d4-300) 1.37(d, J=9.0Hz, 3H), 2.06(t, J=18.0Hz, 3H), 2.15-2.27(m, 1H), 2.94(d, J=9.0Hz, 1H), 7.16-7.28(m, 6H), 7.61(d, J=3.0Hz, 1H), 7.64(d, J=3.0Hz, 1H) |
| 2-10 | | (CD3CN-400) 2.32(dd, J=7.4, 17.5Hz, 1H), 3.08(d, J=10.4Hz, 1H), 3.79(dd, J=7.2, 11.4Hz, 1H), 3.96(dd, J=7.6, 11.3Hz, 1H), 7.16-7.29(m, 5H), 7.44(brs, 1H), 7.57-7.61(m, 1H), 7.68-7.72(m, 1H) |

TABLE 2-3

| Example | Structural formula | NMR |
|---|---|---|
| 2-11 | | (DMSO-d6-300) 1.27(d, J=6.8Hz, 3H), 1.95-2.05(m, 1H), 2.86(d, J=10.5Hz, 1H), 3.05-3.15(m, 4H), 3.44-3.58(m, 4H), 6.93(t, J=7.9Hz, 1H), 7.15-7.30(m, 8H), 7.44(d, J=7.9Hz, 2H), 8.28(s, 1H), 8.59(s, 1H), 12.37(s, 1H) |

TABLE 2-3-continued

| Example | Structural formula | NMR |
|---|---|---|
| 2-12 | | (DMSO-d6-300) 1.39(d, J=3.4Hz, 3H), 1.40(d, J=3.4Hz, 1H), 2.06(d, J=6.4Hz, 1H), 5.56(brs, 2H), 6.89(dd, J=8.3, 2.3Hz, 1H), 7.09(d, J=2.3Hz, 1H), 7.12-7.27(m, 6H), 7.37(d, J=4.1Hz, 1H), 7.50(d, J=4.1Hz, 1H), 9.13(brs, 1H), 12.02(brs, 1H) |
| 2-13 | | (DMSO-d6-300) 2.03(dd, J=6.8, 7.2Hz, 1H), 2.60(d, J=6.8Hz, 1H), 2.99(dd, J=17.3, 7.2Hz, 1H), 3.21-3.36(m, 1H), 5.25(s, 2H), 6.98-7.09(m, 3H), 7.13-7.19(m, 1H), 7.22(d, J=8.7Hz, 2H), 7.49(dd, J=8.3, 2.3Hz, 1H), 7.64(d, J=8.3Hz, 1H), 7.71(d, J=2.3Hz, 1H), 7.81(d, J=8.7Hz, 2H), 8.26(brs, 1H), 8.40(s, 1H), 9.87(s, 1H) |
| 2-14 | | (MeOH-d4-400) 1.95-2.01(m, 1H), 2.08-2.16(m, 1H), 2.69-2.76(m, 1H), 4.03(s, 3H), 6.88(s, 1H), 7.12-7.28(m, 5H), 7.36(d, J=3.9Hz, 1H), 7.65(d, J=3.9Hz, 1H), 8.45(s, 1H) |
| 2-15 | | (MeOH-d4-400) 1.19-1.35(m, 1H), 1.88-1.94(m, 1H), 2.08-2.14(m, 1H), 2.77-2.83(m, 1H), 3.86-3.94(m, 1H), 4.22-4.32(m, 1H), 4.86-4.97(m, 2H), 6.81(d, J=8.6Hz, 1H), 7.14-7.32(m, 8H), 8.39(s, 1H) |

TABLE 2-4

| Example | Structural formula | NMR |
|---|---|---|
| 2-16 | | (MeOH-d4-400) 1.18-1.25(m, 1H), 1.90(dd, J=9.4, 5.5Hz, 1H), 2.12(dd, J=9.4, 5.5Hz, 1H), 2.77(t, J=9.4Hz, 1H), 4.01(s, 3H), 7.12-7.28(m, 6H), 7.39(d, J=3.9Hz, 1H), 7.55(d, J=3.9Hz, 1H), 8.37(s, 1H) |
| 2-17 | | (MeOH-d4-400) 1.93(dd, J=9.4, 5.5Hz, 1H), 2.13(dd, J=9.4, 5.5Hz, 1H), 2.78(t, J=9.4Hz, 1H), 7.12-7.28(m, 5H), 7.34(d, J=9.4Hz, 2H), 7.41(d, J=3.9Hz, 1H), 7.59(d, J=3.9Hz, 1H), 7.77(d, J=9.4Hz, 2H), 8.39(s, 1H) |
| 2-18 | | (CDCl3-400) 2.00-2.07(m, 1H), 2.11-2.13(m, 1H), 2.90-2.96(m, 1H), 6.29(brs, 1H), 7.10-7.85(m, 10H) |
| 2-19 | | (CDCl3-400) 1.25-1.52(m, 2H), 2.11(m, 1H), 2.87(t, J=9.3Hz, 1H), 6.75(d, J=8.7Hz, 1H), 7.14-7.26(m, 5H), 7.59-7.73(m, 6H) |
| 2-20 | | (CDCl3-400) 2.00-2.02(m, 2H), 2.40(s, 3H), 2.89(t, J=9.4Hz, 1H), 5.89(brs, 1H), 7.03-7.26(m, 8H), 7.44-7.48(m, 3H) |

TABLE 2-5

| Example | Structural formula | NMR |
|---|---|---|
| 2-21 | | (CDCl3-400) 1.98-2.06(m, 2H), 2.90(t, J=9.3Hz, 1H), 6.11(brs, 1H), 7.06-7.26(m, 8H), 7.49-7.55(m, 3H) |
| 2-22 | | (DMSO-d6-300) 1.67(dd, J=9.8, 5.7Hz, 1H), 2.01(dd, J=8.7, 5.7Hz, 1H), 2.71(dd, J=9.4, 4.7Hz, 1H), 5.23(d, J=13.2Hz, 1H), 5.28(d, J=13.2Hz, 1H), 6.83(t, J=7.2Hz, 1H), 6.93(d, J=7.5Hz, 1H), 7.07(d, J=7.5Hz, 1H), 7.13(t, J=7.9Hz, 1H), 7.50-7.61(m, 5H), 7.76(d, J=8.7Hz, 2H), 8.13(d, J=7.9Hz, 1H), 8.60(dd, J=5.3, 1.5Hz, 1H), 8.81(d, J=1.5Hz, 1H), 9.01(s, 1H), 12.03-12.29(m, 1H) |
| 2-23 | | (DMSO-d6-300) 1.72(dd, J=9.4, 5.7Hz, 1H), 2.06(dd, J=8.9, 5.8Hz, 1H), 2.79(dd, J=9.2, 4.6Hz, 1H), 5.32(d, J=14.3Hz, 1H), 5.44(d, J=14.3Hz, 1H), 6.88(t, J=7.3Hz, 1H), 6.95(d, J=7.9Hz, 1H), 7.10(d, J=7.5Hz, 1H), 7.16(t, J=7.9Hz, 1H), 7.53(d, J=8.3Hz, 2H), 7.59(s, 2H), 7.67-7.73(m, 1H), 7.76(d, J=8.7Hz, 1H), 7.88(d, J=8.3Hz, 1H), 8.20(t, J=7.7Hz, 1H), 8.79(d, J=5.3Hz, 1H), 9.28(s, 1H) |
| 2-24 | | (DMSO-d6-300) 1.70-1.79(m, 1H), 1.90-1.99(m, 1H), 6.74(d, J=7.2Hz, 1H), 7.04(d, J=6.8Hz, 1H), 7.20-7.33(m, 3H), 7.49-7.54(m, 5H), 7.71-7.74(m, 3H), 8.31-8.32(m, 2H) |

TABLE 2-5-continued

| Example | Structural formula | NMR |
|---|---|---|
| 2-25 | | (DMSO-d6-300)<br>1.23(s, 7H), 1.25(s, 7H), 1.63(dd, J=9.8, 5.7Hz, 1H), 1.99(dd, J=9.0, 5.7Hz, 1H), 2.67(t, J=10.2Hz, 1H), 3.67(dd, J=16.0, 9.2Hz, 2H), 4.62(brs, 1H), 6.79(t, J=7.5Hz, 1H), 6.86(d, J=7.9Hz, 1H), 7.01(d, J=7.2Hz, 1H), 7.13(t, J=7.9Hz, 1H), 7.50-7.54(m, 2H), 7.57(dd, J=5.7, 3.8Hz, 2H), 7.74(dd, J=6.6, 2.1Hz, 2H), 8.75(brs, 1H) |

TABLE 2-6

| Example | Structural formula | NMR |
|---|---|---|
| 2-26 | | (DMSO-d6-300)<br>1.61(dd, J=5.1, 2.6Hz, 1H), 2.01(dd, J=8.7, 5.7Hz, 1H), 2.48(s, 3H), 2.73(t, J=9.0Hz, 1H), 7.14-7.26(m, 5H), 7.53(dd, J=5.8, 4.0Hz, 2H), 7.58-7.58(m, 1H), 12.20(brs, 1H) |
| 2-27 | | (DMSO-d6-300)<br>1.59-1.67(m, 1H), 1.95-2.03(m, 1H), 2.64-2.74(m, 1H), 7.13-7.25(m, 5H), 7.60(s, 1H), 7.62(d, J=4.5Hz, 1H), 7.69(d, J=3.8Hz, 1H), 8.20(dd, J=8.3, 2.6Hz, 1H), 8.81(d, J=2.6Hz, 1H) |
| 2-28 | | (MeOH-d4-400)<br>1.96(dd, J=5.4, 9.6Hz, 1H), 2.10-2.15(m, 1H), 2.80(t, J=9.0Hz, 1H), 3.25-3.45(m, 8H), 7.09(d, J=7.6Hz, 1H), 7.15-7.30(m, 7H), 7.40(t, J=7.9Hz, 1H) |

TABLE 2-6-continued

| Example | Structural formula | NMR |
|---|---|---|
| 2-29 | | (MeOH-d4-400) 1.83-2.19(m, 2H), 2.70-2.84(m, 1H), 3.06-3.53(m, 8H), 7.06-7.50(m, 9H) |
| 2-30 | | (MeOH-d4-400) 1.96(dd, J=5.6, 9.8Hz, 1H), 2.13(dd, J=5.8, 8.5Hz, 1H), 2.80(t, J=9.1Hz, 1H)3.25-3.34(m, 4H), 3.34-3.44(m, 4H), 7.14-7.29(m, 7H), 7.40(d, J=7.4Hz, 1H) |

TABLE 2-7

| Example | Structural formula | NMR |
|---|---|---|
| 2-31 | | (MeOH-d4-400) 1.95(dd, J=5.6, 9.8Hz, 1H), 2.12(dd, J=5.8, 8.3Hz, 1H), 2.79(t, J=9.1Hz, 1H), 3.20-3.42(m, 8H), 6.81(d, J=8.6Hz, 1H), 6.88(d, J=8.6Hz, 1H), 6.95(s, 1H), 7.15-7.29(m, 6H) |
| 2-32 | | (DMSO-d6-300) 1.61(dd, J=9.6, 5.8Hz, 1H), 1.99-2.01(m, 1H), 2.73(t, J=8.9Hz, 1H), 4.31(d, J=5.3Hz, 2H), 7.11-7.56(m, 10H), 7.73(d, J=8.7Hz, 2H), 7.94(d, J=4.9Hz, 1H), 8.00(d, J=2.6Hz, 1H), 9.17(s, 1H) |

TABLE 2-7-continued

| Example | Structural formula | NMR |
|---|---|---|
| 2-33 | | (Aceton-d6-300) 1.94(dd, J=6.0, 9.0Hz, 1H), 2.17(dd, J=6.0, 9.0Hz, 1H), 2.92(t, J=9.0Hz, 1H), 4.11(s, 3H), 7.15-7.33(m, 6H), 7.63(d, J=6.0Hz, 1H), 7.70(d, J=6.0Hz, 1H), 8.15(d, J=9.0Hz, 1H) |
| 2-34 | | (DMSO-d6-300) 1.62(dd, J=9.8, 5.7Hz, 1H), 2.02(dd, J=8.7, 5.7Hz, 1H), 2.74(t, J=9.2Hz, 1H), 7.17-7.27(m, 5H), 7.54-7.55(m, 2H), 7.63(d, J=4.1Hz, 1H), 7.98(d, J=3.8Hz, 1H), 9.31(brs, 1H), 12.23(brs, 1H) |
| 2-35 | | (DMSO-d6-300) 1.56-1.57(m, 1H), 2.00(dd, J=11.7, 6.0Hz, 1H), 2.72(t, J=8.9Hz, 1H), 3.58(d, J=18.5Hz, 1H), 3.96(d, J=18.5Hz, 1H), 7.19-7.25(m, 5H), 7.49(d, J=4.1Hz, 1H), 7.59(d, J=4.1Hz, 1H) |

TABLE 2-8

| Example | Structural formula | NMR |
|---|---|---|
| 2-36 | | (DMSO-d6-300) 1.61(dd, J=9.9, 5.1Hz, 1H), 1.91(dd, J=8.3, 5.3Hz, 1H), 2.59(t, J=9.0Hz, 1H), 5.00(s, 2H), 6.74-6.87(m, 3H), 7.11(t, J=7.9Hz, 1H), 7.26-7.44(m, 5H), 7.46-7.57(m, 4H), 7.73(d, J=8.4Hz, 2H) |

TABLE 2-8-continued
| Example | Structural formula | NMR |
|---|---|---|
| 2-37 | 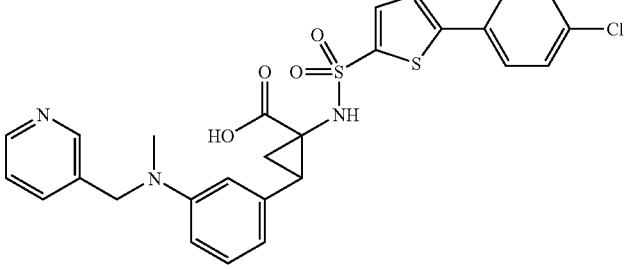 | (DMSO-d6-400) 1.60(dd, J=10.2, 4.6Hz, 1H), 1.81(dd, J=8.3, 4.6Hz, 1H), 2.42(t, J=9.3Hz, 1H), 2.88(s, 3H), 4.50(s, 2H), 6.47-6.52(m, 2H), 6.67(s, 1H), 6.94(t, J=7.9Hz, 1H), 7.29(dd, J=7.7, 4.9Hz, 1H), 7.47-7.59(m, 5H), 7.72(d, J=8.8Hz, 2H), 8.40-8.45(m, 2H) |
| 2-38 | 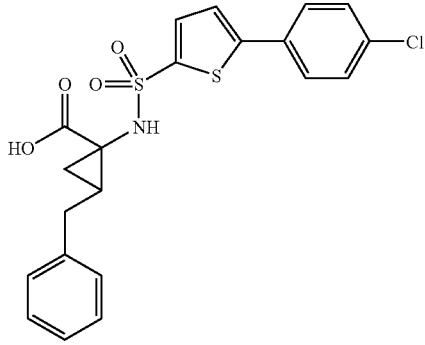 | (DMSO-d6-400) 1.19-1.26(m, 1H), 1.24-1.25(m, 2H), 1.36-1.49(m, 2H), 7.09-7.25(m, 5H), 7.45-7.54(m, 4H), 7.72(d, J=8.3Hz, 2H) |
| 2-39 | 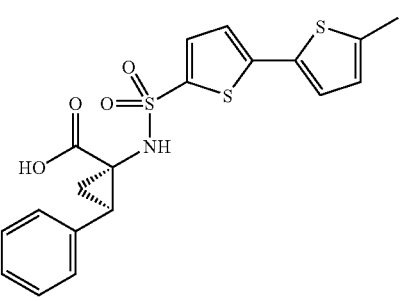 | (DMSO-d6-300) 1.61(dd, J=9.6, 5.5Hz, 1H), 1.95-2.04(m, 1H), 2.47(s, 3H), 2.69(t, J=9.6Hz, 1H), 6.83(d, J=2.6Hz, 1H), 7.12-7.29(m, 7H), 7.47(d, J=3.8Hz, 1H), 12.22(brs, 1H) |
| 2-40 | 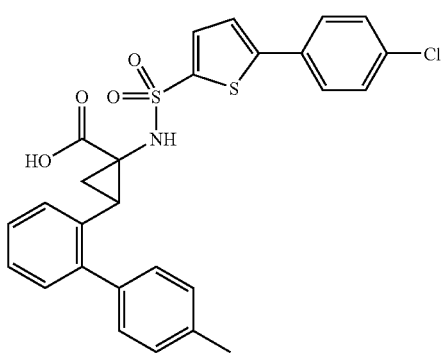 | (DMSO-d6-300) 1.65-1.80(m, 2H), 2.37(s, 3H), 7.09-7.22(m, 4H), 7.22-7.31(m, 4H), 7.51-7.56(m, 4H), 7.75(d, J=10.0Hz, 2H) |

TABLE 2-9

| Example | Structural formula | NMR |
|---|---|---|
| 2-41 | | (DMSO-d6-300)<br>0.67-1.68(m, 13H), 7.46-7.56(m, 4H), 7.73(d, J=7.2Hz, 2H) |
| 2-42 | | (DMSO-d6-300)<br>1.18(s, 6H), 1.61(dd, J=9.8, 5.7Hz, 1H), 2.00(dd, J=8.5, 5.7Hz, 1H), 2.71(dd, J=9.8, 8.5Hz, 1H), 3.63(s, 2H), 4.61(brs, 1H), 6.72-6.82(m, 3H), 7.14(dd, J=7.9, 7.9Hz, 1H), 7.52(d, J=8.7Hz, 2H), 7.56(d, J=3.8Hz, 1H), 7.58(d, J=3.8Hz, 1H), 7.75(d, J=8.7Hz, 2H), 9.17(s, 1H), 12.23(s, 1H) |
| 2-43 | | (DMSO-d6-300)<br>1.61-1.63(m, 1H), 2.04(dd, J=8.8, 5.5Hz, 1H), 2.76(t, J=8.8Hz, 1H), 7.19-7.24(m, 5H), 7.69(d, J=4.0Hz, 1H), 7.85(d, J=4.0Hz, 1H), 8.16(s, 1H), 9.39(brs, 1H), 12.22(brs, 1H) |
| 2-44 | | (DMSO-d6-300)<br>1.63(dd, J=6.0, 9.0Hz, 1H), 2.04(dd, J=6.0, 9.0Hz, 1H), 2.75(t, J=9.0Hz, 1H), 7.10-7.27(m, 5H), 7.70(d, J=3.0Hz, 1H), 7.94(d, J=3.0Hz, 1H) |

TABLE 2-9-continued

| Example | Structural formula | NMR |
|---|---|---|
| 2-45 | | (DMSO-d6-300)<br>1.62(dd, J=6.0, 9.0Hz, 1H),<br>2.03(dd, J=6.0, 9.0Hz, 1H),<br>2.75(t, J=9.0Hz, 1H), 7.11-<br>7.27(m, 5H), 7.70(d, J=3.0Hz,<br>1H), 7.94(d, J=3.0Hz, 1H) |

TABLE 2-10

| Example | Structural formula | NMR |
|---|---|---|
| 2-46 | | (CDCl3-300)<br>1.73(dd, J=6.0, 9.0Hz, 1H), 1.99-<br>2.05(m, 1H), 2.33(q, J=9.0Hz,<br>1H), 5.14(d, J=9.0Hz, 1H),<br>5.30(d, J=18.0Hz, 1H), 5.50-<br>5.59(m, 1H), 5.63(brs, 1H),<br>7.20(d, J=3.0Hz, 1H), 7.41(d,<br>J=9.0Hz, 2H), 7.49-7.56(m, 3H) |
| 2-47 | | (MeOH-d4-300)<br>1.62-1.75(m, 2H), 2.18-2.34(m,<br>1H), 4.67(dd, J=6.0, 12.0Hz, 1H),<br>4.74-4.84(m, 1H), 7.33(d,<br>J=3.0Hz, 1H), 7.40-7.47(m, 3H),<br>7.63(d, J=9.0Hz, 2H), 7.89(t,<br>J=7.5Hz, 1H), 8.04(t, J=7.5Hz,<br>1H), 8.15(d, J=9.0Hz, 1H),<br>8.32(d, J=9.0Hz, 1H) |
| 2-48 | | (CDCl3-300)<br>0.92(t, J=7.5Hz, 3H), 1.36-<br>1.70(m, 4H), 1.79(dd, J=6.0,<br>9.0Hz, 1H), 5.59(brs, 1H),<br>7.21(d, J=3.0Hz, 1H), 7.37-<br>7.44(m, 2H), 7.50-7.57(m, 3H) |

TABLE 2-10-continued

| Example | Structural formula | NMR |
|---|---|---|
| 2-49 | 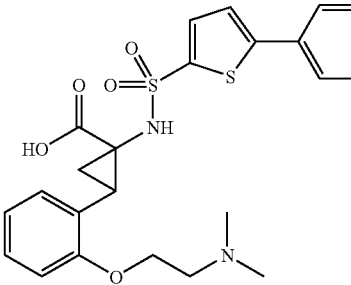 | (DMSO-d6-300) 1.59(dd, J=5.3, 2.6Hz, 1H), 1.98(dd, J=8.7, 5.7Hz, 1H), 2.79-2.86(m, 1H), 2.87(s, 3H), 3.51-3.70(m, 2H), 4.14-4.24(m, 1H), 4.34-4.45(m, 1H), 6.87(t, J=7.3Hz, 1H), 6.95(d, J=7.9Hz, 1H), 7.07(d, J=7.2Hz, 1H), 7.20(t, J=7.7Hz, 1H), 7.54(d, J=8.7Hz, 2H), 7.61(d, J=4.1Hz, 1H), 7.62(d, J=4.1Hz, 1H), 7.76(d, J=8.7Hz, 2H) |
| 2-50 | 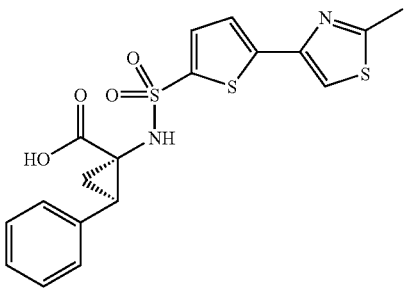 | (DMSO-d6-300) 1.59(dd, J=9.8, 5.5Hz, 1H), 2.01(dd, J=8.5, 5.5Hz, 1H), 2.66-2.77(m, 1H), 2.70(s, 3H), 7.14-7.30(m, 5H), 7.53(d, J=3.8Hz, 1H), 7.55(d, J=3.8Hz, 1H), 8.05(s, 1H), 9.13(s, 1H), 12.17(s, 1H) |

TABLE 2-11

| Example | Structural formula | NMR |
|---|---|---|
| 2-51 | 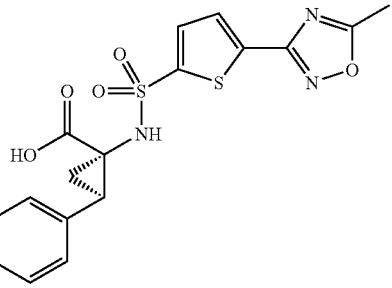 | (DMSO-d6-300) 1.62(dd, J=10.0, 6.5Hz, 1H), 2.03(dd, J=10.0, 6.5Hz, 2H), 2.65(s, 3H), 2.75(t, J=10.0Hz, 1H), 7.12-7.28(m, 5H), 7.63(d, J=3.8Hz, 1H), 7.75(d, J=10.0Hz, 1H), 9.34(brs, 1H), 12.20(brs, 1H) |
| 2-52 | 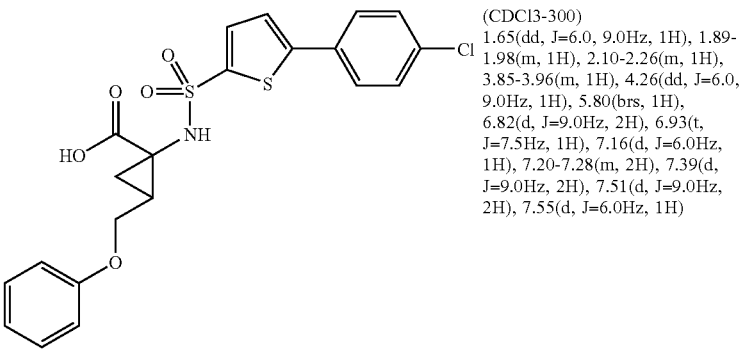 | (CDCl3-300) 1.65(dd, J=6.0, 9.0Hz, 1H), 1.89-1.98(m, 1H), 2.10-2.26(m, 1H), 3.85-3.96(m, 1H), 4.26(dd, J=6.0, 9.0Hz, 1H), 5.80(brs, 1H), 6.82(d, J=9.0Hz, 2H), 6.93(t, J=7.5Hz, 1H), 7.16(d, J=6.0Hz, 1H), 7.20-7.28(m, 2H), 7.39(d, J=9.0Hz, 2H), 7.51(d, J=9.0Hz, 2H), 7.55(d, J=6.0Hz, 1H) |

TABLE 2-11-continued

| Example | Structural formula | NMR |
|---|---|---|
| 2-53 | | (DMSO-d6-300) 1.38(s, 9H), 1.59(dd, J=9.6, 5.5Hz, 1H), 2.00(dd, J=8.5, 5.8Hz, 1H), 2.84(dd, J=9.4, 4.7Hz, 1H), 3.33-3.53(m, 2H), 4.09-4.21(m, 1H), 4.21-4.32(m, 1H), 6.88(t, J=7.5Hz, 1H), 6.95(d, J=7.9Hz, 1H), 7.08(d, J=7.5Hz, 1H), 7.21(t, J=7.5Hz, 1H), 7.54(d, J=8.7Hz, 2H), 7.60(s, 2H), 7.76(d, J=8.7Hz, 2H), 8.44-8.74(m, 1H), 8.83-9.24(m, 1H), 12.31(brs, 1H) |
| 2-54 | | (DMSO-d6-300) 1.26(s, 6H), 1.58(dd, J=9.8, 5.7Hz, 1H), 2.01(dd, J=8.7, 5.3Hz, 1H), 2.74(t, J=9.2Hz, 1H), 4.13(s, 2H), 7.17-7.27(m, 5H), 7.51(d, J=3.8Hz, 1H), 7.53(d, J=4.1Hz, 1H), 9.32(brs, 1H), 12.20(brs, 1H) |
| 2-55 | | (DMSO-d6-300) 1.61(dd, J=9.8, 5.7Hz, 1H), 2.03(dd, J=8.7, 5.7Hz, 1H), 2.68(s, 3H), 2.75(dd, J=9.8, 8.7Hz, 1H), 7.14-7.30(m, 5H), 7.33(d, J=4.1Hz, 1H), 7.52(d, J=4.1Hz, 1H), 8.02(s, 1H), 9.22(s, 1H), 12.22(s, 1H) |

TABLE 2-12

| Example | Structural formula | NMR |
|---|---|---|
| 2-56 | | (DMSO-d6-300) 1.61(dd, J=8.9, 5.8Hz, 1H), 1.99(dd, J=8.9, 5.8Hz, 1H), 2.69(d, J=8.9Hz, 1H), 5.25(s, 2H), 6.24(t, J=2.1Hz, 1H), 6.98(d, J=7.5Hz, 1H), 7.10-7.23(m, 3H), 7.43(d, J=1.5Hz, 1H), 7.56(d, J=3.8Hz, 1H), 7.72(d, J=1.9Hz, 1H), 7.83(d, J=3.8Hz, 1H), 8.01-8.10(m, 2H), 8.62(d, J=1.5Hz, 1H), 9.20(s, 1H), 12.20(brs, 1H) |

TABLE 2-12-continued

| Example | Structural formula | NMR |
|---|---|---|
| 2-57 | | (DMSO-d6-300)<br>1.62(dd, J=9.0, 5.7Hz, 1H),<br>2.00(dd, J=9.0, 5.7Hz, 1H),<br>2.71(t, J=9.0Hz, 1H), 3.24(s,<br>3H), 4.33(s, 2H), 7.06-7.24(m,<br>4H), 7.56(d, J=3.8Hz, 1H),<br>7.83(d, J=4.1Hz, 1H), 8.00-<br>8.10(m, 2H), 8.62(d, J=2.3Hz,<br>1H), 9.18(brs, 1H), 12.17(brs,<br>1H) |
| 2-58 | | (DMSO-d6-300)<br>1.13(m, 1H), 1.26(q, J=4.8Hz,<br>1H), 1.46(d, J=7.9Hz, 1H), 1.66-<br>1.86(m, 5H), 1.91-2.06(m, 1H),<br>2.15-2.27(m, 1H), 7.45-7.55(m,<br>4H), 7.73(d, J=8.7Hz, 2H),<br>8.78(brs, 1H), 12.33(brs, 2H) |
| 2-59 | | (DMSO-d6-300)<br>0.87-0.90(m, 6H), 1.15-1.23(m,<br>3H), 1.37-1.40(m, 1H), 7.48-<br>7.54(m, 4H), 7.73(dd, J=6.8,<br>1.9Hz, 2H), 8.89(s, 1H), 12.52(s,<br>1H) |
| 2-60 | | (CDCl3-300)<br>2.04-2.16(m, 2H), 2.95(t,<br>J=9.6Hz, 1H), 6.11(brs, 1H),<br>7.11-7.29(m, 5H), 7.39(d,<br>J=4.1Hz, 1H), 7.51(d, J=3.8Hz,<br>1H), 7.79(s, 1H) |

TABLE 2-13

| Example | Structural formula | NMR |
|---|---|---|
| 2-61 | | (CDCl3-300)<br>1.17-1.37(m, 2H), 1.42-1.84(m,<br>10H), 5.63(brs, 1H), 7.20(d,<br>J=6.0Hz, 1H), 7.41(d, J=9.0Hz,<br>2H), 7.49-7.58(m, 3H) |

TABLE 2-13-continued

| Example | Structural formula | NMR |
|---|---|---|
| 2-62 | | (CDCl3-300) 0.92(s, 9H), 1.49(t, J=9.0Hz, 1H), 1.62-1.73(m, 2H), 5.70(brs, 1H), 7.22(d, J=3.0Hz, 1H), 7.41(d, J=9.0Hz, 2H), 7.51-7.57(m, 3H) |
| 2-63 | | (DMSO-d6-300) 1.67(dd, J=9.6, 5.8Hz, 1H), 2.09(dd, J=8.5, 5.8Hz, 1H), 2.66(t, J=9.0Hz, 1H), 4.52(d, J=14.7Hz, 1H), 4.73(d, J=14.7Hz, 1H), 5.05(brs, 1H), 7.04(d, J=7.2Hz, 1H), 7.11(t, J=7.3Hz, 1H), 7.19(t, J=7.5Hz, 1H), 7.37(d, J=6.8Hz, 1H), 7.53(d, J=8.7Hz, 2H), 7.58(q, J=3.8Hz, 2H), 7.76(d, J=8.7Hz, 2H), 9.25(brs, 1H), 12.17(brs, 1H) |
| 2-64 | | (acetone-d6-400) 1.58-2.04(m, 2H), 2.51-3.47(complexm, 12H), 6.81-7.41 (m, 9H) |
| 2-65 | | (DMSO-d6-400) 1.60(dd, J=5.5, 9.7Hz, 1H), 2.01(dd, J=5.6, 8.6Hz, 1H), 2.72(t, J=9.2Hz, 1H), 6.83(d, J=8.7Hz, 2H), 7.16-7.33(m, 7H), 7.47-7.54(m, 3H), 9.09(bs, 1H), 9.87(bs, 1H), 12.2(bs, 1H) |

TABLE 2-14

| Example | Structural formula | NMR |
|---|---|---|
| 2-66 | | (MeOH-d4-400)<br>1.89(dd, J=5.8, 9.8Hz, 1H), 2.14(dd, J=5.8, 8.6Hz, 1H), 2.57(s, 3H), 2.83(t, J=9.2Hz, 1H), 7.15-7.27(m, 5H), 7.61(d, J=4.0Hz, 1H), 7.77(d, J=4.0Hz, 1H) |
| 2-67 | | (MeOH-d4-400)<br>1.96(dd, J=5.4, 9.5Hz, 1H), 2.06(dd, J=6.0, 8.2Hz, 1H), 2.53-2.57(m, 1H), 3.10-3.19(m, 4H), 3.34-3.49(m, 4H), 6.93-6.99(m, 4H), 7.10-7.28(m, 5H) |
| 2-68 | | (MeOH-d4-400)<br>1.96(dd, J=5.7, 9.8Hz, 1H), 2.12(dd, J=5.7, 8.5Hz, 1H), 2.75-2.79(m, 1H), 3.12-3.41(m, 4H), 3.46-3.83(m, 4H), 6.91(d, J=9.1Hz, 1H), 7.15-7.29(m, 5H), 7.73(dd, J=2.5, 9.0Hz, 1H), 8.34(s, 1H) |
| 2-69 | | (DMSO-d6-300)<br>1.67(q, J=5.1Hz, 1H), 2.05(q, J=5.1Hz, 1H), 2.69-3.60(m, 11H), 7.15-7.31(m, 4H), 7.51-7.61(m, 4H), 7.72-7.79(m, 2H), 9.13(brs, 1H), 12.31(brs, 1H) |

TABLE 2-14-continued
| Example | Structural formula | NMR |
|---|---|---|
| 2-70 | 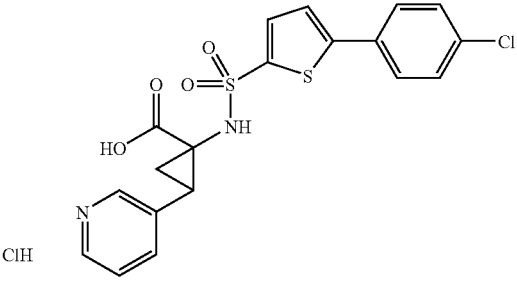 | (MeOH-d4-300) 2.14(dd, J=6.0, 9.0Hz, 1H), 2.31(dd, J=6.0, 9.0Hz, 1H), 3.18(t, J=9.0Hz, 1H), 7.38-7.46(m, 3H), 7.61(d, J=6.0Hz, 1H), 7.66(d, J=9.0Hz, 2H), 8.04(t, J=6.0Hz, 1H), 8.63(d, J=6.0Hz, 1H), 8.73(d, J=6.0Hz, 1H), 8.80(s, 1H) |
TABLE 2-15
| Example | Structural formula | NMR |
|---|---|---|
| 2-71 | 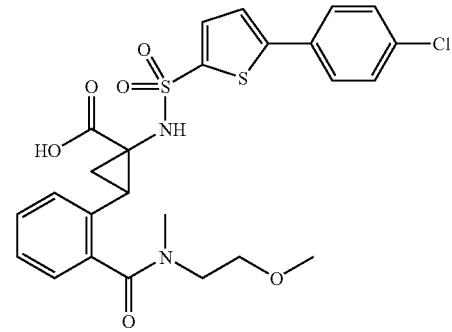 | (DMSO-d6-300) 1.46-1.76(m, 1H), 1.77-2.00(m, 1H), 2.65-2.75(m, 4H), 2.95-3.43(m, 5H), 3.53-3.64(m, 2H), 7.12-7.28(m, 3H), 7.53-7.57(m, 4H), 7.72-7.78(m, 3H), 8.97(brs, 1H), 12.41(brs, 1H) |
| 2-72 | 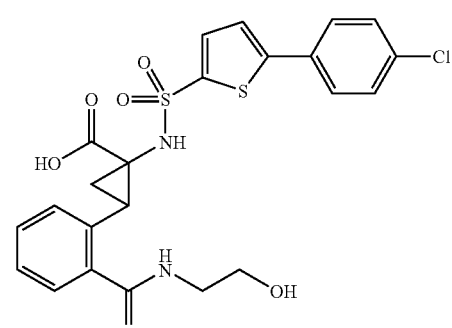 | (DMSO-d6-300) 1.69(dd, J=5.1, 2.6Hz, 1H), 1.87(dd, J=8.9, 5.8Hz, 1H), 2.96(t, J=9.0Hz, 1H), 3.28-3.31(m, 2H), 3.53-3.55(m, 2H), 4.98(brs, 1H), 7.20-7.34(m, 5H), 7.53-7.57(m, 4H), 7.75-7.76(m, 2H), 8.10(t, J=5.7Hz, 1H), 8.85(brs, 1H), 12.31(brs, 1H) |
| 2-73 | 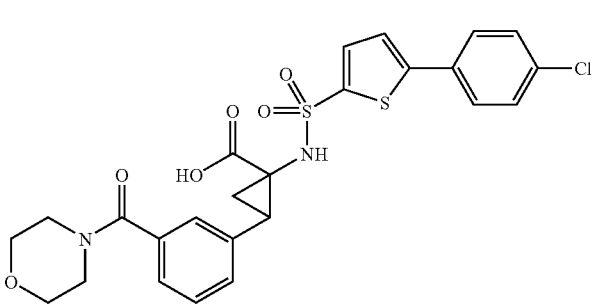 | (DMSO-d6-300) 1.66(dd, J=9.6, 5.8Hz, 1H), 2.08(dd, J=8.5, 6.2Hz, 1H), 2.81(t, J=8.9Hz, 1H), 3.49-3.64(m, 8H), 7.22-7.33(m, 4H), 7.49-7.59(m, 4H), 7.76(d, J=8.7Hz, 2H), 9.20(brs, 1H), 12.30(brs, 1H) |

TABLE 2-15-continued

| Example | Structural formula | NMR |
|---|---|---|
| 2-74 | | (DMSO-d6-300) 1.30(s, 6H), 1.68(dd, J=9.0, 5.7Hz, 1H), 2.08(dd, J=8.1, 7.0Hz, 1H), 2.80(t, J=9.0Hz, 1H), 3.49(d, J=6.0Hz, 2H), 4.92(t, J=6.2Hz, 1H), 7.29-7.35(m, 2H), 7.40-7.80(m, 9H), 9.22(brs, 1H), 12.25(brs, 1H) |
| 2-75 | | (DMSO-d6-300) 1.67(dd, J=9.8, 5.7Hz, 1H), 2.09(dd, J=8.3, 5.7Hz, 1H), 2.80(t, J=9.4Hz, 1H), 3.30(t, J=5.8Hz, 2H), 3.49(brt, J=5.7Hz, 2H), 4.71(brs, 1H), 7.30-7.36(m, 2H), 7.50-7.59(m, 4H), 7.65-7.78(m, 4H), 8.37(t, J=5.1Hz, 1H), 9.23(brs, 1H), 12.25(brs, 1H) |

TABLE 2-16

| Example | Structural formula | NMR |
|---|---|---|
| 2-76 | | (DMSO-d6-300) 1.25(brs, 1H), 1.97(brs, 1H), 2.73(brs, 1H), 3.40-3.64(m, 8H), 7.14-7.30(m, 4H), 7.52(d, J=8.7Hz, 2H), 7.58(s, 2H), 7.76(d, J=8.7Hz, 2H) |
| 2-77 | | (DMSO-d6-300) 1.33(s, 3H), 1.37(s, 3H), 1.75(dd, J=5.0, 2.5Hz, 1H), 2.03(dd, J=9.0, 5.7Hz, 1H), 3.00(t, J=9.4Hz, 1H), 4.02-4.15(m, 2H), 7.28-7.33(m, 2H), 7.53(d, J=8.7Hz, 2H), 7.60-7.61(m, 2H), 7.74-7.76(m, 4H) |

TABLE 2-16-continued

| Example | Structural formula | NMR |
|---|---|---|
| 2-78 | | (DMSO-d6-300) 1.28(s, 3H), 1.29(s, 3H), 1.63(dd, J=5.1, 2.6Hz, 1H), 1.89(dd, J=8.5, 5.5Hz, 1H), 2.75-2.88(m, 1H), 3.48(d, J=10.9Hz, 1H), 3.55(d, J=10.5Hz, 1H), 7.14-7.27(m, 4H), 7.55(dt, J=12.4, 4.8Hz, 4H), 7.75(d, J=8.7Hz, 2H) |
| 2-79 | | (DMSO-d6-300) 1.61(dd, J=8.9, 6.0Hz, 1H), 2.00(dd, J=8.3, 6.0Hz, 1H), 2.48(s, 3H), 2.70(dd, J=8.9, 8.3Hz, 1H), 7.13-7.28(m, 5H), 7.39(d, J=4.1Hz, 1H), 7.56(d, J=4.1Hz, 1H), 7.58(s, 1H) |
| 2-80 | | (MeOH-d4-400) 1.78-1.84(m, 1H), 2.05-2.08(m, 1H), 2.63(s, 3H), 2.71(t, J=8.7Hz, 1H), 7.12-7.24(m, 5H), 7.99(d, J=8.3Hz, 2H), 8.11(d, J=8.1Hz, 2H) |

TABLE 2-17

| Example | Structural formula | NMR |
|---|---|---|
| 2-81 | | (MeOH-d4-400) 1.86(dd, J=5.8, 9.9Hz, 1H), 2.13(dd, J=5.8, 8.7Hz, 1H), 2.83(t, J=9.3Hz, 1H), 7.14-7.26(m, 5H), 7.57-7.70(m, 5H), 7.98-8.02(m, 2H) |

TABLE 2-17-continued

| Example | Structural formula | NMR |
|---|---|---|
| 2-82 | | (MeOH-d4-400)<br>1.90(dd, J=5.8, 9.8Hz, 1H),<br>2.12(dd, J=5.8, 8.7Hz, 1H),<br>2.81(t, J=9.2Hz, 1H), 7.02(d,<br>J=4.0Hz, 1H), 7.14-7.27(m, 5H),<br>7.43(d, J=4.1Hz, 1H) |
| 2-83 | | (MeOH-d4-400)<br>1.83(dd, J=5.7, 9.8Hz, 1H),<br>2.09(dd, J=5.7, 8.6Hz, 1H),<br>2.78(t, J=9.2Hz, 1H), 7.09-<br>7.26(m, 6H), 7.62(dd, J=1.3,<br>3.7Hz, 1H), 7.75(dd, J=1.3,<br>5.0Hz, 1H) |
| 2-84 | | (DMSO-d6-300)<br>1.61-1.73(m, 1H), 1.92-2.02(m,<br>1H), 2.12(t, J=19.2Hz, 3H), 7.07-<br>7.27(m, 5H), 7.67(d, J=3.8Hz,<br>1H), 7.70(s, 1H), 7.80(d,<br>J=3.8Hz, 1H) |
| 2-85 | | (DMSO-d6-300)<br>1.60(dd, J=9.6, 5.5Hz, 1H),<br>2.02(dd, J=8.7, 5.7Hz, 1H),<br>2.45(s, 3H), 2.74(t, J=9.2Hz,<br>1H), 6.82(s, 1H), 7.16-7.25(m,<br>5H), 7.59(d, J=4.0Hz, 1H),<br>7.64(d, J=4.0Hz, 1H), 9.28(s,<br>1H), 12.20(brs, 1H) |

TABLE 2-18

| Example | Structural formula | NMR |
|---|---|---|
| 2-86 | | (DMSO-d6-300) 1.69(dd, J=9.6, 5.5Hz, 1H), 2.05(dd, J=8.7, 5.3Hz, 1H), 2.40(s, 3H), 2.79(t, J=8.5Hz, 1H), 7.24-7.30(m, 2H), 7.35(t, J=9.0Hz, 1H), 7.51(d, J=9.0Hz, 2H), 7.56(s, 2H), 7.68-7.81(m, 4H), 9.21(s, 1H), 12.29(brs, 1H) |
| 2-87 | | (DMSO-d6-300) 1.55-1.63(m, 1H), 1.96-2.04(m, 1H), 2.46(s, 3H), 2.65-2.76(m, 1H), 7.13-7.29(m, 6H), 7.38(d, J=4.1Hz, 1H), 7.54(d, J=4.1Hz, 1H), 8.55(s, 1H), 9.12(s, 1H), 12.19(s, 1H) |
| 2-88 | | (DMSO-d6-300) 1.59(dd, J=5.5, 9.2Hz, 1H), 2.02(dd, J=9.2, 5.5Hz, 1H), 2.47(s, 3H), 2.74(t, J=9.2Hz, 1H), 7.15-7.30(m, 5H), 7.45(d, J=4.1Hz, 1H), 7.59(d, J=4.1Hz, 1H), 9.23(s, 1H), 12.19(s, 1H) |
| 2-89 | | (DMSO-d6-300) 1.71-1.74(m, 1H), 2.07(brs, 1H), 2.11(s, 3H), 2.60-2.67(m, 1H), 3.26(s, 3H), 3.48-3.53(m, 3H), 3.67(d, J=13.2Hz, 1H), 7.08-7.20(m, 4H), 7.54-7.57(m, 4H), 7.75(d, J=9.0Hz, 2H) |
| 2-90 | | (DMSO-d6-300) 0.94(t, J=7.3Hz, 3H), 1.63-1.69(m, 3H), 1.97-2.03(m, 1H), 2.69-2.79(m, 3H), 6.88(s, 1H), 7.16-7.23(m, 5H), 7.60(d, J=4.1Hz, 1H), 7.65(d, J=4.1Hz, 1H), 12.19(brs, 1H) |

TABLE 2-19
| Example | Structural formula | NMR |
|---|---|---|
| 2-91 | 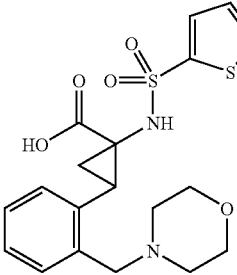 | (DMSO-d6-300) 1.78-1.83(m, 1H), 1.93-1.98(m, 1H), 2.35-2.39(m, 4H), 2.66-2.70(m, 1H), 3.27(d, J=12.1Hz, 1H), 3.48-3.57(m, 4H), 3.72(d, J=13.6Hz, 1H), 7.02-7.09(m, 3H), 7.17-7.20(m, 1H), 7.50(d, J=8.3Hz, 2H), 7.55(s, 2H), 7.73(d, J=8.3Hz, 2H) |
| 2-92 | 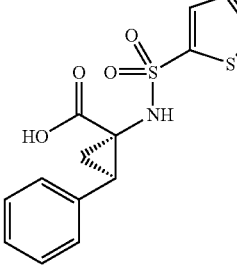 | (DMSO-d6-300) 1.25(t, J=7.7Hz, 3H), 1.61(dd, J=5.1, 2.6Hz, 1H), 2.01(dd, J=8.7, 5.7Hz, 1H), 2.72(t, J=8.9Hz, 1H), 2.80(q, J=7.5Hz, 1H), 6.88(s, 1H), 7.16-7.27(m, 5H), 7.61(d, J=3.8Hz, 1H), 7.66(d, J=4.1Hz, 1H), 12.23(brs, 1H) |
| 2-93 | 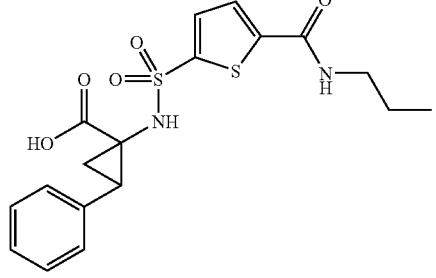 | (MeOH-d4-400) 0.95(t, J=7.41Hz, 3H), 1.57-1.66(m, 2H), 1.89(dd, J=5.6, 9.6Hz, 1H), 2.10(dd, J=5.9, 8.0Hz, 1H), 2.72(t, J=9.0Hz, 1H), 3.28-3.30(m, 2H), 7.12-7.25(m, 5H), 7.56(d, J=3.9Hz, 1H), 7.59(d, J=3.9Hz, 1H) |
| 2-94 | 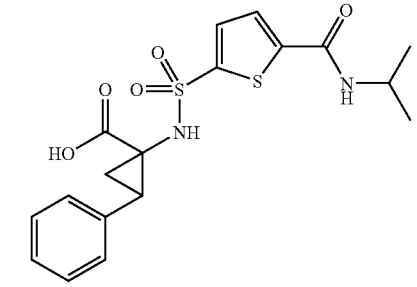 | (MeOH-d4-400) 1.23(d, J=6.6Hz, 6H), 1.85-1.91(m, 1H), 2.09-2.13(m, 1H), 2.76(t, J=7.9Hz, 1H), 4.11-4.18(m, 1H), 7.12-7.27(m, 5H), 7.55(s, 1H), 7.63(s, 1H) |
| 2-95 | 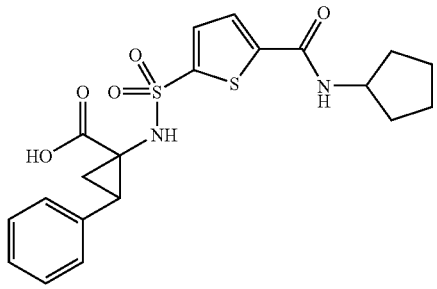 | (MeOH-d4-400) 1.52-2.17(m, 10H), 2.79(t, J=9.3Hz, 1H), 4.22-4.30(m, 1H), 7.12-7.28(m, 5H), 7.55(s, 1H), 7.64(s, 1H), |

TABLE 2-20
| Example | Structural formula | NMR |
|---|---|---|
| 2-96 | 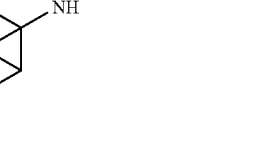 | (MeOH-d4-400) 1.92(dd, J=5.4, 9.2Hz, 1H), 2.13-2.18(m, 1H), 2.81(t, J=8.9Hz, 1H), 7.14-7.37(m, 8H), 7.61-7.66(m, 3H), 7.83(s, 1H) |
| 2-97 | 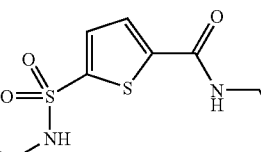 | (MeOH-d4-400) 1.85-1.92(m, 1H), 2.09-2.15(m, 1H), 2.43-2.54(m, 2H), 2.78(t, J=9.3Hz, 1H), 3.59(t, J=6.9Hz, 2H), 7.11-7.29(m, 5H), 7.58(s, 2H) |
| 2-98 |  | (CDCl3-300) 2.15-2.17(m, 1H), 2.35-2.39(m, 1H), 2.87(t, J=9.4Hz, 1H), 5.35-5.46(m, 2H), 6.65(d, J=2.3Hz, 1H), 7.20-7.26(m, 5H), 7.37(d, J=3.8Hz, 1H), 7.61(d, J=3.8Hz, 1H) |
| 2-99 | 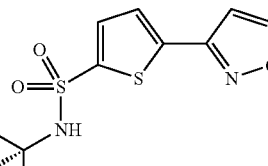 | (DMSO-d6-300) 1.62(dd, J=9.8, 5.7Hz, 1H), 1.99-2.02(m, 1H), 2.71(t, J=8.9Hz, 1H), 7.31-7.43(m, 6H), 7.65(d, J=4.1Hz, 1H), 7.68(s, 1H), 7.82(d, J=4.1Hz, 1H) |
| 2-100 |  | (DMSO-d6-300) 1.27(d, J=5.1Hz, 1H), 1.34(s, 3H), 2.02(d, J=5.1Hz, 1H), 4.03(s, 2H), 7.12-7.19(m, 5H), 7.62(dd, J=8.3, 1.7Hz, 1H), 7.79(dd, J=8.3, 1.7Hz, 1H), 7.86(s, 1H), 7.95-7.97(m, 2H), 8.08(d, J=8.3Hz, 1H), 8.86(s, 1H), 11.91(s, 1H) |

TABLE 2-21

| Example | Structural formula | NMR |
|---|---|---|
| 2-101 | | (DMSO-d6-400) 1.38-1.42(m, 4H), 2.10(d, J=5.6Hz, 1H), 7.11-7.26(m, 5H), 7.49-7.60(m, 4H), 7.72-7.77(m, 2H), 9.20(brs, 1H), 12.11(brs, 1H) |
| 2-102 | | (CDCl3-300) 2.10-2.15(m, 2H), 2.94(t, J=9.4Hz, 1H), 5.85(brs, 1H), 6.83(t, J=55.8Hz, 1H), 7.06(d, J=3.8Hz, 1H), 7.20(d, J=47.5Hz, 7H), 7.49(d, J=4.1Hz, 1H) |
| 2-103 | | (MeOH-d4-400) 1.80-1.84(m, 1H), 2.07-2.13(m, 1H), 2.73(t, J=8.6Hz, 1H), 7.09-7.26(m, 5H), 7.45(s, 1H), 7.51(s, 1H) |
| 2-104 | | (MeOH-d4-400) 1.20(t, J=7.24Hz, 3H), 1.89(dd, J=5.6, 9.8Hz, 1H), 2.12(dd, J=5.8, 8.7Hz, 1H), 2.80(t, J=9.2Hz, 1H), 3.37(q, J=7.2Hz, 2H), 7.13-7.27(m, 5H), 7.56(d, J=4.0Hz, 1H), 7.58(d, J=4.0Hz, 1H) |
| 2-105 | | (MeOH-d4-400) 0.60-0.64(m, 2H), 0.79(dt, J=5.0, 7.1Hz, 2H), 1.89(dd, J=5.7, 9.8Hz, 1H), 2.10(dd, J=5.6, 8.7Hz, 1H), 2.74(t, J=9.1Hz, 1H), 2.77-2.84(m, 1H), 7.12-7.25(m, 5H), 7.54(d, J=4.0Hz, 1H), 7.56(d, J=4.0Hz, 1H) |

TABLE 2-22

| Example | Structural formula | NMR |
|---|---|---|
| 2-106 | | (MeOH-d4-400) 1.91(dd, J=5.8, 9.8Hz, 1H), 2.12-2.18(m, 1H), 2.84(t, J=9.3Hz, 1H), 4.05(dd, J=9.8, 18.9Hz, 2H), 7.15-7.27(m, 5H), 7.59(d, J=4.0Hz, 1H), 7.67(d, J=4.0Hz, 1H) |
| 2-107 | | (DMSO-d6-300) 1.39(s, 3H), 1.42(d, J=5.7Hz, 1H), 2.06-2.19(m, 1H), 2.11(t, J=10.2Hz, 3H), 7.08-7.12(m, 3H), 7.24(t, J=7.3Hz, 2H), 7.65(d, J=3.8Hz, 1H), 7.71(s, 1H), 7.80(d, J=4.1Hz, 1H), 9.37(brs, 1H), 12.12(brs, 1H) |
| 2-108 | | (MeOH-d4-300) 1.92(dd, J=9.8, 5.7Hz, 1H), 1.98(s, 3H), 2.11(dd, J=8.7, 5.7Hz, 1H), 2.75(t, J=9.2Hz, 1H), 2.86(t, J=7.0Hz, 2H), 4.20(t, J=7.0Hz, 2H), 7.02-7.06(m, 1H), 7.08-7.18(m, 3H), 7.36-7.45(m, 3H), 7.58(d, J=3.8Hz, 1H), 7.66(d, J=8.3Hz, 2H) |
| 2-109 | | (MeOH-d4-300) 1.92(dd, J=9.8, 5.7Hz, 1H), 2.08-2.13(m, 1H), 2.71-2.78(m, 3H), 3.69(t, J=6.8Hz, 2H), 7.03(d, J=6.0Hz, 1H), 7.07-7.18(m, 3H), 7.36-7.45(m, 3H), 7.58(dd, J=4.1, 0.4Hz, 1H), 7.62-7.68(m, 2H) |
| 2-110 | | (DMSO-d6-300) 1.62(dd, J=9.8, 5.7Hz, 1H), 1.98-1.99(m, 1H), 2.68(t, J=8.9Hz, 1H), 3.34(s, 3H), 4.59(s, 2H), 7.16-7.23(m, 6H), 7.60(d, J=4.1Hz, 1H), 7.71(d, J=4.1Hz, 1H) |

TABLE 2-23

| Example | Structural formula | NMR |
|---|---|---|
| 2-111 | | (DMSO-d6-300) 1.63(dd, J=8.5, 5.8Hz, 1H), 2.03(dd, J=8.5, 5.8Hz, 1H), 2.75(t, J=8.5Hz, 1H), 6.55(s, 1H), 7.18-7.28(m, 5H), 7.70(d, J=4.1Hz, 1H), 7.89(d, J=4.1Hz, 1H), 8.28(s, 1H) |
| 2-112 | | (DMSO-d6-300) 1.39(s, 3H), 1.42(d, J=5.7Hz, 1H), 2.11(d, J=5.7Hz, 1H), 7.12-7.28(m, 5H), 7.68(d, J=3.8Hz, 1H), 7.89(d, J=3.8Hz, 1H), 8.28(s, 1H), 9.42(s, 1H), 12.13(s, 1H) |
| 2-113 | | (DMSO-d6-300) 1.66(dd, J=9.8, 5.7Hz, 1H), 2.06(dd, J=8.5, 5.5Hz, 1H), 2.78(t, J=9.4Hz, 1H), 7.20-7.30(m, 5H), 7.41-7.43(m, 2H), 7.47(d, J=4.1Hz, 1H), 7.57(d, J=3.8Hz, 1H), 7.87-7.89(m, 2H), 8.00-8.02(m, 1H), 9.29(brs, 1H), 12.26(brs, 1H) |
| 2-114 | | (DMSO-d6-300) 1.66(dd, J=9.8, 5.7Hz, 1H), 2.05(dd, J=8.5, 5.8Hz, 1H), 2.77(t, J=9.4Hz, 1H), 7.19-7.27(m, 5H), 7.56-7.64(m, 3H), 7.68-7.69(m, 2H), 7.74(d, J=3.8Hz, 1H), 7.91-7.93(m, 2H), 12.27(brs, 1H) |

TABLE 2-23-continued

| Example | Structural formula | NMR |
|---|---|---|
| 2-115 | | (DMSO-d6-400)<br>1.64(dd, J=10.2, 5.8Hz, 1H),<br>2.04(dd, J=8.6, 5.8Hz, 1H),<br>2.76(t, J=9.3Hz, 1H), 6.03(d,<br>J=45.5Hz, 2H), 7.14-7.28(m, 5H),<br>7.61(d, J=4.2Hz, 1H), 7.82(d,<br>J=4.2Hz, 1H), 9.35(brs, 1H),<br>12.20(brs, 1H) |

TABLE 2-24

| Example | Structural formula | NMR |
|---|---|---|
| 2-116 | | (acetone-d6-400)<br>1.15(t, J=7.3Hz, 3H), 1.92(dd,<br>J=5.7, 9.8Hz, 1H), 2.16(dd,<br>J=5.7, 8.7Hz, 1H), 2.91(t,<br>J=9.3Hz, 1H), 3.03(q, J=7.3Hz,<br>2H), 7.16-7.29(m, 5H), 8.01(s,<br>1H), 8.41(s, 1H) |
| 2-117 | | (acetone-d6-400)<br>0.98(t, J=7.4Hz, 3H),<br>1.72(sextet, J=7.3Hz, 2H),<br>1.91(dd, J=5.7, 9.8Hz, 1H),<br>2.16(dd, J=5.8, 8.7Hz, 1H),<br>2.91(t, J=9.3Hz, 1H), 2.98(t,<br>J=7.2Hz, 2H), 7.16-7.29(m, 5H),<br>8.03(s, 1H), 8.42(s, 1H) |
| 2-118 | 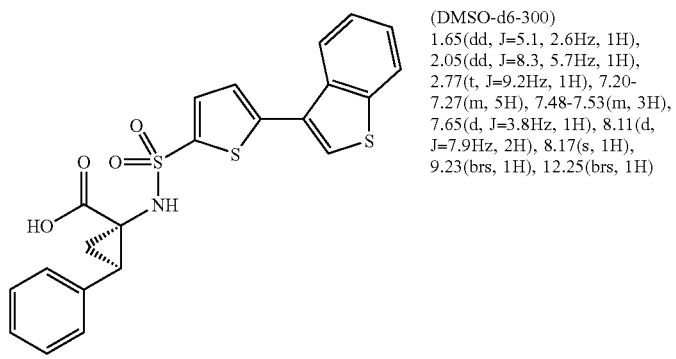 | (DMSO-d6-300)<br>1.65(dd, J=5.1, 2.6Hz, 1H),<br>2.05(dd, J=8.3, 5.7Hz, 1H),<br>2.77(t, J=9.2Hz, 1H), 7.20-<br>7.27(m, 5H), 7.48-7.53(m, 3H),<br>7.65(d, J=3.8Hz, 1H), 8.11(d,<br>J=7.9Hz, 2H), 8.17(s, 1H),<br>9.23(brs, 1H), 12.25(brs, 1H) |

TABLE 2-24-continued

| Example | Structural formula | NMR |
|---|---|---|
| 2-119 | | (CDCl3-300) 2.05-2.16(m, 2H), 2.92(t, J=9.0Hz, 1H), 6.11(brs, 1H), 6.99(t, J=54.0Hz, 1H), 7.12-7.28(m, 5H), 7.36(d, J=3.0Hz, 1H), 7.57(d, J=3.0Hz, 1H), 7.64(s, 1H) |
| 2-120 | | (DMSO-d6-400) 1.63(dd, J=9.7, 5.6Hz, 1H), 2.03(dd, J=8.6, 5.8Hz, 1H), 2.74(t, J=9.3Hz, 1H), 5.83(d, J=46.8Hz, 2H), 7.15-7.28(m, 5H), 7.59(d, J=4.2Hz, 1H), 7.73(d, J=4.2Hz, 1H), 8.03(d, J=2.3Hz, 1H), 9.27(brs, 1H), 12.20(brs, 1H) |

TABLE 2-25

| Example | Structural formula | NMR |
|---|---|---|
| 2-121 | | (DMSO-d6-400) 1.39(s, 3H), 1.42(d, J=5.6Hz, 1H), 2.10(d, J=5.6Hz, 1H), 5.83(d, J=46.4Hz, 2H), 7.10-7.27(m, 5H), 7.57(d, J=3.7Hz, 1H), 7.73(d, J=3.7Hz, 1H), 8.03(d, J=2.3Hz, 1H), 9.27(brs, 1H), 12.11(brs, 1H) |
| 2-122 | | (DMSO-d6-400) 1.66(dd, J=5.1, 2.6Hz, 1H), 2.04(dd, J=8.3, 5.6Hz, 1H), 2.74(t, J=9.5Hz, 1H), 7.14-7.27(m, 5H), 7.30(t, J=7.9Hz, 1H), 7.37(t, J=7.9Hz, 1H), 7.50(s, 1H), 7.61(d, J=3.7Hz, 1H), 7.62-7.71(m, 3H), 12.27(brs, 1H) |

TABLE 2-25-continued

| Example | Structural formula | NMR |
|---|---|---|
| 2-123 | | (MeOH-d4-300) 0.85(d, J=9.0Hz, 3H), 0.92(d, J=9.0Hz, 3H), 1.91-2.05(m, 1H), 1.93(d, J=6.0Hz, 1H), 2.02(d, J=6.0Hz, 1H), 7.09-7.24(m, 5H), 7.36(d, J=6.0Hz, 1H), 7.42(d, J=9.0Hz, 2H), 7.55(d, J=6.0Hz, 1H), 7.64(d, J=9.0Hz, 2H) |
| 2-124 | | (CDCl3-300) 2.08(t, J=18.0Hz, 3H), 2.16-2.25(m, 2H), 2.93-3.01(m, 1H). 6.03(brs, 1H), 7.17-7.32(m, 5H), 7.38(d, J=3.0Hz, 1H), 7.57(s, 1H), 7.62(d, J=3.0Hz, 1H) |
| 2-125 | | (MeOH-d4-400) 1.93(dd, J=5.5, 9.7Hz, 1H), 2.11(dd, J=5.7, 8.4Hz, 1H), 2.77(t, J=9.1Hz, 1H), 2.83-2.86(m, 2H), 3.58-3.70(m, 2H), 4.51(q, J=15.2Hz, 2H), 6.95-7.39(m, 9H) |

TABLE 2-26

| Example | Structural formula | NMR |
|---|---|---|
| 2-126 | | (MeOH-d4-400) 1.94-1.99(m, 1H), 2.14(dd, J=5.8, 8.4Hz, 1H), 2.80(t, J=9.2Hz, 1H), 3.71-3.85(m, 2H), 4.23-4.25(m, 2H), 4.70-4.79(m, 2H), 7.12-7.75(m, 10H) |

TABLE 2-26-continued
| Example | Structural formula | NMR |
|---|---|---|
| 2-127 | 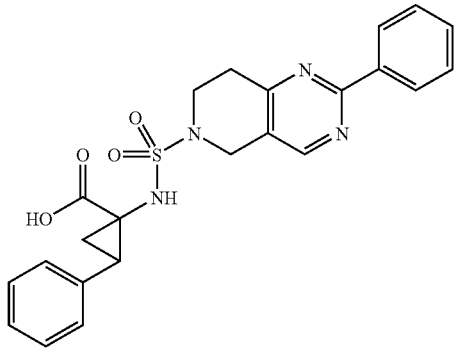 | (MeOH-d4-400) 1.97(dd, J=5.6, 9.8Hz, 1H), 2.13(dd, J=5.7, 8.5Hz, 1H), 2.81(t, J=9.1Hz, 1H), 3.10(t, J=5.6Hz, 2H), 3.70(m, 2H), 4.52(q, J=45.9Hz, 2H), 7.14-8.36(m, 10H), 8.60(s, 1H) |
| 2-128 | 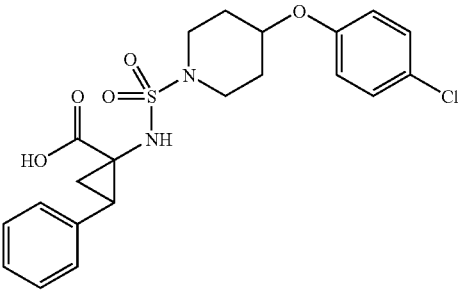 | (MeOH-d4-400) 1.76-1.86(m, 2H), 1.92-1.99(m, 3H), 2.12(dd, J=5.8, 8.5Hz, 1H), 2.82(t, J=9.1Hz, 1H), 3.17-3.27(m, 2H), 3.43-3.52(m, 2H), 4.48(td, J=3.2, 9.9Hz, 1H), 6.90-6.94(m, 2H), 7.16-7.29(m, 7H) |
| 2-129 | 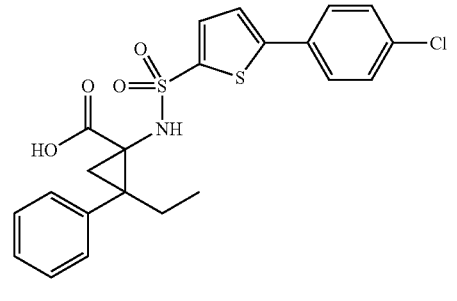 | (MeOH-d4-400) 0.71-0.80(m, 3H), 1.49-1.99(m, 3H), 2.04-2.15(m, 1H), 7.14-7.65(m, 11H) |
| 2-130 | 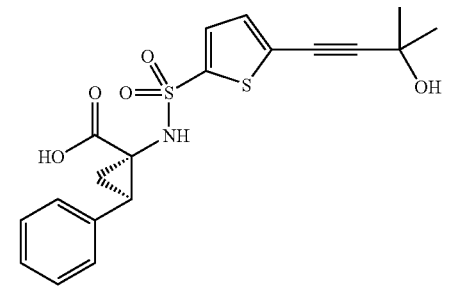 | (DMSO-d6-300) 1.46(s, 6H), 1.61(dd, J=9.8, 5.7Hz, 1H), 2.00-2.02(m, 1H), 2.71(t, J=8.5Hz, 1H), 5.64(brs, 1H), 7.19-7.29(m, 6H), 7.47(d, J=3.8Hz, 1H), 12.24(brs, 1H) |

TABLE 2-27

| Example | Structural formula | NMR |
|---|---|---|
| 2-131 | | (DMSO-d6-300) 1.36(s, 3H), 1.46(d, J=4.5Hz, 1H), 2.03(d, J=4.5Hz, 1H), 7.09-7.25(m, 6H), 7.56(d, J=4.1Hz, 1H), 7.84(d, J=3.4Hz, 1H), 8.07(dd, J=14.5, 8.5Hz, 2H), 8.65(s, 1H), 11.87(brs, 1H) |
| 2-132 | | (DMSO-d6-300) 1.30(s, 9H), 1.59(dd, J=9.8, 5.7Hz, 1H), 2.02(dd, J=8.7, 5.7Hz, 1H), 2.74(t, J=9.2Hz, 1H), 7.19-7.29(m, 5H), 7.44(d, J=3.8Hz, 1H), 9.24(brs, 1H), 12.22(brs, 1H) |
| 2-133 | | (DMSO-d6-300) 0.98(t, J=7.3Hz, 3H), 1.48-1.64(m, 3H), 1.88-2.05(m, 1H), 2.37-2.40(m, 2H), 2.60-2.76(m, 1H), 7.11-7.29(m, 6H), 7.44(d, J=4.1Hz, 1H), 12.23(brs, 1H) |
| 2-134 | | (DMSO-d6-300) 1.68(dd, J=9.6, 5.5Hz, 1H), 1.95(dd, J=6.8, 5.3Hz, 1H), 2.51-2.65(m, 1H), 7.09-7.34(m, 5H), 7.52-7.81(m, 5H), 7.93-8.08(m, 2H), 12.38(brs, 1H) |
| 2-135 | | (DMSO-d6-300) 1.62(dd, J=9.6, 5.5Hz, 1H), 2.02(dd, J=8.5, 5.8Hz, 1H), 2.74(t, J=9.0Hz, 1H), 6.59(t, J=6.4Hz, 1H), 6.68-6.78(m, 2H), 7.15-7.30(m, 5H), 7.34(d, J=3.8Hz, 1H), 7.41(d, J=9.0Hz, 1H), 7.52(d, J=3.8Hz, 1H), 7.99(d, J=1.1Hz, 1H), 8.23(d, J=6.8Hz, 1H), 9.11(brs, 1H), 12.23(brs, 1H) |

TABLE 2-28
| Example | Structural formula | NMR |
|---|---|---|
| 2-136 | 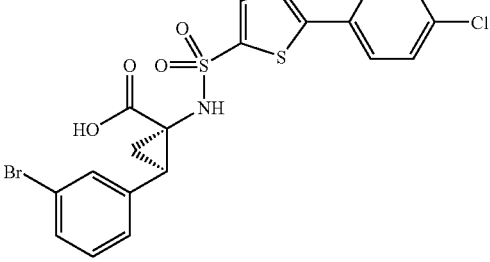 | (DMSO-d6-300) 1.72(dd, J=8.9, 5.5Hz, 1H), 1.90(dd, J=11.9, 5.5Hz, 1H), 2.52-2.60(m, 1H), 7.11-7.22(m, 2H), 7.26-7.38(m, 2H), 7.48-7.63(m, 5H), 7.76(d, J=8.7Hz, 2H), 12.19(brs, 1H) |
| 2-137 | 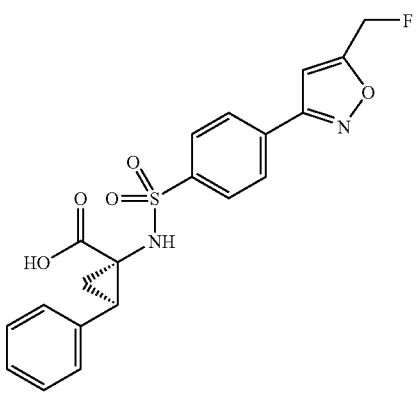 | (DMSO-d6-300) 1.52(dd, J=9.4, 5.7Hz, 1H), 1.92-1.94(m, 1H), 2.61-2.65(m, 1H), 5.65(d, J=47.1Hz, 2H), 7.17-7.22(m, 5H), 7.38(d, J=3.4Hz, 1H), 7.93(d, J=8.7Hz, 2H), 8.08(d, J=8.7Hz, 2H) |
| 2-138 | 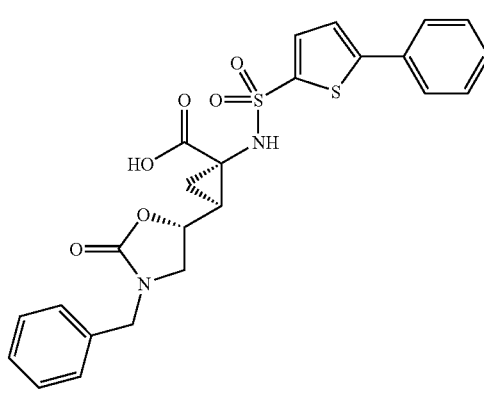 | (CDCl3-300) 1.42-1.52(m, 1H), 1.57-1.66(m, 3.54(m, 2H), 4.33(s, 2H), 4.63-4.76(m, 1H), 6.54(brs, 1H), 7.06(d, J=3.8Hz, 1H), 7.24(q, J=45.2Hz, 6H), 7.36(d, J=8.7Hz, 2H), 7.43(d, J=8.7Hz, 2H) |
| 2-139 | 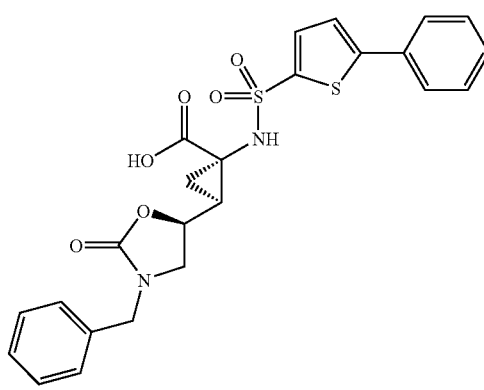 | (CDCl3-300) 1.64-1.82(m, 2H), 1.92-2.04(m, 1H), 3.23(dd, J=8.7, 4.9Hz, 1H), 3.52(dd, J=8.9, 4.4Hz, 1H), 4.33(d, J=14.7Hz, 1H), 4.40(d, J=14.7Hz, 1H), 4.57-4.69(m, 1H), 7.14-7.36(m, 8H), 7.49(d, J=7.9Hz, 2H), 7.64(d, J=3.8Hz, 1H) |

TABLE 2-28-continued

| Example | Structural formula | NMR |
|---|---|---|
| 2-140 | | (CDCl3-300) 2.06(dd, J=6.0, 9.0Hz, 1H), 2.15(dd, J=6.0, 9.0Hz, 1H), 3.04(t, J=9.0Hz, 1H), 5.71(brs, 1H), 6.80(d, J=15.0Hz, 1H), 7.16-7.29(m, 5H), 7.36-7.46(m, 5H), 7.52(d, J=15.0Hz, 1H) |

TABLE 2-29

| Example | Structural formula | NMR |
|---|---|---|
| 2-141 | | (acetone-d6-400) 1.90(dd, J=9.2, 5.7Hz, 1H), 2.14(dd, J=8.8, 5.7Hz, 1H), 2.85(dd, J=9.2, 8.8Hz, 1H), 4.07(s, 2H), 7.15-7.30(m, 6H), 7.44-7.48(m, 1H), 7.68(brs, 1H), 7.92-7.96(m, 1H), 7.99-8.05(m, 2H), 8.07-8.11(m, 1H) |
| 2-142 | | (acetone-d6-400) 1.90(dd, J=9.4, 5.3Hz, 1H), 2.14(dd, J=8.8, 5:3Hz, 1H), 2.85(dd, J=9.4, 8.8Hz, 1H), 4.08(s, 2H), 7.15-7.32(m, 6H), 7.48-7.52(m, 1H), 7.72(s, 1H), 7.94-8.08(m, 3H), 8.10-8.15(m, 1H) |
| 2-143 | | (MeOH-d4-400) 1.76-1.87(m, 2H), 1.95(dd, J=5.7, 9.8Hz, 1H), 1.99-2.06(m, 2H), 2.10(dd, J=5.7, 8.5Hz, 1H), 2.74(t, J=9.1Hz, 1H), 3.16-3.30(m, 2H), 3.45-3.56(m, 2H), 4.47-4.52(m, 1H), 6.89-6.94(m, 3H), 7.15-7.29(m, 7H) |

TABLE 2-29-continued

| Example | Structural formula | NMR |
|---|---|---|
| 2-144 | | (MeOH-d4-400) 1.80-1.89(m, 2H), 1.95(dd, J=5.7, 9.8Hz, 1H), 2.00-2.09(m, 2H), 2.13(dd, J=5.7, 8.6Hz, 1H), 2.81(t, J=9.2Hz, 1H), 3.20-3.30(m, 2H), 3.46-3.55(m, 2H), 4.62(tt, J=3.4, 7.0Hz, 1H), 7.08(d, J=8.7Hz, 2H), 7.16-7.29(m, 5H), 7.56(d, J=8.7Hz, 2H) |
| 2-145 | | (MeOH-d4-400) 1.75-1.85(m, 2H), 1.92-2.03(m, 3H), 2.12(dd, J=5.7, 8.6Hz, 1H), 2.81(t, J=9.2Hz, 1H), 3.16-3.26(m, 2H), 3.44-3.52(m, 2H), 4.42(tt, 3.4, 7.0Hz, 1H), 6.91-7.01(m, 4H), 7.16-7.29(m, 5H) |

TABLE 2-30

| Example | Structural formula | NMR |
|---|---|---|
| 2-146 | | (MeOH-d4-400) 0.69-0.78(m, 3H), 1.52-2.09(m, 4H), 3.93-3.98(m, 2H), 7.09-8.03(m, 11H) |
| 2-147 | | (MeOH-d4-400) 1.13(s, 3H), 1.25(s, 3H), 1.38-1.43(m, 1H), 1.51(d, J=5.5Hz, 1H), 7.38-7.69(m, 6H) |

TABLE 2-30-continued

| Example | Structural formula | NMR |
|---|---|---|
| 2-148 | | (MeOH-d4-400) 1.94(dd, J=5.6, 9.8Hz, 1H), 2.13(dd, J=5.7, 8.5Hz, 1H), 2.58-2.66(m, 2H), 2.84(d, J=9.2Hz, 1H), 3.42-3.55(m, 2H), 3.93(dq, J=3.0, 17.2Hz, 2H), 6.10(s, 1H), 7.15-7.43(m, 10H) |
| 2-149 | | (MeOH-d4-400) 1,94(dd, J=5:6, 9:8Hz, 1H), 2.13(dd, J=5.7, 8.5Hz, 1H), 2.59(brs, 2H), 2.83(t, J=9.2Hz, 1H), 3.42-3.55(m, 2H), 3.93(dq, J=3.1, 17.5Hz, 2H), 6.14(s, 1H), 7.15-7.42(m, 9H) |
| 2-150 | | (DMSO-d6-300) 1.72(dd, J=8.9, 5.5Hz, 1H), 1.90(dd, J=11.9, 5.5Hz, 1H), 2.52-2.60(m, 1H), 7.11-7.22(m, 2H), 7.26-7.38(m, 2H), 7.48-7.63(m, 5H), 7.76(d, J=8.7Hz, 2H), 12.19(brs, 1H) |

TABLE 2-31

| Example | Structural formula | NMR |
|---|---|---|
| 2-151 | | (MeOH-d4-300) 1.83(dd, J=9.8, 5.7 Hz, 1H), 2.07(dd, J=8.5, 5.5 Hz, 1H), 2.75(t, J=9.2 Hz, 1H), 7.10-7.18(m, 4H), 7.27(d, J=7.5 Hz, 2H), 7.38-7.44(m, 3H), 7.57(d, J=8.3 Hz, 2H) |

TABLE 2-31-continued

| Example | Structural formula | NMR |
|---|---|---|
| 2-152 | | (DMSO-d6-300) 1.52(dd, J=8.7, 5.7 Hz, 1H), 1.96(dd, J=8.7, 5.7 Hz, 1H), 2.67(t, J=8.7 Hz, 1H), 7.18-7.22(m, 5H), 7.44(t, J=52.7 Hz, 1H), 7.71(s, 1H), 7.94(d, J=8.7 Hz, 2H), 8.13(d, J=8.7 Hz, 2H) |
| 2-153 | | (CDCl3-400) 1.99(dd, J=9.5, 6.0 Hz, 1H), 2.12(dd, J=8.8, 6.0 Hz, 1H), 3.01(dd, J=9.5, 8.8 Hz, 1H), 5.86(brs, 1H), 6.79(d, J=15.3 Hz, 1H), 7.14-7.23(m, 5H), 7.27-7.44(m, 5H) |
| 2-154 | | (DMSO-d6-300) 1.63-1.65(m, 1H), 1.70-1.88(m, 4H), 1.89-2.01(m, 1H), 2.62(t, J=5.5 Hz, 2H), 2.73(t, J=5.3 Hz, 2H), 7.07-7.26(m, 5H), 7.51(d, J=4.1 Hz, 1H), 7.62(d, J=4.1 Hz, 1H) |
| 2-155 | | (MeOH-d4-400) 1.94(dd, J=5.7, 9.8 Hz, 1H), 2.11(dd, J=5.7, 8.5 Hz, 1H), 2.70-2.78(m, 1H), 3.11-3.30(m, 4H), 3.84-3.86(m, 4H), 7.12-7.28(m, 5H), 8.35-8.40(m, 2H) |

TABLE 2-32
| Example | Structural formula | NMR |
|---------|-------------------|-----|
| 2-156 | 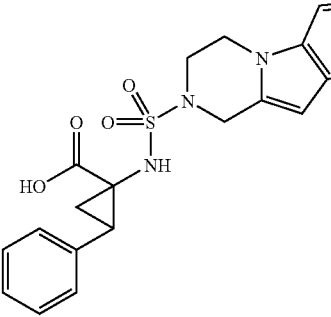 | (MeOH-d4-400) 1.93(dd, J=5.5, 9.8 Hz, 1H), 2.11(dd, J=5.8, 8.2 Hz, 1H), 2.58(t, J=7.7 Hz, 1H), 2.78(t, J=9.1 Hz, 1H), 2.90(t, J=7.7 Hz, 1H), 3.72-3.87(m, 1H), 4.11(t, J=5.2 Hz, 2H), 6.23(s, 1H), 7.06(dd, J=2.0, 8.6 Hz, 1H), 7.13-7.27(m, 6H) 7.44(d, J=1.9 Hz, 1H) |
| 2-157 | 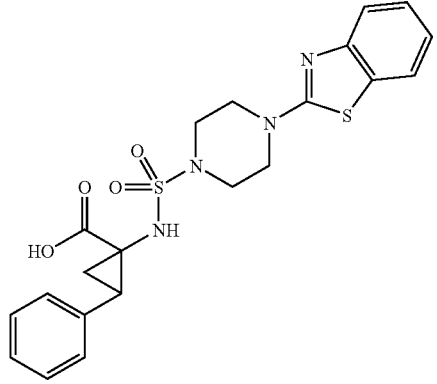 | (MeOH-d4-400) 1.96(dd, J=5.7, 9.8 Hz, 1H), 2.15(dd, J=5.8, 8.6 Hz, 1H), 2.84(t, J=9.2 Hz, 1H), 3.32-3.43(m, 4H), 3.66-3.68(m, 4H), 7.07-7.31(m, 7H), 7.48(d, J=8.0 Hz, 1H), 7.64(d, J=7.9 Hz, 1H) |
| 2-158 | 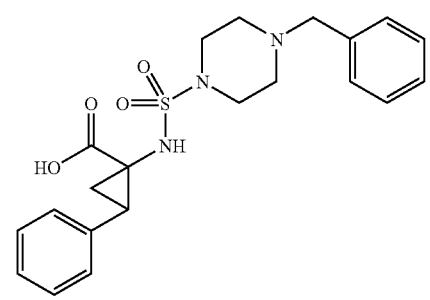 | (MeOH-d4-400) 1.92(dd, J=5.9, 9.9 Hz, 1H), 2.14(dd, J=5.8, 8.6 Hz, 1H), 2.59(t, J=7.7 Hz, 1H), 3.19-3.58(m, 8H), 3.62(s, 2H), 7.14-7.55(m, 10H) |
| 2-159 | 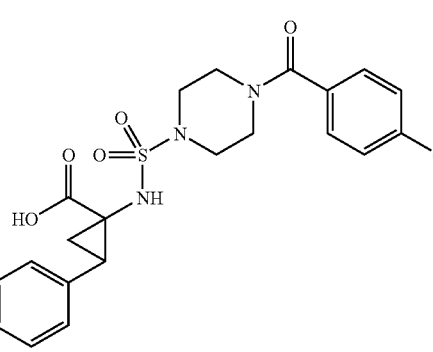 | (MeOH-d4-400) 1.95(dd, J=5.7, 9.8 Hz, 1H), 2.13(dd, J=5.8, 8.5 Hz, 1H), 2.80-2.85(m, 1H), 3.26-3.38(m, 4H), 3.49-3.79(m, 4H), 7.16-7.29(m, 5H), 7.41-7.49(m, 4H) |

TABLE 2-32-continued

| Example | Structural formula | NMR |
|---|---|---|
| 2-160 | | (MeOH-d4-400)<br>1.95(dd, J=5.7, 9.8 Hz, 1H),<br>2.13(dd, J=5.8, 8.6 Hz, 1H), 2.80-<br>2.86(m, 1H), 3.16-3.38(m, 4H),<br>3.41-3.54(m, 2H), 3.67-3.88(m,<br>2H), 7.16-7.53(m, 9H) |

TABLE 2-33

| Example | Structural formula | NMR |
|---|---|---|
| 2-161 | | (DMSO-d6-300)<br>1.70(dd, J=9.0, 5.7 Hz, 1H),<br>2.02(dd, J=8.7, 5.7 Hz, 1H),<br>2.81(dd, J=9.0, 8.7 Hz, 1H), 7.13-<br>7.28(m, 5H), 7.36(d, J=15.4 Hz,<br>1H), 7.45(d, J=15.4 Hz, 1H),<br>7.78(d, J=8.3 Hz, 2H), 7.92(d,<br>J=8.3 Hz, 2H), 8.70(brs, 1H),<br>12.39(brs, 1H) |
| 2-162 | | (CDCl3-300)<br>2.00(dd, J=9.2, 5.3 Hz, 1H),<br>2.15(dd, J=9.0, 5.3 Hz, 1H),<br>3.03(dd, J=9.2, 9.0 Hz, 1H),<br>5.86(brs, 1H), 6.90(d, J=15.4 Hz,<br>1H), 7.14-7.24(m, 5H),<br>7.56(m, 2H), 7.59-7.71(m, 3H) |
| 2-163 | | (CDCl3-300)<br>1.82-1.86(m, 1H), 2.00-2.04(m,<br>1H), 2.17-2.30(m, 2H), 2.61(t,<br>J=7.9 Hz, 2H), 2.73(t, J=8.9 Hz,<br>1H), 3.86(t, J=7.2 Hz, 2H),<br>6.39(d, J=4.1 Hz, 1H), 7.05-<br>7.24(m, 5H), 7.37(d, J=4.1 Hz,<br>1H), 7.45(d, J=4.1 Hz, 1H) |

TABLE 2-33-continued

| Example | Structural formula | NMR |
|---|---|---|
| 2-164 | | (CDCl3-300) 1.91-2.02(m, 9H), 3.76-3.78(m, 2H), 6.51(d, J=4.1 Hz, 1H), 7.17-7.19(m, 5H), 7.38(d, J=4.5 Hz, 1H), 7.47(d, J=4.1 Hz, 1H) |
| 2-165 | | (DMSO-d6-300) 1.45-1.47(m, 1H), 1.91(dd, J=8.7, 6.0 Hz, 1H), 2.63-2.71(m, 1H), 5.79(d, J=4.1 Hz, 1H), 7.07(d, J=4.1 Hz, 1H), 7.20-7.22(m, 5H), 8.48(s, 1H) |

TABLE 2-34

| Example | Structural formula | NMR |
|---|---|---|
| 2-166 | | (CDCl3-300) 0.98-1.20(m, 5H), 1.50-1.79(m, 5H), 1.90-2.02(m, 2H), 2.50-2.74(m, 2H), 3.85-4.09(m, 3H), 6.91(brs, 1H), 7.09-7.24(m, 6H), 7.61(s, 1H), 7.75(d, J=8.7 Hz, 1H) |
| 2-167 | | (DMSO-d6-300) 1.87(dd, J=9.8, 5.7 Hz, 1H), 2.09(dd, J=8.9, 5.5 Hz, 1H), 2.66(t, J=8.7 Hz, 1H), 7.17-7.27(m, 3H), 7.52-7.55(m, 3H), 7.59(s, 2H), 7.76(d, J=8.7 Hz, 2H), 9.07(brs, 1H), 12.31(brs, 1H) |

TABLE 2-34-continued

| Example | Structural formula | NMR |
| --- | --- | --- |
| 2-168 | | (DMSO-d6-300)<br>1.87(dd, J=9.8, 5.7 Hz, 1H),<br>2.09(dd, J=8.9, 5.5 Hz, 1H),<br>2.66(t, J=8.7 Hz, 1H), 7.17-<br>7.27(m, 3H), 7.52-7.55(m, 3H),<br>7.59(s, 2H), 7.76(d, J=8.7 Hz,<br>2H), 9.07(brs, 1H), 12.31(brs, 1H) |
| 2-169 | | (DMSO-d6-300)<br>1.67(dd, J=9.8, 5.7 Hz, 1H),<br>2.03(dd, J=7.5, 5.7 Hz, 1H),<br>2.73(t, J=7.0 Hz, 1H), 7.19-<br>7.25(m, 2H), 7.34-7.41(m, 2H),<br>7.69(q, J=3.6 Hz, 1H), 7.86(d,<br>J=3.8 Hz, 1H), 8.18(d, J=1.1 Hz,<br>1H), 9.33(brs, 1H), 12.44(brs, 1H) |
| 2-170 | | (DMSO-d6-300)<br>1.78(dd, J=9.6, 5.5 Hz, 1H),<br>2.01(dd, J=7.7, 5.5 Hz, 1H),<br>2.71(t, J=7.2 Hz, 1H), 7.43-<br>7.54(m, 1H), 7.52(d, J=8.7 Hz,<br>2H), 7.58(q, J=3.9 Hz, 2H),<br>7.65(d, J=7.2 Hz, 1H), 7.75(d,<br>J=8.7 Hz, 2H), 7.98-8.05(m, 2H),<br>8.80(brs, 1H), 12.32(brs, 1H) |

TABLE 2-35

| Example | Structural formula | NMR |
| --- | --- | --- |
| 2-171 | | (DMSO-d6-300)<br>1.64(dd, J=9.6, 5.5 Hz, 1H), 1.99-<br>2.02(m, 1H), 2.67-2.72(m, 1H),<br>7.17-7.22(m, 5H), 7.69(d,<br>J=3.8 Hz, 1H), 7.80(s, 1H),<br>7.83(d, J=3.8 Hz, 1H) |

TABLE 2-35-continued

| Example | Structural formula | NMR |
|---|---|---|
| 2-172 | | (DMSO-d6-400) 1.53(dd, J=9.7, 5.6 Hz, 1H), 1.98(dd, J=8.3, 5.8 Hz, 1H), 2.70(t, J=9.7 Hz, 1H), 2.71-2.76(m, 5H), 3.26-3.31(m, 2H), 3.67-3.76(m, 2H), 6.26(brs, 1H), 7.16-7.25(m, 6H), 7.47(d, J=4.2 Hz, 1H), 9.16(brs, 1H), 12.18(brs, 1H) |
| 2-173 | ClH | (DMSO-d6-300) 1.51(dd, J=9.6, 5.8 Hz, 1H), 1.90(dd, J=8.7, 5.7 Hz, 1H), 2.61(t, J=9.2 Hz, 1H), 3.09-3.90(brs, 2H), 4.34(s, 2H), 6.39-6.50(m, 3H), 6.93(t, J=7.9 Hz, 1H), 7.51-7.58(m, 4H), 7.65(t, J=6.4 Hz, 1H), 7.75(dt, J=8.8, 2.0 Hz, 2H), 8.07(d, J=7.2 Hz, 1H), 8.60(d, J=5.7 Hz, 1H), 8.69(s, 1H), 9.16(s, 1H), 12.15(brs, 1H) |
| 2-174 | Na$^+$ | (DMSO-d6-300) 1.65-1.72(m, 2H), 2.17(t, J=9.0 Hz, 1H), 4.72(brs, 2H), 6.29(t, J=9.6 Hz, 2H), 6.39(s, 1H), 6.75(t, J=9.6 Hz, 1H), 7.48-7.59(m, 4H), 7.75(d, J=7.9 Hz, 2H), 12.42(brs, 1H) |
| 2-175 | | (DMSO-d6-300) 1.68(q, J=4.9 Hz, 1H), 2.06(dd, J=8.5, 5.5 Hz, 1H), 2.82(t, J=9.2 Hz, 1H), 7.35-7.59(m, 6H), 7.73-7.79(m, 3H), 7.86(s, 1H), 9.21(brs, 1H), 12.43(brs, 1H), 12.93(brs, 1H) |

TABLE 2-36

| Example | Structural formula | NMR |
|---|---|---|
| 2-176 | | (DMSO-d6-300) 1.58(dd, J=9.8, 5.7 Hz, 1H), 1.98(dd, J=8.7, 5.3 Hz, 1H), 2.69(t, J=9.2 Hz, 1H), 2.86(s, 6H), 6.65-6.69(m, 3H), 7.07(t, J=7.5 Hz, 1H), 7.51-7.59(m, 4H), 7.76(d, J=8.7 Hz, 2H), 9.18(s, 1H), 12.16(brs, 1H) |

TABLE 2-36-continued

| Example | Structural formula | NMR |
|---|---|---|
| 2-177 | | (DMSO-d6-300) (120C) 1.64(dd, J=9.2, 5.1 Hz, 1H), 1.98(dd, J=8.8, 5.1 Hz, 1H), 2.04(s, 3H), 2.50-2.54(m, 2H), 2.74(t, J=8.8 Hz, 1H), 3.61-3.68(m, 2H), 4.10-4.15(m, 2H), 6.23-6.29(m, 1H), 7.09(d, J=3.7 Hz, 1H), 7.12-7.27(m, 5H), 7.46(d, J=4.0 Hz, 1H) |
| 2-178 | | (DMSO-d6-300) 1.87(dd, J=9.8, 5.7 Hz, 1H), 2.09(dd, J=8.9, 5.5 Hz, 1H), 2.66(t, J=8.7 Hz, 1H), 7.17-7.27(m, 3H), 7.52-7.55(m, 3H), 7.59(s, 2H), 7.76(d, J=8.7 Hz, 2H), 9.07(brs, 1H), 12.31(brs, 1H) |
| 2-179 | | (DMSO-d6-300) 1.64(dd, J=9.8, 5.7 Hz, 1H), 2.07(dd, J=8.7, 5.3 Hz, 1H), 2.47-2.53(m, 2H), 2.70(t, J=9.4 Hz, 1H), 2.83-2.85(m, 1H), 2.98-3.08(m, 1H), 7.05-7.14(m, 4H), 7.53(d, J=8.3 Hz, 2H), 7.57(d, J=4.1 Hz, 1H), 7.60(d, J=4.1 Hz, 1H), 7.77(d, J=8.3 Hz, 2H), 12.16(brs, 1H) |
| 2-180 | | (DMSO-d6-300) 1.61(dd, J=5.1, 2.6 Hz, 1H), 2.02(dd, J=8.3, 5.7 Hz, 1H), 2.46-2.50(m, 2H), 2.68-2.78(m, 3H), 7.05-7.07(m, 3H), 7.15-7.17(m, 1H), 7.53(d, J=8.7 Hz, 2H), 7.56(d, J=4.1 Hz, 1H), 7.58(d, J=4.1 Hz, 1H), 7.76(d, J=8.7 Hz, 2H), 9.19(brs, 1H), 12.17(brs, 1H) |

TABLE 2-37

| Example | Structural formula | NMR |
|---|---|---|
| 2-181 | | (DMSO-d6-300) 1.66(dd, J=9.4, 3.8 Hz, 1H), 1.78-1.90(m, 1H), 2.33(t, J=9.4 Hz, 1H), 3.07(s, 2H), 6.82(d, J=6.4 Hz, 1H), 6.89-7.06(m, 3H), 7.45-7.60(m, 4H), 7.74(d, J=8.3 Hz, 2H) |
| 2-182 | | (DMSO-d6-300) 1.62(q, J=4.8 Hz, 1H), 2.02(dd, J=8.5, 5.5 Hz, 1H), 2.74(t, J=9.0 Hz, 1H), 4.44(s, 2H), 5.16(brs, 1H), 7.04-7.23(m, 4H), 7.50-7.59(m, 4H), 7.76(d, J=8.3 Hz, 2H), 9.21(brs, 1H), 12.21(brs, 1H) |
| 2-183 | | (DMSO-d6-300) 1.55(dd, J=9.8, 5.7 Hz, 1H), 1.95(dd, J=8.7, 5.3 Hz, 1H), 2.66(t, J=9.1 Hz, 1H), 2.94(s, 3H), 4.54(s, 2H), 6.36-6.71(m, 2H), 6.93-7.07(m, 1H), 7.21-7.89(m, 9H), 8.44(s, 2H), 9.17(brs, 1H), 12.20(brs, 1H) |
| 2-184 | | (DMSO-d6-300) 1.71(dd, J=10.0, 5.5 Hz, 1H), 2.05(dd, J=6.8, 5.3 Hz, 1H), 2.81(t, J=6.4 Hz, 1H), 3.84(s, 3H) 7.38-7.59(m, 6H),. 7.74-7.80(m, 3H), 7.86(s, 1H), 9.25(brs, 1H), 12.32(brs, 1H) |
| 2-185 | | (acetone-d6-400) 1.76(dd, J=5.6, 9.0 Hz, 1H), 2.12-2.16(m, 1H), 2.73-2.77(m, 1H), 3.15(d, J=14.6 Hz, 1H), 3.39-3.42(m, 4H), 3.82-3.85(m, 4H), 4.30(dd, J=0.9, 14.6 Hz, 1H), 7.00(d, J=9.1 Hz, 1H), 7.16-7.32(m, 5H), 7.80(dd, J=2.5, 9.1 Hz, 1H), 8.43(s, 1H) |

TABLE 2-38

| Example | Structural formula | NMR |
|---|---|---|
| 2-186 | | (acetone-d6-400) 1.78(dd, J=5.6, 9.0 Hz, 1H), 2.15(dd, J=6.5, 7.4 Hz, 1H), 2.77(t, J=8.4 Hz, 1H), 3.19(d, J=14.7 Hz, 1H), 3.45-3.48(m, 4H), 3.65-3.67(m, 4H), 4.34(d, J=15.3 Hz, 1H), 7.17-7.46(m, 9H) |
| 2-187 | | (acetone-d6-400) 1.87(dd, J=4.6, 7.2 Hz, 1H), 2.05(td, J=2.2, 4.4 Hz, 1H), 2.54-2.58(m. 1H), 3.71(d, J=11.5 Hz, 1H), 4.02(d, J=11.5 Hz, 1H), 7.14-7.29(m, 5H), 7.49-7.80(m, 6H) |
| 2-188 | | (DMSO-d6-300) 1.62(dd, J=5.0, 2.5 Hz, 1H), 2.00(dd, J=8.3, 6.0 Hz, 1H), 2.71(t, J=8.9 Hz, 1H), 3.60(s, 5H), 7.10(t, J=7.5 Hz, 3H), 7.20(t, J=7.3 Hz, 1H), 7.46-7.60(m, 4H), 7.75(d, J=8.7 Hz, 2H), 9.17(brs, 1H), 12.24(brs, 1H) |
| 2-189 | | (DMSO-d6-300) 1.62(dd, J=5.0, 2.5 Hz, 1H), 1.98(dd, J=8.3, 6.0 Hz, 1H), 2.69(t, J=9.4 Hz, 1H), 2.81(s, 3H), 2.93(s, 3H), 3.61(s, 2H), 7.05(t, J=9.0 Hz, 3H), 7.17(t, J=7.5 Hz, 1H), 7.47-7.60(m, 4H), 7.76(d, J=8.7 Hz, 2H), 12.23(brs, 1H) |
| 2-190 | | (DMSO-d6-300) 1.58-1.70(m, 1H), 1.87-1.99(m, 1H), 2.54-2.67(m, 1H), 3.24-3.56(m, 8H), 3.63(s, 2H), 6.94-7.10(m, 3H), 7.15(t, J=7.0 Hz, 1H), 7.52(d, J=8.7 Hz, 2H), 7.56(s, 2H), 7.75(d, J=8.3 Hz, 2H) |

TABLE 2-39

| Example | Structural formula | NMR |
|---|---|---|
| 2-191 | | (DMSO-d6-300) 1.63(q, J=4.6 Hz, 1H), 1.92-2.02(m, 1H), 2.07-2.30(m, 7H), 2.61-2.75(m, 1H), 3.20-3.56(m, 4H), 3.63(s, 2H), 6.98-7.11(m, 3H), 7.17(t, J=7.5 Hz, 1H), 7.52(d, J=8.7 Hz, 2H), 7.57(s, 2H), 7.76(d, J=8.3 Hz, 2H) |
| 2-192 | | (DMSO-d6-300) 1.62(dd, J=9.8, 5.7 Hz, 1H), 2.03(dd, J=8.1, 5.5 Hz, 1H), 2.75(dd, J=9.2, 4.6 Hz, 1H), 7.15-7.30(m, 5H), 7.53(d, J=8.7 Hz, 2H), 7.56(d, J=4.1 Hz, 1H), 7.58(d, J=4.1 Hz, 1H), 7.76(d, J=8.7 Hz, 2H), 9.21(brs, 1H), 12.21(brs, 1H) |
| 2-193 | | (DMSO-d6-300) 1.89(dd, J=9.6, 5.8 Hz, 1H), 2.10(dd, J=8.7, 5.3 Hz, 1H), 2.66(t, J=11.3 Hz, 1H), 7.17-7.27(m, 3H), 7.54(d, J=7.2 Hz, 1H), 7.72(d, J=4.1 Hz, 1H), 7.87(d, J=3.8 Hz, 1H), 8.18(s, 1H), 12.33(brs, 1H) |
| 2-194 | | (DMSO-d6-300) 1.71-1.76(m, 1H), 2.07-2.10(m, 1H), 2.59-2.64(m, 1H), 3.43-3.59(m, 4H), 3.77(d, J=17.0 Hz, 1H), 3.84(d, J=16.6 Hz, 1H), 6.98-7.00(m, 1H), 7.07-7.15(m, 3H), 7.53(d, J=8.7 Hz, 2H), 7.57(d, J=3.8 Hz, 1H), 7.59(d, J=3.8 Hz, 1H), 7.76(d, J=8.7 Hz, 2H), 12.30(d, J=10.0 Hz, 1H) |

TABLE 2-39-continued

| Example | Structural formula | NMR |
|---------|-------------------|-----|
| 2-195 | | (DMSO-d6-300)<br>1.71-1.76(m, 1H), 2.07-2.10(m, 1H), 2.59-2.64(m, 1H), 3.43-3.59(m, 4H), 3.77(d, J=17.0 Hz, 1H), 3.84(d, J=16.6 Hz, 1H), 6.98-7.00(m, 1H), 7.07-7.15(m, 3H), 7.53(d, J=8.7 Hz, 2H), 7.57(d, J=3.8 Hz, 1H), 7.59(d, J=3.8 Hz, 1H), 7.76(d, J=8.7 Hz, 2H), 12.30(d, J=10.0 Hz, 1H) |

TABLE 2-40

| Example | Structural formula | NMR |
|---------|-------------------|-----|
| 2-196 | | (DMSO-d6-300)<br>1.68(dd, J=9.6, 5.8 Hz, 1H), 1.96(dd, J=8.9, 5.8 Hz, 1H), 3.09(t, J=8.9 Hz, 1H), 7.24-7.34(m, 2H), 7.44-7.46(m, 1H), 7.53(d, J=8.7 Hz, 2H), 7.60(d, J=4.1 Hz, 1H), 7.62(d, J=3.8 Hz, 1H), 7.74-7.78(m, 4H), 8.07(brs, 1H) |
| 2-197 | | (DMSO-d6-300)<br>1.62-1.68(m, 1H), 1.89-1.92(m, 1H), 2.44(t, J=4.5 Hz, 4H), 2.64(t, J=5.8 Hz, 2H), 3.56(t, J=4.5 Hz, 4H), 3.98(t, J=5.8 Hz, 2H), 6.71-6.76(m, 3H), 7.09(t, J=7.9 Hz, 1H), 7.52(d, J=8.7 Hz, 2H), 7.55-7.58(m, 2H), 7.75(d, J=8.7 Hz, 2H) |
| 2-198 | | (DMSO-d6-300)<br>1.63(dd, J=9.8, 5.7 Hz, 1H), 1.92(dd, J=8.1, 5.5 Hz, 1H), 2.13(s, 3H), 2.34-2.43(m, 4H), 2.56-2.66(m, 1H), 2.64(t, J=5.7 Hz, 2H), 3.97(t, J=5.7 Hz, 2H), 6.73-6.76(m, 3H), 7.11(t, J=7.9 Hz, 1H), 7.52-7.56(m, 4H), 7.75(d, J=8.7 Hz, 2H) |

TABLE 2-40-continued
| Example | Structural formula | NMR |
|---------|-------------------|-----|
| 2-199 | 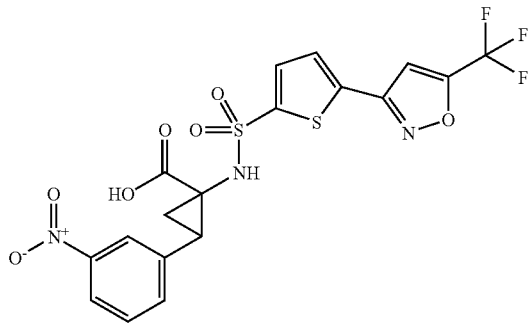 | (DMSO-d6-300) 1.77(dd, J=9.8, 6.0 Hz, 1H), 2.15(dd, J=8.3, 6.0 Hz, 1H), 2.90(t, J=8.7 Hz, 1H), 7.58(t, J=8.3 Hz, 1H), 7.69(d, J=8.3 Hz, 1H), 7.73(d, J=4.1 Hz, 1H), 7.87(d, J=4.1 Hz, 1H), 8.05-8.09 (m, 2H), 8.18(d, J=0.8 Hz, 1H), 9.50(brs, 1H), 12.53(brs, 1H) |
| 2-200 | 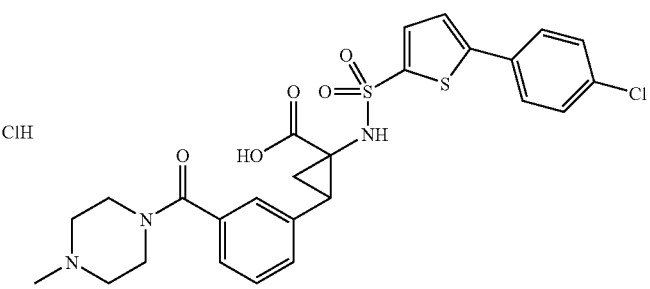 | (DMSO-d6-300) 1.66(q, J=4.8 Hz, 1H), 2.12(dd, J=7.0, 5.5 Hz, 1H), 2.79(s, 3H), 2.70-3.44(m, 9H), 7.23-7.32(m, 2H), 7.38(d, J=4.1 Hz, 2H), 7.53(d, J=8.7 Hz, 2H), 7.58(d, J=4.9 Hz, 1H), 7.59(d, J=4.9 Hz, 1H), 7.76(d, J=8.3 Hz, 2H), 9.23(s, 1H), 10.44(brs, 1H), 12.33(brs, 1H) |
TABLE 2-41
| Example | Structural formula | NMR |
|---------|-------------------|-----|
| 2-201 | 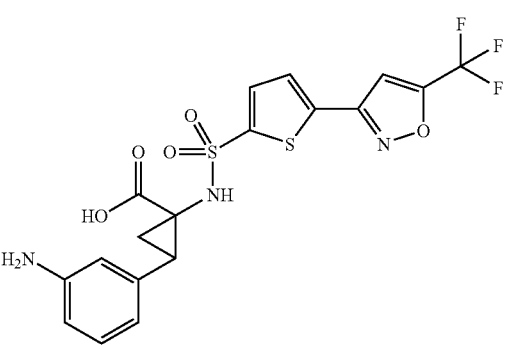 | (DMSO-d6-300) 1.55(dd, J=9.0, 5.3Hz, 1H), 1.88(dd, J=8.9, 5.1Hz, 1H), 2.55(d, J=5.1Hz, 1H), 4.94(brs, 2H), 6.33-6.44(m, 3H), 6.86(t, J=7.5Hz, 1H), 7.69(d, J=3.8Hz, 1H), 7.86(d, J=4.1Hz, 1H), 8.18(s, 1H), 9.26(brs, 1H), 12.18(brs, 1H) |
| 2-202 | 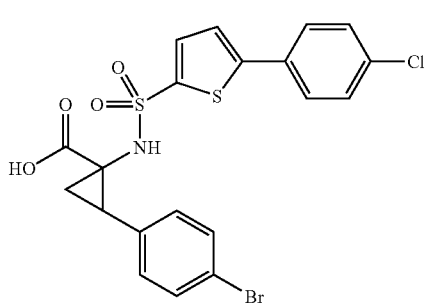 | (MeOH-d4-400) 2.07(dd, J=6.0, 9.7Hz, 1H), 2.27(dd, J=6.1, 7.9Hz, 1H), 2.74-2.78(m, 1H), 7.09(d, J=8.5Hz, 2H), 7.37-7.49(m, 6H), 7.66(d, J=8.6Hz, 2H) |

TABLE 2-41-continued

| Example | Structural formula | NMR |
|---|---|---|
| 2-203 | 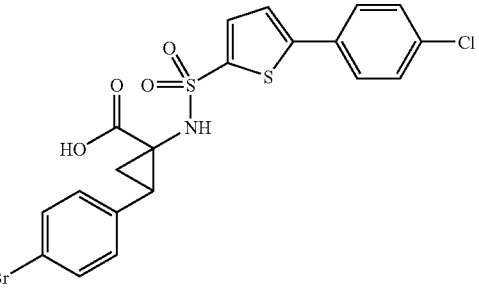 | (MeOH-d4-400)<br>1.94(dd, J=5.8, 9.8Hz, 1H),<br>2.12(dd, J=5.9, 8.6Hz, 1H),<br>2.79(t, J=9.7Hz, 1H), 7.18(d,<br>J=8.3Hz, 2H), 7.36-7.44(m, 5H),<br>7.57(d, J=4.0Hz, 1H), 7.65(d,<br>J=8.6Hz, 2H) |
| 2-204 | 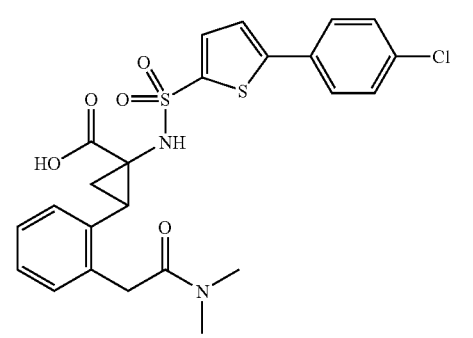 | (DMSO-d6-300)<br>1.71(dd, J=9.8, 5.7Hz, 1H),<br>2.11(dd, J=8.9, 5.5Hz, 1H),<br>2.66(t, J=8.5Hz, 1H), 2.88(s,<br>3H), 2.92(s, 3H), 3.74(d,<br>J=16.2Hz, 1H), 3.82(d, J=17.0Hz,<br>1H), 6.94-6.99(m, 1H), 7.08-<br>7.15(m, 3H), 7.53(d, J=8.7Hz,<br>2H), 7.57(t, J=1.9Hz, 1H),<br>7.60(d, J=3.8Hz, 1H), 7.76(d,<br>J=8.7Hz, 2H), 9.30(brs, 1H),<br>12.26(brs, 1H) |
| 2-205 | 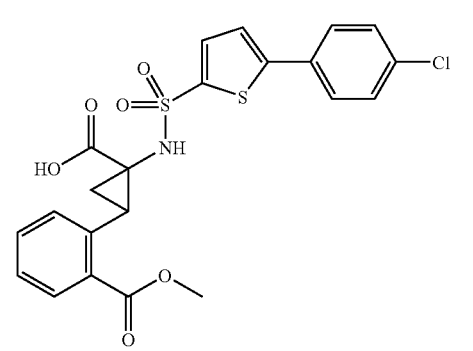 | (DMSO-d6-300)<br>1.70-1.75(m, 1H), 1.91-1.98(m,<br>1H), 3.05-3.08(m, 1H), 3.86(s,<br>3H), 7.31-7.35(m, 2H), 7.45-<br>7.48(m, 1H), 7.53(d, J=8.7Hz,<br>2H), 7.61(s, 2H), 7.72-7.77(m,<br>3H), 8.40(brs, 1H), 12.28(brs,<br>1H) |

TABLE 2-42

| Example | Structural formula | NMR |
|---|---|---|
| 2-206 | 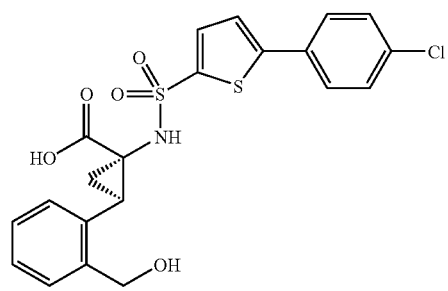 | (DMSO-d6-300)<br>1.68(dd, J=5.1, 2.6Hz, 1H),<br>2.09(dd, J=8.7, 5.3Hz, 1H),<br>2.66(t, J=9.2Hz, 1H), 4.53(d,<br>J=14.7Hz, 1H), 4.73(d, J=14.7Hz,<br>1H), 5.09(brs, 1H), 7.02-7.23(m,<br>3H), 7.37(d, J=7.2Hz, 1H),<br>7.53(d, J=8.7Hz, 2H), 7.57(d,<br>J=4.1Hz, 1H), 7.59(d, J=4.1Hz,<br>1H), 7.76(d, J=8.3Hz, 2H),<br>9.28(brs, 1H), 12.16(brs, 1H) |

TABLE 2-42-continued

| Example | Structural formula | NMR |
|---|---|---|
| 2-207 | | (MeOH-d4-300) 2.00(d, J=6.0Hz, 0.6H), 2.18-2.23(m, 0.4H), 2.20, 2.23(2s, 3H), 2.57(d, J=6.0Hz, 0.4H), 2.58(d, J=6.0Hz, 0.6H), 3.64(d, J=12.0Hz, 0.6H), 3.95(d, J=12.0Hz, 0.6H), 4.12(d, J=12.0Hz, 0.4H), 4.33(d, J=15.0Hz, 0.6H), 4.56(d, J=15.0Hz, 0.4H), 4.67(d, J=15.0Hz, 0.4H), 4.91(d, J=15.0Hz, 0.6H), 7.10-7.24(m, 4H), 7.36-7.49(m, 3H), 7.56-7.70(m, 3H) |
| 2-208 | | (CDCl3-300) 2.09-2.11(m, 2H), 2.54(t, J=7.5Hz, 2H), 2.82-2.92(m, 3H), 3.60(s, 3H), 6.16(brs, 1H), 7.00-7.02(m, 3H), 7.12-7.17(m, 2H), 7.39(d, J=8.3Hz, 2H), 7.51(d, J=8.3Hz, 2H), 7.57(d, J=3.8Hz, 1H) |
| 2-209 | | (DMSO-d6-400) 1.60(dd, J=10.2, 5.6Hz, 1H), 2.01(dd, J=8.8, 5.6Hz, 1H), 2.54(t, J=8.3Hz, 1H), 2.66-2.77(m, 3H), 3.26-3.64(m, 9SH), 7.00-7.09(m, 3H), 7.15(t, J=7.4Hz, 1H), 7.49-7.59(m, 4H), 7.73-7.77(m, 2H), 9.19(s, 1H) |
| 2-210 | | (DMSO-d6-400) 1.61(dd, J=9.7, 5.6Hz, 1H), 2.01(dd, J=8.8, 5.6Hz, 1H), 2.51-3.01(m, 13H), 3.26-3.36(m, 3H), 7.02-7.09(m, 3H), 7.16(t, J=7.4Hz, 1H), 7.50-7.59(m, 4H), 7.73-7.79(m, 2H), 9.20(s, 1H), 10.46(brs, 1H), 12.21(brs, 1H) |

TABLE 2-43
| Example | Structural formula | NMR |
|---|---|---|
| 2-211 | 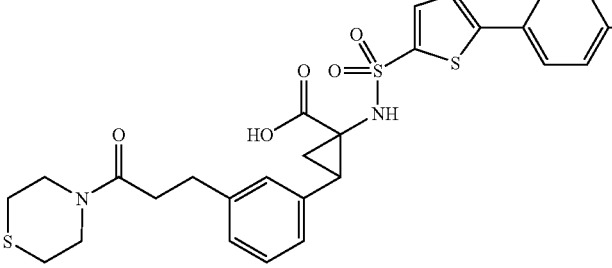 | (DMSO-d6-300) 1.61(dd, J=9.6, 5.5Hz, 1H), 2.02(dd, J=8.7, 5.7Hz, 1H), 2.55(t, J=8.3Hz, 1H), 2.67-2.79(m, 4H), 3.32-3.39(m, 4H), 3H), 7.12-7.19(m, 1H), 7.50-7.60(m, 4H), 7.73-7.78(m, 2H), 9.20(s, 1H), 12.20(brs, 1H) |
| 2-212 | 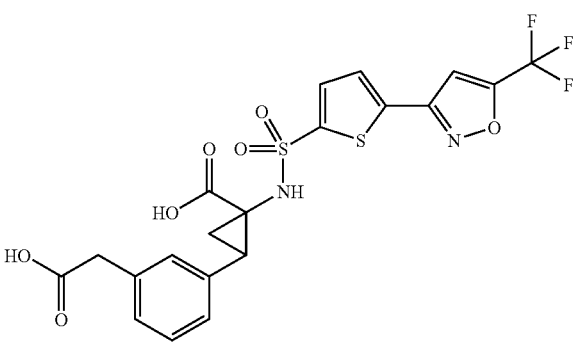 | (DMSO-d6-300) 1.63(dd, J=9.4, 5.7Hz, 1H), 2.04(dd, J=8.5, 5.8Hz, 1H), 2.75(t, J=9.0Hz, 1H), 3.50(s, 2H), 7.07-7.24(m, 4H), 7.70(d, J=3.8Hz, 1H), 7.86(d, J=3.8Hz, 1H), 8.18(d, J=0.8Hz, 1H), 9.43(s, 1H), 12.28(brs, 2H) |
| 2-213 | 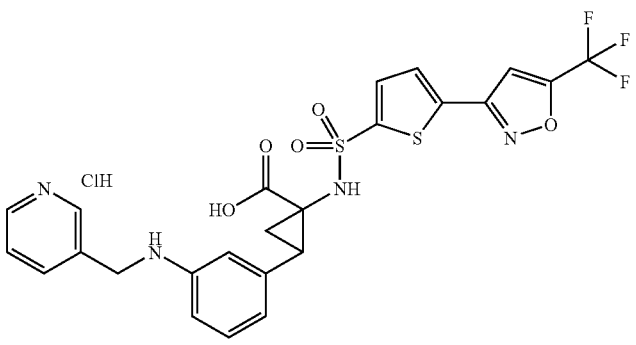 | (DMSO-d6-300) 1.53(dd, J=9.4, 5.3Hz, 1H), 1.92(dd, J=9.2, 5.5Hz, 1H), 2.65(t, J=9.2Hz, 1H), 4.32(brs, 2H), 4.45(s, 2H), 6.40-6.53(m, 3H), 6.96(t, J=7.9Hz, 1H), 7.68(d, J=3.8Hz, 1H), 7.87(d, J=3.8Hz, 1H), 7.98(dd, J=8.1, 5.8Hz, 1H), 8.20(s, 1H), 8.46(d, J=8.3Hz, 1H), 8.79(d, J=5.3Hz, 1H), 8.84(d, J=1.1Hz, 1H), 9.38(s, 1H), 11.92(brs, 1H) |
| 2-214 | 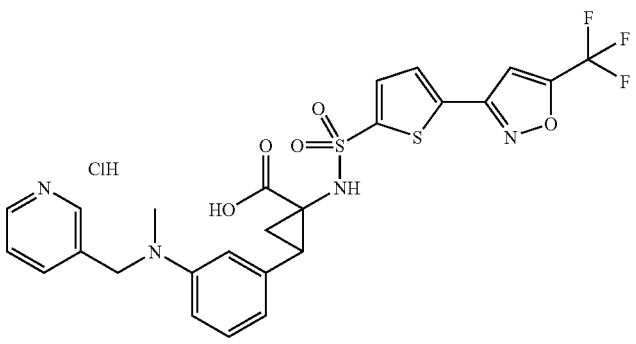 | (DMSO-d6-400) 1.55(dd, J=10.0, 5.8Hz, 1H), 1.97(dd, J=8.8, 5.6Hz, 1H), 2.69(t, J=9.3Hz, 1H), 2.99(s, 3H), 4.26(brs, 1H), 4.70(s, 2H), 6.56-6.60(m, 2H), 6.66(s, 1H), 7.05(t, J=8.1Hz, 1H), 7.67(d, J=3.7Hz, 1H), 7.86(d, J=3.7Hz, 1H), 7.90(d, J=7.4Hz, 1H), 8.18(d, J=0.9Hz, 1H), 8.22(t, J=3.2Hz, 1H), 8.70(s, 1H), 8.75(d, J=5.1Hz, 1H), 9.37(s, 1H), 12.17(brs, 1H) |

TABLE 2-43-continued

| Example | Structural formula | NMR |
|---|---|---|
| 2-215 | | (DMSO-d6-300)<br>1.61-1.65(m, 1H), 1.79-1.83(m, 1H), 2.66-2.70(m, 1H), 2.73(s, 3H), 3.00(s, 3H), 7.10-7.30(m, 4H), 7.53(d, J=8.7Hz, 2H), 7.57(d, J=3.8Hz, 1H), 7.59(d, J=3.8Hz, 1H), 7.76(d, J=9.0Hz, 2H), 9.04(brs, 1H), 12.39(brs, 1H) |

TABLE 2-44

| Example | Structural formula | NMR |
|---|---|---|
| 2-216 | | (DMSO-d6-300)<br>1.48-1.67(m, 1H), 1.73-1.81(m, 1H), 2.04-2.44(m, 4H), 2.65-2.68(m, 1H), 3.17-3.67(m, 7H), 7.12(d, J=7.2Hz, 1H), 7.26-7.35(m, 3H), 7.53(d, J=8.7Hz, 2H), 7.58(s, 2H), 7.76(d, J=8.7Hz, 2H) |
| 2-217 | | (MeOH-d4-300)<br>1.52(s, 9H), 1.96(dd, J=9.8, 5.7Hz, 1H), 2.11(dd, J=8.7, 5.7Hz, 1H), 2.74(t, J=9.2Hz, 1H), 7.00-7.07(m, 1H), 7.17-7.21(m, 2H), 7.41-7.46(m, 4H), 7.63(d, J=4.1Hz, 1H), 7.68(d, J=8.7Hz, 2H) |
| 2-218 | | (DMSO-d6-300)<br>0.92(t, J=5.7Hz, 1H), 1.74(dd, J=5.0, 2.5Hz, 1H), 2.89(dd, J=9.6, 6.2Hz, 1H), 6.84(d, J=7.2Hz, 1H), 6.95(dd, J=8.1, 7.0Hz, 1H), 7.12-7.17(m, 1H), 7.36-7.40(m, 2H), 7.51-7.55(m, 3H), 7.70(d, J=8.7Hz, 2H), 9.26(brs, 1H), 10.13(brs, 1H) |

TABLE 2-44-continued

| Example | Structural formula | NMR |
|---|---|---|
| 2-219 | | (DMSO-d6-300) 1.64 (dd, J=5.3, 2.6Hz, 1H), 1.97-2.06(m, 1H), 2.68-2.77(m, 1H), 3.60(s, 5H), 7.10(t, J=7.3Hz, 3H), 7.20(t, J=7.2Hz, 1H), 7.70(d, J=3.8Hz, 1H), 7.86(d, J=3.8Hz, 1H), 8.17(s, 1H) |
| 2-220 | | (DMSO-d6-300) 1.63(dd, J=9.6, 5.5Hz, 1H), 2.02(dd, J=8.7, 5.3Hz, 1H), 2.76(t, J=9.0Hz, 1H), 3.35-3.54(m, 8H), 3.66(s, 2H), 7.07(t, J=7.9Hz, 3H), 7.20(t, J=7.7Hz, 1H), 7.70(d, J=3.8Hz, 1H), 7.86(d, J=3.8Hz, 1H), 8.18(d, J=1.1Hz, 1H), 9.42(brs, 1H), 12.24(brs, 1H) |

TABLE 2-45

| Example | Structural formula | NNR |
|---|---|---|
| 2-221 | | (DMSO-d6-300) 1.63(dd, J=10.0, 5.8Hz, 1H), 2.03(dd, J=8.3, 5.7Hz, 1H), 2.77(s, 3H), 2.80-3.04(m, 2H), 3.23-3.52(m, 4H), 3.71(s, 2H), 3.98-4.19(m, 1H), 4.33-4.54(m, 1H), 7.02-7.15(m, 3H), 7.22(t, J=7.3Hz, 1H), 7.70(d, J=4.1Hz, 1H), 7.86(d, J=3.8Hz, 1H), 8.18(s, 1H), 9.41(s, 1H), 9.77(brs, 1H), 12.26(brs, 1H) |
| 2-222 | | (DMSO-d6-300) 1.01-1.31(m, 2H), 1.63(q, J=4.9Hz, 1H), 1.95-2.04(m, 1H), 2.71(t, J=8.7Hz, 1H), 2.89-3.01(m, 1H), 3.03-3.14(m, 1H), 3.54-3.70(m, 4H), 3.84-3.97(m, 1H), 7.01-7.12(m, 3H), 7.18(t, J=7.3Hz, 1H), 7.70(d, J=3.8Hz, 1H), 7.86(d, J=3.8Hz, 1H), 8.18(d, J=0.8Hz, 1H) |

TABLE 2-45-continued

| Example | Structural formula | NMR |
|---|---|---|
| 2-223 | | (DMSO-d6-400) 1.61(dd, J=9.7, 5.6Hz, 1H), 1.94(dd, J=8.3, 5.6Hz, 1H), 2.46-2.53(m, 2H), 2.70-2.83(m, 9H), 6.93(d, J=7.9Hz, 1H), 7.19(t, J=8.1Hz, 1H), 7.43-7.47(m, 2H), 7.50-7.55(m, 2H), 7.57(s, 2H), 7.72-7.78(m, 2H), 9.23(s, 1H), 10.17(s, 1H), 12.22(s, 1H) |
| 2-224 | | (DMSO-d6-300) 1.16-1.30(m, 2H), 1.59-1.71(m, 3H), 1.99-2.01(m, 1H), 2.51-2.54(m, 2H), 2.63-2.77(m, 3H), 2.95-3.09(m, 2H), 3.60-3.67(m, 2H), 3.84-3.95(m, 1H), 7.02-7.14(m, 4H), 7.49-7.59(m, 4H), 7.75(d, J=8.3Hz, 2H), 8.32(brs, 1H) |
| 2-225 | | (MeOH-d4-400) 1.89(dd, J=5.7, 9.8Hz, 1H), 2.09(dd, J=5.8, 8.5Hz, 1H), 2.76(t, J=9.2Hz, 1H), 5.01(s, 2H), 6.85-7.67(m, 15H) |

TABLE 2-46

| Example | Structural formula | NMR |
|---|---|---|
| 2-226 | | (MeOH-d4-400) 1.82(dd, J=5.9, 9.8Hz, 1H), 2.05(dd, J=5.8, 8.7Hz, 1H), 2.77(t, J=9.3Hz, 1H), 4.50(s, 2H), 7.16-7.65(m, 7H) |

TABLE 2-46-continued

| Example | Structural formula | NMR |
|---|---|---|
| 2-227 | | (DMSO-d6-300) 1.18-1.24(m, 3H), 1.44(d, J=4.9Hz, 1H), 1.55-1.57(m, 1H), 1.84-1.87(m, 1H), 1.98-2.01(m, 1H), 3.24(t, J=6.2Hz, 2H), 7.11-7.24(m, 5H), 7.50-7.56(m, 4H), 7.74(d, J=8.7Hz, 2H) |
| 2-228 | | (DMSO-d6-300) 1.58(q, J=5.1Hz, 1H), 1.99(dd, J=8.3, 5.7Hz, 1H), 2.71(t, J=9.8Hz, 1H), 2.85(s, 6H), 6.49-6.62(m, 3H), 7.04(t, J=7.7Hz, 1H), 7.69(d, J=4.1Hz, 1H), 7.86(d, J=3.8Hz, 1H), 8.18(s, 1H), 9.38(s, 1H), 12.19(brs, 1H) |
| 2-229 | | (MeOH-d4-300) 1.84(d, J=4.5Hz, 1H), 2.07(d, J=5.3Hz, 1H), 3.76(d, J=11.3Hz, 1H), 3.87(d, J=11.3Hz, 1H), 7.11-7.29(m, 5H), 7.38(d, J=3.0Hz, 1H), 7.42(d, J=9.0Hz, 2H), 7.58(d, J=3.0Hz, 1H), 7.65(d, J=9.0Hz, 2H) |
| 2-230 | | (DMSO-d6-300) 1.65(dd, J=9.4, 5.7Hz, 1H), 2.12(dd, J=8.9, 5.8Hz, 1H), 2.49-2.58(m, 2H), 2.72-3.06(m, 3H), 3.43-3.54(m, 4H), 7.00-7.16(m, 5H), 7.71(d, J=3.8Hz, 1H), 7.88(d, J=4.1Hz, 1H), 8.19(s, 1H), 9.49(brs, 1H), 12.27(brs, 1H) |

TABLE 2-47

| Example | Structural formula | NMR |
|---|---|---|
| 2-231 | | (DMSO-d6-300)<br>1.64(dd, J=9.2, 5.5Hz, 1H), 2.11(dd, J=13.8, 4.7Hz, 1H), 2.53-2.56(m, 1H), 2.74-2.88(m, 2H), 2.84(s, 3H), 2.93(s, 3H), 2.94-3.00(m, 2H), 7.01-7.16(m, 4H), 7.71(d, J=3.8Hz, 1H), 7.88(d, J=3.8Hz, 1H), 8.19(s, 1H), 9.51(brs, 1H), 12.25(brs, 1H) |
| 2-232 | ClH | (DMSO-d6-300)<br>1.65-1.70(m, 1H), 2.14-2.16(m, 1H), 2.59-2.61(m, 1H), 2.84-2.92(m, 7H), 3.27-3.53(m, 4H), 3.99-4.10(m, 2H), 4.43-4.55(m, 2H), 7.05-7.16(m, 4H), 7.72(d, J=3.8Hz, 1H), 7.89(d, J=4.1Hz, 1H), 8.20(s, 1H), 9.52(brs, 1H), 12.30(brs, 1H) |
| 2-233 | | (DMSO-d6-300)<br>1.16(t, J=9.6Hz, 2H), 1.35(t, J=11.5Hz, 1H), 1.45-1.88(m, 5H), 1.92-2.06(m, 2H), 2.59-2.75(m, 1H), 3.17-3.65(m, 3H), 4.85-4.99(m, 1H), 7.00-7.19(m, 4H), 7.69(d, J=3.8Hz, 1H), 7.85(d, J=3.8Hz, 1H), 8.17(s, 1H), 12.26(brs, 1H) |
| 2-234 | | (DMSO-d6-300)<br>1.62(dd, J=9.8, 5.7Hz, 1H), 2.04(dd, J=8.5, 5.8Hz, 1H), 2.54-2.59(m, 2H), 2.69-2.79(m, 3H), 3.34-3.61(m, 8H), 7.04-7.09(m, 3H), 7.13-7.20(m, 1H), 7.70(d, J=4.1Hz, 1H), 7.86(d, J=3.8Hz, 1H), 8.18(s, 1H), 9.40(brs, 1H), 12.24(brs, 1H) |

TABLE 2-47-continued

| Example | Structural formula | NMR |
|---|---|---|
| 2-235 | | (DMSO-d6-300) 1.63(dd, J=9.4, 5.7Hz, 1H), 2.04(dd, J=8.7, 5.7Hz, 1H), 2.62-2.65(m, 2H), 2.71-2.97(m, 10H), 3.28-3.37(m, 2H), 3.99-4.07(m, 1H), 4.41-4.48(m, 1H), 7.05-7.09(m, 3H), 7.16-7.19(m, 1H), 7.70(d, J=4.1Hz, 1H), 7.87(d, J=4.1Hz, 1H), 8.19(s, 1H), 9.42(brs, 1H), 10.51(brs, 1H), 12.23(brs, 1H) |

TABLE 2-48

| Example | Structural formula | NMR |
|---|---|---|
| 2-236 | | (DMSO-d6-300) 1.59-1.71(m, 3H), 2.03(dd, J=8.5, 5.5Hz, 1H), 2.49-2.57(m, 2H), 2.74(t, J=9.0Hz, 1H), 3.39(t, J=6.4Hz, 2H), 4.43(brs, 1H), 6.99-7.07(m, 3H), 7.15(t, J=7.5Hz, 1H), 7.69(d, J=4.1Hz, 1H), 7.86(d, J=4.1Hz, 1H), 8.18(d, J=0.8Hz, 1H), 9.39(brs, 1H), 12.22(brs, 1H) |
| 2-237 | | (DMSO-d6-400) 1.24(d, J=7.0Hz, 3H), 1.96(dq, J=10.7, 7.0Hz, 1H), 2.75(d, J=10.7Hz, 1H), 7.13-7.27(m, 5H), 7.49-7.58(m, 4H), 7.71-7.76(m, 2H) |
| 2-238 | | (DMSO-d6-300) 1.63(q, J=5.3Hz, 1H), 1.85(t, J=7.2Hz, 2H), 2.04(dd, J=8.7, 5.7Hz, 1H), 2.60(t, J=7.5Hz, 1H), 2.77(t, J=6.6Hz, 4H), 2.90-3.36 (m, 7H), 4.02(t, J=6.6Hz, 4H), 7.02-7.09(m, 3H), 7.18(t, J=7.3Hz, 1H), 7.70(d, J=3.8Hz, 1H), 7.87(d, J=4.1Hz, 1H), 8.19(d, J=0.8Hz, 1H), 9.41(s, 1H), 10.53(brs, 1H), 12.24(brs, 1H) |

TABLE 2-48-continued

| Example | Structural formula | NMR |
|---|---|---|
| 2-239 | | (CDCl3-300) 1.25-1.29(m, 2H), 1.75-1.99(m, 2H), 2.12(dd, J=8.7, 6.0Hz, 1H), 2.25(dd, J=9.2, 6.6Hz, 1H), 2.60 (q, J=4.6Hz, 1H), 2.72(dd, 3= 13.0, 7.3Hz, 1H), 2.88(t, J= 9.2Hz, 1H), 3.29-3.32(m, 4H), 3.57(t, J=4.9Hz, 4H), 3.67-3.70 (m, 1H), 6.15(brs, 1H), 6.91(s, 1H), 6.95(s, 1H), 7.01(d, J=7.5 Hz, 1H), 7.10(d, J=7.5Hz, 1H), 7.21(t, J=7.5Hz, 1H), 7.45(d, J= 3.8Hz,1H), 7.66(d, J=3.8Hz, 1H) |
| 2-240 | | (DMSO-d6-300) 1.65-1.76(m, 1H), 2.04-2.16(m, 1H), 2.62-2.82(m, 2H), 2.90-3.05(m, 1H), 3.53-3.67(m, 2H), 4.52(t, J=5.8Hz, 1H), 6.96-7.22(m, 4H), 7.72(d, J=3.0Hz, 1H), 7.87(d, J=3.8Hz, 1H), 8.19(s, 1H), 9.41(brs, 1H), 12.20(brs, 1H) |

TABLE 2-49

| Example | Structural formula | NMR |
|---|---|---|
| 2-241 | | (MeOH-d4-300) 1.94(dd, J=9.8, 5.7Hz, 1H), 2.12-2.14(m, 4H), 2.78(t, J=9.0Hz, 1H), 7.09(d, J=4.1Hz, 1H), 7.16-7.28(m, 5H), 7.48(d, J=4.1Hz, 1H), 7.52(s, 1H), 8.00(s, 1H) |
| 2-242 | | (DMSO-d6-300) 1.64-1.74(m, 1H), 2.05-2.17(m, 1H), 2.65-2.79(m, 1H), 2.80-2.94(m, 1H), 3.06-3.19(m, 1H), 3.26-3.38(m, 4H), 3.46-3.58(m, 4H), 4.16-4.28(m, 2H), 7.04-7.18(m, 4H), 7.71(d, J=3.8Hz, 1H), 7.87(d, J=3.8Hz, 1H), 8.19(s, 1H), 9.46(brs, 1H), 12.26(brs, 1H) |

TABLE 2-49-continued

| Example | Structural formula | NMR |
| --- | --- | --- |
| 2-243 | | (DMSO-d6-300)<br>1.73(dd, J=9.8, 5.7Hz, 1H),<br>2.13(dd, J=7.9, 5.7Hz, 1H),<br>2.69(t, J=9.2Hz, 1H), 3.23-<br>3.62(m, 8H), 3.81(dd, J=21.7,<br>16.4Hz, 2H), 6.95-7.03(m, 1H),<br>7.05-7.21(m, 3H), 7.71(d,<br>J=4.1Hz, 1H), 7.88(d, J=3.8Hz,<br>1H), 8.19(s, 1H), 9.51(brs, 1H),<br>12.32(brs, 1H) |
| 2-244 | | (MeOH-d4-400)<br>1.85-1.90(m, 1H), 2.11(dd, J=5.7,<br>8.6Hz, 1H), 2.81-2.85(m, 1H),<br>3.64(brs, 2H), 7.14-7.27(m, 6H),<br>7.44(dd, J=2.2, 9.0Hz, 1H), 7.91-<br>8.07(m, 4H) |
| 2-245 | | (MeOH-d4-400)<br>1.88(dd, J=6.1, 10.2Hz, 1H),<br>2.08(dd, J=5.7, 8.6Hz, 1H),<br>2.74(t, J=9.2Hz, 1H), 3.05-<br>3.07(m, 4H), 3.77-3.80(m, 4H),<br>6.83(d, J=8.7Hz, 2H), 7.14(d,<br>J=8.6Hz, 2H), 7.37-7.48(m, 3H),<br>7.57(d, J=4.0Hz, 1H), 7.65(d,<br>J=8.6Hz, 2H) |

TABLE 2-50

| Example | Structural formula | NMR |
| --- | --- | --- |
| 2-246 | | (MeOH-d4-400)<br>1.89(dd, J=5.7, 9.8Hz, 1H),<br>2.08(dd, J=5.8, 8.6Hz, 1H),<br>2.77(t, J=9.2Hz, 1H), 2.91-<br>3.04(m, 5H), 3.20-3.31(m, 2H),<br>3.56-3.58(m, 2H), 3.77-3.84(m,<br>2H), 6.90(d, J=8.6Hz, 2H),<br>7.20(d, J=8.4Hz, 2H), 7.39-<br>7.45(m, 3H), 7.57(d, J=4.0Hz,<br>1H), 7.66(d, J=8.6Hz, 2H) |

TABLE 2-50-continued
| Example | Structural formula | NMR |
|---|---|---|
| 2-247 | 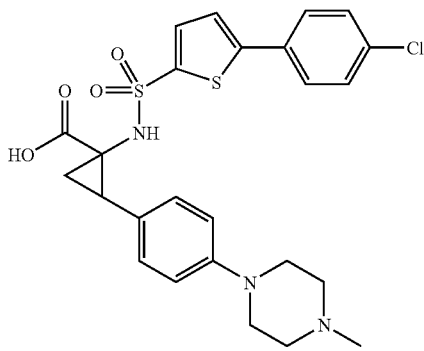 | (MeOH-d4-400) 2.05(dd, J=5.9, 9.7Hz, 1H), 2.26-2.30(m, 1H), 2.69-2.73(m, 1H), 2.88-3.05(m, 5H), 3.18-3.36(m, 2H), 3.52-3.65(m, 2H), 3.74-3.87(m, 2H), 6.93(d, J=8.6Hz, 2H), 7.12(d, J=8.6Hz, 2H), 7.39-7.50(m, 4H), 7.67(d, J=8.6Hz, 2H) |
| 2-248 | 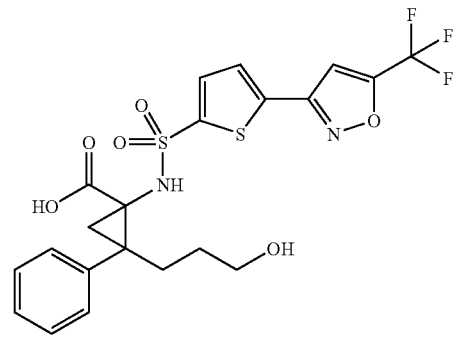 | (MeOH-d4-300) 1.04(t, J=7.2Hz, 1H), 1.31-1.47(m, 2H), 1.75-1.85(m, 2H), 1.98-2.01(m, 1H), 2.22(d, J=6.0Hz, 1H), 3.46(t, J=6.6Hz, 2H), 7.13-7.32(m, 5H), 7.63-7.68(m, 3H) |
| 2-249 | 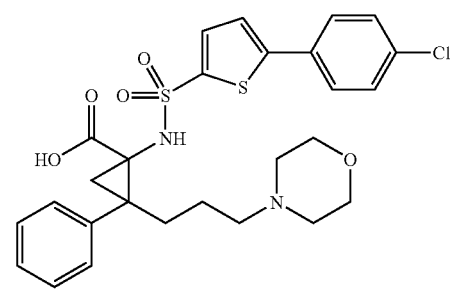 | (MeOH-d4-300) 1.44-1.47(m, 2H), 1.85-1.94(m, 3H), 2.09(d, J=5.7Hz, 1H), 2.39-2.49(m, 6H), 3.68(t, J=4.7Hz, 4H), 7.14-7.21(m, 5H), 7.38(d, J=4.1Hz, 1H), 7.44(d, J=8.7Hz, 2H), 7.59(d, J=4.1Hz, 1H), 7.67(d, J=8.7Hz, 2H) |
| 2-250 | 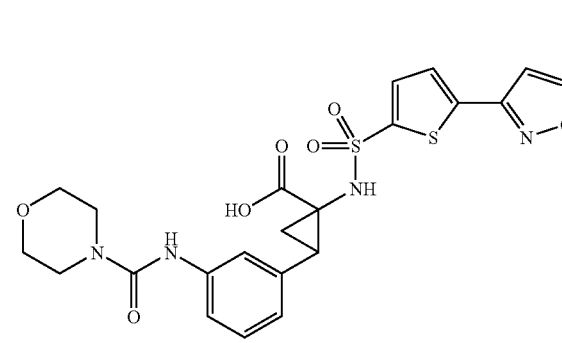 | (DMSO-d6-300) 1.61(dd, J=9.8, 5.7Hz, 1H), 1.97(dd, J=8.7, 5.7Hz, 1H), 2.73(t, J=9.0Hz, 1H), 3.40(t, J=4.5Hz, 4H), 3.60(t, J=4.3Hz, 4H), 6.81(d, J=7.9Hz, 1H), 7.11(t, J=7.9Hz, 1H), 7.30(d, J=7.9Hz, 1H), 7.38(s, 1H), 7.71(d, J=4.1Hz, 1H), 7.86(d, J=4.1Hz, 1H), 8.18(d, J=0.8Hz, 1H), 8.50(s, 1H), 9.43(s, 1H), 12.23(brs, 1H) |

TABLE 2-51

| Example | Structural formula | NMR |
|---------|-------------------|-----|
| 2-251 | | (DMSO-d6-300) 1.60(q, J=5.0Hz, 1H), 1.95(t, J=7.2Hz, 1H), 2.70(t, J=9.0Hz, 1H), 3.40(t, J=4.7Hz, 4H), 3.59(t, J=4.7Hz, 4H), 6.81(d, J=7.5Hz, 1H), 7.10(t, J=7.9Hz, 1H), 7.29(d, J=9.0Hz, 1H), 7.37(s, 1H), 7.53(d, J=8.7Hz, 2H), 7.57(s, 2H), 7.76(d, J=8.7Hz, 2H), 8.50(s, 1H), 9.22(s, 1H), 12.19(brs, 1H) |
| 2-252 | | (DMSO-d6-300) 1.65-1.76(m, 3H), 2.10-2.12(m, 1H), 2.54-2.81(m, 3H), 3.49(t, J=6.4Hz, 2H), 7.04-7.12(m, 4H), 7.71(d, J=3.8Hz, 1H), 7.87(d, J=4.1Hz, 1H), 8.18(s, 1H) |
| 2-253 | | (DMSO-d6-300) 1.70-1.74(m, 1H), 1.84-1.89(m, 2H), 2.08-2.14(m, 1H), 2.60-2.68(m, 2H), 2.76-2.90(m, 1H), 3.31-3.38(m, 4H), 3.49-3.57(m, 4H), 4.06-4.10(m, 2H), 7.06-7.16(m, 4H), 7.71(d, J=4.1Hz, 1H), 7.88(d, J=3.8Hz, 1H), 8.19(s, 1H), 9.48(brs, 1H), 12.21(brs, 1H) |
| 2-254 | | (DMSO-d6-300) 1.68-1.91(m, 7H), 2.08-2.15(m, 1H), 2.62-2.69(m, 1H), 2.76-2.90(m, 2H), 3.26-3.32(m, 2H), 3.47-3.51(m, 1H), 3.70-3.74(m, 1H), 4.02-4.07(m, 2H), 4.70-4.72(m, 1H), 7.04-7.15(m, 4H), 7.71(d, J=4.1Hz, 1H), 7.87(d, J=4.1Hz, 1H), 8.18(s, 1H), 9.50(brs, 1H), 12.20(brs, 1H) |

TABLE 2-51-continued
| Example | Structural formula | NMR |
|---|---|---|
| 2-255 | 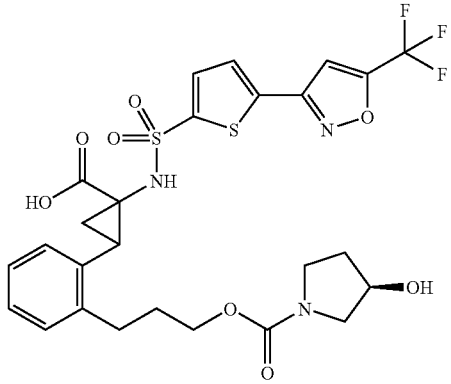 | (DMSO-d6-300)<br>1.70-1.92(m, 5H), 2.08-2.15(m, 1H), 2.61-2.72(m, 2H), 2.80-2.83(m, 1H), 3.16-3.21(m, 1H), 3.31-3.39(m, 3H), 4.04-4.07(m, 1H), 4.22-4.25(m, 1H), 4.91-4.92(m, 1H), 7.05-7.15(m, 4H), 7.71(d, J=3.8Hz, 1H), 7.87(d, J=4.1Hz, 1H), 8.19(s, 1H), 9.51(brs, 1H), 12.20(brs, 1H) |
TABLE 2-52
| Example | Structural formula | NMR |
|---|---|---|
| 2-256 | 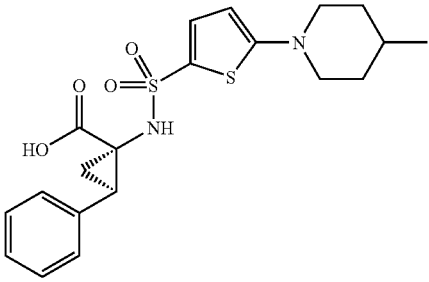 | (MeOH-d4-300)<br>1.00(d, J=6.8Hz, 3H), 1.25-1.85(m, 6H), 2.04(dd, J=9.0, 5.7Hz, 1H), 2.66(t, J=9.0Hz, 1H), 2.90(t, J=11.8Hz, 2H), 3.60(d, J=11.8Hz, 2H), 6.05(d, J=4.1Hz, 1H), 7.13-7.33(m, 6H) |
| 2-257 | 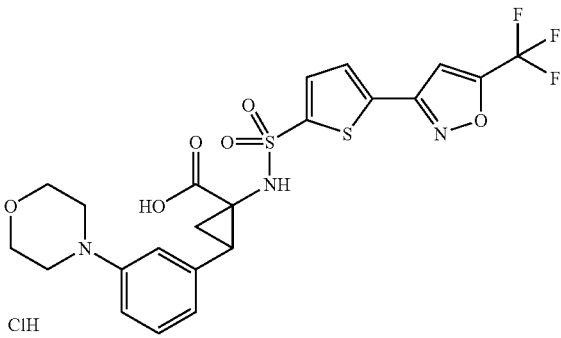 | (DMSO-d6-300)<br>1.60(dd, J=9.8, 5.5Hz, 1H), 2.03(dd, J=8.7, 5.5Hz, 1H), 2.74(dd, J=9.8, 8.7Hz, 1H), 3.03-3.12(m, 4H), 3.70-3.78(m, 4H), 6.72(d, J=7.2Hz, 1H), 6.79-6.88(m, 2H), 7.12(t, J=7.9Hz, 1H), 7.69(d, J=4.1Hz, 1H), 7.87(d, J=4.1Hz, 1H), 8.18(s, 1H), 9.38(brs, 1H) |
| 2-258 | 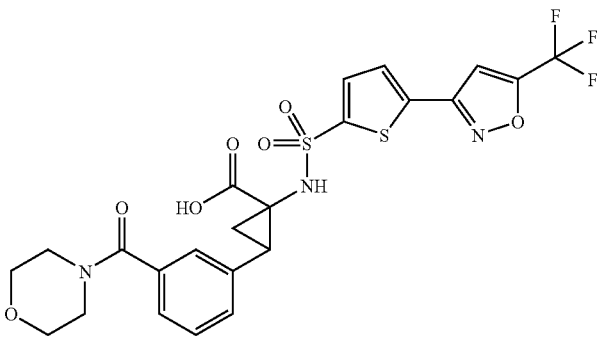 | (DMSO-d6-300)<br>1.67(dd, J=9.7, 5.7Hz, 1H), 2.11(dd, J=8.7, 5.7Hz, 1H), 2.84(dd, J=9.7, 8.7Hz, 1H), 3.17-3.71(m, 8H), 7.20-7.26(m, 2H), 7.31-7.40(m, 2H), 7.71(d, J=4.1Hz, 1H), 7.87(d, J=4.1Hz, 1H), 8.18(s, 1H), 9.41(brs, 1H), 12.32(brs, 1H) |

TABLE 2-52-continued

| Example | Structural formula | NMR |
|---|---|---|
| 2-259 | | (DMSO-d6-300) 1.63(dd, J=10.0, 5.8Hz, 1H), 2.04(dd, J=8.3, 5.8Hz, 1H), 2.65(t, J=7.9Hz, 2H), 2.75(dd, J=10.0, 8.3Hz, 1H), 3.13-3.27(m, 2H), 3.23(t, J=4.7Hz, 4H), 3.52(t, J=4.7Hz, 4H), 6.58-6.64(m, 1H), 6.99-7.09(m, 2H), 7.14-7.22(m, 1H), 7.70(d, J=4.1Hz, 1H), 7.86(d, J=4.1Hz, 1H), 8.18(s, 1H), 9.42(s, 1H), 12.24(s, 1H) |
| 2-260 | | (DMSO-d6-300) 1.64(q, J=4.9Hz, 1H), 1.98(dd, J=8.9, 5.1Hz, 1H), 2.81(t, J=9.6Hz, 1H), 3.18-4.24(m, 11H), 7.00(d, J=7.2Hz, 1H), 7.25(t, J=8.3Hz, 1H), 7.47-7.51(m, 2H), 7.72(d, J=4.1Hz, 1H), 7.87(d, J=3.8Hz, 1H), 8.19(s, 1H), 9.45(s, 1H), 10.56(brs, 1H), 12.28(brs, 1H) |

TABLE 2-53

| Example | Structural formula | NMR |
|---|---|---|
| 2-261 | | (DMSO-d6-300) 1.63(dd, J=10.0, 5.8Hz, 1H), 1.97(dd, J=8.5, 6.2Hz, 1H), 2.77(t, J=9.4Hz, 1H), 3.18-4.23(m, 10H), 7.00(d, J=7.2Hz, 1H), 7.24(t, J=8.1Hz, 1H), 7.46-7.59(m, 6H), 7.76(d, J=8.7Hz, 2H), 9.25(s, 1H), 10.70(brs, 1H), 12.24(brs, 1H) |
| 2-262 | | (DMSO-d6-300) 1.25(d, J=6.8Hz, 3H), 1.97(dd, J=10.2, 6.4Hz, 1H), 2.76(d, J=10.2Hz, 1H), 7.12-7.29(m, 5H), 7.52(d, J=8.7Hz, 2H), 7.56(s, 2H), 7.74(d, J=8.7Hz, 2H) |

TABLE 2-53-continued

| Example | Structural formula | NMR |
|---|---|---|
| 2-263 | | (MeOH-d4-300) 1.85(d, J=6.0Hz, 1H), 1.94-2.04(m, 1H), 2.13-2.21(m, 1H), 2.20(d, J=5.7Hz, 1H), 3.42(t, J=7.0Hz, 2H), 7.18-7.23(m, 5H), 7.40(d, J=4.1Hz, 1H), 7.45(d, J=8.7Hz, 2H), 7.58(d, J=3.8Hz, 1H), 7.67(d, J=8.7Hz, 2H) |
| 2-264 | | (CDCl3-300) 1.26(s, 1H), 1.50(s, 2H), 1.83-1.85(m, 1H), 2.02(s, 3H), 2.21-2.23(m, 1H), 3.97-3.99(m, 2H), 6.09(s, 1H), 6.99(s, 1H), 7.08-7.09(m, 2H), 7.23-7.25(m, 3H), 7.44(d, J=4.0Hz, 1H), 7.63(d, J=4.0Hz, 1H) |
| 2-265 | | (MeOH-d4-400) 1.95(dd, J=5.8, 9.8Hz, 1H), 2.14(dd, J=5.8, 8.6Hz, 1H), 2.87(t, J=9.2Hz, 1H), 4.05(s, 2H), 7.32-7.40(m, 5H), 7.44(d, J=8.6Hz, 2H), 7.58(d, J=4.0Hz, 1H), 7.66(d, J=8.6Hz, 2H) |

TABLE 2-54

| Example | Structural formula | NMR |
|---|---|---|
| 2-266 | | (MeOH-d4-400) 1.97(dd, J=5.8, 9.8Hz, 1H), 2.19(dd, J=5.9, 8.6Hz, 1H), 2.88-2.93(m, 1H), 2.95(s, 3H), 3.07(s, 3H), 7.31(d, J=8.3Hz, 2H), 7.37(d, J=8.1Hz, 2H), 7.65-7.68(m, 3H) |

TABLE 2-54-continued

| Example | Structural formula | NMR |
|---|---|---|
| 2-267 | | (DMSO-d6-300) 1.64(q, J=5.0Hz, 1H), 1.92(dd, J=8.1, 5.8Hz, 1H), 2.67(t, J=7.9Hz, 1H), 3.03(t, J=4.3Hz, 4H), 3.50(t, J=4.5Hz, 4H), 6.91(d, J=7.9Hz, 1H), 7.00(d, J=8.7Hz, 1H), 7.12-7.19(m, 2H), 7.70(d, J=3.8Hz, 1H), 7.85(d, J=4.1Hz, 1H), 8.17(s, 1H), 9.87(brs, 1H), 12.27(brs, 1H) |
| 2-268 | | (DMSO-d6-300) 1.63(q, J=5.1Hz, 1H), 2.02(dd, J=8.7, 6.8Hz, 1H), 2.65(t, J=7.2Hz, 1H), 2.72(t, J=6.8Hz, 1H), 3.54(t, J=7.3Hz, 1H), 4.62(brs, 1H), 7.00-7.08(m, 3H), 7.15(t, J=7.3Hz, 1H), 7.69(d, J=3.8Hz, 1H), 7.86(d, J=3.8Hz, 1H), 8.17(s, 1H), 9.38(brs, 1H), 12.24(brs, 1H) |
| 2-269 | | (DMSO-d6-300) 1.63(q, J=5.1Hz, 1H), 1.91(dd, J=7.7, 6.2Hz, 1H), 2.66(t, J=8.9Hz, 1H), 3.03(t, J=4.1Hz, 4H), 3.50(t, J=4.5Hz, 4H), 6.91(d, J=7.9Hz, 1H), 7.00(d, J=7.9Hz, 1H), 7.12-7.19(m, 2H), 7.52(d, J=8.7Hz, 2H), 7.57(s, 2H), 7.76(d, J=8.7Hz, 2H), 9.91(brs, 1H), 12.28(brs, 1H) |
| 2-270 | | (DMSO-d6-300) 1.63(dd, J=9.6, 5.5Hz, 1H), 2.05(dd, J=8.9, 5.5Hz, 1H), 2.75(t, J=9.0Hz, 1H), 2.79(t, J=7.3Hz, 1H), 4.05(t, J=7.2Hz, 2H), 6.45(brs, 2H), 7.06-7.12(m, 3H), 7.17(d, J=6.8Hz, 1H), 7.69(d, J=4.1Hz, 1H), 7.86(d, J=4.1Hz, 1H), 8.18(d, J=0.8Hz, 1H), 9.41(brs, 1H), 12.12(brs, 1H) |

TABLE 2-55

| Example | Structural formula | NMR |
|---|---|---|
| 2-271 | | (MeOH-d4-400) 1.95(dd, J=5.5, 9.6Hz, 1H), 2.14(dd, J=6.0, 8.0Hz, 1H), 2.78(t, J=9.1Hz, 1H), 2.94-3.72(complexm, 10H), 7.28-7.38(m, 4H), 7.65-7.70(m, 3H) |
| 2-272 | | (MeOH-d4-300) 1.30-1.38(m, 3H), 1.81(d, J=6.0Hz, 1H), 1.88(s, 3H), 1.93-2.03(m, 1H), 2.19(d, J=6.0Hz, 1H), 3.06-3.08(m, 2H), 7.16-7.23(m, 5H), 7.40(d, J=4.1Hz, 1H), 7.45(dd, J=6.6, 2.1Hz, 2H), 7.57(d, J=4.1Hz, 1H), 7.67(dd, J=6.6, 2.1Hz, 2H) |
| 2-273 | | (MeOH-d4-300) 1.71-1.73(m, 4H), 2.19(d, J=6.0Hz, 1H), 4.03-4.05(m, 2H), 6.21(t, J=2.3Hz, 1H), 7.16-7.23(m, 5H), 7.41-7.46(m, 4H), 7.53(d, J=4.1Hz, 1H), 7.67(dd, J=6.6, 2.1Hz, 2H) |
| 2-274 | | (DMSO-d6-300) 1.16(s, 3H), 1.34(s, 3H), 2.56(s, 1H), 7.13-7.29(m, 5H), 7.51(d, J=8.7Hz, 2H), 7.55(s, 2H), 7.73(d, J=8.7Hz, 2H), 9.03(brs, 1H), 12.28(brs, 1H) |

TABLE 2-55-continued

| Example | Structural formula | NMR |
|---|---|---|
| 2-275 | | (DMSO-d6-300)<br>1.17(s, 3H), 1.34(s, 3H), 2.57(s, 1H), 7.13-7.31(m, 5H), 7.69(d, J=4.1Hz, 1H), 7.84(d, J=4.1Hz, 1H), 8.15(s, 1H), 9.23(brs, 1H), 12.31(brs, 1H) |

TABLE 2-56

| Example | Structural formula | NMR |
|---|---|---|
| 2-276 | | (DMSO-d6-300)<br>1.64(dd, J=9.7, 5.7Hz, 1H), 1.97-2.12(m, 3H), 2.43-2.49(m, 2H), 2.70-2.84(m, 1H), 3.71-3.85(m, 2H), 6.98(d, J=7.5Hz, 1H), 7.24(dd, J=7.9, 7.5Hz, 1H), 7.50(d, J=7.9Hz, 1H), 7.53(s, 1H), 7.71(d, J=4.1Hz, 1H), 7.86(d, J=4.1Hz, 1H), 8.18 (s, 1H), 9.41(brs, 1H), 12.26(brs, 1H) |
| 2-277 | | (MeOH-d4-400)<br>2.68(t, J=7.0Hz, 1H), 3.03(d, J=7.0Hz, 1H), 3.18(dd, J=7.0, 17.5Hz, 1H), 3.50(d, J=17.3Hz, 1H), 7.06(s, 3H), 7.24-7.28(m, 1H), 7.65-7.67(m, 3H) |
| 2-278 | | (DMSO-d6-400)<br>1.60(dd, J=5.5, 9.6Hz, 1H), 2.02(dd, J=5.8, 8.2Hz, 1H), 2.31(t, J=7.7Hz, 2H), 2.70-2.75(m, 3H), 6.74(s, 1H), 7.11(q, J=8.1Hz, 4H), 7.26(s, 1H), 7.69(d, J=3.9Hz, 1H), 7.86(d, J=3.9Hz, 1H), 8.17(s, 1H), 9.39(s, 1H) |

TABLE 2-56-continued
| Example | Structural formula | NMR |
| --- | --- | --- |
| 2-279 | 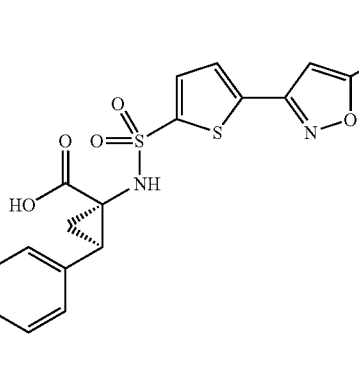 | (DMSO-d6-400) 1.60(dd, J=5.6, 9.7Hz, 1H), 2.02(dd, J=5.7, 8.4Hz, 1H), 2.55-2.59(m, 2H), 2.70-2.77(m, 3H), 3.37-3.43(m, 4H), 3.48-3.53(m, 4H), 7.13(s, 4H), 7.69(d, J=3.9Hz, 1H), 7.86(d, J=3.9Hz, 1H), 8.17(s, 1H), 9.39(s, 1H) |
| 2-280 | 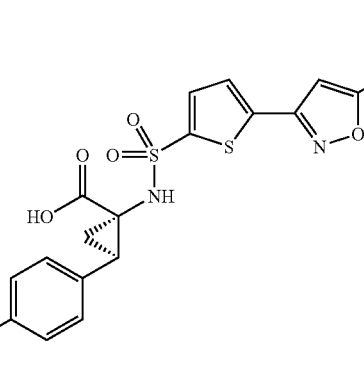 | (DMSO-d6-400) 1.61(dd, J=5.6, 9.8Hz, 1H), 2.02(dd, J=5.7, 8.4Hz, 1H), 2.59-3.60(complexm, 16H), 7.14(s, 4H), 7.87(d, J=3.9Hz, 1H), 8.18(s, 1H), 9.39(s, 1H) |
TABLE 2-57
| Example | Structural formula | NMR |
| --- | --- | --- |
| 2-281 | 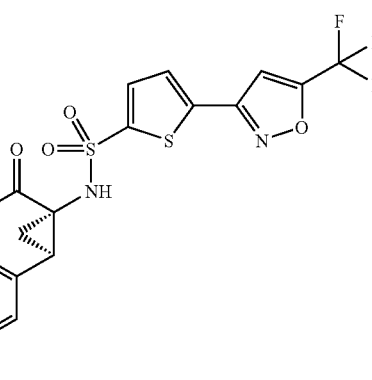 | (DMSO-d6-400) 1.60(dd, J=5.6, 9.7Hz, 1H), 2.02(dd, J=5.8, 8.4Hz, 1H), 2.29-2.33(m, 2H), 2.54(d, J=4.5Hz, 3H), 2.70-2.76(m, 3H), 7.10(dd, J=8.0, 19.3Hz, 4H), 7.69(d, J=3.9Hz, 1H), 7.71-7.73(m, 1H), 7.86(d, J=3.9Hz, 1H), 8.17(s, 1H), 9.38(s, 1H) |

TABLE 2-57-continued

| Example | Structural formula | NMR |
|---|---|---|
| 2-282 | | (DMSO-d6-400) 1.60(dd, J=5.6, 9.8Hz, 1H), 2.02(dd, J=5.7, 8.5Hz, 1H), 2.52-2.56(m, 2H), 2.69-2.75(m, 3H), 2.80(s, 3H), 2.90(s, 3H), 7.12(s, 4H), 7.69(d, J=3.9Hz, 1H), 7.86(d, J=3.9Hz, 1H), 8.18(s, 1H), 9.39(s, 1H) |
| 2-283 | | (DMSO-d6-300) 1.66(dd, J=9.8, 5.7Hz, 1H), 2.07(dd, J=8.7, 5.7Hz, 1H), 2.80(dd, J=9.8, 8.7Hz, 1H), 5.38(s, 2H), 7.23-7.36(m, 4H), 7.70(d, J=3.8Hz, 1H), 7.86(d, J=3.8Hz, 1H), 8.18(s, 1H), 9.43(s, 1H), 12.31(s, 1H) |
| 2-284 | | (DMSO-d6-400) 0.42-0.58(m, 10H), 0.98(d, J=5.6Hz, 1H), 1.07-1.21(m, 1H), 1.35(d, J=5.6Hz, 1H), 2.12-2.14(m, 2H), 6.33-6.40(m, 5H), 6.57(d, J=4.2Hz, 1H), 6.62(d, J=8.8Hz, 2H), 6.75(d, J=4.2Hz, 1H), 6.85(d, J=8.8Hz, 2H) |
| 2-285 | | (MeOH-d4-300) 1.54-1.57(m, 2H), 1.85-1.86(m, 1H), 1.92(d, J=6.0Hz, 1H), 2.01-2.04(m, 1H), 2.24(d, J=6.0Hz, 1H), 2.77-2.88(m, 2H), 7.19-7.24(m, 5H), 7.39(d, J=4.1Hz, 1H), 7.43(dd, J=6.8, 1.9Hz, 2H), 7.56(d, J=4.1Hz, 1H), 7.65(dd, J=6.8, 1.9Hz, 2H) |

TABLE 2-58

| Example | Structural formula | NMR |
|---|---|---|
| 2-286 | | (MeOH-d4-300)<br>1.33(d, J=6.8Hz, 3H), 2.14(dd, J=10.5, 6.8Hz, 1H), 2.84(d, J=10.5Hz, 1H), 4.01(s, 2H), 7.16-7.23(m, 5H), 7.57(dd, J=8.3, 1.9Hz, 1H), 7.79(brs, 1H), 7.83(d, J=7.9Hz, 1H), 7.93-7.97(m, 2H), 8.08(brs, 1H) |
| 2-287 | | (MeOH-d4-400)<br>1.37(d, J=6.5Hz, 3H), 2.14(s, 3H), 2.16-2.24(m, 1H), 2.94(d, J=10.2Hz, 1H), 7.08(d, J=4.2Hz, 1H), 7.16-7.30(m, 5H), 7.48(dd, J=4.2, 0.9Hz, 1H), 7.51(s, 1H), 7.99(brs, 1H) |
| 2-288 | | (DMSO-d6-300)<br>1.27(d, J=6.4Hz, 3H), 2.01(dd, J=10.4, 7.0Hz, 1H), 2.80(d, J=10.2Hz, 1H), 7.11-7.34(m, 5H), 7.70(d, J=3.8Hz, 1H), 7.85(d, J=3.8Hz, 1H), 8.17(s, 1H), 9.28(brs, 1H), 12.35(brs, 1H) |
| 2-289 | | (MeOH-d4-400)<br>1.95(dd, J=5.8, 9.8Hz, 1H), 2.15(dd, J=5.8, 8.6Hz, 1H), 2.91(t, J=9.2Hz, 1H), 4.05(s, 2H), 7.36(dt, J=8.2, 8.2Hz, 4H), 7.65-7.68(m, 3H) |

TABLE 2-58-continued
| Example | Structural formula | NMR |
|---|---|---|
| 2-290 | 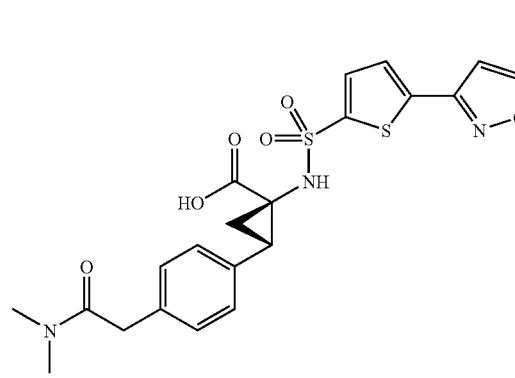 | (DMSO-d6-400) 1.61(dd, J=5.6, 9.6Hz, 1H), 2.03(dd, J=5.8, 8.2Hz, 1H), 2.74(t, J=9.2Hz, 1H), 2.81(s, 3H), 2.96(s, 3H), 3.4-3.8(s, 2H), 7.10(d, J=8.0Hz, 2H), 7.15(d, J=8.0Hz, 2H), 7.69(d, J=3.8Hz, 1H), 7.86(d, J=3.8Hz, 1H), 8.17(s, 1H), 9.40(s, 1H) |
TABLE 2-59
| Example | Structural formula | NMR |
|---|---|---|
| 2-291 | 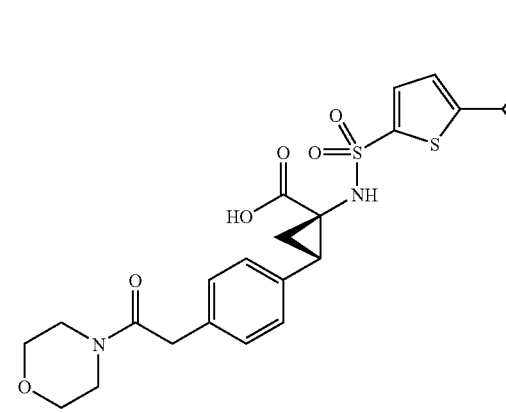 | (DMSO-d6-400) 1.59(dd, J=5.5, 9.4Hz, 1H), 2.00(dd, J=5.9, 7.9Hz, 1H), 2.71(t, J=9.1Hz, 1H), 3.41-3.48(m, 8H), 3.62(s, 2H), 7.07(d, J=7.8Hz, 2H), 7.13(d, J=7.8Hz, 2H), 7.66(d, J=3.7Hz, 1H), 7.82(d, J=3.7Hz, 1H), 8.12(s, 1H), 9.36(s, 1H) |
| 2-292 | 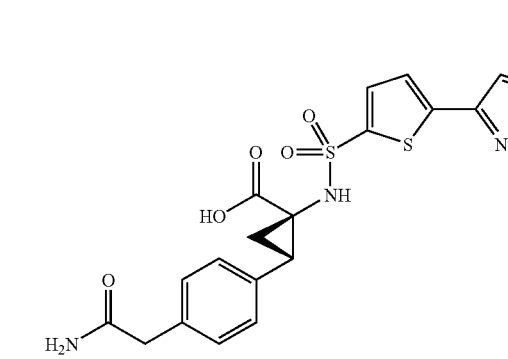 | (MeOH-d4-400) 1.93(dd, J=5.8, 9.8Hz, 1H), 2.14(dd, J=5.9, 8.5Hz, 1H), 2.83(t, J=9.2Hz, 1H), 3.44(s, 2H), 7.18-7.24(m, 4H), 7.65-7.68(m, 3H) |

TABLE 2-59-continued

| Example | Structural formula | NMR |
|---|---|---|
| 2-293 | | (DMSO-d6-400) 1.61(dd, J=5.5, 9.3Hz, 1H), 2.02-2.05(m, 1H), 2.56(s, 3H), 2.74(t, J=9.1Hz, 1H), 3.33(s, 2H), 7.15(m, 4H), 7.70(d, J=3.6Hz, 1H), 7.86(d, J=3.6Hz, 1H), 7.94(s, 1H), 8.17(s.1H), 9.40(s, 1H) |
| 2-294 | | (MeOH-d4-400) 1.91(dd, J=5.8, 9.7Hz, 1H), 2.13(dd, J=5.9, 8.4Hz, 1H), 2.47-4.33(complexm, 14H), 7.16(d, J=8.0Hz, 2H), 7.27(d, J=7.9Hz, 2H), 7.65-7.69(m, 3H), 8.89(s, 2H) |
| 2-295 | | (DMSO-d6-300) 1.58(d, J=5.7Hz, 1H), 1.77-1.87(m, 1H), 2.03-2.20(m, 2H), 3.56-3.70(m, 2H), 6.38(brs, 2H), 7.11-7.26(m, 5H), 7.47-7.56(m, 4H), 7.73(d, J=8.7Hz, 2H), 9.19(brs, 1H), 12.19(brs, 1H) |

TABLE 2-60

| Example | Structural formula | NNR |
|---|---|---|
| 2-296 | | (DMSO-d6-300) 1.23(d, J=6.8Hz, 3H), 1.80(dd, J=10.4, 6.6Hz, 1H), 2.61(d, J=10.5Hz, 1H), 6.85(brs, 1H), 7.04(brs, 1H), 7.12-7.28(m, 5H), 7.74(d, J=3.8Hz, 1H), 7.87(d, J=3.8Hz, 1H), 8.17(s, 1H), 9.11(brs, 1H) |

TABLE 2-60-continued

| Example | Structural formula | NNR |
|---|---|---|
| 2-297 | | (DMSO-d6-300) 1.21(d, J=6.8Hz, 3H), 1.77(dd, J=10.7, 6.6Hz, 1H), 2.39(d, J=4.1Hz, 3H), 2.58(d, J=10.5Hz, 1H), 7.09-7.27(m, 5H), 7.49(d, J=4.9Hz, 1H), 7.72(d, J=3.8Hz, 1H), 7.87(d, J=3.8Hz, 1H), 8.16(s, 1H), 9.01(brs, 1H) |
| 2-298 | | (MeOH-d4-300) 1.61-1.76(m, 10H), 2.17(d, J=5.7Hz, 1H), 2.96-2.99(m, 1H), 4.95-4.98(m, 1H), 7.19(t, J=7.9Hz, 5H), 7.38(d, J=4.1Hz, 1H), 7.43(d, J=8.7Hz, 2H), 7.55(d, J=4.1Hz, 1H), 7.66(d, J=8.7Hz, 2H) |
| 2-299 | | (MeOH-d4-400) 1.07(t, J=7.3Hz, 3H), 1.70-1.80(m, 1H), 1.82-1.93(m, 1H), 2.03-2.10(m, 1H), 2.98(d, J=10.5Hz, 1H), 7.15-7.28(m, 5H), 7.64-7.68(m, 3H) |
| 2-300 | | (MeOH-d4-400) 1.93(dd, J=6.0, 9.9Hz, 1H), 2.12(dd, J=5.8, 8.5Hz, 1H), 2.88(dd, J=8.0, 15.0Hz, 1H), 3.13(t, J=7.8Hz, 2H), 3.18-3.24(m, 2H), 7.17(d, J=7.9Hz, 2H), 7.28(d, J=7.9Hz, 2H), 7.65-7.68(m, 3H) |

TABLE 2-61

| Example | Structural formula | NMR |
|---|---|---|
| 2-301 | | (MeOH-d4-400) 1.91(dd, J=5.8, 9.7Hz, 1H), 2.13(dd, J=6.1, 8.4Hz, 1H), 2.75(t, J=7.0Hz, 2H), 2.81(t, J=9.2Hz, 1H), 3.69(t, J=7.0Hz, 2H), 7.10(d, J=7.9Hz, 2H), 7.19(d, J=7.8Hz, 2H), 7.64-7.67(m, 3H) |
| 2-302 | | (MeOH-d4-400) 1.73-1.81(m, 2H), 1.91(dd, J=5.3, 9.4Hz, 1H), 2.11-2.15(m, 1H), 2.61(t, J=7.6Hz, 2H), 2.80(t, J=8.9Hz, 1H), 3.52(t, J=6.4Hz, 2H), 7.08(d, J=7.7Hz, 2H), 7.17(d, J=7.8Hz, 2H), 7.65-7.67(m, 3H) |
| 2-303 | | (DMSO-d6-300) 1.48(d, J=6.0Hz, 1H), 1.83(q, J=7.4Hz, 1H), 2.11(d, J=5.3Hz, 1H), 2.16-2.25(m, 1H), 2.65(s, 6H), 3.62(q, J=8.3Hz, 1H), 3.81(q, J=5.4Hz, 1H), 7.11-7.19(m, 3H), 7.23(d, J=7.2Hz, 1H), 7.27(d, J=4.1Hz, 1H), 7.48-7.57(m, 4H), 7.74(d, J=8.3Hz, 2H), 9.23(s, 1H), 12.19(brs, 1H) |
| 2-304 | | (DMSO-d6-300) 1.26(d, J=6.0Hz, 6H), 1.68(dd, J=8.7, 5.8Hz, 1H), 2.13(dd, J=8.5, 5.8Hz, 1H), 2.83(dd, J=8.7, 8.5Hz, 1H), 3.14-3.98(m, 3H), 7.27-7.49(m, 4H), 7.72(d, J=3.8Hz, 1H), 7.88(d, J=3.8Hz, 1H), 8.19(s, 1H), 9.45(s, 1H) |

TABLE 2-61-continued

| Example | Structural formula | NMR |
|---|---|---|
| 2-305 | | (DMSO-d6-400) 1.41-1.91(m, 5H), 2.43-2.53(m, 1H), 2.76(d, J=9.7Hz, 1H), 2.99(td, J=13.0, 7.4Hz, 1H), 7.04-7.18(m, 4H), 7.70(d, J=3.7Hz, 1H), 7.85(d, J=3.7Hz, 1H), 8.17(s, 1H), 9.26(brs, 1H), 12.43(brs, 1H) |

TABLE 2-62

| Example | Structural formula | NMR |
|---|---|---|
| 2-306 | | (DMSO-d6-300) 1.80(d, J=6.0Hz, 1H), 2.13(d, J=5.7Hz, 1H), 3.20-3.44(m, 8H), 4.21(d, J=11.3Hz, 1H), 4.26(d, J=11.3Hz, 1H), 7.15-7.29(m, 5H), 7.70(d, J=3.8Hz, 1H), 7.86(d, J=4.1Hz, 1H), 8.18(s, 1H), 9.52(brs, 1H), 12.43(brs, 1H) |
| 2-307 | | (DMSO-d6-300) 1.63(dd, J=10.2, 6.0Hz 1H), 2.06(dd, J=8.7, 5.7Hz, 1H), 2.79(t, J=9.4Hz, 1H), 7.15-7.31(m, 5H), 7.62-7.73(m, 4H), 7.89(d, J=8.7Hz, 2H), 9.49(brs, 1H), 12.27(brs, 1H) |
| 2-308 | | (DMSO-d6-300) 1.02(s, 3H), 1.04(s, 3H), 1.75(d, J=5.7Hz, 1H), 2.14(d, J=5.3Hz, 1H), 2.93-3.00(m, 2H), 3.20-3.29(m, 2H), 3.43-3.50(m, 1H), 4.15(d, J=11.7Hz, 1H), 4.26(d, J=10.9Hz, 1H), 6.92(t, J=5.7Hz, 1H), 7.16-7.25(m, 5H), 7.70(d, J=3.8Hz, 1H), 7.86(d, J=4.1Hz, 1H), 8.17(s, 1H), 9.38(brs, 1H), 12.40(brs, 1H) |

TABLE 2-62-continued

| Example | Structural formula | NMR |
|---|---|---|
| 2-309 | | (DMSO-d6-300)<br>1.68-1.79(m, 5H), 2.11-2.16(m, 1H), 2.87-2.92(m, 2H), 3.54-3.72(m, 3H), 4.15(d, J=11.3Hz, 1H), 4.25(d, J=12.8Hz, 1H), 6.96-7.01(m, 1H), 7.17-7.25(m, 5H), 7.70(d, J=3.8Hz, 1H), 7.86(d, J=3.8Hz, 1H), 8.17(s, 1H), 9.35(brs, 1H), 12.40(brs, 1H) |
| 2-310 | | (DMSO-d6-300)<br>1.21-1.37(m, 4H), 1.39-1.51(m, 2H), 1.77(d, J=6.0Hz, 1H), 2.15(d, J=6.0Hz, 1H), 3.13-3.24(m, 4H), 4.16(d, J=12.0Hz, 1H), 4.25(d, J=12.0Hz, 1H), 7.11-7.32(m, 5H), 7.70(d, J=3.0Hz, 1H), 7.87(d, J=3.0Hz, 1H), 8.18(s, 1H), 9.49(s, 1H), 12.40(brs, 1H) |

TABLE 2-63

| Example | Structural formula | NMR |
|---|---|---|
| 2-311 | | (acetone-d6-400)<br>2.14-2.19(m, 5H), 2.89(t, J=9.2Hz, 1H), 6.06(s, 1H), 7.73-7.74(m, 1H), 7.81-7.82(m, 2H) |
| 2-312 | | (CD3CN-400)<br>2.95(dd, J=5.0, 9.0Hz, 1H), 3.21(d, J=9.0Hz, 1H), 4.03(d, J=10.3Hz, 1H), 4.46(dd, 5.0, 10.3Hz, 1H), 7.28-7.41(m, 5H), 7.47(s, 1H), 7.65(d, J=3.9Hz, 1H), 7.75(d, J=3.9Hz, 1H) |

TABLE 2-63-continued

| Example | Structural formula | NMR |
|---|---|---|
| 2-313 | | (acetone-d6-400)<br>2.05(m, 1H), 2.11-2.15(m, 1H),<br>2.33(s, 3H), 2.77-2.82(m, 1H),<br>6.00(s, 1H), 7.74-7.82(m, 3H) |
| 2-314 | | (acetone-d6-400)<br>2.16(dd, J=5.8, 9.7Hz, 1H), 2.27-<br>2.31(m, 1H), 2.37(s, 3H),<br>2.80(dd, J=7.9, 9.6Hz, 1H),<br>5.97(s, 1H), 7.68-7.83(m, 3H) |
| 2-315 | | (acetone-d6-400)<br>2.05-2.07(m, 1H), 2.12-2.15(m, 1H), 2.81(t, J=9.3Hz, 1H),<br>2.88(t, J=6.4Hz, 2H), 3.79(t, J=6.2Hz, 2H), 6.09(s, 1H), 7.74-7.81(m, 3H) |

TABLE 2-64

| Example | Structural formula | NMR |
|---|---|---|
| 2-316 | | (acetone-d6-400)<br>2.17(dd, J=5.7, 9.6Hz, 1H), 2.25-<br>2.31(m, 1H), 2.82(t, J=8.8Hz,<br>1H), 2.92(t, J=6.4Hz, 2H),<br>3.82(t, J=6.5Hz, 2H), 6.05(s,<br>1H), 7.68-7.82(m, 3H) |

TABLE 2-64-continued
| Example | Structural formula | NMR |
|---------|-------------------|-----|
| 2-317 | 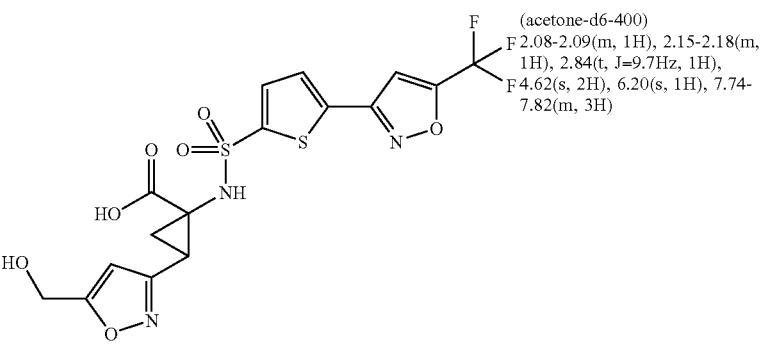 | (acetone-d6-400)<br>2.08-2.09(m, 1H), 2.15-2.18(m, 1H), 2.84(t, J=9.7Hz, 1H), 4.62(s, 2H), 6.20(s, 1H), 7.74-7.82(m, 3H) |
| 2-318 | 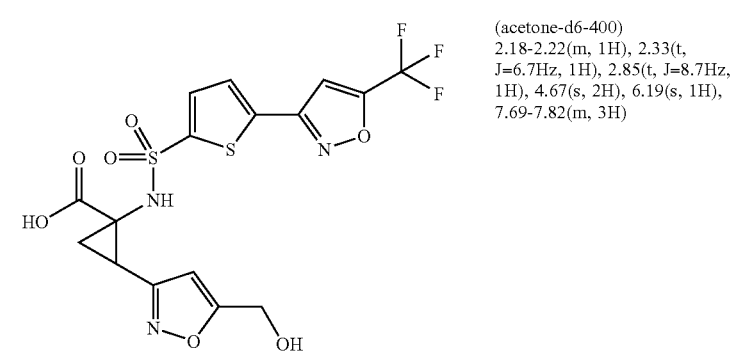 | (acetone-d6-400)<br>2.18-2.22(m, 1H), 2.33(t, J=6.7Hz, 1H), 2.85(t, J=8.7Hz, 1H), 4.67(s, 2H), 6.19(s, 1H), 7.69-7.82(m, 3H) |
| 2-319 | 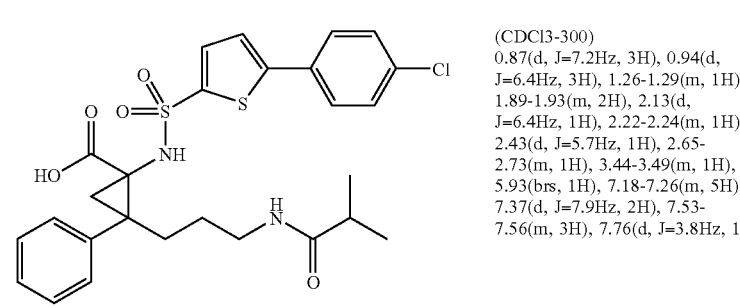 | (CDCl3-300)<br>0.87(d, J=7.2Hz, 3H), 0.94(d, J=6.4Hz, 3H), 1.26-1.29(m, 1H), 1.89-1.93(m, 2H), 2.13(d, J=6.4Hz, 1H), 2.22-2.24(m, 1H), 2.43(d, J=5.7Hz, 1H), 2.65-2.73(m, 1H), 3.44-3.49(m, 1H), 5.93(brs, 1H), 7.18-7.26(m, 5H), 7.37(d, J=7.9Hz, 2H), 7.53-7.56(m, 3H), 7.76(d, J=3.8Hz, 1H) |
| 2-320 | 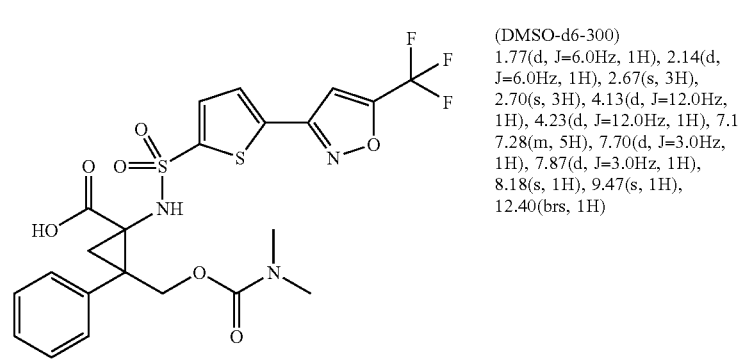 | (DMSO-d6-300)<br>1.77(d, J=6.0Hz, 1H), 2.14(d, J=6.0Hz, 1H), 2.67(s, 3H), 2.70(s, 3H), 4.13(d, J=12.0Hz, 1H), 4.23(d, J=12.0Hz, 1H), 7.16-7.28(m, 5H), 7.70(d, J=3.0Hz, 1H), 7.87(d, J=3.0Hz, 1H), 8.18(s, 1H), 9.47(s, 1H), 12.40(brs, 1H) |

TABLE 2-65

| Example | Structural formula | NMR |
|---|---|---|
| 2-321 | | (DMSO-d6-300)<br>0.91(t, J=7.5Hz, 3H), 1.75(d, 6.0Hz, 1H), 2.16(d, J=6.0Hz, 1H), 2.81-2.96(m, 2H), 4.13(d, J=12.0Hz, 1H), 4.28(d, J=12.0Hz, 1H), 6.89-6.97(m, 1H), 7.13-7.28(m, 5H), 7.70(d, J=3.0Hz, 1H), 7.87(d, J=3.0Hz, 1H), 8.18(s, 1H), 9.38(s, 1H), 12.37(brs, 1H) |
| 2-322 | | (DMSO-d6-300)<br>2.10-2.23(m, 1H), 2.90-4.11(m, 10H), 7.14-7.47(m, 5H), 7.69(d, J=4.1Hz, 1H), 7.86(d, J=4.1Hz, 1H), 8.19(s, 1H), 9.53(brs, 1H), 9.75(brs, 1H), 12.49(brs, 1H) |
| 2-323 | | (DMSO-d6-300)<br>1.20(d, J=6.4Hz, 2H), 1.73(dt, J=10.5, 6.5Hz, 1H), 2.56(d, J=10.5Hz, 1H), 7.11-7.27(m, 5H), 7.74(d, J=3.8Hz, 1H), 7.86(d, J=3.8Hz, 1H), 8.15(s, 1H), 8.62(brs, 1H), 8.92(brs, 1H), 10.21(brs, 1H) |
| 2-324 | | (DMSO-d6-300)<br>1.21(d, J=6.8Hz, 3H), 1.82(dd, J=10.4, 6.6Hz, 1H), 2.62(d, J=9.8Hz, 1H), 5.21(s, 2H), 7.12-7.30(m, 7H), 7.49(dd, J=8.5, 1.7Hz, 1H), 7.63(d, J=8.3Hz, 1H), 7.69-7.78(m, 3H), 8.60(brs, 1H), 12.18(brs, 1H) |

TABLE 2-65-continued

| Example | Structural formula | NMR |
|---|---|---|
| 2-325 | | (DMSO-d6-300) 1.14(d, J=6.4Hz, 3H), 1.53(dd, J=10.9, 6.4Hz, 1H), 2.38(d, J=10.5Hz, 1H), 5.21(s, 2H), 7.07-7.25(m, 7H), 7.48(d, J=8.3Hz, 1H), 7.62(d, J=8.3Hz, 1H), 7.70(s, 1H), 7.78(d, J=8.3Hz, 2H), 8.36(brs, 1H), 8.60(brs, 1H), 10.13(brs, 1H) |

TABLE 2-66

| Example | Structural formula | NMR |
|---|---|---|
| 2-326 | | (CDCl3-300) 1.25(d, J=5.3Hz, 3H), 2.18-2.29(m, 1H), 2.77-2.89(m, 1H), 7.11-7.34(m, 6H), 7.37(d, J=8.3Hz, 2H), 7.48(d, J=8.3Hz, 2H), 7.60(d, J=3.0Hz, 1H) |
| 2-327 | | (MeOH-d4-400) 1.07(t, J=7.3Hz, 3H), 1.68-1.80(m, 1H), 1.83-1.93(m, 1H), 2.07(ddd, J=5.8, 9.9, 10.1Hz, 1H), 2.99(d, J=10.5Hz, 1H), 7.15-7.27(m, 5H), 7.65-7.68(m, 3H) |
| 2-328 | | (MeOH-d4-400) 1.07(t, J=7.3Hz, 3H), 1.68-1.80(m, 1H), 1.82-1.93(m, 1H), 2.07(ddd, J=5.8, 9.9, 10.1Hz, 1H), 2.99(d, J=10.5Hz, 1H), 7.15-7.27(m, 5H), 7.64-7.68(m, 3H) |

TABLE 2-66-continued
| Example | Structural formula | NMR |
|---|---|---|
| 2-329 | 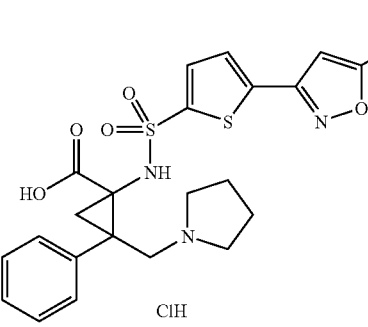 ClH | (DMSO-d6-300) 1.62-1.94(m, 4H), 2.12(d, J=6.8Hz, 1H), 2.41(d, J=6.8Hz, 1H), 2.53-2.68(m, 2H), 2.92-3.16(m, 2H), 3.42-3.57(m, 1H), 3.81-3.95(m, 1H), 7.21-7.43(m, 5H), 7.71(d, J=4.1Hz, 1H), 7.87(d, J=4.1Hz, 1H), 8.20(s, 1H), 9.53(brs, 1H), 9.76(brs, 1H), 12.50(brs, 1H) |
| 2-330 | 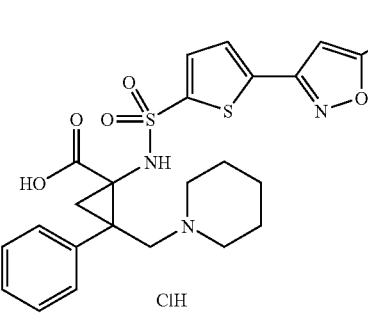 ClH | (DMSO-d6-300) 1.14-1.35(m, 1H), 1.47-1.76(m, 5H), 2.12(d, J=6.8Hz, 1H), 2.70-2.97(m, 2H), 3.07-3.44(m, 3H), 3.77-3.91(m, 1H), 7.16-7.46(m, 5H), 7.70(d, J=3.8Hz, 1H), 7.87(d, J=3.8Hz, 1H), 8.20(s, 1H), 9.16(brs, 1H), 9.52(brs, 1H), 12.50(brs, 1H) |
TABLE 2-67
| Example | Structural formula | NMR |
|---|---|---|
| 2-331 | 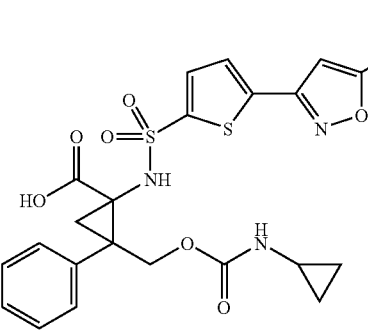 | (DMSO-d6-300) 0.25-0.30(m, 1H), 0.44-0.49(m, 1H), 1.75-1.81(m, 1H), 2.09-2.14(m, 1H), 2.29-2.36(m, 1H), 4.12(d, J=11.3Hz, 1H), 4.29(d, J=10.2Hz, 1H), 7.12-7.23(m, 6H), 7.69(d, J=3.8Hz, 1H), 7.86(d, J=3.8Hz, 1H), 8.17(s, 1H), 12.43(brs, 1H) |
| 2-332 | 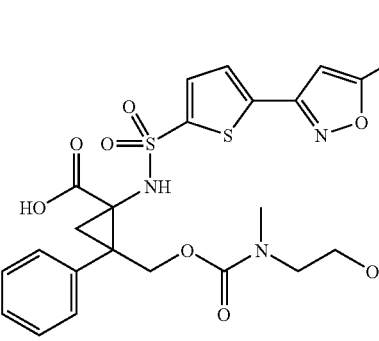 | (DMSO-d6-300) 1.79(d, J=5.7Hz, 1H), 2.11(d, J=4.5Hz, 1H), 2.68-2.79(m, 2H), 3.06-3.17(m, 2H), 3.36(s, 3H), 4.13(d, J=8.7Hz, 1H), 4.22(d, J=11.3Hz, 1H), 7.18-7.25(m, 5H), 7.69(d, J=4.1Hz, 1H), 7.86(d, J=3.8Hz, 1H), 8.17(s, 1H), 12.43(brs, 1H) |

TABLE 2-67-continued

| Example | Structural formula | NMR |
|---|---|---|
| 2-333 | | (DMSO-d6-300) 1.77(d, J=5.7Hz, 1H), 2.13(d, J=4.9Hz, 1H), 2.93(dd, J=6.3, 3.1Hz, 2H), 3.30(t, J=6.0Hz, 2H), 4.15(d, J=11.3Hz, 1H), 4.24(d, J=10.5Hz, 1H), 6.87(t, J=5.5Hz, 1H), 7.16-7.24(m, 5H), 7.69(d, J=4.1Hz, 1H), 7.85(d, J=3.8Hz, 1H), 8.17(s, 1H), 12.41(brs, OH) |
| 2-334 | | (DMSO-d6-300) 1.04(d, J=6.0Hz, 1H), 1.78(d, J=5.7Hz, 1H), 2.07-2.17(m, 4H), 2.12(s, 3H), 3.17-3.22(m, 4H), 4.19(d, J=10.9Hz, 1H), 4.25(d, J=11.7Hz, 1H), 7.13-7.28(m, 5H), 7.70(d, J=3.8Hz, 1H), 7.86(d, J=3.8Hz, 1H), 8.18(s, 1H) |
| 2-335 | | (DMSO-d6-300) 1.76(d, J=6.0Hz, 1H), 2.13(d, J=5.3Hz, 1H), 4.11(d, J=11.3Hz, 1H), 4.25(d, J=11.7Hz, 1H), 6.36(brs, 2H), 7.12-7.28(m, 5H), 7.69(d, J=3.8Hz, 1H), 7.85(d, J=4.1Hz, 1H), 8.17(s, 1H), 12.41(brs, 1H) |

TABLE 2-68

| Example | Structural formula | NMR |
|---|---|---|
| 2-336 | | (DMSO-d6-300) 2.08-2.13(m, 1H), 2.73-2.76(m, 1H), 3.23-3.33(m, 2H), 3.28(s, 3H), 3.35(s, 3H), 3.51-3.61(m, 2H), 3.76-3.85(m, 1H), 4.14-4.18(m, 1H), 7.33-7.37(m, 5H), 7.70(d, J=3.8Hz, 1H), 7.88(d, J=3.8Hz, 1H), 8.21(s, 1H), 9.50(brs, 1H), 12.51(brs, 1H) |

TABLE 2-68-continued
| Example | Structural formula | NMR |
|---|---|---|
| 2-337 | 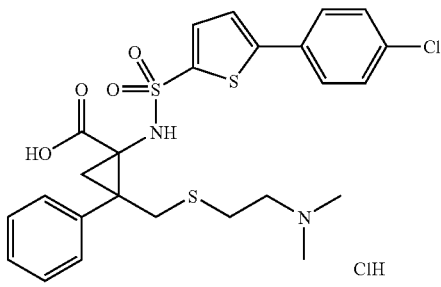 | (MeOH-d4-300) 2.12(d, J=6.0Hz, 1H), 2.30(d, J=6.0Hz, 1H), 2.61-2.63(m, 2H), 2.80(brs, 6H), 3.13-3.15(m, 3H), 3.59-3.75(m, 3H), 7.31-7.40(m, 8H), 7.57-7.67(m, 3H) |
| 2-338 | 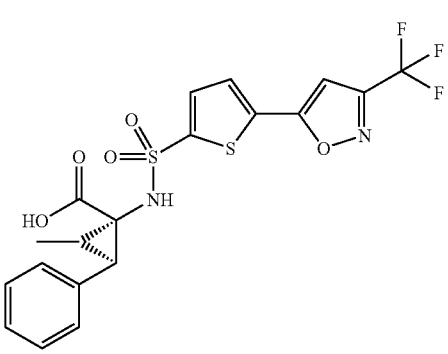 | (DMSO-d6-300) 1.28(d, J=6.8Hz, 3H), 2.02(dd, J=10.2, 6.8Hz, 1H), 2.81(d, J=10.2Hz, 1H), 7.19-7.30(m, 5H), 7.71(d, J=3.8Hz, 1H), 7.81(s, 1H), 7.85(d, J=3.8Hz, 1H) |
| 2-339 | 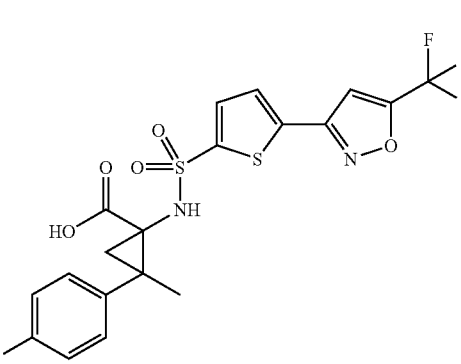 | (MeOH-d4-400) 1.50(s, 3H), 1.75(d, J=5.8Hz, 1H), 2.19(d, J=5.8Hz, 1H), 6.93(t, J=8.8Hz, 2H), 7.23(dd, J=5.4, 8.7Hz, 2H), 7.62-7.66(m, 3H) |
| 2-340 | 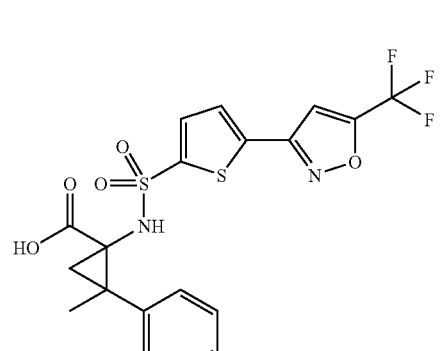 | (MeOH-d4-400) 1.44(s, 3H), 1.82(d, J=6.1Hz, 1H), 2.16(d, J=6.2Hz, 1H), 7.00(t, J=8.8Hz, 2H), 7.21-7.25(m, 2H), 7.44(d, J=3.9Hz, 1H), 7.62-7.64(m, 2H) |

TABLE 2-69
| Example | Structural formula | NMR |
|---|---|---|
| 2-341 | 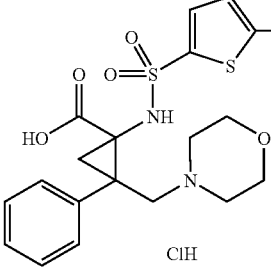 | (DMSO-d6-300) 2.15(d, J=6.4Hz, 1H), 2.42-2.49(m, 1H), 2.90-3.13(m, 3H), 3.24-3.37(m, 2H), 3.60-3.97(m, 5H), 7.21-7.42(m, 5H), 7.53(d, J=8.7Hz, 2H), 7.57(d, J=4.1Hz, 1H), 7.58(d, J=4.1Hz, 1H), 7.75(d, J=8.7Hz, 2H), 9.32(brs, 1H), 10.17(brs, 1H), 12.48(brs, 1H) |
| 2-342 | 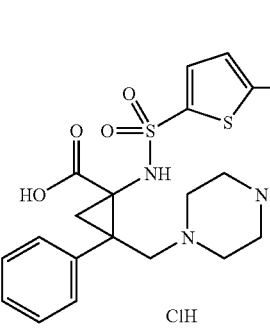 | (DMSO-d6-300) 1.73-1.93(m, 1H), 2.61-2.94(m, 6H), 3.24-3.37(m, 4H), 3.82-4.01(m, 4H), 7.17-7.29(m, 5H), 7.70(d, J=4.1Hz, 1H), 7.88(d, J=3.8Hz, 1H), 8.21(s, 1H), 9.42(brs, 1H) |
| 2-343 | 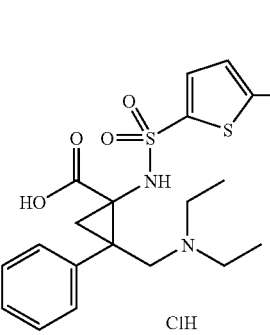 | (MeOH-d4-300) 1.14-1.34(m, 6H), 2.37(d, J=7.2Hz, 1H), 2.66(d, J=6.0Hz, 1H), 3.18-3.30(m, 4H), 3.52(d, J=13.9Hz, 1H), 3.99(d, J=14.3Hz, 1H), 7.34-7.45(m, 5H), 7.70-7.71(m, 3H) |
| 2-344 | 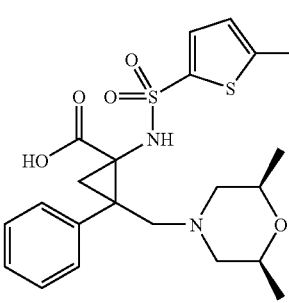 | (MeOH-d4-300) 1.09(d, J=6.0Hz, 3H), 1.15-1.25(m, 3H), 2.40(d, J=6.0Hz, 1H), 2.59-2.80(m, 3H), 3.13(d, J=12.0Hz, 1H), 3.50(d, J=15.0Hz, 1H), 3.57(d, J=12.0Hz, 1H), 3.69-3.83(m, 2H), 4.02(d, J=12.0Hz, 1H), 7.27-7.47(m, 8H), 7.58(d, J=3.0Hz,.1H), 7.65(d, J=9.0Hz, 2H) |

TABLE 2-69-continued

| Example | Structural formula | NMR |
|---|---|---|
| 2-345 | | (MeOH-d4-300) 1.93(d, J=6.0Hz, 1H), 2.23(d, J=6.0Hz, 1H), 2.30(dd, J=6.0, 12.0Hz, 1H), 2.39(dd, J=6.0, 12.0Hz, 1H), 2.99(d, J=12.0Hz, 1H), 3.11(d, J=12.0Hz, 1H), 3.46(t, J=6.0Hz, 2H), 7.12-7.29(m, 5H), 7.38(d, J=3.0Hz, 1H), 7.43(d, J=9.0Hz, 2H), 7.57(d, J=3.0Hz, 1H), 7.66(d, J=9.0Hz, 2H) |

TABLE 2-70

| Example | Structural formula | NMR |
|---|---|---|
| 2-346 | | (DMSO-d6-300) 2.21-2.31(m, 2H), 4.36(d, J=14.3Hz, 1H), 4.77(d, J=14.3Hz, 1H), 6.98-7.06(m, 2H), 7.15-7.23(m, 3H), 7.48-7.56(m, 4H), 7.60(s, 2H), 7.76(d, J=9.0Hz, 2H), 8.78(s, 1H), 9.46(brs, 1H), 12.56(brs, 1H) |
| 2-347 | | (MeOH-d4-300) 1.99(d, J=6.0Hz, 1H), 2.20(d, J=6.0Hz, 1H), 3.41-3.42(m, 2H), 3.60-3.62(m, 2H), 3.74-3.79(m, 2H), 7.17-7.33(m, 5H), 7.40(d, J=4.1Hz, 1H), 7.45(d, J=8.7Hz, 2H), 7.59(d, J=4.1Hz, 1H), 7.67(d, J=8.7Hz, 2H) |
| 2-348 | | (MeOH-d4-300) 1.03(d, J=6.8Hz, 3H), 1.15(d, J=6.8Hz, 3H), 2.36(d, J=7.2Hz, 1H), 2.48-2.57(m, 2H), 3.40(d, J=14.7Hz, 1H), 3.91(d, J=14.7Hz, 1H), 7.23-7.30(m, 3H), 7.35-7.46(m, 5H), 7.60(d, J=3.8Hz, 1H), 7.67(d, J=8.7Hz, 2H) |
| 2-349 | | (MeOH-d4-300) 1.06-1.07(m, 6H), 1.90(d, J=6.0Hz, 1H), 2.25(d, J=6.0Hz, 1H), 2.53-2.55(m, 1H), 2.94(d, J=12.8Hz, 1H), 3.12(d, J=12.8Hz, 1H), 7.18-7.27(m, 5H), 7.41(d, J=4.1Hz, 1H), 7.45(d, J=8.7Hz, 2H), 7.59(d, J=4.1Hz, 1H), 7.67(d, J=8.7Hz, 2H) |

TABLE 2-70-continued
| Example | Structural formula | NMR |
|---|---|---|
| 2-350 | 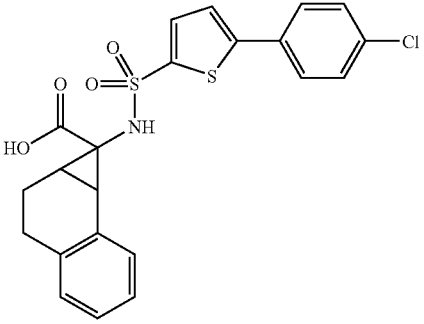 | (CDCl3-300) 1.98-2.11(m, 1H), 2.20-2.34(m, 1H), 2.47-2.58(m, 2H), 2.68-2.86(m, 1H), 2.98(d, J=9.8Hz, 1H), 5.81(s, 1H), 7.01-7.16(m, 3H), 7.19(d, J=3.8Hz, 1H), 7.29-7.35(m, 1H), 7.39(d, J=8.7Hz, 2H), 7.50(d, J=8.7Hz, 2H), 7.61(d, J=3.8Hz, 1H) |
TABLE 2-71
| Example | Structural formula | NMR |
|---|---|---|
| 2-351 | 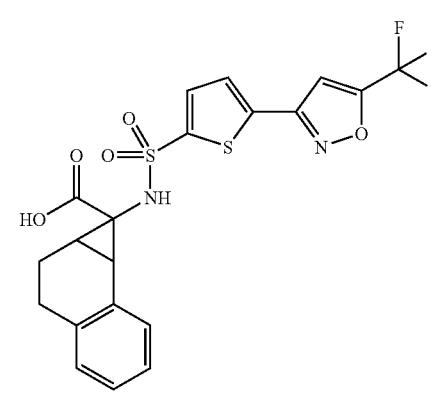 | (CDCl3-300) 1.87-2.33(m, 2H), 2.44-2.58(m, 2H), 2.69-2.85(m, 1H), 2.96(d, J=9.8Hz, 1H), 5.90(s, 1H), 6.98(s, 1H), 7.01-7.07(m, 1H), 7.09-7.19(m, 2H), 7.28-7.34(m, 1H), 7.44(d, J=3.8Hz, 1H), 7.65(d, J=3.8Hz, 1H) |
| 2-352 | 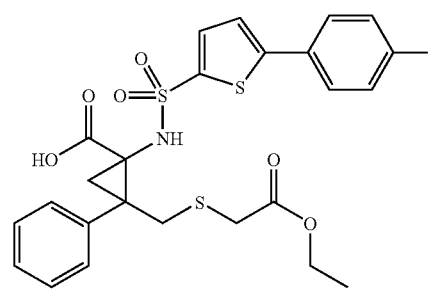 | (MeOH-d4-300) 1.21(t, J=7.5Hz, 3H), 1.91(d, J=6.0Hz, 1H), 2.14(d, J=6.0Hz, 1H), 2.86(d, J=15.0Hz, 1H), 2.96(d, J=15.0Hz, 1H), 3.08(d, J=12.0Hz, 1H), 3.17(d, J=12.0Hz, 1H), 4.07(q, J=7.0Hz, 2H), 7.10-7.28(m, 5H), 7.36(d, J=3.0Hz, 1H), 7.42(d, J=9.0Hz, 2H), 7.58(d, J=3.0Hz, 1H), 7.66(d, J=9.0Hz, 2H) |
| 2-353 | 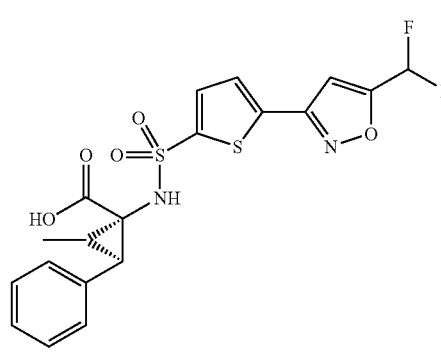 | (MeOH-d4-300) 1.38(d, J=6.8Hz, 3H), 2.21(dd, J=10.5, 6.8Hz, 1H), 2.94(d, J=10.5Hz, 1H), 6.90-7.36(m, 7H), 7.64-7.65(m, 2H) |

TABLE 2-71-continued
| Example | Structural formula | NMR |
|---|---|---|
| 2-354 | 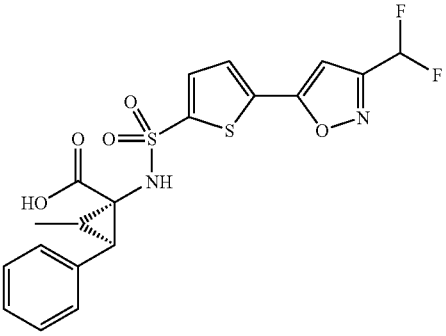 | (MeOH-d4-300)<br>1.39(d, J=6.8Hz, 3H), 2.22(dd, J=10.5, 6.8Hz, 1H), 2.94(d, J=10.5Hz, 1H), 6.93-7.15(m, 7H), 7.67-7.68(m, 2H) |
| 2-355 | 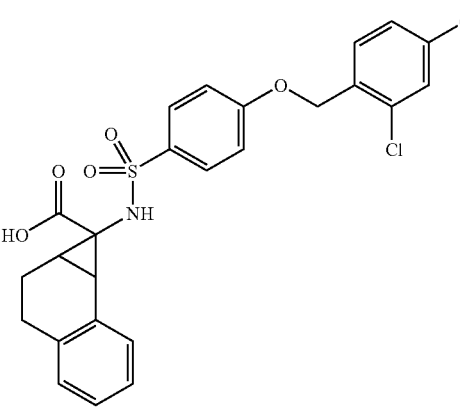 | (DMSO-d6-300)<br>1.85-2.06(m, 4H), 2.25-2.64(m, 2H), 5.23(s, 2H), 6.95-7.14(m, 4H), 7.22(d, J=8.7Hz, 2H), 7.49(dd, J=8.3, 2.3Hz, 1H), 7.64 (d, J=8.3Hz, 1H), 7.71(d, J=2.3Hz, 1H), 7.76(d, J=8.7Hz, 2H), 8.54(s, 1H), 12.02(brs, 1H) |
TABLE 2-72
| Example | Structural formula | NMR |
|---|---|---|
| 2-356 | 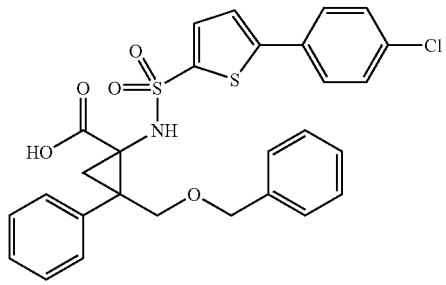 | (CDCl3-300)<br>1.87(d, J=6.0Hz, 1H), 2.10(d, J=6.0Hz, 1H), 3.56(d, J=9.8Hz, 1H), 3.74(d, J=9.8Hz, 1H), 4.35(d, J=12.1Hz, 1H), 4.46(d, J=12.1Hz, 1H), 6.10(s, 1H), 7.13-7.35(m, 11H), 7.37-7.43(m, 3H), 7.50(d, J=8.7Hz, 2H) |
| 2-357 | 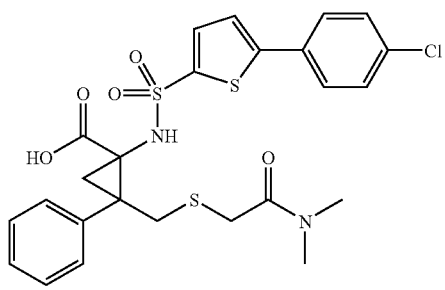 | (MeOH-d4-300)<br>1.93(d, J=6.0Hz, 1H), 2.24(d, J=6.0Hz, 1H), 2.82(s, 3H), 2.88(s, 3H), 3.03-3.10(m, 3H), 3.19(d, J=12.0Hz, 1H), 7.14-7.27(m, 5H), 7.38(d, J=3.0Hz, 1H), 7.43(d, J=9.0Hz, 2H), 7.57(d, J=3.0Hz, 1H), 7.65(d, J=9.0Hz, 2H) |

TABLE 2-72-continued

| Example | Structural formula | NMR |
|---|---|---|
| 2-358 | | (MeOH-d4-300) 1.89(d, J=6.0Hz, 1H), 2.20(d, J=6.0Hz, 1H), 2.89(d, J=15.0Hz, 1H), 2.99(d, J=15.0Hz, 1H), 3.07(d, J=12.0Hz, 1H), 3.20(d, J=12.0Hz, 1H), 7.11-7.30(m, 5H), 7.38(d, J=3.0Hz, 1H), 7.42(d, J=9.0Hz, 2H), 7.57(d, J=3.0Hz, 1H), 7.65(d, J=9.0Hz, 2H) |
| 2-359 | | (MeOH-d4-300) 1.73(d, J=6.0Hz, 1H), 2.15(d, J=6.0Hz, 1H), 2.98-3.14(m, 4H), 3.35-3.58(m, 8H), 7.12-7.29(m, 5H), 7.40(d, J=3.0Hz, 1H), 7.44(d, J=9.0Hz, 2H), 7.60(d, J=3.0Hz, 1H), 7.68(d, J=9.0Hz, 2H) |
| 2-360 | | (DMSO-d6-300) 1.64-1.79(m, 2H), 1.95-2.15(m, 2H), 2.24-2.59(m, 2H), 5.26(s, 2H), 6.90-7.07(m, 4H), 7.24(d, J=9.0Hz, 2H), 7.48(dd, J=8.3, 2.3Hz, 1H), 7.65(d, J=8.3Hz, 1H), 7.72(d, J=2.3Hz, 1H), 7.81(d, J=9.0Hz, 2H), 8.23(brs, 1H), 8.64(brs, 1H), 9.75(brs, 1H) |

TABLE 2-73

| Example | Structural formula | NMR |
|---|---|---|
| 2-361 | | (DMSO-d6-300) 1.82(d, J=6.4Hz, 1H), 2.17(d, J=6.0Hz, 1H), 3.01(d, J=13.6Hz, 1H), 7.26-7.32(m, 6H), 7.53(d, J=8.7Hz, 2H), 7.60(d, J=4.1Hz, 3H), 7.76(d, J=8.3Hz, 2H) |

TABLE 2-73-continued
| Example | Structural formula | NMR |
|---|---|---|
| 2-362 | 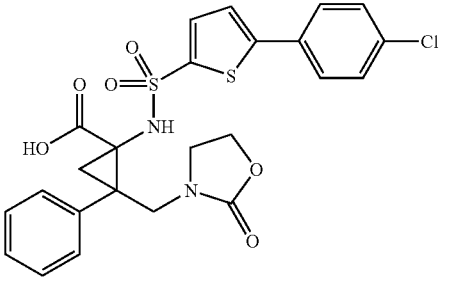 | (CDCl3-300) 1.75(d, J=6.4Hz, 1H), 2.17(d, J=6.8Hz, 1H), 2.57-2.68(m, 1H), 3.14-3.17(m, 1H), 3.34(d, J=14.7Hz, 1H), 3.78(d, J=15.1Hz, 1H), 4.02(dd, J=8.3, 4.1Hz, 1H), 4.14(dd, J=15.6, 8.9Hz, 1H), 7.18-7.29(m, 6H), 7.39(d, J=8.7Hz, 2H), 7.53(d, J=8.3Hz, 2H), 7.59(d, J=3.8Hz, 1H), 7.97(brs, 1H) |
| 2-363 | 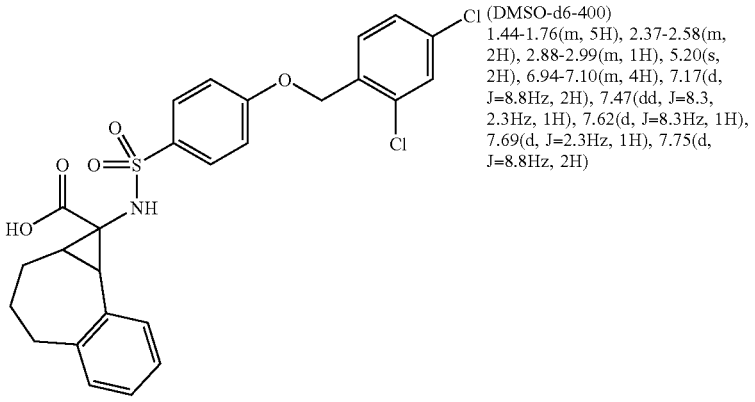 | (DMSO-d6-400) 1.44-1.76(m, 5H), 2.37-2.58(m, 2H), 2.88-2.99(m, 1H), 5.20(s, 2H), 6.94-7.10(m, 4H), 7.17(d, J=8.8Hz, 2H), 7.47(dd, J=8.3, 2.3Hz, 1H), 7.62(d, J=8.3Hz, 1H), 7.69(d, J=2.3Hz, 1H), 7.75(d, J=8.8Hz, 2H) |
| 2-364 | 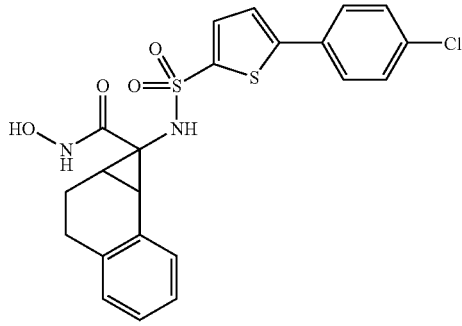 | (DMSO-d6-300) 1.69-1.92(m, 2H), 2.08-2.59(m, 4H), 6.91-6.98(m, 1H), 7.00-7.12(m, 3H), 7.54(d, J=8.7Hz, 2H), 7.62-7.67(m, 2H), 7.78(d, J=8.7Hz, 2H), 8.70(brs, 1H), 9.78(brs, 1H) |
| 2-365 | 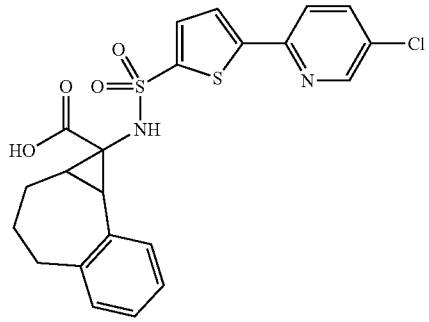 | (DMSO-d6-300) 1.47-1.69(m, 3H), 1.71-1.90(m, 2H), 2.43-2.51(m, 1H), 2.74(d, J=9.9Hz, 1H), 2.95-3.02(m, 1H), 7.02-7.21(m, 4H), 7.59(d, J=4.0Hz, 1H), 7.84(d, J=4.0Hz, 1H), 8.03(dd, J=8.1, 1.0Hz, 1H), 8.08(d, J=8.1Hz, 1H), 8.63(d, J=1.0Hz, 1H), 12.38(brs, 1H) |

TABLE 2-74

| Example | Structural formula | NMR |
|---|---|---|
| 2-366 | | (DMSO-d6-300)<br>1.25(d, J=6.6Hz, 3H), 1.98(dq, J=10.6, 6.6Hz, 1H), 2.77(d, J=10.6Hz, 1H), 7.14-7.30(m, 5H), 7.57(d, J=4.0Hz, 1H), 7.82(d, J=4.0Hz, 1H), 8.01-8.08(m, 1H), 8.07(d, J=9.2Hz, 1H), 8.62(d, J=1.5Hz, 1H), 9.05(s, 1H), 12.26(s, 1H) |
| 2-367 | | (MeOH-d4-300)<br>1.36(d, J=6.6Hz, 3H), 2.12-2.25(m, 4H), 2.86(d, J=10.6Hz, 1H), 7.17-7.21(m, 7H), 7.53(d, J=4.0Hz, 1H), 7.98(d, J=1.5Hz, 1H) |
| 2-368 | | (MeOH-d4-300)<br>2.02(d, J=6.6Hz, 1H), 2.22(d, J=5.9Hz, 1H), 3.80(dd, J=14.3, 4.4Hz, 1H), 3.94(d, J=13.9Hz, 1H), 7.14-7.24(m, 5H), 7.39(d, J=4.0Hz, 1H), 7.43(d, J=8.4Hz, 2H), 7.50-7.66(m, 1H), 7.60(d, J=4.0Hz, 1H), 7.66(d, J=8.4Hz, 2H), 7.95-8.03(m, 2H), 8.56-8.60(m, 1H) |
| 2-369 | | (DMSO-d6-300)<br>1.95-2.30(m, 3H), 2.78 (d, J=9.9Hz, 1H), 3.99-4.18(m, 2H), 6.81(d, J=7.7Hz, 1H), 6.96(t, J=6.8Hz, 1H), 7.11(t, J=6.8Hz, 1H), 7.28(d, J=7.0Hz, 1H), 7.52(d, J=8.8Hz, 2H), 7.57(s, 2H), 7.75(d, J=8.4Hz, 2H), 9.08(brs, 1H), 12.42(brs, 1H) |

TABLE 2-74-continued

| Example | Structural formula | NMR |
|---|---|---|
| 2-370 | | (DMSO-d6-300)<br>1.95-2.29(m, 3H), 2.80(d, J=9.5Hz, 1H), 4.01-4.18(m, 2H), 6.81(dd, J=7.9, 1.3Hz, 1H), 6.97(td, J=7.4, 1.2Hz, 1H), 7.12(td, J=7.8, 1.6Hz, 1H), 7.28(d, J=7.3Hz, 1H), 7.70(d, J=3.7Hz, 1H), 7.86(d, J=4.0Hz, 1H), 8.16(s, 1H), 9.30(brs, 1H), 12.45(brs, 1H) |

TABLE 2-75

| Example | Structural formula | NMR |
|---|---|---|
| 2-371 | | (DMSO-d6-300)<br>1.63(dd, J=10.0, 5.5Hz, 1H), 2.05(dd, J=10.4, 2.9Hz, 1H), 2.84(t, J=9.2Hz, 1H), 7.14-7.27(m, 5H), 7.31(d, J=3.8Hz, 1H), 7.43(d, J=3.8Hz, 1H), 7.97(s, 1H), 9.53(s, 1H), 12.20(s, 1H) |
| 2-372 | | (DMSO-d6-300)<br>1.26(d, J=6.8Hz, 3H), 2.01(dt, J=17.0, 6.8Hz, 1H), 2.88(d, J=17.0Hz, 1H), 7.15-7.29(m, 5H), 7.31(d, J=4.1Hz, 1H), 7.43(d, J=3.8Hz, 1H), 7.95(s, 1H), 9.39(s, 1H), 12.23(s, 1H) |
| 2-373 | | (DMSO-d6-300)<br>1.43-1.96(m, 6H), 2.84(d, J=9.8Hz, 1H), 2.94-3.10(m, 1H), 7.03-7.22(m, 5H), 7.32(d, J=3.8Hz, 1H), 7.44(d, J=3.8Hz, 1H), 7.97(s, 1H), 9.40(s, 1H), 12.38(s, 1H) |

TABLE 2-75-continued

| Example | Structural formula | NMR |
| --- | --- | --- |
| 2-374 | | (CDCl3-300)<br>1.32(d, J=7.0Hz, 3H), 2.27-2.39(m, 1H), 2.48(s, 3H), 3.05(d, J=10.3Hz, 1H), 6.26(s, 1H), 7.11-7.28(m, 6H), 7.32(d, J=4.0Hz, 1H), 7.59(d, J=4.0Hz, 1H) |
| 2-375 | | (CDCl3-300)<br>1.41-1.94(m, 4H), 2.09-2.29(m, 1H), 2.33-2.72(m, 4H), 2.89-3.14(m, 2H), 6.27(s, 1H), 6.94-7.69(m, 7H) |

TABLE 2-76

| Example | Structural formula | NNR |
| --- | --- | --- |
| 2-376 | | (DMSO-d6-400)<br>1.55(d, J=5.6Hz, 1H), 1.69(s, 3H), 1.97(d, J=5.6Hz, 1H), 3.20(dd, J=13.7, 4.4Hz, 1H), 3.50(dd, J=13.9, 7.0Hz, 1H), 7.08-7.31(m, 5H), 7.49-7.60(m, 4H), 7.72-7.78(m, 3H), 9.21(s, 1H), 12.34(brs, 1H) |
| 2-377 | | (DMSO-d6-400)<br>0.72(t, J=7.4Hz, 3H), 1.37(sextet, J=7.4Hz, 2H), 1.55(d, J=5.6Hz, 1H), 1.92(t, J=7.2Hz, 2H), 1.97(d, J=5.6Hz, 1H), 3.23(dd, J=13.9, 4.6Hz, 1H), 3.50(dd, J=13.9, 7.0Hz, 1H), 7.07-7.22(m, 5H), 7.49-7.54(m, 2H), 7.56-7.60(m, 2H), 7.68(t, J=6.3Hz, 1H), 7.73-7.78(m, 2H), 9.23(s, 1H), 12.33(brs, 1H) |

TABLE 2-76-continued

| Example | Structural formula | NMR |
|---|---|---|
| 2-378 | | (DMSO-d6-400)<br>1.37(d, J=5.1Hz, 1H), 1.94(d, J=5.1Hz, 1H), 2.69(s, 6H), 3.17(dd, J=14.4, 5.1Hz, 1H), 3.40(dd, J=14.4, 7.0Hz, 1H), 6.17(t, J=5.8Hz, 1H), 7.05-7.10(m, 2H), 7.13-7.25(m, 3H), 7.49-7.54(m, 2H), 7.55-7.60(m, 2H), 7.74-7.79(m, 2H), 9.73(s, 1H), 12.25(brs, 1H) |
| 2-379 | | (DMSO-d6-400)<br>0.50-0.61(m, 4H), 1.38-1.46(m, 1H), 1.53(d, J=6.0Hz, 1H), 1.97(d, J=6.0Hz, 1H), 3.24(dd, J=14.4, 5.1Hz, 1H), 3.52(dd, J=14.4, 7.4Hz, 1H), 7.08-7.24(m, 5H), 7.49-7.54(m, 2H), 7.56-7.59(m, 2H), 7.73-7.78(m, 2H), 7.95(t, J=6.0Hz, 1H), 9.25(s, 1H), 12.31(brs, 1H) |
| 2-380 | | (DMSO-d6-400)<br>1.00-1.27(m, 5H), 1.44-1.66(m, 5H), 1.54(d, J=6.0Hz, 1H), 1.90-1.99(m, 1H), 1.96(d, J=5.6Hz, 1H), 3.18(dd, J=14.4, 4.6Hz, 1H), 3.51 (dd, J=14.4, 7.4Hz, 1H), 7.06-7.23(m, 4H), 7.49-7.64(m, 6H), 7.73-7.78(m, 2H), 9.24(s, 1H), 12.31(brs, 1H) |

TABLE 2-77

| Example | Structural formula | NMR |
|---|---|---|
| 2-381 | | (DMSO-d6-400)<br>1.46(d, J=5.6Hz, 1H), 1.96(d, J=5.6Hz, 1H), 3.10-3.56(m, 10H), 6.36(t, J=5.8Hz, 1H), 7.06-7.24(m, 5H), 7.52(d, J=8.8Hz, 2H), 7.57-7.58(m, 2H), 7.76(d, J=8.3Hz, 2H), 9.43(s, 1H), 12.28(brs, 1H) |

TABLE 2-77-continued

| Example | Structural formula | NMR |
|---|---|---|
| 2-382 | | (CDCl3-300)<br>1.50(s, 3H), 1.83(d, J=5.9Hz, 1H), 2.17(d, J=5.9Hz, 1H), 6.12(s, 1H), 6.79(t, J=53.6Hz, 1H), 6.90(s, 1H), 7.02-7.10(m, 2H), 7.15-7.24(m, 3H), 7.41(d, J=4.0Hz, 1H), 7.58(d, J=4.0Hz, 1H) |
| 2-383 | | (CDCl3-300)<br>1.42-1.97(m, 4H), 2.14-2.29(m, 1H), 2.50-2.62(m, 1H), 2.94-3.10(m, 2H), 5.96(s, 1H), 6.79(t, J=53.9Hz, 1H), 6.88(s, 1H), 7.03-7.21(m, 4H), 7.44(d, J=4.0Hz, 1H), 7.66(d, J=4.0Hz, 1H) |
| 2-384 | | (MeOH-d4-300)<br>1.13(t, J=7.0Hz, 3H), 1.92(d, J=5.9Hz, 1H), 2.14(d, J=6.2Hz, 1H), 3.46(d, J=14.3Hz, 1H), 3.57(d, J=14.7Hz, 1H), 3.94(q, J=7.2Hz, 2H), 7.15-7.19(m, 5H), 7.38(d, J=4.0Hz, 1H), 7.43(d, J=8.4Hz, 2H), 7.57(d, J=4.0Hz, 1H), 7.66(d, J=8.4Hz, 2H) |
| 2-385 | | (DMSO-d6-300)<br>1.46-2.04(m, 6H); 3.09-3.54(m, 2H), 3.64-3.81(m, 2H), 3.96-4.10(m, 1H), 7.06-7.26(m, 5H), 7.52(d, J=8.4Hz, 2H), 7.57(s, 2H), 7.76(d, J=8.4Hz, 2H), 9.36(brs, 1H), 12.31(brs, 1H) |

TABLE 2-78

| Example | Structural formula | NMR |
|---|---|---|
| 2-386 | | (DMSO-d6-300)<br>1.68(d, J=5.7Hz, 1H), 2.06-2.15(m, 1H), 3.07(s, 3H), 3.39(d, J=10.5Hz, 1H), 3.77(d, J=10.5Hz, 1H), 7.10-7.26(m, 5H), 7.52(d, J=8.7Hz, 2H), 7.56(d, J=4.1Hz, 1H), 7.58(d, J=4.1Hz, 1H), 7.75(d, J=8.7Hz, 2H), 9.11(brs, 1H), 12.29(brs, 1H) |
| 2-387 | | (DMSO-d6-300)<br>1.59(q, J=5.3Hz, 1H), 2.01(dd, J=8.3, 5.3Hz, 1H), 2.72(t, J=8.5Hz, 1H), 3.87(s, 3H), 7.16-7.29(m, 6H), 7.48(d, J=3.8Hz, 1H), 7.84(s, 1H), 8.19(s, 1H), 9.07(brs, 1H), 12.19(brs, 1H) |
| 2-388 | | (MeOH-d4-300)<br>1.97(dd, J=9.8, 5.7Hz, 1H), 2.18(dd, J=8.7, 6.0Hz, 1H), 2.86(t, J=9.2Hz, 1H), 7.17-7.31(m, 5H), 7.63(d, J=3.8Hz, 1H), 7.66(d, J=3.8Hz, 1H), 7.95(d, J=9.0Hz, 2H), 8.33(d, J=9.0Hz, 2H) |
| 2-389 | | (MeOH-d4-400)<br>1.98-2.08(m, 1H), 2.17-2.27(m, 1H), 2.32-2.46(m, 1H), 2.90(d, J=10.2Hz, 1H), 3.16-3.28(m, 2H), 6.65(d, J=8.3Hz, 1H), 6.73(t, J=7.4Hz, 1H), 6.95(t, J=7.7Hz, 1H), 7.31(d, J=7.9Hz, 1H), 7.38(d, J=4.2Hz, 1H), 7.47-7.41(m, 2H), 7.58(d, J=4.2Hz, 1H), 7.68-7.62(m, 2H) |

TABLE 2-78-continued

| Example | Structural formula | NMR |
|---------|-------------------|-----|
| 2-390 | | (DMSO-d6-300) 1.32-1.70(m, 5H), 2.32-2.56(m, 2H), 2.75-2.88(m, 1H), 6.95-7.02(m, 1H), 7.04-7.10(m, 2H), 7.20-7.28(m, 1H), 7.21(d, J=9.0Hz, 2H), 7.46(dd, J=8.3, 2.3Hz, 1H), 7.62(d, J=8.3Hz, 1H), 7.70(d, J=2.3Hz, 1H), 7.79(d, J=9.0Hz, 2H), 8.25(s, 1H), 8.58(s, 1H), 10.11(s, 1H) |

TABLE 2-79

| Example | Structural formula | NMR |
|---------|-------------------|-----|
| 2-391 | | (DMSO-d6-300) 1.22-1.79(m, 5H), 2.36-2.59(m, 2H), 2.82-2.98(m, 1H), 6.96-7.03(m, 1H), 7.05-7.14(m, 2H), 7.30-7.39(m, 1H), 7.52(d, J=8.7Hz, 2H), 7.59(d, J=3.8Hz, 1H), 7.63(d, J=3.8Hz, 1H), 7.75(d, J=8.7Hz, 2H), 8.63(s, 1H), 8.70(s, 1H), 10.14(s, 1H) |
| 2-392 | | (DMSO-d6-300) 1.08(t, J=5.8Hz, 6H), 1.85(d, J=6.4Hz, 1H), 2.26(d, J=7.9Hz, 1H), 3.01-3.10(m, 1H), 3.12-3.23(m, 1H), 3.36-3.47(m, 1H), 7.20-7.38(m, 7H), 7.54(d, J=9.0Hz, 3H), 7.58-7.63(m, 2H), 7.76(d, J=9.0Hz, 3H), 8.23(brs, 1H), 8.42(brs, 1H), 9.15(s, 1H), 12.57(s, 1H) |
| 2-393 | | (DMSO-d6-300) 1.90(d, J=6.8Hz, 1H), 2.27(d, J=6.8Hz, 1H), 3.18-3.35(m, 1H), 3.59-3.72(m, 1H), 4.44-4.53(m, 2H), 7.21-7.37(m, 5H), 7.50-7.60(m, 4H), 7.77-7.80(m, 2H), 7.79-7.87(m, 2H), 9.15(s, 1H) |

TABLE 2-79-continued

| Example | Structural formula | NMR |
|---|---|---|
| 2-394 | 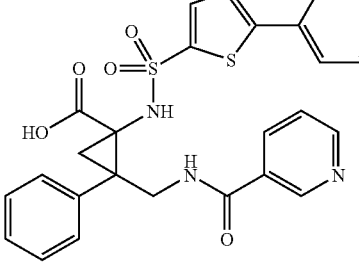 | (DMSO-d6-300) 1.74(d, J=6.0Hz, 1H), 2.06(d, J=6.0Hz, 1H), 3.50-3.60(m, 1H), 3.73-3.82(m, 1H), 7.10-7.21(m, 5H), 7.49-7.63(m, 4H), 7.77(d, J=8.7Hz, 2H), 8.02-8.09(m, 1H), 8.44-8.52(m, 1H), 8.71(dd, J=4.9, 1.5Hz, 1H), 8.81(d, J=2.3Hz, 1H), 9.19(s, 1H) |
| 2-395 | 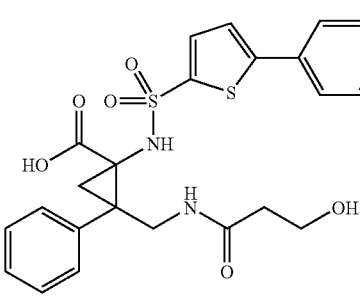 | (DMSO-d6-300) 1.56(d, J=6.0Hz, 1H), 1.98(d, J=6.0Hz, 1H), 2.14(t, J=6.8Hz, 2H), 3.16-3.26(m, 1H), 3.44-3.58(m, 3H), 4.49(t, J=5.3Hz, 1H), 7.09-7.25(m, 5H), 7.53(d, J=8.9Hz, 2H), 7.56-7.61(m, 2H), 7.70-7.80(m, 3H), 9.24(s, 1H), 12.32(s, 1H) |

TABLE 2-80

| Example | Structural formula | NMR |
|---|---|---|
| 2-396 | 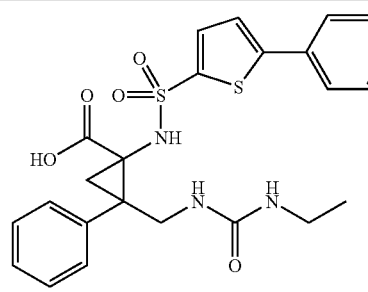 | (DMSO-d6-300) 0.94(t, J=6.8Hz, 3H), 1.36(d, J=6.4Hz, 1H), 1.95(d, J=6.4Hz, 1H), 2.91-3.03(m, 2H), 3.21(dd, J=6.8, 3.4Hz, 1H), 3.36(dd, J=6.8, 3.4Hz, 1H), 5.76-5.91(m, 2H), 7.09-7.28(m, 2H), 7.52(d, J=8.7Hz, 1H); 7.58(dd, J=4.5, 3.8Hz, 1H), 7.77(d, J=8.3Hz, 2H), 9.70(s, 1H), 12.24(brs, 1H) |
| 2-397 | 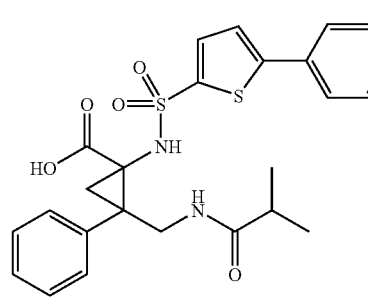 | (DMSO-d6-300) 0.87(d, J=4.1Hz, 3H), 0.89(d, J=4.1Hz, 3H), 1.57(d, J=5.7Hz, 1H), 1.99(d, J=6.0Hz, 1H), 2.19-2.28(m, 1H), 3.25(dd, J=14.1, 4.7Hz, 1H), 3.50(dd, J=13.6, 6.8Hz, 1H), 7.09-7.26(m, 5H), 7.51-7.69(m, 4H), 7.78(d, J=8.7Hz, 2H), 9.27(brs, 1H), 12.34(brs, 1H) |
| 2-398 | 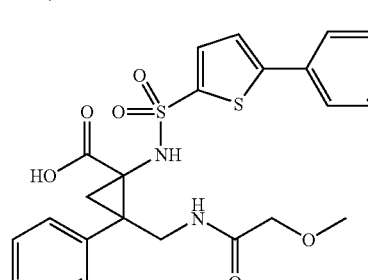 | (DMSO-d6-300) 1.62(d, J=5.7Hz, 1H), 2.02(d, J=5.7Hz, 1H), 3.28(dd, J=12.8, 3.4Hz, 1H), 3.62-3.69(m, 6H), 7.13-7.34(m, 5H), 7.52-7.67(m, 4H), 7.78(d, J=8.3Hz, 2H), 9.35(brs, 1H), 12.36(brs, 1H) |

TABLE 2-80-continued

| Example | Structural formula | NMR |
| --- | --- | --- |
| 2-399 | | (DMSO-d6-300) 1.58(d, J=5.7Hz, 1H), 2.01(d, J=6.4Hz, 1H), 3.22(dd, J=13.8, 4.3Hz, 1H), 3.66(d, J=5.7Hz, 2H), 3.75(dd, J=13.9, 7.9Hz, 1H), 5.42(brs, 1H), 7.11-7.26(m, 5H), 7.54(d, J=8.7Hz, 2H), 7.59(s, 2H), 7.69-7.81(m, 3H), 9.47(brs, 1H), 12.33(brs, 1H) |
| 2-400 | | (CDCl3-400) 1.66(d, J=6.5Hz, 1H), 1.99-2.01(m, 1H), 2.15(d, J=6.0Hz, 1H), 2.97-3.01(m, 1H), 3.04(d, J=14.8Hz, 1H), 3.20-3.24(m, 1H), 3.51-3.53(m, 1H), 4.07(d, J=17.2Hz, 1H), 4.11(d, J=14.8Hz, 1H), 4.15(d, J=17.2Hz, 1H), 7.05-7.10(m, 2H), 7.19(d, J=4.2Hz, 1H), 7.24-7.26(m, 3H), 7.39(d, J=8.3Hz, 2H), 7.53(d, J=8.3Hz, 2H), 7.56(d, J=3.7Hz, 1H), 8.82(brs, 1H) |

TABLE 2-81

| Example | Structural formula | NMR |
| --- | --- | --- |
| 2-401 | | (DMSO-d6-300) 1.25(d, J=6.4Hz, 3H), 1.92(dd, J=10.4, 6.6Hz, 1H), 2.70(d, J=10.2Hz, 1H), 7.17-7.29(m, 5H), 7.45(s, 1H), 7.71(s, 1H), 7.95(d, J=8.7Hz, 2H), 8.15(d, J=8.7Hz, 2H), 8.94(brs, 1H), 12.23(brs, 1H) |
| 2-402 | | (DMSO-d6-400) 1.35-1.40(m, 4H), 2.02-2.07(m, 4H), 7.11-7.24(m, 5H), 7.41(d, J=3.7Hz, 1H), 7.49(d, J=3.7Hz, 1H), 7.64(s, 2H), 9.11(brs, 1H), 10.11(brs, 1H), 12.10(brs, 1H) |

TABLE 2-81-continued

| Example | Structural formula | NMR |
|---|---|---|
| 2-403 | | (MeOH-d4-300) 1.52(s, 3H), 1.76(d, J=6.0Hz, 1H), 2.21(d, J=6.0Hz, 1H), 3.44(s, 3H), 4.60(s, 2H), 6.85(s, 1H), 7.18-7.21(m, 5H), 7.55(d, J=4.1Hz, 1H), 7.61(d, J=4.1Hz, 1H) |
| 2-404 | | (MeOH-d4-300) 1.38(d, J=6.8Hz, 3H), 2.21(dd, J=10.5, 6.8Hz, 1H), 2.94(d, J=10.5Hz, 1H), 3.45(s, 3H), 4.61(s, 2H), 6.86(s, 1H), 7.20-7.27(m, 5H), 7.56(d, J=4.1Hz, 1H), 7.64(d, J=4.1Hz, 1H) |
| 2-405 | | (DMSO-d6-300) 1.58(d, J=5.7Hz, 1H), 2.10(d, J=5.7Hz, 1H), 3.65(d, J=10.2Hz, 1H), 3.74(d, J=10.2Hz, 1H), 3.80(d, J=17.3Hz, 1H), 3.86(d, J=17.3Hz, 1H), 7.20(m, 5H), 7.53(d, J=8.7Hz, 2H), 7.57(s, 2H), 7.75(d, J=8.7Hz, 2H) |

TABLE 2-82

| Example | Structural formula | NMR |
|---|---|---|
| 2-406 | | (DMSO-d6-300) 1.39(s, 4H), 2.09(d, J=5.7Hz, 1H), 7.11-7.27(m, 5H), 7.42(d, J=8.3Hz, 1H), 7.56-7.69(m, 3H), 7.92(t, J=8.5Hz, 1H), 9.25(brs, 1H), 12.12(brs, 1H) |
| 2-407 | | (DMSO-d6-300) 1.26(d, J=6.8Hz, 3H), 1.92-2.05(m, 1H), 2.78(d, J=10.5Hz, 1H), 7.15-7.31(m, 5H), 7.42(dd, J=8.7, 1.9Hz, 1H), 7.58-7.69(m, 3H), 7.92(t, J=8.5Hz, 1H), 9.10(brs, 1H), 12.31(brs, 1H) |

TABLE 2-82-continued

| Example | Structural formula | NMR |
|---|---|---|
| 2-408 | | (MeOH-d4-300) 1.28-1.40(m, 9H), 2.13-2.23(m, 1H), 2.93(d, J=9.0Hz, 1H), 3.05-3.17(m, 1H), 6.57(s, 1H), 7.11-7.28(m, 5H), 7.51(d, J=3.0Hz, 1H), 7.61(d, J=3.0Hz, 1H) |
| 2-409 | | (MeOH-d4-300) 1.22(t, J=7.5Hz, 3H), 1.98(d, J=6.0Hz, 1H), 2.29(d, J=6.0Hz, 1H), 2.86(d, J=12.0Hz, 1H), 2.99-3.13(m, 2H), 3.24(d, J=12.0Hz, 1H), 4.08(q, J=8.0Hz, 2H), 7.14-7.35(m, 5H), 7.61-7.68(m, 3H) |
| 2-410 | | (MeOH-d4-300) 1.97(d, J=6.0Hz, 1H), 2.28(d, J=6.0Hz, 1H), 2.83(d, J=15.0Hz, 1H), 2.98(d, J=15.0Hz, 1H), 3.07(d, J=12.0Hz, 1H), 3.24(d, J=12.0Hz, 1H), 7.13-7.31(m, 5H), 7.61-7.68(m, 3H) |

TABLE 2-83

| Example | Structural formula | NMR |
|---|---|---|
| 2-411 | | (DMSO-d6-400) 1.58-1.67(m, 2H), 1.79-1.97(m, 3H), 2.43-2.54(m, 1H), 2.76(d, J=9.7Hz, 1H), 4.65(brs, 1H), 7.01-7.27(m, 4H), 7.51(d, J=8.3Hz, 2H), 7.54(d, J=3.7Hz, 1H), 7.56(d, J=3.7Hz, 1H), 7.73(d, J=8.3Hz, 2H) |

TABLE 2-83-continued

| Example | Structural formula | NMR |
|---|---|---|
| 2-412 | | (DMSO-d6-400) 1.20-1.36(m, 1H), 1.41-1.68(m, 2H), 1.82-1.91(m, 1H), 2.06-2.19(m, 1H), 2.43-2.55(m, 1H), 2.64(d, J=9.7Hz, 1H), 4.99-5.04(m, 1H), 7.06-7.12(m, 2H), 7.16-7.22(m, 1H), 7.38(d, J=7.4Hz, 1H), 7.51(d, J=8.3Hz, 2H), 7.54-7.57(m, 2H), 7.73(d, J=8.3Hz, 2H) |
| 2-413 | | (DMSO-d6-300) 1.36-1.43(m, 1H), 1.39(s, 3H), 2.08(d, J=5.3Hz, 1H), 7.11-7.27(m, 5H), 7.46-7.56(m, 1H), 7.54(d, J=4.1Hz, 1H), 7.61(d, J=4.1Hz, 1H), 7.68-7.76(m, 1H), 8.00(dd, J=6.8, 2.3Hz, 1H), 9.22(s, 1H), 12.11(s, 1H) |
| 2-414 | | (MeOH-d4-300) 1.52(d, J=8.3Hz, 3H), 1.76(d, J=5.7Hz, 1H), 2.23(d, J=5.7Hz, 1H), 7.11-7.25(m, 5H), 7.61(d, J=4.1Hz, 1H), 7.93(d, J=4.1Hz, 1H), 8.89(s, 2H) |
| 2-415 | | (DMSO-d6-300) 0.81(t, J=6.2Hz, 1H), 1.55(q, J=5.3Hz, 1H), 2.63(t, J=8.9Hz, 1H), 3.69(q, J=7.2Hz, 1H), 4.92(dd, J=14.9, 5.1Hz, 1H), 7.11-7.18(m, 2H), 7.24(t, J=7.0Hz, 1H), 7.35(d, J=7.5Hz, 1H), 7.52(d, J=8.7Hz, 2H), 7.57(dd, J=6.0, 4.1Hz 7.74(d, J=8.7Hz, 2H), 8.06(t, J=5.5Hz, 1H), 9.34(brs, 1H) |

TABLE 2-84

| Example | Structural formula | NMR |
|---|---|---|
| 2-416 | | (DMSO-d6-300) 1.38(s, 3H), 1.39(d, J=6.4Hz, 1H), 2.08(d, J=5.7Hz, 1H), 7.12-7.26(m, 5H), 7.55(d, J=3.8Hz, 1H), 7.78(d, J=3.8Hz, 1H), 7.87(td, J=8.7, 3.0Hz, 1H), 8.13(dd, J=4.4, 2.2Hz, 1H), 8.60(d, J=3.0Hz, 1H), 9.19(brs, 1H), 12.08(brs, 1H) |
| 2-417 | | (CDCl3-400) 1.44(d, J=7.0Hz, 3H), 2.35(s, 3H), 2.49-2.51(m, 1H), 3.06(d, J=10.7Hz, 1H), 6.33(brs, 1H), 6.79(s, 1H), 7.22-7.28(m, 6H), 7.36(d, J=4.2Hz, 1H), 7.57(d, J=4.2Hz, 1H) |
| 2-418 | | (CDCl3-400) 2.07-2.10(m, 1H), 2.27-2.32(m, 4H), 6.27(brs, 1H), 6.65(s, 1H), 7.17-7.24(m, 6H), 7.53(d, J=4.2Hz, 1H) |
| 2-419 | | (MeOH-d4-300) 1.35(d, J=6.6Hz, 3H), 2.16(dd, J=10.5, 6.6Hz, 1H), 2.91(d, J=10.5Hz, 1H), 3.02(s, 6H), 7.17-7.23(m, 6H), 7.43(d, J=4.0Hz, 1H), 7.59(d, J=4.0Hz, 1H) |
| 2-420 | | (DMSO-d6-300) 1.39(s, 3H), 1.40(d, J=3.4Hz, 1H), 2.09(d, J=5.7Hz, 1H), 7.12-7.26(m, 5H), 7.59-7.63(m, 3H), 8.11(ddd, J=8.9, 4.4, 2.2Hz, 1H), 8.38(dd, J=6.0, 2.3Hz, 1H), 9.25(brs, 1H), 12.12(brs, 1H) |

TABLE 2-85
| Example | Structural formula | NMR |
|---|---|---|
| 2-421 | 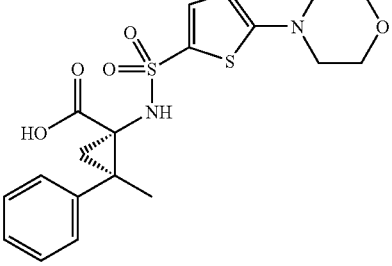 | (DMSO-d6-300) 1.25(d, J=5.7Hz, 1H), 1.37(s, 3H), 2.00(d, J=5.3Hz, 1H), 3.11-3.19(m, 4H), 3.69-3.75(m, 4H), 6.16(d, J=4.5Hz, 1H), 7.14-7.23(m, 6H), 8.72(brs, 1H), 12.03(brs, 1H) |
| 2-422 | 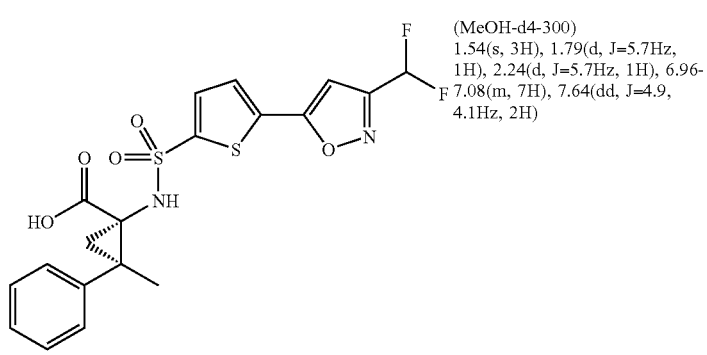 | (MeOH-d4-300) 1.54(s, 3H), 1.79(d, J=5.7Hz, 1H), 2.24(d, J=5.7Hz, 1H), 6.96-7.08(m, 7H), 7.64(dd, J=4.9, 4.1Hz, 2H) |
| 2-423 | 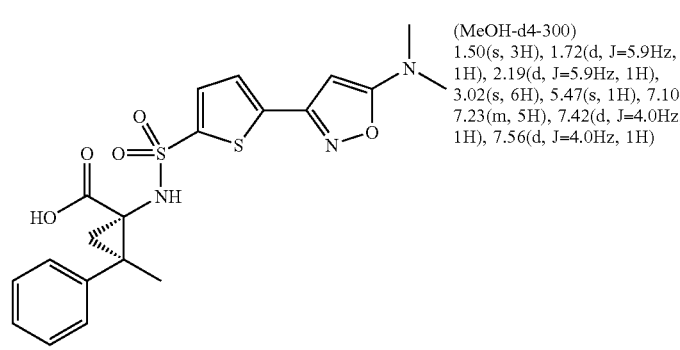 | (MeOH-d4-300) 1.50(s, 3H), 1.72(d, J=5.9Hz, 1H), 2.19(d, J=5.9Hz, 1H), 3.02(s, 6H), 5.47(s, 1H), 7.10-7.23(m, 5H), 7.42(d, J=4.0Hz, 1H), 7.56(d, J=4.0Hz, 1H) |
| 2-424 | 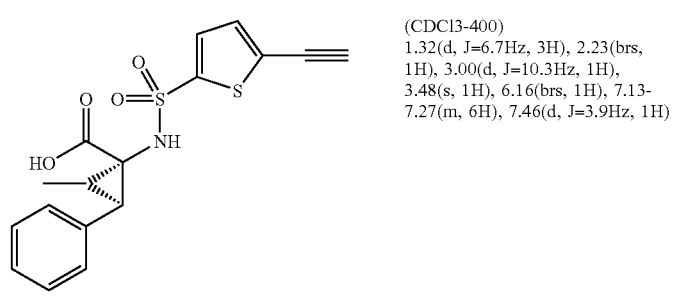 | (CDCl3-400) 1.32(d, J=6.7Hz, 3H), 2.23(brs, 1H), 3.00(d, J=10.3Hz, 1H), 3.48(s, 1H), 6.16(brs, 1H), 7.13-7.27(m, 6H), 7.46(d, J=3.9Hz, 1H) |
| 2-425 | 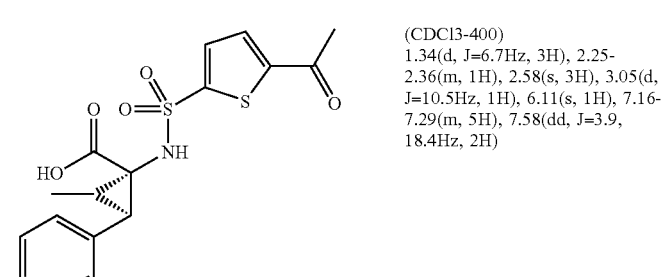 | (CDCl3-400) 1.34(d, J=6.7Hz, 3H), 2.25-2.36(m, 1H), 2.58(s, 3H), 3.05(d, J=10.5Hz, 1H), 6.11(s, 1H), 7.16-7.29(m, 5H), 7.58(dd, J=3.9, 18.4Hz, 2H) |

TABLE 2-86
| Example | Structural formula | NMR |
|---|---|---|
| 2-426 | 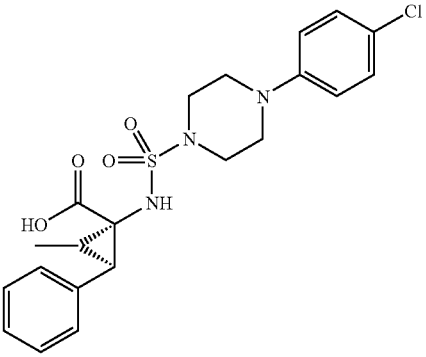 | (CDCl3-400) 1.34(d, J=6.7Hz, 3H), 2.19-2.28(m, 1H), 3.11-3.20(m, 5H), 3.36-3.43(m, 4H), 5.58(s, 1H), 6.83(d, J=8.9Hz, 2H), 7.21-7.29(m, 7H) |
| 2-427 | 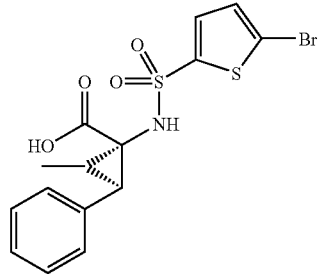 | (CDCl3-400) 1.32-1.35(m, 3H), 2.17-2.28(m, 1H), 3.01(d, J=10.3Hz, 1H), 6.11(brs, 1H), 7.00(d, J=4.0Hz, 1H), 7.18-7.32(m, 5H), 7.38(d, J=4.0Hz, 1H) |
| 2-428 | 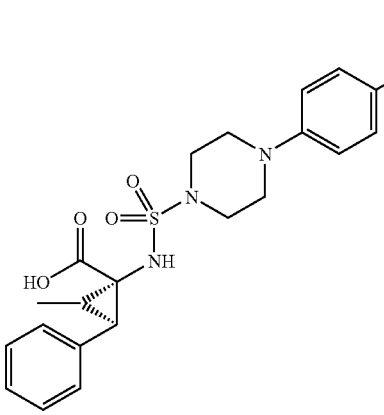 | (CDCl3-400) 1.33-1.36(m, 3H), 2.21-2.29(m, 1H), 3.17(d, J=10.5Hz, 1H), 3.30-3.32(m, 4H), 3.40-3.42(m, 4H), 5.59(s, 1H), 6.94(d, J=8.6Hz, 2H), 7.14-7.29(m, 5H), 7.50(d, J=8.7Hz, 2H) |
| 2-429 | 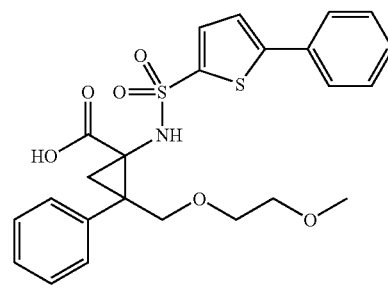 | (CDCl3-300) 1.93(d, J=5.9Hz, 1H), 2.14(d, J=5.9Hz, 1H), 3.35-3.67(m, 5H), 3.38(s, 3H), 3.88(d, J=9.5Hz, 1H), 7.11-7.25(m, 5H), 7.39(d, J=8.8Hz, 2H), 7.54(d, J=8.8Hz, 2H), 7.57(d, J=3.7Hz, 2H) |

TABLE 2-86-continued

| Example | Structural formula | NMR |
|---|---|---|
| 2-430 | | (MeOH-d4-400) 1.86-1.96(m, 1H), 2.08-2.21(m, 1H), 2.62-2.68(m, 1H), 2.81(d, J=9.7Hz, 1H), 3.21-3.31(m, 2H), 6.86-6.95(m, 2H), 7.17(t, J=7.7Hz, 1H), 7.23(d, J=7.4Hz, 1H), 7.40(d, J=4.2Hz, 1H), 7.47-7.42(m, 2H), 7.60(d, J=3.7Hz, 1H), 7.70-7.64(m, 2H) |

TABLE 2-87

| Example | Structural formula | NMR |
|---|---|---|
| 2-431 | | (DMSO-d6-300) 2.41(dd, J=6.8, 7.2Hz, 1H), 2.95(d, J=6.8Hz, 1H), 3.11(dd, J=17.3, 7.2Hz, 1H), 3.24-3.40(m, 1H), 7.04-7.10(m, 3H), 7.20-7.26(m, 1H), 7.53(d, J=8.7Hz, 2H), 7.57(d, J=3.8Hz, 1H), 7.60(d, J=3.8Hz, 1H), 7.76(d, J=8.7Hz, 2H), 9.07(s, 1H), 12.10(s, 1H) |
| 2-432 | | (MeOH-d4-300) 1.77(s, 3H), 1.92(d, J=6.0Hz, 1H), 2.25(d, J=6.0Hz, 1H), 2.93(d, J=12.0Hz, 1H), 3.05(d, J=12.0Hz, 1H), 7.12-7.28(m, 5H), 7.38(d, J=3.0Hz, 1H), 7.43(d, J=9.0Hz, 2H), 7.56(d, J=3.0Hz, 1H), 7.65(d, J=9.0Hz, 2H) |
| 2-433 | | (MeOH-d4-300) 0.90-0.94(m, 2H), 1.05-1.12(m, 2H), 1.32(d, J=6.6Hz, 3H), 2.09-2.15(m, 2H), 2.88(d, J=10.6Hz, 1H), 6.44(s, 1H), 7.09-7.33(m, 5H), 7.43(d, J=4.0Hz, 1H), 7.56(d, J=4.0Hz, 1H) |

TABLE 2-87-continued

| Example | Structural formula | NMR |
|---|---|---|
| 2-434 | | (DMSO-d6-300) 1.39(s, 4H), 2.08(d, J=5.7Hz, 1H), 7.11-7.27(m, 5H), 7.53-7.71(m, 4H), 7.88(dd, J=10.5, 2.3Hz, 1H), 9.24(brs, 1H), 12.14(brs, 1H) |
| 2-435 | | (DMSO-d6-300) 1.27(d, J=6.4Hz, 3H), 1.92-2.06(m, 1H), 2.78(d, J=10.2Hz, 1H), 7.13-7.31(m, 5H), 7.53-7.71(m, 4H), 7.87(dd, J=10.5, 1.9Hz, 1H), 9.10(brs, 1H), 12.31(brs, 1H) |

TABLE 2-88

| Example | Structural formula | NMR |
|---|---|---|
| 2-436 | | (CDCl3-400) 0.94-1.03(m, 3H), 1.08-1.13(m, 1H), 1.39-2.11(m, 13H), 2.50-2.59(m, 1H), 5.94(brs, 1H), 7.07(d, J=7.4Hz, 2H), 7.19-7.30(m, 5H), 7.77-7.78(m, 2H) |
| 2-437 | | (DMSO-d6-400) 1.55-1.67(m, 2H), 1.80-1.99(m, 3H), 2.42-2.54(m, 1H), 2.77(d, J=10.2Hz, 1H), 4.66(brs, 1H), 7.04(d, J=6.5Hz, 1H), 7.10(dd, J=7.0, 6.5Hz, 1H), 7.16(dd, J=7.0, 6.5Hz, 1H), 7.23(d, J=6.5Hz, 1H), 7.68(d, J=3.7Hz, 1H), 7.85(d, J=3.7Hz, 1H), 8.15(s, 1H) |

TABLE 2-88-continued

| Example | Structural formula | NMR |
|---|---|---|
| 2-438 | | (DMSO-d6-400) 1.55-1.67(m, 2H), 1.80-1.99(m, 3H), 2.42-2.54(m, 1H), 2.77(d, J=10.2Hz, 1H), 4.66(brs, 1H), 7.04(d, J=6.5Hz, 1H), 7.10(dd, J=7.0, 6.5Hz, 1H), 7.16(dd, J=7.0, 6.5Hz, 1H), 7.23(d, J=6.5Hz, 1H), 7.68(d, J=3.7Hz, 1H), 7.85(d, J=3.7Hz, 1H), 8.15(s, 1H) |
| 2-439 | | (DMSO-d6-400) 1.66-1.83(m, 2H), 1.88-2.00(m, 1H), 2.49(s, 3H), 2.71(d, J=9.3Hz, 1H), 2.94(ddd, J=13.0, 4.6, 2.8Hz, 1H), 4.39(td, J=12.5, 5.6Hz, 1H), 7.15-7.21(m, 1H), 7.25-7.37(m, 3H), 7.49-7.54(m, 2H), 7.55-7.59(m, 2H), 7.71-7.76(m, 2H), 9.11(brs, 1H), 12.59(brs, 1H) |
| 2-440 | | (MeOH-d4-300) 2.31(d, J=6.0Hz, 1H), 2.34(s, 3H), 2.48(d, J=6.0Hz, 1H), 3.42(d, J=15.0Hz, 1H), 3.95(d, J=15.0Hz, 1H), 7.13-7.46(m, 8H), 7.58(d, J=3.0Hz, 1H), 7.65(d, J=9.0Hz, 2H) |

TABLE 2-89

| Example | Structural formula | NMR |
|---|---|---|
| 2-441 | | (CDCl3-400) 1.24-1.42(m, 3H), 2.19(brs, 1H), 2.56(s, 2H), 3.13(d, J=11.3Hz, 1H), 3.49(s, 2H), 3.93(s, 2H), 5.64(brs, 1H), 6.01(s, 1H), 7.24-7.31(m, 9H) |

TABLE 2-89-continued
| Example | Structural formula | NMR |
|---|---|---|
| 2-442 | 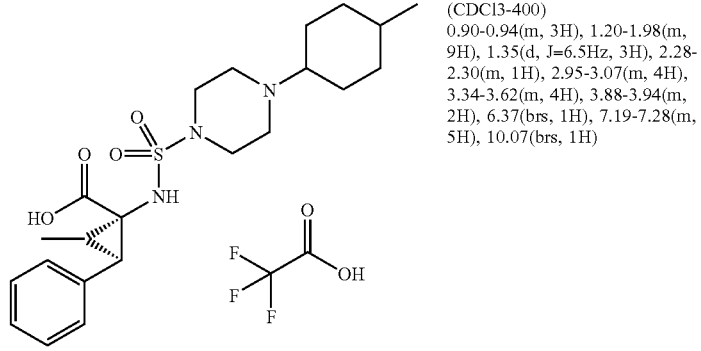 | (CDCl3-400) 0.90-0.94(m, 3H), 1.20-1.98(m, 9H), 1.35(d, J=6.5Hz, 3H), 2.28-2.30(m, 1H), 2.95-3.07(m, 4H), 3.34-3.62(m, 4H), 3.88-3.94(m, 2H), 6.37(brs, 1H), 7.19-7.28(m, 5H), 10.07(brs, 1H) |
| 2-443 | 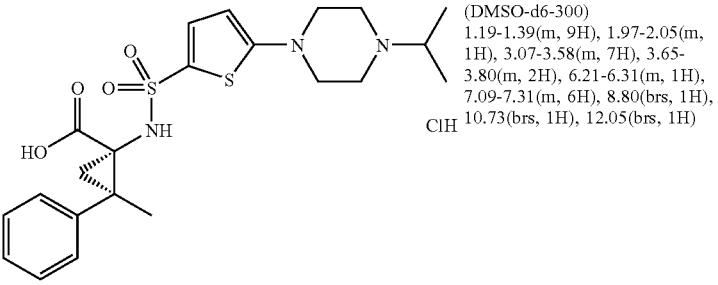 | (DMSO-d6-300) 1.19-1.39(m, 9H), 1.97-2.05(m, 1H), 3.07-3.58(m, 7H), 3.65-3.80(m, 2H), 6.21-6.31(m, 1H), 7.09-7.31(m, 6H), 8.80(brs, 1H), 10.73(brs, 1H), 12.05(brs, 1H) |
| 2-444 | 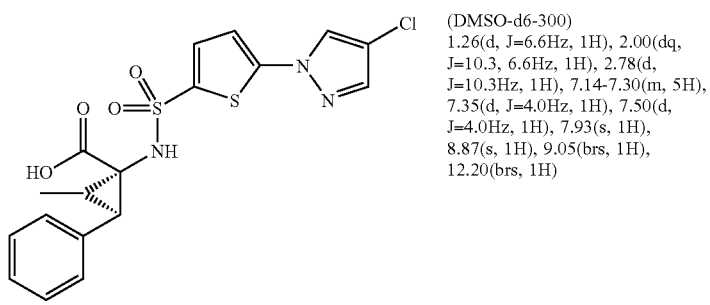 | (DMSO-d6-300) 1.26(d, J=6.6Hz, 1H), 2.00(dq, J=10.3, 6.6Hz, 1H), 2.78(d, J=10.3Hz, 1H), 7.14-7.30(m, 5H), 7.35(d, J=4.0Hz, 1H), 7.50(d, J=4.0Hz, 1H), 7.93(s, 1H), 8.87(s, 1H), 9.05(brs, 1H), 12.20(brs, 1H) |
| 2-445 | 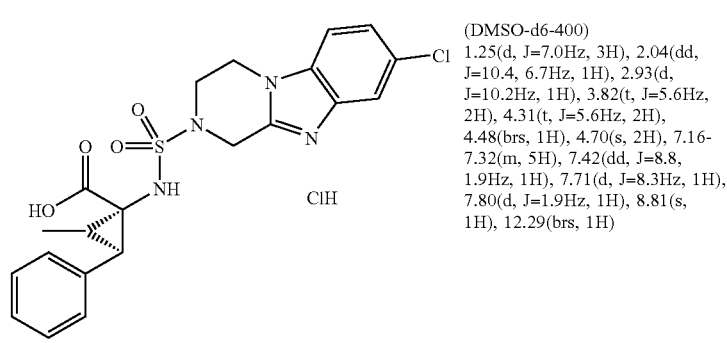 | (DMSO-d6-400) 1.25(d, J=7.0Hz, 3H), 2.04(dd, J=10.4, 6.7Hz, 1H), 2.93(d, J=10.2Hz, 1H), 3.82(t, J=5.6Hz, 2H), 4.31(t, J=5.6Hz, 2H), 4.48(brs, 1H), 4.70(s, 2H), 7.16-7.32(m, 5H), 7.42(dd, J=8.8, 1.9Hz, 1H), 7.71(d, J=8.3Hz, 1H), 7.80(d, J=1.9Hz, 1H), 8.81(s, 1H), 12.29(brs, 1H) |

TABLE 2-90
| Example | Structural formula | NMR |
|---|---|---|
| 2-446 | 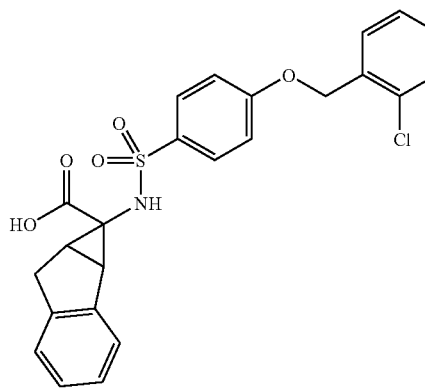 | (DMSO-d6-300)<br>2.20(dd, J=6.4, 7.2Hz, 1H), 2.78(d, J=6.4Hz, 1H), 3.03(dd, J=17.3, 7.2Hz, 1H), 3.19-3.44(m, 1H), 5.22(s, 2H), 7.01-7.09(m, 3H), 7.16-7.22(m, 1H), 7.20(d, J=9.0Hz, 2H), 7.48(dd, J=8.3, 2.3Hz, 1H), 7.63(d, J=8.3Hz, 1H), 7.71(d, J=2.3Hz, 1H), 7.75(d, J=9.0Hz, 2H), 8.61(brs, 1H) |
| 2-447 | 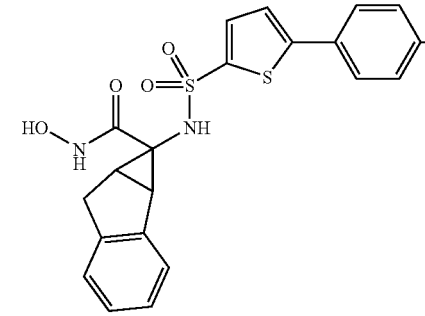 | (DMSO-d6-300)<br>2.23(dd, J=7.2, 7.3Hz, 1H), 2.78(d, J=7.2Hz, 1H), 3.06(dd, J=17.9, 7.3Hz, 1H), 3.22-3.40(m, 1H), 7.00-7.11(m, 3H), 7.19-7.26(m, 1H), 7.53(d, J=8.7Hz, 2H), 7.62(d, J=4.1Hz, 1H), 7.66(d, J=4.1Hz, 1H), 7.77(d, J=8.7Hz, 2H), 8.48(s, 1H), 8.74(brs, 1H), 9.92(s, 1H) |
| 2-448 | 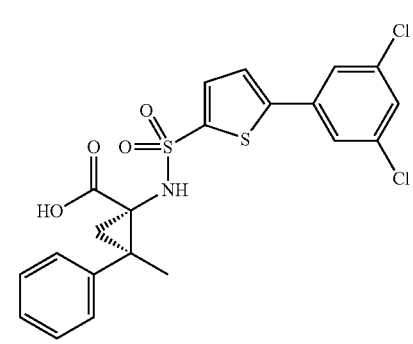 | (DMSO-d6-300)<br>1.37-1.43(m, 1H), 1.40(s, 3H), 2.10(d, J=5.7Hz, 1H), 7.12-7.27(m, 5H), 7.56(d, J=3.8Hz, 1H), 7.65(t, J=1.9Hz, 1H), 7.73(d, J=3.8Hz, 1H), 7.81(d, J=1.9Hz, 2H), 9.26(s, 1H), 12.11(brs, 1H) |
| 2-449 | 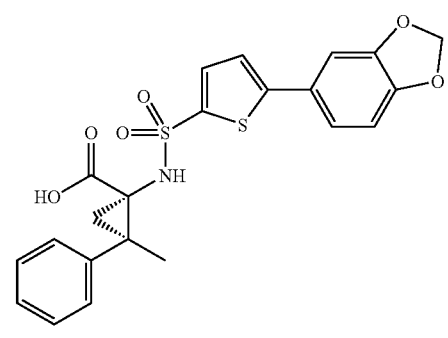 | (DMSO-d6-400)<br>1.36-1.38(m, 1H), 1.37(s, 3H), 2.06(d, J=5.1Hz, 1H), 6.07(s, 2H), 6.97(d, J=7.9Hz, 1H), 7.11-7.25(m, 6H), 7.32(d, J=1.9Hz, 1H), 7.40(d, J=3.7Hz, 1H), 7.47(d, J=3.7Hz, 1H), 9.11(s, 1H), 12.10(s, 1H) |

TABLE 2-90-continued

| Example | Structural formula | NMR |
|---------|-------------------|-----|
| 2-450 | | (DMSO-d6-400)<br>1.23(d, J=6.5Hz, 3H), 1.93(dd, J=10.4, 6.7Hz, 1H), 2.73(d, J=10.2Hz, 1H), 3.70(s, 3H), 7.14-7.20(m, 3H), 7.22-7.27(m, 3H), 7.47(d, J=3.7Hz, 1H), 7.77(s, 1H), 7.97(s, 1H), 8.92(s, 1H), 12.27(brs, 1H) |

TABLE 2-91

| Example | Structural formula | NMR |
|---------|-------------------|-----|
| 2-451 | | (DMSO-d6-400)<br>1.25(d, J=7.0Hz, 3H), 1.99(dd, J=10.4, 6.7Hz, 1H), 2.65(s, 3H), 2.78(d, J=10.7Hz, 1H), 7.14-7.20(m, 3H), 7.22-7.28(m, 2H), 7.62(t, J=2.1Hz, 1H), 7.75(q, J=1.9Hz, 1H), 9.25(brs, 1H), 12.31(brs, 1H) |
| 2-452 | | (DMSO-d6-300)<br>1.39(s, 4H), 2.07(d, J=5.3Hz, 1H), 5.30(brs, 2H), 6.56-6.61(m, 1H), 6.80-6.88(m, 2H), 7.04-7.27(m, 6H), 7.34(d, J=4.1Hz, 1H), 7.50(d, J=3.8Hz, 1H), 9.11(brs, 1H), 12.11(brs, 1H) |
| 2-453 | | (DMSO-d6-400)<br>1.40(s, 4H), 2.09(d, J=5.5Hz, 1H), 3.05(s, 3H), 7.11-7.27(m, 6H), 7.39-7.50(m, 4H), 7.54(d, J=4.0Hz, 1H), 9.18(brs, 1H), 9.91(brs, 1H), 12.10(brs, 1H) |

TABLE 2-91-continued
| Example | Structural formula | NMR |
|---|---|---|
| 2-454 | 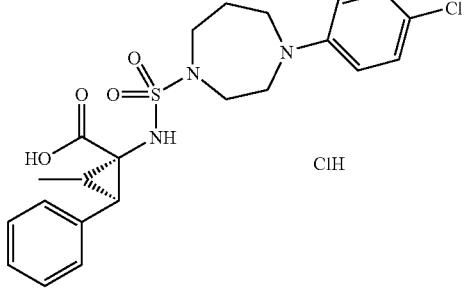 | (DMSO-d6-300) 1.19(d, J=6.0Hz, 3H), 1.78-1.94(m, 3H), 2.68(d, J=9.7Hz, 1H), 3.06-3.19(m, 2H), 3.28-3.41(m, 2H), 3.53(t, J=5.8Hz, 2H), 3.59(t, J=5.1Hz, 2H), 6.71(d, J=9.3Hz, 2H), 7.10-7.19(m, 5H), 7.23(d, J=7.0Hz, 2H), 8.10(s, 1H) |
| 2-455 | 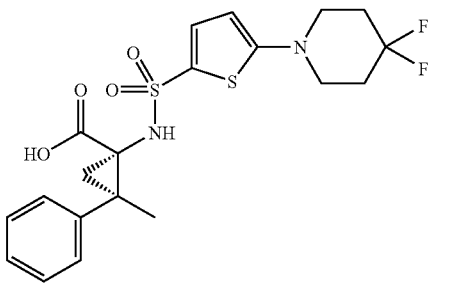 | (DMSO-d6-400) 1.27(d, J=5.1Hz, 1H), 1.36(s, 3H), 2.00(d, J=5.6Hz, 1H), 2.03-2.13(m, 4H), 3.28-3.33(m, 4H), 6.19(d, J=4.2Hz, 1H), 7.12-7.16(m, 3H), 7.20-7.23(m, 3H), 8.71(brs, 1H), 12.01(brs, 1H) |
TABLE 2-92
| Example | Structural formula | NMR |
|---|---|---|
| 2-456 | 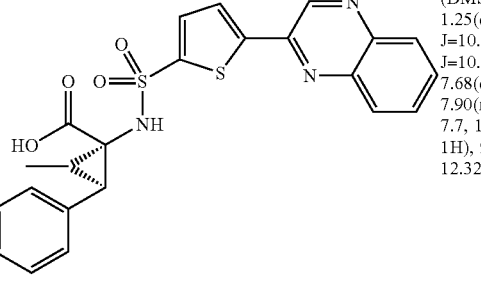 | (DMSO-d6-400) 1.25(d, J=7.0Hz, 3H), 1.99(dd, J=10.4, 6.7Hz, 1H), 2.78(d, J=10.7Hz, 1H), 7.14-7.27(m, 5H), 7.68(d, J=4.2Hz, 1H), 7.82-7.90(m, 2H), 8.09(ddd, J=11.6, 7.7, 1.9Hz, 2H), 8.20(d, J=4.2Hz, 1H), 9.18(brs, 1H), 9.62(s, 1H), 12.32(brs, 1H) |
| 2-457 | 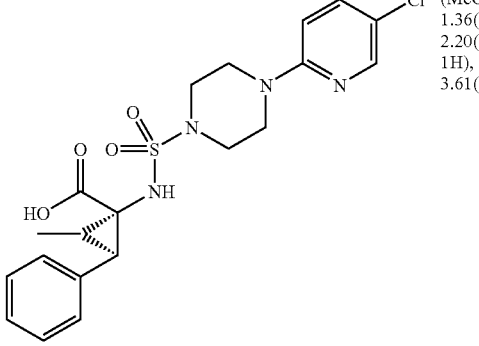 | (MeOH-d4-400) 1.36(d, J=6.8Hz, 3H), 2.13-2.20(m, 1H), 3.03(d, J=10.5Hz, 1H), 3.30-3.35(m, 4H), 3.58-3.61(m, 4H), 6.81-8.06(m, 8H) |

TABLE 2-92-continued

| Example | Structural formula | NMR |
|---|---|---|
| 2-458 | | (MeOH-d4-400) 1.35-1.38(m, 3H), 2.12-2.20(m, 1H), 3.03(d, J=10.4Hz, 1H), 3.20-3.23(m, 4H), 3.35-3.38(m, 4H), 6.88-6.91(m, 2H), 7.16-7.34(m, 8H) |
| 2-459 | | (CDCl3-400) 1.34(d, J=7.0Hz, 3H), 2.21-2.29(m, 1H), 3.15-3.21(m, 5H), 3.37-3.40(m, 4H), 5.56(s, 1H), 6.64(ddd, J=2.7, 10.4, 11.6Hz, 2H), 7.20-7.30(m, 6H) |
| 2-460 | | (MeOH-d4-400) 1.36(d, J=7.0Hz, 3H), 2.14-2.22(m, 1H), 3.04(d, J=10.5Hz, 1H), 3.10-3.12(m, 4H), 3.37-3.40(m, 4H), 6.99-7.33(m, 8H) |

TABLE 2-93

| Example | Structural formula | NMR |
|---|---|---|
| 2-461 | | (CDCl3-400) 1.20-1.32(m, 2H), 1.33(d, J=6.5Hz, 3H), 1.97-2.12(m, 2H), 2.24-2.35(m, 1H), 2.99(d, J=10.2Hz, 1H), 3.29-3.92(m, 6H), 6.04(brs, 1H), 6.83(dd, J=9.7, 1.9Hz, 1H), 7.14-7.33(m, 5H), 7.71(dt, J=9.7, 2.3Hz, 1H), 7.92(t, J=2.3Hz, 1H) |

TABLE 2-93-continued
| Example | Structural formula | NMR |
|---|---|---|
| 2-462 | 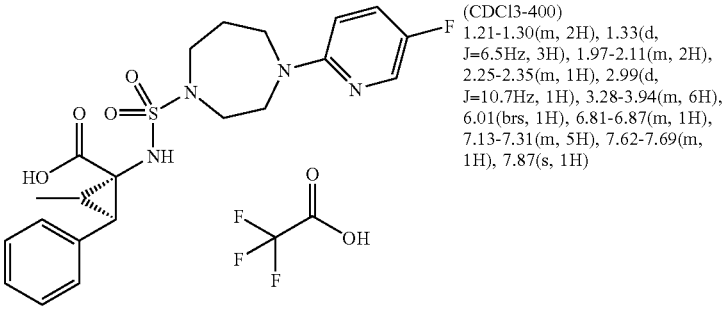 | (CDCl3-400) 1.21-1.30(m, 2H), 1.33(d, J=6.5Hz, 3H), 1.97-2.11(m, 2H), 2.25-2.35(m, 1H), 2.99(d, J=10.7Hz, 1H), 3.28-3.94(m, 6H), 6.01(brs, 1H), 6.81-6.87(m, 1H), 7.13-7.31(m, 5H), 7.62-7.69(m, 1H), 7.87(s, 1H) |
| 2-463 | 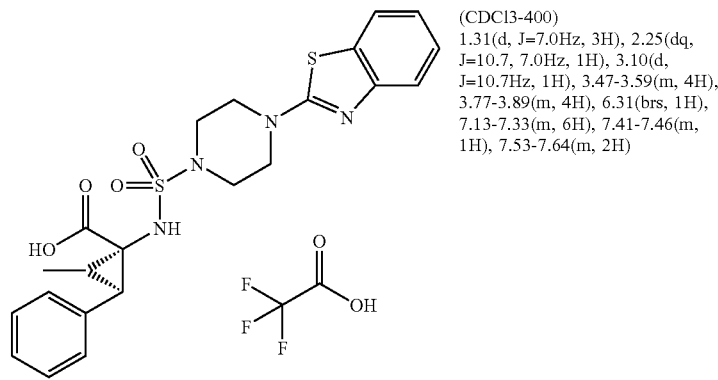 | (CDCl3-400) 1.31(d, J=7.0Hz, 3H), 2.25(dq, J=10.7, 7.0Hz, 1H), 3.10(d, J=10.7Hz, 1H), 3.47-3.59(m, 4H), 3.77-3.89(m, 4H), 6.31(brs, 1H), 7.13-7.33(m, 6H), 7.41-7.46(m, 1H), 7.53-7.64(m, 2H) |
| 2-464 | 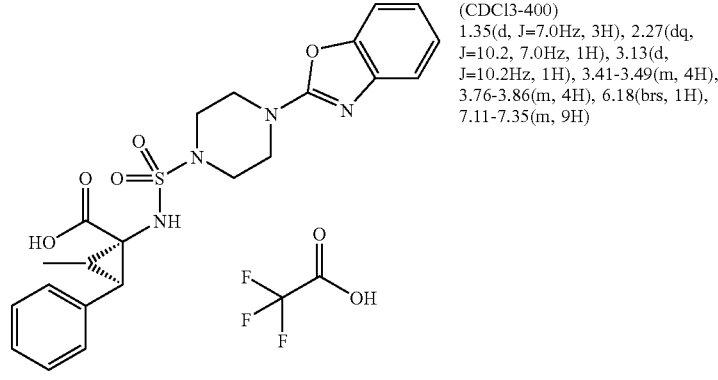 | (CDCl3-400) 1.35(d, J=7.0Hz, 3H), 2.27(dq, J=10.2, 7.0Hz, 1H), 3.13(d, J=10.2Hz, 1H), 3.41-3.49(m, 4H), 3.76-3.86(m, 4H), 6.18(brs, 1H), 7.11-7.35(m, 9H) |
| 2-465 | 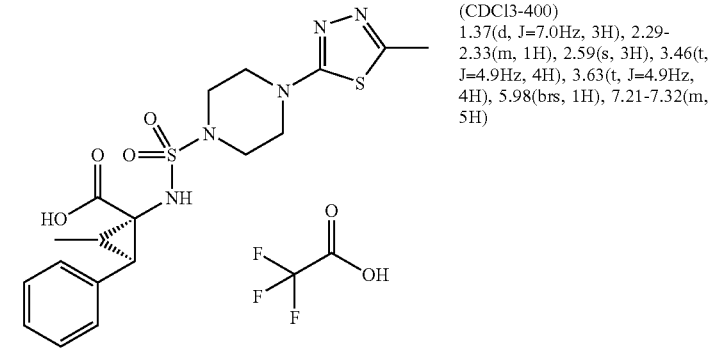 | (CDCl3-400) 1.37(d, J=7.0Hz, 3H), 2.29-2.33(m, 1H), 2.59(s, 3H), 3.46(t, J=4.9Hz, 4H), 3.63(t, J=4.9Hz, 4H), 5.98(brs, 1H), 7.21-7.32(m, 5H) |

TABLE 2-94

| Example | Structural formula | NMR |
|---|---|---|
| 2-466 | | (DMSO-d6-300) 1.39(s, 3H), 1.40(d, J=4.9Hz, 1H), 2.10(d, J=5.7Hz, 1H), 7.16-7.25(m, 5H), 7.60(d, J=4.1Hz, 1H), 7.65-7.68(m, 1H), 8.13-8.19(m, 1H), 8.60(d, J=2.3Hz, 1H), 9.27(brs, 1H), 12.10(brs, 1H) |
| 2-467 | | (DMSO-d6-300) 1.24(d, J=5.3Hz, 1H), 1.37(s, 3H), 2.00(d, J=5.3Hz, 1H), 2.59-2.61(m, 1H), 3.49(t, J=7.2Hz, 2H), 3.73(t, J=12.8Hz, 2H), 5.90(d, J=4.1Hz, 1H), 7.14-7.26(m, 6H), 8.69(brs, 1H), 12.02(brs, 1H) |
| 2-468 | | (DMSO-d6-300) 1.26(d, J=6.4Hz, 3H), 1.98(dd, J=10.4, 6.6Hz, 1H), 2.78(d, J=10.5Hz, 1H), 7.14-7.30(m, 6H), 7.45(d, J=3.8Hz, 1H), 7.54(d, J=3.8Hz, 1H), 7.61(dd, J=8.3, 1.9Hz, 1H), 8.00(d, J=1.9Hz, 1H), 9.01(brs, 1H), 12.22(brs, 1H) |
| 2-469 | | (DMSO-d6-300) 1.28(d, J=6.4Hz, 3H), 2.01(dd, J=10.2, 6.8Hz, 1H), 2.81(d, J=10.2Hz, 1H), 2.83(s, 3H), 7.16-7.31(m, 5H), 7.58(d, J=3.8Hz, 1H), 7.65(d, J=4.1Hz, 1H), 7.73(dd, J=8.5, 1.7Hz, 1H), 8.12(d, J=8.7Hz, 1H), 8.24(d, J=1.5Hz, 1H), 9.05(s, 1H), 12.31(brs, 1H) |
| 2-470 | | (DMSO-d6-300) 1.26(d, J=6.8Hz, 3H), 1.97(dd, J=10.5, 6.8Hz, 1H), 2.77(d, J=10.5Hz, 1H), 6.08(s, 2H), 6.99(d, J=7.9Hz, 1H), 7.15-7.30(m, 6H), 7.33(d, J=1.5Hz, 1H), 7.41(d, J=3.8Hz, 1H), 7.50(d, J=3.8Hz, 1H), 8.98(brs, 1H), 12.30(brs, 1H) |

TABLE 2-95

| Example | Structural formula | NMR |
|---|---|---|
| 2-471 | | (DMSO-d6-300) 1.21(d, J=6.0Hz, 3H), 1.80-2.01(m, 3H), 2.70(d, J=11.3Hz, 1H), 3.10-3.21(m, 2H), 3.30-3.43(m, 2H), 3.51-3.66(m, 4H), 6.53-6.78(m, 3H), 7.09-7.30(m, 6H), 8.13(s, 1H) |
| 2-472 | | (DMSO-d6-300) 1.22(d, J=6.8Hz, 3H), 1.81-2.00(m, 3H), 2.71(d, J=10.9Hz, 1H), 3.10-3.19(m, 2H), 3.32-3.43(m, 2H), 3.48-3.65(m, 4H), 6.65-6.77(m, 2H), 6.92-7.02(m, 2H), 7.12-7.30(m, 5H), 8.11(s, 1H) |
| 2-473 | | (DMSO-d6-300) 1.39-1.52(m, 1H), 1.91-2.00(m, 1H), 2.61-2.71(m, 1H), 7.11-7.28(m, 5H), 7.49-7.65(m, 3H), 7.77(d, J=8.7Hz, 2H), 7.91-8.01(m, 4H), 8.78(s, 1H), 10.58(s, 1H), 12.07(s, 1H) |
| 2-474 | | (DMSO-d6-300) 1.41-1.51(m, 1H), 1.92-2.01(m, 1H), 2.64-2.74(m, 2H), 7.10-7.29(m, 6H), 7.37(t, J=8.1Hz, 2H), 7.77(d, J=8.1Hz, 2H), 7.93(d, J=8.3Hz, 2H), 8.11(d, J=8.3Hz, 2H), 9.05(s, 1H), 10.42(s, 2H), 12.16(s, 1H) |

TABLE 2-95-continued

| Example | Structural formula | NMR |
|---|---|---|
| 2-475 | | (DMSO-d6-300) 1.26(d, J=6.8Hz, 3H), 1.93-2.07(m, 1H), 2.86(d, J=10.2Hz, 1H), 3.11-3.19(m, 2H), 3.20-3.27(m, 2H), 3.28-3.34(m, 4H), 6.05(s, 1H), 7.12-7.31(m, 5H), 8.31(s, 1H), 12.37(s, 1H) |

TABLE 2-96

| Example | Structural formula | NMR |
|---|---|---|
| 2-476 | | (DMSO-d6-300) 1.26(d, J=7.5Hz, 3H), 1.98-2.11(m, 1H), 2.91(d, J=9.8Hz, 1H), 3.51-3.62(m, 3H), 3.82-3.93(m, 2H), 3.96(s, 2H), 6.80(s, 1H), 7.13-7.32(m, 5H), 8.66(s, 1H), 12.47(s, 1H) |
| 2-477 | | (DMSO-d6-300) 1.39(s, 3H), 1.42(d, J=5.7Hz, 1H), 2.08(d, J=4.9Hz, 1H), 7.12-7.25(m, 5H), 7.58(d, J=4.1Hz, 1H), 7.74(d, J=3.8Hz, 1H), 7.84(d, J=8.7Hz, 1H), 8.03(dd, J=8.7, 2.3Hz, 1H), 8.44(d, J=2.3Hz, 1H), 9.29(brs, 1H), 12.16(brs, 1H) |
| 2-478 | | (DMSO-d6-300) 1.34-1.42(m, 1H), 1.35(t, J=7.2Hz, 3H), 1.40(s, 3H), 2.09(d, J=5.3Hz, 1H), 4.36(q, J=7.2Hz, 2H), 7.10-7.28(m, 5H), 7.56(d, J=3.8Hz, 1H), 7.61-7.65(m, 1H), 7.64(d, J=3.8Hz, 1H), 7.94-8.04(m, 2H), 8.18(brs, 1H), 9.25(s, 1H), 12.14(s, 1H) |

TABLE 2-96-continued

| Example | Structural formula | NMR |
|---|---|---|
| 2-479 | | (DMSO-d6-300)<br>1.40(s, 3H), 1.42(d, J=5.7Hz, 1H), 2.10(d, J=5.7Hz, 1H), 7.13-7.27(m, 5H), 7.55-7.63(m, 1H), 7.56(d, J=4.1Hz, 1H), 7.62(d, J=4.1Hz, 1H), 7.93-8.00(m, 2H), 8.15-8.18(m, 1H), 9.22(s, 1H) |
| 2-480 | | (DMSO-d6-300)<br>1.37-1.41(m, 4H), 2.06(s, 3H), 2.09(d, J=5.7Hz, 1H), 7.13-7.27(m, 5H), 7.36-7.41(m, 2H), 7.44(d, J=3.8Hz, 1H), 7.53-7.56(m, 1H), 7.54(d, J=3.8Hz, 1H), 7.97(brs, 1H), 9.18(s, 1H), 10.08(s, 1H), 12.11(brs, 1H) |

TABLE 2-97

| Example | Structural formula | NMR |
|---|---|---|
| 2-481 | ClH | (DMSO-d6-400)<br>1.64(q, J=5.1Hz, 1H), 1.97(t, J=7.2Hz, 1H), 2.10(s, 3H), 2.69(t, J=8.6Hz, 1H), 7.11-7.24(m, 5H), 7.72(s, 1H), 7.98(d, J=8.8Hz, 1H), 8.24(dd, J=8.8, 2.3Hz, 1H), 8.44(s, 1H), 8.73(d, J=2.3Hz, 1H), 12.20(brs, 1H) |

TABLE 2-97-continued

| Example | Structural formula | NMR |
|---|---|---|
| 2-482 | | (CDCl3-300)<br>1.67(dd, J=9.6, 5.5Hz, 1H),<br>2.04(dd, J=8.5, 5.5Hz, 1H),<br>2.79(t, J=9.4Hz, 1H), 3.80(s,<br>3H), 7.15-7.29(m, 5H), 7.76(s,<br>1H), 8.00(d, J=8.7Hz, 1H),<br>8.25(dd, J=8.9, 2.4Hz, 1H),<br>8.36(s, 1H), 8.73(d, J=2.3Hz,<br>1H), 9.19(s, 1H), 12.30(brs, 1H) |
| 2-483 | | (CDCl3-400)<br>1.39(d, J=7.0Hz, 4H), 2.31(dd,<br>J=10.0, 6.7Hz, 1H), 2.68(s, 3H),<br>3.15(d, J=10.2Hz, 1H), 3.23-<br>3.24(m, 4H), 3.48-3.49(m, 4H),<br>6.10(brs, 1H), 6.94(dd, J=8.8,<br>2.3Hz, 1H), 7.19-7.31(m, 5H),<br>7.53(d, J=2.3Hz, 1H), 7.59(d,<br>J=8.8Hz, 1H) |
| 2-484 | | (CDCl3-400)<br>1.41(d, J=7.0Hz, 3H), 2.23(d,<br>J=1.4Hz, 3H), 2.30-2.35(m, 1H),<br>3.09(d, J=10.7Hz, 1H), 3.41-<br>3.46(m, 8H), 6.07(brs, 1H),<br>6.62(d, J=0.9Hz, 1H), 7.26-<br>7.30(m, 5H) |
| 2-485 | | (DMSO-d6-300)<br>1.36(s, 3H), 1.43(d, J=4.9Hz,<br>1H), 1.99(d, J=4.9Hz, 1H),<br>4.28(s, 4H), 6.92(d, J=8.3Hz,<br>1H), 7.07-7.24(m, 7H), 7.38(d,<br>J=3.8Hz, 1H), 7.48(d, J=3.8Hz,<br>1H) |

TABLE 2-98

| Example | Structural formula | NMR |
|---|---|---|
| 2-486 | | (DMSO-d6-300)<br>1.73-1.92(m, 2H), 2.08-2.55(m, 4H), 6.91-6.99(m, 1H), 7.01-7.16(m, 3H), 7.77(d, J=3.8Hz, 1H), 7.91(d, J=3.8Hz, 1H), 8.18(s, 1H), 8.70(s, 1H), 8.90(brs, 1H), 9.80(s, 1H) |
| 2-487 | | (DMSO-d6-300)<br>1.37(s, 3H), 1.41(d, J=5.1Hz, 1H), 2.07(d, J=5.6Hz, 1H), 7.07-7.22(m, 6H), 7.34(d, J=10.2Hz, 1H), 7.41-7.48(m, 2H), 7.58-7.63(m, 2H), 9.10(brs, 1H), 12.26(brs, 1H) |
| 2-488 | | (DMSO-d6-300)<br>1.38(d, J=5.3Hz, 1H), 1.39(s, 3H), 2.09(d, J=5.3Hz, 1H), 2.79(s, 6H), 7.14-7.27(m, 5H), 7.30(dd, J=8.1, 2.1Hz, 1H), 7.37(d, J=2.3Hz, 1H), 7.45(d, J=8.3Hz, 1H), 7.54(d, J=4.1Hz, 1H), 7.58(d, J=3.8Hz, 1H), 9.18(s, 1H), 12.10(brs, 1H) |
| 2-489 | | (DMSO-d6-400)<br>1.68(dd, J=10.2, 5.1Hz, 1H), 1.95(dd, J=8.3, 5.1Hz, 1H), 2.59(t, J=9.3Hz, 1H), 7.09-7.21(m, 5H), 7.25-7.31(m, 1H), 7.37-7.43(m, 2H), 7.81-7.86(m, 2H), 8.23(s, 1H), 8.58(s, 1H) |

TABLE 2-98-continued

| Example | Structural formula | NMR |
|---|---|---|
| 2-490 | | (DMSO-d6-400) 1.67(dd, J=9.7, 5.1Hz, 1H), 1.96(dd, J=8.3, 5.1Hz, 1H), 2.61(t, J=9.0Hz, 1H), 7.08-7.24(m, 5H), 7.46(d, J=8.8Hz, 2H), 7.86(d, J=8.8Hz, 2H), 8.27(s, 1H), 8.60(s, 1H) |

TABLE 2-99

| Example | Structural formula | NMR |
|---|---|---|
| 2-491 | | (DMSO-d6-400) 1.69(dd, J=9.7, 5.6Hz, 1H), 1.98(dd, J=8.6, 5.3Hz, 1H), 2.64(t, J=9.0Hz, 1H), 7.11-7.27(m, 7H), 7.84-7.91(m, 2H), 8.21(s, 1H), 8.60(s, 1H) |
| 2-492 | | (MeOH-d4-300) 1.38(d, J=6.8Hz, 3H), 2.15-2.25(m, 1H), 2.93(d, J=10.5Hz, 1H), 3.81(s, 3H), 7.05(d, J=4.1Hz, 1H), 7.20-7.24(m, 5H), 7.47-7.49(m, 2H), 7.97(d, J=0.8Hz, 1H) |
| 2-493 | | (DMSO-d6-300) 1.27(d, J=6.8Hz, 3H), 1.99(dd, J=10.9, 6.8Hz, 1H), 2.79(d, J=10.9Hz, 1H), 6.86(d, J=1.5Hz, 1H), 7.02(t, J=7.0Hz, 1H), 7.11-7.30(m, 6H), 7.39(d, J=8.3Hz, 1H), 7.48(d, J=3.8Hz, 1H), 7.51-7.58(m, 2H), 9.03(brs, 1H), 11.73(brs, 1H), 12.32(brs, 1H) |

TABLE 2-99-continued

| Example | Structural formula | NMR |
|---|---|---|
| 2-494 | | (MeOH-d4-300) 1.36(d, J=9.0Hz, 3H), 2.14-2.26(m, 1H), 2.93(d, J=9.0Hz, 1H), 7.12-7.28(m, 6H), 7.49(d, J=3.0Hz, 1H), 7.69(s, 1H), 8.41(s, 1H) |
| 2-495 | | (DMSO-d6-300) 2.26(dd, J=6.8, 7.3Hz, 1H), 2.81(d, J=6.8Hz, 1H), 3.08(dd, J=17.5, 7.3Hz, 1H), 3.26-3.38(m, 1H), 7.01-7.11(m, 3H), 7.20-7.29(m, 1H), 7.76(d, J=3.8Hz, 1H), 7.89(d, J=3.8Hz, 1H), 8.17(s, 1H), 8.46(s, 1H), 8.96(brs, 1H), 9.97(s, 1H) |

TABLE 2-100

| Example | Structural formula | NMR |
|---|---|---|
| 2-496 | | (MeOH-d4-300) 1.42(d, J=6.8Hz, 3H), 2.20(dd, J=10.0, 7.0Hz, 1H), 2.93(d, J=10.2Hz, 1H), 6.90(dd, J=8.3, 1.9Hz, 1H), 7.10(d, J=1.9Hz, 1H), 7.18-7.32(m, 7H), 7.56(d, J=4.1Hz, 1H) |
| 2-497 | | (DMSO-d6-300) 1.27(d, J=6.8Hz, 3H), 2.01(dd, J=10.4, 6.6Hz, 1H), 2.80(d, J=10.5Hz, 1H), 7.15-7.29(m, 5H), 7.62(d, J=4.1Hz, 1H), 7.83(d, J=3.8Hz, 1H), 8.09(t, J=4.7Hz, 1H), 8.17(d, J=9.0Hz, 1H), 8.45(s, 1H), 9.12(brs, 1H), 12.31(brs, 1H) |

TABLE 2-100-continued

| Example | Structural formula | NMR |
|---|---|---|
| 2-498 | | (DMSO-d6-300)<br>1.40(s, 3H), 1.42(d, J=5.7Hz, 1H), 2.09(d, J=5.7Hz, 1H), 7.10-7.28(m, 5H), 7.35(d, J=4.1Hz, 1H), 7.49(d, J=4.1Hz, 1H), 7.94(s, 1H), 8.88(s, 1H), 9.20(brs, 1H), 12.08(brs, 1H) |
| 2-499 | | (DMSO-d6-400)<br>1.24(d, J=6.5Hz, 3H), 1.94(dq, J=10.4, 6.7Hz, 1H), 2.66(d, J=10.7Hz, 1H), 7.04-7.21(m, 5H), 7.26-7.32(m, 1H), 7.38-7.43(m, 2H), 7.82-7.86(m, 2H), 8.23(s, 1H), 8.56(s, 1H) |
| 2-500 | | (CDCl3-400)<br>1.27-1.31(m, 3H), 2.16(m, 3H), 3.11(dd, J=10.5, 16.6Hz, 1H), 3.45-3.63(m, 4H), 4.85(s, 1H), 5.71(brs, 1H), 6.71(m, 2H), 7.16-7.30(m, 7H) |

TABLE 2-101

| Example | Structural formula | NMR |
|---|---|---|
| 2-501 | | (CDCl3-400)<br>1.29-1.34(m, 3H), 2.17(m, 3H), 3.14(dd, J=11.1, 19.9Hz, 1H), 3.49-3.74(m, 4H), 4.89(s, 1H), 5.65(brs, 1H), 6.65-7.00(m, 2H), 7.13-7.25(m, 7H) |

TABLE 2-101-continued

| Example | Structural formula | NMR |
|---|---|---|
| 2-502 | | (MeOH-d4-400)<br>1.38(d, J6.7Hz, 3H), 2.17-2.24(m, 1H), 3.04(d, J=10.5Hz, 1H), 3.70-3.72(m, 2H), 3.73-3.81(m, 2H), 4.02-4.11(m, 2H), 7.17-7.33(m, 7H), 7.41-7.45(m, 2H) |
| 2-503 | | (MeOH-d4-400)<br>1.36(d, J6.7Hz, 3H), 2.10-2.16(m, 1H), 2.93(d, J=10.4Hz, 1H), 3.37-3.39(m, 4), 3.71-3.74(m, 4H), 7.14-7.47(m, 7H) |
| 2-504 | | (MeOH-d4-400)<br>1.39(d, J=6.67Hz, 3H), 2.21(qd, J=6.4, 12.9Hz, 1H), 3.05(d, J=10.5Hz, 1H), 3.72-3.74(m, 2H), 3.86(t, J=5.2Hz, 2H), 4.05-4.14(m, 2H), 7.17-7.30(m, 5H), 7.55(d, J=8.4Hz, 2H), 7.73(d, J=8.4Hz, 2H) |
| 2-505 | | (MeOH-d4-400)<br>1.35-1.38(m, 3H), 2.07(s, 1H), 2.84(d, J=10.4Hz, 1H), 4.57-4.73(m, 4H), 7.12-7.45(m, 8H) |

TABLE 2-102

| Example | Structural formula | NMR |
|---------|-------------------|-----|
| 2-506 | | (MeOH-d4-400)<br>1.51(s, 3H), 1.70(d, J=5.5Hz, 1H), 2.17(d, J=5.5Hz, 1H), 7.17-7.21(m, 5H), 8.01(s, 4H), 8.02(s, 1H), 8.90(s, 1H) |
| 2-507 | | (MeOH-d4-400)<br>1.35(d, J=7.0Hz, 3H), 2.15(qd, J=6.7, 13.4Hz, 1H), 2.87(d, J=10.5Hz, 1H), 7.14-7.20(m, 1H), 7.23(d, J=4.3Hz, 4H), 8.03(s, 5H), 8.90(s, 1H) |
| 2-508 | | (DMSO-d6-300)<br>1.19(d, J=6.8Hz, 3H), 1.85(dq, J=10.2, 6.8Hz, 1H), 2.66(d, J=10.2Hz, 1H), 4.18(s, 2H), 6.90(d, J=3.8Hz, 1H), 7.04-7.35(m, 10H), 7.40(d, J=3.8Hz, 1H) |
| 2-509 | | (DMSO-d6-300)<br>1.24(d, J=6.4Hz, 3H), 1.96(dq, J=10.2, 6.4Hz, 1H), 2.73(d, J=10.2Hz, 1H), 6.79(d, J=7.2Hz, 1H), 6.90-7.29(m, 8H), 7.43(d, J=3.8Hz, 1H), 7.53(d, J=3.8Hz, 1H) |

TABLE 2-102-continued

| Example | Structural formula | NMR |
|---|---|---|
| 2-510 | | (DMSO-d6-300) 1.19(d, J=5.7Hz, 6H), 1.72(dd, J=9.6, 5.3Hz, 1H), 2.02(dd, J=9.4, 5.3Hz, 1H), 2.74(t, J=9.4Hz, 1H), 2.95-3.11(m, 4H), 3.35-3.44(m, 4H), 4.74-4.82(m, 1H), 7.12-7.30(m, 5H), 8.47(s, 1H), 12.25(s, 1H) |

TABLE 2-103

| Example | Structural formula | NMR |
|---|---|---|
| 2-511 | | (DMSO-d6-300) 0.86(d, J=6.4Hz, 6H), 1.24-1.35(m, 2H), 1.50-1.62(m, 1H), 1.71(dd, J=5.5, 2.4Hz, 1H), 2.01(dd, J=9.0, 5.5Hz, 1H), 2.24-2.32(m, 2H), 2.34-2.44(m, 4H), 2.73(t, J=9.0Hz, 1H), 2.95-3.11(m, 4H), 7.10-7.31(m, 5H), 8.34(s, 1H) |
| 2-512 | | (DMSO-d6-300) 1.00(t, J=7.2Hz, 3H), 1.72(dd, J=5.1, 8.5Hz, 1H), 2.01(dd, J=8.5, 5.1Hz, 1H), 2.72(t, J=8.5Hz, 1H), 2.92-3.11(m, 6H), 3.24-3.38(m, 4H), 6.53(t, J=5.3Hz, 1H), 7.13-7.31(m, 5H), 8.42(s, 1H), 12.28(s, 1H) |
| 2-513 | | (DMSO-d6-300) 0.89(d, J=6.8Hz, 6H), 1.71(dd, J=8.9, 5.7Hz, 1H), 1.92-2.06(m, 2H), 2.20(d, J=6.8Hz, 2H), 2.75(t, 5=8.9Hz, 1H), 2.90-3.12(m, 4H), 3.42-3.61(m, 4H), 7.13-7.32(m, 5H), 12.27(s, 1H), 12.27(s, 1H) |

TABLE 2-103-continued
| Example | Structural formula | NMR |
|---|---|---|
| 2-514 | 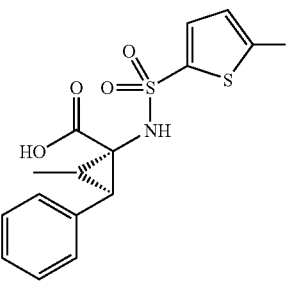 | (DMSO-d6-300) 1.27(d, J=6.8Hz, 3H), 2.01(dq, J=10.2, 6.8Hz, 1H), 2.79(d, J=10.2Hz, 1H), 7.11-7.31(m, 6H), 7.54(d, J=4.1Hz, 1H), 7.55(d, J=4.1Hz, 1H), 8.80(s, 1H), 9.13(brs, 1H), 12.31(brs, 1H) |
| 2-515 | 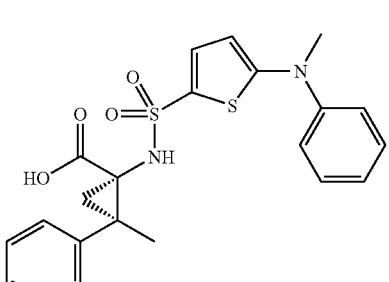 | (DMSO-d6-300) 1.31(d, J=5.3Hz, 1H), 1.37(s, 3H), 2.02(d, J=5.3Hz, 1H), 3.34(s, 3H), 6.21(d, J=4.1Hz, 1H), 7.17-7.22(m, 7H), 7.33-7.42(m, 4H), 8.71(brs, 1H), 12.04(brs, 1H) |
TABLE 2-104
| Example | Structural formula | NMR |
|---|---|---|
| 2-516 | 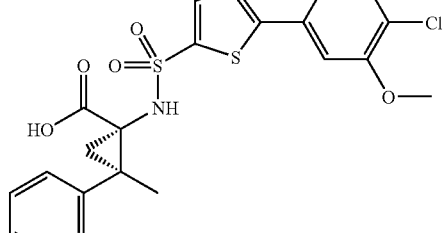 | (DMSO-d6-300) 1.39(s, 3H), 1.41(d, J=4.1Hz, 1H), 2.08(d, J=6.0Hz, 1H), 3.95(s, 3H), 7.13-7.24(m, 5H), 7.28 (dd, J=8.3, 1.9Hz, 1H), 7.41(d, J=1.9Hz, 1H), 7.50(d, J=8.3Hz, 1H), 7.55(d, J=3.8Hz, 1H), 7.63(d, J=3.8Hz, 1H), 9.17(brs, 1H), 12.13(brs, 1H) |
| 2-517 | 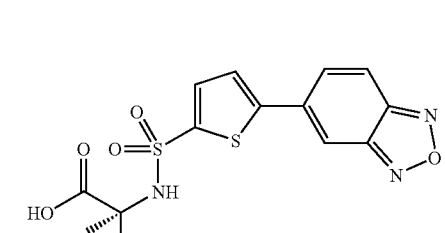 | (DMSO-d6-300) 1.28(d, J=6.8Hz, 3H), 2.02(dd, J=10.4, 6.6Hz, 1H), 2.81(d, J=10.5Hz, 1H), 7.14-7.30(m, 5H), 7.65(d, J=4.1Hz, 1H), 7.89(d, J=4.1Hz, 1H), 8.02(d, J=10.2Hz, 1H), 8.17(d, J=9.4Hz, 1H), 8.45(s, 1H), 9.18(s, 1H), 12.31(brs, 1H) |

TABLE 2-104-continued

| Example | Structural formula | NMR |
|---|---|---|
| 2-518 | | (DMSO-d6-400)<br>1.42(s, 3H), 1.48(d, J=5.6Hz, 1H), 2.13(d, J=5.6Hz, 1H), 7.13-7.30(m, 6H), 7.40(t, J=7.7Hz, 2H), 7.84(d, J=7.4Hz, 2H), 8.23(s, 1H), 8.59(s, 1H), 9.52(brs, 1H), 12.24(brs, 1H) |
| 2-519 | | (DMSO-d6-400)<br>1.41(s, 3H), 1.45(d, J=5.6Hz, 1H), 2.12(d, J=6.0Hz, 1H), 3.27(s, 3H), 4.36(s, 2H), 7.12-7.27(m, 5H), 7.73(s, 1H), 8.53(s, 1H), 9.49(brs, 1H), 12.24(brs, 1H) |
| 2-520 | | (DMSO-d6-400)<br>1.18-1.27(m, 4H), 1.83-1.95(m, 1H), 5.28(s, 2H), 7.18-7.04(m, 5H), 7.51(s, 1H), 7.73(s, 1H), 7.99(s, 1H), 8.48(s, 1H) |

TABLE 2-105

| Example | Structural formula | NMR |
|---|---|---|
| 2-521 | | (CDCl3-300)<br>1.34(d, J=6.7Hz, 3H), 1.37(t, J=7.1Hz, 3H), 2.36(dq, J=10.6, 6.7Hz, 1H), 3.08(d, J=10.6Hz, 1H), 4.34(q, J=7.1Hz, 2H), 6.11(brs, 1H), 7.01(d, J=4.0Hz, 1H), 7.12-7.31(m, 5H), 7.52(d, J=4.0Hz, 1H), 8.04(s, 1H), 8.33(s, 1H) |

TABLE 2-105-continued

| Example | Structural formula | NMR |
|---|---|---|
| 2-522 | | (DMSO-d6-300) 1.27(d, J=6.2Hz, 3H), 2.01(dq, J=10.3, 6.2Hz, 1H), 2.79(d, J=10.3Hz, 1H), 7.13-7.31(m, 7.51(d, J=4.0Hz, 1H), 7.55(d, J=4.0Hz, 1H), 8.09(s, 1H), 9.06(brs, 1H), 9.12(s, 1H) |
| 2-523 | | (CDCl3-300) 1.37(d, J=7.0Hz, 3H), 1.56(s, 3H), 1.58(s, 3H), 2.45(dq, J=10.6, 7.0Hz, 1H), 3.06(d, J=10.6Hz, 1H), 6.16(s, 1H), 6.85(d, J=4.0Hz, 1H), 7.09-7.30(m, 5H), 7.46(d, J=4.0Hz, 1H), 7.59(s, 1H), 7.78(s, 1H) |
| 2-524 | | (MeOH-d4-300) 1.36(d, J=6.0Hz, 3H), 2.12-2.22(m, 1H), 2.91(d, J=9.0Hz, 1H), 3.21(s, 3H), 7.14-7.28(m, 5H), 7.35(d, J=3.0Hz, 1H), 7.53(d, J=3.0Hz, 1H), 8.07(s, 1H), 8.91(s, 1H) |
| 2-525 | | (DMSO-d6-300) 1.26(d, J=6.8Hz, 3H), 1.98(dq, J=10.5, 6.8Hz, 1H), 2.78(d, J=10.5Hz, 1H), 4.55(s, 2H), 5.28(brs, 1H), 7.14-7.45(m, 7H), 7.48-7.65(m, 2H), 7.50(d, J=3.8Hz, 1H), 7.55(d, J=3.8Hz, 1H), 9.00(brs, 1H), 12.29(brs, 1H) |

TABLE 2-106

| Example | Structural formula | NNR |
|---|---|---|
| 2-526 | | (DMSO-d6-300)<br>1.40(s, 3H), 1.42(d, J=5.7Hz, 1H), 2.12(d, J=5.7Hz, 1H), 7.12-7.28(m, 5H), 7.67(d, J=4.1Hz, 1H), 8.01(d, J=4.1Hz, 1H), 8.06(d, J=6.8Hz, 2H), 8.78(d, J=6.8Hz, 2H), 9.39(s, 1H)<br>ClH |
| 2-527 | | (DMSO-d6-300)<br>1.35-1.46(m, 4H), 2.10(d, J=6.0Hz, 1H), 7.11-7.28(m, 5H), 7.56-7.63(m, 2H), 7.71(d, J=3.8Hz, 1H), 8.24(dt, J=8.0, 1.9Hz, 1H), 8.64(dd, J=4.9, 1.9Hz, 1H), 9.02(d, J=1.9Hz, 1H), 9.25(s, 1H)<br>ClH |
| 2-528 | | (CDCl3-300)<br>1.30(d, J=6.8Hz, 3H), 2.13-2.26(m, 1H), 2.84(t, J=5.8Hz, 2H), 3.13(d, J=10.5Hz, 1H), 3.53(t, J=5.8Hz, 2H), 3.82(s, 3H), 3.84(s, 3H), 4.36(s, 2H), 5.62(s, 1H), 6.53(s, 3H), 6.59(s, 3H), 7.15-7.28(m, 5H) |
| 2-529 | | (DMSO-d6-300)<br>1.26(d, J=6.8Hz, 3H), 1.95-2.06(m, 1H), 2.84(d, J=10.5Hz, 1H), 2.98-3.07(m, 4H), 3.34-3.46(m, 4H), 4.23(d, J=5.7Hz, 2H), 7.09-7.36(m, 11H), 8.25(s, 1H), 12.32(s, 1H) |
| 2-530 | | (DMSO-d6-300)<br>0.86(d, J=6.0Hz, 6H), 1.20-1.35(m, 5H), 1.48-1.62(m, 1H), 1.92-2.06(m, 1H), 2.22-2.31(m, 2H), 2.33-2.44(m, 4H), 2.85(d, J=10.5Hz, 1H), 2.99-3.08(m, 4H), 7.11-7.32(m, 5H), 8.14(s, 1H) |

TABLE 2-107

| Example | Structural formula | NMR |
|---|---|---|
| 2-531 | | (DMSO-d6-300) 1.26(d, J=6.8Hz, 3H), 1.93-2.05(m, 1H), 2.41-2.56(m, 6H), 2.72(t, J=7.5Hz, 2H), 2.86(d, J=10.2Hz, 1H), 2.98-3.12(m, 4H), 7.09-7.33(m, 11H), 8.16(s, 1H) |
| 2-532 | | (DMSO-d6-300) 1.26(d, J=7.2Hz, 3H), 1.94-2.06(m, 1H), 2.84(d, J=10.9Hz, 1H), 3.01-3.10(m, 4H), 3.39-3.51(m, 4H), 5.09(s, 2H), 7.15-7.42(m, 10H), 8.28(s, 1H), 12.30(s, 1H) |
| 2-533 | | (DMSO-d6-300) 1.27(d, J=6.8Hz, 3H), 1.96-2.09(m, 1H), 2.87(d, J=10.2Hz, 1H), 3.13-3.26(m, 4H), 3.73-3.81(m, 4H), 7.15-7.31(m, 7H), 8.28(d, J=7.5Hz, 2H), 8.42(s, 1H), 12.37(s, 1H) |
| 2-534 | | (DMSO-d6-300) 1.28(d, J=6.2Hz, 3H), 1.95-2.07(m, 1H), 2.86(d, J=10.6Hz, 1H), 2.98-3.73(m, 15H), 7.12-7.31(m, 5H), 8.50(s, 1H), 10.26(s, 1H), 12.39(s, 1H) |
| 2-535 | | (DMSO-d6-300) 1.25(d, J=7.0Hz, 3H), 1.95-2.08(m, 1H), 2.87(t, J=6.1Hz, 2H), 3.40(t, J=6.1Hz, 2H), 4.30(s, 2H), 7.11-7.29(m, 9H), 8.32(s, 1H), 12.32(s, 1H) |

TABLE 2-108

| Example | Structural formula | NMR |
|---------|-------------------|-----|
| 2-536 | | (DMSO-d6-300) 1.25(d, J=6.8Hz, 3H), 1.96(dq, J=6.8, 10.2Hz, 1H), 2.34-2.42(m, 4H), 2.83(d, J=10.2Hz, 1H), 3.01-3.10(m, 4H), 3.40(s, 2H), 3.73(s, 3H), 6.87(d, J=9.0Hz, 2H), 7.14-7.29(m, 5H), 7.19(d, J=9.0Hz, 2H), 8.13(brs, 1H) |
| 2-537 | | (DMSO-d6-300) 1.25(d, J=6.8Hz, 3H), 1.97(dq, J=6.8, 10.5Hz, 1H), 2.41-2.54(m, 4H), 2.85(d, J=10.5Hz, 1H), 3.02-3.15(m, 6H), 6.22-6.32(m, 1H), 6.54(d, J=16.2Hz, 1H), 7.14-7.36(m, 8H), 7.39-7.46(m, 2H), 8.16(brs, 1H) |
| 2-538 | | (CD2Cl2-400) 1.18-1.20(m, 3H), 1.96-2.00(m, 1H), 2.92(d, J=10.4Hz, 1H), 4.53(s, 4H), 7.05-7.24(m, 8H) |
| 2-539 | | (MeOH-d4-400) 1.74-1.81(m, 1H), 3.06(d, J=12.3Hz, 1H), 3.37(s, 3H), 3.77-3.91(m, 2H), 7.15-7.30(m, 5H), 7.63-7.73(m, 3H) |

TABLE 2-108-continued

| Example | Structural formula | NMR |
|---------|-------------------|-----|
| 2-540 | | (DMSO-d6-300) 1.26(d, J=6.8Hz, 3H), 1.98(dq, J=10.2, 6.8Hz, 1H), 2.31-2.47(m, 2H), 2.78(d, J=10.2Hz, 1H), 3.46-3.72(m, 6H), 7.13-7.31(m, 6H), 7.32-7.49(m, 1H), 7.50-7.71(m, 2H), 7.52(d, J=3.8Hz, 1H), 7.56(d, J=3.8Hz, 1H), 9.03(s, 1H), 12.30(brs, 1H) |

TABLE 2-109

| Example | Structural formula | NMR |
|---------|-------------------|-----|
| 2-541 | | (DMSO-d6-300) 1.21(d, J=6.4Hz, 3H), 1.82(dq, J=10.5, 6.4Hz, 1H), 2.64(d, J=10.5Hz, 1H), 2.91(t, J=7.5Hz, 2H), 3.13(t, J=7.5Hz, 2H), 6.84(d, J=3.4Hz, 1H), 7.07-7.30(m, 10H), 7.36(d, J=3.4Hz, 1H) |
| 2-542 | | (MeOH-d4-400) 1.38(d, J=6.5Hz, 3H), 2.19-2.23(m, 1H), 2.95(d, J=10.2Hz, 1H), 6.54(t, J=2.1Hz, 1H), 7.16-7.30(m, 6H), 7.51(d, J=4.2Hz, 1H), 7.70(d, J=2.1Hz, 1H), 8.23(d, J=2.1Hz, 1H) |
| 2-543 | | (DMSO-d6-300) 1.26(d, J=6.6Hz, 3H), 1.91-2.06(m, 1H), 2.78(d, J=10.6Hz, 1H), 7.14-7.30(m, 5H), 7.35(d, J=4.0Hz, 1H), 7.48(d, J=4.0Hz, 1H), 7.87(s, 1H), 8.79(s, 1H), 9.03(brs, 1H), 12.27(brs, 1H) |

TABLE 2-109-continued

| Example | Structural formula | NMR |
|---|---|---|
| 2-544 | | (DMSO-d6-300)<br>1.37-1.42(m, 4H), 2.09(d, J=5.7Hz, 1H), 7.11-7.27(m, 5H), 7.49(d, J=8.3Hz, 1H), 7.52-7.59(m, 3H), 7.88(d, J=1.5Hz, 1H), 9.19(brs, 1H), 12.12(brs, 1H) |
| 2-545 | | (MeOH-d4-300)<br>1.37(d, J=6.6Hz, 3H), 2.21(dq, J=10.6, 6.6Hz, 1H), 2.95(d, J=10.6Hz, 1H), 5.40(d, J=2.2Hz, 1H), 5.84(d, J=2.2Hz, 1H), 7.11-7.30(m, 6H), 7.50(d, J=4.0Hz, 1H), 7.92(s, 1H), 8.44(s, 1H) |

TABLE 2-110

| Example | Structural formula | NMR |
|---|---|---|
| 2-546 | | (DMSO-d6-300)<br>1.27(d, J=6.8Hz, 3H), 2.01(dq, J=10.2, 6.8Hz, 1H), 2.46(s, 3H), 2.79(d, J=10.2Hz, 1H), 7.14-7.31(m, 5H), 7.51(d, J=4.1Hz, 1H), 7.54(d, J=4.1Hz, 1H), 8.21(s, 1H), 9.10(brs, 1H), 9.27(s, 1H), 12.30(brs, 1H) |
| 2-547 | | (DMSO-d6-300)<br>1.26(d, J=6.4Hz, 3H), 1.37(d, J=6.4Hz, 3H), 1.99(dq, J=10.5, 6.4Hz, 1H), 2.78(d, J=10.5Hz, 1H), 4.74(dq, J=4.9, 6.4Hz, 1H), 5.14(d, J=4.9Hz, 1H), 7.14-7.28(m, 5H), 7.30(d, J=4.1Hz, 1H), 7.46(d, J=4.1Hz, 1H), 7.68(s, 1H), 8.38(s, 1H), 8.99(brs, 1H), 12.27(brs, 1H) |

TABLE 2-110-continued
| Example | Structural formula | NMR |
|---|---|---|
| 2-548 | 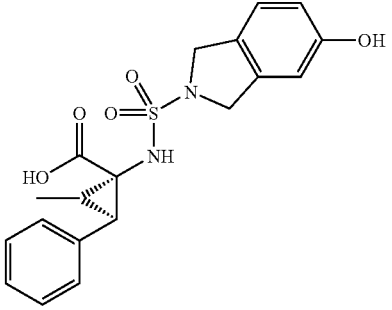 | (MeOH-d4-400) 1.29(s, 3H), 2.15(m, 1H), 2.93-2.96(d, J=10.8Hz, 1H), 4.55-4.63(m, 4H), 6.67-7.28(m, 8H) |
| 2-549 | 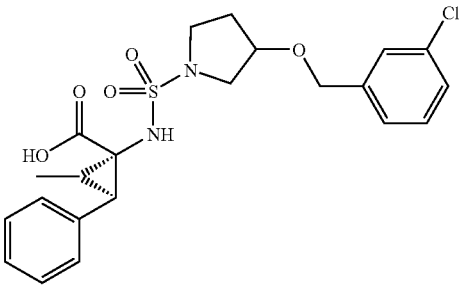 | (MeOH-d4-400) 1.29(t, J=6.4Hz, 3H), 2.03-2.13(m, 3H), 2.99(t, J=9.7Hz, 1H), 3.40-3.50(m, 4H), 4.17-4.24(m, 1H), 4.41-4.50(m, 2H), 7.16-7.33(m, 9H) |
| 2-550 | 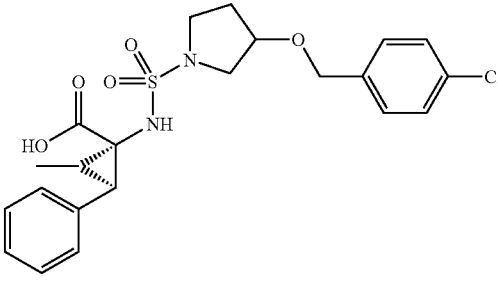 | (MeOH-d4-400) 1.30(t, J=7.04Hz, 3H), 2.04-2.13(m, 3H), 2.99(dd, J=10.5, 13.1Hz, 1H), 3.41-3.48(m, 4H), 4.19-4.22(m, 1H), 4.41-4.51(m, 2H), 7.15-7.37(m, 9H) |
TABLE 2-111
| Example | Structural formula | NMR |
|---|---|---|
| 2-551 | 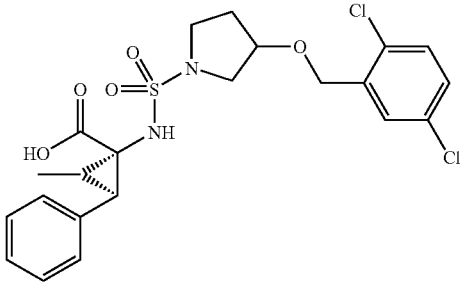 | (MeOH-d4-400) 1.29(t, J=6.44Hz, 3H), 2.06-2.16(m, 3H), 3.00(dd, J=10.5, 12.9Hz, 1H), 3.43-3.56(m, 4H), 4.26-4.30(m, 1H), 4.44-4.58(m, 2H), 7.13-7.52(m, 8H) |

TABLE 2-111-continued
| Example | Structural formula | NMR |
|---|---|---|
| 2-552 | 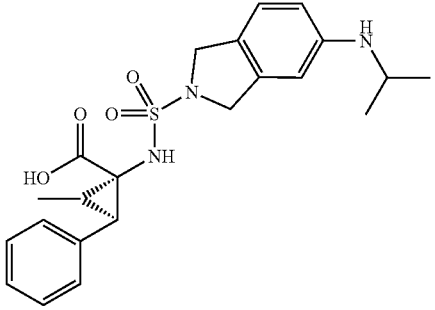 | (MeOH-d4-400) 1.19-1.38(m, 9H), 2.18-2.22(m, 1H), 3.00(d, J=10.5Hz, 1H), 3.70-3.76(m, 1H), 4.72-4.85(m, 4H), 7.16-7.44(m, 8H) |
| 2-553 | 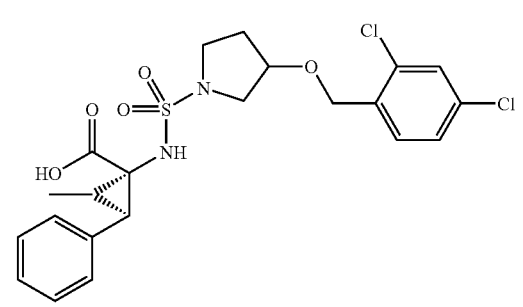 | (MeOH-d4-400) 1.29(t, J=6.3Hz, 3H), 2.06-2.17(m, 3H), 3.00(dd, J=4.9, 10.4Hz, 1H), 3.39-3.54(m, 4H), 4.24-4.28(m, 1H), 4.45-4.58(m, 2H), 7.16-7.47(m, 8H) |
| 2-554 | 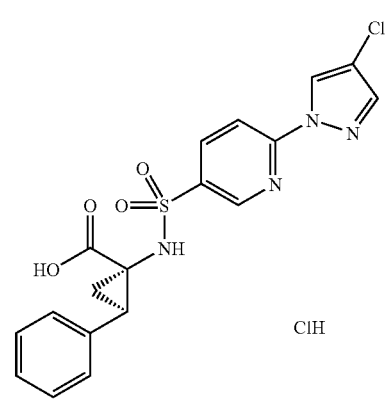 | (DMSO-d6-400) 1.65(dd, J=10.0, 5.8Hz, 1H), 2.02(dd, J=8.6, 5.8Hz, 1H), 2.79(t, J=9.3Hz, 1H), 7.14-7.26(m, 5H), 8.03-8.07(m, 2H), 8.32(dd, J=8.8, 2.3Hz, 1H), 8.77(d, J=2.3Hz, 1H), 8.88(d, J=1.4Hz, 1H), 9.23(s, 1H), 12.13(brs, 1H) |
| 2-555 | 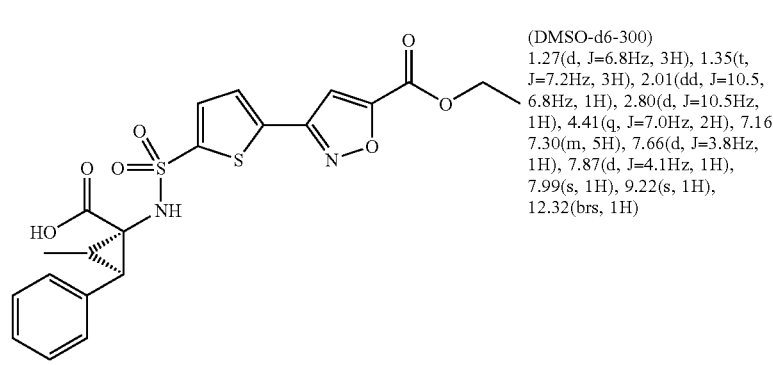 | (DMSO-d6-300) 1.27(d, J=6.8Hz, 3H), 1.35(t, J=7.2Hz, 3H), 2.01(dd, J=10.5, 6.8Hz, 1H), 2.80(d, J=10.5Hz, 1H), 4.41(q, J=7.0Hz, 2H), 7.16-7.30(m, 5H), 7.66(d, J=3.8Hz, 1H), 7.87(d, J=4.1Hz, 1H), 7.99(s, 1H), 9.22(s, 1H), 12.32(brs, 1H) |

TABLE 2-112
| Example | Structural formula | NMR |
|---|---|---|
| 2-556 | 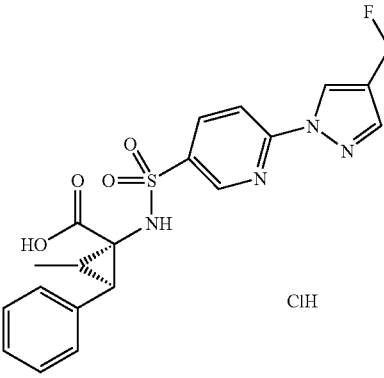 ClH | (DMSO-d6-300) 1.27(d, J=6.4Hz, 3H), 2.05(dq, J=10.5, 6.4Hz, 1H), 2.83(d, J=10.5Hz, 1H), 7.13-7.32(m, 5H), 8.17(d, J=8.7Hz, 1H), 8.39(s, 1H), 8.39(dd, J=8.7, 1.9Hz, 1H), 8.85(d, J=1.9Hz, 1H), 9.17(s, 1H), 9.30(s, 1H), 12.24(s, 1H) |
| 2-557 | 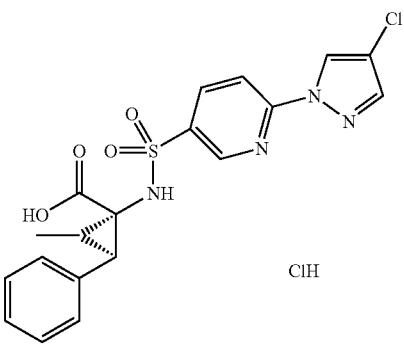 ClH | (DMSO-d6-400) 1.25(d, J=7.0Hz, 3H), 2.02(dq, J=10.2, 7.0Hz, 1H), 2.80(d, J=10.2Hz, 1H), 7.13-7.28(m, 5H), 8.05(s, 1H), 8.07(d, J=8.8Hz, 1H), 8.32(dd, J=8.8, 2.3Hz, 1H), 8.78(d, J=2.3Hz, 1H), 8.89(s, 1H), 9.11(s, 1H), 12.24(brs, 1H) |
| 2-558 | 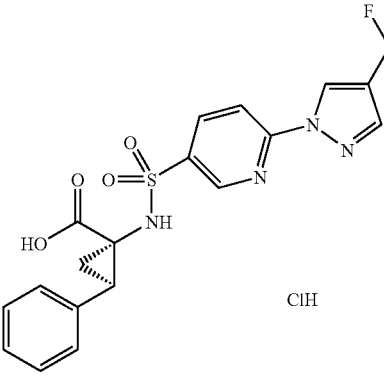 ClH | (DMSO-d6-400) 1.65(dd, J=9.3, 5.8Hz, 1H), 2.02(dd, J=9.3, 5.8Hz, 1H), 2.79(t, J=9.3Hz, 1H), 7.13-7.27(m, 5H), 8.13(d, J=8.8Hz, 1H), 8.37(dd, J=8.8, 2.3Hz, 1H), 8.37(s, 1H), 8.81(d, J=2.3Hz, 1H), 9.27(s, 2H), 12.11(brs, 1H) |
| 2-559 | 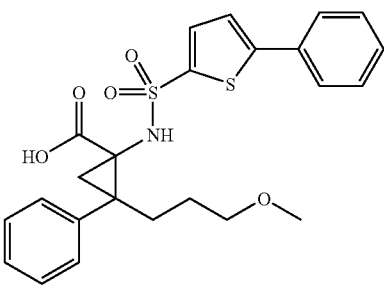 | (MeOH-d4-300) 1.32-1.46(m, 2H), 1.68-1.85(m, 1H), 1.73(d, J=6.0Hz, 1H), 1.91-2.06(m, 1H), 2.18(d, J=6.0Hz, 1H), 3.19(s, 3H), 3.21-3.34(m, 2H), 7.09-7.26(m, 5H), 7.37(d, J=3.0Hz, 1H), 7.43(d, J=9.0Hz, 2H), 7.55(d, J=3.0Hz, 1H), 7.65(d, J=9.0Hz, 2H) |

TABLE 2-112-continued

| Example | Structural formula | NMR |
|---|---|---|
| 2-560 | | (MeOH-d4-300)<br>1.37-1.42(m, 2H), 1.73(d, J=5.9Hz, 1H), 1.74-1.80(m, 1H), 1.96-1.98(m, 1H), 2.17(d, J=5.9Hz, 1H), 3.20(s, 3H), 7.14-7.19(m, 6H), 7.45(d, J=4.0Hz, 1H), 7.66(s, 1H), 8.38(s, 1H) |

TABLE 2-113

| Example | Structural formula | NMR |
|---|---|---|
| 2-561 | | (MeOH-d4-300)<br>1.36(d, J=7.0Hz, 3H), 2.17-2.20(m, 1H), 2.92(d, J=10.3Hz, 1H), 4.55(s, 2H), 7.12(d, J=4.0Hz, 1H), 7.23-7.24(m, 5H), 7.49(d, J=4.4Hz, 1H), 7.66(s, 1H), 8.15(s, 1H) |
| 2-562 | | (DMSO-d6-300)<br>1.37(d, J=7.5Hz, 1H), 1.38(s, 3H), 2.08(d, J=5.3Hz, 1H), 6.69-6.77(m, 1H), 7.16-7.23(m, 6H), 7.50-7.53(m, 2H), 9.27(brs, 1H), 12.11(brs, 1H) |
| 2-563 | | (DMSO-d6-300)<br>1.34(d, J=5.7Hz, 1H), 1.38(s, 3H), 2.09(d, J=5.7Hz, 1H), 6.10-6.14(m, 1H), 7.13-7.31(m, 6H), 7.39(d, J=4.1Hz, 1H), 7.54(d, J=3.8Hz, 1H), 9.30(brs, 1H), 12.12(brs, 1H) |

TABLE 2-113-continued

| Example | Structural formula | NMR |
|---|---|---|
| 2-564 | | (DMSO-d6-300) 1.37-1.43(m, 1H), 1.40(s, 3H), 2.10(d, J=5.3Hz, 1H), 4.59(d, J=5.3Hz, 2H), 5.53(t, J=5.3Hz, 1H), 7.13-7.27(m, 5H), 7.49(d, J=8.3Hz, 1H), 7.53-7.55(m, 2H), 7.65(dd, J=8.3, 2.3Hz, 7.81(d, J=2.3Hz, 1H), 9.19(s, 1H), 12.09(s, 1H) |
| 2-565 | | (DMSO-d6-300) 1.26(d, J=6.8Hz, 3H), 1.99(dq, J=10.2, 6.8Hz, 1H), 2.78(d, J=10.2Hz, 1H), 4.59(d, J=5.3Hz, 2H), 5.52(t, J=5.3Hz, 1H), 7.17-7.30(m, 5H), 7.49(d, J=8.3Hz, 1H), 7.53(d, J=3.8Hz, 1H), 7.56(d, J=3.8Hz, 1H), 7.64(dd, J=8.3, 2.3Hz, 1H), 7.81(d, J=2.3Hz, 1H), 9.04(s, 1H), 12.30(s, 1H) |

TABLE 2-114

| Example | Structural formula | NMR |
|---|---|---|
| 2-566 | | (CDCl3-300) 1.55(s, 4H), 1.98(d, J=5.7Hz, 1H), 2.24(d, J=5.7Hz, 1H), 5.87(s, 1H), 7.07-7.13(m, 2H), 7.16-7.35(m, 5H), 7.39-7.45(m, 1H), 7.49-7.58(m, 2H) |
| 2-567 | | (CDCl3-300) 1.56(s, 3H), 1.98(d, J=6.0Hz, 1H), 2.26(d, J=6.0Hz, 1H), 5.90(s, 1H), 7.07-7.14(m, 2H), 7.19-7.28(m, 3H), 7.30-7.36(m, 1H), 7.58-7.63(m, 1H), 7.65-7.74(m, 4H) |

TABLE 2-114-continued

| Example | Structural formula | NMR |
|---|---|---|
| 2-568 | | (DMSO-d6-300)<br>1.28(d, J=5.3Hz, 1H), 1.35(s, 3H), 2.03(d, J=5.3Hz, 1H), 4.04(s, 2H), 7.08-7.26(m, 5H), 7.50(dd, J=8.1, 2.1Hz, 1H), 7.73(d, J=2.1Hz, 1H), 7.80(dd, J=8.1, 2.1Hz, 1H), 7.98(d, J=2.1Hz, 1H), 8.03(d, J=8.1Hz, 1H), 8.09(d, J=8.1Hz, 1H), 8.87(s, 1H) |
| 2-569 | | (DMSO-d6-300)<br>1.22(d, J=6.4Hz, 3H), 1.88(d, J=38.4Hz, 1H), 2.66(d, J=10.9Hz, 1H), 4.04(s, 2H), 7.13-7.28(m, 5H), 7.50(dd, J=8.3, 1.9Hz, 1H), 7.72(d, J=1.9Hz, 1H), 7.84(dd, J=8.3, 1.9Hz, 1H), 8.00(d, J=1.9Hz, 1H), 8.02(d, J=8.3Hz, 1H), 8.09(d, J=8.3Hz, 1H), 8.72(s, 1H) |
| 2-570 | | (DMSO-d6-300)<br>1.27(d, J=6.4Hz, 3H), 1.99(dd, J=10.5, 6.0Hz, 1H), 2.79(d, J=9.8Hz, 1H), 7.02(t, J=7.0Hz, 1H), 7.16-7.31(m, 5H), 7.39(t, J=7.9Hz, 1H), 7.56(q, J=3.9Hz, 2H), 7.64(d, J=9.4Hz, 1H), 8.50(s, 1H), 8.58(d, J=7.2Hz, 1H), 9.02(s, 1H), 12.24(brs, 1H) |

TABLE 2-115

| Example | Structural formula | NMR |
|---|---|---|
| 2-571 | | (DMSO-d6-300)<br>1.27(d, J=6.8Hz, 3H), 2.00(dd, J=9.8, 6.8Hz, 1H), 2.79(d, J=10.2Hz, 1H), 3.59(brs, 2H), 7.11(t, J=5.5Hz, 1H), 7.16-7.30(m, 4H), 7.59(dd, J=9.4, 3.8Hz, 2H), 8.42(s, 1H), 8.53-8.60(m, 1H), 8.93-9.03(m, 2H), 12.25(brs, 1H) |

TABLE 2-115-continued

| Example | Structural formula | NMR |
|---|---|---|
| 2-572 | | (DMSO-d6-300) 1.39-1.42(m, 1H), 1.40(s, 3H), 2.10(d, J=5.7Hz, 1H), 7.11-7.28(m, 5H), 7.59(d, J=3.8Hz, 1H), 7.70(d, J=3.8Hz, 1H), 7.81(d, J=8.3Hz, 2H), 7.95(d, J=8.3Hz, 2H), 9.24(brs, 1H), 12.12(brs, 1H) |
| 2-573 | | (DMSO-d6-300) 1.39-1.42(m, 1H), 1.40(s, 3H), 2.10(d, J=5.3Hz, 1H), 2.60(s, 3H), 7.10-7.28(m, 5H), 7.58(d, J=4.1Hz, 1H), 7.70(d, J=4.1Hz, 1H), 7.87(d, J=8.3Hz, 2H), 8.02(d, J=8.3Hz, 2H), 9.23(brs, 1H), 12.11(brs, 1H) |
| 2-574 | | (DMSO-d6-300) 1.38-1.42(m, 1H), 1.39(s, 3H), 2.08(d, J=4.1Hz, 1H), 4.53(s, 2H), 7.10-7.27(m, 5H), 7.39(d, J=8.3Hz, 2H), 7.50(d, J=3.8Hz, 1H), 7.53(d, J=3.8Hz, 1H), 7.67(d, J=8.3Hz, 2H), 9.14(brs, 1H), 12.09(brs, 1H) |
| 2-575 | | (DMSO-d6-300) 1.37-1.44(m, 1H), 1.40(s, 3H), 2.09(d, J=5.7Hz, 1H), 3.73(dt, J=4.9, 5.5Hz, 2H), 4.06(t, J=4.9Hz, 2H), 4.86(t, J=5.5Hz, 1H), 6.96-7.02(m, 1H), 7.13-7.29(m, 7H), 7.33-7.40(m, 1H), 7.53(d, J=3.8Hz, 1H), 7.56(d, J=3.8Hz, 1H), 9.16(s, 1H), 12.10(s, 1H) |

TABLE 2-116
| Example | Structural formula | NMR |
|---|---|---|
| 2-576 | 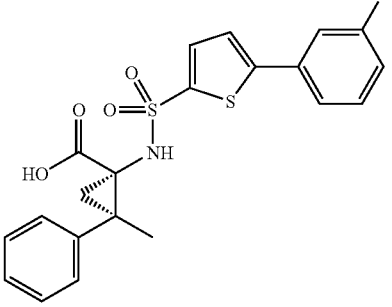 | (DMSO-d6-300) 1.37-1.43(m, 1H), 1.39(s, 3H), 1.88(tt, J=6.2, 6.4Hz, 2H), 2.09(d, J=5.7Hz, 1H), 3.53-3.60(m, 2H), 4.10(t, J=6.4Hz, 2H), 4.54(brs, 1H), 6.95-7.01(m, 1H), 7.11-7.28(m, 7H), 7.32-7.39(m, 1H), 7.53(d, J=3.8Hz, 1H), 7.56(d, J=3.8Hz, 1H), 9.15(s, 1H), 12.10(s, 1H) |
| 2-577 | 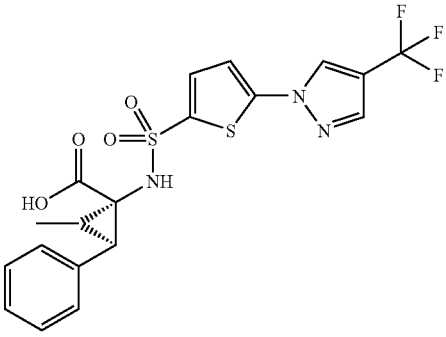 | (DMSO-d6-300) 1.27(d, J=6.8Hz, 3H), 2.01(dq, J=10.2, 6.8Hz, 1H), 2.80(d, J=10.2Hz, 1H), 7.14-7.32(m, 5H), 7.50(d, J=4.1Hz, 1H), 7.54(d, J=4.1Hz, 1H), 8.27(s, 1H), 9.11(brs, 1H), 9.29(s, 1H), 12.26(brs, 1H) |
| 2-578 | 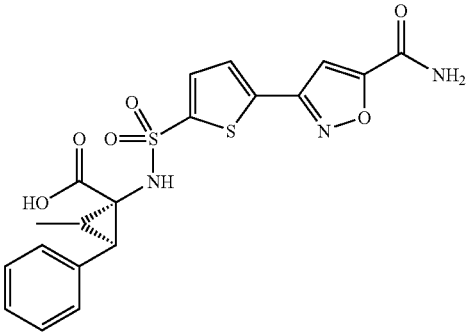 | (MeOH-d4-300) 1.39(d, J=6.8Hz, 3H), 2.23(dq, J=10.5, 6.8Hz, 1H), 2.97(d, J=10.5Hz, 1H), 7.18-7.30(m, 5H), 7.40(s, 1H), 7.62-7.68(m, 2H) |
| 2-579 | 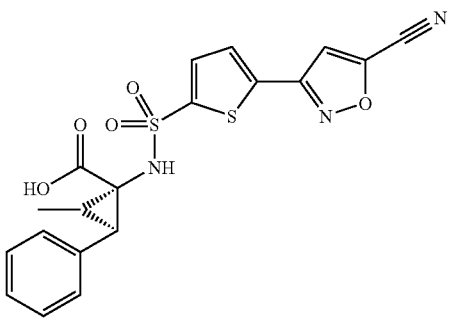 | (CDCl3-300) 1.33(d, J=6.8Hz, 3H), 2.22-2.33(m, 1H), 3.03(d, J=10.9Hz, 1H), 7.13-7.30(m, 6H), 7.44(d, J=3.8Hz, 1H), 7.65(d, J=3.8Hz, 1H) |

TABLE 2-116-continued
| Example | Structural formula | NMR |
|---|---|---|
| 2-580 |  | (CDCl3-300) 1.33(d, J=6.0Hz, 3H), 2.27-2.39(m, 1H), 3.06(d, J=12.0Hz, 1H), 5.98(brs, 1H), 7.09(d, J=6.0Hz, 1H), 7.11-7.29(m, 5H), 7.55(d, J=6.0Hz, 1H), 7.96(s, 1H), 8.30(s, 1H) |
TABLE 2-117
| Example | Structural formula | NMR |
|---|---|---|
| 2-581 | | (DMSO-d6-300) 1.35-1.43(m, 4H), 2.09(d, J=5.3Hz, 1H), 7.11(s, 5H), 7.11-7.29(m, 5H), 7.46-7.62(m, 2H), 7.55(d, J=3.8Hz, 1H), 7.59(d, J=3.8Hz, 1H), 7.84-7.95(m, 1H), 9.20(s, 1H), 12.10(brs, 1H) |
| 2-582 | | (DMSO-d6-300) 1.35-1.42(m, 1H), 1.39(s, 3H), 2.06(d, J=6.0Hz, 1H), 6.83(d, J=8.7Hz, 2H), 7.10-7.27(m, 5H), 7.32(d, J=3.8Hz, 1H), 7.47(d, J=3.8Hz, 1H), 7.53(d, J=8.7Hz, 2H), 9.07(brs, 1H), 9.84(brs, 1H), 12.08(brs, 1H) |
| 2-583 | | (DMSO-d6-300) 1.37-1.46(m, 1H), 1.41(s, 3H), 2.09(d, J=5.7Hz, 1H), 5.16(brs, 2H), 6.63(dd, J=8.3, 7.2Hz, 1H), 6.81(d, J=8.3Hz, 1H), 7.06-7.27(m, 8H), 7.51(d, J=4.1Hz, 1H), 9.08(brs, 1H) |

TABLE 2-117-continued

| Example | Structural formula | NMR |
|---|---|---|
| 2-584 | | (DMSO-d6-300) 1.27(d, J=6.8Hz, 3H), 2.01(dq, J=10.5, 6.8Hz, 1H), 2.80(d, J=10.5Hz, 1H), 7.15-7.31(m, 7H), 7.53(d, J=7.2Hz, 1H), 7.61-7.68(m, 1H), 7.64(d, J=3.8Hz, 1H), 7.77(d, J=3.8Hz, 1H), 9.12(brs, 1H), 12.30(brs, 1H), 13.20(brs, 1H) |
| 2-585 | | (DMSO-d6-300) 0.99(d, J=5.3Hz, 1H), 1.16(s, 3H), 1.99(d, J=5.7Hz, 1H), 7.13-7.21(m, 5H), 7.42(t, J=7.3Hz, 1H), 7.54(t, J=7.5Hz, 2H), 7.80-7.82(m, 3H), 8.18(d, J=8.7Hz, 1H), 8.47(d, J=1.9Hz, 1H), 8.51(s, 1H), 9.44(brs, 1H), 12.07(brs, 1H) |

TABLE 2-118

| Example | Structural formula | NMR |
|---|---|---|
| 2-586 | | (DMSO-d6-300) 1.41(s, 3H), 1.42(d, J=7.5Hz, 1H), 2.12(d, J=5.7Hz, 1H), 4.15(s, 3H), 7.13-7.27(m, 5H), 7.54(d, J=4.1Hz, 1H), 7.63(d, J=3.8Hz, 1H), 8.11(s, 1H), 9.31(brs, 1H), 12.09(brs, 1H) |
| 2-587 | | (DMSO-d6-300) 1.38(d, J=4.1Hz, 1H), 1.39(s, 3H), 2.09(d, J=5.7Hz, 1H), 4.10(s, 3H), 7.12-7.26(m, 5H), 7.41(d, J=4.1Hz, 1H), 7.54(d, J=3.8Hz, 1H), 8.59(s, 1H), 9.16(brs, 1H) |

TABLE 2-118-continued

| Example | Structural formula | NMR |
|---|---|---|
| 2-588 | | (CDCl3-300) 1.30-1.50(m, 2H), 1.69(d, J=6.0Hz, 1H), 1.82(t, J=7.5Hz, 2H), 2.08(d, J=6.0Hz, 1H), 3.20-3.34(m, 2H), 3.24(s, 3H), 6.73(brs, 1H), 6.99-7.10(m, 3H), 7.14-7.22(m, 3H), 7.46(d, J=6.0Hz, 1H), 7.60(d, J=6.0Hz, 1H) |
| 2-589 | | (CDCl3-300) 1.55(s, 3H), 1.98(d, J=6.0Hz, 1H), 2.24(d, J=6.0Hz, 1H), 5.84(s, 1H), 7.00-7.13(m, 4H), 7.17-7.35(m, 5H), 7.53(d, J=4.1Hz, 1H) |
| 2-590 | | (CDCl3-300) 1.33(d, J=7.2Hz, 3H), 2.26-2.40(m, 1H), 3.09(d, J=10.9Hz, 1H), 5.82(s, 1H), 7.14-7.31(m, 6H), 7.62(d, J=4.1Hz, 1H), 7.67-7.70(m, 4H) |

TABLE 2-119

| Example | Structural formula | NMR |
|---|---|---|
| 2-591 | | (CDCl3-300) 1.37(d, J=6.4Hz, 3H), 2.32-2.45(m, 1H), 3.11(d, J=10.5Hz, 1H), 6.19(s, 1H), 7.22(d, J=59.5Hz, 4H), 7.39-7.54(m, 4H), 7.60(d, J=4.1Hz, 1H), 7.86(d, J=8.3Hz, 1H), 8.00(d, J=8.3Hz, 1H) |

TABLE 2-119-continued

| Example | Structural formula | NMR |
|---------|-------------------|-----|
| 2-592 | | (CDCl3-300) 1.38(s, 3H), 1.99(d, J=6.4Hz, 2H), 2.03(d, J=6.4Hz, 2H), 3.88(s, 3H), 4.78(d, J=13.6Hz, 1H), 4.91(d, J=13.6Hz, 1H), 6.63-6.70(m, 3H), 6.92-6.98(m, 2H), 7.02-7.13(m, 3H), 7.40(d, J=3.8Hz, 1H), 7.54(dd, J=8.3, 2.3Hz, 1H), 7.73(d, J=2.3Hz, 1H) |
| 2-593 | | (CDCl3-300) 1.50(s, 3H), 1.80(d, J=6.0Hz, 1H), 2.16(d, J=6.0Hz, 1H), 5.95(s, 1H), 7.01-7.08(m, 2H), 7.18-7.24(m, 3H), 7.35(d, J=4.1Hz, 1H), 7.43-7.51(m, 2H), 7.58(d, J=4.1Hz, 1H), 7.68(dd, J=8.5, 6.6Hz, 1H) |
| 2-594 | | (CDCl3-300) 1.53(s, 3H), 1.97(d, J=6.0Hz, 1H), 2.19(d, J=6.0Hz, 1H), 4.77(s, 2H), 5.79(s, 1H), 7.02-7.09(m, 2H), 7.15-7.30(m, 5H), 7.37(dd, J=8.1, 1.7Hz, 1H), 7.48(d, J=7.5Hz, 1H), 7.51(d, J=4.1Hz, 1H) |
| 2-595 | | (DMSO-d6-300) 1.36-1.43(m, 4H), 2.08(d, J=5.7Hz, 1H), 3.90(s, 3H), 7.10-7.27(m, 6H), 7.48-7.52(m, 2H), 7.65(dd, J=8.7, 2.3Hz, 1H), 7.82(d, J=2.3Hz, 1H), 9.15(brs, 1H), 12.09(brs, 1H) |

TABLE 2-120
| Example | Structural formula | NMR |
|---|---|---|
| 2-596 | 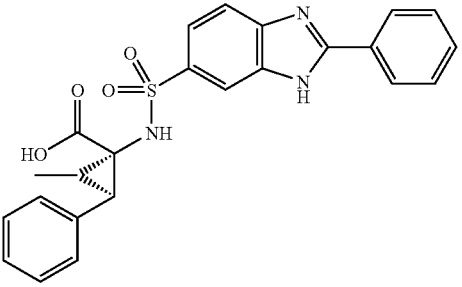 | (DMSO-d6-400)<br>1.21(d, J=6.7Hz, 3H), 1.84(dq, J=10.2, 6.7Hz, 3H), 2.62(d, J=10.2Hz, 1H), 7.12-7.27(m, 5H), 7.48-7.81(m, 5H), 8.01(brs, 1H), 8.18(d, J=6.5Hz, 2H), 8.64(s, 1H), 12.10(s, 1H), 13.30(s, 1H) |
| 2-597 | 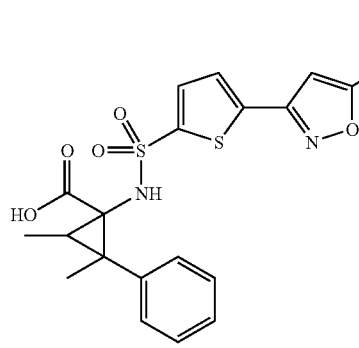 | (DMSO-d6-300)<br>1.30(s, 3H), 1.45(d, J=6.8Hz, 3H), 2.32(q, J=6.8Hz, 1H), 7.18-7.32(m, 5H), 7.34(d, J=3.8Hz, 1H), 7.78(d, J=3.8Hz, 1H), 8.15(s, 1H), 8.49(brs, 1H), 12.50(brs, 1H) |
| 2-598 | 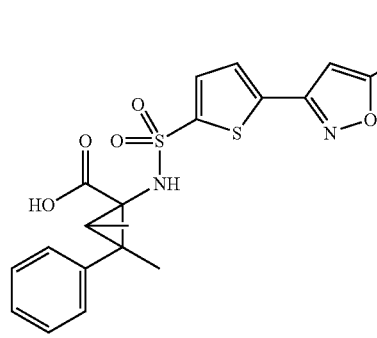 | (DMSO-d6-300)<br>1.15(d, J=6.8Hz, 3H), 1.30(s, 3H), 2.39(q, J=6.8Hz, 1H), 7.13-7.27(m, 5H), 7.68(d, J=4.1Hz, 1H), 7.83(d, J=4.1Hz, 1H), 8.16(s, 1H), 8.96(s, 1H), 12.08(brs, 1H) |
| 2-599 | 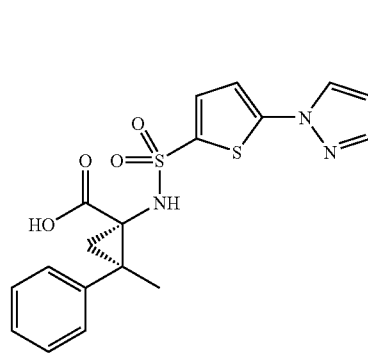 | (DMSO-d6-300)<br>1.40(s, 3H), 1.43(d, J=5.5Hz, 1H), 2.10(d, J=5.5Hz, 1H), 7.11-7.28(m, 5H), 7.51(d, J=4.0Hz, 1H), 7.53(d, J=4.0Hz, 1H), 8.26(s, 1H), 9.24(brs, 1H), 9.30(s, 1H), 12.09(brs, 1H) |

TABLE 2-120-continued

| Example | Structural formula | NMR |
|---|---|---|
| 2-600 | | (DMSO-d6-300)<br>1.36-1.44(m, 1H), 1.38(s, 3H),<br>2.01-2.09(m, 1H), 7.08-7.26(m,<br>8H), 7.38(d, J=3.8Hz, 1H),<br>7.50(d, J=3.8Hz, 1H) |

TABLE 2-121

| Example | Structural formula | NMR |
|---|---|---|
| 2-601 | | (DMSO-d6-300)<br>1.37-1.43 (m, 1H), 1.39 (s, 3H),<br>2.08 (d, J = 5.3Hz, 1H),<br>7.03-7.08 (m, 1H), 7.13-7.27 (m, 6H),<br>7.44-7.48 (m, 1H), 7.5l (d,<br>J = 3.8Hz, 1H) |
| 2-602 | | (CDCl3-300)<br>1.51 (s, 3H), 1.85 (d, J = 6.0Hz,<br>1H), 2.21 (d, J = 6.0Hz, 1H),<br>3.17 (s, 3H), 6.24 (brs, 1H),<br>6.99-7.11 (m, 3H), 7.15-7.23 (m, 3H),<br>7.50 (d, J = 6.0Hz, 1H), 8.00 (s,<br>1H), 8.42 (s, 1H) |
| 2-603 | | (CDCl3-300)<br>1.58 (s, 3H), 2.04 (d, J = 6.0Hz,<br>1H), 2.25 (d, J = 6.0Hz, 1H),<br>4.62 (s, 2H), 6.04 (brs, 1H),<br>6.84 (d, J = 6.0Hz, 1H),<br>7.09-7.28 (m, 5H), 7.43 (d, J = 6.0Hz,<br>1H), 7.63 (s, 1H), 7.77 (s, 1H) |

TABLE 2-121-continued

| Example | Structural formula | NMR |
|---|---|---|
| 2-604 | (structure) | (DMSO-d6-300)<br>1.27 (d, J = 6.8Hz, 3H), 2.02 (dq, J = 10.5, 6.8Hz, 1H), 2.79 (d, J = 10.5Hz, 1H), 7.14-7.31 (m, 7H), 7.54-7.71 (m, 1H), 7.65 (d, J = 3.8Hz, 1H), 7.80 (d, J = 3.8Hz, 1H) |
| 2-605 | (structure) | (MeOH-d4-300)<br>2.08 (dd, J = 9.4, 5.7Hz, 1H), 2.30 (dd, J = 8.3, 5.7Hz, 1H), 2.75 (dd, J = 9.4, 8.3Hz, 1H), 7.18-7.30 (m, 6H), 7.41 (d, J = 4.1Hz, 1H), 7.72 (s, 1H), 8.45 (s, 1H) |

TABLE 2-122

| Example | Structural formula | NMR |
|---|---|---|
| 2-606 | (structure) | (DMSO-d6-300)<br>1.40 (s, 3H), 1.41 (d, J = 5.7Hz, 1H), 2.10 (d, J = 5.7Hz, 1H), 3.92 (td, J = 13.9, 6.2Hz, 2H), 5.64 (t, J = 6.2Hz, 1H), 7.11-7.27 (m, 5H), 7.52-7.65 (m, 4H), 7.78-7.88 (m, 2H), 9.20 (brs, 1H), 12.10 (brs, 1H) |
| 2-607 | (structure) | (DMSO-d6-300)<br>1.28 (d, J = 6.8Hz, 3H), 2.01(dq, J = 10.2, 6.8Hz, 1H), 2.80 (d, J = 10.2Hz, 1H), 3.81 (s, 3H), 6.87 (d, J = 8.7Hz, 1H), 7.07 (s, 1H), 7.15-7.32 (m, 5H), 7.49 (d, J = 8.7Hz, 1H), 7.62 (d, J = 3.8Hz, 1H), 7.71 (d, J = 3.8Hz, 1H), 9.12 (s, 1H), 12.30 (brs, 1H) |

TABLE 2-122-continued

| Example | Structural formula | NMR |
|---|---|---|
| 2-608 | | (DMSO-d6-300)<br>1.39 (s, 3H), 1.45 (d, J = 5.5Hz, 1H), 2.11 (d, J = 5.5Hz, 1H), 7.19 (d, J = 8.4Hz, 2H), 7.30 (d, J = 8.4Hz, 2H), 7.68 (d, J = 4.0Hz, 1H), 7.85 (d, J = 4.0Hz, 1H), 8.15 (s, 1H) |
| 2-609 | | (DMSO-d6-300)<br>1.16 (d, J = 6.6Hz, 3H), 1.91 (dd, J = 10.6, 6.6Hz, 1H), 2.12 (t, J = 19.3Hz, 3H), 2.57 (d, J = 10.6Hz, 1H), 7.00-7.10 (m, 6H), 7.67 (d, J = 4.0Hz, 2H), 7.79 (d, J = 4.0Hz, 1H) |
| 2-610 | | (DMSO-d6-300)<br>1.37 (s, 3H), 1.39 (d, J = 5.7Hz, 1H), 2.08 (d, J = 5.7Hz, 1H), 3.67 (s, 3H), 6.68-6.77 (m, 3H), 7.10-7.18 (m, 1H), 7.66 (d, J = 4.1Hz, 1H), 7.84 (d, J = 4.1Hz, 1H), 8.15 (s, 1H), 9.36 (brs, 1H), 12.13 (brs, 1H) |

TABLE 2-123

| Example | Structural formula | NMR |
|---|---|---|
| 2-611 | | (DMSO-d6-300)<br>1.40 (s, 3H), 1.45 (d, J = 5.7Hz, 1H), 2.14 (d, J = 5.7Hz, 1H), 6.91-7.06 (m, 3H), 7.21-7.35 (m, 1H), 7.68 (d, J = 4.1Hz, 1H), 7.86 (d, J = 4.1Hz, 1H), 8.17 (s, 1H), 12.26 (s, 1H), 12.26 (s, 1H) |

TABLE 2-123-continued

| Example | Structural formula | NMR |
|---|---|---|
| 2-612 | | (DMSO-d6-300)<br>1.40 (s, 3H), 1.45 (d, J = 5.7Hz, 1H), 2.13 (d, J = 5.7Hz, 1H), 7.10-7.33 (m, 4H), 7.69 (d, J = 4.1Hz, 1H), 7.86 (d, J = 4.1Hz, 1H), 8.17 (s, 1H), 9.34 (s, 1H), 12.31 (s, 1H) |
| 2-613 | | (DMSO-d6-300)<br>1.36 (s, 3H), 1.59 (d, J = 5.5Hz, 1H), 2.02( d, J = 5.5Hz, 1H), 3.72 (s, 3H), 6.74-6.88 (m, 2H), 7.05-7.15 (m, 2H), 7.63 (d, J = 3.7Hz, 1H), 7.76(d, J = 3.7Hz, 1H), 7.89 (s, 1H), 8.52(brs, 1H) |
| 2-614 | | (DMSO-d6-300)<br>1.44 (s, 3H), 1.54 (d, J = 5.7Hz, 1H), 2.17 (d, J = 5.7Hz, 1H), 3.13 (s, 3H), 7.51-7.56 (m, 2H), 7.67-7.76 (m, 2H), 7.69 (d, J = 3.8Hz, 1H), 7.86 (d, J = 3.8Hz, 1H), 8.17 (s, 1H), 9.43 (brs, 1H), 12.34 (brs, 1H) |
| 2-615 | | (MeOH-d4-300)<br>1.51 (s, 3H), 1.89 (d, J = 6.0Hz, 1H), 2.18 (d, J = 6.0Hz, 1H), 6.96-7.05 (m, 2H), 7.17-7.24 (m, 2H), 7.62-7.67 (m, 3H) |

TABLE 2-124
| Example | Structural formula | NMR |
|---|---|---|
| 2-616 | 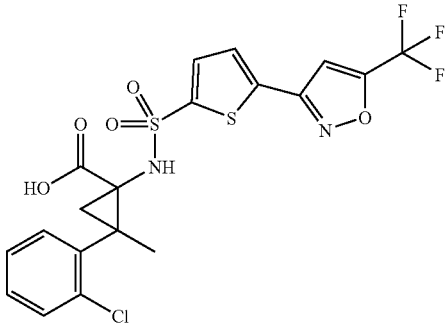 | (DMSO-d6-300)<br>1.35 (d, J = 16.2Hz, 3H), 1.66 (dd, J = 13.9, 5.3Hz, 1H), 2.05 (t, J = 7.0Hz, 1H), 7.13-7.37 (m, 4H), 7.68 (d, J = 3.0Hz, 1H), 7.84 (d, J = 1.5Hz, 1H), 8.15 (s, 1H), 9.28 (brs, 1H), 12.15 (brs, 1H) |
| 2-617 | 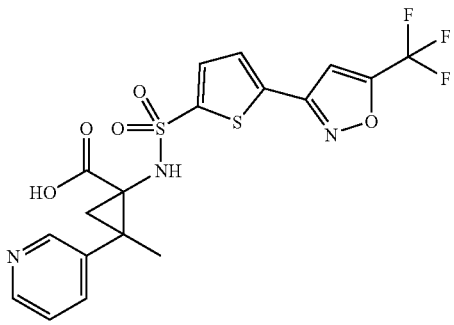 | (MeOH-d4-300)<br>1.54 (s, 3H), 1.85 (d, J = 5.7Hz, 1H), 2.22 (d, J = 6.0Hz, 1H), 77.29 (dd, J = 7.7, 5.1Hz, 1H), 7.62-7.66 (m, 3H), 7.70 (dt, J = 8.0, 1.7Hz, 1H), 8.30 (dd, J = 4.9, 1.5Hz, 1H), 8.41 (d, J = 1.9Hz, 1H) |
| 2-618 | 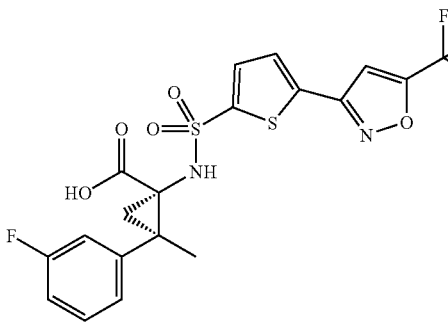 | (DMSO-d6-300)<br>1.40 (s, 3H), 1.44 (d, J = 5.7Hz, 1H), 2.14 (d, J = 5.7Hz, 1H), 6.92-7.05 (m, 3H), 7.23-7.34 (m, 1H), 7.69 (d, J = 4.1Hz, 1H), 7.86 (d, J = 4.1Hz, 1H), 8.17 (s, 1H), 9.38 (s, 1H), 12.28 (s, 1H) |
| 2-619 | 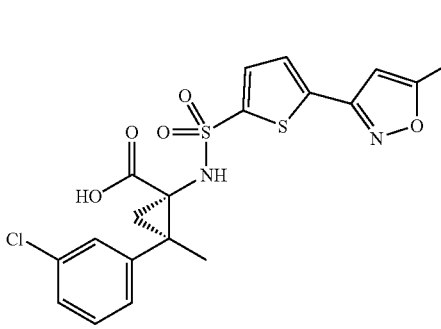 | (DMSO-d6-300)<br>1.40 (s, 3H), 1.45 (d, J = 5.7Hz, 1H), 2.13 (d, J = 5.7Hz, 1H), 7.10-7.33 (m, 4H), 7.69 (d, J = 4.1Hz, 1H), 7.86 (d, J = 4.1Hz, 1H), 8.17 (s, 1H), 9.36 (s, 1H), 12.30 (s, 1H) |

TABLE 2-124-continued
| Example | Structural formula | NMR |
|---|---|---|
| 2-620 | 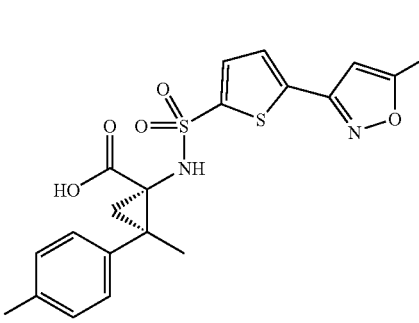 | (DMSO-d6-300)<br>1.40 (s, 3H), 1.44 (d, J = 5.7Hz, 1H), 2.13 (d, J = 5.7Hz, 1H), 7.19 (d, J = 8.3Hz, 2H), 7.32 (d, J = 8.7Hz, 2H), 7.69 (d, J = 4.1Hz, 1H), 7.86 (d, J = 3.8Hz, 1H), 8.17 (s, 1H), 9.39 (brs, 1H), 12.22 (brs, 1H) |
TABLE 2-125
| Example | Structural formula | NMR |
|---|---|---|
| 2-621 | 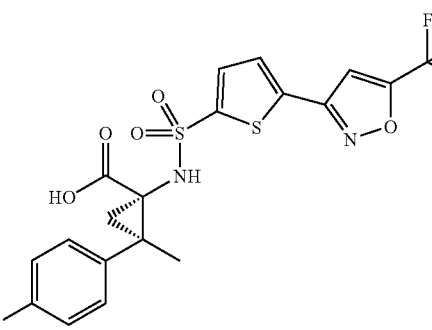 | (DMSO-d6-400)<br>1.38 (s, 3H), 1.42 (d, J = 5.6Hz, 1H), 2.11 (d, J = 5.6Hz, 1H), 7.02-7.10 (m, 2H), 7.15-7.23 (m, 2H), 7.67 (d, J = 3.7Hz, 1H), 7.85 (d, J = 3.7Hz, 1H), 8.16 (q, J = 0.9Hz, 1H), 9.38 (brs, 1H), 12.19 (brs, 1H) |
| 2-622 | 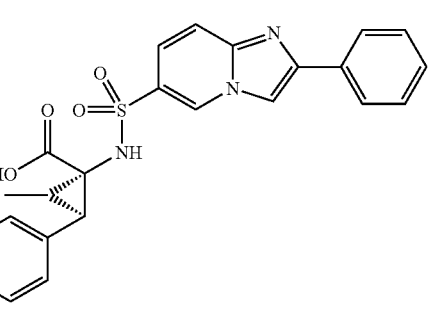 | (DMSO-d6-400)<br>1.23 (d, J = 7.0Hz, 3H), 1.97 (dq, J = 10.2, 6.5Hz, 1H), 2.74 (d, J = 10.7Hz, 1H), 7.09-7.27 (m, 5H), 7.32-7.38 (m, 1H), 7.43-7.49 (m, 3H), 7.71 (d, J = 9.7Hz, 1H), 7.93-7.97 (m, 2H), 8.58 (s, 1H), 9.12-9.09 (m, 1H) |
| 2-623 | 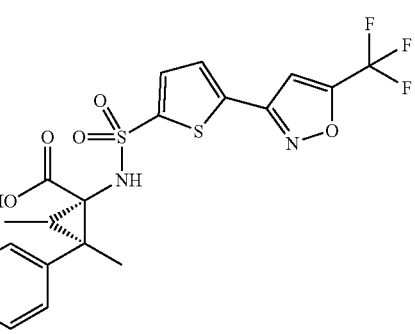 | (DMSO-d6-400)<br>1.31-1.39 (m, 6H), 1.85 (q, J = 6.7Hz, 1H), 7.06-7.29 (m, 5H), 7.67 (d, J = 3.8Hz, 1H), 7.86 (d, J = 3.8Hz, 1H), 8.17 (s, 1H), 9.23 (brs, 1H), 12.17 (brs, 1H) |

TABLE 2-125-continued

| Example | Structural formula | NMR |
|---|---|---|
| 2-624 | (structure) | (DMSO-d6-300) 1.35-1.37 (m, 6H), 1.85 (q, J = 6.4Hz, 1H), 2.13 (t, J = 19.3Hz, 3H), 7.08-7.28 (m, 5H), 7.64 (d, J = 4.0Hz, 1H), 7.71 (s, 1H), 7.80 (d, J = 4.0Hz, 1H), 9.19 (s, 1H), 12.17 (s, 1H) |
| 2-625 | (structure) | (DMSO-d6-300) 1.35-1.37 (m, 6H), 1.85 (q, J = 6.4Hz, 1H), 2.13 (t, J = 19.3Hz, 3H), 7.08-7.28 (m, 5H), 7.64 (d, J = 4.0Hz, 1H), 7.71 (s, 1H), 7.80 (d, J = 4.0Hz, 1H), 9.19 (s, 1H), 12.17 (s, 1H) |

The following show the results of experiments performed with regard to the aggrecanase-1 inhibitory action, matrix metalloproteinase-1 (MMP-1) inhibitory action and matrix metalloproteinase-13 (MMP-13) inhibitory action of the compound of the present invention.

(Pharmacological Tests)

EXPERIMENTAL EXAMPLE 1

Aggrecanase-1 Inhibitory Action

Particle Assay was used for determination of aggrecanase activity.

The enzyme and substrate were diluted with Tris-HCl buffer, and test compounds were diluted with dimethyl sulfoxide (DMSO).

Test compounds and the enzyme were added into 96-well plate, and polyacrylamide particles containing aggrecan were added as a substrate and the mixture was incubated at 37° C. for 15 hr.

After incubation, the supernatant was transferred to another plate, and mixed with 1,9-dimethylmethylene blue. The absorbance at 595 nm was measured to quantify the amount of glycosaminoglycan (GAG) released in the reaction supernatant. Whale chondroitin sulfate was used as the standard of GAG. The inhibitory activity of the compound in each well (%) was calculated based on the values of enzyme-free well and inhibitor-free well. The inhibitory activity of the compound was represented as $IC_{50}$ (μM).

EXPERIMENTAL EXAMPLE 2

MMP-1 Inhibitory Action

For MMP-1 Assay, Type I collagen Activity Measurement kit (YAGAI YU-72013) modified to a 96-well plate format was used.

The principle of the kit is based on the property of collagen that becomes soluble in ethanol after being cleaved by MMP-1.

The enzyme and substrate were diluted with Tris-HCl buffer, and test compounds were diluted with dimethyl sulfoxide (DMSQ).

The enzyme and test compounds were added into 96-well plate, and fluorescein isothiocianate (FITC)-labeled collagen type I was added as a substrate and the mixture was incubated at 37° C. for 3 hr.

The reaction was terminated by addition of Tris-HCl buffer containing ethanol. After centrifugation, the supernatant containing denatured substrate was transferred to another 96-well plate. The collagenase activity of MMP-1 was determined by measuring FITC fluorescence intensity (excitation wavelength 485 nm, emission wavelength 530 nm) of each well. The inhibitory activity of the compound in each well (%) was calculated based on the values of enzyme-free well and inhibitor-free well. The inhibitory activity of the compound was represented as $IC_{50}$ (μM).

EXPERIMENTAL EXAMPLE 3

Inhibitory activity of tested compounds on MMP-13 was measured using MMP-13 specific fluorescent substrate with quencher.

The enzyme and substrate were diluted with Tris-HCl buffer, and test compounds were diluted with dimethyl sulfoxide (DMSO).

Test compounds and the enzyme (Recombinant Human MMP-13: R&D systems, 511-MM) were added into 96-well plate. The reaction was initiated by adding synthetic substrate (7-MCA-Pro-CHA-Gly-NVal-His-Ala-DPA: enzyme systems products, Met-06) into the plate. After incubation at 25° C. for 1 h, the reaction was terminated by addition of reaction terminating solution containing acetic acid. Fluorescence intensity of each well was measured (Ex: 325 nm, Em: 405 nm) and the MMP-13 inhibitory activity of the compound in each well (%) was calculated based on the values of enzyme-free well and inhibitor-free well. The inhibitory activity of the compound was represented as IC$_{50}$ (μM).

The results of the aforementioned Experimental Examples 1 to 3 are shown in Tables 3-1 to 3-19. In the table, + means less than 1 μM, ++ means less than 0.1 μM, − means not less than 1 μM, −− means not less than 10 μM and blank column means "not tested".

TABLE 3-1

| Example | Experimental Example 1 IC$_{50}$ AG1 | Experimental Example 2 IC$_{50}$ MMP1 | Experimental Example 3 IC$_{50}$ MMP13 |
| --- | --- | --- | --- |
| 1 | + | − | |
| 1-2 | ++ | − | ++ |
| 1-3 | ++ | − | ++ |
| 1-4 | ++ | − | |
| 1-7 | + | −− | |
| 1-10 | + | − | + |
| 1-11 | + | − | + |
| 1-12 | + | − | ++ |
| 1-13 | + | − | |
| 1-14 | + | −− | |
| 1-16 | + | − | ++ |
| 1-18 | + | − | ++ |
| 1-21 | + | − | |
| 1-26 | + | −− | + |
| 1-31 | + | −− | |
| 1-38 | ++ | −− | ++ |
| 1-40 | + | − | ++ |
| 1-41 | + | − | ++ |
| 1-42 | + | − | |
| 1-43 | + | − | |
| 1-44 | + | − | |
| 1-54 | + | − | + |
| 1-61 | + | − | ++ |
| 1-62 | + | − | ++ |
| 1-63 | + | − | ++ |
| 1-64 | + | − | ++ |
| 1-65 | | −− | |
| 1-66 | + | − | ++ |
| 1-68 | + | − | ++ |
| 1-69 | ++ | −− | + |
| 1-72 | ++ | − | + |
| 1-74 | + | − | ++ |
| 1-75 | + | − | ++ |
| 1-76 | + | −− | ++ |
| 1-80 | ++ | −− | |
| 1-83 | + | − | ++ |
| 1-84 | + | −− | + |
| 1-85 | ++ | − | ++ |
| 1-86 | + | − | + |
| 1-88 | ++ | −− | + |
| 1-90 | + | − | ++ |

TABLE 3-2

| Example | Experimental Example 1 IC$_{50}$ AG1 | Experimental Example 2 IC$_{50}$ MMP1 | Experimental Example 3 IC$_{50}$ MMP13 |
| --- | --- | --- | --- |
| 1-91 | ++ | − | ++ |
| 1-94 | ++ | − | ++ |
| 1-98 | + | −− | |
| 1-100 | + | − | |
| 1-101 | + | −− | |
| 1-102 | ++ | − | + |
| 1-103 | + | −− | + |
| 1-104 | + | −− | |
| 1-105 | + | − | |
| 1-107 | ++ | − | ++ |
| 1-108 | ++ | − | ++ |
| 1-109 | + | −− | + |
| 1-110 | + | − | |
| 1-112 | + | − | |
| 1-113 | ++ | − | + |
| 1-114 | + | − | |
| 1-115 | + | − | |
| 1-116 | + | − | |
| 1-117 | ++ | − | |
| 1-118 | ++ | − | |
| 1-119 | ++ | − | ++ |
| 1-121 | ++ | − | ++ |
| 1-122 | ++ | − | ++ |
| 1-125 | ++ | −− | |
| 1-127 | ++ | − | + |
| 1-128 | ++ | − | + |
| 1-129 | ++ | − | ++ |
| 1-130 | ++ | − | ++ |
| 1-131 | ++ | − | ++ |
| 1-132 | ++ | − | ++ |
| 1-133 | ++ | − | ++ |
| 1-134 | ++ | − | ++ |
| 1-135 | + | − | |
| 1-136 | ++ | − | ++ |
| 1-137 | + | − | |
| 1-138 | ++ | − | + |
| 1-139 | ++ | −− | + |
| 1-145 | + | −− | |
| 1-146 | ++ | −− | |
| 1-147 | + | −− | |

TABLE 3-3

| Example | Experimental Example 1 IC$_{50}$ AG1 | Experimental Example 2 IC$_{50}$ MMP1 | Experimental Example 3 IC$_{50}$ MMP13 |
| --- | --- | --- | --- |
| 2 | − | −− | −− |
| 2-2 | −− | −− | −− |
| 2-3 | − | −− | − |
| 2-4 | ++ | + | ++ |
| 2-5 | + | − | ++ |
| 2-6 | ++ | − | + |
| 2-7 | ++ | + | ++ |
| 2-8 | ++ | − | ++ |
| 2-9 | ++ | ++ | ++ |
| 2-10 | ++ | + | ++ |
| 2-11 | − | − | − |
| 2-12 | ++ | + | ++ |
| 2-13 | ++ | −− | ++ |
| 2-14 | −− | −− | −− |
| 2-15 | −− | −− | − |
| 2-16 | −− | −− | + |
| 2-17 | − | −− | ++ |
| 2-18 | + | − | + |
| 2-19 | + | −− | + |
| 2-20 | + | − | ++ |
| 2-21 | + | − | + |
| 2-22 | ++ | −− | ++ |
| 2-23 | + | −− | + |
| 2-24 | + | −− | + |
| 2-25 | ++ | −− | + |

TABLE 3-3-continued

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-26 | + | -- | |
| 2-27 | + | -- | + |
| 2-28 | - | | -- |
| 2-29 | - | | ++ |
| 2-30 | - | | - |
| 2-31 | - | | - |
| 2-32 | ++ | -- | ++ |
| 2-33 | - | | + |
| 2-34 | - | | + |
| 2-35 | + | -- | + |
| 2-36 | + | -- | + |
| 2-37 | ++ | -- | ++ |
| 2-38 | - | | + |

TABLE 3-4

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-39 | + | - | ++ |
| 2-40 | + | -- | + |
| 2-41 | + | -- | + |
| 2-42 | ++ | -- | ++ |
| 2-43 | ++ | + | ++ |
| 2-44 | - | -- | - |
| 2-45 | - | -- | - |
| 2-46 | - | -- | - |
| 2-47 | - | -- | + |
| 2-48 | + | -- | - |
| 2-49 | - | -- | -- |
| 2-50 | - | -- | - |
| 2-51 | - | -- | - |
| 2-52 | + | -- | + |
| 2-53 | - | -- | - |
| 2-54 | - | -- | -- |
| 2-55 | - | -- | -- |
| 2-56 | ++ | -- | ++ |
| 2-57 | + | -- | ++ |
| 2-58 | + | -- | + |
| 2-59 | + | -- | + |
| 2-60 | -- | -- | - |
| 2-61 | + | -- | + |
| 2-62 | + | -- | + |
| 2-63 | ++ | - | ++ |
| 2-64 | -- | -- | - |
| 2-65 | + | -- | + |
| 2-66 | - | -- | - |
| 2-67 | -- | -- | + |
| 2-68 | - | -- | ++ |
| 2-69 | ++ | - | ++ |
| 2-70 | + | -- | |
| 2-71 | ++ | -- | + |
| 2-72 | ++ | -- | + |
| 2-73 | ++ | -- | + |
| 2-74 | + | -- | ++ |
| 2-75 | + | -- | + |
| 2-76 | ++ | -- | + |

TABLE 3-5

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-77 | ++ | - | + |
| 2-78 | ++ | -- | + |
| 2-79 | -- | -- | -- |
| 2-80 | -- | -- | -- |
| 2-81 | -- | -- | -- |

TABLE 3-5-continued

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-82 | -- | -- | -- |
| 2-83 | -- | -- | -- |
| 2-84 | ++ | + | ++ |
| 2-85 | + | - | ++ |
| 2-86 | ++ | -- | + |
| 2-87 | -- | -- | - |
| 2-88 | -- | -- | -- |
| 2-89 | - | -- | - |
| 2-90 | - | - | ++ |
| 2-91 | + | -- | + |
| 2-92 | ++ | + | ++ |
| 2-93 | -- | -- | - |
| 2-94 | -- | -- | -- |
| 2-95 | -- | -- | -- |
| 2-96 | -- | -- | + |
| 2-97 | -- | -- | -- |
| 2-98 | ++ | - | ++ |
| 2-99 | ++ | + | + |
| 2-100 | ++ | + | ++ |
| 2-101 | ++ | -- | + |
| 2-102 | + | + | |
| 2-103 | -- | -- | -- |
| 2-104 | -- | -- | -- |
| 2-105 | -- | -- | -- |
| 2-106 | -- | -- | -- |
| 2-107 | ++ | + | ++ |
| 2-108 | ++ | - | ++ |
| 2-109 | ++ | -- | ++ |
| 2-110 | + | - | ++ |
| 2-111 | - | -- | + |
| 2-112 | + | -- | - |
| 2-113 | ++ | + | ++ |
| 2-114 | - | + | ++ |

TABLE 3-6

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-115 | - | | + |
| 2-116 | -- | -- | -- |
| 2-117 | -- | -- | -- |
| 2-118 | - | - | |
| 2-119 | ++ | + | ++ |
| 2-120 | ++ | + | ++ |
| 2-121 | ++ | + | ++ |
| 2-122 | - | + | |
| 2-123 | + | -- | + |
| 2-124 | ++ | - | ++ |
| 2-125 | -- | -- | -- |
| 2-126 | -- | -- | -- |
| 2-127 | -- | -- | |
| 2-128 | -- | -- | -- |
| 2-129 | + | -- | + |
| 2-130 | - | | - |
| 2-131 | ++ | - | + |
| 2-132 | -- | -- | -- |
| 2-133 | -- | -- | + |
| 2-134 | -- | -- | + |
| 2-135 | - | | ++ |
| 2-136 | + | - | ++ |
| 2-137 | - | + | ++ |
| 2-138 | -- | | |
| 2-139 | - | -- | - |
| 2-140 | -- | -- | - |
| 2-141 | + | - | ++ |
| 2-142 | ++ | - | + |
| 2-143 | -- | -- | |
| 2-144 | -- | -- | - |
| 2-145 | -- | -- | - |
| 2-146 | + | -- | + |

TABLE 3-6-continued

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-147 | − | −− | − |
| 2-148 | − | −− | + |
| 2-149 | − | −− | ++ |
| 2-150 | + | − | + |
| 2-151 | −− | −− | − |
| 2-152 | + | −− | ++ |

TABLE 3-7

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-153 | −− | −− | − |
| 2-154 | − | −− | + |
| 2-155 | − | −− | + |
| 2-156 | − | −− | − |
| 2-157 | − | −− | − |
| 2-158 | −− | −− | −− |
| 2-159 | −− | −− | −− |
| 2-160 | −− | −− | −− |
| 2-161 | −− | −− | − |
| 2-162 | −− | −− | −− |
| 2-163 | −− | −− | −− |
| 2-164 | −− | −− | −− |
| 2-165 | −− | −− | − |
| 2-166 | −− | −− | −− |
| 2-167 | + | −− | − |
| 2-168 | + | −− | − |
| 2-169 | ++ | − | ++ |
| 2-170 | ++ | −− | ++ |
| 2-171 | + | −− | + |
| 2-172 | −− | −− | − |
| 2-173 | ++ | − | ++ |
| 2-174 | ++ | −− | ++ |
| 2-175 | ++ | − | + |
| 2-176 | ++ | −− | ++ |
| 2-177 | − | −− | − |
| 2-178 | ++ | −− | + |
| 2-179 | ++ | −− | + |
| 2-180 | ++ | −− | ++ |
| 2-181 | ++ | − | ++ |
| 2-182 | ++ | −− | ++ |
| 2-183 | ++ | − | ++ |
| 2-184 | ++ | − | + |
| 2-185 | − | −− | + |
| 2-186 | − | −− | − |
| 2-187 | −− | −− | −− |
| 2-188 | ++ | − | ++ |
| 2-189 | ++ | −− | ++ |
| 2-190 | ++ | − | ++ |

TABLE 3-8

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-191 | ++ | −− | ++ |
| 2-192 | + | −− | + |
| 2-193 | + | −− | + |
| 2-194 | + | −− | + |
| 2-195 | + | −− | + |
| 2-196 | ++ | − | ++ |
| 2-197 | + | −− | + |
| 2-198 | + | −− | + |
| 2-199 | + | −− | + |
| 2-200 | + | −− | + |
| 2-201 | + | −− | ++ |
| 2-202 | + | −− | + |

TABLE 3-8-continued

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-203 | + | −− | ++ |
| 2-204 | ++ | −− | + |
| 2-205 | ++ | −− | + |
| 2-206 | ++ | − | ++ |
| 2-207 | + | −− | + |
| 2-208 | ++ | − | ++ |
| 2-209 | ++ | − | ++ |
| 2-210 | + | −− | ++ |
| 2-211 | ++ | −− | ++ |
| 2-212 | ++ | − | + |
| 2-213 | ++ | + | ++ |
| 2-214 | ++ | + | ++ |
| 2-215 | ++ | −− | + |
| 2-216 | + | −− | + |
| 2-217 | + | −− | + |
| 2-218 | − | −− | |
| 2-219 | + | − | ++ |
| 2-220 | ++ | − | ++ |
| 2-221 | + | − | ++ |
| 2-222 | ++ | − | ++ |
| 2-223 | + | −− | + |
| 2-224 | ++ | − | ++ |
| 2-225 | − | −− | + |
| 2-226 | + | −− | + |
| 2-227 | ++ | − | + |
| 2-228 | + | − | + |

TABLE 3-9

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-229 | + | −− | + |
| 2-230 | + | −− | ++ |
| 2-231 | + | − | ++ |
| 2-232 | + | − | ++ |
| 2-233 | + | − | ++ |
| 2-234 | ++ | − | ++ |
| 2-235 | + | − | ++ |
| 2-236 | + | − | ++ |
| 2-237 | ++ | − | ++ |
| 2-238 | + | − | ++ |
| 2-239 | ++ | − | ++ |
| 2-240 | + | − | + |
| 2-241 | + | − | ++ |
| 2-242 | ++ | − | ++ |
| 2-243 | + | − | ++ |
| 2-244 | + | −− | + |
| 2-245 | − | −− | + |
| 2-246 | − | −− | + |
| 2-247 | −− | −− | −− |
| 2-248 | ++ | − | + |
| 2-249 | ++ | −− | + |
| 2-250 | + | − | ++ |
| 2-251 | + | −− | + |
| 2-252 | ++ | − | + |
| 2-253 | ++ | − | ++ |
| 2-254 | ++ | − | ++ |
| 2-255 | ++ | − | ++ |
| 2-256 | − | −− | −− |
| 2-257 | ++ | − | + |
| 2-258 | + | − | + |
| 2-259 | ++ | − | ++ |
| 2-260 | + | − | ++ |
| 2-261 | + | −− | + |
| 2-262 | ++ | + | ++ |
| 2-263 | ++ | − | + |
| 2-264 | ++ | − | ++ |
| 2-265 | + | −− | + |
| 2-266 | + | − | + |

TABLE 3-10

| Example | Experimental Example 1 IC$_{50}$ AG1 | Experimental Example 2 IC$_{50}$ MMP1 | Experimental Example 3 IC$_{50}$ MMP13 |
| --- | --- | --- | --- |
| 2-267 | ++ | − | ++ |
| 2-268 | ++ | − | ++ |
| 2-269 | ++ | − | ++ |
| 2-270 | ++ | − | ++ |
| 2-271 | − | −− | + |
| 2-272 | ++ | −− | ++ |
| 2-273 | ++ | + | ++ |
| 2-274 | ++ | −− | − |
| 2-275 | ++ | − | + |
| 2-276 | + | − | ++ |
| 2-277 | + | − | + |
| 2-278 | ++ | + | ++ |
| 2-279 | ++ | + | ++ |
| 2-280 | + | −− | ++ |
| 2-281 | ++ | + | ++ |
| 2-282 | ++ | + | ++ |
| 2-283 | + | − | ++ |
| 2-284 | ++ | − | ++ |
| 2-285 | + | − | − |
| 2-286 | ++ | − | ++ |
| 2-287 | ++ | + | ++ |
| 2-288 | ++ | + | ++ |
| 2-289 | + | − | + |
| 2-290 | ++ | + | ++ |
| 2-291 | ++ | + | ++ |
| 2-292 | ++ | + | ++ |
| 2-293 | ++ | + | ++ |
| 2-294 | ++ | − | ++ |
| 2-295 | ++ | − | ++ |
| 2-296 | − | −− | − |
| 2-297 | − | −− | − |
| 2-298 | ++ | − | ++ |
| 2-299 | ++ | ++ | ++ |
| 2-300 | + | − | ++ |
| 2-301 | ++ | − | ++ |
| 2-302 | ++ | + | ++ |
| 2-303 | ++ | − | ++ |
| 2-304 | + | − | + |

TABLE 3-11

| Example | Experimental Example 1 IC$_{50}$ AG1 | Experimental Example 2 IC$_{50}$ MMP1 | Experimental Example 3 IC$_{50}$ MMP13 |
| --- | --- | --- | --- |
| 2-305 | ++ | − | ++ |
| 2-306 | + | − | + |
| 2-307 | − | −− | − |
| 2-308 | + | − | + |
| 2-309 | + | − | + |
| 2-310 | + | + | ++ |
| 2-311 | + | − | + |
| 2-312 | − | −− | −− |
| 2-313 | + | − | + |
| 2-314 | − | −− | −− |
| 2-315 | + | −− | + |
| 2-316 | − | −− | −− |
| 2-317 | + | − | + |
| 2-318 | − | −− | −− |
| 2-319 | ++ | − | ++ |
| 2-320 | + | − | + |
| 2-321 | + | − | + |
| 2-322 | ++ | − | + |
| 2-323 | − | − | ++ |
| 2-324 | − | −− | − |
| 2-325 | − | −− | − |
| 2-326 | + | − | + |
| 2-327 | + | + | ++ |
| 2-328 | ++ | ++ | ++ |
| 2-329 | − | −− | − |
| 2-330 | − | −− | − |
| 2-331 | + | − | + |

TABLE 3-11-continued

| Example | Experimental Example 1 IC$_{50}$ AG1 | Experimental Example 2 IC$_{50}$ MMP1 | Experimental Example 3 IC$_{50}$ MMP13 |
| --- | --- | --- | --- |
| 2-332 | + | − | + |
| 2-333 | + | − | + |
| 2-334 | + | − | + |
| 2-335 | + | − | + |
| 2-336 | − | −− | − |
| 2-337 | + | −− | + |
| 2-338 | ++ | − | + |
| 2-339 | ++ | − | + |
| 2-340 | + | −− | − |
| 2-341 | ++ | −− | − |
| 2-342 | + | − | − |

TABLE 3-12

| Example | Experimental Example 1 IC$_{50}$ AG1 | Experimental Example 2 IC$_{50}$ MMP1 | Experimental Example 3 IC$_{50}$ MMP13 |
| --- | --- | --- | --- |
| 2-343 | − | −− | − |
| 2-344 | ++ | −− | + |
| 2-345 | ++ | −− | + |
| 2-346 | + | −− | + |
| 2-347 | ++ | −− | + |
| 2-348 | + | −− | + |
| 2-349 | ++ | −− | + |
| 2-350 | + | − | ++ |
| 2-351 | ++ | + | ++ |
| 2-352 | ++ | − | ++ |
| 2-353 | ++ | + | ++ |
| 2-354 | ++ | − | + |
| 2-355 | − | − | + |
| 2-356 | + | + | + |
| 2-357 | ++ | − | ++ |
| 2-358 | ++ | − | + |
| 2-359 | + | − | ++ |
| 2-360 | ++ | −− | + |
| 2-361 | − | −− | − |
| 2-362 | + | −− | ++ |
| 2-363 | − | −− | + |
| 2-364 | + | + | ++ |
| 2-365 | ++ | + | ++ |
| 2-366 | ++ | + | ++ |
| 2-367 | − | −− | − |
| 2-368 | + | − | + |
| 2-369 | ++ | − | ++ |
| 2-370 | ++ | + | ++ |
| 2-371 | − | −− | − |
| 2-372 | − | −− | − |
| 2-373 | − | −− | − |
| 2-374 | ++ | + | ++ |
| 2-375 | ++ | + | ++ |
| 2-376 | + | −− | + |
| 2-377 | +− | + | |
| 2-378 | + | − | + |
| 2-379 | + | − | + |
| 2-380 | + | −− | + |

TABLE 3-13

| Example | Experimental Example 1 IC$_{50}$ AG1 | Experimental Example 2 IC$_{50}$ MMP1 | Experimental Example 3 IC$_{50}$ MMP13 |
| --- | --- | --- | --- |
| 2-381 | + | −− | + |
| 2-382 | ++ | + | + |
| 2-383 | ++ | + | ++ |
| 2-384 | + | −− | ++ |
| 2-385 | + | −− | + |
| 2-386 | + | − | |
| 2-387 | − | −− | + |

TABLE 3-13-continued

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-388 | + | − | + |
| 2-389 | ++ | − | ++ |
| 2-390 | + | −− | − |
| 2-391 | − | −− | + |
| 2-392 | − | −− | − |
| 2-393 | + | − | ++ |
| 2-394 | + | − | ++ |
| 2-395 | + | −− | + |
| 2-396 | + | −− | + |
| 2-397 | + | −− | + |
| 2-398 | + | −− | + |
| 2-399 | + | − | + |
| 2-400 | − | − | + |
| 2-401 | ++ | + | ++ |
| 2-402 | − | −− | |
| 2-403 | + | + | ++ |
| 2-404 | ++ | + | ++ |
| 2-405 | ++ | −− | + |
| 2-406 | ++ | + | ++ |
| 2-407 | ++ | + | ++ |
| 2-408 | ++ | + | ++ |
| 2-409 | + | + | ++ |
| 2-410 | ++ | − | − |
| 2-411 | ++ | + | ++ |
| 2-412 | ++ | − | ++ |
| 2-413 | ++ | − | + |
| 2-414 | + | − | + |
| 2-415 | − | −− | |
| 2-416 | + | − | + |
| 2-417 | + | − | |
| 2-418 | − | − | |

TABLE 3-14

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-419 | ++ | + | ++ |
| 2-420 | − | −− | − |
| 2-421 | − | −− | − |
| 2-422 | ++ | + | + |
| 2-423 | + | + | ++ |
| 2-424 | −− | + | + |
| 2-425 | −− | −− | − |
| 2-426 | + | − | ++ |
| 2-427 | −− | + | − |
| 2-428 | + | − | ++ |
| 2-429 | + | − | + |
| 2-430 | ++ | − | ++ |
| 2-431 | + | − | + |
| 2-432 | ++ | − | + |
| 2-433 | ++ | + | ++ |
| 2-434 | ++ | − | + |
| 2-435 | ++ | + | ++ |
| 2-436 | − | −− | − |
| 2-437 | ++ | + | ++ |
| 2-438 | ++ | + | ++ |
| 2-439 | ++ | − | ++ |
| 2-440 | + | −− | + |
| 2-441 | ++ | − | ++ |
| 2-442 | − | −− | − |
| 2-443 | − | −− | − |
| 2-444 | ++ | + | ++ |
| 2-445 | + | −− | + |
| 2-446 | − | −− | − |
| 2-447 | + | + | ++ |
| 2-448 | − | −− | − |
| 2-449 | ++ | − | ++ |
| 2-450 | + | −− | + |
| 2-451 | − | −− | − |
| 2-452 | + | + | ++ |

TABLE 3-14-continued

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-453 | − | −− | + |
| 2-454 | + | −− | − |
| 2-455 | − | | − |
| 2-456 | − | | − |

TABLE 3-15

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-457 | ++ | − | ++ |
| 2-458 | + | −− | ++ |
| 2-459 | + | − | ++ |
| 2-460 | + | − | ++ |
| 2-461 | + | − | − |
| 2-462 | + | − | − |
| 2-463 | − | −− | − |
| 2-464 | − | −− | − |
| 2-465 | − | −− | −− |
| 2-466 | + | − | − |
| 2-467 | − | −− | −− |
| 2-468 | + | − | |
| 2-469 | − | −− | |
| 2-470 | ++ | + | ++ |
| 2-471 | − | −− | − |
| 2-472 | + | − | −− |
| 2-473 | − | −− | − |
| 2-474 | − | −− | − |
| 2-475 | − | −− | − |
| 2-476 | − | −− | −− |
| 2-477 | − | −− | − |
| 2-478 | − | −− | −− |
| 2-479 | − | −− | −− |
| 2-480 | + | + | ++ |
| 2-481 | − | −− | ++ |
| 2-482 | − | −− | ++ |
| 2-483 | − | −− | − |
| 2-484 | − | −− | + |
| 2-485 | + | −− | − |
| 2-486 | + | + | ++ |
| 2-487 | − | −− | − |
| 2-488 | − | −− | − |
| 2-489 | − | −− | ++ |
| 2-490 | − | −− | ++ |
| 2-491 | − | −− | ++ |
| 2-492 | ++ | ++ | ++ |
| 2-493 | ++ | + | ++ |
| 2-494 | ++ | ++ | ++ |

TABLE 3-16

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-495 | ++ | ++ | ++ |
| 2-496 | ++ | + | ++ |
| 2-497 | ++ | − | ++ |
| 2-498 | ++ | − | + |
| 2-499 | + | + | ++ |
| 2-500 | − | − | + |
| 2-501 | − | − | − |
| 2-502 | − | − | − |
| 2-503 | + | − | + |
| 2-504 | − | − | + |
| 2-505 | − | − | + |
| 2-506 | − | + | ++ |
| 2-507 | − | + | ++ |
| 2-508 | − | − | − |

TABLE 3-16-continued

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-509 | + | − | ++ |
| 2-510 | − | − | − |
| 2-511 | − | − | − |
| 2-512 | − | − | − |
| 2-513 | − | − | − |
| 2-514 | + | − | + |
| 2-515 | − | − | − |
| 2-516 | + | − | + |
| 2-517 | ++ | − | + |
| 2-518 | + | + | ++ |
| 2-519 | − | − | − |
| 2-520 | − | − | − |
| 2-521 | + | − | ++ |
| 2-522 | − | − | ++ |
| 2-523 | + | + | ++ |
| 2-524 | ++ | ++ | ++ |
| 2-525 | ++ | ++ | ++ |
| 2-526 | − | − | − |
| 2-527 | − | − | − |
| 2-528 | − | − | − |
| 2-529 | − | − | − |
| 2-530 | − | − | − |
| 2-531 | − | − | − |
| 2-532 | − | − | − |

TABLE 3-17

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-533 | − | − | − |
| 2-534 | − | − | − |
| 2-535 | − | − | − |
| 2-536 | − | − | − |
| 2-537 | − | − | − |
| 2-538 | − | − | + |
| 2-539 | ++ | + | ++ |
| 2-540 | − | − | + |
| 2-541 | − | − | − |
| 2-542 | + | − | ++ |
| 2-543 | ++ | ++ | ++ |
| 2-544 | + | − | + |
| 2-545 | ++ | ++ | ++ |
| 2-546 | ++ | ++ | ++ |
| 2-547 | ++ | ++ | ++ |
| 2-548 | − | − | − |
| 2-549 | − | − | − |
| 2-550 | − | − | − |
| 2-551 | − | − | − |
| 2-552 | − | − | + |
| 2-553 | − | − | − |
| 2-554 | − | − | + |
| 2-555 | + | − | + |
| 2-556 | − | − | ++ |
| 2-557 | + | − | ++ |
| 2-558 | − | − | + |
| 2-559 | ++ | − | + |
| 2-560 | + | − | + |
| 2-561 | ++ | ++ | ++ |
| 2-562 | − | − | − |
| 2-563 | − | − | − |
| 2-564 | ++ | − | ++ |
| 2-565 | ++ | + | ++ |
| 2-566 | + | − | − |
| 2-567 | ++ | − | + |
| 2-568 | ++ | + | ++ |
| 2-569 | ++ | + | ++ |
| 2-570 | + | − | ++ |

TABLE 3-18

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-571 | − | − | + |
| 2-572 | ++ | − | ++ |
| 2-573 | + | − | ++ |
| 2-574 | + | + | ++ |
| 2-575 | − | | |
| 2-576 | − | | |
| 2-577 | ++ | + | ++ |
| 2-578 | + | − | ++ |
| 2-579 | ++ | + | ++ |
| 2-580 | + | − | ++ |
| 2-581 | ++ | − | + |
| 2-582 | + | − | + |
| 2-583 | − | − | − |
| 2-584 | + | − | ++ |
| 2-585 | − | | − |
| 2-586 | − | | −− |
| 2-587 | − | − | + |
| 2-588 | ++ | + | + |
| 2-589 | + | − | − |
| 2-590 | ++ | − | ++ |
| 2-591 | − | − | ++ |
| 2-592 | − | | |
| 2-593 | + | − | + |
| 2-594 | + | − | + |
| 2-595 | − | − | ++ |
| 2-596 | + | − | + |
| 2-597 | − | − | −− |
| 2-598 | ++ | − | + |
| 2-599 | ++ | − | + |
| 2-600 | + | − | + |
| 2-601 | + | − | − |
| 2-602 | ++ | + | + |
| 2-603 | + | + | + |
| 2-604 | + | − | |
| 2-605 | − | −− | − |
| 2-606 | − | −− | − |
| 2-607 | − | − | ++ |
| 2-608 | ++ | + | + |

TABLE 3-19

| Example | Experimental Example 1 IC$_{50}$ AG1 | Experimental Example 2 IC$_{50}$ MMP1 | Experimental Example 3 IC$_{50}$ MMP13 |
|---|---|---|---|
| 2-609 | ++ | ++ | ++ |
| 2-610 | ++ | + | − |
| 2-611 | ++ | + | − |
| 2-612 | ++ | + | − |
| 2-613 | ++ | + | − |
| 2-614 | ++ | + | − |
| 2-615 | ++ | ++ | ++ |
| 2-616 | ++ | + | + |
| 2-617 | + | − | − |
| 2-618 | ++ | + | + |
| 2-619 | ++ | + | + |
| 2-620 | ++ | + | ++ |
| 2-621 | ++ | + | ++ |
| 2-622 | − | − | + |
| 2-623 | ++ | + | ++ |
| 2-624 | ++ | | |
| 2-625 | ++ | | |

The compound (1) of the present invention described in the results above has superior aggrecanase inhibitory activity and MMP-13 inhibitory activity, and high selectivity to aggrecanase as compared to the activity of MMP-1.

INDUSTRIAL APPLICABILITY

According to the present invention, a compound useful as a prophylactic or therapeutic agent for diseases mediated by aggrecanase, such as osteoarthritis (OA), rheumatoid arthritis (RA), joint injury, reactive arthritis, cancer, asthma, allergic reaction, chronic pulmonary emphysema, fibroid lung, acute respiratory distress (ARDS), lung infection, interstitial pneumonia, bone resorption disorder, etc. is provided.

What is claimed is:

1. A cyclopropane compound of formula (1):

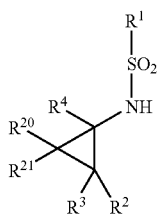

(1)

wherein
$R^1$ is
—$(CH_2)_m$—X—$(CH_2)_n$-$A^1$,
wherein
m and n are the same or different and each is selected from 0 and an integer ranging from 1 to 6,
X is a linker selected from the following group A,
group A:
(a) a single bond,
(b) a $C_{1-6}$ alkylene group,
(c) a $C_{2-6}$ alkenylene group,
(d) a $C_{2-6}$ alkynylene group,
(e) —O—,
(f) —$N(R^5)$—,
(g) —$S(O)_{m1}$—,
(j) —OCO—,
(l) —$N(R^5)CO$—,
(m) —$SO_2N(R^5)$—,
(n) —$N(R^5)SO_2$—,
(o) —$N(R^5)CON(R^6)$—,
(p) —$N(R^5)SO_2N(R^6)$—,
(q) —$OCON(R^5)$—,
(r) —$N(R^5)COO$—,
and
(s) —$S(O)_{m1}$—$(CH_2)_{n1}$—CO—;
wherein
$R^5$ and $R^6$ are the same or different and each is selected from a hydrogen atom, a $C_{1-6}$ alkyl group optionally substituted by halogen atoms or hydroxyl groups, a $C_{3-14}$ hydrocarbon ring group and a heterocyclic group,
m1 is selected from 0 and an integer ranging from 1 to 2 and
n1 is selected from an integer ranging from 1 to 2, and
$A^1$ is selected from a substituted $C_{3-14}$ hydrocarbon ring group and a substituted heterocyclic group;
$R^2$ and $R^3$ are the same or different and each is selected from
(1) —$(CH_2)_p$—$X_1$—$(CH_2)_q$-$A^2$,
wherein
p and q are the same or different and each is selected from 0 and an integer ranging from 1 to 6, $X_1$ is a linker selected from the above-mentioned group A and
$A^2$ is selected from an optionally substituted $C_{3-14}$ hydrocarbon ring group and an optionally substituted heterocyclic group, and
(2) —$(CH_2)_{m8}$—$X_8$—$(CH_2)_{n8}$—$R^{27}$,
wherein
m8 and n8 are the same or different and each is selected from 0 and an integer ranging from 1 to 6,
$X_8$ is a linker selected from the above-mentioned group A and
$R^{27}$ is a substituent selected from the following group B,
group B:
(a) a hydrogen atom,
(b) a halogen atom,
(c) a hydroxyl group,
(d) a nitro group,
(e) a cyano group,
(g) an amino group,
(i) a $C_{2-6}$ acyl group,
(j) a halogenated $C_{1-6}$ alkyl group,
(k) a $C_{1-6}$ alkyl group optionally substituted by hydroxyl groups,
(l) a $C_{2-6}$ alkenyl group optionally substituted by halogen atoms,
(m) a $C_{2-6}$ alkynyl group,
(n) a $C_{1-6}$ alkoxy group optionally substituted by hydroxyl groups,
(o) a $C_{1-6}$ alkoxy-$C_{1-6}$ alkyl group,
(p) a $C_{1-6}$ alkoxy-carbonyl group,
(q) a $C_{1-6}$ alkyl-aminocarbonyl group optionally substituted by halogen atoms,
(r) a mono($C_{1-6}$ alkyl)amino group,
(s) a di($C_{1-6}$ alkyl)amino group,
(t) a $C_{1-6}$ alkyl-carbonylamino group optionally substituted by halogen atoms,
(u) a $C_{1-6}$ alkylsulfonyl group, and
(v) a $C_{1-6}$ alkylsulfonylamino group;
or $A^2$ and $R^{27}$ may be taken together to form an optionally substituted fused ring group,
or $R^2$ and $R^3$ may be taken together with a carbon atom bonded thereto to form the following ring

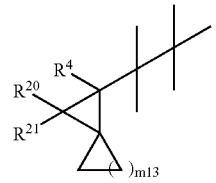

wherein m13 is selected from an integer ranging from 1 to 6, provided that $R^2$ and $R^3$ are not hydrogen atoms at the same time;
$R^4$ is selected from
(1) —$CO_2R^9$,
(2) —$C(O)NHOR^9$,
(3) —$C(O)NH$—$SO_2$—$R^9$,
(4) —$C(O)NHR^9$,
(5) —SH,
(6) —$CH_2CO_2R^9$,
(7) —$C(O)R^9$,
(8) —$N(OH)COR^9$,
(9) —$SN_2H_2R^9$,

(10) —SONHR$^9$,
(11) —CH$_2$CO$_2$H,
(12) —PO(OH)$_2$,
(13) —PO(OH)NHR$^9$,
(14) —CH$_2$SH,
(15) —CH$_2$OH,
(16) —(CH$_2$)$_{r1}$—PO(OH)—(CH$_2$)$_{r2}$—R$^9$,
(17) —NHR$^9$,
(18) —NH—NHR$^9$,
and
(19) —(CH$_2$)$_{r1}$—R$^{50}$;
wherein
r1 and r2 are the same or different and each is selected from 0 and an integer ranging from 1 to 6,
R$^9$ is selected from
(1) a hydrogen atom,
(2) an optionally substituted C$_{1-10}$ alkyl group,
(3) an optionally substituted C$_{6-14}$ aryl-C$_{1-6}$ alkyl group, and
(4) —(CH$_2$)$_{m9}$—X$_9$—(CH$_2$)$_{n9}$—R$^{28}$;
wherein
m9 and n9 are the same or different and each is selected from 0 and an integer ranging from 1 to 6,
X$_9$ is a linker selected from the above-mentioned group A and
R$^{28}$ is a substituent selected from the following group C,
group C:
(a) a hydrogen atom,
(b) a halogen atom,
(c) a hydroxyl group,
(d) a nitro group,
(e) a cyano group,
(f) a carboxyl group,
(g) an amino group,
(h) an amido group,
(i) a C$_{2-6}$ acyl group,
(j) a halogenated C$_{1-6}$ alkyl group,
(k) a C$_{1-6}$ alkyl group optionally substituted by hydroxyl groups,
(l) a C$_{2-6}$ alkenyl group optionally substituted by halogen atoms,
(m) a C$_{2-6}$ alkynyl group,
(n) a C$_{1-6}$ alkoxy group optionally substituted by hydroxyl groups,
(o) a C$_{1-6}$ alkoxy-C$_{1-6}$ alkyl group,
(p) a C$_{1-6}$ alkoxy-carbonyl group,
(q) a C$_{1-6}$ alkyl-aminocarbonyl group optionally substituted by halogen atoms,
(r) a mono(C$_{1-6}$ alkyl)amino group,
(s) a di(C$_{1-6}$ alkyl)amino group,
(t) a C$_{1-6}$ alkyl-carbonylamino group optionally substituted by halogen atoms,
(u) a C$_{1-6}$ alkylsulfonyl group,
(v) a C$_{1-6}$ alkylsulfonylamino group,
(w) a C$_{3-14}$ hydrocarbon ring group optionally substituted by 1 to 5 substituent(s) selected from the above-mentioned group B, and
(x) a heterocyclic group optionally substituted by 1 to 5 substituent(s) selected from the above-mentioned group B, and
R$^{50}$ is selected from an optionally substituted C$_{3-14}$ hydrocarbon ring group and an optionally substituted heterocyclic group;
or R$^9$ of —C(O)NHR$^9$, A$^2$ and the cyclopropane ring may be taken together to form an optionally further substituted fused ring;

R$^{20}$ and R$^{21}$ are the same or different and each is selected from
(1) —(CH$_2$)$_{m10}$—X$_{10}$—(CH$_2$)$_{n10}$-A$^3$,
wherein
m10 and n10 are the same or different and each is selected from 0 and an integer ranging from 1 to 6,
X$_{10}$ is a linker selected from the above-mentioned group A and
A$^3$ is selected from an optionally substituted C$_{3-14}$ hydrocarbon ring group and an optionally substituted heterocyclic group, and
—(CH$_2$)$_{m12}$—X$_{12}$—(CH$_2$)$_{n12}$—R$^{30}$,
wherein
m12 and n12 are the same or different and each is selected from 0 and an integer ranging from 1 to 6,
X$_{12}$ is a linker selected from the above-mentioned group A and
R$^{30}$ is a substituent selected from the above-mentioned group B;
or A$^2$, R$^{30}$ and the cyclopropane ring may be taken together to form a optionally further substituted fused ring,
or R$^9$ of —CO$_2$R$^9$, R$^{20}$ and the cyclopropane ring may be taken together to form an optionally further substituted fused ring,
or R$^{20}$ and R$^{21}$ may be taken together with a carbon atom bonded thereto to form the following ring

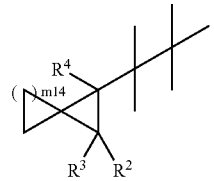

wherein m14 is selected from an integer ranging from 1 to 6;
or a pharmaceutically acceptable salt thereof.

2. The compound of claim 1, wherein the substituted C$_{3-14}$ hydrocarbon ring group or the substituted heterocyclic group in A$^1$ is a group of the following formula:

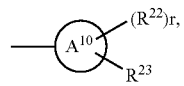

wherein
ring A$^{10}$ is selected from a C$_{3-14}$ hydrocarbon ring group and a heterocyclic group,
r is selected from an integer ranging from 1 to 4,
R$^{22}$ is —(CH$_2$)$_{m4}$—X$_4$—(CH$_2$)$_{n4}$—R$^{24}$,
wherein
m4 and n4 are the same or different and each is selected from 0 and an integer ranging from 1 to 6,
X$_4$ is a linker selected from the above-mentioned group A and
R$^{24}$ is a substituent selected from the above-mentioned group B,
wherein the substituents R$^{22}$ are the same or different when r is an integer selected from the range of 2 to 4, and $R^{23}$ is

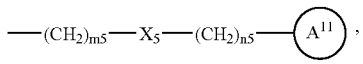

wherein
m5 and n5 are the same or different and each is selected from 0 and an integer ranging from 1 to 6,
$X_5$ is a linker selected from the above-mentioned group A and
ring $A^{11}$ is selected from a $C_{3-14}$ hydrocarbon ring group and a heterocyclic group, and the ring $A^{11}$ is optionally substituted by 1 to 5 groups of the formula "—$(CH_2)_{m6}$—$X_6$—$(CH_2)_{n6}$—$R^{25}$", which are the same or different,
wherein
m6 and n6 are the same or different and each is selected from 0 and an integer ranging from 1 to 6,
$X_6$ is a linker selected from the above-mentioned group A and
$R^{25}$ is a substituent selected from the above-mentioned group C;
or the ring $A^{10}$ and the ring $A^{11}$ may be taken together with a substituent thereof to form an optionally substituted fused ring group;
the optionally substituted $C_{3-14}$ hydrocarbon ring group or the optionally substituted heterocyclic group in $A^2$ is a group of the following formula:

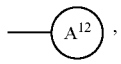

wherein
ring $A^{12}$ is selected from a $C_{3-14}$ hydrocarbon ring group and a heterocyclic group, and the ring $A^{12}$ is optionally substituted by 1 to 5 groups of the formula "—$(CH_2)_{m7}$—$X_7$—$(CH_2)_{n7}$—$R^{26}$", which are the same or different,
wherein
m7 and n7 are the same or different and each is selected from 0 and an integer ranging from 1 to 6,
$X_7$ is a linker selected from the above-mentioned group A and
$R^{26}$ is a substituent selected from the above-mentioned group C;
or $R^{26}$ may be linked with $R^{27}$, together with ring $A^{12}$ to form an optionally substituted fused ring group,
or $R^{26}$ may be linked with $R^9$ of —C(O)NHR$^9$ or $R^{30}$, together with the ring $A^{12}$ and the cyclopropane ring to form an optionally further substituted fused ring;
the optionally substituted $C_{3-14}$ hydrocarbon ring group or the optionally substituted heterocyclic group in $A^3$ is a group of the following formula:

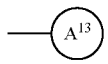

wherein
ring $A^{13}$ is selected from a $C_{3-14}$ hydrocarbon ring group and a heterocyclic group, and the ring $A^{13}$ is optionally substituted by 1 to 5 groups of the formula "—$(CH_2)_{m11}$—$X_{11}$—$(CH_2)_{n11}$—$R^{29}$", which are the same or different,
wherein
m11 and n11 are the same or different and each is selected from 0 and an integer ranging from 1 to 6,
$X_{11}$ is a linker selected from the above-mentioned group A and
$R^{29}$ is a substituent selected from the above-mentioned group C;
or a pharmaceutically acceptable salt thereof.

3. The compound of claim 2, wherein m and n are 0 and X is a single bond; or a pharmaceutically acceptable salt thereof.

4. The compound of claim 3, wherein $A^1$ is

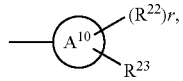

$R^{23}$ is 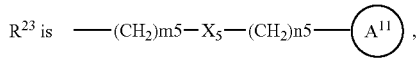

m5 and n5 are 0 and $X_5$ is a single bond; or a pharmaceutically acceptable salt thereof.

5. The compound of claim 4, wherein $R^4$ is selected from —$CO_2R^9$ and —C(O)NHOR$^9$; or a pharmaceutically acceptable salt thereof.

6. The compound of claim 5, wherein $R^9$ is a hydrogen atom; or a pharmaceutically acceptable salt thereof.

7. The compound of claim 6, wherein $R^2$ is —$(CH_2)_p$—$X_1$—$(CH_2)_q$-$A^2$; or a pharmaceutically acceptable salt thereof.

8. The compound of claim 7, wherein p and q are 0 and $X_1$ is a single bond; or a pharmaceutically acceptable salt thereof.

9. The compound of claim 1, which is selected from the group consisting of
4-[5-((1S,2R)-1-Carboxy-2-phenyl-cyclopropylsulfamoyl)-thiophen-2-yl]-3,6-dihydro-2H-pyridine-1-carboxylic acid tert-butyl ester,
(1S,2R)-2-Phenyl-1-[5-(1,2,3,6-tetrahydro-pyridin-4-yl)-thiophene-2-sulfonylamino]-cyclopropanecarboxylic acid,
4-[5-((1S,2R)-1-Carboxy-2-phenyl-cyclopropylsulfamoyl)-thiophen-2-yl]-3,6-dihydro-2H-pyridine-1-carboxylic acid methyl ester,
(1S,2R,3R)-1-[5-(4-Ethynyl-pyrazol-1-yl)-thiophene-2-sulfonylamino]-2-methyl-3-phenyl-cyclopropanecarboxylic acid,
(1S,2R,3R)-2-Methyl-3-phenyl-1-[4-(5-trifluoromethyl-pyridin-2-yl)-piperazine-1-sulfonylamino]-cyclopropanecarboxylic acid,
(1S,2R)-2-Methyl-2-phenyl-1-[5-(5-trifluoromethyl-isoxazol-3-yl)-thiophene-2-sulfonylamino]-cyclopropanecarboxylic acid,
(1S,2R,3R)-2-Methyl-3-phenyl-1-[5-(5-trifluoromethyl-isoxazol-3-yl)-thiophene-2-sulfonylamino]-cyclopropanecarboxylic acid,
(1R*,1aS*,8bS*)-1-[5-(4-Chloro-phenyl)-thiophene-2-sulfonylamino]-1,1a,2,3,4,8b-hexahydro-benzo[a]cyclopropan[c]cycloheptene-1-carboxylic acid,
(1S,2R,3R)-1-{5-[5-(1,1-Difluoro-ethyl)-isoxazol-3-yl]-thiophene-2-sulfonylamino}-2-methyl-3-phenyl-cyclopropanecarboxylic acid, (1R*,2R*,3R*)-2-Hydroxymethyl-3-phenyl-1-[5-(5-trifluoromethyl-isoxazol-3-yl)-thiophene-2-sulfonylamino]-cyclopropanecarboxylic acid,
(1S,2R,3R)-2-Methyl-3-phenyl-1-(4-phenylcarbamoyl-piperazine-1-sulfonylamino)-cyclopropanecarboxylic acid,
(1S,2R)-1-[5-(3-Amino-4-chloro-phenyl)-thiophene-2-sulfonylamino]-2-methyl-2-phenyl-cyclopropanecarboxylic acid,
(1R*,1aS*,6aS*)-1-[4-(3,5-Dichloro-benzyloxy)-benzenesulfonylamino]-1,1a,6,6a-tetrahydro-cyclopropa[a]indene-1-carboxylic acid hydroxyamide,
(1R*,2S*)-1-[5-(2-Methyl-5-trifluoromethyl-2H-pyrazol-3-yl)-thiophene-2-sulfonylamino]-2-phenyl-cyclopropanecarboxylic acid,
(1R*,2S*)-1-[3-(4-Chloro-phenoxy)-azetidine-1-sulfonylamino]-2-phenyl-cyclopropanecarboxylic acid,
(1R*,2S*)-1-[5-(1-Methyl-5-trifluoromethyl-1H-pyrazol-3-yl)-thiophene-2-sulfonylamino]-2-phenyl-cyclopropanecarboxylic acid,
(1R*,2S*)-2-Phenyl-1-[5-(4-trifluoromethoxy-phenyl)-thiophene-2-sulfonylamino]-cyclopropanecarboxylic acid,
(1R*,2S*)-1-[5-(3,4-Dichloro-phenyl)-thiophene-2-sulfonylamino]-2-phenyl-cyclopropanecarboxylic acid,
(1R*,2S*)-2-Phenyl-1-[5-(4-trifluoromethyl-phenyl)-thiophene-2-sulfonylamino]-cyclopropanecarboxylic acid,
(1R*,2S*)-2-Phenyl-1-(5-p-tolyl-thiophene-2-sulfonylamino)-cyclopropanecarboxylic acid,
(1R*,2S*)-1-[5-(4-Fluoro-phenyl)-thiophene-2-sulfonylamino]-2-phenyl-cyclopropanecarboxylic acid,
(1R*,2S*)-1-[5-(4-Chloro-phenyl)-thiophene-2-sulfonylamino]-2-[2-(pyridin-3-ylmethoxy)-phenyl]-cyclopropanecarboxylic acid,
(1R*,2S*)-1-[5-(4-Chloro-phenyl)-thiophene-2-sulfonylamino]-2-[2-(pyridin-2-ylmethoxy)-phenyl]-cyclopropanecarboxylic acid,
(1R*,2S*)-1-[5-(4-Chloro-phenyl)-thiophene-2-sulfonylamino]-2-[2-(pyridin-3-yloxy)-phenyl]-cyclopropanecarboxylic acid,
(1R*,2S*)-1-[5-(4-Chloro-phenyl)-thiophene-2-sulfonylamino]-2-[2-(2-hydroxy-2-methyl-propoxy)-phenyl]-cyclopropanecarboxylic acid,
(1S,2R)-1-[5-(5-Methyl-thiazol-2-yl)-thiophene-2-sulfonylamino]-2-phenyl-cyclopropanecarboxylic acid,
(1S,2R)-1-[5-(6-Chloro-pyridin-3-yl)-thiophene-2-sulfonylamino]-2-phenyl-cyclopropanecarboxylic acid,
(1R*,2S*)-2-Phenyl-1-[4-(3-trifluoromethyl-phenyl)-piperazine-1-sulfonylamino]-cyclopropanecarboxylic acid,
(1R*,2S*)-2-Phenyl-1-[4-(4-trifluoromethyl-phenyl)-piperazine-1-sulfonylamino]-cyclopropanecarboxylic acid,
(1R*,2S*)-1-[4-(4-Chloro-3-trifluoromethyl-phenyl)-piperazine-1-sulfonylamino]-2-phenyl-cyclopropanecarboxylic acid,
(1R*,2S*)-1-[4-(3-Chloro-phenyl)-piperazine-1-sulfonylamino]-2-phenyl-cyclopropanecarboxylic acid,
(1R*,2S*)-1-[5-(4-Chloro-phenyl)-thiophene-2-sulfonylamino]-2-[3-(pyridin-3-ylaminomethyl)-phenyl]-cyclopropanecarboxylic acid,
(1S,2R)-1-[5-(6-Methoxy-pyridazin-3-yl)-thiophene-2-sulfonylamino]-2-phenyl-cyclopropanecarboxylic acid,
(1S,2R)-1-(5'-Cyano-[2,2']bithiophenyl-5-sulfonylamino)-2-phenyl-cyclopropanecarboxylic acid,
(1S,2R)-1-[5-(5-Hydroxy-5-trifluoromethyl-4,5-dihydro-isoxazol-3-yl)-thiophene-2-sulfonylamino]-2-phenyl-cyclopropanecarboxylic acid,
(1R*,2S*)-2-(3-Benzyloxy-phenyl)-1-[5-(4-chloro-phenyl)-thiophene-2-sulfonylamino]-cyclopropanecarboxylic acid,
(1R*,2S*)-1-[5-(4-Chloro-phenyl)-thiophene-2-sulfonylamino]-2-[3-(methyl-pyridin-3-ylmethyl-amino)-phenyl]-cyclopropanecarboxylic acid,
(1R*,2S*)-2-Benzyl-1-[5-(4-chloro-phenyl)-thiophene-2-sulfonylamino]-cyclopropanecarboxylic acid,
(1S,2R)-1-(5'-Methyl-[2,2']bithiophenyl-5-sulfonylamino)-2-phenyl-cyclopropanecarboxylic acid,
(1R*,2S*)-1-[5-(4-Chloro-phenyl)-thiophene-2-sulfonylamino]-2-(4'-methyl-biphenyl-2-yl)-cyclopropanecarboxylic acid,
(1R*,2S*)-1-[5-(4-Chloro-phenyl)-thiophene-2-sulfonylamino]-2-cyclohexyl-cyclopropanecarboxylic acid,
(1R*,2S*)-1-[5-(4-Chloro-phenyl)-thiophene-2-sulfonylamino]-2-[3-(2-hydroxy-2-methyl-propoxy)-phenyl]-cyclopropanecarboxylic acid,
(1S,2R)-2-Phenyl-1-[5-(5-trifluoromethyl-isoxazol-3-yl)-thiophene-2-sulfonylamino]-cyclopropanecarboxylic acid,
(1S,2R)-2-Phenyl-1-[5-(5-trifluoromethyl-[1,2,4]oxadiazol-3-yl)-thiophene-2-sulfonylamino]-cyclopropanecarboxylic acid,
(1S,2R)-1-[5-(5-Pentafluoroethyl-[1,2,4]oxadiazol-3-yl)-thiophene-2-sulfonylamino]-2-phenyl-cyclopropanecarboxylic acid,
(1R*,2S*)-1-[5-(4-Chloro-phenyl)-thiophene-2-sulfonylamino]-2-vinyl-cyclopropanecarboxylic acid,
(1R*,2S*)-1-[5-(4-Chloro-phenyl)-thiophene-2-sulfonylamino]-2-(4-oxo-4H-benzo[d][1,2,3]triazin-3-ylmethyl)-cyclopropanecarboxylic acid,
(1R*,2R*)-1-[5-(4-Chloro-phenyl)-thiophene-2-sulfonylamino]-2-ethyl-cyclopropanecarboxylic acid,
(1R*,2S*)-1-[5-(4-Chloro-phenyl)-thiophene-2-sulfonylamino]-2-[2-(2-dimethylamino-ethoxy)-phenyl]-cyclopropanecarboxylic acid,
(1S,2R)-1-[5-(2-Methyl-thiazol-4-yl)-thiophene-2-sulfonylamino]-2-phenyl-cyclopropanecarboxylic acid,
(1S,2R)-1-[5-(5-Methyl-[1,2,4]oxadiazol-3-yl)-thiophene-2-sulfonylamino]-2-phenyl-cyclopropanecarboxylic acid,
(1R*,2R*)-1-[5-(4-Chloro-phenyl)-thiophene-2-sulfonylamino]-2-phenoxymethyl-cyclopropanecarboxylic acid,
(1R*,2S*)-2-[2-(2-tert-Butylamino-ethoxy)-phenyl]-1-[5-(4-chloro-phenyl)-thiophene-2-sulfonylamino]-cyclopropanecarboxylic acid,
(1S,2R)-1-[5-(4,4-Dimethyl-4,5-dihydro-oxazol-2-yl)-thiophene-2-sulfonylamino]-2-phenyl-cyclopropanecarboxylic acid,
(1S,2R)-1-[5-(2-Methyl-thiazol-5-yl)-thiophene-2-sulfonylamino]-2-phenyl-cyclopropanecarboxylic acid,
(1R*,2S*)-1-[5-(5-Chloro-pyridin-2-yl)-thiophene-2-sulfonylamino]-2-(3-pyrazol-1-ylmethyl-phenyl)-cyclopropanecarboxylic acid,
(1R*,2S*)-1-[5-(5-Chloro-pyridin-2-yl)-thiophene-2-sulfonylamino]-2-(3-methoxymethyl-phenyl)-cyclopropanecarboxylic acid,
(1R*,2S*)-1-[5-(4-Chloro-phenyl)-thiophene-2-sulfonylamino]-2-cyclobutyl-cyclopropanecarboxylic acid,
(1R*,2S*)-1-[5-(4-Chloro-phenyl)-thiophene-2-sulfonylamino]-2-isopropyl-cyclopropanecarboxylic acid, (1S,2R)-2-Phenyl-1-[5-(4-trifluoromethyl-thiazol-2-yl)-thiophene-2-sulfonylamino]-cyclopropanecarboxylic acid,
(1R*,2S*)-1-[5-(4-Chloro-phenyl)-thiophene-2-sulfonylamino]-2-cyclopentyl-cyclopropanecarboxylic acid,
(1R*,2S*)-2-tert-Butyl-1-[5-(4-chloro-phenyl)-thiophene-2-sulfonylamino]-cyclopropanecarboxylic acid,
(1R*,2S*)-1-[5-(4-Chloro-phenyl)-thiophene-2-sulfonylamino]-2-(2-hydroxymethyl-phenyl)-cyclopropanecarboxylic acid,
(1R*,2S*)-1-[4-(4-Methoxy-phenyl)-piperazine-1-sulfonylamino]-2-phenyl-cyclopropanecarboxylic acid,
(1R*,2S*)-1-[5-(4-Hydroxy-phenyl)-thiophene-2-sulfonylamino]-2-phenyl-cyclopropanecarboxylic acid,
(1R*,2S*)-1-(5-Acetyl-thiophene-2-sulfonylamino)-2-phenyl-cyclopropanecarboxylic acid,
(1R*,2S*)-1-[4-(4-Fluoro-phenyl)-piperazine-1-sulfonylamino]-2-phenyl-cyclopropanecarboxylic acid,
(1R*,2S*)-2-Phenyl-1-[4-(5-trifluoromethyl-pyridin-2-yl)-piperazine-1-sulfonylamino]-cyclopropanecarboxylic acid,
(1R*,2S*)-1-[5-(4-Chloro-phenyl)-thiophene-2-sulfonylamino]-2-{3-[(2-methoxy-ethyl)-methyl-carbamoyl]-phenyl}-cyclopropanecarboxylic acid,
(1R*,2S*)-1-[5-(4-Chloro-phenyl)-thiophene-2-sulfonylamino]-2-pyridin-3-yl-cyclopropanecarboxylic acid,
(1R*,2S*)-1-[5-(4-Chloro-phenyl)-thiophene-2-sulfonylamino]-2-{2-[(2-methoxy-ethyl)-methyl-carbamoyl]-phenyl}-cyclopropanecarboxylic acid,
(1R*,2S*)-1-[5-(4-Chloro-phenyl)-thiophene-2-sulfonylamino]-2-[2-(2-hydroxy-ethylcarbamoyl)-phenyl]-cyclopropanecarboxylic acid,
(1R*,2S*)-1-[5-(4-Chloro-phenyl)-thiophene-2-sulfonylamino]-2-[3-(morpholine-4-carbonyl)-phenyl]-cyclopropanecarboxylic acid,
(1R*,2S*)-1-[5-(4-Chloro-phenyl)-thiophene-2-sulfonylamino]-2-[3-(2-hydroxy-1,1-dimethyl-ethylcarbamoyl)-phenyl]-cyclopropanecarboxylic acid,
(1R*,2S*)-1-[5-(4-Chloro-phenyl)-thiophene-2-sulfonylamino]-2-[3-(2-hydroxy-ethylcarbamoyl)-phenyl]-cyclopropanecarboxylic acid,
(1R*,2S*)-1-[5-(4-Chloro-phenyl)-thiophene-2-sulfonylamino]-2-[2-(morpholine-4-carbonyl)-phenyl]-cyclopropanecarboxylic acid,
(1R*,2S*)-1-[5-(4-Chloro-phenyl)-thiophene-2-sulfonylamino]-2-[2-(4,4-dimethyl-4,5-dihydro-oxazol-2-yl)-phenyl]-cyclopropanecarboxylic acid,
(1R*,2S*)-1-[5-(4-Chloro-phenyl)-thiophene-2-sulfonylamino]-2-[2-(2-hydroxy-1,1-dimethyl-ethylcarbamoyl)-phenyl]-cyclopropanecarboxylic acid,
(1R*,2S*)-1-[5-(2-Methyl-oxazol-5-yl)-thiophene-2-sulfonylamino]-2-phenyl-cyclopropanecarboxylic acid,
(1R*,2S*)-1-(4-Acetyl-benzenesulfonylamino)-2-phenyl-cyclopropanecarboxylic acid,
(1R*,2S*)-1-(5-Benzenesulfonyl-thiophene-2-sulfonylamino)-2-phenyl-cyclopropanecarboxylic acid,
(1R*,2S*)-1-(5-Chloro-thiophene-2-sulfonylamino)-2-phenyl-cyclopropanecarboxylic acid,
(1R*,2S*)-2-Phenyl-1-(thiophene-2-sulfonylamino)-cyclopropanecarboxylic acid,
(1S,2R)-1-{5-[5-(1,1-Difluoro-ethyl)-isoxazol-3-yl]-thiophene-2-sulfonylamino}-2-phenyl-cyclopropanecarboxylic acid,
(1S,2R)-1-[5-(5-Methyl-isoxazol-3-yl)-thiophene-2-sulfonylamino]-2-phenyl-cyclopropanecarboxylic acid,
(1R*,2S*)-1-[5-(4-Chloro-phenyl)-thiophene-2-sulfonylamino]-2-[3-(4-methyl-thiazol-2-yl)-phenyl]-cyclopropanecarboxylic acid,
(1R*,2S*)-1-[5-(2-Methyl-oxazol-4-yl)-thiophene-2-sulfonylamino]-2-phenyl-cyclopropanecarboxylic acid,
(1R*,2S*)-1-[5-(5-Chloro-2-methyl-oxazol-4-yl)-thiophene-2-sulfonylamino]-2-phenyl-cyclopropanecarboxylic acid,
(1R*,2S*)-1-[5-(4-Chloro-phenyl)-thiophene-2-sulfonylamino]-2-(2-{[(2-methoxy-ethyl)-methyl-amino]-methyl}-phenyl)-cyclopropanecarboxylic acid,
(1S,2R)-2-Phenyl-1-[5-(5-propyl-isoxazol-3-yl)-thiophene-2-sulfonylamino]-cyclopropanecarboxylic acid,
(1R*,2S*)-1-[5-(4-Chloro-phenyl)-thiophene-2-sulfonylamino]-2-(2-morpholin-4-ylmethyl-phenyl)-cyclopropanecarboxylic acid,
(1S,2R)-1-[5-(5-Ethyl-isoxazol-3-yl)-thiophene-2-sulfonylamino]-2-phenyl-cyclopropanecarboxylic acid,
(1R*,2S*)-2-Phenyl-1-(5-propylcarbamoyl-thiophene-2-sulfonylamino)-cyclopropanecarboxylic acid,
(1R*,2S*)-1-(5-Isopropylcarbamoyl-thiophene-2-sulfonylamino)-2-phenyl-cyclopropanecarboxylic acid,
(1R*,2S*)-1-(5-Cyclopentylcarbamoyl-thiophene-2-sulfonylamino)-2-phenyl-cyclopropanecarboxylic acid,
(1R*,2S*)-2-Phenyl-1-(5-phenylcarbamoyl-thiophene-2-sulfonylamino)-cyclopropanecarboxylic acid,
(1R*,2S*)-2-Phenyl-1-[5-(3,3,3-trifluoro-propylcarbamoyl)-thiophene-2-sulfonylamino]-cyclopropanecarboxylic acid,
(1S,2R)-1-[5-(5-Fluoromethyl-isoxazol-3-yl)-thiophene-2-sulfonylamino]-2-phenyl-cyclopropanecarboxylic acid,
(1S,2R)-1-[5-(5-Difluoromethyl-isoxazol-3-yl)-thiophene-2-sulfonylamino]-2-phenyl-cyclopropanecarboxylic acid,
(1S,2R)-1-(7-Bromo-9H-fluorene-2-sulfonylamino)-2-methyl-2-phenyl-cyclopropanecarboxylic acid,
(1S,2R)-1-[5-(4-Chloro-phenyl)-thiophene-2-sulfonylamino]-2-methyl-2-phenyl-cyclopropanecarboxylic acid,
(1S,2R)-1-(5'-Difluoromethyl-[2,2']bithiophenyl-5-sulfonylamino)-2-phenyl-cyclopropanecarboxylic acid,
5-((1R*,2S*)-1-Carboxy-2-phenyl-cyclopropylsulfamoyl)-thiophene-2-carboxylic acid,
(1R*,2S*)-1-(5-Ethylcarbamoyl-thiophene-2-sulfonylamino)-2-phenyl-cyclopropanecarboxylic acid,
(1R*,2S*)-1-(5-Cyclopropylcarbamoyl-thiophene-2-sulfonylamino)-2-phenyl-cyclopropanecarboxylic acid,
(1R*,2S*)-2-Phenyl-1-[5-(2,2,2-trifluoro-ethylcarbamoyl)-thiophene-2-sulfonylamino]-cyclopropanecarboxylic acid,
(1S,2R)-1-{5-[5-(1,1-Difluoro-ethyl)-isoxazol-3-yl]-thiophene-2-sulfonylamino}-2-methyl-2-phenyl-cyclopropanecarboxylic acid,
(1R*,2S*)-2-[3-(2-Acetoxy-ethyl)-phenyl]-1-[5-(4-chloro-phenyl)-thiophene-2-sulfonylamino]-cyclopropanecarboxylic acid,
(1R*,2S*)-1-[5-(4-Chloro-phenyl)-thiophene-2-sulfonylamino]-2-[3-(2-hydroxy-ethyl)-phenyl]-cyclopropanecarboxylic acid,
(1S,2R)-1-[5-(5-Methoxymethyl-isoxazol-3-yl)-thiophene-2-sulfonylamino]-2-phenyl-cyclopropanecarboxylic acid,
(1S,2R)-1-[5-(5-Pentafluoroethyl-isoxazol-3-yl)-thiophene-2-sulfonylamino]-2-phenyl-cyclopropanecarboxylic acid, (1S,2R)-2-Methyl-1-[5-(5-pentafluoroethyl-isoxazol-3-yl)-thiophene-2-sulfonylamino]-2-phenyl-cyclopropanecarboxylic acid,
(1S,2R)-1-(5-Benzo[b]thiophen-2-yl-thiophene-2-sulfonylamino)-2-phenyl-cyclopropanecarboxylic acid,
(1S,2R)-2-Phenyl-1-[5-(5-phenyl-isoxazol-3-yl)-thiophene-2-sulfonylamino]-cyclopropanecarboxylic acid,
(1S,2R)-1-[5-(5-Fluoromethyl-[1,2,4]thiadiazol-3-yl)-thiophene-2-sulfonylamino]-2-phenyl-cyclopropanecarboxylic acid,
(1R*,2S*)-2-Phenyl-1-(5-propionyl-thiophene-2-sulfonylamino)-cyclopropanecarboxylic acid,
(1R*,2S*)-1-(5-Butyryl-thiophene-2-sulfonylamino)-2-phenyl-cyclopropanecarboxylic acid,
(1S,2R)-1-(5-Benzo[b]thiophen-3-yl-thiophene-2-sulfonylamino)-2-phenyl-cyclopropanecarboxylic acid,
(1S,2R)-1-[5-(5-Difluoromethyl-isothiazol-3-yl)-thiophene-2-sulfonylamino]-2-phenyl-cyclopropanecarboxylic acid,
(1S,2R)-1-[5-(5-Fluoromethyl-isothiazol-3-yl)-thiophene-2-sulfonylamino]-2-phenyl-cyclopropanecarboxylic acid,
(1S,2R)-1-[5-(5-Fluoromethyl-isothiazol-3-yl)-thiophene-2-sulfonylamino]-2-methyl-2-phenyl-cyclopropanecarboxylic acid,
(1S,2R)-1-(5-Benzofuran-2-yl-thiophene-2-sulfonylamino)-2-phenyl-cyclopropanecarboxylic acid,
(1R*,2R*)-1-[5-(4-Chloro-phenyl)-thiophene-2-sulfonylamino]-2-isopropy-2-phenyl-cyclopropanecarboxylic acid,
(1S,2R)-1-{5-[5-(1,1-Difluoro-ethyl)-isothiazol-3-yl]-thiophene-2-sulfonylamino}-2-phenyl-cyclopropanecarboxylic acid,
(1R*,2S*)-2-Phenyl-1-(1,3,4,9-tetrahydro-beta-carboline-2-sulfonylamino)-cyclopropanecarboxylic acid,
(1R*,2S*)-2-Phenyl-1-(3-phenyl-5,6-dihydro-8H-[1,2,4]triazolo[4,3-a]pyrazine-7-sulfonylamino)-cyclopropanecarboxylic acid,
(1R*,2S*)-2-Phenyl-1-(2-phenyl-7,8-dihydro-5H-pyrido[4,3-d]pyrimidine-6-sulfonylamino)-cyclopropanecarboxylic acid,
(1R*,2S*)-1-[4-(4-Chloro-phenoxy)-piperidine-1-sulfonylamino]-2-phenyl-cyclopropanecarboxylic acid,
(1R*,2S*)-1-[5-(4-Chloro-phenyl)-thiophene-2-sulfonylamino]-2-ethyl-2-phenyl-cyclopropanecarboxylic acid,
(1S,2R)-1-[5-(3-Hydroxy-3-methyl-but-1-ynyl)-thiophene-2-sulfonylamino]-2-phenyl-cyclopropanecarboxylic acid,
(1S,2R)-1-[5-(5-Chloro-pyridin-2-yl)-thiophene-2-sulfonylamino]-2-methyl-2-phenyl-cyclopropanecarboxylic acid,
(1S,2R)-1-[5-(3,3-Dimethyl-but-1-ynyl)-thiophene-2-sulfonylamino]-2-phenyl-cyclopropanecarboxylic acid,
(1S,2R)-1-(5-Pent-1-ynyl-thiophene-2-sulfonylamino)-2-phenyl-cyclopropanecarboxylic acid,
(1S,2R)-2-Phenyl-1-[5-(3-trifluoromethyl-phenyl)-thiophene-2-sulfonylamino]-cyclopropanecarboxylic acid,
(1S,2R)-1-(5-Indolizin-2-yl-thiophene-2-sulfonylamino)-2-phenyl-cyclopropanecarboxylic acid,
(1S,2R)-2-(3-Bromo-phenyl)-1-[5-(4-chloro-phenyl)-thiophene-2-sulfonylamino]-cyclopropanecarboxylic acid,
(1S,2R)-1-[4-(5-Fluoromethyl-isoxazol-3-yl)-benzenesulfonylamino]-2-phenyl-cyclopropanecarboxylic acid,
(1S,2S)-2-((R)-3-Benzyl-2-oxo-oxazolidin-5-yl)-1-[5-(4-chloro-phenyl)-thiophene-2-sulfonylamino]-cyclopropanecarboxylic acid,
(1S,2S)-2-((S)-3-Benzyl-2-oxo-oxazolidin-5-yl)-1-[5-(4-chloro-phenyl)-thiophene-2-sulfonylamino]-cyclopropanecarboxylic acid,
(1S,2R)-2-Phenyl-1-((E)-2-phenyl-ethenesulfonylamino)-cyclopropanecarboxylic acid,
(1S,2R)-1-(7-Fluoro-9H-fluorene-2-sulfonylamino)-2-phenyl-cyclopropanecarboxylic acid,
(1S,2R)-1-(7-Chloro-9H-fluorene-2-sulfonylamino)-2-phenyl-cyclopropanecarboxylic acid,
(1R*,2S*)-1-(4-Phenoxy-piperidine-1-sulfonylamino)-2-phenyl-cyclopropanecarboxylic acid,
(1R*,2S*)-2-Phenyl-1-[4-(4-trifluoromethyl-phenoxy)-piperidine-1-sulfonylamino]-cyclopropanecarboxylic acid,
(1R*,2S*)-1-[4-(4-Fluoro-phenoxy)-piperidine-1-sulfonylamino]-2-phenyl-cyclopropanecarboxylic acid,
(1R*,2S*)-2-Ethyl-1-(7-fluoro-9H-fluorene-2-sulfonylamino)-2-phenyl-cyclopropanecarboxylic acid,
1-[5-(4-Chloro-phenyl)-thiophene-2-sulfonylamino]-2,2-dimethyl-cyclopropanecarboxylic acid,
(1R*,2S*)-2-Phenyl-1-(4-phenyl-3,6-dihydro-2H-pyridine-1-sulfonylamino)-cyclopropanecarboxylic acid,
(1R*,2S*)-1-[4-(4-Chloro-phenyl)-3,6-dihydro-2H-pyridine-1-sulfonylamino]-2-phenyl-cyclopropanecarboxylic acid,
(1R,2S)-2-(3-Bromo-phenyl)-1-[5-(4-chloro-phenyl)-thiophene-2-sulfonylamino]-cyclopropanecarboxylic acid,
(1S,2R)-1-[(E)-2-(4-Chloro-phenyl)-ethenesulfonylamino]-2-phenyl-cyclopropanecarboxylic acid,
(1S,2R)-1-[4-(5-Difluoromethyl-isoxazol-3-yl)-benzenesulfonylamino]-2-phenyl-cyclopropanecarboxylic acid,
(1S,2R)-1-[(E)-2-(3-Chloro-phenyl)-ethenesulfonylamino]-2-phenyl-cyclopropanecarboxylic acid,
(1S,2R)-2-Phenyl-1-[5-(4,5,6,7-tetrahydro-benzo[d]isoxazol-3-yl)-thiophene-2-sulfonylamino]-cyclopropanecarboxylic acid,
(1R*,2S*)-1-[4-(5-Bromo-pyrimidin-2-yl)-piperazine-1-sulfonylamino]-2-phenyl-cyclopropanecarboxylic acid,
(1R*,2S*)-1-(8-Chloro-3,4-dihydro-1H-pyrazino[1,2-a]indole-2-sulfonylamino)-2-phenyl-cyclopropanecarboxylic acid,
(1R*,2S*)-1-(4-Benzothiazol-2-yl-piperazine-1-sulfonylamino)-2-phenyl-cyclopropanecarboxylic acid,
(1R*,2S*)-1-(4-Benzyl-piperazine-1-sulfonylamino)-2-phenyl-cyclopropanecarboxylic acid,
(1R*,2S*)-1-[4-(4-Chloro-benzoyl)-piperazine-1-sulfonylamino]-2-phenyl-cyclopropanecarboxylic acid,
(1R*,2S*)-1-[4-(3-Chloro-benzoyl)-piperazine-1-sulfonylamino]-2-phenyl-cyclopropanecarboxylic acid,
(1S,2R)-2-Phenyl-1-[(E)-2-(4-trifluoromethyl-phenyl)-ethenesulfonylamino]-cyclopropanecarboxylic acid,
(1S,2R)-2-Phenyl-1-[(E)-2-(3-trifluoromethyl-phenyl)-ethenesulfonylamino]-cyclopropanecarboxylic acid,
(1S,2R)-1-[5-(2-Oxo-pyrrolidin-1-yl)-thiophene-2-sulfonylamino]-2-phenyl-cyclopropanecarboxylic acid,
(1S,2R)-1-[5-(2-Oxo-piperidin-1-yl)-thiophene-2-sulfonylamino]-2-phenyl-cyclopropanecarboxylic acid, (1R*,2S*)-1-(5-Amino-thiophene-2-sulfonylamino)-2-phenyl-cyclopropanecarboxylic acid,
(1S,2R)-1-(2-Cyclohexyl-2,3-dihydro-1H-isoindole-5-sulfonylamino)-2-phenyl-cyclopropanecarboxylic acid,
(1R*,2S*)-2-(2-Bromo-phenyl)-1-[5-(4-chloro-phenyl)-thiophene-2-sulfonylamino]-cyclopropanecarboxylic acid,
(1R,2S)-2-(2-Bromo-phenyl)-1-[5-(4-chloro-phenyl)-thiophene-2-sulfonylamino]-cyclopropanecarboxylic acid,
(1S,2R)-2-(3-Bromo-phenyl)-1-[5-(5-trifluoromethyl-isoxazol-3-yl)-thiophene-2-sulfonylamino]-cyclopropanecarboxylic acid,
(1S,2R)-1-[5-(4-Chloro-phenyl)-thiophene-2-sulfonylamino]-2-(3-nitro-phenyl)-cyclopropanecarboxylic acid,
(1S,2R)-2-Phenyl-1-[5-(3-trifluoromethyl-isoxazol-5-yl)-thiophene-2-sulfonylamino]-cyclopropanecarboxylic acid,
(1S,2R)-1-[5-(1-Methyl-1,2,3,6-tetrahydro-pyridin-4-yl)-thiophene-2-sulfonylamino]-2-phenyl-cyclopropanecarboxylic acid,
(1S,2R)-1-[5-(4-Chloro-phenyl)-thiophene-2-sulfonylamino]-2-{3-[(pyridin-3-ylmethyl)-amino]-phenyl}-cyclopropanecarboxylic acid,
(1S,2R)-2-(3-amino-phenyl)-1-[5-(4-chloro-phenyl)-thiophene-2-sulfonylamino]-cyclopropanecarboxylic acid,
3-{(1R,2S)-2-Carboxy-2-[5-(4-chloro-phenyl)-thiophene-2-sulfonylamino]-cyclopropyl}-benzoic acid,
(1S,2R)-1-[5-(4-Chloro-phenyl)-thiophene-2-sulfonylamino]-2-(3-dimethylamino-phenyl)-cyclopropanecarboxylic acid,
(1S,2R)-1-[5-(1-Acetyl-1,2,3,6-tetrahydro-pyridin-4-yl)-thiophene-2-sulfonylamino]-2-phenyl-cyclopropanecarboxylic acid,
(1S,2R)-2-(2-Bromo-phenyl)-1-[5-(4-chloro-phenyl)-thiophene-2-sulfonylamino]-cyclopropanecarboxylic acid,
(1R*,2S*)-2-[2-(2-Carboxy-ethyl)-phenyl]-1-[5-(4-chloro-phenyl)-thiophene-2-sulfonylamino]-cyclopropanecarboxylic acid,
(1R*,2S*)-2-[3-(2-Carboxy-ethyl)-phenyl]-1-[5-(4-chloro-phenyl)-thiophene-2-sulfonylamino]-cyclopropanecarboxylic acid,
(1R*,2S*)-2-(3-Carboxymethyl-phenyl)-1-[5-(4-chloro-phenyl)-thiophene-2-sulfonylamino]-cyclopropanecarboxylic acid,
(1S,2R)-1-[5-(4-Chloro-phenyl)-thiophene-2-sulfonylamino]-2-(3-hydroxymethyl-phenyl)-cyclopropanecarboxylic acid,
(1S,2R)-1-[5-(4-Chloro-phenyl)-thiophene-2-sulfonylamino]-2-[3-(methyl-pyridin-3-ylmethyl-amino)-phenyl]-cyclopropanecarboxylic acid,
(1R*,2S*)-3-{2-Carboxy-2-[5-(4-chloro-phenyl)-thiophene-2-sulfonylamino]-cyclopropyl}-benzoic acid methyl ester,
(1R*,2S*)-2-Phenyl-1-[4-(5-trifluoromethyl-pyridin-2-yl)-piperazine-1-sulfonylmethyl]-cyclopropanecarboxylic acid,
(1R*,2S*)-1-[4-(4-Chloro-phenyl)-piperazine-1-sulfonylmethyl]-2-phenyl-cyclopropanecarboxylic acid,
(1R*,2S*)-1-[5-(4-Chloro-phenyl)-thiophene-2-sulfonylmethyl]-2-phenyl-cyclopropanecarboxylic acid,
(1R*,2S*)-1-[5-(4-Chloro-phenyl)-thiophene-2-sulfonylamino]-2-(3-methoxycarbonylmethyl-phenyl)-cyclopropanecarboxylic acid,
(1R*,2S*)-1-[5-(4-Chloro-phenyl)-thiophene-2-sulfonylamino]-2-(3-dimethylcarbamoylmethyl-phenyl)-cyclopropanecarboxylic acid,
(1R*,2S*)-1-[5-(4-Chloro-phenyl)-thiophene-2-sulfonylamino]-2-[3-(2-morpholin-4-yl-2-oxo-ethyl)-phenyl]-cyclopropanecarboxylic acid,
(1R*,2S*)-1-[5-(4-Chloro-phenyl)-thiophene-2-sulfonylamino]-2-{3-[2-(4-methyl-piperazin-1-yl)-2-oxo-ethyl]-phenyl}-cyclopropanecarboxylic acid,
(1R,2S)-1-[5-(4-Chloro-phenyl)-thiophene-2-sulfonylamino]-2-phenyl-cyclopropanecarboxylic acid,
(1S,2R)-2-(2-Bromo-phenyl)-1-[5-(5-trifluoromethyl-isoxazol-3-yl)-thiophene-2-sulfonylamino]-cyclopropanecarboxylic acid,
(1R*,2S*)-1-[5-(4-Chloro-phenyl)-thiophene-2-sulfonylamino]-2-[2-(2-morpholin-4-yl-2-oxo-ethyl)-phenyl]-cyclopropanecarboxylic acid,
(1R*,2S*)-1-[5-(4-Chloro-phenyl)-thiophene-2-sulfonylamino]-2-{2-[2-(4-methyl-piperazin-1-yl)-2-oxo-ethyl]-phenyl}-cyclopropanecarboxylic acid,
(1R*,2S*)-2-{2-Carboxy-2-[5-(4-chloro-phenyl)-thiophene-2-sulfonylamino]-cyclopropyl}-benzoic acid,
(1R*,2S*)-1-[5-(4-Chloro-phenyl)-thiophene-2-sulfonylamino]-2-[3-(2-morpholin-4-yl-ethoxy)-phenyl]-cyclopropanecarboxylic acid,
(1R*,2S*)-1-[5-(4-Chloro-phenyl)-thiophene-2-sulfonylamino]-2-{3-[2-(4-methyl-piperazin-1-yl)-ethoxy]-phenyl}-cyclopropanecarboxylic acid,
(1R*,2S*)-2-(3-Nitro-phenyl)-1-[5-(5-trifluoromethyl-isoxazol-3-yl)-thiophene-2-sulfonylamino]-cyclopropanecarboxylic acid,
(1R*,2S*)-1-[5-(4-Chloro-phenyl)-thiophene-2-sulfonylamino]-2-[3-(4-methyl-piperazine-1-carbonyl)-phenyl]-cyclopropanecarboxylic acid,
(1R*,2S*)-2-(3-Amino-phenyl)-1-[5-(5-trifluoromethyl-isoxazol-3-yl)-thiophene-2-sulfonylamino]-cyclopropanecarboxylic acid,
(1R*,2R*)-2-(4-Bromo-phenyl)-1-[5-(4-chloro-phenyl)-thiophene-2-sulfonylamino]-cyclopropanecarboxylic acid,
(1R*,2S*)-2-(4-Bromo-phenyl)-1-[5-(4-chloro-phenyl)-thiophene-2-sulfonylamino]-cyclopropanecarboxylic acid,
(1R*,2S*)-1-[5-(4-Chloro-phenyl)-thiophene-2-sulfonylamino]-2-(2-dimethylcarbamoylmethyl-phenyl)-cyclopropanecarboxylic acid,
(1R*,2S*)-2-{2-Carboxy-2-[5-(4-chloro-phenyl)-thiophene-2-sulfonylamino]-cyclopropyl}-benzoic acid methyl ester,
(1S,2R)-1-[5-(4-Chloro-phenyl)-thiophene-2-sulfonylamino]-2-(2-hydroxymethyl-phenyl)-cyclopropanecarboxylic acid,
(1'R*,2'S*)-2-Acetyl-1,2,3,4-tetrahydro-isoquinoline-4-spiro-2'-{1-[5-(4-chloro-phenyl)-hiophene-2-sulfonylamino]-1'-cyclopropanecarboxylic acid},
(1R*,2S*)-1-[5-(4-Chloro-phenyl)-thiophene-2-sulfonylamino]-2-[3-(2-methoxycarbonyl-ethyl)-phenyl]-cyclopropanecarboxylic acid,
(1R*,2S*)-1-[5-(4-Chloro-phenyl)-thiophene-2-sulfonylamino]-2-[3-(3-morpholin-4-yl-3-oxo-propyl)-phenyl]-cyclopropanecarboxylic acid, (1R*,2S*)-1-[5-(4-Chloro-phenyl)-thiophene-2-sulfonylamino]-2-{3-[3-(4-methyl-piperazin-1-yl)-3-oxo-propyl]-phenyl}-cyclopropanecarboxylic acid, (1R*,2S*)-1-[5-(4-Chloro-phenyl)-thiophene-2-sulfonylamino]-2-[3-(3-oxo-3-thiomorpholin-4-yl-propyl)-phenyl]-cyclopropanecarboxylic acid, (1R*,2S*)-2-(3-Carboxymethyl-phenyl)-1-[5-(5-trifluoromethyl-isoxazol-3-yl)-thiophene-2-sulfonylamino]-cyclopropanecarboxylic acid, (1R*,2S*)-2-{3-[(Pyridin-3-ylmethyl)-amino]-phenyl}-1-[5-(5-trifluoromethyl-isoxazol-3-yl)-thiophene-2-sulfonylamino]-cyclopropanecarboxylic acid, (1R*,2S*)-2-[3-(Methyl-pyridin-3-ylmethyl-amino)-phenyl]-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-(2-dimethylcarbamoyl-phenyl)-cyclopropanecarboxylic acid, (1R*,2S*)-1-[5-(4-Chloro-phenyl)-thiophene-2-sulfonylamino]-2-[2-(4-methyl-piperazine-1-carbonyl)-phenyl]-cyclopropanecarboxylic acid, (1R*,2S*)-2-(2-tert-Butoxycarbonylamino-phenyl)-1-[5-(4-chloro-phenyl)-thiophene-2-sulfonylamino]-cyclopropanecarboxylic acid, (1aR*,7bS*)-5-(4-Chloro-phenyl)-thiophene-2-sulfonic acid (2-oxo-1,2,3,7b-tetrahydro-3-aza-cyclopropa[a]naphthalen-1a-yl)-amide, (1R*,2S*)-2-(3-Methoxycarbonylmethyl-phenyl)-1-[5-(5-trifluoromethyl-isoxazol-3-yl)-thiophene-2-sulfonylamino]-cyclopropanecarboxylic acid, (1R*,2S*)-2-[3-(2-Morpholin-4-yl-2-oxo-ethyl)-phenyl]-1-[5-(5-trifluoromethyl-isoxazol-3-yl)-thiophene-2-sulfonylamino]-cyclopropanecarboxylic acid, (1R*,2S*)-2-{3-[2-(4-Methyl-piperazin-1-yl)-2-oxo-ethyl]-phenyl}-1-[5-(5-trifluoromethyl-isoxazol-3-yl)-thiophene-2-sulfonylamino]-cyclopropanecarboxylic acid, (1R*,2S*)-2-{3-[2-(4-Hydroxy-piperidin-1-yl)-2-oxo-ethyl]-phenyl}-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-[3-(3-dimethylamino-propionylamino)-phenyl]-cyclopropanecarboxylic acid, (1R*,2S*)-1-[5-(4-Chloro-phenyl)-thiophene-2-sulfonylamino]-2-{3-[3-(4-hydroxy-piperidin-1-yl)-3-oxo-propyl]-phenyl}-cyclopropanecarboxylic acid, (1R*,2S*)-2-(4-Benzyloxy-phenyl)-1-[5-(4-chloro-phenyl)-thiophene-2-sulfonylamino]-cyclopropanecarboxylic acid, (1R*,2S*)-1-[5-(4-Chloro-phenyl)-thiophene-2-sulfonylamino]-2-(4-hydroxymethyl-phenyl)-cyclopropanecarboxylic acid, (1R*,2S*)-1-[5-(4-Chloro-phenyl)-thiophene-2-sulfonylamino]-2-(3-hydroxy-propyl)-2-phenyl-cyclopropanecarboxylic acid, (1R*,2S*)-2-(3-Dimethylamino-phenyl)-1-[5-(5-trifluoromethyl-isoxazol-3-yl)-thiophene-2-sulfonylamino]-cyclopropanecarboxylic acid, (1R*,2R*)-1-[5-(4-Chloro-phenyl)-thiophene-2-sulfonylamino]-2-hydroxymethyl-2-phenyl-cyclopropanecarboxylic acid, (1R*,2S*)-2-[2-(3-Morpholin-4-yl-3-oxo-propyl)-phenyl]-1-[5-(5-trifluoromethyl-isoxazol-3-yl)-thiophene-2-sulfonylamino]-cyclopropanecarboxylic acid, (1R*,2S*)-2-[2-(2-Dimethylcarbamoyl-ethyl)-phenyl]-1-[5-(5-trifluoromethyl-isoxazol-3-yl)-thiophene-2-sulfonylamino]-cyclopropanecarboxylic acid, (1R*,2S*)-2-{2-[3-(4-Methyl-piperazin-1-yl)-3-oxo-propyl]-phenyl}-1-[5-(5-trifluoromethyl-isoxazol-3-yl)-thiophene-2-sulfonylamino]-cyclopropanecarboxylic acid, (1R*,2S*)-2-{3-[(4-trans-Hydroxy-cyclohexylcarbamoyl)-methyl]-phenyl}-1-[5-(5-trifluoromethyl-isoxazol-3-yl)-thiophene-2-sulfonylamino]-cyclopropanecarboxylic acid, (1R*,2S*)-2-[3-(3-Morpholin-4-yl-3-oxo-propyl)-phenyl]-1-[5-(5-trifluoromethyl-isoxazol-3-yl)-thiophene-2-sulfonylamino]-cyclopropanecarboxylic acid, (1R*,2S*)-2-{3-[3-(4-Methyl-piperazin-1-yl)-3-oxo-propyl]-phenyl}-1-[5-(5-trifluoromethyl-isoxazol-3-yl)-thiophene-2-sulfonylamino]-cyclopropanecarboxylic acid, (1R*,2S*)-2-[3-(3-Hydroxy-propyl)-phenyl]-1-[5-(5-trifluoromethyl-isoxazol-3-yl)-thiophene-2-sulfonylamino]-cyclopropanecarboxylic acid, (1R*,2S*,3S*)-1-[5-(4-Chloro-phenyl)-thiophene-2-sulfonylamino]-2-methyl-3-phenyl-cyclopropanecarboxylic acid, (1R*,2S*)-4-Methyl-piperazine-1-carboxylic acid 3-(3-{2-carboxy-2-[5-(5-trifluoromethyl-isoxazol-3-yl)-thiophene-2-sulfonylamino]-cyclopropyl}-phenyl)-propyl ester, (1R*,2S*)-Morpholine-4-carboxylic acid 3-(3-{2-carboxy-2-[5-(5-trifluoromethyl-isoxazol-3-yl)-thiophene-2-sulfonylamino]-cyclopropyl}-phenyl)-propyl ester, (1R*,2S*)-2-[2-(2-Hydroxy-ethyl)-phenyl]-1-[5-(5-trifluoromethyl-isoxazol-3-yl)-thiophene-2-sulfonylamino]-cyclopropanecarboxylic acid, (1S,2R)-1-[5-(4-Methyl-pyrazol-1-yl)-thiophene-2-sulfonylamino]-2-phenyl-cyclopropanecarboxylic acid, (1R*,2S*)-Morpholine-4-carboxylic acid 2-(2-{2-carboxy-2-[5-(5-trifluoromethyl-isoxazol-3-yl)-thiophene-2-sulfonylamino]-cyclopropyl}-phenyl)-ethyl ester, (1R*,2S*)-2-[2-(2-Morpholin-4-yl-2-oxo-ethyl)-phenyl]-1-[5-(5-trifluoromethyl-isoxazol-3-yl)-thiophene-2-sulfonylamino]-cyclopropanecarboxylic acid, (1R,2S)-1-(7-Fluoro-9H-fluorene-2-sulfonylamino)-2-phenyl-cyclopropanecarboxylic acid, (1R*,2S*)-1-[5-(4-Chloro-phenyl)-thiophene-2-sulfonylamino]-2-(4-morpholin-4-yl-phenyl)-cyclopropanecarboxylic acid, (1R*,2S*)-1-[5-(4-Chloro-phenyl)-thiophene-2-sulfonylamino]-2-[4-(4-methyl-piperazin-1-yl)-phenyl]-cyclopropanecarboxylic acid, (1R*,2R*)-1-[5-(4-Chloro-phenyl)-thiophene-2-sulfonylamino]-2-[4-(4-methyl-piperazin-1-yl)-phenyl]-cyclopropanecarboxylic acid, (1R*,2S*)-2-(3-Hydroxy-propyl)-2-phenyl-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-(3-morpholin-4-yl-propyl)-2-phenyl-cyclopropanecarboxylic acid, (1R*,2S*)-2-{3-[(Morpholine-4-carbonyl)-amino]-phenyl}-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-{3-[(morpholine-4-carbonyl)-amino]-phenyl}-cyclopropanecarboxylic acid, (1R*,2S*)-2-[2-(3-Hydroxy-propyl)-phenyl]-1-[5-(5-trifluoromethyl-isoxazol-3-yl)-thiophene-2-sulfonylamino]-cyclopropanecarboxylic acid, (1R*,2S*)-Morpholine-4-carboxylic acid 3-(2-{2-carboxy-2-[5-(5-trifluoromethyl-isoxazol-3-yl)-thiophene-2-sulfonylamino]-cyclopropyl}-phenyl)-propyl ester, (S)-2-Hydroxymethyl-pyrrolidine-1-carboxylic acid 3-(2-{(1R*,2S*)-2-carboxy-2-[5-(5-trifluoromethyl-isoxazol-3-yl)-thiophene-2-sulfonylamino]-cyclopropyl}-phenyl)-propyl ester, (R)-3-Hydroxy-pyrrolidine-1-carboxylic acid 3-(2-{(1R*,2S*)-2-carboxy-2-[5-(5-trifluoromethyl-isoxazol-3-yl)-thiophene-2-sulfonyiamino]-cyclopropyl}-phenyl)-propyl ester, (1S,2R)-1-[5-(4-Methyl-piperidin-1-yl)-thiophene-2-sulfonylamino]-2-phenyl-cyclopropanecarboxylic acid, (1R*,2S*)-2-(3-Morpholin-4-yl-phenyl)-1-[5-(5-trifluoromethyl-isoxazol-3-yl)-thiophene-2-sulfonylamino]-cyclopropanecarboxylic acid, (1R*,2S*)-2-[3-(Morpholine-4-carbonyl)-phenyl]-1-[5-(5-trifluoromethyl-isoxazol-3-yl)-thiophene-2-sulfonylamino]-cyclopropanecarboxylic acid, (1R*,2S*)-2-(3-{2-[(Morpholine-4-carbonyl)-amino]-ethyl}-phenyl)-1-[5-(5-trifluoromethyl-isoxazol-3-yl)-thiophene-2-sulfonylamino]-cyclopropanecarboxylic acid, (1R*,2S*)-2-[3-(2-Morpholin-4-yl-acetylamino)-phenyl]-1-[5-(5-trifluoromehyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-[3-(2-morpholin-4-yl-acetylamino)-phenyl]-cyclopropanecarboxylic acid, (1S,2R,3R)-1-[5-(4-Chloro-phenyl)-thiophene-2-sulfonylamino]-2-methyl-3-phenyl-cyclopropanecarboxylic acid, (1R*,2R*)-1-[5-(4-Chloro-phenyl)-thiophene-2-sulfonylamino]-2-(2-hydroxy-ethyl)-2-phenyl-cyclopropanecarboxylic acid, (1R*,2S*)-2-(3-Acetoxy-propyl)-2-phenyl-1-[5-(5-trifluoromethyl-isoxazol-3-yl)-thiophene-2-sulfonylamino]-cyclopropanecarboxylic acid, (1R*,2S*)-2-(4-Aminomethyl-phenyl)-1-[5-(4-chloro-phenyl)-thiophene-2-sulfonylamino]-cyclopropanecarboxylic acid, (1R*,2S*)-2-(4-Dimethylcarbamoyl-phenyl)-1-[5-(5-trifluoromethyl-isoxazol-3-yl)-thiophene-2-sulfonylamino]-cyclopropanecarboxylic acid, (1R*,2S*)-2-[3-(Morpholine-4-sulfonylamino)-phenyl]-1-[5-(5-trifluoromethyl-isoxazol-3-yl)-thiophene-2-sulfonylamino]-cyclopropanecarboxylic acid, (1R*,2S*)-2-[3-(2-Hydroxy-ethyl)-phenyl]-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-[3-(morpholine-4-sulfonylamino)-phenyl]-cyclopropanecarboxylic acid, (1R*,2S*)-2-[3-(2-Carbamoyloxy-ethyl)-phenyl]-1-[5-(5-trifluoromethyl-isoxazol-3-yl)-thiophene-2-sulfonylamino]-cyclopropanecarboxylic acid, (1R*,2S*)-2-(3-Acetoxy-propyl)-2-{4-[(2-methoxyethyl)-methyl-carbamoyl]-phenyl}-1-[5-(5-trifluoromethyl-isoxazol-3-yl)-thiophene-2-sulfonylamino]-cyclopropanecarboxylic acid, (1R*,2S*)-2-(3-Acetylamino-propyl)-1-[5-(4-chlorophenyl)-thiophene-2-sulfonylamino]-2-phenyl-cyclopropanecarboxylic acid, (1R*,2S*)-1-[5-(4-Chloro-phenyl)-thiophene-2-sulfonylamino]-2-phenyl-2-(3-pyrazol-1-yl-propyl)-cyclopropanecarboxylic acid, (1R*,3S*)-1-[5-(4-Chloro-phenyl)-thiophene-2-sulfonylamino]-2,2-dimethyl-3-phenyl-cyclopropanecarboxylic acid, (1R*,3S*)-2,2-Dimethyl-3-phenyl-1-[5-(5-trifluoromethyl-isoxazol-3-yl)-thiophene-2-sulfonylamino]-cyclopropanecarboxylic acid, (1R*,2S*)-2-[3-(2-Oxo-pyrrolidin-1-yl)-phenyl]-1-[5-(5-trifluoromethyl-isoxazol-3-yl)-thiophene-2-sulfonylamino]-cyclopropanecarboxylic acid, (1R*,1aS*,6aS*)-1-[5-(5-Trifluoromethyl-isoxazol-3-yl)-thiophene-2-sulfonylamino]-1,1a,6,6a-tetrahydrocyclopropa[a]indene-1-carboxylic acid, (1S,2R)-2-[4-(2-Carbamoyl-ethyl)-phenyl]-1-[5-(5-trifluoromethyl-isoxazol-3-yl)-thiophene-2-sulfonylamino]-cyclopropanecarboxylic acid, (1S,2R)-2-[4-(3-Morpholin-4-yl-3-oxo-propyl)-phenyl]-1-[5-(5-trifluoromethyl-isoxazol-3-yl)-thiophene-2-sulfonylamino]-cyclopropanecarboxylic acid, (1S,2R)-2-{4-[3-(4-Methyl-piperazin-1-yl)-3-oxo-propyl]-phenyl}-1-[5-(5-trifluoromethyl-isoxazol-3-yl)-thiophene-2-sulfonylamino]-cyclopropanecarboxylic acid, (1S,2R)-2-[4-(2-Methylcarbamoyl-ethyl)-phenyl]-1-[5-(5-trifluoromethyl-isoxazol-3-yl)-thiophene-2-sulfonylamino]-cyclopropanecarboxylic acid, (1S,2R)-2-[4-(2-Dimethylcarbamoyl-ethyl)-phenyl]-1-[5-(5-trifluoromethyl-isoxazol-3-yl)-thiophene-2-sulfonylamino]-cyclopropanecarboxylic acid, (1R*,2S*)-2-(3-Hydroxymethyl-phenyl)-1-[5-(5-trifluoromethyl-isoxazol-3-yl)-thiophene-2-sulfonylamino]-cyclopropanecarboxylic acid, (1R*,2S*)-2-(3-tert-Butoxycarbonylamino-propyl)-1-[5-(4-chloro-phenyl)-thiophene-2-sulfonylamino]-2-phenyl-cyclopropanecarboxylic acid, (1R*,2S*)-2-(3-Amino-propyl)-1-[5-(4-chloro-phenyl)-thiophene-2-sulfonylamino]-2-phenyl-cyclopropanecarboxylic acid, (1S,2R,3R)-1-(7-Bromo-9H-fluorene-2-sulfonylamino)-2-methyl-3-phenyl-cyclopropanecarboxylic acid, (1S,2R,3R)-2-Methyl-1-[5-(4-methyl-pyrazol-1-yl)-thiophene-2-sulfonylamino]-3-phenyl-cyclopropanecarboxylic acid, (1R,2S,3S)-2-Methyl-3-phenyl-1-[5-(5-trifluoromethyl-isoxazol-3-yl)-thiophene-2-sulfonylamino]-cyclopropanecarboxylic acid, (1R,2S)-2-(4-Aminomethyl-phenyl)-1-[5-(5-trifluoromethyl-isoxazol-3-yl)-thiophene-2-sulfonylamino]-cyclopropanecarboxylic acid, (1R,2S)-2-(4-Dimethylcarbamoylmethyl-phenyl)-1-[5-(5-trifluoromethyl-isoxazol-3-yl)-thiophene-2-sulfonylamino]-cyclopropanecarboxylic acid, (1R,2S)-2-[4-(2-Morpholin-4-yl-2-oxo-ethyl)-phenyl]-1-[5-(5-trifluoromethyl-isoxazol-3-yl)-thiophene-2-sulfonylamino]-cyclopropanecarboxylic acid, (1R,2S)-2-(4-Carbamoylmethyl-phenyl)-1-[5-(5-trifluoromethyl-isoxazol-3-yl)-thiophene-2-sulfonylamino]-cyclopropanecarboxylic acid, (1R,2S)-2-(4-Methylcarbamoylmethyl-phenyl)-1-[5-(5-trifluoromethyl-isoxazol-3-yl)-thiophene-2-sulfonylamino]-cyclopropanecarboxylic acid, (1R,2S)-2-{4-[2-(4-Methyl-piperazin-1-yl)-2-oxo-ethyl]-phenyl}-1-[5-(5-trifluoromethyl-isoxazol-3-yl)-thiophene-2-sulfonylamino]-cyclopropanecarboxylic acid, (1R*,2R*)-2-(2-Carbamoyloxy-ethyl)-1-[5-(4-chloro-phenyl)-thiophene-2-sulfonylamino]-2-phenyl-cyclopropanecarboxylic acid, (1S,2R,3R)-2-Methyl-3-phenyl-1-[5-(5-trifluoromethyl-isoxazol-3-yl)-thiophene-2-sulfonylamino]-cyclopropanecarboxylic acid amide, (1S,2R,3R)-2-Methyl-3-phenyl-1-[5-(5-trifluoromethyl-isoxazol-3-yl)-thiophene-2-sulfonylamino]-cyclopropanecarboxylic acid methylamide, (1R*,2S*)-1-[5-(4-Chloro-phenyl)-thiophene-2-sulfonylamino]-2-(3-cyclopentyloxycarbonylamino-propyl)-2-phenyl-cyclopropanecarboxylic acid, (1R*,2S*,3S*)-2-Ethyl-3-phenyl-1-[5-(5-trifluoromethyl-isoxazol-3-yl)-thiophene-2-sulfonylamino]-cyclopropanecarboxylic acid, (1S,2R)-2-[4-(2-Amino-ethyl)-phenyl]-1-[5-(5-trifluoromethyl-isoxazol-3-yl)-thiophene-2-sulfonylamino]-cyclopropanecarboxylic acid, (1R,2S)-2-[4-(2-Hydroxy-ethyl)-phenyl]-1-[5-(5-trifluoromethyl-isoxazol-3-yl)-thiophene-2-sulfonylamino]-cyclopropanecarboxylic acid, (1S,2R)-2-[4-(3-Hydroxy-propyl)-phenyl]-1-[5-(5-trifluoromethyl-isoxazol-3-yl)-thiophene-2-sulfonylamino]-cyclopropanecarboxylic acid, (1R*,2R*)-1-[5-(4-Chloro-phenyl)-thiophene-2-sulfonylamino]-2-(2-dimethylcarbamoyloxy-ethyl)-2-phenyl-cyclopropanecarboxylic acid, (1S,2R)-2-[3-(4-Isopropyl-piperazin-1-ylmethyl)-phenyl]-1-[5-(5-trifluoromethyl-isoxazol-3-yl)-thiophene-2-sulfonylamino]-cyclopropanecarboxylic acid, (1R*,1aS*,8bS*) 1-[5-(5-Trifluoromethyl-isoxazol-3-yl)-thiophene-2-sulfonylamino]-1,1a,2,3,4,8b-hexahydro-benzo[a]cyclopropan[c]cycloheptene-1-carboxylic acid, (1R*,2R*)-Morpholine-4-carboxylic acid 2-carboxy-1-phenyl-2-[5-(5-trifluoromethyl-isoxazol-3-yl)-thiophene-2-sulfonylamino]-cyclopropylmethyl ester, (1S,2R)-1-[5-(4-Chloro-benzoyl)-thiophene-2-sulfonylamino]-2-phenyl-cyclopropanecarboxylic acid, (1R*,2R*)-2-(2-Isopropoxy-ethylcarbamoyloxymethyl)-2-phenyl-1-[5-(5-trifluoromethyl-isoxazol-3-yl)-thiophene-2-sulfonylamino]-cyclopropanecarboxylic acid, (1R*,2R*)-2-Phenyl-2-[(R)-1-(tetrahydro-furan-2-yl)methylcarbamoyloxymethyl]-1-[5-(5-trifluoromethyl-isoxazol-3-yl)-thiophene-2-sulfonylamino]-cyclopropanecarboxylic acid, (1R*,2R*)-Piperidine-1-carboxylic acid 2-carboxy-1-phenyl-2-[5-(5-trifluoromethyl-isoxazol-3-yl)-thiophene-2-sulfonylamino]-cyclopropylmethyl ester, (1R*,2R*)-2-(3-Methyl-isoxazol-5-yl)-1-[5-(5-trifluoromethyl-isoxazol-3-yl)-thiophene-2-sulfonylamino]-cyclopropanecarboxylic acid, 5-(5-Trifluoromethyl-isoxazol-3-yl)-thiophene-2-sulfonic acid ((1S*,5S*,6S*)-2-oxo-6-phenyl-3-oxa-bicyclo[3.1.0]hex-1-yl)-amide, (1R*,2R*)-2-(5-Methyl-isoxazol-3-yl)-1-[5-(5-trifluoromethyl-isoxazol-3-yl)-thiophene-2-sulfonylamino]-cyclopropanecarboxylic acid, (1R*,2S*)-2-(5-Methyl-isoxazol-3-yl)-1-[5-(5-trifluoromethyl-isoxazol-3-yl)-thiophene-2-sulfonylamino]-cyclopropanecarboxylic acid, (1R*,2R*)-2-[5-(2-Hydroxy-ethyl)-isoxazol-3-yl]-1-[5-(5-trifluoromethyl-isoxazol-3-yl)-thiophene-2-sulfonylamino]-cyclopropanecarboxylic acid, (1R*,2S*)-2-[5-(2-Hydroxy-ethyl)-isoxazol-3-yl]-1-[5-(5-trifluoromethyl-isoxazol-3-yl)-thiophene-2-sulfonylamino]-cyclopropanecarboxylic acid, (1R*,2R*)-2-(5-Hydroxymethyl-isoxazol-3-yl)-1-[5-(5-trifluoromethyl-isoxazol-3-yl)-thiophene-2-sulfonylamino]-cyclopropanecarboxylic acid, (1R*,2S*)-2-(5-Hydroxymethyl-isoxazol-3-yl)-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-(3-isobutyrylamino-propyl)-2-phenyl-cyclopropanecarboxylic acid, (1R*,2R*)-2-Dimethylcarbamoyloxymethyl-2-phenyl-1-[5-(5-trifluoromethyl-isoxazol-3-yl)-thiophene-2-sulfonylamino]-cyclopropanecarboxylic acid, (1R*,2R*)-2-Ethylcarbamoyloxymethyl-2-phenyl-1-[5-(5-trifluoromethyl-isoxazol-3-yl)-thiophene-2-sulfonylamino]-cyclopropanecarboxylic acid, (1R*,2S*)-2-Morpholin-4-ylmethyl-2-phenyl-1-[5-(5-trifluoromethyl-isoxazol-3-yl)-thiophene-2-sulfonylamino]-cyclopropanecarboxylic acid, (1S,2R,3R)-2-Methyl-3-phenyl-1-[5-(5-trifluoromethyl-isoxazol-3-yl)-thiophene-2-sulfonylamino]-cyclopropanecarboxylic acid hydroxyamide, (1S,2R,3R)-1-[4-(2,4-Dichloro-benzyloxy)-benzenesulfonylamino]-2-methyl-3-phenyl-cyclopropanecarboxylic acid, (1S,2R,3R)-1-[4-(2,4-Dichloro-benzyloxy)-benzenesulfonylamino]-2-methyl-3-phenyl-cyclopropanecarboxylic acid hydroxyamide, (1R*,2R*,3S*)-1-[5-(4-Chloro-phenyl)-thiophene-2-sulfonylamino]-2-methyl-3-phenyl-cyclopropanecarboxylic acid, (1R*,2S*,3S*)-2-Ethyl-3-phenyl-1-[5-(5-trifluoromethyl-isoxazol-3-yl)-thiophene-2-sulfonylamino]-cyclopropanecarboxylic acid, (1S*,2R*,3R*)-2-Ethyl-3-phenyl-1-[5-(5-trifluoromethyl-isoxazol-3-yl)-thiophene-2-sulfonylamino]-cyclopropanecarboxylic acid, (1R*,2S*)-2-Phenyl-2-pyrrolidin-1-ylmethyl-1-[5-(5-trifluoromethyl-isoxazol-3-yl)-thiophene-2-sulfonylamino]-cyclopropanecarboxylic acid, (1R*,2S*)-2-Phenyl-2-piperidin-1-ylmethyl-1-[5-(5-trifluoromethyl-isoxazol-3-yl)-thiophene-2-sulfonylamino]-cyclopropanecarboxylic acid, (1R*,2R*)-2-Cyclopropylcarbamoyloxymethyl-2-phenyl-1-[5-(5-trifluoromethyl-isoxazol-3-yl)-thiophene-2-sulfonylamino]-cyclopropanecarboxylic acid, (1R*,2R*)-2-{[(2-Hydroxy-ethyl)-methyl-carbamoyloxy]-methyl}-2-phenyl-1-[5-(5-trifluoromethyl-isoxazol-3-yl)-thiophene-2-sulfonylamino]-cyclopropanecarboxylic acid, (1R*,2R*)-2-(2-Hydroxy-ethylcarbamoyloxymethyl)-2-phenyl-1-[5-(5-trifluoromethyl-isoxazol-3-yl)-thiophene-2-sulfonylamino]-cyclopropanecarboxylic acid, (1R*,2R*)-4-Methyl-piperazine-1-carboxylic acid 2-carboxy-1-phenyl-2-[5-(5-trifluoromethyl-isoxazol-3-yl)-thiophene-2-sulfonylamino]-cyclopropylmethyl ester, (1R*,2R*)-2-Carbamoyloxymethyl-2-phenyl-1-[5-(5-trifluoromethyl-isoxazol-3-yl)-thiophene-2-sulfonylamino]-cyclopropanecarboxylic acid, (1R*,2S*)-2-{[(2-Methoxy-ethyl)-methyl-amino]-methyl}-2-phenyl-1-[5-(5-trifluoromethyl-isoxazol-3-yl)-thiophene-2-sulfonylamino]-cyclopropanecarboxylic acid, (1R*,2R*)-1-[5-(4-Chloro-phenyl)-thiophene-2-sulfonylamino]-2-(2-dimethylamino-ethylsulfanylmethyl)-2-phenyl-cyclopropanecarboxylic acid, (1S,2R,3R)-2-Methyl-3-phenyl-1-[5-(3-trifluoromethyl-isoxazol-5-yl)-thiophene-2-sulfonylamino]-cyclopropanecarboxylic acid, (1R*,2S*)-2-(4-Fluoro-phenyl)-2-methyl-1-[5-(5-trifluoromethyl-isoxazol-3-yl)-thiophene-2-sulfonylamino]-cyclopropanecarboxylic acid, (1R*,2R*)-2-(4-Fluoro-phenyl)-2-methyl-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-morpholin-4-ymethyl-2-phenyl-cyclopropanecarboxylic acid, (1R*,2S*)-2-(4-Methyl-piperazin-1-ylmethyl)-2-phenyl-1-[5-(5-trifluoromethyl-isoxazol-3-yl)-thiophene-2-sulfonylamino]-cyclopropanecarboxylic acid, (1R*,2S*)-2-Diethylaminomethyl-2-phenyl-1-[5-(5-trifluoromethyl-isoxazol-3-yl)-thiophene-2-sulfonylamino]-cyclopropanecarboxylic acid, (1R*,2S*)-1-[5-(4-Chloro-phenyl)-thiophene-2-sulfonylamino]-2-((2R,6S)-2,6-dimethyl-morpholin-4-ylmethyl)-2-phenyl-cyclopropanecarboxylic acid, (1R*,2R*)-1-[5-(4-Chloro-phenyl)-thiophene-2-sulfonylamino]-2-(2-hydroxy-ethylsulfanylmethyl)-2-phenyl-cyclopropanecarboxylic acid, (1R*,2S*)-1-[5-(4-Chloro-phenyl)-thiophene-2-sulfonylamino]-2-imidazol-1-ylmethyl-2-phenyl-cyclopropanecarboxylic acid, (1R*,2R*)-1-[5-(4-Chloro-phenyl)-thiophene-2-sulfonylamino]-2-(2-hydroxy-ethoxymethyl)-2-phenyl-cyclopropanecarboxylic acid, (1R*,2R*)-1-[5-(4-Chloro-phenyl)-thiophene-2-sulfonylamino]-2-phenyl-2-(propane-2-sulfonylmethyl)-cyclopropanecarboxylic acid, (1R*,2R*)-1-[5-(4-Chloro-phenyl)-thiophene-2-sulfonylamino]-2-isopropylsulfanylmethyl-2-phenyl-cyclopropanecarboxylic acid, (1R*,1aS*,7bS*)-1-[5-(4-Chloro-phenyl)-thiophene-2-sulfonylamino]-1a,2,3,7b-tetrahydro-1H-cyclopropa[a]naphthalene-1-carboxylic acid, (1R*,1aS*,7bS*)-1-[5-(5-Trifluoromethyl-isoxazol-3-yl)-thiophene-2-sulfonylamino]-1a,2,3,7b-tetrahydro-1H-cyclopropa[a]naphthalene-1-carboxylic acid, (1R*,2R*)-1-[5-(4-Chloro-phenyl)-thiophene-2-sulfonylamino]-2-ethoxycarbonylmethylsulfanylmethyl-2-phenyl-cyclopropanecarboxylic acid, (1S,2R,3R)-1-[5-(5-Difluoromethyl-isoxazol-3-yl)-thiophene-2-sulfonylamino]-2-methyl-3-phenyl-cyclopropanecarboxylic acid, (1S,2R,3R)-1-[5-(3-Difluoromethyl-isoxazol-5-yl)-thiophene-2-sulfonylamino]-2-methyl-3-phenyl-cyclopropanecarboxylic acid, (1R*,1aS*,7bS*)-1-[4-(2,4-Dichloro-benzyloxy)-benzenesulfonylamino]-1a,2,3,7b-tetrahydro-1H-cyclopropa[a]naphthalene-1-carboxylic acid, (1R*,2R*)-2-Benzyloxymethyl-1-[5-(4-chloro-phenyl)-thiophene-2-sulfonylamino]-2-phenyl-cyclopropanecarboxylic acid, (1R*,2R*)-1-[5-(4-Chloro-phenyl)-thiophene-2-sulfonylamino]-2-dimethylcarbamoylmethylsulfanylmethyl-2-phenyl-cyclopropanecarboxylic acid, (1R*,2R*)-2-Carboxymethylsulfanylmethyl-1-[5-(4-chloro-phenyl)-thiophene-2-sulfonylamino]-2-phenyl-cyclopropanecarboxylic acid, (1R*,2R*)-1-[5-(4-Chloro-phenyl)-thiophene-2-sulfonylamino]-2-(2-morpholin-4-yl-2-oxo-ethylsulfanylmethyl)-2-phenyl-cyclopropanecarboxylic acid, (1R*,1aS*,7bS*)-1-[4-(2,4-Dichloro-benzyloxy)-benzenesulfonylamino]-1a,2,3,7b-tetrahydro-1H-cyclopropa[a]naphthalene-1-carboxylic acid hydroxyamide, (1R*,2S*)-2-Aminomethyl-1-[5-(4-chloro-phenyl)-thiophene-2-sulfonylamino]-2-phenyl-cyclopropanecarboxylic acid, (1R*,2S*)-1-[5-(4-Chloro-phenyl)-thiophene-2-sulfonylamino]-2-(2-oxo-oxazolidin-3-ylmethyl)-2-phenyl-cyclopropanecarboxylic acid, (1R*,1aS*,8bS*)-1-[4-(2,4-Dichloro-benzyloxy)-benzenesulfonylamino]-1,1a,2,3,4,8b-hexahydro-benzo[a]cyclopropan[c]cycloheptene-1-carboxylic acid, (1R*,1aS*,7bS*)-1-[5-(4-Chloro-phenyl)-thiophene-2-sulfonylamino]-1a,2,3,7b-tetrahydro-1H-cyclopropa[a]naphthalene-1-carboxylic acid hydroxyamide, (1R*,1aS*,8bS*)-1-[5-(5-Chloro-pyridin-2-yl)-thiophene-2-sulfonylamino]-1,1a,2,3,4,8b-hexahydro-benzo[a]cyclopropan[c]cycloheptene-1-carboxylic acid, (1S,2R,3R)-1-[5-(5-Chloro-pyridin-2-yl)-thiophene-2-sulfonylamino]-2-methyl-3-phenyl-cyclopropanecarboxylic acid, (1S,2R,3R)-2-Methyl-1-[5-(4-methyl-imidazol-1-yl)-thiophene-2-sulfonylamino]-3-phenyl-cyclopropanecarboxylic acid, (1R*,2S*)-1-[5-(4-Chloro-phenyl)-thiophene-2-sulfonylamino]-2-phenyl-2-{[(pyridine-2-carbonyl)-amino]-methyl}-cyclopropanecarboxylic acid, (1R*,1aS*,8bS*)-1-[5-(4-Chloro-phenyl)-thiophene-2-sulfonylamino]-1a,2,3,8b-tetrahydro-1H-4-oxa-benzo[a]cyclopropan[c]cycloheptene-1-carboxylic acid, (1R*,1aS*,8bS*)-1-[5-(5-Trifluoromethyl-isoxazol-3-yl)-thiophene-2-sulfonylamino]-1a,2,3,8b-tetrahydro-1H-4-oxa-benzo[a]cyclopropan[c]cycloheptene-1-carboxylic acid, (1S,2R)-2-Phenyl-1-[5-(5-trifluoromethyl-isoxazol-3-yl)-furan-2-sulfonylamino]-cyclopropanecarboxylic acid, (1S,2R,3R)-2-Methyl-3-phenyl-1-[5-(5-trifluoromethyl-isoxazol-3-yl)-furan-2-sulfonylamino]-cyclopropanecarboxylic acid, (1R*,1aS*,8bS*)-1-[5-(5-Trifluoromethyl-isoxazol-3-yl)-furan-2-sulfonylamino]-1,1a,2,3,4,8b-hexahydro-benzo[a]cyclopropan[c]cycloheptene-1-carboxylic acid, (1S,2R,3R)-2-Methyl-1-[5-(5-methyl-isoxazol-3-yl)-thiophene-2-sulfonylamino]-3-phenyl-cyclopropanecarboxylic acid, (1R*,1aS*,8bS*)-1-[5-(5-Methyl-isoxazol-3-yl)-thiophene-2-sulfonylamino]-1,1a,2,3,4,8b-hexahydro-benzo[a]cyclopropan[c]cycloheptene-1-carboxylic acid, (1R*,2S*)-2-(Acetylamino-methyl)-1-[5-(4-chloro-phenyl)-thiophene-2-sulfonylamino]-2-phenyl-cyclopropanecarboxylic acid, (1R*,2S*)-2-(Butyrylamino-methyl)-1-[5-(4-chloro-phenyl)-thiophene-2-sulfonylamino]-2-phenyl-cyclopropanecarboxylic acid, (1R*,2S*)-1-[5-(4-Chloro-phenyl)-thiophene-2-sulfonylamino]-2-(3,3-dimethyl-ureidomethyl)-2-phenyl-cyclopropanecarboxylic acid, (1R*,2S*)-1-[5-(4-Chloro-phenyl)-thiophene-2-sulfonylamino]-2-[(cyclopropanecarbonyl-amino)-methyl]-2-phenyl-cyclopropanecarboxylic acid, (1R*,2S*)-1-[5-(4-Chloro-phenyl)-thiophene-2-sulfonylamino]-2-[(cyclohexanecarbonyl-amino)-methyl]-2-phenyl-cyclopropanecarboxylic acid, (1R*,2S*)-1-[5-(4-Chloro-phenyl)-thiophene-2-sulfonylamino]-2-{[(morpholine-4-carbonyl)-amino]-methyl}-2-phenyl-cyclopropanecarboxylic acid, (1S,2R)-1-[5-(5-Difluoromethyl-isoxazol-3-yl)-thiophene-2-sulfonylamino]-2-methyl-2-phenyl-cyclopropanecarboxylic acid, (1R*,1aS*,8bS*)-1-[5-(5-Difluoromethyl-isoxazol-3-yl)-thiophene-2-sulfonylamino]-1,1a,2,3,4,8b-hexahydro-benzo[a]cyclopropan[c]cycloheptene-1-carboxylic acid, (1R*,2S*)-1-[5-(4-Chloro-phenyl)-thiophene-2-sulfonylamino]-2-(ethoxycarbonylamino-methyl)-2-phenyl-cyclopropanecarboxylic acid, (1R*,2S*)-1-[5-(4-Chloro-phenyl)-thiophene-2-sulfonylamino]-2-phenyl-2-{[((S)-tetrahydro-furan-2-carbonyl)-amino]-methyl}-cyclopropanecarboxylic acid, (1R*,2R*)-1-[5-(4-Chloro-phenyl)-thiophene-2-sulfonylamino]-2-methoxymethyl-2-phenyl-cyclopropanecarboxylic acid, (1S,2R)-1-[5-(1-Methyl-1H-pyrazol-4-yl)-thiophene-2-sulfonylamino]-2-phenyl-cyclopropanecarboxylic acid, (1S,2R)-1-[5-(4-Nitro-phenyl)-thiophene-2-sulfonylamino]-2-phenyl-cyclopropanecarboxylic acid, (1R*,1aS*,8bS*)-1-[5-(4-Chloro-phenyl)-thiophene-2-sulfonylamino]-1,1a,2,3,4,8b-hexahydro-4-aza-benzo[a]cyclopropan[c]cycloheptene-1-carboxylic acid, (1R*,1aS*,8bS*)-1-[4-(2,4-Dichloro-benzyloxy)-benzenesulfonylamino]-1,1a,2,3,4,8b-hexahydro-benzo[a]cyclopropan[c]cycloheptene-1-carboxylic acid hydroxyamide, (1R*,1aS*,8bS*)-1-[5-(4-Chloro-phenyl)-thiophene-2-sulfonylamino]-1,1a,2,3,4,8b-hexahydro-benzo[a]cyclopropan[c]cycloheptene-1-carboxylic acid hydroxyamide, (1R*,2S*)-1-[5-(4-Chloro-phenyl)-thiophene-2-sulfonylamino]-2-(isopropylamino-methyl)-2-phenyl-cyclopropanecarboxylic acid, (1R*,2S*)-1-[5-(4-Chloro-phenyl)-thiophene-2-sulfonylamino]-2-phenyl-2-{[(thiazol-2-ylmethyl)-amino]-methyl}-cyclopropanecarboxylic acid, (1R*,2S*)-1-[5-(4-Chloro-phenyl)-thiophene-2-sulfonylamino]-2-phenyl-2-{[(pyridine-3-carbonyl)-amino]-methyl}-cyclopropanecarboxylic acid, (1R*,2S*)-1-[5-(4-Chloro-phenyl)-thiophene-2-sulfonylamino]-2-[(3-hydroxy-propionylamino)-methyl]-2-phenyl-cyclopropanecarboxylic acid, (1R*,2S*)-1-[5-(4-Chloro-phenyl)-thiophene-2-sulfonylamino]-2-[(3-ethyl-ureido)-methyl]-2-phenyl-cyclopropanecarboxylic acid, (1R*,2S*)-1-[5-(4-Chloro-phenyl)-thiophene-2-sulfonylamino]-2-(isobutyrylamino-methyl)-2-phenyl-cyclopropanecarboxylic acid, (1R*,2S*)-1-[5-(4-Chloro-phenyl)-thiophene-2-sulfonylamino]-2-[(2-methoxy-acetylamino)-methyl]-2-phenyl-cyclopropanecarboxylic acid, (1R*,2S*)-1-[5-(4-Chloro-phenyl)-thiophene-2-sulfonylamino]-2-[(2-hydroxy-acetylamino)-methyl]-2-phenyl-cyclopropanecarboxylic acid, (1R*,2S*)-1-[5-(4-Chloro-phenyl)-thiophene-2-sulfonylamino]-2-(3-oxo-morpholin-4-ylmethyl)-2-phenyl-cyclopropanecarboxylic acid, (1S,2R,3R)-1-[4-(5-Difluoromethyl-isoxazol-3-yl)-benzenesulfonylamino]-2-methyl-3-phenyl-cyclopropanecarboxylic acid, (1S,2R)-1-[5-(4-Acetylamino-phenyl)-thiophene-2-sulfonylamino]-2-methyl-2-phenyl-cyclopropanecarboxylic acid, (1S,2R)-1-[5-(5-Methoxymethyl-isoxazol-3-yl)-thiophene-2-sulfonylamino]-2-methyl-2-phenyl-cyclopropanecarboxylic acid, (1S,2R,3R)-2-methyl-1-[5-(5-Methoxymethyl-isoxazol-3-yl)-thiophene-2-sulfonylamino]-3-phenyl-cyclopropanecarboxylic acid, (1S,2R)-1-[5-(4-Chloro-2-fluoro-phenyl)-thiophene-2-sulfonylamino]-2-methyl-2-phenyl-cyclopropanecarboxylic acid, (1S,2R,3R)-1-[5-(4-Chloro-2-fluoro-phenyl)-thiophene-2-sulfonylamino]-2-methyl-3-phenyl-cyclopropanecarboxylic acid, (1S,2R,3R)-1-[5-(5-Isopropyl-isoxazol-3-yl)-thiophene-2-sulfonylamino]-2-methyl-3-phenyl-cyclopropanecarboxylic acid, (1R*,2R*)-2-Ethoxycarbonylmethylsulfanylmethyl-2-phenyl-1-[5-(5-trifluoromethyl-isoxazol-3-yl)-thiophene-2-sulfonylamino]-cyclopropanecarboxylic acid, (1R*,2R*)-2-Carboxymethylsulfanylmethyl-2-phenyl-[5-(5-trifluoromethyl-isoxazol-3-yl)-thiophene-2-sulfonylamino]-cyclopropanecarboxylic acid, (1R*,1aS*,4R*,8bS*)-1-[5-(4-Chloro-phenyl)-thiophene-2-sulfonylamino]-4-hydroxy-1,1a,2,3,4,8b-hexahydro-benzo[a]cyclopropan[c]cycloheptene-1-carboxylic acid, (1R*,1aS*,4S*,8bS*)-1-[5-(4-Chloro-phenyl)-thiophene-2-sulfonylamino]-4-hydroxy-1,1a,2,3,4,8b-hexahydro-benzo[a]cyclopropan[c]cycloheptene-1-carboxylic acid, (1S,2R)-1-[5-(3-Chloro-4-fluoro-phenyl)-thiophene-2-sulfonylamino]-2-methyl-2-phenyl-cyclopropanecarboxylic acid, (1S,2R)-1-[5-(5-Bromo-pyrimidin-2-yl)-thiophene-2-sulfonylamino]-2-methyl-2-phenyl-cyclopropanecarboxylic acid, (1 aR*,8bS*)-5-(4-Chloro-phenyl)-thiophene-2-sulfonic acid (2-oxo-2,3,4,8b-tetrahydro-1H-3-aza-benzo[a]cyclopropan[c]cyclohepten-1a-yl)-amide, (1S,2R)-1-[5-(5-Fluoro-pyridin-2-yl)-thiophene-2-sulfonylamino]-2-methyl-2-phenyl-cyclopropanecarboxylic acid, (1S,2R,3R)-2-Methyl-1-[5-(5-methyl-oxazol-2-yl)-thiophene-2-sulfonylamino]-3-phenyl-cyclopropanecarboxylic acid, (1S,2R)-2-Methyl-1-[5-(5-methyl-oxazol-2-yl)-thiophene-2-sulfonylamino]-2-phenyl-cyclopropanecarboxylic acid, (1S,2R,3R)-1-[5-(5-Dimethylamino-isoxazol-3-yl)-thiophene-2-sulfonylamino]-2-methyl-3-phenyl-cyclopropanecarboxylic acid, (1S,2R)-1-[5-(3-Cyano-4-fluoro-phenyl)-thiophene-2-sulfonylamino]-2-methyl-2-phenyl-cyclopropanecarboxylic acid, (1S,2R)-2-Methyl-1-(5-morpholin-4-yl-thiophene-2-sulfonylamino)-2-phenyl-cyclopropanecarboxylic acid, (1S,2R)-1-[5-(3-Difluoromethyl-isoxazol-5-yl)-thiophene-2-sulfonylamino]-2-methyl-2-phenyl-cyclopropanecarboxylic acid, (1S,2R)-1-[5-(5-Dimethylamino-isoxazol-3-yl)-thiophene-2-sulfonylamino]-2-methyl-2-phenyl-cyclopropanecarboxylic acid,
(1S,2R,3R)-1-(5-Ethynyl-thiophene-2-sulfonylamino)-2-methyl-3-phenyl-cyclopropanecarboxylic acid,
(1S,2R,3R)-1-(5-Acetyl-thiophene-2-sulfonylamino)-2-methyl-3-phenyl-cyclopropanecarboxylic acid,
(1S,2R,3R)-1-[4-(4-Chloro-phenyl)-piperazine-1-sulfonylamino]-2-methyl-3-phenyl-cyclopropanecarboxylic acid,
(1S,2R,3R)-1-(5-Bromo-thiophene-2-sulfonylamino)-2-methyl-3-phenyl-cyclopropanecarboxylic acid,
(1S,2R,3R)-2-Methyl-3-phenyl-1-[4-(4-trifluoromethyl-phenyl)-piperazine-1-sulfonylamino]-cyclopropanecarboxylic acid,
(1R*,2R*)-1-[5-(4-Chloro-phenyl)-thiophene-2-sulfonylamino]-2-(2-methoxy-ethoxymethyl)-2-phenyl-cyclopropanecarboxylic acid,
(1R*,1aS*,8bS*)-1-[5-(4-Chloro-phenyl)-thiophene-2-sulfonylamino]-4-methyl-1,1a,2,3,4,8b-hexahydro-4-aza-benzo[a]cyclopropan[c]cycloheptene-1-carboxylic acid,
(1R*,1aS*,6aS*)-1-[5-(4-Chloro-phenyl)-thiophene-2-sulfonylamino]-1,1a,6,6a-tetrahydro-cyclopropa[a]indene-1-carboxylic acid,
(1R*,2R*)-1-[5-(4-Chloro-phenyl)-thiophene-2-sulfonylamino]-2-methylsulfanylmethyl-2-phenyl-cyclopropanecarboxylic acid,
(1S,2R,3R)-1-[5-(5-Cyclopropyl-isoxazol-3-yl)-thiophene-2-sulfonylamino]-2-methyl-3-phenyl-cyclopropanecarboxylic acid,
(1S,2R)-1-[5-(4-Chloro-3-fluoro-phenyl)-thiophene-2-sulfonylamino]-2-methyl-2-phenyl-cyclopropanecarboxylic acid,
(1S,2R,3R)-1-[5-(4-Chloro-3-fluoro-phenyl)-thiophene-2-sulfonylamino]-2-methyl-3-phenyl-cyclopropanecarboxylic acid,
(1S,2R)-2-Methyl-1-[4-(4-methyl-cyclohexyl)-benzenesulfonylamino]-2-phenyl-cyclopropanecarboxylic acid,
(1R*,1aS*,4R*,8bS*)-4-Hydroxy-1-[5-(5-trifluoromethyl-isoxazol-3-yl)-thiophene-2-sulfonylamino]-1,1a,2,3,4,8b-hexahydro-benzo[a]cyclopropan[c]cycloheptene-1-carboxylic acid,
(1R*,1aS*,4S*,8bS*)-4-Hydroxy-1-[5-(5-trifluoromethyl-isoxazol-3-yl)-thiophene-2-sulfonylamino]-1,1a,2,3,4,8b-hexahydro-benzo[a]cyclopropan[c]cycloheptene-1-carboxylic acid,
(1R*,1aS*,8bS*)-4-Acetyl-1-[5-(4-chloro-phenyl)-thiophene-2-sulfonylamino]-1,1a,2,3,4,8b-hexahydro-4-aza-benzo[a]cyclopropan[c]cycloheptene-1-carboxylic acid,
(1R*,2R*)-1-[5-(4-Chloro-phenyl)-thiophene-2-sulfonylamino]-2-methanesulfonylmethyl-2-phenyl-cyclopropanecarboxylic acid,
(1S,2R,3R)-1-[4-(4-Chloro-phenyl)-3,6-dihydro-2H-pyridine-1-sulfonylamino]-2-methyl-3-phenyl-cyclopropanecarboxylic acid,
(1S,2R,3R)-2-Methyl-1-[4-(4-methyl-cyclohexyl)-piperazine-1-sulfonylamino]-3-phenyl-cyclopropanecarboxylic acid,
(1S,2R)-1-[5-(4-Isopropyl-piperazin-1-yl)-thiophene-2-sulfonylamino]-2-methyl-2-phenyl-cyclopropanecarboxylic acid,
(1S,2R,3R)-1-[5-(4-Chloro-pyrazol-1-yl)-thiophene-2-sulfonylamino]-2-methyl-3-phenyl-cyclopropanecarboxylic acid,
(1S,2R,3R)-1-(8-Chloro-3,4-dihydro-1H-benzo[4,5]imidazol[1,2-a]pyrazine-2-sulfonylamino)-2-methyl-3-phenyl-cyclopropanecarboxylic acid,
(1R*,1aS*,6aS*)-1-[4-(2,4-Dichloro-benzyloxy)-benzenesulfonylamino]-1,1a,6,6a-tetrahydro-cyclopropa[a]indene-1-carboxylic acid,
(1R*,1aS*,6aS*)-1-[5-(4-Chloro-phenyl)-thiophene-2-sulfonylamino]-1,1a,6,6a-tetrahydro-cyclopropa[a]indene-1-carboxylic acid hydroxyamide,
(1S,2R)-1-[5-(3,5-Dichloro-phenyl)-thiophene-2-sulfonylamino]-2-methyl-2-phenyl-cyclopropanecarboxylic acid,
(1S,2R)-1-(5-Benzo[1,3]dioxol-5-yl-thiophene-2-sulfonylamino)-2-methyl-2-phenyl-cyclopropanecarboxylic acid,
(1S,2R,3R)-2-Methyl-1-[5-(1-methyl-1H-imidazol-4-yl)-thiophene-2-sulfonylamino]-3-phenyl-cyclopropanecarboxylic acid,
(1S,2R,3R)-2-Methyl-1-[5-(5-methyl-[1,2,4]oxadiazol-3-yl)-thiophene-2-sulfonylamino]-3-phenyl-cyclopropanecarboxylic acid,
(1S,2R)-1-[5-(3-Amino-phenyl)-thiophene-2-sulfonylamino]-2-methyl-2-phenyl-cyclopropanecarboxylic acid,
(1S,2R)-1-[5-(3-Methanesulfonylamino-phenyl)-thiophene-2-sulfonylamino]-2-methyl-2-phenyl-cyclopropanecarboxylic acid,
(1S,2R,3R)-1-[4-(4-Chloro-phenyl)-[1,4]diazepane-1-sulfonylamino]-2-methyl-3-phenyl-cyclopropanecarboxylic acid,
(1S,2R)-1-[5-(4,4-Difluoro-piperidin-1-yl)-thiophene-2-sulfonylamino]-2-methyl-2-phenyl-cyclopropanecarboxylic acid,
(1S,2R,3R)-2-Methyl-3-phenyl-1-(5-quinoxalin-2-yl-thiophene-2-sulfonylamino)-cyclopropanecarboxylic acid,
(1S,2R,3R)-1-[4-(5-Chloro-pyridin-2-yl)-piperazine-1-sulfonylamino]-2-methyl-3-phenyl-cyclopropanecarboxylic acid,
(1S,2R,3R)-1-[4-(4-Bromo-phenyl)-piperazine-1-sulfonylamino]-2-methyl-3-phenyl-cyclopropanecarboxylic acid,
(1S,2R,3R)-1-[4-(4-Chloro-3-fluoro-phenyl)-piperazine-1-sulfonylamino]-2-methyl-3-phenyl-cyclopropanecarboxylic acid,
(1S,2R,3R)-1-[4-(4-Chloro-2-fluoro-phenyl)-piperazine-1-sulfonylamino]-2-methyl-3-phenyl-cyclopropanecarboxylic acid,
(1S,2R,3R)-1-[4-(5-Chloro-pyridin-2-yl)-[1,4]diazepane-1-sulfonylamino]-2-methyl-3-phenyl-cyclopropanecarboxylic acid,
(1S,2R,3R)-1-[4-(5-Fluoro-pyridin-2-yl)-[1,4]diazepane-1-sulfonylamino]-2-methyl-3-phenyl-cyclopropanecarboxylic acid,
(1S,2R,3R)-1-(4-Benzothiazol-2-yl-piperazine-1-sulfonylamino)-2-methyl-3-phenyl-cyclopropanecarboxylic acid,
(1S,2R,3R)-1-(4-Benzoxazol-2-yl-piperazine-1-sulfonylamino)-2-methyl-3-phenyl-cyclopropanecarboxylic acid,
(1S,2R,3R)-2-Methyl-1-[4-(5-methyl-[1,3,4]thiadiazol-2-yl)-piperazine-1-sulfonylamino]-3-phenyl-cyclopropanecarboxylic acid,
(1S,2R)-1-[5-(3,5-Difluoro-pyridin-2-yl)-thiophene-2-sulfonylamino]-2-methyl-2-phenyl-cyclopropanecarboxylic acid, (1S,2R)-1-[5-(3,3-Difluoro-pyrrolidin-1-yl)-thiophene-2-sulfonylamino]-2-methyl-2-phenyl-cyclopropanecarboxylic acid, (1S,2R,3R)-2-Methyl-1-[5-(2-oxo-2,3-dihydro-benzothiazol-6-yl)-thiophene-2-sulfonylamino]-3-phenyl-cyclopropanecarboxylic acid, (1S,2R,3R)-2-Methyl-1-[5-(2-methyl-benzothiazol-5-yl)-thiophene-2-sulfonylamino]-3-phenyl-cyclopropanecarboxylic acid, (1S,2R,3R)-1-(5-Benzo[1,3]dioxol-5-yl-thiophene-2-sulfonylamino)-2-methyl-3-phenyl-cyclopropanecarboxylic acid, (1S,2R,3R)-1-[4-(3-Chloro-phenyl)-[1,4]diazepane-1-sulfonylamino]-2-methyl-3-phenyl-cyclopropanecarboxylic acid, (1S,2R,3R)-1-[4-(4-Fluoro-phenyl)-[1,4]diazepane-1-sulfonylamino]-2-methyl-3-phenyl-cyclopropanecarboxylic acid, (1S,2R)-1-(4-Benzoylamino-benzenesulfonylamino)-2-phenyl-cyclopropanecarboxylic acid, (1S,2R)-2-Phenyl-1-(4-phenylcarbamoyl-benzenesulfonylamino)-cyclopropanecarboxylic acid, (1S,2R,3R)-2-Methyl-1-[4-(5-methyl-isoxazol-3-yl)-piperazine-1-sulfonylamino]-3-phenyl-cyclopropanecarboxylic acid, (1S,2R,3R)-2-Methyl-1-[4-(5-methyl-isoxazol-3-yl)-3-oxo-piperazine-1-sulfonylamino]-3-phenyl-cyclopropanecarboxylic acid, (1S,2R)-1-[5-(4-Chloro-3-nitro-phenyl)-thiophene-2-sulfonylamino]-2-methyl-2-phenyl-cyclopropanecarboxylic acid, (1S,2R)-3-[5-((1S,2R)-1-Carboxy-2-methyl-2-phenyl-cyclopropylsulfamoyl)-thiophen-2-yl]-benzoic acid ethyl ester, 3-[5-((1S,2R)-1-Carboxy-2-methyl-2-phenyl-cyclopropylsulfamoyl)-thiophen-2-yl]-benzoic acid, (1S,2R)-1-[5-(3-Acetylamino-phenyl)-thiophene-2-sulfonylamino]-2-methyl-2-phenyl-cyclopropanecarboxylic acid, (1S,2R)-1-[6-(4-Methyl-pyrazol-1-yl)-pyridine-3-sulfonylamino]-2-phenyl-cyclopropanecarboxylic acid, (1S,2R)-1-[6-(4-Methoxy-pyrazol-1-yl)-pyridine-3-sulfonylamino]-2-phenyl-cyclopropanecarboxylic acid, (1S,2R,3R)-2-Methyl-1-[4-(2-methyl-benzothiazol-5-yl)-piperazine-1-sulfonylamino]-3-phenyl-cyclopropanecarboxylic acid, (1S,2R,3R)-2-Methyl-1-[4-(5-methyl-thiazol-2-yl)-piperazine-1-sulfonylamino]-3-phenyl-cyclopropanecarboxylic acid, (1S,2R)-1-[5-(2,3-Dihydro-benzo[1,4]dioxin-6-yl)-thiophene-2-sulfonylamino]-2-methyl-2-phenyl-cyclopropanecarboxylic acid, (1R*,1aS*,7bS*)-1-[5-(5-Trifluoromethyl-isoxazol-3-yl)-thiophene-2-sulfonylamino]-1a,2,3,7b-tetrahydro-1H-cyclopropa[a]naphthalene-1-carboxylic acid hydroxyamide, (1S,2R)-1-[5-(3-Hydroxy-3H-benzotriazol-5-yl)-thiophene-2-sulfonylamino]-2-methyl-2-phenyl-cyclopropanecarboxylic acid, (1S,2R)-1-[5-(4-Chloro-3-dimethylamino-phenyl)-thiophene-2-sulfonylamino]-2-methyl-2-phenyl-cyclopropanecarboxylic acid, (1R*,2S*)-2-Phenyl-1-(6-phenyl-imidazo[2,1-b]thiazole-2-sulfonylamino)-cyclopropanecarboxylic acid, (1R*,2S*)-1-[6-(4-Chloro-phenyl)-imidazol[2,1-b]thiazole-2-sulfonylamino]-2-phenyl-cyclopropanecarboxylic acid, (1R*,2S*)-1-[6-(4-Fluoro-phenyl)-imidazol[2,1-b]thiazole-2-sulfonylamino]-2-phenyl-cyclopropanecarboxylic acid, (1S,2R,3R)-1-[5-(4-Methoxy-pyrazol-1-yl)-thiophene-2-sulfonylamino]-2-methyl-3-phenyl-cyclopropanecarboxylic acid, (1S,2R,3R)-1-[5-(1H-Indol-2-yl)-thiophene-2-sulfonylamino]-2-methyl-3-phenyl-cyclopropanecarboxylic acid, (1S,2R,3R)-1-[5-(4-Bromo-pyrazol-1-yl)-thiophene-2-sulfonylamino]-2-methyl-3-phenyl-cyclopropanecarboxylic acid, (1R*,1aS*,6aS*)-1-[5-(5-Trifluoromethyl-isoxazol-3-yl)-thiophene-2-sulfonylamino]-1,1a,6,6a-tetrahydro-cyclopropa[a]indene-1-carboxylic acid hydroxyamide, (1S,2R,3R)-1-[5-(3-Amino-4-chloro-phenyl)-thiophene-2-sulfonylamino]-2-methyl-3-phenyl-cyclopropanecarboxylic acid, (1S,2R,3R)-1-(5-Benzo[2,1,3]thiadiazol-5-yl-thiophene-2-sulfonylamino)-2-methyl-3-phenyl-cyclopropanecarboxylic acid, (1S,2R)-1-[5-(4-Chloro-pyrazol-1-yl)-thiophene-2-sulfonylamino]-2-methyl-2-phenyl-cyclopropanecarboxylic acid, (1S,2R,3R)-2-Methyl-3-phenyl-1-(6-phenyl-imidazo[2,1-b]thiazole-2-sulfonylamino)-cyclopropanecarboxylic acid, (1S,2R,3R)-1-[3-(4-Chloro-phenoxy)-pyrrolidine-1-sulfonylamino]-2-methyl-3-phenyl-cyclopropanecarboxylic acid, (1S,2R,3R)-1-[3-(3-Chloro-phenoxy)-pyrrolidine-1-sulfonylamino]-2-methyl-3-phenyl-cyclopropanecarboxylic acid, (1S,2R,3R)-1-[4-(4-Chloro-phenyl)-3-oxo-piperazine-1-sulfonylamino]-2-methyl-3-phenyl-cyclopropanecarboxylic acid, (1S,2R,3R)-1-[4-(6-Chloro-pyridazin-3-yl)-piperazine-1-sulfonylamino]-2-methyl-3-phenyl-cyclopropanecarboxylic acid, (1S,2R,3R)-2-Methyl-1-[3-oxo-4-(4-trifluoromethyl-phenyl)-piperazine-1-sulfonylamino]-3-phenyl-cyclopropanecarboxylic acid, (1S,2R,3R)-1-(5-Bromo-1,3-dihydro-isoindole-2-sulfonylamino)-2-methyl-3-phenyl-cyclopropanecarboxylic acid, (1S,2R)-2-Methyl-2-phenyl-1-[4-(4-trifluoromethyl-pyrazol-1-yl)-benzenesulfonylamino]-cyclopropanecarboxylic acid, (1S,2R,3R)-2-Methyl-3-phenyl-1-[4-(4-trifluoromethyl-pyrazol-1-yl)-benzenesulfonylamino]-cyclopropanecarboxylic acid, (1R*,2S*,3S*)-1-(5-Benzyl-thiophene-2-sulfonylamino)-2-methyl-3-phenyl-cyclopropanecarboxylic acid, (1R*,2S*,3S*)-1-[5-(3-Hydroxy-phenyl)-thiophene-2-sulfonylamino]-2-methyl-3-phenyl-cyclopropanecarboxylic acid, 4-((1S,2R)-1-Carboxy-2-phenyl-cyclopropylsulfamoyl)-piperazine-1-carboxylic acid isopropyl ester, (1S,2R)-1-[4-(3-Methyl-butyl)-piperazine-1-sulfonylamino]-2-phenyl-cyclopropanecarboxylic acid, (1S,2R)-1-(4-Ethylcarbamoyl-piperazine-1-sulfonylamino)-2-phenyl-cyclopropanecarboxylic acid, (1S,2R)-1-[4-(3-Methyl-butyryl)-piperazine-1-sulfonylamino]-2-phenyl-cyclopropanecarboxylic acid, (1S,2R,3R)-2-Methyl-3-phenyl-1-[5-(3-trifluoromethyl-pyrazol-1-yl)-thiophene-2-sulfonylamino]-cyclopropanecarboxylic acid, (1S,2R)-2-Methyl-1-[5-(methyl-phenyl-amino)-thiophene-2-sulfonylamino]-2-phenyl-cyclopropanecarboxylic acid, (1S,2R)-1-[5-(4-Chloro-3-methoxy-phenyl)-thiophene-2-sulfonylamino]-2-methyl-2-phenyl-cyclopropanecarboxylic acid, (1S,2R,3R)-1-(5-Benzo[2,1,3]oxadiazol-5-yl-thiophene-2-sulfonylamino)-2-methyl-3-phenyl-cyclopropanecarboxylic acid, (1S,2R)-2-Methyl-2-phenyl-1-(6-phenyl-imidazo[2,1-b]thiazole-2-sulfonylamino)-cyclopropanecarboxylic acid, (1S,2R)-1-(6-Methoxymethyl-imidazo[2,1-b]thiazole-2-sulfonylamino)-2-methyl-2-phenyl-cyclopropanecarboxylic acid, (1S,2R,3R)-1-[6-(4-Chloro-pyrazol-1-ylmethyl)-imidazol[2,1-b]thiazole-2-sulfonylamino]-2-methyl-3-phenyl-cyclopropanecarboxylic acid, 1-[5-((1S,2R,3R)-1-Carboxy-2-methyl-3-phenyl-cyclopropylsulfamoyl)-thiophen-2-yl]-1H-pyrazole-4-carboxylic acid ethyl ester, 1-[5-((1S,2R,3R)-1-Carboxy-2-methyl-3-phenyl-cyclopropylsulfamoyl)-thiophen-2-yl]-1H-pyrazole-4-carboxylic acid, (1S,2R,3R)-1-{5-[4-(1-Hydroxy-1-methyl-ethyl)-pyrazol-1-yl]-thiophene-2-sulfonylamino}-2-methyl-3-phenyl-cyclopropanecarboxylic acid, (1S,2R,3R)-1-[5-(4-Methanesulfonyl-pyrazol-1-yl)-thiophene-2-sulfonylamino]-2-methyl-3-phenyl-cyclopropanecarboxylic acid, (1R*,2S*,3S*)-1-[5-(3-Hydroxymethyl-phenyl)-thiophene-2-sulfonylamino]-2-methyl-3-phenyl-cyclopropanecarboxylic acid, (1S,2R)-2-Methyl-2-phenyl-1-(5-pyridin-4-yl-thiophene-2-sulfonylamino)-cyclopropanecarboxylic acid, (1S,2R)-2-Methyl-2-phenyl-1-(5-pyridin-3-yl-thiophene-2-sulfonylamino)-cyclopropanecarboxylic acid, (1S,2R,3R)-1-(6,7-Dimethoxy-3,4-dihydro-1H-isoquinoline-2-sulfonylamino)-2-methyl-3-phenyl-cyclopropanecarboxylic acid, (1S,2R,3R)-1-(4-Benzylcarbamoyl-piperazine-1-sulfonylamino)-2-methyl-3-phenyl-cyclopropanecarboxylic acid, (1S,2R,3R)-2-Methyl-1-[4-(3-methyl-butyl)-piperazine-1-sulfonylamino]-3-phenyl-cyclopropanecarboxylic acid, (1S,2R,3R)-2-Methyl-1-(4-phenethyl-piperazine-1-sulfonylamino)-3-phenyl-cyclopropanecarboxylic acid, 4-((1S,2R,3R)-1-Carboxy-2-methyl-3-phenyl-cyclopropylsulfamoyl)-piperazine-1-carboxylic acid benzyl ester, (1S,2R,3R)-2-Methyl-3-phenyl-1-(4-pyridin-4-yl-piperazine-1-sulfonylamino)-cyclopropanecarboxylic acid, (1S,2R,3R)-1-[4-(2-Methoxy-ethyl)-piperazine-1-sulfonylamino]-2-methyl-3-phenyl-cyclopropanecarboxylic acid, (1S,2R,3R)-1-(3,4-Dihydro-1H-isoquinoline-2-sulfonylamino)-2-methyl-3-phenyl-cyclopropanecarboxylic acid, (1S,2R,3R)-1-[4-(4-Methoxy-benzyl)-piperazine-1-sulfonylamino]-2-methyl-3-phenyl-cyclopropanecarboxylic acid, (1S,2R,3R)-2-Methyl-3-phenyl-1-[4-((E)-3-phenyl-allyl)-piperazine-1-sulfonylamino]-cyclopropanecarboxylic acid, (1S,2R,3R)-1-(5-Chloro-1,3-dihydro-isoindole-2-sulfonylamino)-2-methyl-3-phenyl-cyclopropanecarboxylic acid, (1R*,2R*,3R*)-2-Methoxymethyl-3-phenyl-1-[5-(5-trifluoromethyl-isoxazol-3-yl)-thiophene-2-sulfonylamino]-cyclopropanecarboxylic acid, (1R*,2S*,3S*)-2-Methyl-1-[5-(3-morpholin-4-ylmethyl-phenyl)-thiophene-2-sulfonylmethyl]-3-phenyl-cyclopropanecarboxylic acid, (1R*,2S*,3S*)-2-Methyl-1-(5-phenethyl-thiophene-2-sulfonylamino)-3-phenyl-cyclopropanecarboxylic acid, (1S,2R,3R)-2-Methyl-3-phenyl-1-(5-pyrazol-1-yl-thiophene-2-sulfonylamino)-cyclopropanecarboxylic acid, (1S,2R,3R)-1-[5-(4-Iodo-pyrazol-1-yl)-thiophene-2-sulfonylamino]-2-methyl-3-phenyl-cyclopropanecarboxylic acid, (1S,2R)-1-[5-(2,2-Difluoro-benzo[1,3]dioxol-5-yl)-thiophene-2-sulfonylamino]-2-methyl-2-phenyl-cyclopropanecarboxylic acid, (1S,2R,3R)-1-{5-[4-(1-Chloro-vinyl)-pyrazol-1-yl]-thiophene-2-sulfonylamino}-2-methyl-3-phenyl-cyclopropanecarboxylic acid, (1S,2R,3R)-1-[5-(4-Acetyl-pyrazol-1-yl)-thiophene-2-sulfonylamino]-2-methyl-3-phenyl-cyclopropanecarboxylic acid, (1S,2R,3R)-1-{5-[4-(1-Hydroxy-ethyl)-pyrazol-1-yl]-thiophene-2-sulfonylamino}-2-methyl-3-phenyl-cyclopropanecarboxylic acid, (1S,2R,3R)-1-(5-Hydroxy-1,3-dihydro-isoindole-2-sulfonylamino)-2-methyl-3-phenyl-cyclopropanecarboxylic acid, (1S,2R,3R)-1-[3-(3-Chloro-benzyloxy)-pyrrolidine-1-sulfonylamino]-2-methyl-3-phenyl-cyclopropanecarboxylic acid, (1S,2R,3R)-1-[3-(4-Chloro-benzyloxy)-pyrrolidine-1-sulfonylamino]-2-methyl-3-phenyl-cyclopropanecarboxylic acid, (1S,2R,3R)-1-[3-(2,5-Dichloro-benzyloxy)-pyrrolidine-1-sulfonylamino]-2-methyl-3-phenyl-cyclopropanecarboxylic acid, (1S,2R,3R)-1-(5-Isopropylamino-1,3-dihydro-isoindole-2-sulfonylamino)-2-methyl-3-phenyl-cyclopropanecarboxylic acid, (1S,2R,3R)-1-[3-(2,4-Dichloro-benzyloxy)-pyrrolidine-1-sulfonylamino]-2-methyl-3-phenyl-cyclopropanecarboxylic acid, (1S,2R)-1-[6-(4-Chloro-pyrazol-1-yl)-pyridine-3-sulfonylamino]-2-phenyl-cyclopropanecarboxylic acid, 3-[5-((1S,2R,3R)-1-Carboxy-2-methyl-3-phenyl-cyclopropylsulfamoyl)-thiophen-2-yl]-isoxazole-5-carboxylic acid ethyl ester, (1S,2R,3R)-2-Methyl-3-phenyl-1-[6-(4-trifluoromethyl-pyrazol-1-yl)-pyridine-3-sulfonylamino]-cyclopropanecarboxylic acid, (1S,2R,3R)-1-[6-(4-Chloro-pyrazol-1-yl)-pyridine-3-sulfonylamino]-2-methyl-3-phenyl-cyclopropanecarboxylic acid, (1S,2R)-2-Phenyl-1-[6-(4-trifluoromethyl-pyrazol-1-yl)-pyridine-3-sulfonylamino]-cyclopropanecarboxylic acid, (1R*,2S*)-1-[5-(4-Chloro-phenyl)-thiophene-2-sulfonylamino]-2-(3-methoxy-propyl)-2-phenyl-cyclopropanecarboxylic acid, (1R*,2S*)-1-[5-(4-Chloro-phenyl)-thiophene-2-sulfonylamino]-2-(3-methoxy-propyl)-2-phenyl-cyclopropanecarboxylic acid,
(1S,2R,3R)-1-[5-(4-Hydroxymethyl-pyrazol-1-yl)-thiophene-2-sulfonylamino]-2-methyl-3-phenyl-cyclopropanecarboxylic acid,
(1S,2R)-2-Methyl-2-phenyl-1-[5-((E)-3,3,3-trifluoro-propenyl)-thiophene-2-sulfonylamino]-cyclopropanecarboxylic acid,
(1S,2R)-2-Methyl-2-phenyl-1-[5-((Z)-3,3,3-trifluoro-propenyl)-thiophene-2-sulfonylamino]-cyclopropanecarboxylic acid,
(1S,2R)-1-[5-(4-Chloro-3-hydroxymethyl-phenyl)-thiophene-2-sulfonylamino]-2-methyl-2-phenyl-cyclopropanecarboxylic acid,
(1S,2R,3R)-1-[5-(4-Chloro-3-hydroxymethyl-phenyl)-thiophene-2-sulfonylamino]-2-methyl-3-phenyl-cyclopropanecarboxylic acid,
(1S,2R)-1-[5-(2,4-Dichloro-phenyl)-thiophene-2-sulfonylamino]-2-methyl-2-phenyl-cyclopropanecarboxylic acid,
(1S,2R)-1-[5-(4-Cyano-phenyl)-thiophene-2-sulfonylamino]-2-methyl-2-phenyl-cyclopropanecarboxylic acid,
(1S,2R)-1-(7-Chloro-9H-fluorene-2-sulfonylamino)-2-methyl-2-phenyl-cyclopropanecarboxylic acid,
(1S,2R,3R)-1-(7-Chloro-9H-fluorene-2-sulfonylamino)-2-methyl-3-phenyl-cyclopropanecarboxylic acid,
(1S,2R,3R)-1-(5-Imidazo[1,2-a]pyridin-2-yl-thiophene-2-sulfonylamino)-2-methyl-3-phenyl-cyclopropanecarboxylic acid,
(1S,2R,3R)-1-(5-Imidazo[1,2-a]pyrimidin-2-yl-thiophene-2-sulfonylamino)-2-methyl-3-phenyl-cyclopropanecarboxylic acid,
(1S,2R)-2-Methyl-2-phenyl-1-[5-(4-trifluoromethyl-phenyl)-thiophene-2-sulfonylamino]-cyclopropanecarboxylic acid,
(1S,2R)-1-[5-(4-Acetyl-phenyl)-thiophene-2-sulfonylamino]-2-methyl-2-phenyl-cyclopropanecarboxylic acid,
(1S,2R)-1-[5-(4-Hydroxymethyl-phenyl)-thiophene-2-sulfonylamino]-2-methyl-2-phenyl-cyclopropanecarboxylic acid,
(1S,2R)-1-{5-[3-(2-Hydroxy-ethoxy)-phenyl]-thiophene-2-sulfonylamino}-2-methyl-2-phenyl-cyclopropanecarboxylic acid,
(1S,2R)-1-{5-[3-(3-Hydroxy-propoxy)-phenyl]-thiophene-2-sulfonylamino}-2-methyl-2-phenyl-cyclopropanecarboxylic acid,
(1S,2R,3R)-2-Methyl-3-phenyl-1-[5-(4-trifluoromethyl-pyrazol-1-yl)-thiophene-2-sulfonylamino]-cyclopropanecarboxylic acid,
(1S,2R,3R)-1-[5-(5-Carbamoyl-isoxazol-3-yl)-thiophene-2-sulfonylamino]-2-methyl-3-phenyl-cyclopropanecarboxylic acid,
(1S,2R,3R)-1-[5-(5-Cyano-isoxazol-3-yl)-thiophene-2-sulfonylamino]-2-methyl-3-phenyl-cyclopropanecarboxylic acid,
(1S,2R,3R)-1-[5-(4-Cyano-pyrazol-1-yl)-thiophene-2-sulfonylamino]-2-methyl-3-phenyl-cyclopropanecarboxylic acid,
(1S,2R)-1-[5-(3,4-Difluoro-phenyl)-thiophene-2-sulfonylamino]-2-methyl-2-phenyl-cyclopropanecarboxylic acid,
(1S,2R)-1-[5-(4-Hydroxy-phenyl)-thiophene-2-sulfonylamino]-2-methyl-2-phenyl-cyclopropanecarboxylic acid,
(1S,2R)-1-[5-(4-Amino-phenyl)-thiophene-2-sulfonylamino]-2-methyl-2-phenyl-cyclopropanecarboxylic acid,
(1S,2R,3R)-1-[5-(1H-Benzoimidazol-2-yl)-thiophene-2-sulfonylamino]-2-methyl-3-phenyl-cyclopropanecarboxylic acid,
(1S,2R)-2-Methyl-2-phenyl-1-(5-phenyl-benzo[b]thiophene-3-sulfonylamino)-cyclopropanecarboxylic acid,
(1S,2R)-2-Methyl-1-[5-(3-methyl-3H-[1,2,3]triazol-4-yl)-thiophene-2-sulfonylamino]-2-phenyl-cyclopropanecarboxylic acid,
(1S,2R)-2-Methyl-1-[5-(1-methyl-1H-[1,2,3]triazol-4-yl)-thiophene-2-sulfonylamino]-2-phenyl-cyclopropanecarboxylic acid,
(1R*,2S*)-2-(3-Methoxy-propyl)-2-phenyl-1-[5-(5-trifluoromethyl-isoxazol-3-yl)-thiophene-2-sulfonylamino]-cyclopropanecarboxylic acid,
(1S,2R)-1-[5-(3-Fluoro-4-hydroxy-phenyl)-thiophene-2-sulfonylamino]-2-methyl-2-phenyl-cyclopropanecarboxylic acid,
(1S,2R,3R)-2-Methyl-3-phenyl-1-[5-(4-trifluoromethyl-phenyl)-thiophene-2-sulfonylamino]-cyclopropanecarboxylic acid,
(1S,2R,3R)-1-(5-Benzothiazol-2-yl-thiophene-2-sulfonylamino)-2-methyl-3-phenyl-cyclopropanecarboxylic acid,
(1S,2R)-1-[5-(3-Hydroxymethyl-4-methoxy-phenyl)-thiophene-2-sulfonylamino]-2-methyl-2-phenyl-cyclopropanecarboxylic acid,
(1S,2R)-1-[5-(4-Cyano-3-fluoro-phenyl)-thiophene-2-sulfonylamino]-2-methyl-2-phenyl-cyclopropanecarboxylic acid,
(1S,2R)-1-[5-(3-Fluoro-4-hydroxymethyl-phenyl)-thiophene-2-sulfonylamino]-2-methyl-2-phenyl-cyclopropanecarboxylic acid,
(1S,2R)-1-[5-(3-Chloro-4-methoxy-phenyl)-thiophene-2-sulfonylamino]-2-methyl-2-phenyl-cyclopropanecarboxylic acid,
(1S,2R,3R)-2-Methyl-3-phenyl-1-(2-phenyl-3H-benzoimidazole-5-sulfonylamino)-cyclopropanecarboxylic acid,
(1R*,2R*,3S*)-2,3-Dimethyl-2-phenyl-1-[5-(5-trifluoromethyl-isoxazol-3-yl)-thiophene-2-sulfonylamino]-cyclopropanecarboxylic acid,
(1R*,2S*,3R*)-2,3-Dimethyl-2-phenyl-1-[5-(5-trifluoromethyl-isoxazol-3-yl)-thiophene-2-sulfonylamino]-cyclopropanecarboxylic acid,
(1S,2R)-2-Methyl-2-phenyl-1-[5-(4-trifluoromethyl-pyrazol-1-yl)-thiophene-2-sulfonylamino]-cyclopropanecarboxylic acid,
(1S,2R)-1-[5-(4-Fluoro-3-hydroxy-phenyl)-thiophene-2-sulfonylamino]-2-methyl-2-phenyl-cyclopropanecarboxylic acid,
(1S,2R)-1-[5-(3,4-Difluoro-5-hydroxy-phenyl)-thiophene-2-sulfonylamino]-2-methyl-2-phenyl-cyclopropanecarboxylic acid,
(1S,2R)-1-[5-(4-Methanesulfonyl-pyrazol-1-yl)-thiophene-2-sulfonylamino]-2-methyl-2-phenyl-cyclopropanecarboxylic acid,
(1S,2R)-1-[5-(4-Hydroxymethyl-pyrazol-1-yl)-thiophene-2-sulfonylamino]-2-methyl-2-phenyl-cyclopropanecarboxylic acid,
(1S,2R,3R)-1-[5-(5-Chloro-1H-benzoimidazol-2-yl)-thiophene-2-sulfonylamino]-2-methyl-3-phenyl-cyclopropanecarboxylic acid, (1S,2R)-1-[5-(4-Bromo-pyrazol-1-yl)-thiophene-2-sulfonylamino]-2-phenyl-cyclopropanecarboxylic acid,
(1S,2R)-1-{5-[3-(1,1-Difluoro-2-hydroxy-ethyl)-phenyl]-thiophene-2-sulfonylamino}-2-methyl-2-phenyl-cyclopropanecarboxylic acid,
(1S,2R,3R)-1-[5-(5-Methoxy-1H-benzoimidazol-2-yl)-thiophene-2-sulfonylamino]-2-methyl-3-phenyl-cyclopropanecarboxylic acid,
(1R*,2S*)-2-(4-Chloro-phenyl)-2-methyl-1-[5-(5-trifluoromethyl-isoxazol-3-yl)-thiophene-2-sulfonylamino]-cyclopropanecarboxylic acid,
(1R*,2S*)-2-(3-ethoxy-phenyl-2-methyl-1-[5-(5-trifluoromethyl-isoxazol-3-yl)-thiophene-2-sulfonylamino]-cyclopropanecarboxylic acid,
(1R*,2S*)-2-(3-Fluoro-phenyl)-2-methyl-1-[5-(5-trifluoromethyl-isoxazol-3-yl)-thiophene-2-sulfonylamino]-cyclopropanecarboxylic acid,
(1R*,2S*)-2-(3-Chloro-phenyl)-2-methyl-1-[5-(5-trifluoromethyl-isoxazol-3-yl)-thiophene-2-sulfonylamino]-cyclopropanecarboxylic acid,
(1R*,2S*)-2-(2-Methoxy-phenyl)-2-methyl-1-[5-(5-trifluoromethyl-isoxazol-3-yl)-thiophene-2-sulfonylamino]-cyclopropanecarboxylic acid,
(1R*,2S*)-2-(3-Methanesulfonyl-phenyl)-2-methyl-1-[5-(5-trifluoromethyl-isoxazol-3-yl)-thiophene-2-sulfonylamino]-cyclopropanecarboxylic acid,
(1R*,2S*)-2-(2-Fluoro-phenyl)-2-methyl-1-[5-(5-trifluoromethyl-isoxazol-3-yl)-thiophene-2-sulfonylamino]-cyclopropanecarboxylic acid,
(1R*,2S*)-2-(2-Chloro-phenyl)-2-methyl-1-[5-(5-trifluoromethyl-isoxazol-3-yl)-thiophene-2-sulfonylamino]-cyclopropanecarboxylic acid,
(1R*,2S*)-2-Methyl-2-pyridin-3-yl-1-[5-(5-trifluoromethyl-isoxazol-3-yl)-thiophene-2-sulfonylamino]-cyclopropanecarboxylic acid,
(1S,2R)-2-(3-Fluoro-phenyl)-2-methyl-1-[5-(5-trifluoromethyl-isoxazol-3-yl)-thiophene-2-sulfonylamino]-cyclopropanecarboxylic acid,
(1S,2R)-2-(3-Chloro-phenyl)-2-methyl-1-[5-(5-trifluoromethyl-isoxazol-3-yl)-thiophene-2-sulfonylamino]-cyclopropanecarboxylic acid,
(1S,2R)-2-(4-Chloro-phenyl)-2-methyl-1-[5-(5-trifluoromethyl-isoxazol-3-yl)-thiophene-2-sulfonylamino]-cyclopropanecarboxylic acid,
(1S,2R)-2-(4-Fluoro-phenyl)-2-methyl-1-[5-(5-trifluoromethyl-isoxazol-3-yl)-thiophene-2-sulfonylamino]-cyclopropanecarboxylic acid,
(1S,2R,3R)-2-Methyl-3-phenyl-1-(2-phenyl-imidazo[1,2-a]pyridine-6-sulfonylamino)-cyclopropanecarboxylic acid,
(1S,2R,3R)-2,3-Dimethyl-2-phenyl-1-[5-(5-trifluoromethyl-isoxazol-3-yl)-thiophene-2-sulfonylamino]-cyclopropanecarboxylic acid,
(1S,2R)-2-(3-Methoxy-phenyl)-2-methyl-1-[5-(5-trifluoromethyl-isoxazol-3-yl)-thiophene-2-sulfonylamino]-cyclopropanecarboxylic acid, and
(1S,2R,3R)-1-{5-[5-(1,1-Difluoro-ethyl)-isoxazol-3-yl]-thiophene-2-sulfonylamino}-2,3-dimethyl-2-phenyl-cyclopropanecarboxylic acid;
or a pharmaceutically acceptable salt thereof.

10. A compound represented by the formula (1'):

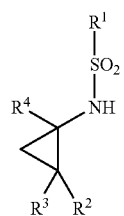

wherein
$R^1$ is
—$(CH_2)_m$—X—$(CH_2)_n$-$A^1$,
wherein
m and n are the same or different and each is selected from 0 and an integer ranging from 1 to 6,
X is selected from a single bond, a $C_{1-6}$ alkylene group, a $C_{2-6}$ alkenylene group, a $C_{2-6}$ alkynylene group, —O—, —N($R^5$)—, —S(O)$_{m1}$—, —CO—, —CON($R^5$)—, —N($R^5$)CO—, —SO$_2$N($R^5$)—, —N($R^5$)SO$_2$—, —N($R^5$)CON($R^6$)—, —N($R^5$)SO$_2$N($R^6$)—, —OCON($R^5$)— and —N($R^5$)COO—,
wherein
$R^5$ and $R^6$ are the same or different and each is selected from a hydrogen atom and a $C_{1-6}$ alkyl group,
m1 is selected from 0 and an integer ranging from 1 to 2,
$A^1$ is selected from a substituted $C_{3-14}$ hydrocarbon ring group and a substituted heterocyclic group;
$R^2$ and $R^3$ are the same or different and each is selected from
(1) a hydrogen atom,
(2) a $C_{1-6}$ alkyl group,
(3) a halogenated $C_{1-6}$ alkyl group, and
(4) —$(CH_2)_p$—$X_1$—$(CH_2)_q$-$A^2$,
provided that $R^2$ and $R^3$ are not hydrogen atoms at the same time,
wherein
p and q are the same or different and each is selected from 0 and an integer ranging from 1 to 6,
$X_1$ is selected from a single bond, a $C_{1-6}$ alkylene group, a $C_{2-6}$ alkenylene group, a $C_{2-6}$ alkynylene group, —O—, —N($R^7$)—, —S(O)$_{m2}$—, —CO—, —CON($R^7$)—, —N($R^7$)CO—, —SO$_2$N($R^7$)—, —N($R^7$)SO$_2$—, —N($R^7$)CON($R^8$)—, —N($R^7$)SO$_2$N($R^8$)—, —OCON($R^7$)— and —N($R^7$)COO—,
wherein
$R^7$ and $R^8$ are the same or different and each is selected from a hydrogen atom and a $C_{1-6}$ alkyl group,
m2 is selected from 0 and an integer ranging from 1 to 2,
r is selected from 0 and an integer ranging from 1 to 2, and
$A^2$ is selected from an optionally substituted $C_{3-14}$ hydrocarbon ring group and an optionally substituted heterocyclic group; and
$R^4$ is selected from
(1) —CO$_2R^9$,
(2) —C(O)NHOR$^9$,
(3) —C(O)NH—SO$_2$—R$^9$,
(4) —C(O)NHR$^9$,
(5) —SH,
(6) —CH$_2$CO$_2$R$^9$,
(7) —C(O)R$^9$,
(8) —N(OH)COR$^9$,
(9) —SN$_2$H$_2$R$^9$,

(10) —SONHR$^9$,
(11) —CH$_2$CO$_2$H,
(12) —PO(OH)$_2$,
(13) —PO(OH)NHR$^9$,
(14) —CH$_2$SH,
and
(15) —CH$_2$OH;
wherein
R$^9$ is selected from a hydrogen atom, an optionally substituted C$_{1-10}$ alkyl group and an optionally substituted C$_{6-14}$ aryl-C$_{1-6}$ alkyl group;
or a pharmaceutically acceptable salt thereof.

11. The compound of claim 10, wherein A$^1$ is selected from
(1) an optionally substituted fused C$_{6-14}$ hydrocarbon ring group,
(2) an optionally substituted fused heterocyclic group, and
(3) —V—W-Z,
wherein
V is selected from an optionally substituted C$_{3-14}$ hydrocarbon ring group and an optionally substituted heterocyclic group;
W is —(CH$_2$)$_t$—X$_2$—(CH$_2$)$_u$—;
wherein
t and u are the same or different and each is selected from 0 and an integer ranging from 1 to 6,
X$_2$ is selected from a single bond, a C$_{1-6}$ alkylene group, a C$_{2-6}$ alkenylene group, a C$_{2-6}$ alkynylene group, —O—, —N(R$^{10}$)—, —S(O)$_{m3}$—, —CO—, —CON(R$^{10}$)—, —N(R$^{10}$)CO—, —SO$_2$N(R$^{10}$)—, —N(R$^{10}$)SO$_2$—, —N(R$^{10}$)CON(R$^{11}$)—, —N(R$^{10}$)SO$_2$N(R$^{11}$)—, —OCON(R$^{10}$)— and —N(R$^{10}$)COO—,
wherein
R$^{10}$ and R$^{11}$ are the same or different and each is selected from a hydrogen atom and a C$_{1-6}$ alkyl group,
m3 is selected from 0 and an integer ranging from 1 to 2,
Z is selected from an optionally substituted C$_{1-6}$ alkyl group, a halogen atom, a nitro group, a cyano group, a C$_{1-6}$ alkoxy group, a hydroxyl group, a halogenated C$_{1-6}$ alkyl group, a halogenated C$_{1-6}$ alkoxy group, a carboxyl group, a C$_{1-6}$ alkoxy-carbonyl group, an amino group, a mono(C$_{1-6}$ alkyl)amino group, a di(C$_{1-6}$ alkyl)amino group, an optionally substituted C$_{3-14}$ hydrocarbon ring group and an optionally substituted heterocyclic group;
or a pharmaceutically acceptable salt thereof.

12. The compound of claim 11, wherein m and n are 0, and X is a single bond; or a pharmaceutically acceptable salt thereof.

13. The compound of claim 12, wherein t and u are 0; or a pharmaceutically acceptable salt thereof.

14. The compound of claim 13, wherein R$^4$ is selected from —CO$_2$R$^9$ and —C(O)NHOR$^9$; or a pharmaceutically acceptable salt thereof.

15. The compound of claim 14, wherein R$^9$ is a hydrogen atom; or a pharmaceutically acceptable salt thereof.

16. The compound of claim 15, wherein R$^2$ is —(CH$_2$)$_p$—X$_1$—(CH$_2$)$_q$-A$^2$; or a pharmaceutically acceptable salt thereof.

17. The compound of claim 10, which is selected from the group consisting of
(1S,2R)-1-(4'-chloro-biphenyl-4-sulfonylamino)-2-phenyl-cyclopropanecarboxylic acid,
(1R*,2S*)-1-[4-(2,4-dichloro-benzyloxy)-benzenesulfonylamino]-2-phenyl-cyclopropanecarboxylic acid hydroxyamide,
(1R*,2S*)-1-(4'-chloro-biphenyl-4-sulfonylamino)-2-{3-[(pyridin-3-ylmethyl)-amino]-phenyl}-cyclopropanecarboxylic acid,
(1R*,2S*)-1-[5-(4-chloro-phenyl)-thiophene-2-sulfonylamino]-2-(2-methoxy-phenyl)-cyclopropanecarboxylic acid,
(1S,2R)-1-(4'-chloro-biphenyl-4-sulfonylamino)-2-phenyl-cyclopropanecarboxylic acid,
(1R,2R)-1-(4'-chloro-biphenyl-4-sulfonylamino)-2-phenyl-cyclopropanecarboxylic acid,
(1R,2S)-1-(4'-chloro-biphenyl-4-sulfonylamino)-2-phenyl-cyclopropanecarboxylic acid,
(1R,2R)-2-benzyl-1-(4'-chloro-biphenyl-4-sulfonylamino)-cyclopropanecarboxylic acid,
(1S,2S)-2-benzyl-1-(4'-chloro-biphenyl-4-sulfonylamino)-cyclopropanecarboxylic acid,
(1R*,2S*)-1-(4'-chloro-biphenyl-4-sulfonylamino)-2-(3-phenoxy-phenyl)-cyclopropanecarboxylic acid,
(1R*,2S*)-1-(4'-chloro-biphenyl-4-sulfonylamino)-2-[3-(4-chloro-phenoxy)-phenyl]-cyclopropanecarboxylic acid,
(1R*,2S*)-1-(4'-chloro-biphenyl-4-sulfonylamino)-2-(3-methoxy-phenyl)-cyclopropanecarboxylic acid,
(1R*,2S*)-1-(4'-chloro-biphenyl-4-sulfonylamino)-2-(2-methoxy-phenyl)-cyclopropanecarboxylic acid,
(1R*,2S*)-1-(4'-chloro-biphenyl-4-sulfonylamino)-2-(2-phenoxy-phenyl)-cyclopropanecarboxylic acid,
(1R*,2S*)-1-(4'-chloro-biphenyl-4-sulfonylamino)-2-(4-methoxy-phenyl)-cyclopropanecarboxylic acid,
(1R*,2S*)-1-(4'-chloro-biphenyl-4-sulfonylamino)-2-(4-phenoxy-phenyl)-cyclopropanecarboxylic acid,
(1R*,2S*)-1-(4'-chloro-biphenyl-4-sulfonylamino)-2-(3-nitro-phenyl)-cyclopropanecarboxylic acid,
(1R*,2S*)-2-(3-amino-phenyl)-1-(4'-chloro-biphenyl-4-sulfonylamino)-cyclopropanecarboxylic acid,
(1R*,2S*)-1-(4'-chloro-biphenyl-4-sulfonylamino)-2-piperidine-4-yl-cyclopropanecarboxylic acid,
(1R*,2S*)-1-(4'-chloro-biphenyl-4-sulfonylamino)-2-(3-isobutoxy-phenyl)-cyclopropanecarboxylic acid,
(1R*,2S*)-1-(4'-chloro-biphenyl-4-sulfonylamino)-2-(3-dimethylamino-phenyl)-cyclopropanecarboxylic acid,
(1R*,2S*)-1-(4'-chloro-biphenyl-4-sulfonylamino)-2-(3-trifluoromethyl-phenyl)-cyclopropanecarboxylic acid,
(1R*,2S*)-2-(3-bromo-phenyl)-1-(4'-chloro-biphenyl-4-sulfonylamino)-cyclopropanecarboxylic acid,
(1R*,2S*)-1-(4'-chloro-biphenyl-4-sulfonylamino)-2-phenyl-cyclopropanecarboxylic acid,
(1R*,2S*)-1-(4'-chloro-biphenyl-4-sulfonylamino)-2-(3,5-diphenoxy-phenyl)-cyclopropanecarboxylic acid,
(1R*,2S*)-2-biphenyl-3-yl-1-(4'-chloro-biphenyl-4-sulfonylamino)-cyclopropanecarboxylic acid,
(1R,2S*)-2-(3-benzyloxycarbonylamino-phenyl)-1-(4'-chloro-biphenyl-4-sulfonylamino)-cyclopropanecarboxylic acid,
(1R*,2S*)-1-(4'-chloro-biphenyl-4-sulfonylamino)-2-(3-isobutoxycarbonylamino-phenyl)-cyclopropanecarboxylic acid,
(1R*,2S*)-1-(biphenyl-4-sulfonylamino)-2-phenyl-cyclopropanecarboxylic acid,
(1R*,2S*)-1-(4-phenoxy-benzenesulfonylamino)-2-phenyl-cyclopropanecarboxylic acid,
(1R*,2S*)-1-(4'-bromo-biphenyl-4-sulfonylamino)-2-phenyl-cyclopropanecarboxylic acid,
(1S,2R)-2-phenyl-1-[5-(5-trifluoromethyl-[1,2,4]oxadiazol-3-yl)-thiophene-2-sulfonylamino]-cyclopropanecarboxylic acid, (1R*,2S*)-1-[4-(2-methyl-2H-tetrazol-5-yl)-benzenesulfonylamino]-2-phenyl-cyclopropanecarboxylic acid,
(1R*,2S*)-1-[4-(2-ethyl-2H-tetrazol-5-yl)-benzenesulfonylamino]-2-phenyl-cyclopropanecarboxylic acid,
(1R*,2S*)-2-phenyl-1-[4-(2-propyl-2H-tetrazol-5-yl)-benzenesulfonylamino]-cyclopropanecarboxylic acid,
(1R*,2S*)-1-[4-(2-isopropyl-2H-tetrazol-5-yl)-benzenesulfonylamino]-2-phenyl-cyclopropanecarboxylic acid,
(1R*,2S*)-1-(dibenzofurane-2-sulfonylamino)-2-phenyl-cyclopropanecarboxylic acid,
(1R*,2S*)-1-(4'-chloro-biphenyl-4-sulfonylamino)-2-(3-methanesulfonylamino-phenyl)-cyclopropanecarboxylic acid,
(1S,2R)-1-[5-(5-pentafluoroethyl-[1,2,4]oxadiazol-3-yl)-thiophene-2-sulfonylamino]-2-phenyl-cyclopropanecarboxylic acid,
(1R*,2S*)-2-(3-acetylamino-phenyl)-1-(4'-chloro-biphenyl-4-sulfonylamino)-cyclopropanecarboxylic acid,
(1R*,2S*)-1-(4'-chloro-biphenyl-4-sulfonylamino)-2-(3-methoxycarbonylamino-phenyl)-cyclopropanecarboxylic acid,
(1R*,2S*)-4-{3-[2-carboxy-2-(4'-chloro-biphenyl-4-sulfonylamino)-cyclopropyl]-phenylamino}-piperidine-1-carboxylic acid tert-butyl ester,
(1R*,2S*)-2-(3-benzylamino-phenyl)-1-(4'-chloro-biphenyl-4-sulfonylamino)-cyclopropanecarboxylic acid,
(1R*,2S*)-1-(4'-chloro-biphenyl-4-sulfonylamino)-2-(3-hydroxy-phenyl)-cyclopropanecarboxylic acid,
(1R*,2S*)-1-(4'-chloro-biphenyl-4-sulfonylamino)-2-cyclohexyl-cyclopropanecarboxylic acid,
(1R*,2S*)-2-phenyl-1-(4-thiophen-2-yl-benzenesulfonylamino)-cyclopropanecarboxylic acid,
(1R*,2S*)-2-phenyl-1-(4-thiophen-3-yl-benzenesulfonylamino)-cyclopropanecarboxylic acid,
(1R*,2S*)-1-[4-(4-methyl-thiophen-2-yl)-benzenesulfonylamino]-2-phenyl-cyclopropanecarboxylic acid,
5-[4-((1R*,2S*)-1-Carboxy-2-phenyl-cyclopropylsulfamoyl)-phenyl]-thiophene-2-carboxylic acid,
(1R*,2S*)-1-(9-oxo-9H-fluorene-2-sulfonylamino)-2-phenyl-cyclopropanecarboxylic acid,
(1R*,2S*)-4-[2-carboxy-2-(4'-chloro-biphenyl-4-sulfonylamino)-cyclopropyl]-piperidine-1-carboxylic acid tert-butyl ester,
(1R*,2S*)-2-(3-benzenesulfonylamino-phenyl)-1-(4'-chloro-biphenyl-4-sulfonylamino)-cyclopropanecarboxylic acid,
(1R*,2S*)-1-(4'-methoxy-biphenyl-4-sulfonylamino)-2-phenyl-cyclopropanecarboxylic acid,
(1R*,2S*)-1-(9H-fluorene-2-sulfonylamino)-2-phenyl-cyclopropanecarboxylic acid,
(1R*,2S*)-1-[4-(5-methyl-[1,2,4]oxadiazol-3-yl)-benzenesulfonylamino]-2-phenyl-cyclopropanecarboxylic acid,
(1R*,2S*)-2-phenyl-1-[4-(5-phenyl-[1,2,4]oxadiazol-3-yl)-benzenesulfonylamino]-cyclopropanecarboxylic acid,
(1R*,2S*)-2-phenyl-1-(5-phenyl-thiophene-2-sulfonylamino)-cyclopropanecarboxylic acid,
(1R*,2S*)-1-(4'-chloro-biphenyl-4-sulfonylamino)-2-(2-hydroxy-phenyl)-cyclopropanecarboxylic acid,
(1R*,2S*)-2-phenyl-1-[4-(5-phenyl-[1,3,4]oxadiazol-2-yl)-benzenesulfonylamino]-cyclopropanecarboxylic acid,
(1R*,2S*)-1-(5-bromo-thiophene-2-sulfonylamino)-2-phenyl-cyclopropanecarboxylic acid,
(1R*,2S*)-1-(4'-chloro-biphenyl-4-sulfonylamino)-2-[3-(pyridin-2-ylamino)-phenyl]-cyclopropanecarboxylic acid,
(1R*,2S*)-1-(4-chloro-biphenyl-4-sulfonylamino)-2-{3-[(pyridin-2-carbonyl)-amino]-phenyl}-cyclopropanecarboxylic acid,
(1R*,2S*)-1-(4'-chloro-biphenyl-4-sulfonylamino)-2-{3-[(pyridin-4-carbonyl)-amino]-phenyl}-cyclopropanecarboxylic acid,
(1R*,2S*)-1-(4'-chloro-biphenyl-4-sulfonylamino)-2-{3-[(pyridin-3-carbonyl)-amino]-phenyl}-cyclopropanecarboxylic acid,
(1R*,2S*)-1-[4-(2,4-dichloro-benzyloxy)-benzenesulfonylamino]-2-phenyl-cyclopropanecarboxylic acid,
(1R*,2S*)-1-(4'-chloro-biphenyl-4-sulfonylamino)-2-[3-(2-hydroxy-ethoxy)-phenyl]-cyclopropanecarboxylic acid,
(1R*,2S*)-1-(4'-chloro-biphenyl-4-sulfonylamino)-2-[3-(2-dimethylamino-acetylamino)-phenyl]-cyclopropanecarboxylic acid,
(1R*,2S)-1-(4'-chloro-biphenyl-4-sulfonylamino)-2-[3-(pyridin-3-yloxy)-phenyl]-cyclopropanecarboxylic acid,
(1R*,2S*)-1-[5-(4-chloro-phenyl)-thiophene-2-sulfonylamino]-2-phenyl-cyclopropanecarboxylic acid,
(1R*,2S*)-1-[5-(4-methoxy-phenyl)-thiophene-2-sulfonylamino]-2-phenyl-cyclopropanecarboxylic acid,
(1R*,2S*)-1-[5-(4-dimethylamino-phenyl)-thiophene-2-sulfonylamino]-2-phenyl-cyclopropanecarboxylic acid,
(1R*,2S*)-1-(7-bromo-9H-fluorene-2-sulfonylamino)-2-phenyl-cyclopropanecarboxylic acid,
(1R*,2S*)-1-(4'-chloro-biphenyl-4-sulfonylamino)-2-[3-(2-pyrrolidin-1-yl-ethoxy)-phenyl]-cyclopropanecarboxylic acid,
(1R*,2S*)-1-(4'-chloro-biphenyl-4-sulfonylamino)-2-[3-(2-morpholin-4-yl-ethoxy)-phenyl]-cyclopropanecarboxylic acid,
(1R*,2S*)-1-(4'-chloro-biphenyl-4-sulfonylamino)-2-[3-(2-pyrazol-1-yl-ethoxy)-phenyl]-cyclopropanecarboxylic acid,
(1R*,2S*)-1-(4'-chloro-biphenyl-4-sulfonylamino)-2-[3-(pyridin-3-ylmethoxy)-phenyl]-cyclopropanecarboxylic acid,
(1R*,2S*)-1-(4'-chloro-biphenyl-4-sulfonylamino)-2-(2-methyl-1,2,3,4-tetrahydro-isoquinolin-7-yl)-cyclopropanecarboxylic acid,
(1R*,2S*)-1-(4'-chloro-biphenyl-4-sulfonylamino)-2-(2-isopropyl-1,2,3,4-tetrahydro-isoquinolin-7-yl)-cyclopropanecarboxylic acid,
(1R*,2S*)-2-(2-benzyl-1,2,3,4-tetrahydro-isoquinolin-7-yl)-1-(4'-chloro-biphenyl-4-sulfonylamino)-cyclopropanecarboxylic acid,
(1R*,2S*)-1-(7-fluoro-9H-fluorene-2-sulfonylamino)-2-phenyl-cyclopropanecarboxylic acid,
(1S*,2S*)-1-(7-fluoro-9H-fluorene-2-sulfonylamino)-2-phenyl-cyclopropanecarboxylic acid,
(1R*,2S*)-1-[4-(2-ethyl-thiazol-4-yl)-benzenesulfonylamino]-2-phenyl-cyclopropanecarboxylic acid,
(1R*,2S*)-1-(4'-chloro-biphenyl-4-sulfonylamino)-2-[3-(2-imidazol-1-yl-ethoxy)-phenyl]-cyclopropanecarboxylic acid,
(1R*,2S*)-2-(2-benzyloxy-phenyl)-1-[5-(4-chloro-phenyl)-thiophene-2-sulfonylamino]-cyclopropanecarboxylic acid,
(1S,2R)-1-[5-(4-chloro-phenyl)-thiophene-2-sulfonylamino]-2-phenyl-cyclopropanecarboxylic acid, (1R*,2S*)-1-[5-(4-chloro-phenyl)-thiophene-2-sulfonylamino]-2-[3-(2-hydroxy-ethoxy)-phenyl]-cyclopropanecarboxylic acid,
(1R*,2S*)-2-(2-benzyloxy-phenyl)-1-[5-(4-chloro-phenylethynyl)-thiophene-2-sulfonylamino]-cyclopropanecarboxylic acid,
(1R*,2S*)-1-[5-(4-chloro-phenyl)-thiophene-2-sulfonylamino]-2-[3-(pyridin-3-yloxy)-phenyl]-cyclopropanecarboxylic acid,
(1S,2R)-2-phenyl-1-(1-phenyl-1H-pyrazole-4-sulfonylamino)-cyclopropanecarboxylic acid,
(1R*,2S*)-1-(4'-chloro-biphenyl-4-sulfonylamino)-2-{3-[(3H-imidazol-4-ylmethyl)-amino]-phenyl}-cyclopropanecarboxylic acid,
(1S,2R)-1-(7-bromo-9H-fluorene-2-sulfonylamino)-2-phenyl-cyclopropanecarboxylic acid,
(1R*,2S*)-1-[4-(2-methyl-thiazol-4-yl)-benzenesulfonylamino]-2-phenyl-cyclopropanecarboxylic acid,
(1R*,2S*)-1-[4-(1-hydroxy-ethyl)-benzenesulfonylamino]-2-phenyl-cyclopropanecarboxylic acid,
(1R*,2S*)-1-(7-chloro-9H-fluorene-2-sulfonylamino)-2-phenyl-cyclopropanecarboxylic acid,
(1R*,2S*)-1-[3-(6-chloro-pyridazin-3-yl)-benzenesulfonylamino]-2-phenyl-cyclopropanecarboxylic acid,
(1S*,2S*)-1-(7-chloro-9H-fluorene-2-sulfonylamino)-2-phenyl-cyclopropanecarboxylic acid,
(1S,2R)-1-[1-(4-chloro-phenyl)-1H-pyrazole-4-sulfonylamino]-2-phenyl-cyclopropanecarboxylic acid,
(1R*,2S*)-1-[5-(4-chloro-phenyl)-thiophene-2-sulfonylamino]-2-(3-dimethylaminomethyl-phenyl)-cyclopropanecarboxylic acid,
(1R*,2S*)-1-(4'-chloro-biphenyl-4-sulfonylamino)-2-[3-(1-methyl-piperidine-4-ylamino)-phenyl]-cyclopropanecarboxylic acid,
(1S,2R)-1-[2-(4-chloro-phenyl)-thiazole-5-sulfonylamino]-2-phenyl-cyclopropanecarboxylic acid,
(1R*,2S*)-1-(4'-chloro-biphenyl-4-sulfonylamino)-2-{3-[(1-methyl-1H-imidazol-2-ylmethyl)-amino]-phenyl}-cyclopropanecarboxylic acid,
(1R*,2S*)-1-[5-(4-chloro-phenyl)-thiophene-2-sulfonylamino]-2-(2-hydroxy-phenyl)-cyclopropanecarboxylic acid,
(1R*,2S*)-1-[5-(4-chloro-phenyl)-thiophene-2-sulfonylamino]-2-[3-(4-methyl-piperazin-1-ylmethyl)-phenyl]-cyclopropanecarboxylic acid,
(1R*,2S*)-1-[5-(4-chloro-phenyl)-thiophene-2-sulfonylamino]-2-(3-{[methyl-(1-methyl-piperidine-4-yl)-amino]-methyl}-phenyl)-cyclopropanecarboxylic acid,
(1R*,2S*)-1-(4'-chloro-biphenyl-4-sulfonylamino)-2-[3-(2-hydroxy-acetylamino)-phenyl]-cyclopropanecarboxylic acid,
(1S,2R)-1-[5-(4-chloro-phenyl)-4-methyl-thiophene-2-sulfonylamino]-2-phenyl-cyclopropanecarboxylic acid,
(1R*,2S*)-1-[5-(4-chloro-phenyl)-thiophene-2-sulfonylamino]-2-[3-(pyridin-3-ylmethoxy)-phenyl]-cyclopropanecarboxylic acid,
(1R*,2S*)-1-[5-(4-chloro-phenyl)-thiophene-2-sulfonylamino]-2-[3-(pyridin-2-ylmethoxy)-phenyl]-cyclopropanecarboxylic acid,
(1R,2S)-1-(7-bromo-9H-fluorene-2-sulfonylamino)-2-phenyl-cyclopropanecarboxylic acid,
(1S,2R)-1-[5-(3-chloro-phenyl)-thiophene-2-sulfonylamino]-2-phenyl-cyclopropanecarboxylic acid,
(1R*,2S)-1-(4'-chloro-biphenyl-4-sulfonylamino)-2-[3-(pyridine-3-sulfonylamino)-phenyl]-cyclopropanecarboxylic acid,
(1R*,2S*)-1-(4'-chloro-biphenyl-4-sulfonylamino)-2-{3-[(1H-imidazol-2-ylmethyl)-amino]-phenyl}-cyclopropanecarboxylic acid,
(1R*,2S*)-3-{2-carboxy-2-[5-(4-chloro-phenyl)-thiophene-2-sulfonylamino]-cyclopropyl}-benzoic acid,
(1R*,2S*)-1-(4'-chloro-biphenyl-4-sulfonylamino)-2-(3-dimethylcarbamoylmethoxy-phenyl)-cyclopropanecarboxylic acid,
(1R*,2S*)-1-[5-(4-chloro-phenyl)-thiophene-2-sulfonylamino]-2-(3-methoxy-phenyl)-cyclopropanecarboxylic acid,
(1R*,2S*)-1-[5-(4-chloro-phenyl)-thiophene-2-sulfonylamino]-2-(3-hydroxy-phenyl)-cyclopropanecarboxylic acid,
(1R*,2S*)-2-(3-carbamoylmethoxy-phenyl)-1-(4'-chloro-biphenyl-4-sulfonylamino)-cyclopropanecarboxylic acid,
(1R*,2S*)-1-(4'-chloro-biphenyl-4-sulfonylamino)-2-(3-methylcarbamoylmethoxy-phenyl)-cyclopropanecarboxylic acid,
(1R*,2S*)-2-(3-carboxymethoxy-phenyl)-1-(4'-chloro-biphenyl-4-sulfonylamino)-cyclopropanecarboxylic acid,
(1R*,2S*)-1-(5-isooxazol-3-yl-thiophene-2-sulfonylamino)-2-phenyl-cyclopropanecarboxylic acid,
(1R*,2S*)-2-phenyl-1-[5-(5-trifluoromethyl-isooxazol-3-yl)-thiophene-2-sulfonylamino]-cyclopropanecarboxylic acid,
(1S*,2R*)-1-(7-chloro-dibenzofurane-3-sulfonylamino)-2-phenyl-cyclopropanecarboxylic acid,
(1S*,2S*)-1-(7-chloro-dibenzofurane-3-sulfonylamino)-2-phenyl-cyclopropanecarboxylic acid,
(1S,2R)-1-[5-(2-chloro-phenyl)-thiophene-2-sulfonylamino]-2-phenyl-cyclopropanecarboxylic acid,
(1S,2R)-1-[5-(2,4-dichloro-phenyl)-thiophene-2-sulfonylamino]-2-phenyl-cyclopropanecarboxylic acid,
(1S,2R)-1-(2-benzofuran-2-yl-ethansulfonylamino)-2-phenyl-cyclopropanecarboxylic acid,
(1R*,2S*)-1-[5-(4-chloro-phenyl)-thiophene-2-sulfonylamino]-2-(3-nitro-phenyl)-cyclopropanecarboxylic acid,
(1R*,2S*)-2-(3-amino-phenyl)-1-[5-(4-chloro-phenyl)-thiophene-2-sulfonylamino]-cyclopropanecarboxylic acid,
(1R*,2S*)-1-[5-(4-chloro-phenyl)-thiophene-2-sulfonylamino]-2-{3-[(pyridin-3-ylmethyl)-amino]-phenyl}-cyclopropanecarboxylic acid,
(1R*,2S*)-1-[5-(4-chloro-phenyl)-thiophene-2-sulfonylamino]-2-(3-methanesulfonylamino-phenyl)-cyclopropanecarboxylic acid,
(1S,2R)-1-[5-(5-chloro-pyridin-2-yl)-thiophene-2-sulfonylamino]-2-phenyl-cyclopropanecarboxylic acid,
(1R*,2S*)-1-[5-(4-chloro-phenyl)-thiophene-2-sulfonylamino]-2-(3-trifluoromethanesulfonylamino-phenyl)-cyclopropanecarboxylic acid,
(1R*,2S*)-1-[5-(4-chloro-phenyl)-thiophene-2-sulfonylamino]-(3-dimethylamino-phenyl)-cyclopropanecarboxylic acid,
(1R*,2S*)-1-[5-(4-chloro-phenyl)-thiophene-2-sulfonylamino]-2-(3-hydroxymethyl-phenyl)-cyclopropanecarboxylic acid,
(1R*,2S*)-1-[5-(4-chloro-phenyl)-thiophene-2-sulfonylamino]-2-(3-ureido-phenyl)-cyclopropanecarboxylic acid, (1R*,2S*)-1-[5-(4-chloro-phenyl)-thiophene-2-sulfonylamino]-2-[3-(pyridine-3-sulfonylamino)-phenyl]-cyclopropanecarboxylic acid, (1R*,2S*)-2-(3-carbamoyl-phenyl)-1-[5-(4-chloro-phenyl)-thiophene-2-sulfonylamino]-cyclopropanecarboxylic acid, (1R*,2S*)-1-[5-(4-chloro-phenyl)-thiophene-2-sulfonylamino]-2-[2-(2-hydroxy-ethoxy)-phenyl]-cyclopropanecarboxylic acid, (1R*,2S*)-2-(2-carboxymethoxy-phenyl)-1-[5-(4-chloro-phenyl)-thiophene-2-sulfonylamino]-cyclopropanecarboxylic acid, (1R*,2S*)-1-(3-phenoxy-benzenesulfonylamino)-2-phenyl-cyclopropanecarboxylic acid, (1R*,2S*)-1-[3-(4-fluoro-phenoxy)-benzenesulfonylamino]-2-phenyl-cyclopropanecarboxylic acid, (1R*,2S*)-1-[3-(4-chloro-phenoxy)-benzenesulfonylamino]-2-phenyl-cyclopropanecarboxylic acid, (1R*,2S*)-1-[3-(3,4-dichloro-phenoxy)-benzenesulfonylamino]-2-phenyl-cyclopropanecarboxylic acid, (1R*,2S*)-1-[4-(4-chloro-phenyl)-piperazin-1-sulfonylamino]-2-phenyl-cyclopropanecarboxylic acid, (1R*,2S)-2-[2-(benzylcarbamoyl-methoxy)-phenyl]-1-[5-(4-chloro-phenyl)-thiophene-2-sulfonylamino]-cyclopropanecarboxylic acid, (1R*,2S*)-1-[5-(4-chloro-phenyl)-thiophene-2-sulfonylamino]-2-[2-(2-morpholin-4-yl-2-oxo-ethoxy)-phenyl]-cyclopropanecarboxylic acid, (1R*,2S*)-1-[5-(4-chloro-phenyl)-thiophene-2-sulfonylamino]-2-[2-(isopropylcarbamoyl-methoxy)-phenyl]-cyclopropanecarboxylic acid, (1R*,2S*)-1-[5-(4-chloro-phenyl)-thiophene-2-sulfonylamino]-2-[3-(pyridin-3-ylaminomethyl)-phenyl]-cyclopropanecarboxylic acid, and (1R*,2S*)-1-[5-(4-chloro-phenyl)-thiophene-2-sulfonylamino]-2-methyl-2-phenyl-cyclopropanecarboxylic acid;

or a pharmaceutically acceptable salt thereof.

18. A pharmaceutical composition comprising a compound of any claims 1, 2, and 3 to 17, or a pharmaceutically acceptable salt thereof, and a pharmaceutically acceptable carrier.

19. A method of inhibiting aggrecanase comprising administering a compound of any of claims 1, 2, and 3 to 17, or a pharmaceutically acceptable salt thereof as an active ingredient, to a mammal.

20. A method of inhibiting MMP comprising administering a compound of claim 1 or claim 10, or a pharmaceutically acceptable salt thereof as an active ingredient, to a mammal.

21. The method of claim 20, wherein MMP is MMP-13.

22. A pharmaceutical composition for treating osteoarthritis comprising a compound of claim 1 or claim 10, or a pharmaceutically acceptable salt thereof as an active ingredient.

23. A pharmaceutical composition for treating rheumatoid arthritis comprising a compound of claim 1 or claim 10, or a pharmaceutically acceptable salt thereof as an active ingredient.

24. A method for treating osteoarthritis, which comprises administering a compound of any of claims 1, 2, and 3 to 17, or a pharmaceutically acceptable salt thereof to a mammal in ned thereof.

25. A method for treating rheumatoid arthritis, which comprises administering a compound of any of claims 1, 2, and 3 to 17, or a pharmaceutically acceptable salt thereof to a mammal in need thereof.

26. The pharmaceutical composition of claim 22, further comprising at least one other therapeutic agent for osteoarthritis.

27. The pharmaceutical composition of claim 22, further comprising at least one therapeutic agent for rheumatoid arthritis.

28. The pharmaceutical composition of claim 23, further comprising at least one therapeutic agent for osteoarthritis.

29. The pharmaceutical composition of claim 23, further comprising at least one other therapeutic agent for rheumatoid arthritis.

30. A method for treating osteoarthritis, which comprises administering a compound of calim 1 or claim 10, or a pharmaceutically acceptable salt thereof and at least one other therapeutic agent for rheumatoid arthritis to a mammal in need thereof.

31. A method for treating osteoarthritis, which comprises administering a compound of claim 1 or claim 10, or a pharmaceutically acceptable salt thereof and at least one therapeutic agent for rheumatoid arthritis to a mammal in need thereof.

32. A method for treating rheumatoid arthritis, which comprises administering a compound of claim 1 or claim 10, or a pharmaceutically acceptable salt thereof and at least one therapeutic agent for osteoarthritis to a mammal in need thereof.

33. A method for treating rheumatoid arthritis, which comprises administering a compound of claim 1 or claim 10, or a pharmaceutically acceptable salt thereof and at least one other therapeutic agent for rheumatoid arthritis to a mammal in need thereof.

* * * * *